(12) United States Patent
Altermann et al.

(10) Patent No.: US 10,590,170 B2
(45) Date of Patent: Mar. 17, 2020

(54) VACCINES AND VACCINE COMPONENTS FOR INHIBITION OF MICROBIAL CELLS

(71) Applicant: Pastoral Greenhouse Gas Research Limited, Wellington (NZ)

(72) Inventors: Eric Heinz Altermann, Palmerston North (NZ); Graeme Trevor Attwood, Ashhurst (NZ); Dong Li, Palmerston North (NZ); William John Kelly, Ashhurst (NZ); Zhanhao Kong, Shanghai (CN); Sinead Christine Leahy, Palmerston North (NZ)

(73) Assignee: PASTORAL GREENHOUSE GAS RESEARCH LIMITED, Wellington (NZ)

( * ) Notice: Subject to any disclaimer, the term of this patent is extended or adjusted under 35 U.S.C. 154(b) by 0 days.

(21) Appl. No.: 15/082,373

(22) Filed: Mar. 28, 2016

(65) Prior Publication Data

US 2017/0342112 A1   Nov. 30, 2017

Related U.S. Application Data

(63) Continuation of application No. 12/678,976, filed as application No. PCT/NZ2008/000249 on Sep. 25, 2008, now Pat. No. 9,296,789.

(60) Provisional application No. 60/989,841, filed on Nov. 22, 2007, provisional application No. 60/989,840, filed on Nov. 22, 2007, provisional application No. 60/975,104, filed on Sep. 25, 2007.

(51) Int. Cl.
| | |
|---|---|
| *C07K 14/005* | (2006.01) |
| *C12N 7/00* | (2006.01) |
| *A61K 35/13* | (2015.01) |
| *C12N 9/64* | (2006.01) |
| *C12N 1/20* | (2006.01) |

(52) U.S. Cl.
CPC .............. *C07K 14/005* (2013.01); *C12N 1/20* (2013.01); *C12N 7/00* (2013.01); *C12N 9/641* (2013.01); *A61K 35/13* (2013.01); *C07K 2319/00* (2013.01); *C12N 2795/10021* (2013.01); *C12N 2795/10022* (2013.01)

(58) Field of Classification Search
None
See application file for complete search history.

(56) References Cited

U.S. PATENT DOCUMENTS

| | | | |
|---|---|---|---|
| 8,586,709 B2 | 11/2013 | Oh et al. | |
| 8,592,556 B2 | 11/2013 | Altermann et al. | |
| 9,296,789 B2* | 3/2016 | Altermann | C07K 14/005 |
| 9,441,016 B2* | 9/2016 | Altermann | C07K 14/195 |
| 2003/0219467 A1 | 11/2003 | Miner et al. | |
| 2006/0068386 A1 | 3/2006 | Slesarev et al. | |
| 2010/0209999 A1 | 8/2010 | Altermann et al. | |
| 2010/0221185 A1* | 9/2010 | Altermann | C07K 14/005 424/9.1 |
| 2013/0127612 A1 | 5/2013 | Stadler et al. | |
| 2013/0217612 A1* | 8/2013 | Altermann | C07K 14/195 514/1.1 |
| 2017/0157225 A1* | 6/2017 | Altermann | A61K 39/0001 |
| 2017/0342112 A1* | 11/2017 | Altermann | C12N 1/20 |

FOREIGN PATENT DOCUMENTS

| | | | |
|---|---|---|---|
| CN | 101864362 A | 10/2010 | |
| EP | 2203470 A2 | 7/2010 | |
| JP | 2010539928 A | 12/2010 | |
| WO | 9511041 | 4/1995 | |
| WO | 9700086 | 1/1997 | |
| WO | 1998007830 A2 | 3/1998 | |
| WO | 03038109 | 5/2003 | |
| WO | 06102350 | 9/2006 | |
| WO | 2009041832 A2 | 4/2009 | |
| WO | WO-2009041832 A2 * | 4/2009 | ........... C07K 14/005 |
| WO | 2009041832 A3 | 6/2009 | |
| WO | 2011025394 A1 | 3/2011 | |
| WO | WO-2011025394 A1 * | 3/2011 | ........... C07K 14/195 |
| WO | WO-2014100726 A2 * | 6/2014 | .............. C12P 5/007 |

OTHER PUBLICATIONS

Zhang et al, Recombinant Protein. PLoS One 10(10): e0140086. (2015) doi:10.1371/journal.pone.0140086. published: Oct. 7, 2015 (Year: 2015).*
Leahy et al, Standards in Genomic Sciences (2013) 8:215-227 (Year: 2013).*
McAllister et al, J. Anim. Sci. 2015.93:1431-1449. doi:10.2527/jas2014-8329. published; May 1, 2015 (Year: 2015).*
Attwood et al, Animal Feed Science and Technology 166-167 (2011) 65-75 (Year: 2011).*
Subharat et al, Veterinary Immunology and Immunopathology 164 (2015) 201-207. (Year: 2015).*
Subharat et al. (2016) PLoS ONE 11(7): e0159861. doi:10.1371/journal.pone.0159861. published Jul. 29, 2016 (Year: 2016).*
Wedlock et al, New Zealand Veterinary Journal (2010), 58(1), 29-36. (abstract only) (Year: 2010).*

(Continued)

*Primary Examiner* — Nita M. Minnifield
(74) *Attorney, Agent, or Firm* — Arent Fox LLP

(57) ABSTRACT

The invention encompasses components from microbial cells which are useful for antibody production, including peptides, polypeptides comprising these peptides, polynucleotides which encode these peptides or polypeptides, and antibodies directed to these peptides, polypeptides, or polynucleotides. The invention also encompasses to expression vectors and host cells for producing these peptides, polypeptides, polynucleotides, and antibodies. The invention further encompasses methods and compositions, especially vaccine compositions, for detecting, targeting, and inhibiting microbial cells, especially methanogen cells, using one or more of the disclosed peptides, polypeptides, polynucleotides, antibodies, expression vectors, and host cells.

8 Claims, 304 Drawing Sheets

Specification includes a Sequence Listing.

(56) References Cited

OTHER PUBLICATIONS

Wedlock et al, Animal (2013), 7:s2, pp. 244-252. (Year: 2013).*
Wright et al. Vaccine 22 (2004) 3976-3985. Available online Apr. 27, 2004 (Year: 2004).*
Buddie et al, Vet. J., 2011, 188:11-17 (Year: 2011).*
Greenspan et al, Nature Biotechnology 7: 936-937, 1999. (Year: 1999).*
Williams et al., Applied and Environmental Microbiology, Apr. 2009, 75/7:1860-1866 (Year: 2009).*
Smith et al, PNAS, Jun. 19, 2007. vol. 104, No. 25, pp. 10643-10648 (Year: 2007).*
Attwood GT et al. "Analysis of the Methanobrevibacter Ruminantium Draft Genome: Understanding Methanogen Biology to Inhibit Their Action in the Rumen", Australian Journal of Experimental Agriculture, Jan. 2, 2008, 48(1-2):83-88.
Samuel BS et al. "Genomic and Metabolic Adaptations of Methanobrevibacter Smithii to the Human Gut", Proceedings of the National Academy of Sciences of the United States of America, Jun. 19, 2007, 104 (25): 10643-48.
Uniprot Database. XP002624118; Accession No. A5UKB4, Jul. 10, 2007.
Smith DR et al. "Complete Genome Sequence of Methanobacterium Thermoautotrophicum Deltah: Functional Analysis and Comparative Genomics", Journal of Bacteriology, American Society for Microbiology, Washington, DC; US, Nov. 1, 1997, 179(22):7135-55.
Uniprot Database. XP002624120; Accession No. 027038, Jan. 1, 1998.
Fricke WF et al. "The Genome Sequence of Methanosphaera Stadtmanae Reveals Why This Human Intestinal Archaeon Is Restricted to Methanol and H-2 for Methane Formation and ATP Synthesis", Journal of Bacteriology, Jan. 2006, 188(2):642-58.
Uniprot Database XP002624121; Accession No. Q2NF85, Feb. 7, 2006.

Bult CJ et al. "Complete Genome Sequence of the Methanogenic Archaeon, Methanococcus Jannaschii", Science, American Association for the Advancement of Science, Washington, DC; US, Aug. 23, 1996, 273(5278):1058-73.
Uniprot Database XP002624122; Accession No. Q57672, Nov. 1, 1997.
Wright AD et al. "Reducing Methane Emissions in Sheep by Immunization Against Rumen Methanogens", Vaccine, Elsevier LTD; GB, Sep. 28, 2004, 22 (29-30)3976-85.
Leahy SC et al. "The Genome Sequence of the Rumen Methanogen Methanobrevibacter Ruminantium Reveals New Possibilities for Controlling Ruminant Methane Emissions", PLoS ONE, Jan. 2010, 5(1):E8926/1-17.
Uniprot Database XP002624123; Accession No. D3E1Y9, Mar. 23, 2010.
European Search Report corresponding to related EP Application No. 08833501.3; dated Mar. 11, 2011.
NCBI Genpept Accession No. ABQ87219; Jun. 21, 2007.
NCBI Genpept Accession No. ABQ87409; Jun. 21, 2007.
NCBI Genpept Accession No. ABQ86777; Jun. 21, 2007.
NCBI Genpept Accession No. ABQ87512; Jun. 21, 2007.
NCBI Genpept Accession No. ABQ87815; Jun. 21, 2007.
NCBI Genpept Accession No. ABQ86644; Jun. 21, 2007.
NCBI Genpept Accession No. ABQ86506; Jun. 21, 2007.
NCBI Genbank Accession No. X84218, Aug. 23, 1995.
NCBI Genbankaccession No. DQ419923, Jun. 28, 2006.
NCBI DBEST Accession No. CO004855, Jun. 9, 2004.
NCBI Genbank Accession No. DQ516856, Jun. 4, 2006.
International Preliminary Report on Patentability corresponding to related International Application No. PCT/NZ2008/000249; dated Jan. 20, 2010.
Attwood et al. Animal Feed Science and Technology (2011) 166-167:65-75.
Buddle et al. The Veterinary Journal (2011) 188:11-17.
Greenspan et al. Nature Biotechnology (1999) 7:936-937.
Wedlock et al. Animal (2013) 7:s2, pp. 244-252.
Williams et al. Applied Environmental Microbiology (Apr. 2009) 75(7):1860-1866.

* cited by examiner

FIG. 1A

Comparison of Methanobacteriales genomes

| Methanogen | Mb | ORFs | %G+C | rRNAs | tRNAs |
|---|---|---|---|---|---|
| Methanobrevibacter ruminantium M1[a] | 2.9 | 2239 | 32.6 | 2 | 59 |
| Methanobrevibacter smithii PS[b] | 1.9 | 1795 | 31.0 | 2 | 34 |
| Methanothermobacter thermoautotrophicus ΔH[c] | 1.8 | 1873 | 49.5 | 2 | 39 |
| Methanosphaera stadtmanae DSM3091[d] | 1.8 | 1534 | 27.6 | 4 | 40 |

[a] genome size and number of ORFs are based on analysis of the single contig M. ruminantium draft genome sequence
[b] Samuel et al., 2007
[c] Smith et al., 1997
[d] Fricke et al., 2006

FIG. 1B

M. ruminantium draft genome statistics

| | |
|---|---|
| Genome size (bp) | 2937347 |
| Open reading frames | 2239 |
| Proteins with trans-membrane domains | 503 (22.5) |
| Terminator structures | 334 (14.9) |
| TIGRfams | 2304 |
| Pfams | 3315 |
| COGs | 1834 |

[a] Numbers in parentheses indicate the feature as a % of the total ORF number

FIG. 2

Vaccination protocol.

| *Week* | *Activity* | *Description* |
|---|---|---|
| Week 0 | Bleed | Pre-bleed (2-5 ml) and initial imm. in CFA 200 μg, ID 10-15 sites |
| Week 2 | Immunize | 200 μg Boost in IFA, 10-15 sites ID |
| Week 4 | Immunize | 200 μg Boost in CFA, 15 sites ID |
| Week 6 | Bleed | Test bleed 2-5 ml |
| Week 8 | Bleed/Immunize | Test bleed 2-5 ml, 200 μg Boost in IFA, ID 10-15 sites |
| Week 10 | Immunize | 200 μg Boost in IFA, 10-15 sites ID |
| Week 12 | Bleed/Immunize | Test bleed 2-5 ml, 200 μg Boost in IFA, ID 10-15 sites |
| Week 14 | Immunize | 200 μg Boost in IFA, 10-15 sites ID |
| Week 16 | Bleed/Immunize | Test bleed 2-5 ml, 200 μg Boost in IFA, ID 10-15 sites |
| Week 17 | Verify/Plasmapheresis | Project review, Plasmapheresis (if titer OK) |

FIG. 3

**Sheep antibody responses to vaccination with *M. ruminantium* cell wall preparation and peptides designed against *M. ruminantium mtr* and surface proteins.***

| | | | | Week | | |
|---|---|---|---|---|---|---|
| Sheep # | Antigen | 0 | 6 | 12 | 15 | 16 |
| T0040 | Cell wall prep | <50 | 3200 | 12800 | 12800 | 50 |
| T0041 | mtrD peptide | 100 | 51200 | 102400 | 102400 | 25600 |
| T0042 | mtrE peptide | <50 | 3200 | 1600 | 800 | 400 |
| T0043 | mtrC peptide | <50 | 1600 | 3200 | 3200 | 3200 |
| T0044 | ORF818 surface protein peptide 1 | <50 | 6400 | 6400 | 6400 | 3200 |
| T0045 | ORF818 surface protein peptide 2 | <50 | 1600 | 3200 | 6400 | 3200 |
| T0046 | ORF508 surface protein peptide | <50 | 1600 | 3200 | 3200 | 1600 |
| T0047 | ORF820 surface protein peptide | <50 | 6400 | 6400 | 6400 | 3200 |
| T0048 | ORF1850 surface protein peptide | <50 | 3200 | 6400 | 6400 | 6400 |
| T0049 | ORF819 surface protein peptide | <50 | 3200 | 3200 | 3200 | 1600 |

*Assay: Antibody titer was determined with an ELISA with Peptide-GGG (goat gamma globulin) bound in solid phase (0.1 μg/100 μl/well) on high binding 96 well plates. The serum was first diluted 50 fold and then further diluted in 2 fold serial dilutions. The ELISA Titer was calculated as the estimated dilution factor that resulted in an $OD_{405}$ of 0.2 and was derived from nonlinear regression analysis of the serial dilution curve. Detection was obtained using an HRP conjugated secondary antibody and ABTS substrate.

FIG. 4

Peptide sequences used for antibody production.

| ORF | ORF Annotation | Peptide Sequence | SEQ ID No. |
|---|---|---|---|
| Contig40_gene_697 | tetrahydromethanopterin S-methyltransferase subunit C MtrC (=ORF898) | IIAAF KLKGL EMLC | 1 |
| Contig40_gene_698 | tetrahydromethanopterin S-methyltransferase subunit D MtrD (=ORF897) | YNIGG TIEGF VDPKC | 2 |
| Contig40_gene_699 | tetrahydromethanopterin S-methyltransferase subunit E MtrE (=ORF896) | CTLPL DGLGH PFPLP | 3 |
| Contig40_gene_828 | cobaltochelatase CobN subunit (=ORF820) | YQSST YGSDG GYDDK C | 4 |
| Contig40_gene_829 | adhesin-like protein (=ORF819) | VQSGE VSGGV DIASS C | 5 |
| Contig40_gene_830 | adhesin-like protein (=ORF818) | VADIW NGSSN SVDAY C | 6 |
| Contig40_gene_830 | adhesin-like protein (=ORF818) | FTDNQ ATGSS NGGGA IC | 7 |
| Contig40_gene_1158 | adhesin-like protein with cysteine protease domain (=ORF1850) | SKSNF VINGN GHTID C | 8 |
| Contig49_gene_43 | adhesin-like protein (=ORF508) | CYKIS ENNGN KSYDI | 9 |

FIG. 5A-1

ORFs selected for antibody production: Nucleotide sequences.

| ORF | SEQ ID NO: | Nucleotide sequence |
|---|---|---|
| Contig40_gene_697 | 703 | ttggaccaagtcattgcatgtcttggtgtgcagtttgtgcaattcttgggagttcttgctattcgtagtgtagcaagttacgttaggtact<br>ggtgtaccttctattgttgttacatgtcttaggtatggtaatcggtgcattagcaggtgtaattgcagcatttaaattaaagga<br>ttagaaatgctcgaccaatactgcattagtatttgcaatgctcattggtttattagttgcaattgttgctaagaagattgttgaatgaaa<br>atccctgttatggaaagatgcacagctgaaatcgctggtgtgctcgatcctgttctcgattctcctctgcaattgcaggtgatctct<br>attgattttattattaccgctgttgtagctcctgtagtcttaaatgtggtcatccactgcattcttaaccatgattattactgttctgcaatt<br>tgtttaggacctaacgaagatcaagttgcaatcttagttgttggacttagttgttggacttagttgttggactctcatttaaatgtttgttaatgcttcctacgaa<br>gctgcagcatctgttaaatgtccgattatgtccgatttgaggaataa |
| Contig40_gene_698 | 704 | atggatctttaatattattatgtgttgtaatcgcagtattattaggtgaggtgtacacttcattcctgtaggtgtgctcctgca<br>gctatggctaccgtacggtgtaggaactggtaccgcaatgttagcagctgtgcaggattaactgactaattaccgcagcttctatgacc<br>ggtcaaccagtatggtaatcgtattagcaggtcagttgtgttccatgtaatgatggtatcaccatgctatttgtaacttttatttatatt<br>ttcggtggttggtagtagcagcagcatctgttaaagcagcatggtatcataagtggtatctactggttagcgctcgtgttactggtgtctactgggcaattaat<br>ggacacggtattcctaccgtctgttacataagtggtatcatcggtgttatcgctggttagcgctattctctctgtaggtatgttcttatcaattca<br>gaattgctactgcaaacttaactgattgacgctactgttatgaagtttcgtagaccctaaattcaaaagactccaactgaatcctcgcttgtcgtt<br>gttctcttgtagctgctattttcatggttcttaatgatagaggtatttaa |
| Contig40_gene_699 | 705 | atgacccctattacattagtgtcagtcagtcagtcattgatggtgcagcagcaccattgcaggtgctgcagagacttagaatctgacatcggttca<br>caagtaaccctaactcccaagttcagctcagctcgctcagtattcgccgcctccacaaatggacacttacacgtatgataataaggcagcttctgggaaccagtagca<br>tacgatgctgtgtgttgtattccggtcgtattccagctcctgctattgcagctcctgtatgcagctcctatggtatatacctatagtgcaattgcaattgcaatgtgttctact<br>gtcgctgcacttgttcacgcaattctaagagttgttcggttcgttattgtcgtcaatctcaattgaacaaccattattgactgac<br>gtattaaccaatcctaggcctaccatgccagctcatgttttatagcttcgtatttgtagaatctgttatttaatgactcttcatta<br>gacgacttggacacccttcacaccattcaccattcccaataaatagttccgctgtactgcttgggaattactattggtcaatcgggatatcgtaactcaacagggatgttcat<br>tatggtcagaagtgaataccaaaaattcgactacggtgaggtactcctgtagcgattcaagggatatcgtaactaaagctcctctcggt<br>gctaaaaactctatcgatgtaggtaactcttgtctaaaatggtgacctttacctttaaccgatcgtgtttgactcagttttaacgttttcgtaagtgctt<br>tggattactgtttgtattcggagcttaggaaggacaaattgtagttatttgtcatccgtatttattaatcgctgctaattactctcttgaaag<br>tctacaagagcaaattcggaccatatggagaataa |
| Contig40_gene_828 | 706 | atgaaatataatcaaaagatattctttttttattttatatgcctcatattcctcaagctctatttatgcaggggatgttgatgattatcg<br>gatgctggtaattacactagagataattcaccttttaacaataagttccacttatccaagttctatgattgatgatgatgat<br>aaaaatgagaatttatattttagataaaagttagtgatgggataaatctcaaaacatgctgttctaaggaactctcttagataatgctgt<br>tctatgataaatcttctgttctaaggacatcttatagcttaaggcatataaagattcatcaactgtctaatcatat<br>ttagttctgaaaaattacaaattatattgattttaataagttgatagatgataaacttcagatttgatcaaacatttcaagtctgatctt<br>aataagtattaactctttaattaaatcaataagatgtcttttaaaatcaatcaagatgttcaaaatgatgattcttttaaataacagatctaacgatttaaaatcc<br>gagagcgattggatgaaactcgatcaactctatttaaacgagtcattcttttatatcaaacagagaaatcctttttgaccagtggcatgtgaaatcttagac |

FIG. 5A-2

```
aattccaattttctaatgtcaaattcaatataagaagcgaaacaaataatgcaatgagcgaggatgaaatctatgaactgatgctcct
tgcgatgcattcatcgccagtgggtaagctcaatgtgatgcagttcagtattaaccagtcttttaacaatcatcctgaattgtcaataagaaa
ctgttccttatctggaaccactactggaaacatcaattcaagctccagttcattgaattggttagaaactctacaattgactataagaag
atattcaatgaatttccaatgacgatttgataaattatttcaaggctaccaaagaggaaacaacttcgaaagcattcaagaatacattgac
aatgaaggagctctttaatagcatcttaataattggttctctataaggatataaacgataagcaaatcttaaaaacgaattgctctat
atcctttatctattgggacatgatgttcctcaagaaatcgtcaaacttttacaggatacaggcatcgaatattccgtgacaggtgtattca
tttgataatacgttctcacctttctccatgagtccagaaatcgtaccataggattttggaagtacaatgtatatccaatccaacaattg
gatttggtaaatgaaatcacagaacgcctttgaatcaaaaggataaatgtcattcctattttctccggcaggtaacgccgaacagctaaat
atcatgtgaaatattggaccagtgcctgttcgagagaacttcaccaatcttgaagatgcaaatgtcctatattcagagcggttcac
tccatggtgcatatgtgtcggtggagcaatggaattaagccctgtagtctctctacactaaaagtgataaatggcacgttacaattgcagag
tctgaatacattaccaatgagcaattgttggtggtgtttgactcttatatttcaaataggacaggagcaatcatatttgactttgttccagtt
tcccagggaattttgatgctacatatgttggtgtgttggactgcgctgggtggactagaacgctgggtggacttactctctaataggtatac
catgagaatataagaactcttgactgatagggtagacagtgcaagctactggatgcaatcacaagtctctataatgcttatacctaaggatgaa
tacaactacccctgtaagacttgccaaacaatgtttcagaacttgaagatatgatgattgcctgctgcgtataaacgtagctaactggctcctga
gaagtcgaaagttagctaaccgttcagtgtcgctctcttctcctgtagatgttaggcgtgttcctaatcaactcaccgatgaggtgagacaatggtc
aatgattggtacaatcaaatcaggcattgcttcctgaaatcagactgcttgctgcaacaaatatattggataagcttgtaaacagcctgaag
ctctatcaaacgcatcctccgatggcgatgaagctcctgaaatgcatcctttactatcatgctggttaatcgaatgaaccgattacttgtaattccaggtcttaca
gtttctgattaaacgatgggtgaagctgccctgaacctcaaagaggttggaggctgacaatcaaatgccatgtatttgtcgaagcacgcaaccacgaatggttgccagcc
ttcggtaatgtcttcattggctgcttactattatatgcagaccaggcaatcaaatgccatggttctattgattgattttccacttgatttcctccaagttcctcaagtaaatcatcatatattctatattactgatgtttagcagag
caatatttggctgcttactattatatgcagaccaggcaatcaaatgccatggttctattgattgattttccacttgatttcctccaagttcctcaagtaaatcatcatatattctatattactgatgtttagcagag
aaggaagttttattatcataagaagaggattttgcagtagtgatgatgataataatcatcaagtagtcgagagaacatcaatcaagagttagaggacaatctaacaagagcaatcaagagacttggtaattgcaaacaat
gctatacaagctaattggagagtatgatgataataatcatcaagtagtcgagagaacatcaatcaagagcaatcaagagacttggtaattgcaaacaat
ttgcaactctattggagagtatgatgataataatcatcaagtagtcgagagaacatcaatcaagagcaatcaagagacttggtaattgcaaacaat
aaggataatcagactatcacttacttgatcactgcagagaatactacgaacatgttctccctaagctcaacttaaatgcttcttaagaacact
tactaccttacaattggattcactgcagaacttcatgcaatggacatgtcagagatgaggattggcgaacaccgttgcaatcatagtctctcat
caaataccctatatccattaggacttcatgcaatgtcagagatgaggattggcgaacaccgttgcaatcatagtctctcat
gactttgaatatgccgcaagagacaatctattcgatcagctatcctgtattactaggacagagagagtgtctgatacaattggtataggagt
cgtgattatatccctaaacaggtcagtggatgtctgtaaggcttaatctat:gggacacagagacagtgctgatacaattggtataggagt
ccagagttcattggcttgagtcattaaacatggcagagaaaataacattgaccttacaatcaatgtatcagcctgagctgaagagatggtttccgcc
ttaaatggagatatgtccagtcaatagccttgaggattatgctaagacggtcgtcctcaggtgctcctacagtctctacacctcaccttaggattgtcatagcattggaaatggttacagaccag
tcatctgagctccgactcaggttgtgtagaagaagaaatagacgttacttgcaatatcatctcgacatctgtaaacctgaatcgcattacctattgtcaggatcgcattacagaccag
atcatggtatctgtgtgtagagacttgacgaagagagaatagacgttcatgctctcacctttagaaatggaatgagcctgtctggcat
aactcatcaagtgcaggatgcttgttcatattacactatcgtaaacaataagacaattgatagcacatgccgaatatgcgcctcaagtcat
cgtcctgacgatgcataacaggatgcttgttcatattacactatcgtaaacaataagacaattgatagcacatgccgaatatgcgcctcaagtcat
gacaatgcatacaggatgcttgttcatattacactatcgtaaacaataagacaattgatagcacatgccgaatatgcgcctcaagtcat
gatgcacttagatccatcatgagaagcattagcttcaaggaatgtcaacgaatcattagaagacaagaagaacaatgtgctaagcattggctagag
```

FIG. 5A-3

| | | |
|---|---|---|
| | | gattgcatctattatctaagcctagctataactctacagtctctgagaatgcaataaccgtatctttgcacctcctaacgggattat<br>ggtgctgaatatcaaagcttgtgtcaatgtcatgacctgaacgatacagatgagcttcagagttctatattgcagaatgggaaacatg<br>tattcaaaatattactgggagataacaaacccgtctgtattcatgagggcgctatccgatacagacacatattgtgtaagcgtaataccaac<br>caatacgagtattggataacgatgacttctttgattactgggagtctctcaatgacagttgaatacctatccaacagactcctacaatg<br>aatgtattgatgtatgcaaataaggacaatgcatatgttgcaacattcgagaatgtttctataacgagcttaatacaagtatctaaaccct<br>gaatggatcaaggagaatgatgcaggaaggctacagcggttccagatatatgtccaacagttcattccaacctatgggatgcaggtaacc<br>agacctt catctgtctctgaaacagtttgggatgacgtttacaatacctattataaggacaaatacgattaggagtaaaatcatggctcaa<br>tctgaaacaatgcatattcattgatatccatggcacaggctacagttgcaaatgggtagcacatgttgactgcgctgcgaactcaaatccgctcttctatacaaatagcagt<br>agtgatatagctaacacttggcacagttgcaaatgggtagcacatgttgactgcgctgcgaactcaaatccgctcttctatacaaatagcagt<br>gcattcaagtatgtgaatgctgatttgcttgctaagttgatgcctaagttgtatgacgaaacatactgaactgttcagactaactcaagc<br>gatatgcctacaaactcttcgaatattgacccgccaactacaaacagcagtgcagagtcaaacatactgaactgttcagactaactcaagc<br>tctaacagtcagcaaagcgctaacggaaaactacttaatattccaggagcaagcagatctgtagaggtcactaagagcacactccagtgctcca<br>atggccagtgcgatcagatgcaggaatgaacgatgcaaatggagaatgaacgatctgtagaggtcactaagagcacactccagtgctcca<br>aaggacgtaagtatgcctatagctattcattgttgtgttattgtttagtggcattaataggattcggttatttcagaaacagaaaagacgac<br>gatgattattataatgatgatgacgatgatgattatgaatataaatag |
| Contig40_<br>gene_829 | 707 | atgtcttttgagctgtctcagcagctgacctaaatacagtccggtgagtttcaggtgagttgacatagccagctcaaatcctga<br>gtcgaaatgaagaattgacttacgaagtccgaagcaaattccagatagtgttgaaacattcagtatgcaggctcttgttgacagctatactgcaggatcc<br>tctaatttgtatatgacggtgaaagcaaagctcatcactttgacaaaaaacgcgaacagatgaagcttttgcagactatatgatgaacagactt<br>ggaagtgcagaccggtagttatgtcattaacgacactgtaaatgcactcctatcgaagatacacattctataataaatcaagctgataggcttgta<br>caggtgcaaaggaaatatcacaatcactgtaaatgccaattccattattggtaaatgcaggttcatcttgataacttgtccctttcaagcagtcagcaggatggtctatacttc<br>tttacatatgatgatggagatggagacgaattacgacccaactgtagccaactgtataactcattgtcctgaaacacagttgacatattgataagattaagaac<br>gctacattttaagctgtgaaacgtgaatacgacccaactgtagccaactgtataactcattgtcctgaaacacagttgacatattgataagattaagaac<br>aatgccaggagatggatgagtccatagtcactgaggaggctcatactcattgtcctgaaacacagttgacatattgataagattaagaac<br>atgacaaacccctgtatacactcaaggaggctcatactcattgtcttttcaggaaacagatcgaaaaagtaaacagttctcaaatctcattagctgtctaaggtggcataacaatatgtaca<br>tatgctaaagtcaacatactctggattattatgccgatgcagatgcagcatctgaataaaagagatcaattacactgtagttgtattagcgat<br>gcctctgcatcctatcctcttgattattatgccgatgcagatgcagcatctgaataaagaagatcaattacactgtagttgtattagcgat<br>tccttgattgacaatacaattagccatcgacagcatctccataatcctctataacgtgtcagataataagaagatcaattacactgtagttgtcattagcagcttatctctgcagaa<br>agaacactggagaggtttagatgaacactgtaagcgtgtcagataataacgttaggcaaggtatgcaaatataggcagcttgcttaatcaaggggctaaggcattgtattgct<br>agataagttcattaagaatataacgttaatggagcatgatcattgaagtcaggtgatccaccattatagcagcttgctaggcaagcttcaatcagcactgtaggcgatcaaatagaagtgcggcattat<br>aaaccgattcttgactattcttgactgctgaatgcgcttaatcctataggtccatattgtctgcatgcatttgtctatcgcatataaatcatgggatgtctaccagtgaaaatgaagtgagaaaatgctaaaaacgga<br>cctatgttcacaagacattcaatgggcggcagttaatcctataggtccatatagcagcagattcaatcagcagctattcatcgagtttat<br>tacggatcgtgctgtttatgatgttggaggcgcattaaggcagtgtaattgtctcttatcaagaagcaggttgctgagtttat<br>caagcaccctaattgcattttacaattcacagattcagacttctaacagcgcattcatcaatgggcagactattatccaatgaa<br>tacaattcacttgaagatgtttcaagcgataatatattatctcatcgcgcttttgatgattggaagtgctaagcttcatgtattgct<br>gccgattgccaagctggagaggagacttgactgttaatgcaaagctatagacgttcattttatttccacagcaatagaagtgcggcattat<br>gtgtgattaggaaatccactaatgactaatgcatcaaatgaggtgcattttatttccacacgctatttgcagtaccacatttctagccttgtctcttaat<br>gttcaatataatgtccctcagttaaggcacagtcttgtctctgaatattcacagccaccatctcttgtcttcttaat<br>ataacaataacgtaaattgattctatctatacgttgactctatctatacgttgactctgtcattggatgcaaaagcaaacagcactgaaatatcct |

FIG. 5A-4

| | | |
|---|---|---|
| | 708 | ggtgctaataaggattatatcttattgatgatacaataaggcctattgatgcaagcacagtaaatgggcagacaatcctaagtcaattat<br>acagttgtcatcattgacaagagaaaatcaatggtattagatgagattaccataatcctagcctcttatataatgaaatctaggaaggac<br>ttggcttatccggcagagaatcacttcatttagaaatataactgtaaggtggcgtgattgtcgatacattagatgattccacatatatt<br>aactctcaagcaacacaacagaacagatatttggaatgtggcgatgcatgcacagatgcctttgttatgttccttacaat<br>tgggataagaccaacgtacatgccagtttgaatgcaagtcaatggttgttgagcagttcaatggttgtcctctcctataggaccaatcaaat<br>ataggattcttcggcaagaaccgatatgattggtgttctatgatgtgagcaagcttatcaaatcagggaaaacactttcactttagaaaa<br>gaagctgaatcactgctgtatatccaagcaccctatgcattctataatgcaacagttccaatagcttaaagaccatttatatctataat<br>ggtgcagacctattgcaaatgagataaacttcctaaacagactgttgcatctgactagatatctcctctttaaggaagtaatt<br>agcgctaagctttatgttttagtgccggtgctcaaaaggtgaaggaaatattatatttaataataataaacatataaagatgttgaatggt<br>actgtaaacagttgtagtagttcatcattgatttaggcaagtctccaagtgtcctgtcctttgtctctacaggtcaaccatt<br>atgcacttcagcagctcattgttcttgactattatgttatcctctgttaaggcaaatgtgtcctctgaatattctggtgctgtatttgcaggt<br>acgataatgtattaaaagttgactgaccaatgacgtcaggaggatctgttatgtgcttgactttctatattgatgcaagattgtaaac<br>agcacagaaatcctcttgatgcaggtaaaagcactgaaatctttttagttgatgataaaataaggcctgttgatgcaagcactgtaaatggt<br>gcaaataatgccaagtcaattatacaataactgtaactgataaggccagccagttgttttatatgaggccagtctcaatctcattgtatta<br>tataatgaaatctaggaaaggactttggcttatccggcagagaatatcagcttcttttgatgccataactgtaaatggggcgtaatcattgat<br>gattgtttatgtatcatcaatggataaggccagtccaatatggtactatgggcaaatatggcttatgcagttcttatgtgtcttttagcattctataatcgtacagaatcaatcagct<br>gccactatagagaccagtccaatatggtactatgggcaaatatggcttatgcagttccaagacactcttttagcattctataatcgtacagaatcaaataat<br>gaaaacaagtttaccttagaaaaagagaatggaactactgcagacttatgtccaatgccaagtcttcaagcgttgcaagcaatgccgctttagat<br>ttgccttgaatccaaatgatgagattaaaagctcaaagcttatgttttttgctgcaagcggccaatctgagaagcaatctgcaagcaatgctcattgtcaac<br>aacaagacattttaacaatgtctacaatgcagttggagtgtcagtgcaaatagtgtggatgccttatattatttgattaggcaagtcccctagcgcatcaataat<br>gtgtcatttatagctacaggctcaaccattcttgctctctcagcaattcgttgttgatgctatacaccagtccagtgaagagcttcaaaag<br>atgatcaattcagctaggcaggctctacattgaatttgggaagcaacgtattcaaggatgtctcaaatgtaatcatcaataaggaccttaca<br>ataacaggcgaacaatatgcaagagaggagagacaattcttcgttgtcaccgaccgctctgcaggagtcctaaggaagtgaatatcact<br>ggagtcaagttcgtttttagataatgcaaaacacaattcttcaagcaaggctaaagcgtccacacaccactcaattgatgtgcttcaatc<br>aacatcaaaaagaataatatctctttgttgatgatgtggttccagaatcaataaccgttcttgacttaagtccaaagtcttcaatt<br>gccccaactagaaactttgaccataagcgcaatatccagataaaaaagcttctgtaatacattatgaagacatgttacaactgcatcaatacaaat<br>tctgtagttgttccagaaggaggcaaatacttgaagtgaacttacagattccaatgaacttcagatcctattgaaggataagaggtccagataggatttaat<br>attgaaggaagagtgggcaaatacttgaagtgaacttacagattccaatgaacttcagatcctattgaaggataagaggtccagataggatttaat<br>ggtgttgtatatgataggacaacaaatgccacaggagttcaagctcaagaatcaaagaggaacatacacctttgcaattgca<br>ttccttggtgatgattattataatgcagctttgtttgtagctaagtaaggttaacactcaaaagacaaagatttccacttcttctagaca<br>tataaggcaagtgctaagcaaagcattctgccaccctaaggatgcaagcagtaatcctataagcgtaagaagcttagttcactgtt<br>aatgaaaaacctatagcgctacaactaattcaaaaggcactgcaactgtgaatgtaagctaagcaagaagggaacttatagcttactgta<br>aagtatgctggcgatgatatgtatgctgggccacttcaaggcagtaaggtggttataaatag |
| Contig40_gene_830 | | atgaagatagaaaattttgatagttagcttaattcttattgttctaatgctgcttaggatctgcttatgccgcagattaagtccagtg<br>actaatgaactgttctgaggtggatgtggcaactgccaatccatacgcttctcaaacaggaggccaagaaatacaatctgagaatta<br>agctatgatgtcccggagatgttagtgatgtccagtatgtcaggactctttgtaaatgtttatggaggtctgcacaggagactatggtgcc |

FIG. 5A-5

```
cagtccaatgtctcaataacatccaatggtgagacaagtcaaattgcaagcgaaagtttaattatactgatggcgacggcactgtc
tatatagtaaatgaccacatccaccaagtctattccgactatcagatgatttatatatcactgataggttcaaggtgcaacggtcaaata
aagatcaatgtaacaacaccaaacttgaaggatatgctaattttgatgcagaatcaattaatcggttggtctttgcttataatgacga
agcaataatagatttgattattggtggattccggtcaggcttggtcaaatagtgcgattcagttacaaagctaattttactgtgggaact
gtaagtccttcttaagtgctaacataagaaatattgcacttcaagcactgacggtaactattcattcaataagcaagagtaactggtggg
gaactcatctctgattccatgtcaaatacccataagtgggatgtaactagaagaacttagagagaaatatttgtaagtcctgacgtactggtactact
aaatcttttaagaatgtacttctgtcttgacagttacaaagaactaaaaaatattgtaagtcctgacgtactgtacctacaccaatccaaa
gcagatgatcctaccactatggataaggcagctcctgcttgtcagtaaatcctgtgaaatgtatatctgtgaaacaattctgttgcaaacattaga
cgttatgacattaggccaaactacttttgacgcttactttcaaagacattaataatacccggaggcgcaatctacattgctgagacaatgccaccgttctacatatccgttctaaaaatgttatgattgaa
gtatatggtgccaatgtaacttttgacgcttactttcaaagacattaataatacccggaggcgcaatctacattgctgagacaatgccaccgttctacatatccgttctaaaaatgttatgattgaa
ggccttgtgacaaattgtattttcaaagacattaataatacccggaggcgcaatctacattgctgagacaatgccaccgttctacatatccgttctaaaaatgttatgattgaa
aattgtaaattcataaacaccactttcacaggtggtgcaatccgtgtaaattctagagatttgcggttgtaagagactctaacttcactggttgttgca
gaaaatgctactggaaaggatgtgtggtaggaaaatatggaaaatcaataactgtacattacagacaatcaagctacgtttatggaggcgctgttaat
actaccggcggagccatttagttggtaggagaatgtgaaaatcaataactgtacattacagacaatcaagctacgtttatggaggcgctgttaat
ggaggagctatctattgcaggtaaatcaacgtacaatagtcactgctcattgaagacaatgaggcagatgaagcgagttgctcattccaatgtcatgcaatttcctggtatt
tgggctgcagttaaatcaacgtacaatagtcactgctcattgaagacaatgaggcagatgaagcgagttgctcattccaatgtcatgcaatttcctggtatt
ggtgcaaatgaaatgctaattatgtcctgcatttatagacgtaactgaacttgattgatgatacaatcaagacaaagctacacaccaagtgaaatagtact
taccttctgattgtaacttattaccagcaccatgcaaccatgaagtgctgtaatgctctattccaatgtagccaattcctggtatt
ggaaactgtaattttgatagataactctgcagacgtattgaactattccattgtaacaatgcaggaaaattaaaattatctgaaaataacatc
acaaccaatgatcttcgatgaatctacacaaacggttcaatatatgactgacgttatttatatctcattgtcaatgaaaccaatgatgct
gcatccaatgtagtatgtcagacatcggcgatgaagtgcctattgacgttgacccttgtagatgacaacagcaatctcattaacggcataggc
ttaagcgtagagatcaatgaaccaacatcactgaattgattgatgatacaatcaagacaaagctacacaccaagtgaaatagtact
tattatgtaactgaaactattccaaggctgagctttagcaatatcctaacaggatcaatcgttgtgagagaaacctgttctgctatagaa
atgctttagagcgaatatgtaaatacactgcaggtgtgaaaacctattgcagttcattgcataacaccgatcttagatgga
aactatctttgaatttatgtgatggcgagcttgcaggaacttgcagaatctaagtaaaatgctgctacaacaagcgatattaacttattt
gatgagaaataaggatctaaacgaatcaactataagtggacattggacatgaacatcaggctaattacactgtaattgttaaggataatgaaacc
caagaagttataggggaatccagctattccaatatggcctaactgtatttatctaagaaatacgaatattcagatgaattcataagc
tcattcagaaatgctgacctccacttcaatgaggctattcattaacaccactgaagctctgtgaagctactcctgaagcaaccctgattgactgacatttgg
actcttcctgctctttgcgaagggcaagctttgcaggagcttatatgttcaggacttatgtatgttgataacctgggataagacagaaatgaccatctgac
tggcctactctgcagctttaatgatgactcctattgtagctcaatagcgaacaatcccaatagggtacaagcggttcatatggatacggt
cttgtgtctgacgtttcctcttgattaaggaagacaaaacaatactcattacaaagggacacagctatatatccacgtaccctt
gtgcattctataatgtgactgatcaagcactgtaaaacccatgtaaacattgagagtgttgaacggtactaccgcactccaccatttagcactttatatttgctaatgtt
ttggaaagacttgttatgacagattcgttgcaacggcaaaactatcctttgtatctaccggatctacagctccacagtctaccagctcctctgaaaatgcttagaagagaagtctttgat
cagcaggtgaagtaacttgcttgcatccaatgaaatctcctttgtatctaccggatctacagctccacagtctaccagctcctctgaaaatgcttagaagagaagtctttgat
ttggagacaatccctctgcagttacaatagcttctgaattattgtcgacggttgacgttggacgtcgactatgaacatgttaagtgtgacgttggcgaagc
gacggtttgaaaagccattatttgattgaattattgtcgacggttgacgttggacgtcgactatgaacatgttaagtgtgacgttggcgaagc
aatgtcctaacttaatcgacgaccatcaggccagtgactgaagacactgtaaatgccagtgcgagacactgtaaattacacagtctat
```

FIG. 5A-6

```
gtaagtgctgctggagtctttagctgaaagacaatcactcctaccatatgtataacgttacttaggcaaggactacgcttatcctaat
gagacaatcagctatttcgacaccattaacgtggagttatcattgaaactttaaatgatcaccacttatatggcgctacagttctt
aacagaactgatgtatgggagcttgatgtcccagatgatgttgaattgcagatgcattatctatattggataacactggataagaccggt
gcaaacatccctgtcttgaacttaacattcaatggagaaactgttgctcctatgaaagctataggatcaatcaacttaggcagctcgc
aaatacggataacgttaatcgtttatgatgtgtctggcttgtgaagctgaagctctgatgtcattacaacagtttatatgatcatgtgtctgacttgtta
gcagtttaccaagcactcttgtagcattctataaccaagaggtccctgatgtcattacaacagtttatatgtatcatcatgtgtctgacttgtta
tataacagctacaacctattaggaaggacgttgaaagtaacagcgttgtaaataatgaacatatgaagaatgtctggctggaacacaaacagact
gtattgctgcaagcgctcaagcaggtgaaggtaacttgattgtaaatatgaacatatgaagaatgtctggctggaacacaaacagact
aatgtattgtgtcgatatattggacagtctcaagcaatccaatgaagtctccttgtttcaactggaggaactatcctagcacttcaacaa
ttcattgtcttcgaatacgatgcacttctgctaaagctaacactgtctatcatattgacttatgctgatgcgacttggtagacagcatagaagctgaa
aaacttgattaaccaatcacgtgtaatcagtagaacagtacactattgactatacagccagtgaaataacagaaacactagaagctgaa
atcgattgcggtgaaaacagtacactatacttgattgatcaaccgatgagatattgtatgatatattggaacactatcatgaagatgcacttaaaacactactga
gtaaactacacagttgtaatcagtgataatgcaaccgtatcaatttctcacgcgctatcacagttgttcaaaatgttcacttgatgataccagaatgatac
ggtaaggactacgcttatcctaatgacaaccaaccgtgcacctgcaaaatacggctatgattgcttgttctctatgtttcagaatgtgcactgtttga
caatcaaacttgaaccagtctgaccagtccagttacctgcaccgccgaacctcaaaatcgatcagttcaatgctcactgcctatagctcattacagaatgttt
gcatacaactggataagaccagtctgactgtcactgttgctgactactcagatgtatgtttcagagtacgtctgcaggcgaaatgttt
gagcttctaaaggattatgatgctactgtctgtctatcaatgcatataattcttgtagcattctatgattgaagactcacctatattgacaactgct
tacatgttcaatgctatcacgtgactattactacaatgtagttttgctgctccagcgcgttgtaacgtttatatatgatggaataccaat
gacgatacgatgaaggaacaagcaatagtgcagctgcgcttatatgtctgccagcggcgtcagcggcaaggtaaactgattgatccaatatgtgtcctgttcact
gtttggaggaactatcctagcccctcacaaatgctcttaaagtcttgaattgaaagtaggccgttcatagttttcatagtttcaagaacgtctgccatatatctgaataatacgcctaaggctgacattatctctgaatataaggccgtt
ggaggaacttaccctcacaaatgtcttaaagtgaagtaggccgttcatagttttcatagttcaatgaacagtcgaagactccaatctctgaataataggcgtt
gcatttgcaggcacaaccatgtcttaaagtcaatgaagtaggccgttcatagttcatagtcgagcgttaccgatgcacttgcattgcaagactttaccgatgagagatcagaccggttacagaaaac
gttgaataggcagtcagctcatagaaccagaaccagcttagtcgcttagcattacgctaccttgcatatcctgagcaccaatatgacagcattgccatcacagtaaggtggc
acagtcaaagggcagacaatgaaaagtcaatagcactttaggcaaggactacctggcgtatagcaagctaccttgcatctggagctaccaacgaactgacatatgaacattgaagcacctgaagacgct
ccggatatcctctataaatccaaatgaatcaaggtaacttggcgtacctgtcatctggagctaccaacgaactgacatatgaacattgaagcacctgaagacgct
atttacattgaaatccaaaatgattcaagctacctcaatcaaggactacctgtcatctggagctaccaacctctcgaggatatcacgagccttaatacacatcacatggtgtatct
gatttcgtagctgatttgtatatgtggctacaagaccaatcaatccaataatggacaatgccaaatatggaactctgcactgcaagccttgtattcaacttgacagctgatatcgaagaatcc
gtcgctcctgttgcacattacagagatcaatatgggaccatcaatggacaaatatggaaccaaatatggcagtgttgctaaattcaattccatgttgtttctgttgacgctaaa
ttagaagcagggataatgtattcacctaccaagatgctaacatgactcagtgttgttgttgcaggctacgaccaagaa
gtatctgacagcatgaaaaccattacatgttcaacgcgcagacttatgtccaatgcaacaacttcttaggagagttgttgcatctaac
agtgttagacattgaattgcctgatgatgttgcacttgcacttgaattgtgcactgcaagctcaaaaagggcaagcaatctaata
gtaaacggagagaagctttgaagatgttgaaccgagatcttccaactcagtcaggcgttcttcaagctcatcttcaacttgaatacgagctctgttttctgttgacgctaaa
aacacagtatcattgttcaaccgaagcactatactagccctcagcaatgtcttagaatttaacattaccaatgacgaacgcctaccttcctaccgatac
ttaggctctgaatacaataacgttgcatttgctgaaccgacacacttagaactttaaaccttgatgatcttagaatttaacattaccaatgacgaacgcctaccttcctaccgatac
accatttgagttctatatcgatgtcgatgtgcagaccactgtaaacgcgcagacaatgcagacattgcttagaagtcaactgcttaatcacagacaattcaactgagat
accatcagaccagttgatgaaccactctgctatggaaccactgttaaacgcgcagacaatgcagacattgcttagaagtcaactgcttaatcacagacaattcaactgagat
gtcttagatataatcactatcacctcctctgtactctacaaacgtaactataggcaagactagctttagaacaagaccaatccatcctgctgagaaatcacttcttc
```

FIG. 5A-7

| Contig40_gene_1158 | 709 | gatgtaattacagtaaatggagatatcattgtcataggaatgattccacttatcttggctctaagacaacaggacgtactgacgtatgg<br>gactaaccactaatgaagatattatctttgcagccggatacctttatgttgcatcaactggataagaccctgctgaatgctgtatgg<br>acaccacattcaatggcgtaactgtcactcctgttgcacattacagagaccaatccaattgggaacctacggcaaatatggctacggactt<br>atcgtttacgatgtatctgacttattgtagctggtgaaaacattcacctgaaaagaaaatgaaccactgcagtatatccaagtacc<br>cttgtagcattctataatatgccgaatccagcacattggatatcgattcattgtgacatatagtcgcgctgaccttttagtatttgcagctagcgct<br>ttaggaagacttgttgcatctaacagcacattggatatcgattcattgtgacatatagtcgcgctgaccttttagtatttgcagctagcgct<br>caagctggagaaggtagccttgtcataaatgcgatctgtgagctgtgacaacgtagtgcaacagcgtagatgcatatgctattgac<br>ttaggcaaaaacctaagcatctaatgaggtatcattgttgcaaccggatctaccattctagcattgcaacagttcaacagtcattgttgaatac<br>aatgttccttcagctgaggcaagcctcgttagcgaatattctaatgttgacggcaagaagtaaacagcactcaaattgcactcaactctgcgaagc<br>aacggcgctcttaacacttcatgatgataacatcaggccagtgtgacttgacgcaagcactgtaaacgcgcagcaatgcgcagaaatggactacacagtctta<br>tttgccaatacttatcgatgataacatcaggccagtgaagtgacccctcactcctctgtattatatacaatacattagtgatgattcagttctactatctggatacat<br>gtcagcgataaggatccgacttatattgacacaatcactgtaaacgttcctttcagatgcttcagatgtcataccttttgcatacaactgggataag<br>cctcagaagaaatcgtcctattgacaatcactgtaaacgttccttcagatgcttcagatgtcataccttttgcatacaactgggataag<br>acaacggactactgatgaatggaactactccttgtgatgctgattcagatgctaaatgtcactcctgtgctcatttacagagaccaatccaatatgggaacc<br>actgcaagtgaatgcctgaatacggacttactactcttgagcattatgattgtatcagaactgttgcaagcaatgtcaagtaatgtcttcactctatcc<br>tatgcaaatatggactacccagcttcaaacaacttctcttaaacagaactgttgcaagcaatgtcttagaattagatcctataaacatagaattcactctatcc<br>actacagcggtatacccagcttcaaacaacttctcttaaacagaactgttgcaagcaatgaaactctcatgatgattatcattgtaccggttctacaatcctt<br>ttattatccaatctatgtatttgcttgcaagcgctcaagctgaaaatgacccttagcttattgaaacatgaaacattcactatgtctgaatgaact<br>agccaactctatgtatttgcttgcaagcgctcaagctgaaaatgaccctagcttatccaatgatgtatcattgtaccggttctacaatcctt<br>tctaatagcgtagatgcttatattgtcgttgttgaaaatccaaatatcaaacaacctagcttatccaatgatgtatcattgtaccggttctacaatcctt<br>gcattagagcaacttgtcgttgttgaaaatccaaatatcaaacaacctagcttatccaatgatgtatcattgtaccggttctacaatcctt<br>gattagttgacaacgtattccagatgttgctaatgtagtaatcgctaatgtagtgaggtaaacataacggcgttgacttattgtgaagatgcaaatgta<br>atgttcaagcaactgctgacaatgaagcagccaacttcaatcgacactcaaactcagaatcagtcagtgacaactcattgacatgatagac<br>gaagcgtttgtacctgatcagtagtcagtgtatttgaaacttgacagctagggatcccacgcagcgcaccaatattccagaaggcgtacttccgaaagtc<br>gcaattgcagctgaatcaaacaccattcagtttgatgtaactgcgttaactctcaagatttgaagaagtgggcaaatacttcgaagtc<br>actgaaacaggcttctgtaatccactatcaagatatgaaacactgcttaactctcaagatttgaagaagtgggcaaatacttcgaagtc<br>aacttgacagacacaatgaaacccattagaacaagactttacaccttgctatctcctacctgagatgactactacaacgtagcttt<br>gcggagtcaaactccaaatcaacttaagacacaaaagaactacactttgtctatctcctacctgagatgactactacaacgtagcttt<br>gttgtatctaagatcaagctaagcacacaaaagaactacacctttgctgcaaaaacctataagcaagcgctaagacaaaaacattaact<br>caacactcaagtcaagcgtgtaacaacaatcaacgttaagaaagtaacatcaacactttcacgtaaacgcaaatcctactcagcactacaaac<br>gctaaagtgtagcactgttaagtaagctccaccaagaaaaactacagtttcaccagcaaattcgctgagacgatatgtacaccaaa<br>tcaagtgttacagtaagtaactataaataga |
| Contig40_gene_1158 | | atgaaggtctaaagatagcaattatcatgcttatttaatcatatctctggagcggtttcagcaacagagaatttaataatgatttaagt<br>gataatgactaagctaacacattaagcgacaacagcttaagcgacaacatccttaagtgataaagcttaagcgaa<br>agcacaatcatccaaatgatcatgataattaaaagatacaaataataatgataataaagctcaaaagatcctgcgaagacatttaca<br>gacttacaaatgaaataataaatgcaagtgaccttttagaattgacagacgactataacaacatgaaactgacaatatcacattaaca<br>atctctaaaagcaattttcgtaattaacgaagtgccatacatagacggagacaatcaatgtgccatttccaatcaacgaactaacata |

FIG. 5A-8

| | | |
|---|---|---|
| | | accctaaaaaatctcaatataataaatgcaaactctacaaggacagcgccctattactcaaccagctctgagcttgagacaaacaatgta |
| | | accttcatcaacgacagctcagacaaaagtaatatttgcattggagcaaaatacaagcaatatgcaaatgatagtttatagactgcacatcc |
| | | ctcaatgatggagtaataaactcatacctggtgaaataactatcaacaacgatatttgaagctccaagccattggactggcttcgtc |
| | | aacagtttggaaattcctccatctacgtttaaacacaacacattgcaaatcccaaatacgtacagcaatcaaggagatcgagaa |
| | | acagtaattcatgattctaaattcattaatctctatgcaaacctactgcaggagcaatagattcctgacatattcagatagcgaagacgtaccaataatgatt |
| | | aattgcacattcatttaatgtgagttcacaaaaaatggagggcaatattccttgacatattcagatagcgaagacgtaccaataatgatt |
| | | tcaagatcctccttgttaattgctacagcgaattcggaggagcaatcctatttcctctcacagcttacaattcacagacaatctttgacaataactctgtagaa |
| | | aacaatgggcattcttttgacggaggagcaatctattctcctctcacagcttacaattcacagacaatctttgacaataactctgtagaa |
| | | ttagatgatgatagaggttccttggaggggcaatattcaggctacactgatttcaggccaatatccacttcaaagacaatacaacaagagagtgagtttgat |
| | | caactggaggagccctatatacatatgattcaggctacactgaaaactaagctatagcggaggattcaatatgcctgaacaacgaaagtat |
| | | gatatcttcacagacttcgatgggaaatcgccacacttaccctcatagaaaatgaaatcaatgtgacaaacctcctcgaaatttgacctacgtgaa |
| | | gaatcagtaatcgccgtttctgaatgaacttaccctcatagaaaatgaaatcaatgtgacaaacctcctcgaaatttgacctacgtgaa |
| | | tgggatgggtgactccagttaaaaaccaaggctacatggttcatgtgggcattgtgaactgtaggagctgtagaatcttcaatattaaga |
| | | ttttaggcctgaaatggacatctcctatgcaagagcagcttatttgcaatatatcgctatgaacctaggagcagaagaggg |
| | | ggagagtataactaggcccttccatcattgcaggacgagtctttggagtattccctgctcctctctatgaattcactgacaagataaattaaagcaa |
| | | gcaataatgcaacagatgacagcatccattgcaggacgtactatgccgaacctgatgatattctatatgacgcaagttgcaaccctagtgcct |
| | | tcccttaaaatatgcgcttagcagtaagcttagtggatgggataagataggatatcattacaatatcaatatcaatatcggacattagggcct |
| | | aaaatgatagtaaccatcgcgttcttttagtgcagtaagcttagtggatgggataagataggatatcattacaatatcaatatcggacattagggcct |
| | | tgataataccaaaaaacagctgggagaagaatcattacaataaaactatcaatatgacatcggaacatatctctattgatcagagttcaccctagtgcct |
| | | tctgtcgattcccaaataatgaacagtcattacaataaaactatcaatatgacatcggaacatatctcattgctgctcgattcactagtggaaat |
| | | gaatacgtcaatgaatttgaggcttggaagatgattcattgcagcagtcggaacatacttcattgctgctcgattcactagtggaaat |
| | | atctatgtcaatgatgaattgaaatacagccaagatgaacttcaccattttggattccatacaatccaattgattcatatgtccatc |
| | | aaggaaggggatgaatttgacgttaagatcacatcagactgcattccaatttttagaagtctgtgctataaagtatataccaagtgaagacaggagcagct |
| | | gcaaatctaaatggagaatagatactgctttagccaatagatttcaatgaagatagttcaatgaaggtcttaggatggatgaaacaaagaagaa |
| | | tcttctagaatcaatcaaagatagatactgctttagccaatagatttcaatgaagatagttcaatgaaggtcttaggatggatgaaacaaagaagaa |
| | | acttaaaagacgaaaacgaacttgcttacaaagcacataacactttgcaatagaattctggatggatgaggaatactggagcttt |
| | | gcagtcaaagctacagataacactttgcttacaaagcacataacactttgcaatagaattctggatggatgaggaatactggagcttt |
| | | gaagttgctaagattactgtaaagtacagacccctaaattgactgccaaatagtcatatagtaaggtaagtgcaaaacatactcagctaaaaccaattcc |
| | | gcaagcttcaagacagcaaacgaaaagccgtaagcgtaagcaagaaggaacttatagcttactgcaagtttactgtcagttgcagaaatgagctaaaccaattc |
| | | aaggaactgctactgtaaatgtaagcttaagcaagaaggaacttatagcttactgtcagttgcagtgagatacatttgctacttct |
| | | agtgcaaaggctaattgacattaaaatag |
| Contig49_gene_43 | 710 | atgagattaagatatttgcaataattagtttaattctttaatatttttagttccagttagttttgcagtgaactaatctgattcaata |
| | | gaattaaatgattagctgattctttcactgaaatagatgattctactgattaatcaggattatagttctaatcaagattaagtcttaat |
| | | cagaattctgattctaattaagcaatgaacaagaattatatttctaataaactagttgaaaactctctgattcaattcacaagttcaaat |
| | | gattatcaaactccttatatttgtcttcaaatggagtaaggctagctgatttgaattcaagcttgccagttcaataacaagcttaacgat |
| | | tcaaatacgatctatgtaactcatcctatattggttctgatgagtttggaactcaatctaatccaataagacagtattgctggaataaat |
| | | gctgcaactactgatttaaataatgtctatattgcaaatgggtttatataatacaacaataactgttttaaatccataaatataata |
| | | ggagaaagtcttaatgttatattaaatgcttcaacgaaacaatattcaggtaaagaagtctgcaggtgacgatacattgctactcct |

FIG. 5A-9

```
acattcaggaatggctatgcaaataaggagggcaatatatgtggataaatcttcctaaacattattggaagccttttttgattcaaacatt
gcatatgtcacaagcgataacgatagtgtgggctatctacaataatgcaggctttttaaagctctataacaccacattcaaaaacataag
gtgtagcagcatacaacatagtctctgaagtttgaagtgcaatctctataatgactgtgaaatgactgttcttaattctaagttctat
ataactcaatagacatagaaaacatataagaaactcaatcaaaatcatcatatcatcatgtgctgaggagcaatattcaaccgtgcaggattgtcacaatattcaac
tcaagcatcagcaataattcaatctataccaactactcacttgagggtctatccactggaagccgcaatgtctatataatcaattcc
acaataaacgacaacataattagcgaagctctgtggagaattcaacaatctacaataaacggcaatttcaatctgataaactctaagatggaaaac
tcaaacaacaatataaatgcaagctctgtggagaattcaacaatctacaatataaacggcaatttcaatctgataaactctaagatggaaaac
aataagataaagacaattaagaccaatctccttatgtgtcttgaggatcagcttattgtaaacagcagcttcaatctgcaaacgagttaaaa
ggccttaatatgacttcctacttcccattacgacttaaggaggaaggattggttactgcagtaaagaatcaggaagctctgagcttgc
tggcatttgcattctactctgcaatgaatcatatcttttgaagtgaaaacataagctatgacttctctgaaaacaatatgaaaaactgt
atgggagacggcagcgaaacagtaccgactggatgacggcgagcatatgtgttgcactgcttatctctccgttggagcggacgata
aacgaaacagacgatccattcaatgccgctctaaagttccctaccaatctaactaggtcaaatacctcactgatgcattatacatacca
ttgcgtcttggagcattgacaatgaccaaatcaagactgctatcctaaagtatgtgctatatttgtgccagtatattcaaatatcattaaa
gcaaattccaaatcaggatattccgatatcctgagacggcgctttcatcataaaaaacagctgggaacaagcgggagaacaggatcatattcagcaagcaac
tttaaggacactccacctgagacggcgctttcatcataaaaaacagctgggaacaagcgggagaacaggatactattacatttcctat
tatgacgcttcatttgcagcttcaatagagacatctgctgcagttgctgtgacaaatgttgtaaatacaacaggtgaatacagaaacaactat
tactatgacacattcggcaatacatttgaaaccatagggatacaattcagatacaatatgtttgcaaatcagttactgccataagtgacaat
cctttaaatgccttggcctttatcctatggagattccacatatctatgagactaagctaagacatcactgtaaacaacaagtcagttacacatctagcgga
aagatagtgggagcaggcttccataacaataaagctaagacaaactacagcggattaccccaaggcaaagtccgactacaaccagtcattcataagc
accccttccacttattccacttgccgttgagacaatgtgatgacctagaaatagctctaacaacaggctgtaaagttctatggagatatgtattctatacattaaagaat
ccagacgtaagacatgtatgacttgccttaaggcatatactgcatttgccgatgcattgccgatgaattgccatgaattgccaagcaattcatctatagcggttccttagacaagtcttatagcatcgtgtcc
gcaagcgtttgccttaaggcatatactgcatttgccgatgcattgccgatgaattgccaagcaattcatctatagcggttccttagacaagtcttatagcatcgtgtcc
attaaacttaatctcactgtcactaaccgtgggattgcaagcaataagtcatatgaataagttcaagcttaataatgatgttaacattaagtatgcatcaaatatccatccataaatacaact
tataagatatctgaaaatgaggagtctgtaagcttaatctgtaagttcatatgaataagtctaagatgaatgaatgttaacattaagtatgcatcaagtctagtgaatttggtccattcct
tatttggaaaatgaggagtctgtaagcttaatctgtaagttcatatgaatgctttaagtcttaatatgggagattcagggaatttggtccattcct
tcatgcagcgtaaagaccaatgtatatgcaaatttctctaaaatataaaacataacaaagcccctagcaatagcccctagcaaataagaatgtgaatctttgctcttaaagtta
gcaagtcttatgggctcttaaacttttaccattgttgataactaattttatattcagttcaagcattccagcaattcactggagaaatactactcaagctgcattctggataccaaatctg
gatgatggaagatgaagcttaagcttaacagttgtacagtacaaattgataactaaaattgatcttacattggagaatacctattcagctctctaggacatgtaactattcagtc
acctaaaaaccaacgcaatgaaccttcagactcaggaattattccttaacataacaaagagaaagtcaactaagattcactttgtaaggacatgtaacctatcagtc
atatcaagcttcagactcaagctctcgtaatgctatctgtctttcaagctaaagctggagatcaagatccttgaagtcaggcagatcgttatagagcctattcagtc
gttcagaggtgatggaagaacggagaatactcaatgtccgaggcaaggcaagctccaatgtgacgagctgtgaaatacctaaagaaccttaagaatcaaatgcttacacattt
gattcaatgaaggatatataacagaaccactgattccgagggcaaggcaagctccagataaactaagaatcaaatgcttacacattt
gcaatctgtttcctaagcgatgatgactattgcctcatttgaagtgctaagatacttaacgaacaattctaacagattctaacgacttatgcctcatttgaagtgctaagataactgtaaataagaagagaacagttgcaataagtcctgaatgttcg
aataaggcttatataagcctctgaaagtcaaagattctaacagaagattctaacagactattgcaaagatcgttgaagtgctatcagtcatttgagttctgaagctgaaagctgaatagcagaagaacagttgtctagcagagcatttgcaaacaggtattgact
tttacagtcgatgaaagccttatcagtcaacggatgatgacctattcagcttatgcctaagaattctaacagactattgctagatagaagagaacagatctgaagaaaaatgtcctgaagttctagcagattctgcaaagttctgagttctgcaaagttatccaagttctgctaccaagttctgaagagttctattattca
```

FIG. 5B-1

ORFs selected for antibody production: Amino acid sequences.

| ORF | SEQ ID No. | Amino acid sequences |
|---|---|---|
| Contig40_gene_697 | 10 | mdqviaclgavcailwgvlairsvasyglgtgvpsigymslgigvigalagvgiiaafklkglemlgpilalvfamligllvaivakkivgmkipvmerctaeiagaaalavlgfssaiaggysidllltavvapgfialfyilvtmaiqhpfnaclgpnedqvrtlkcgastafltmiitgilaisaggyawfailvvgligwyvsfkmfvnasyeaaasvkwsglwpkvee |
| Contig40_gene_698 | 11 | mdllificvviagilmggvhfipvggapaamatatgvtgtamlaagagltglitaasmtgqpvwlivlagavgsmlnmgitmlignfiyifgvgvvpasgkaavdpitgwnqekyktpgteghgiptvcyisggliggllggagglvywainefatanltgfdatviaglaailsvgmffinsvtasyniggtiegfvdpkfkrlptgilacavvslvaaifmvlmiggi |
| Contig40_gene_699 | 12 | mdpitlgvvalmgaaatiagaaedlesdigsqsnpnsqvqlapqmghlhrminkaasgepvaygcwcgisgaiaalamgmgiipivaiamgstvaalvhaiytvtshmgrivggsqfeqplfmdvltqslgpiaahgfiasfgivgiaylmtlpldglghpfplpllavlwgitigaigsstgdvhygaeseyqkfdyggqtpvaigqdivtkaplgaknsidvgnfcakyggplgfcfglivfvsfwitvvfgalggqivgivivllliaanyllekstrakfgpyee |
| Contig40_gene_828 | 13 | mkynkkiffflfllllclliipqaiyagdvddlsdagnytrdnspltisstyqsstygsdggyddknenyildkvsdgdksktccskdlsldnacsmdksscsksnsacskgisssdkdssnlsntyvsennyndfnvdidlndklsdldinndlslnkdltlnlnsnndmdylnleevigtdgtltyegdldqtylndeslnqdvqnddslnkndlksplsdentfnifiisdntgnnldavaceildnsnfsnvkfnirsgnqinamsedeiyelmapcdafigqvwssnvdavltslnnhpelsnklflileptgninsssslnlvrnstidykkifngisnddliinyfkatkrgnfesigeyidnegssfnsifnnlvlykdindkanlknellyilylghgcsyesantfgvqasgifrdrwysfdeyvltfnesrnrtiglestmyiqsqqldlvneiterleskgynvipiycpagnaeqlnimvkywtsacsnisgflenpqfdiyvdgiismvaygvggenftnatkffedanvpifravhseyitneqwelspvglstkdskwwhvtiaesggifdatyvggvdsyisnrtgaiiltfvpvheniellttdrvdawvdlkytpnedknisivyynyppgkniqasyldaitsvynmlytlkdegyyltdlpnnvseledmmiacginvanwapgeveklanrsgvallpvdeylewfdslddivkvqitegpvayigqmvrravlinytdevetmvndwynqikallpenqtvaatnlldklvnslklyanassdgdenaslyydeflryydefksinvsglngwgeapgniimlvnrngtdyfvipgltfgnvfigpepgrgweadienlyhctavapthqylaayyymqtrgsnamvfvgrhathewlpgkevllsyndygsivvgkvpqvfyitdglaeaigakrrgfavllishldspksythlygnitvlatlleeydnnhilesdsdkdnqaityqvikdnqtityqvinqelednltraikdlviannyltigftaeelnntdmfslsstlnaflknqntlyplglhaigqkwtdedlantvaiivshdfeyggktnlfdqlslyyygekysnltpklkrdyiilnrsvdvckaliywdtetvsdtigigspefilesiniiakkyidlynqcisleleemvsalngayvpvniggesvtpqvlptgannygdqsselptqkawdyaktlslltladlndttekiimgiwcvetarddgalvstvlyllgmepvwhnsssagfdeegiptgkkvedilpnvialenltrpdgwakkridvtvitsglifdlyssqarlmdnayrmalacsyytivnnktimdseygpqvydalrsimrsisfkgmsnesledhyvakhwiedciyylslgynstvsgeyaitrifappngdygagisklvsmswtwndtdelsefyigrmgnmyskyywgdtnpvvfmralsdtdhivvsrntnqygvldnddffdywgclsmtveylsnktptmnvlmyankdnayvatfenvfynelntrylnpewikgmmqegysgsrymsnkfisnlwgwqvtrpssvsetvwddvyntyykdkyglgvkswlqsgnnayslismsgtmlnsaysgywdaddatlsdiantwagatvangvaccdcscgnvamnqwafkyvnadllaklmpkiydatqnplfytnssdmptnssnidrrttnssaesnntetvqtnsssnsqqsangrtnipgasggymvgteadaqsdmasdsdagmndangegrsvevtksstpvapkdvsmpiaiivcviclvaligfgyfrnrkddddyndddddyeyk |
| Contig40_gene_829 | 14 | msfgavsaadlntvqsgevsggvdiassnpgvengeltyeipdsveniqyaglfvdsytagssnlvygseanitlkngeseqiaserlvasvgsadgevyvindhttkcfadymmtynltdrlqdakgnititvnatpiegytfynkikligvftyddgdgdqfhywvnagsswvktdsgetskatfklgnvnydptvatlcnfalssgdqvyftngkemdesivtetgvyyihkfdildkikmmtntlvytpgegsysfrnvlsvvklvktvpv |

FIG. 5B-2

| | | |
|---|---|---|
| | | yakvnisseyddivfsgtenllkvgitnngtgsasylldlyadgkkvnssqislaagreavislidntirpsaadtvsgadnkkinytvvsd
kntgevldessifpnllyngylgkglaypaekissfknitvngmileslgdstyldasmtgktdswtidlpdgafftdafvypynldngnv
pmftstfngaavnpiasyrdqpnigenakngyllvydvgelikagvnsfalskeagiagvypstliafynltdsdlltsafifngadllsne
ynslgrdvssdnilsigafdglvsaklhvfaadcqagegdltvngksyknvwagtnrsvgdyvvdlgkstnasnevsfistasnilalqqlav
vqynvpsvkaslvseysnavfagtnnvlslnitnngkfdsiytvdfyvdgkkqnsteislksgankqlyliddtirpidastvngadnpkvny
tvviidkeksmvldeititpsllyngnlgkdlaypaenitsfrnitvsggvivdtlddstyinsqatnrtdiwnvnvadgdvftdafvyvpyn
wdktngympvwnarfngvavsplvsyrdqsnigffgkngylvvydvskliksgentftlekeagitavypstlmafynatssnslktiyiyn
gadllanennflnrtvasdshldissfkevisaklyvfsagaqkgegnilfnnktykdvwngtvnsvdsfiidlgkspsvsndvsfvstgsti
malqqlivldyyvssvkanvsseysgavfagtdnvlkvdltndggggsvyvldfyidgkivnsteipldagksteiflvddkirpvdastvng
annakvnytitvtdkasglvlyeaslnpivlyngnlgkdlaypaenisffdaitvngvildtlddstylgakttgrtdvwkveipkdgkivd
gfvyvsynwdktngsmpiwnvsfngvsvspvahyrdqsnmgtygkygyglvvydvgeliksaenkftlekengttavypstllafynrtesnn
rttvymngadllsnannflgrtvasnaaldlalnpndeikssrlyvfaasgqsgegklivnnktfnnvyngsansvdayiidlgkspsasnn
vsfiatgstilalqqfvvdaihqsseelqkminsaragstlnlgsnvfkdvsnviinkdltitggtiyaregetifvvtdrsaggpkevnit
gvkfvldnantilqaravngstptsidvasinikknnisfvdddvvpesitvldlksqrssiaptrnltisgnnliagicpfmfevtsfngkd
svvpegnnipdkkasvihyedmvttaintniegrvgkyfevnltdsngnplkdkvvqifngvvydrttnatggvklqinlgykgtytfaia
flgddyyngsfvvakikvntqktkistssktykasaktkaisatlkdassnpisgkklsftvngktysattnskgtatvnvlskkgtysftv
kyagddmyagatssskvvik |
| Contig40_
gene_830 | 15 | mknrkflivsliliivlmlalgsayaadlspvtngtvsggvdvatanpyasqtggeigsgelsydvpedvsdvqyaglfvnvyggsaggdyga
qsnvsitsngetsqiaseslnytdgsgdgtvyivndhitkvysdyqmiynitdrvggatggikinvtnklegyanfdgrikliglvfayndg
snnrfdywvdsgqawsnsadsvtkanftvgtvspflsanirnialsstdgnysfnkqeltggelisdsmfkyhkwdvtdllknktnnltfnst
ksfknvlsvltvtknleeifvspdgtgtgtfydsdangglvtncifkdinntgaggavyisgsknvmlenckfinttsgtggaiyiagdnatvkecsf
vyganvtldgltfthgktgggvyfdsdangglvtncifkdinntgaggavyisgsknvmlenckfinttsgtggaiyiagdnatvkecsf
enatgkdgairvnsrdfavvrdsnftgcvattgaaganemlimycsfedneadanggamgfiradqcylldcnftsnhakqngsavmlysnvanflgi
waagkingtivnsifkensagrdggayysaaganemlimycsfedneadanggamgfiradqcylldcnftsnhakqngsavmlysnvanflgi
gncnfvdnsadvlnysivnnagklksennittndlrdgiytngsiltdvlylivnetndaasnvvyadigdevpidvylvddnsnlingig
lsveingtnitefdldgytyktsytpseigtyyvtgnyskaelsniltgsivvgeepvsaieiafrgeyvnttyagvenliavslhntgsldg
nylvefyvdgelagteeskvnagytsdinfidekirdlnestilghdnlqanytvivkdnetqevigessyfpyvlyngylskkyeysdefis
sfrnvtfnggyfinttgsysgnsnpgltdiwtlpalgegasfagayvvaytwdktengpsdwassfndesipivaqyrdqsnmgtgsgsygyg
lvvydvsslikeqnkysltkgdtaiyprtlvafynvtesstvktmynggadllyygsynvlerlvmtdsvlnistegnvlgsnlyvfaasa
qagegnllvngekyedvwngttsseveekvfdlgdnplasneisfvstgstilalqfvleveyasadvtiaseyngacyagtenalkvnvtn
dglekanylielyadgrvdvehveidvgesnvltiddtirpvtedtvngadcnqkvnytvyvsaagsllaektitptiwyngylgkdyaypn
etisyfdtitvnggvlietlndttymgatvlnrtdvweldvpddvefadafiyignwdktganipvlnltfngetvapmesyrdqsnlgssg
kygyglivydvsglveagentlliekefnktavypstlvafyngevpdvittvmyhgadllynsynllgrdvesnsvlevelvddlasadll
vfaasaqagegnllvnnetyenvwsgstnstnvfgvdildslkqsnevsfvstgtilalqqflvfeydvtsakakvsteysnsayagtdnvl
kldltnngtvdtvyhidlyadgdlvdsieaeidcgenstlylliddtirpvtentingnnakvnytvvisdnatdeildeititpvlvnvgyl
gkdyaypndtiqffdaitvnggvliidtlndttylgtkttnrtdvwtvdvpndaefveafvylaynwdktngtcpvfnttfngetvtpiahyrd
qsnlgtssakygygllvydvseyiaagensfellkdydvtavypstlvafydvedspilttaymfngadllynaynflgrpvesnsvlidsv
ddideatlvfaasgqagegnllvngdeytnvwegtsnsaaayminltdsiaesnnvsfvstgtilalqqfvivseyapyakadiiseykgv |

FIG. 5B-3

| | | |
|---|---|---|
| | | afagtnnvlkvntvaeedavfnvtlyadgveigsqlievgaysgaiamftdekirpvtentvkgadnekvnytavvrdvddlivedaeatit<br>pdilyngnlgkdlaypaeeitffdsitvnggiyieiqndssylasgatnrtdiwnieapedadfvagfvyvaynwdktsagipalnitfngvs<br>vapvahyrdqsnmgtygkygygllvydvsdlleagdnvftltkdanmtaiypsvlvagydqevsdmktiymfngadllsnannflgrvvasn<br>svldielpddvidcalgifaassqkgegnlivngesfedvwngssnsvqacvfnltddieesntvsfvatgstilalqqfifveyelvsvdak<br>lgseynnvafagtdnvlefnitndgtiptaytiefyidgeladtlelelangesdslyIvdptirpvdettvngadnakvnytvvitdnstgd<br>vlditltpsvlyngnlgkdlaypageitffdvitvngdiivigmndstylgskttgrtdvwdlttnediifaaglyvaynwdktpagmpvw<br>nttfngvtvtpvahyrdqsnmgtygkygyglivydvsdllivagentftlekengttavpstlvafynmpesstyvttylyngadllsnannf<br>lgrlvasnstldidsfdnivgadllvfaasaqagegslvingdlvadiwngssnsvdayaidlgknpkasnevsfvatgstilalqqfivvey<br>nvpsaeaslvseysnvafagtnnvlqfnltnngalntsyivdfyidgkkvnstqialnsgesfgqyfiddtirpvdastvngaanakvnytvl<br>vsdkdtglildevtltpsvlyngnlgkdlahppeeivlfdtitvngdviidtlddstylgakttgrtdewnltvpsdadfevaylyvaynwdk<br>tasgmpewnttfngvnvtpvahyrdqsnmgtygkygyglyiydvsdlikagintftlgkengttavypstlvalynvnesnvlttvslfngad<br>llsnannflnrtvasnnvleldftvfdeilssqlyvfaasagagegnlivnnetffnvwngtsnsvdayivdlgndpslsndvsfvatgstil<br>aleqfvvvkskygtssdlqklidaaepgstldlgdnvfgdvanvvidknltikggsimgkagetifvipaksangpdevnitgvdfivedanv<br>ivqatadngssptsidtpnirisdnfidmidgsvvpesvtvlkldsergvlaptgelkvtdnalaagikpfefdvtgvsngsdtnipeggnip<br>akqasvihyqdmettavnskiegrvgkyfevnltdtngnplankfvqigfngvvynrttnetgvkiqinlgykgtyfaisylgddyngsf<br>vvskikvstqntkltbaaktykasaktkltatlkssvynkpingkkvtftvngksysattnakgvatvkvslstkktysftakfagddmytk<br>ssvtgkvtik |
| Contig40_<br>gene_115<br>8 | 16 | mkvlkiaimlliliislgavsatenfnndlsdnglndntlsdnslnentlsdntlsdkslsestiiqpdhdnlkdtnnndnnkalkdpaktft<br>dlqmeiinasdlleltddykynnetdnitltisksnfviingnghtidgdnqcgifqingtnitiklnliinanstkdsallInpgseletnnv<br>tfindssdkrvifafgakytsnndkfidctslndgvinsylgeitinngyfesskpldwafvnslgnssiyvlnttfanttskyataikgdre<br>tvihdskfinlyanltagaiglkrieeaeidnctfinvssqkngaifldiysdsedvpimisrssfvncysefggailslggkitleednft<br>nngaffdggaiyssfsqltisqtifdnnsveldddrgsfggaifsdisalilincsfsnnmagtggalytydsgyyianstfkdntnkesefd<br>diftdfdgeiatlennsysgedsiclnneryesviavsgmnftlieneinvtnpprkfdlrewgwvtpvknqgymgscwafgtvgaiessilr<br>flglemdisennmqdslqyyrgtlgaeeggeynlgpsyalswfgvfpseydvydelgkisaliatddsihlqdavfvpplmnstdkdklkq<br>sllkygalavsyyaetdepglnentssqyslkndsnhrvllvgwdddyskdnfymtppgdgawiiknswgeelgdkgyyyisyydasfatlvp<br>svgfpimntviynknyyqydiggtleftdmgneyvnefealeddfiaavgtyfidagvdynieiyvndelkysqdgtspffgfhtiqldsyvpi<br>kegdefdvkitsdcipilesgrqhyienksaanlngewdltsdgkvcaikvyttdedkkessrintridcknmttavasedgrigeyfqv<br>tlkdengtalankpikigfngrvydrttdengsaklqinlaykgtyfaigflgdeeylgafevakitvkvqtpkltapnksykvsaktkslt<br>asfktangkavsgkkisftvngktysaktnskgtatvnvslnkkgtysftvkfagddtfatssakakltlk |
| Contig49_<br>gene_43 | 17 | mrlryfaiisllilliflvpvsfasetnlcsielndladssteiddstdlnqdyssnqdlslnqnsdnslnneqelysnklsensldsnsqssn<br>dlsnslylssngvrladnssfaqfntslndsntiyvnssyigsdefgtqsnpyktvlaginaattdlnnvyianqvyninttitvlksinii<br>geslnvilnasnennilsvkgssvevsifnltfrngyankggaiyvdkssIniigslfdsniayvtsdngyggaiynnagfiklynttfknnk<br>vvaayniveegfggaiynelgemtvlnskfynnsidirnisksssygagaifnragfvtifnssisnnsiytnyslggaisiwasrnvyiins<br>tindniisgsygfasvisnkgtllqienstisnnninassvenstiyningnfnlinskmennkiktiknllmcledqlivnssfnlanelk<br>glnmtslpshydlreeglvtavknqgssgacwafafysamesyllkvenisydfsennmkncmgdgsenstdwddgayvvalayllrwsgai<br>netddpfnarskvsptnltrvkyltdalyiplrlgaldndqiktailkygaifvpvysnikansksgysdiqyicnhavaivgwddnysasn<br>fkdtppgdgafliknswgtsggeqggyyyisyydasfaasietsaavatvnvnttgeyrnnyydfgntfetigvnsdtiwfanqftaisdn<br>plnafglytygdstytvnitvnnksvytssgkivgagfhtiklsryvplktkgdtfriivklttpstlfplavetnysgftpraksydynqsfis |

FIG. 5B-4

| | | |
|---|---|---|
| | | pdgktwydlrnssnnravkfyedmyfytlknasvclkaytafadelelnlssnspiyytgdtiklnltvtnrgdlasnssiavpldksysivs<br>ykisenngnksydihyngssfnmasgiwsipyleneesvslilslkmnsnndvnikvsanssscsvkdnvyanislkykipskfanipsintt<br>arsygllnftlldinnkplanknvnllllklddeededlslndtnlyysdssisnasvisnltlktngngivqyklnltlgeylfklafdedk<br>nyqasdynyslnitkrkstkilckdmvtysvvaevdgrsgeyfnvtltdcdgyamadkfiqigfngriynrttdsegkarlqinlknpnaytf<br>aicflsdddyyasfevakitvnkkkmslnvpnkaykasekskiltatliennkktvanklltftvdgktysaktnsagvasvkvslsskkiys<br>ftvkfagddcygsatksakviik |

FIG. 6A

ORFs encoding methanogenesis pathway enzymes identified from *M. ruminantium*: Annotation.

| ORF | ORF Annotation |
|---|---|
| Contig40_gene_238 | formylmethanofuran-tetrahydromethanopterin formyltransferase FtrII |
| Contig40_gene_692 | tetrahydromethanopterin S-methyltransferase subunit H MtrH |
| Contig40_gene_693 | tetrahydromethanopterin S-methyltransferase subunit G MtrG |
| Contig40_gene_694 | tetrahydromethanopterin S-methyltransferase subunit F MtrF |
| Contig40_gene_695 | tetrahydromethanopterin S-methyltransferase subunit A MtrA |
| Contig40_gene_696 | tetrahydromethanopterin S-methyltransferase subunit B MtrB |
| Contig40_gene_697 | tetrahydromethanopterin S-methyltransferase subunit C MtrC |
| Contig40_gene_698 | tetrahydromethanopterin S-methyltransferase subunit D MtrD |
| Contig40_gene_699 | tetrahydromethanopterin S-methyltransferase subunit E MtrE |
| Contig40_gene_700 | methyl-coenzyme M reductase alpha subunit McrA |
| Contig40_gene_701 | methyl-coenzyme M reductase gamma subunit McrG |
| Contig40_gene_702 | methyl-coenzyme M reductase C subunit McrC |
| Contig40_gene_703 | methyl-coenzyme M reductase D subunit McrD |
| Contig40_gene_704 | methyl-coenzyme M reductase beta subunit McrB |
| Contig40_gene_802 | formylmethanofuran-tetrahydromethanopterin formyltransferase Ftr |
| Contig40_gene_925 | F420-dependent methylenetetrahydromethanopterin dehydrogenase Mtd |
| Contig40_gene_1365 | tungsten formylmethanofuran dehydrogenase subunit E FwdE |
| Contig40_gene_1366 | tungsten formylmethanofuran dehydrogenase subunit F FwdF |
| Contig40_gene_1367 | tungsten formylmethanofuran dehydrogenase subunit G FwdG |
| Contig40_gene_1368 | tungsten formylmethanofuran dehydrogenase subunit D FwdD |
| Contig40_gene_1369 | tungsten formylmethanofuran dehydrogenase subunit B FwdB |
| Contig40_gene_1370 | tungsten formylmethanofuran dehydrogenase subunit A FwdA |
| Contig40_gene_1371 | tungsten formylmethanofuran dehydrogenase subunit C FwdC |
| Contig47_gene_224 | 5,10-methylenetetrahydromethanopterin reductase |
| Contig47_gene_269 | coenzyme F420-dependent N(5),N(10)-methenyltetrahydromethanopterin reductase Hmd |
| Contig47_gene_358 | tetrahydromethanopterin S-methyltransferase subunit A |
| Contig49_gene_209 | methenyltetrahydromethanopterin cyclohydrolase Mch |

FIG. 6B-1

ORFs encoding methanogenesis pathway enzymes identified from *M. ruminantium*: nucleotide sequences

| ORF | SEQ ID No. | Nucleotide sequences |
|---|---|---|
| Contig40_gene_238 | 711 | atggtaaattatgataaggttgaagatacctctttgaatcattgatgaatgtatataagagcattgattacagcagaagacgaattgact gtaaggaagcagcatatgatgctacagctgtcagttgttgcaggtgaagcaggtgtagagtccttgtaagtggagataag actccagagcagaagcctgagccattgttcagttctggctaagtttgaaaaggaactgtcctataggattcgccag gacattccttgtaaagcaattacaaggtattcagcatagcagaaatccatgttcctattccagttccgatttcaatcgagtcagagcttgct tatcagaaggaatcatggaggaaactctgtatatgtgttccactaaggagcatgtattgaaggcaggaagaataataagacaccatt atgaagttgatggtctgcactccattgcaggaaagacttgcaggtcaaagttccagaggagtcaaagttaaactatattccagagattgttattaatgca cattccttgagaggcataagacaattgcttgtatctttaaaggaatga gggcgttaggagagagcataagaccaattgcttgtatctttaaaggaatga |
| Contig40_gene_692 | 712 | atgtttagatttgataaagaacaactcgtcgtagatattgctgtagatattgctgtatagagtaggacaacctggagaatacccctaccgtttttagcagga actatcttttacgcggacacaaaattattagtgatgaaaagcaggagactttgataaagacgctgctgaaggattaattaaacaatgaa gaaatgtctgatgtaaccggaaaccctttgtgtttgtacaaactttcgtgctactgcagaagctatgttaaatactagaatttgtagggac atctgtgacaaaacctttcctatcgactcaactgctcgagtcgcagaagattgcagtgtagaatacgtagaagaagcaggattagctgaaaga gctgtatacaaactccttaagtatgcagaagctgaagaatcgaagctgtagctaactctgacatcgacgcatccattctctttaggtttc aacccaatgacccctggttgtacctgtaaactcgaaatctggaaaacggtgatctgttatcgacgaggtattctcgaaatggcagaaga tgtgtattaccaaccttgatggacgtagcagttacttccttagtcaggtgcaggtcctgcagtaagaatcctcacgctgtaaagct aaatgggataccctgtaggttctaacatcgtacaacaaatgctggtggagacttcgtacttcgtcctatcgaaaactcaagactcgcatc ccctgtatgtgatataggttctaacatcgtacaacaaatgctggtggagacttcgtacttcgtcctatcgaaaactcaagactcgcatc ccagcatgtggatgcagatattatgattgctgaagcagcagaagatccggtaccgaacctattgaagcaccaccattgaacttgttatta taa |
| Contig40_gene_693 | 713 | atgtctgaagaagaatcagtacctcaaattattgtatctaccgatgatatgcagctgcaattaataattggatgaagctgaagaaaagta gaattcgctgttggtgaatacttccaacgtttaggacaacaaacgtagagatattgttatttttatatgtatttagtcttgtaatt ttaatagtacttattgaattgttttggtaagtgcaatgagtactatgcttacaagcttagtctaa |
| Contig40_gene_694 | 714 | atggttagatttcaaacaaccaaatactcgtggtattagaaatgtcttctaataatgtagaataccgtgcaaagctcttaggtagagaagga agattatttgctgcgtaatcagcaccagattttctgaatgctattggtattagttgcttgcttagcagttgttattccatactta gctaaattatgtggtttatag |
| Contig40_gene_695 | 715 | atggctgacaaaaacctgctgctgataactgcctgtagtaagtggagactacattgtagggagaccctgaagtcctgttgctgttaactacc ttagcttctcacaatgaagatattccagctgctgctgagcagctattgctgaccttgtaagactgaaactaggtattgaaaagttgtt gcaaacattattcaaaccaacatcagattcttaatccttggtgctgaaggtcacattactggtcaaagtatccaagcatta catgaaaatgttgcgaccctgaaaagaaagatcactgtctaccgggtgctattccttcgtagaaacattcctatggaaggtgtagaa agattccaacaacaagtagaaacttgttgactgtgttgactgatcgacaacgaagacgtgagcaatcactcgaaagtaaaagtatgcagaaagat cctggtgcttttgaagaagatgctatgtattgaagtgaagtgacgaagatgacgacgaagatgaaggtgaagaagtgaaggtcgctcctatttccgct gaactgcattacttgaagcaagtacttgaagcactcagtcaagtaaattagttggtgctgtacaaagaaatatggtcagttaactattca |

| | | |
|---|---|---|
| | | ggaaaagtccaaggtatcatgattgattaatattcacttagtaatcggtttcttgttattaatgcaccattattaggtgcataa |
| Contig40_gene_696 | 716 | atggtattaccttaatacaattattcctgaattaaacttaaatcttgatcctgaaaccgtctctctcggtgtgcaggtggtggagatttaatc<br>attcttcaatgatgatgagataaatggagaaatcgaagcgctgctgatgaattcctagatcctaattccgcacca<br>ttaggttccttcccagaagagagaagtaacttgttattgcaggaacattgaccaatatgtttatgatttattataggaatgttccttatc<br>atgcagcaatgcctattattaacagctatggggttttatag |
| Contig40_gene_697 | 717 | ttggaccaagtcattgcatgtcttggtgcagttgttgtgcaattcttgggagttcttgctattcgtagtgtagcaagttacggtttaggtact<br>ggtgtaccttctattggttacatgtcttaggtatcttaggtgtaatcggtgcattagcaggtgtaggtataattgcagcattaaattaaaagga<br>ttagaaatgctcgaccaatacttgcattagtatttgcattggtttattagttgcaattgttgctaagaagattgttggaatgaaa<br>atccctgttatggaaagatgcacagctgaaatcgctgtcctgagaaatcgctcaatgttctgctctctcgcaattgcaggtggatactct<br>attgattattattaaccgctgttgtagctctggtgagcttcattgctctcttttacatattagttactactagtctatcaacaccattcaacgca<br>tgtttagacctaacgaagatcaagttagaactcttagttgtcatccactgcatcctactgatatttctgcaatt<br>tccgctgagcatacgcatgtttgcaatttagttgtgactgttgtactgtctcattaaaatgtttgttaatgcttcctacgaa<br>gctcagcatctgttaatgtccgattatcagtgccaaaagttgaggaataa |
| Contig40_gene_698 | 718 | atggatcttttaatattattattgtgttgtaatcgcaggtattattgtgcaggtgtacacttcattcctgtaggtgtgctcctgca<br>gctatgctaccgctacggtgtaggaactgtacggcaatgttagcagctggtcaggattaactgacttaactaccgcagcttctatgacc<br>ggtcaaccagtatgcttaatcgtattagcaggtgcagttggttccatgtcattgattgtatcaccatgcttattgtaacttttatatattt<br>ttcggtgttgttgtaagcagcatctggtaagcagcagtcagtcatcgtgttactgtgtcaagcttaggtgctgtggagaattagtcactggcaattaat<br>ggacacgtattcctaccgtctgttacataactggattgacgctactggtatcatcggtggttacttgcgtgttatcgccgttaatcttctgttacgtctgttatcaattca<br>gaattgctactgcaaacttaactggaggtactatttgaagtttcgtagacccctaaattcaaaagactcccaactggaatcctcgcttgtctgtt<br>gtaactgcttcctataacattgaggtgctatttcatgtttcaatgatagaggtatttaa |
| Contig40_gene_699 | 719 | atggaccctattacattaggtgtagtcgcattgatggtgcagcagcaaccattgcaggtgctgcagaggacttagaatctgacatcggttca<br>caagtaacctaactctcaggttcagctgctctccacaaatggacacttacaccgtatgataaaatggcagcttctggggaacagtagca<br>tacggatgctggtgtgtattccggtgcttgttcacgcaatttatacagtcacatcctcttgcagctctgctattatacctatagtgcaattgcaattggttctact<br>gtcgctgcacttgttcacgcaatttatacagtcacatcctcttgttcacgcaatctcaattgaacaaccattattatgac<br>gtattaaccaatcctcaggccatttataccattacggttttatagctagttgggaattactattggtgcaatgcttatttaatgactcttccatta<br>gacgacttggacaccattccattaccattactgcgtctgtacttgggaattactattggtcaatgggatatcgatcatccacaggatgtcat<br>tatggtgcagaaagtgaataccaaaaattgcactacgggtgaggtactcctgcagcttaaaccgattctgtttttgactattgtttcgtaagcttc<br>gctaaaactctatcgatgtaggtaggtaacttctgtgctaatatgtggacctttaaccgattcatcgttcatcgttattaatcgctgttattaatcgctgtaattacttgaaaag<br>tggattactgttgtattcggagcttagcgagaggacaaattgtaggtattgtcatcgttcatcgttattaatcgctgtaattacttgaaaag<br>tctacaagagcaaaattcggaccatatgaggaataa |

FIG. 6B-3

| | | |
|---|---|---|
| Contig40_gene_700 | 1374 | atggctgatataaaattcttagatgcaatgactaaaagttcaaagagcctccagaagaaaaaactactacctctctatatatggcggttgg<br>actcaatctgaaagaaaaactgaatttgtaaacgaagttaaagcaatgctgaagcaagaagaattccaatgtacaaccagacattgtaac<br>ccacttggtcaaagagctttaatgtcctaccaattatccggtactgacacttcgtagaagggacgacttacacttttattaacaacgcagca<br>atgcaacaagcttggacgatatcagaaaaactgtaatcgtaggtttaaacactgctcacaactgctcacaagttagtgtatgaagta<br>actcctgaaaccattaccaactacttagaagttgtaaccacgctatgcctgctgcagctgcagcagaaatcgaccctgcattgtattagacattaacaa<br>ttactcgtagacgactcctacgtaaaagtattaccggtgacgactagcgacgactgcagatgctatttgcaaattgtaagagttccatctgttgtagtagatc<br>tgtgacggtgtacaacctccagatggtctgctatgcaagaagttgtatgtggtacttacttaccaatcagaagagcaagagcaagtaacgactcggt<br>ggtgactccatcgcatccaaaacacgcagaagttctgtcaagcaacagagtaaccgacgacccgtagaatctgcattagagtagtagctttagt<br>gctgctcttatacgaccaaatctgttaggttcttacatgtctgtggtgtggttaggattttactcaatatgctaccgcagcatacaccgataacgtat |
| Contig40_gene_701 | 720 | atggcacaatattatccaggaacttctcaggtagctgaaaacagagagaaatttactaaccagatgttgagttagaagtttaagagaaata<br>tctgatgaagtgtagtaaaattattaggtcacagagctccaggtgaagaatacaaatccgttcacccacctctgacgaactcgatgaacct<br>gatgacattattagacaaggatccacgctatttgacggtgcaaaagcagatacagaggagcagagtaagatacaggtaagattcaattccatgtacttt<br>gctccagtcaacctttcttaagagcaagcaagatctttagaaagatttagaaaacgataaatactttgacactgcacgtacgactgaatcagaggtgcaggtgta<br>gctcgtgaaagagatgtgaaagactcctttaagactgcacgaaaacggtttaatgttgacatgttaagagacaagtactcaacaagaaaacgtaacgttgaaatg<br>cacggtcaactctttagaagagaccaaattgtcgtgaattagtaacgactgaatgtagttagtgaaccattagaagcgaagaaactctcagagctaaaccaatcta<br>gtaaaagaccaaattagattaacattagagatgcataa<br>cagatgtga |
| Contig40_gene_702 | 721 | atgattgaagatgcacacatcttgtagactgcaggcgaacaagaggactggtgaaggaggaattgccaaagaggaactttttgcagaa<br>tgtgaagcgatgttttgcagttgcagtcgtccaggtagaacacattaccaagccagtctgtgaaatcaccttcggtctcttcgcgaagcc<br>aacctattgaccagcaccagtcgatattcgatgcaggaagcggctaccgcatgtgtcctgctgaggtgcggtaatgcattgcggcttgact<br>gacaaggaagtcgagcagcagtagacaaacccttgttgttcttattttgtgaatatcatccagtagtcaactttgaagatttgcaaaaatcggtgtcaaaaaccgcaagtc<br>ttgctaacgttaacaaacagacaggtaaagacaggtaaaatcatcaacattagcaatttcaggggttattagggacaacagtctctcaagaaaaattagatgag<br>atgcctgataggtaggtaaagtagaacaggtaaactcaggggttattagggacaacagtctctcaagaaaaattagatgag<br>attattagaaaagttagattaacattagagatgcataa |
| Contig40_gene_703 | 722 | atgatattgaaatatttccacacagaacattttaggtacagacaagatggttatttaaatgatcttgtgtaaatgcgagaagttt<br>actgtaattcaagggccaagactccaccacagactgtgacagaattcatgagaatcatgagatcgcagaattcattgtgtaaatgcgagaagttt<br>gaattaaagttaaaactgttagaactgtagaattgtagactctatgtagaactatacatcatgtgatgaatcgtgttattgagcgcatatgcgataagcatattgac<br>actgtttttgatttaatactacagagctcaataactcgtaagcaaaaacagttactgatggattgatatgtgaaaatacagaaatt<br>cctgaagaactgatttgattgctaccgataccccgttctaaattaatgaacatgtctctattctaagaaaagatgtgtctgaataa |
| Contig40_gene_704 | 723 | ttgcaagtttgatgatataaagtcgattagaggttcattagttcagtagacgacagaggttcattagttaaatatcttaaaaactgttccgtt<br>aacctgctatttaagaacattattagcggtgttaaaagaacttgagctgtaacttgacatttgtgctaagctgactccattaacgctcattacgatcttcaactatcagattagattcttc<br>ggtggagcaaatctaaaatcttaggaagagaaatggatcttgctctgtggtgaaaagattttgaaaactgtaccgataactaaatgtaccgactataaatgtaccgtaagactggacagagttgacgtacgttaatactaaatgtaccgactataaatgtaccgactataaat<br>caagtaactgaacgatgaagagcgttaaccaagctgatatactctctgtgaaaagatttagtcaactatcagattagattatcatcaactatcagattcttcc<br>ggaatactcgtagagcgatgatactaaatgtaccgatataactacgccaatctcattaacctagcatgctgtaccaacttgtaagcatacaaatgtaaagctccaactatcagattcttcc<br>gtaaagctgctatcttaggaagataccccacatctgtagaatacctagatgaatcatgtgaaaaacaaatgtaaaaatttagaa |

FIG. 6B-4

| | | |
|---|---|---|
| | | ggtccagttactctttaagaaacattaaagcaaacgactcgtagctgctacccttaaagaatactttacaagcaactgctcttgcaagtatc<br>tttgaacaaactgctatgttgaatggtgacgcagtcgtgcatacgaaagaatgcacttattagtttagctaccaaggattaaacgca<br>gacaacatggtattaggtctcgtacaagacaacgcaaagaaggaaccgtagttctatcgtacaagacacatcattgctaagctgaagctgat<br>ggtgttatcgctgtagaaaaagaattaaccgactacaacatgtacgcaaccaacgatgcagctaaatgaacgcatacgctgctggatgt<br>actgctgctattatggttaacgtaggtcgcagcaagagctgctcaagtattccatctactattttatacttcaacgacaacatcgaattcgct<br>a |
| Contig40_<br>gene_802 | 724 | atgaaattaatggtgtagaaattaaagaaacttacgcagaaggattcggaattaaagtaactagaattttagtaactgcagcaactgcaaaa<br>cttgcaaaaattgcagcaacggaagaccttggttatgcaactgctcgtaatcgatgtcctgctgaagcaggtattgactgttttgtaccatct<br>gaatgcactccagacggaagaccttggttacgcaatcattcaactcatcgaatctgaagacgaattaaaaaccgcttcaaactcaaatacttcggt<br>atgtgtcttaactgctcctactgcagcagcattcaactcactcgaatctgaagacgaattaaaaaccgcttcaaactcaaatacttcggt<br>gacggtttcgaaaaagactgttgcattgagggaagaaactacatccatccaatcatgtctgtgactcattgtgaatccacttcgga<br>ttcaaagcaggtgtagctggaggaaactcttcattttagctaagacaaattactggtgttaaagtctcaaatgctgttgcagtatt<br>agaaacatccaagtactatcactccatccctgaggtatgttgcatccggttcaaagtaggatccaacaatactcattcttaccagca<br>tccactaacgaaaaatgtgttaacttcaaaaaagctatgaaagcaggtatgcatcttgttgacgaagtgtattttgaaatcagcgcagtaac<br>ggtttagatgaagaatctgtcaaaaaagctatgaaagcaggtatgcttgtgacggagttcttgaaatcagcgcagtaac<br>tttgacgtaagttaggtgcatacatcttaaacttacacgacttattctaa |
| Contig40_<br>gene_925 | 725 | atgtgtgatattatgtgtagtaatgttgtatcgtaaaagtgtactccaccagtgatttattatattagaacgaagagca<br>gacagacaaacatcgatgtaagagtattgatctgagcaaaaatgaacctgaacagtgaagacgtcgtacctaaactgaccattc<br>gaccctgacttctgtatttcattagcgcacccaaaccagtgatcatcgagtttggacaacagctgaagacgtcgtacctaaactgaccattc<br>attatcattggtgacgcacctgtaaagtaaaagatgaaaagatgctatcttaaagtattagcagaaactggtgtcttagatta<br>ggtcaaaaagaaaactctcgacgctgttattgctgctgatgctggcaaagacaaaattgaattaccaactcattgttactgctgaaaagctgtt<br>gtacaaaaaactctcgacgctgttattgctgctgatgctggcaaagacaaaattgaattaccaactcattgttactgctgaaaagctgtt<br>gaagctgcaggatttgcaaaccatacgacaaagcaaaacttcatccaccattagttgctgctgtcacacgaagaagaaactggtgagctgtcgcaggcttagacgaaaggt<br>tgtttcatgaccaaaggcttcgaaaaatccaacgacactgtcttaagaactcctcaagactgtcttaatccaatgaactcctcaagactgtcttaatcagcaaacct<br>gtagacaaataa |
| Contig40_<br>gene_136<br>5 | 726 | atgtcaaaacatatcgtatcaggactaaaatatttagaaagtgtcgagctgttgaagtgtcgagtgttgaaaaaagaggctgtcccaaaggagattctcatcgaatt<br>ggtggacagatcaactatttctcactacttgaacgcggaaacattctgccgattcaatcgagctgcaatcgagcttgctaagttatttagcgaat<br>cctaaggatttatattaattgcaagagtttgtttgagattataacgaaattcgtcaacttatcgtcaacttcaacttaatatgaatcattatgac<br>ccgcagatagatgacggatgtatttggttgtgagttgtgtgattgggattgcgagactcattagactcattaaaagcaagata<br>aaccctcgttattgttgctcttatgtgtcttatgtgttgaagattgccgacaaattcaataaagatttggaggtaa |
| Contig40_<br>gene_136<br>6 | 727 | atggtcaaaatattaaagaaacagaaggcaaaaacttctgcattaaaagatccattaggcgaagaaagagtattgtctttcaaagatcacgtc<br>tgtcggttgcggactctgtgaagcaacctgtcctgtagaagctatcctcttgatgaagtagctcctatcgaacgtaaatatgtagacact<br>tatttcagtggtcatgaaagattgctcaaaactatgctctttcactaatgataacgaaatcaaagcaaaattagatatttgcaagataa<br>tgtctctgtggtttatgtagtgaatgtccagcaggttgcattgaactgtctattgatgggtatccattaaagaaaatgaagcttac<br>ccacatcttgtcacttcagctgaaattgatgaagacaaatgtttattctgtaagaaatgtgaagctgcatgtcctaggagtcattactatc<br>gacagaaaattacctaaccgtgcagaccttgtaaccggtgaatgtgatgaagaaatgtatctactgtggcgcttgtgctgatta<br>tgtcctgaagctatcgtggacaaggcaaccggcaacgtgcattgcattgacaagaaagcattgtcattgacaagaaagcattgtcattgacaagaaagcattgtcattgacaagaaagcattgtcaagaatgtgtatactgtctgtatgtaag |

FIG. 6B-5

| | | |
|---|---|---|
| Contig40_gene_1367 | 728 | aaagcatgtcctgttgacgctatcaaagcagtatgtagatcctgttcctacggcgaatacgatctgacctgctaaagcagcaattacaggt aacgctatcattgattctgaaacctgtattctgatggtgttgaaggagtctgtcctgctgatgcagctactgtaaacaagcattcaa ggtactctcgaaatcgacgaggaaactcacttagttaaagaagaagattactgacatgtatgtccatgtcttcctcctaaatcaact ggtcctggagacagaggaactcacttagttaaagaagaagattactgacatgtatgtccatgtcctaacgaagcatta a |
| Contig40_gene_1368 | 729 | atgaaacttaaagtagatcaagataaatgtttaggttgtggagtatgttgttatcgcatgtcctgtaaacgcttccatcagtccgaaacgct ggaggacggttccaaaacaaccgaaactattatgatgttgaaaacgatttattaaatattcagtgtggacaaatgtgataatgtggt acttgccaaatgttctgtccaactgaagctatatggttagaatag |
| Contig40_gene_1368 | 729 | atgcattacgcaaatacttattttagaaagaccagtagtggactttggagtttgagaaacgtagctcaagaaggtactaccaagtactcaaatgtatg ttaaacaccgttctgacatgtctcaagagcttgtaagaaaaagagttccaccttaaagaagaatataagaacgcttccgtacctgttat atggatcctcgtgacatgtcctcacgaagtacccattttttgtatgtaaagtccatggctaacactatcgtaagccacgaaacctactgctgttca aatcaagagatgtcctcacgaagtattcacgtcacgactgttattgaaaaaaccgaacagaaaagttctactcatgcagacttaatgagatgggcatacaaaaaa gaccctacctacaaagtattcacgtcacgactgttattgaaaaaacatgaatcccttaggtgaaagaccagttataactga tatgttgacgaagaagatgacgacgttattgaaaacatgaatcctaggtgaaagaccagttataactga |
| Contig40_gene_1369 | 730 | atgacatgagccaccctgtaactgttaactgttatattgtagaaaactgtactttgtcatttgcggttgtaactgtgacgacttagattc ttagtaaaacggtcacgtggttgccgtaagacacgcatgcagttgcagttaaggtcaagtaatggaagatatggaccaaagattacttgtg ccaatggtaagaaacgaagaaggagttcttgaagagttcctgaaacttccacgttggtctgaaacttcgcagctgaatacatcagagcagttctcgataaccaa cctgtatctacggttggtctgaaacttgtctgaaacttccacgttggtctgaaacttcgcagctgaatacatcgagcagttctcgataaccaa gcaaccatctgtcacggtccagttcacgtccaagtctacaagctactcacccagctcagtcataacgcagcttaccctatggggaagttaaaaacagagctgacgtt attgcatactctggaagcaaccgttatcactatggacctcaccgcaagaccgttagctggtacgttaggtgaaaacgttgttactgaagagtatgtctgcatttccctcgtggatacttcagacaagagga agttcgacagaaccgttatcactatgagcctttaagagctgtactcaaagtaaacctaaaaaatgtctgaaatgtgttccagatccgttttcagcagaagacatctatgaa tacggttctcacaacgctttaagagctgcagaatgcgaaaattcggttgtttctcttcgttagttaaaccacacctctaagtaaggcaaagaaaactgaca ttagctgctgaaatggaagctgacgatcaaacaccaacaagacttaaaaacaccaacagtaaacaccaacagtaacctaagtaaggcaaagaaaactgaca gcgattaaattggtacaagacttaaaacaccaacagtaaggtaaatgggactcactccaatgagaggtcacttaactaacgtttcaacatcttc atggcttacgaaccggttggcatttcggtgtagacttcggtgtagacttcggtgtagacgtcctagaggatacggaagatatatgatggtgaaccaacaatcgacttactc g |
| Contig40_gene_1370 | 731 | atggaatatatacttaaaaatggtattgttacgacctgctaatgaagtaaacggagaaaaaatggatatctgcttcaaggatgtaaaatc gttgaagacgtatccgctgacgcagaagttattagacgtcactgatataaattgtaatgcctgctgtgtgtagacctcacgttgcagga ccaaattggttggtagttatacagaccagaagatgaaagaagaggtagctcaaaaacaaccagagcagagctggtttc tctatccaagttgtcctaccactgtcgatacagatactccaaccattgcacattcctaacactttggaagcagctacgtgctccttagaagcaaa cacacacagaagaaattaacactattcctaacactttggcagcattcattgcagcaatgttaaggatatctaaagatacgtttgtaatgcaacctgttgtaatgctaga gaaaacgtagaaattgacgattggcatgtgtaaccatgataagctccatctttgacgtaacctcagagttgtaagagcttagca aagcaacgaaaattaggactccactactcatacaccatctgcttcgtaagatacaaccatccacctgaaagttaggtcaccgtgaaacgttctactaccattgcaact tagactcaatcaaagacattgcaaatcaactaataccatctgttcgtgcgaaatctgctgactcattaacaagaaccatatgtaacttgtgacgtaggt tacaggaaacagctgaaggatgcagcatctggtgctgaaggatgctgaacagcatctggtgctgaaggatgcagactcattaacaagaaccatatgtaactttgtgacgtaggt caagtaacctcgacgaaacactacaatgactgcagacgctcctatgaatcagctgactttaagattctgattaaatgggctaacaag g |

FIG. 6B-6

| | | |
|---|---|---|
| Contig40_gene_137 | 732 | atgaaaactattacttttgatcaaagaaaacttcttcaattgctttagaatttgatgagttaatcactgataacattacgcttgaccgaa<br>gaggactttgcagaatacaaagttcctatagaaactccagattccaatcactgattactttgacatcaccgttgaaggagagcagaatct<br>cctgctgaagtcaaaatgatttaaacggagatgtaacagatgtaaaatacatcggctgtaaaatgagcgctgtgaagctgttaacggt<br>gacgctgaccttcacgtaggtgcagaaatgtctgcggaattgttaccgtattcgtaatgtagcagctcacgccggtcgtgaatgaaagt<br>ggaaaactcgaaattatgggtaatacaaagaattctgtggtcgcatcctatacggtaatggaagaggtatgtccggtggaaatcatcatc<br>cacggaaacgctgaaaacaatgtggtgaatgttaacggttgaatgtttagtcgtcgttgaagatccacgttttagttgactgtgtatattctgcagtattcacatg<br>actaaagtaccattgaaatcgatggtaatgtaacggttgcctggcgtgcagatgaaaacgtaacatagtcatccacgtaagtagga<br>agattacttgaaggtttcgtagaacaaggaatcgtcacagaccctgaattagatggtcacttatcctgcagatacatcgaatacaaaggg<br>gacattgctttaaacggtaaagttaccttattaatcgatgctgagaaaaacagagacagattatctacctgattgaagagacgacgaatat<br>aacgcaattagaagaatacagagaccaataa |
| Contig47_gene_224 | 733 | atgaaattggtatagaattcgtacctccaatactagtagaactcgtaagattagtaaaaatagcagaagacgtcggtttgaatacgca<br>tggatcactgaccactacaacaacaaaaacgtatacgaaaccttagcattgcagcaaaccattaaaatggtcctgtgta<br>accaacccatacgtaagaagtcctgcaattcccgctccgcaattgcatggaaaaacctgtatccacaattaaagcagcaatgcagacatacctta<br>cctgtgacaaagcaacctttgacgcattagttatgcatggaaaaacctgtatccacaattaaagcagcaatgcagacattaccactta<br>ttagacgtgtgaaaaacgaagctgagcagctgctgacggtgtattaattaacgctctactctcatggctatgactgtctatgcctatgattaaa<br>aaatgttagaaaactgctgtgaaatcgtgaaatgagtttcgatgcagagttcaccactccagtaattgcaagacacgattaccagaagattcaacgacaatggtgaa<br>ttcttagcacaagtaacttcggtggagctattggtggctgacatggtgtaactcaatacgtagcaggatctcctgtagtaaaacgtagaagaatctattaaatta<br>taggagacgtaattgctagcttctaa |
| Contig47_gene_269 | 734 | atgaaagtagcaattttagtgctgctgttacagaactcacgcagctagtgaattacaaattttctagagctgtgaagtagcagacgca<br>acggtaagaaacattcaatgaccactctaccattgaaatggtgcagaacttttagaattagcaggtgtagacaggttgtagtagct<br>gacccgtatttgacgcgaattcactgtagtagaagactttgactatgcagaagtaatcgcagctcacaaagctgaaacctgaagatgta<br>atgctgcaatcagagcaaaagtaggagaattagctgaaacgtaccgtgaaacctaaacagctaacgtgctatccacttcactcacctgaagactta<br>ggaatgaaatgtactactgacgaaccgtgaacgtgaacgtagctgcctgactgactggatcatgacgtggttaccagaaggagtgtcaactcttgaagac<br>atcgaaaaattcgctgatgtaattaaagacgtcctaccaccagtgcaatgctacctccgcatgtaacctcctgattaaccaaatctttgaagac<br>ttagcaaaaacgtaaacgtaagctcctacacaagagttcgaaagcaagagttccgcattccgcatggtaaacatgtagttcctgtatgtatatg<br>gcagctatcgacacacttaaaagctaggtgcaaagacaagagttccgcattccgcatggtaaactctaggtgcaccagcaggattcgctcaa<br>tgttccgcagtaactgcaattactgctacgtgcgtcttttatctcacagagacactgtaactcaaatctaagtgatgcttaacctggcatta<br>atgctgctaacgaagcattaaccaacgtaacaattaatgctgataaggcattgacaaaatctagaatcttagaaatccaaatag<br>ttaggtactgctgactcaatgaacttcgtcaatctgaattgtacctactatcttgaatctttagaaaagatccaatag |
| Contig47_gene_358 | 735 | atggcggataaaaactactgcagaaaactggcctgttgtaagtggagattatattgtaggagatccagaaagccctgttgctgtaaccaca<br>ttgcttctcacatgaagacattcctgcagctgctggcgcagccattgctgacctgcaagactgcaaaaccttgaatgaaaggttgtt<br>gcaaacatcattcaaaccctaacaataagatttgattttatgtgtgctgaagtgcaagacacattacagttcaagtcattaaggcatta<br>tatgaaacggctgtgacctgaggaaaatcactgagctactgacgtggagctattccttttgtagaaaaacattccaatggaaggtgttgaa<br>tgattccaacaacaattgttgttgatattgattgacaacgaagacggtggagcaacgtcaaagttaaggaatgcataaaaagat<br>cctggtgctttgaagaggattctttagtgattaagattgatgaagaagatattctaaaaaaagcagtttgtgaatcttcatctgaagt |

FIG. 6B-7

| | | |
|---|---|---|
| | | gaaaaaatagaatccgaagcataa |
| Contig49_gene_209 | 736 | atggttagtgtcaatttagaagctaaaaaaactgtagatgtaatgattgaaaaggctgacgatcttaacattgctgtttccaaattagaaaac<br>ggcgcaactgtcattgactgtggtgtaaatgtcgcaggtagttcaaagcaggtgaattatatactaaagtatgtcttggaggattagctgat<br>gtaggcattccattcctgagacttatctgaaaaattcgcattgcattgcctctgtaaaataaaaacagactttcccagctatttccaccttagt<br>gcacaaaagcaggttgttccgtcagtgaagactttcttgcattagttccgtccagtcagctagagctcagcattatccttaaaaccagctgaaacc<br>tatgaagaaattgattacaaagatgaagctgatcttgcaaacgtattcttctaactttagaagctgactattgcctggtgaagatgtagctcaatacatt<br>gcagatgaatgtggcgtagatgttgcaaacgtattcttaaagttcttgctgtagctcctacgcttcctttagttgcatgcaggaacttactattgtcaaatcaggaagaggatc<br>gttgaaaacgtacctacaaaatgttagaattcttaaagttcgatgttaaaaggttgtacatgcagcaggtattgcaccatcgctcctatc<br>gacccagacgcagttggcgattaaaggctatggtaaaaccaacgatgcagtgctcttttggcggataacgcaaaccattctttgacgtatttaaagatgcaggatttgac<br>gacattgcagcagttgcagctcaattaccatcctcagcagctgacgagctgacggataacgcaaaccattctttgacgtatttaaagatgcaggatttgac<br>ttctaccaatcgacaaaggaatgtttgcaccagtgttatcaacgattgttatcaacactgttaaccactgtaaattatacaaagaaggtttcgttaac<br>gctgaattgcttaaaaatcctttggtatagaataa |

FIG. 6C-1

ORFs encoding methanogenesis pathway enzymes identified from *M. ruminantium*: amino acid sequences

| ORF | SEQ ID No. | Amino acid sequences |
|---|---|---|
| Contig40_gene_238 | 18 | mvnydkvedtffesfdgmyiralitaedeltvkeaaydatatpsavigrveagvesfvsgdktpdgrpgaivqfwltddlakfekelsyrirq dilvkpftrvfsitenpvgsipmmesvghcgdgyeweieeygrkminvpiavpdfqieselayaegimggnfwymcstkeavlkagriiidti mevdgvctpfgicsaaskpetnfpeigpstnhpycpslrerlgkeskvpegvnyipeivinavsgeamnlaikkavdaiidggverisagnf egglgehktnlldilke |
| Contig40_gene_692 | 19 | mfrfdkeqlvvdiagvkmggqpgeyptvlagtifygghklisdekagdfcdkdaaegliktmeemsdvtgnpcvvqtfgataeamvkylefvgd icdkpflidstaaaakiagveyvqeaglaeravynslsmaaeageieavansdidasillgfnpmtpgvpgkleiwetgsvideglemaer cgitkpwmdvavtplggqagpavrtsyavkakwgypvgsgihnvpsawdwlrqykkehkeawpvcdigsnivqqmaggdfvlfgpiensrlaf pacgmadimiaeaardigtepieahplnlll |
| Contig40_gene_693 | 20 | mseeesvpqiivstddmaaainkldeaeekvefavgeyfqrlgqqngrdigilygiilglvilivsiefglvsamstmltslv |
| Contig40_gene_694 | 21 | mvrfsnkpntrgirnasnnveyraklgregrlfagvistrfsgmaigiglalalavvipylaklcgl |
| Contig40_gene_695 | 22 | madknwpvvsgdyivgdpespvavttlashnedipaaagaaiagpcktenlgiekvvaniisnpnirfliilcgaevqghitgqsiqal hengcdpekkitgatgaipfvenipmegverfgqqvelvdlidnedgaitakvkeciekdpgafeedamvievkegdddedegeeirpisa etalleariirnidtqvklvgavqrnmagnysgkvqgimigliftlvigfllmapllga |
| Contig40_gene_696 | 23 | mvlpliqfipelnlnldpetgllgaggdliilsmdeingeiakveaaadelmnsldpnsaplgsfpgregnfviagtltnmvygfiigmfli maampiltamgvl |
| Contig40_gene_697 | 24 | mdqviaclgavcailwgvlairsvasyglgtgvpsigymslg,gvigalagvgliaafklkglemlgpilalvfamlligllvaivakkivgmk ipvmerctaeiagaaalavlgfssaiaggysidllltavvapgfialfyilvtmaighpfnaclgpnedqvrtlkcgastafltmiitgilai saggyawfailvvgligwyvsfkmfvnasyeaaasvkwsglwpkvee |
| Contig40_gene_698 | 25 | mdllifiicvviagliimggvhfipvggapaamatatgvgtamlaagagltgliitaasmtgqpvwliviagavgsmlmngitmlignfiyi fgvgvvpasgkaavdpitgwnqekyktpgteghgiptvcyisgiinggllggagglvywainefatanltgfdatviaglaailsvgmffins vtasyniggtiegfvdpkfkrlptgilacavvslvaaifmvlmiggi |
| Contig40_gene_699 | 26 | mdpitlgvvalmgaaatiagaaedlesdigsqsnpnsqvqlapqmglhrminkaasgepvaygcwcgisgaiaalamgmgiplvalamgst vaalvhaiytvtshmgrivgqsqfeqplfmdvltqslgpiaahgfiasfgivgiaylmtlpldglghpfplpllavlwgitigaigsstgdvh ygaeseyqkfdyggtpvaigqdivtkapligaknsidvgnfcakyggpltgfcfglivfvsfwitvvfgalggqivgivivilliaanyllek strakfgpyee |
| Contig40_gene_700 | 27 | madkkfldamtkkfkeapeektttfynmggwtqserktefvnegkaiaeargipmynpdignplgqralmsyqlsgtdtfvegddlhfinnaa mqqawddirktvivglntahnvlekrlgmevtpetitnylevvnhampgaaavqehmvetnpllvddsyvkvftgdddlaaeidpafvldink efpeeqaealkaevggaiwqivrvpsvvgrvcdggttsrwsamqigmsmisaygqcagegatgdfayaskhaevigmgtylpirraragnelg gvpfgfmadicqatrvtddpvesalevvalgaalydqiwlgsymsggvftqataaytdnvlddfsyfgkdyvedkygdlcsapndmdtvld vgsavtfysleqyeeypallethfggsqraavvsaasgistafatgnaqtglsawylaqylhkeqhsrlgfygydlqdcgaanvfairndeg lplelrgpnypnyamvghqqeyagiagaphsargdafavnplvkiafadknlpfdftkvraefakgalrefepagersilipak |

FIG. 6C-2

| | | |
|---|---|---|
| Contig40_gene_701 | 28 | magyypgtsqvaenrrkftnpdvelevlreisdedvvkllghrapgeeyksvhppldeldepddiireivepidgakagdrvryiqfvdsmyf apaqpflrarsyvyryrgidtgtlsgrqiiearerdveriskeileneyfdtartgirgagvhghslrldenglmfdmlrrqvlnketgnvem vkdqigreldepvvlgepldeetlraknhnlqm |
| Contig40_gene_702 | 29 | migrcthlvdcretrglgeggiaqrgtfaecgsdvlavamspgrrhitkpvceitfglreanlltstmildagsgvphdapaggagnafglt dkeveqmqkfkvivvhlggvrnhitykarlllrnvnkpcviiceypvdfedfakigvktakvmpdevktegkimnivsgvirgqtvsqeklde iirkvrltlgda |
| Contig40_gene_703 | 30 | mdieifphrilgtdttekvlndlesldsvkrtviqgprlppqdeidriygdrrlivvngeevelkvktgrifvelydesgieeiraicdkhid tgfdintskaqyirkqktvtdglkygenteipeeligiadtrskfnehvsilrkdgle |
| Contig40_gene_704 | 31 | makfddkvdlyddrgslvesdvpiealsplrrpaikniisgvkrtvavnlegiekslktasvggakskilgremdldivaqadsinaslkeml qvtedddtkceilsggkrilvqiptirldssaeysvatlatataltgaiikefdvsmydanmvkaailgrypqsveymgsnlktmldvpqkle gpgyslrniikandfvaatlkntlqatalasifeqtamfemgdavgayermhllglayqlnadnmvlglvqdnakegtvgsivqdtiakaead gviavekeltdynmyatndaakwnayaaagctaaimvnvgaaraaggipstilyfndniefatglpgidfgraegvavgfsffshsiygggp glfngnhvtrhskgftipcvaagmaldagtqlfspeatsglikevyseidefreplkyvalaaaeikgdi |
| Contig40_gene_802 | 32 | meingveiketyaegfgikvtrilvtaataklaiateatgyatsvigcpaeagidcfvpsectpdgrpgyaimichasskaldhelmerig mcvltaptaaafnllesedelktafklkyfgdgfekdccidgrkvhsipimsgdfivestfgfkagvaggnffilakdqitgvkaaqmavaai rnipgtitpfpggmvasgskvgsnkysflpastnekmcvtlkdqvdsdiredaegvfeividgldeesvkkamkagivaacsvdgvleisagn fdgklgayilnlhdlf |
| Contig40_gene_925 | 33 | mcdimvvkigivksgnigtspvldillderadrpnidvrvfgsgakmnpeqvedvvpkldqfdpdfcifispnpgapgpararellsekdlpa iiigdapgkgkkdemdeqglgyiivmsdpmigakrewldptemaifnadilkvlaetgalrlvqktldaviaaadageeielpklivtaekav eaagfanpyakakaiaayemagavagldmkgcfmtkgfenfiplvaaaheiasaaaklaqeareieksndtvlrtphmkegnlgckvdliskp vdk |
| Contig40_gene_1365 | 34 | mpkhivsglkylesvelrkrglsqkeisseigvdrstishylngrnisadsielakvilelnpkdfiliarvlfgdyneirqlisifnmnhyd pqiddgcigcglcvdlcevksisldslkakinpryccglmcvedcptnsikilev |
| Contig40_gene_1366 | 35 | mvkniketegknfcikrslgeervlsfkdhvcvcglceatcpveaisldevapierkyvdtyfsghekiaqnyalftndneikakldicedk cvlcglcsgvcpagalelaidgvsikeneayphlvtsaeidedkclfckkceaacpresitidrklpnradlvtgeievdeeeclycgacael cpaeaivvdkatgeesividkekcvyclvckkacpvdaikavcrscsygeyldpakaaitgnaiidsetcikcgwcegvcpadaatvkqafk gtleideekcgtcgacidvcpcnvlsfpkstgpgdrgthlvkeedycihcgacakvcpnealtvtrtdvdytptssksWiaafealkn |
| Contig40_gene_1367 | 36 | melkvdqdkclcgcvciacpvnasispenagghgskttetimmvengfiklfsvdkcdkcgtcqmfcpteaiwle |
| Contig40_gene_1368 | 37 | mhyantylerpvvgdlenvaqegttkvlkcmlntgsdiyqgackkrgstlkeeyknasgtcymdprdmvklgvknwdtvlvktdygevvlnaa ksrdaphegtifvckgpwantivshetyccsdptykgihatvektdrkvllmadlmrwaykkyvdeeddvienmeslgerpvyn |

FIG. 6C-3

| | | |
|---|---|---|
| Contig40_gene_1369 | 38 | mtyeppvtdydyivenctcafcgcncddldflvknghvvavrhacrlgaskvmedmdqrllvpmvrneegvleevdwtaldtaaeyiansir pvfygwsetstecmkegvelgeyigavldnqatichqpslqamqnagypiqtlgevknradviaysgsnamnshprhlaryaafprgyfrqrg rfdrtvitmdpkfsdtakmsdkwigfeqngdygfynalravlkgkklqsesvsgipaediyelaaemeaaefgvlffglglthtlgkqrnidi aiklvqdlntnskwgltpmrghfnvngfnifmayetgwafgvdfcrgygrymngetntidllvrkepdcfmviaadpgahfpnganqhladip viqidihwgpsteladvvlpgsfisvecggtsyrmdgvpiwmkkaidkpetcrddewivrelkervmklreepnvadeyvpneglaclldk |
| Contig40_gene_1370 | 39 | meyilkngivydpanevngekmdicfkdgkivedvsadaevldvtdkivmpagvdphahvagpklvvgrlyrpederrgvaqktkttraeagf sipscpttgyrysrmgygtvceaampleakhtheeintipnidinplpflgnnwfvmeyarenriddlaafiaamlrvskgygvkivnpcgs eawgmnvhgyddkapyfdvtsrevvralakaneklglphsihihpndlghpgnvpttiatldsikdiakstkpsasvrdqtihchlqfhs ytgnswkdaasgaeecadfinknpyvtcdvgqvtfdettmtadapmeydlfkisglkwankdiecetaagiipciyspktpvstlqwaigle lflhienpwqvclttdhpnagpfirypkiiswlmsapkrmemidngevhkwaskrtglaglereydfyeiatisraaparihgfadrgaltpg ynadiavydinpndfdpsrdpegvekafsnayytikdgqivvkdgdivstkqshtiwtnvigyeeeekqiidsimpfftqyysvkwenyqvhd hyvpnptvvdveak |
| Contig40_gene_1371 | 40 | mktitfdqkktssialefdelitdniyawteedfaeykvpignsrfpitdyfditvegeaespaevkmilngdcnrvkyigckmsagevvng dadlhvgaemsggivtvfgnvaahagremkggkleimgntkefcgasyigewrgmsggeiihgnagkqcgeclvggkihvlgdcdilagihm tkgtieldgnvnrwpggqmkngnivihgkvgrllegfveggivtdpeldgvtypgryieykgdialngkgtllidaeknrdlstwieeddey naireyrdq |
| Contig47_gene_224 | 41 | mkfgiefvpqipldelvrlvkiaedvgfeyawitdhynnknvyetlaliaantetikmgpgvtnpyvrspaisasaiatideisngratfgig pgdkatfdalgiawekpvstikaaiadittlldggkteagalggakvqdaipiymgagpkmletageiadgvlinasnpkdyeaampmik kgigdqdkdfdvaaytatsigtdseeaaknaakivvafiaagspppviarhglpegfneqmgeflaggnfggaigavtpealdafsvcgtpdef ipkiealadmgvtqyvagspvgknveesikllgdviasf |
| Contig47_gene_269 | 42 | mkvailgagcyrthaasgitnfsracevadatgkenismthstiemgaellelagvdevvvadpvfdgeftvvedfdyaeviaahkagnpedv mpairakvgelaetvpkpangaihfthpedlgmkcttddreavadadwimtwlpeggmqpaiiekfadvikdgaivtsactiptpglnqifed lgknvnvasyhpgavpemkgqvyiaegfadqaaidtlkdlgakargsaftlpanmvgpvcdmcsavtaityagllsyrdtvtqilgapagfaq mmanealtnvtklmadegidkmddalnpgallgtadsmnfgplseivptileslekrsk |
| Contig47_gene_358 | 43 | madkkptaenwpvvsgdyivgdpespvavttlashnedipaaagaaiagpcktenlgiekvvaniisnpnirflilcgaevgghitgqsfkal yengcdpekkkitgatgaipfvenipmegverfgqqlelvdmidnedggaitakvkecieknkpgafeedslvikideeryskksfvessses ekiesea |
| Contig49_gene_209 | 44 | mvsvnleakktvdvmiekaddlniavsklengatvidcgvnvagsfkagelytkvclggladvgisipgdlsekfalpsvkiktdfpaistlg aqkagwsvsvgdffalgsgparalslkpaetyeeidykdeadlailtleadvlpgedvaqyiadecgvdvanvfllvaptaslvgsiqiagrv vengtykmleflkfdvkkvvhaagiapiapidpdglkamgktndavlfggrtyyvkseegddiaavaaqlpssaadgygkpffdvfkdagfd fyqidkgmfapaevvindlttgklykegfvnaellkksfgie |

FIG. 7A-1

**ORFs for cell surface proteins identified from *M. ruminantium*: Annotation.**

| ORF | Annotation |
| --- | --- |
| Contig40_gene_34 | hypothetical protein |
| Contig40_gene_35 | LemA family protein |
| Contig40_gene_39 | hypothetical protein |
| Contig40_gene_40 | hypothetical protein |
| Contig40_gene_41 | hypothetical protein |
| Contig40_gene_51 | adhesin-like protein |
| Contig40_gene_54 | hypothetical protein |
| Contig40_gene_63 | adhesin-like protein |
| Contig40_gene_70 | hypothetical protein |
| Contig40_gene_72 | hypothetical protein |
| Contig40_gene_75 | hypothetical protein |
| Contig40_gene_87 | adhesin-like protein |
| Contig40_gene_88 | adhesin-like protein |
| Contig40_gene_105 | adhesin-like protein |
| Contig40_gene_119 | molybdopterin-guanine dinucleotide biosynthesis protein A MobA |
| Contig40_gene_141 | adhesin-like protein |
| Contig40_gene_155 | adhesin-like protein |
| Contig40_gene_156 | adhesin-like protein |
| Contig40_gene_157 | adhesin-like protein |
| Contig40_gene_158 | adhesin-like protein |
| Contig40_gene_161 | hypothetical protein |
| Contig40_gene_163 | 2-dehydropantoate 2-reductase PanE |
| Contig40_gene_164 | hypothetical protein |
| Contig40_gene_165 | hypothetical protein |
| Contig40_gene_169 | hypothetical protein |
| Contig40_gene_179 | hypothetical protein |
| Contig40_gene_187 | hypothetical protein |
| Contig40_gene_203 | adhesin-like protein |
| Contig40_gene_221 | adhesin-like protein |
| Contig40_gene_228 | SNase domain-containing protein |
| Contig40_gene_231 | adhesin-like protein |
| Contig40_gene_232 | adhesin-like protein with cysteine protease domain |
| Contig40_gene_248 | hypothetical protein |
| Contig40_gene_251 | hypothetical protein |
| Contig40_gene_252 | hypothetical protein |
| Contig40_gene_260 | hypothetical protein |
| Contig40_gene_261 | adhesin-like protein |
| Contig40_gene_269 | adhesin-like protein |
| Contig40_gene_296 | hypothetical protein |
| Contig40_gene_297 | hypothetical protein |
| Contig40_gene_306 | UDP-glucose pyrophosphorylase GalU |
| Contig40_gene_310 | adhesin-like protein |
| Contig40_gene_317 | geranylgeranyl reductase family protein |
| Contig40_gene_342 | adhesin-like protein with transglutaminase domain |
| Contig40_gene_344 | adhesin-like protein with transglutaminase domain |
| Contig40_gene_346 | adhesin-like protein |
| Contig40_gene_349 | hypothetical protein |

FIG. 7A-2

| | |
|---|---|
| Contig40_gene_352 | adhesin-like protein |
| Contig40_gene_359 | adhesin-like protein |
| Contig40_gene_411 | hypothetical protein |
| Contig40_gene_431 | signal peptidase I |
| Contig40_gene_448 | peptidase S49 family |
| Contig40_gene_466 | hypothetical protein |
| Contig40_gene_483 | ABC transporter substrate-binding protein |
| Contig40_gene_501 | adhesin-like protein |
| Contig40_gene_553 | ABC transporter substrate-binding protein |
| Contig40_gene_636 | hypothetical protein |
| Contig40_gene_721 | ABC transporter substrate-binding protein |
| Contig40_gene_730 | CBS domain-containing protein |
| Contig40_gene_732 | hypothetical protein |
| Contig40_gene_733 | hypothetical protein |
| Contig40_gene_749 | hypothetical protein |
| Contig40_gene_750 | adhesin-like protein |
| Contig40_gene_762 | DGC domain-containing protein |
| Contig40_gene_766 | dihydroorotate dehydrogenase PyrD |
| Contig40_gene_769 | coenzyme A biosynthesis bifunctional protein CoaBC |
| Contig40_gene_776 | adhesin-like protein |
| Contig40_gene_787 | energy-converting hydrogenase B subunit H EhbH |
| Contig40_gene_815 | hypothetical protein |
| Contig40_gene_824 | adhesin-like protein |
| Contig40_gene_828 | cobaltochelatase CobN subunit |
| Contig40_gene_829 | adhesin-like protein |
| Contig40_gene_830 | adhesin-like protein |
| Contig40_gene_834 | adhesin-like protein |
| Contig40_gene_835 | adhesin-like protein |
| Contig40_gene_836 | adhesin-like protein |
| Contig40_gene_837 | adhesin-like protein |
| Contig40_gene_841 | adhesin-like protein |
| Contig40_gene_847 | hypothetical protein |
| Contig40_gene_848 | hypothetical protein |
| Contig40_gene_867 | hypothetical protein |
| Contig40_gene_872 | adhesin-like protein |
| Contig40_gene_900 | signal peptidase I |
| Contig40_gene_906 | hypothetical protein |
| Contig40_gene_909 | ribonuclease |
| Contig40_gene_917 | adhesin-like protein |
| Contig40_gene_930 | adhesin-like protein |
| Contig40_gene_964 | adhesin-like protein |
| Contig40_gene_975 | glycerol-3-phosphate dehydrogenase (NAD) |
| Contig40_gene_976 | adhesin-like protein |
| Contig40_gene_982 | hypothetical protein |
| Contig40_gene_996 | hypothetical protein |
| Contig40_gene_1008 | adhesin-like protein |
| Contig40_gene_1021 | adhesin-like protein with cysteine protease domain |
| Contig40_gene_1025 | adhesin-like protein |
| Contig40_gene_1026 | adhesin-like protein with cysteine protease domain |
| Contig40_gene_1029 | hypothetical protein |

FIG. 7A-3

| | |
|---|---|
| Contig40_gene_1036 | hypothetical protein |
| Contig40_gene_1037 | adhesin-like protein |
| Contig40_gene_1038 | adhesin-like protein |
| Contig40_gene_1039 | adhesin-like protein |
| Contig40_gene_1042 | adhesin-like protein |
| Contig40_gene_1044 | adhesin-like protein |
| Contig40_gene_1054 | adhesin-like protein |
| Contig40_gene_1073 | adhesin-like protein |
| Contig40_gene_1074 | adhesin-like protein |
| Contig40_gene_1084 | adhesin-like protein |
| Contig40_gene_1088 | adhesin-like protein |
| Contig40_gene_1089 | adhesin-like protein |
| Contig40_gene_1093 | adhesin-like protein |
| Contig40_gene_1096 | adhesin-like protein |
| Contig40_gene_1097 | adhesin-like protein |
| Contig40_gene_1098 | adhesin-like protein |
| Contig40_gene_1099 | adhesin-like protein |
| Contig40_gene_1100 | adhesin-like protein |
| Contig40_gene_1104 | adhesin-like protein |
| Contig40_gene_1106 | hypothetical protein |
| Contig40_gene_1158 | adhesin-like protein with cysteine protease domain |
| Contig40_gene_1176 | adhesin-like protein |
| Contig40_gene_1198 | protein disulfide-isomerase thioredoxin-related |
| Contig40_gene_1215 | molybdate ABC transporter substrate-binding protein ModA |
| Contig40_gene_1238 | adhesin-like protein with cysteine protease domain |
| Contig40_gene_1247 | hypothetical protein |
| Contig40_gene_1254 | hypothetical protein |
| Contig40_gene_1264 | adhesin-like protein |
| Contig40_gene_1270 | ABC transporter substrate-binding protein |
| Contig40_gene_1274 | adhesin-like protein |
| Contig40_gene_1296 | hypothetical protein |
| Contig40_gene_1331 | hypothetical protein |
| Contig40_gene_1350 | adhesin-like protein |
| Contig40_gene_1351 | adhesin-like protein |
| Contig40_gene_1355 | adhesin-like protein |
| Contig40_gene_1362 | adhesin-like protein |
| Contig40_gene_1363 | adhesin-like protein |
| Contig40_gene_1364 | adhesin-like protein |
| Contig40_gene_1367 | tungsten formylmethanofuran dehydrogenase subunit G FwdG |
| Contig45_gene_8 | conserved hypothetical protein |
| Contig45_gene_20 | conserved hypothetical secreted protein |
| Contig45_gene_21 | conserved hypothetical protein |
| Contig45_gene_30 | hypothetical secreted protein |
| Contig45_gene_35 | conserved hypothetical secreted protein |
| Contig45_gene_36 | peptidase C39 family |
| Contig45_gene_60 | poly-gamma-glutamate biosynthesis protein |
| Contig45_gene_64 | UDP-glucose/GDP-mannose dehydrogenase |
| Contig45_gene_89 | UDP-glucose/GDP-mannose dehydrogenase |
| Contig45_gene_91 | adhesin-like protein |
| Contig45_gene_93 | adhesin-like protein |

FIG. 7A-4

| | |
|---|---|
| Contig45_gene_100 | hypothetical protein |
| Contig45_gene_106 | hypothetical protein |
| Contig45_gene_116 | conserved hypothetical protein |
| Contig45_gene_142 | adhesin-like protein |
| Contig45_gene_159 | homoserine dehydrogenase |
| Contig47_gene_98 | adhesin-like protein |
| Contig47_gene_7 | adhesin-like protein with cysteine protease domain |
| Contig47_gene_8 | adhesin-like protein with cysteine protease domain |
| Contig47_gene_13 | hypothetical protein |
| Contig47_gene_57 | adhesin-like protein with cysteine protease domain |
| Contig47_gene_60 | hypothetical protein |
| Contig47_gene_62 | adhesin-like protein |
| Contig47_gene_4 | adhesin-like protein |
| Contig47_gene_125 | hypothetical protein |
| Contig47_gene_140 | hypothetical protein |
| Contig47_gene_146 | hypothetical protein |
| Contig47_gene_160 | hypothetical protein |
| Contig47_gene_197 | hypothetical protein |
| Contig47_gene_208 | hypothetical protein |
| Contig47_gene_253 | cobalt ABC transporter permease protein |
| Contig47_gene_269 | coenzyme F420-dependent N(5),N(10)-methenyltetrahydromethanopterin reductase Hmd |
| Contig47_gene_304 | adhesin-like protein |
| Contig47_gene_306 | hydrolase alpha/beta fold family |
| Contig47_gene_309 | hypothetical protein |
| Contig47_gene_348 | adhesin-like protein |
| Contig47_gene_349 | adhesin-like protein |
| Contig47_gene_353 | OB fold nucleic acid binding domain-containing protein |
| Contig47_gene_356 | short-chain dehydrogenase/reductase family protein |
| Contig47_gene_375 | hypothetical protein |
| Contig47_gene_380 | adhesin-like protein |
| Contig47_gene_381 | adhesin-like protein |
| Contig47_gene_382 | adhesin-like protein |
| Contig47_gene_383 | adhesin-like protein |
| Contig47_gene_391 | hypothetical protein |
| Contig49_gene_3 | hypothetical protein |
| Contig49_gene_4 | conserved hypothetical protein |
| Contig49_gene_12 | adhesin-like protein |
| Contig49_gene_25 | adhesin-like protein with transglutaminase domain |
| Contig49_gene_29 | adhesin-like protein with transglutaminase domain |
| Contig49_gene_40 | adhesin-like protein with cysteine protease domain |
| Contig49_gene_43 | adhesin-like protein with cysteine protease domain |
| Contig49_gene_44 | adhesin-like protein with cysteine protease domain |
| Contig49_gene_81 | adhesin-like protein |
| Contig49_gene_96 | adhesin-like protein |
| Contig49_gene_128 | hypothetical protein |
| Contig49_gene_152 | ABC transporter substrate-binding protein |
| Contig49_gene_167 | adhesin-like protein |
| Contig49_gene_168 | adhesin-like protein |
| Contig49_gene_172 | conserved hypothetical protein |
| Contig49_gene_175 | adhesin-like protein |

FIG. 7A-5

| Contig49_gene_180 | hypothetical protein |
|---|---|
| Contig49_gene_181 | adhesin-like protein |
| Contig49_gene_182 | adhesin-like protein |
| Contig49_gene_183 | adhesin-like protein |
| Contig49_gene_184 | adhesin-like protein |
| Contig49_gene_194 | hypothetical secreted protein |
| Contig49_gene_208 | ABC transporter substrate-binding protein |
| Contig49_gene_226 | conserved hypothetical secreted protein |
| Contig49_gene_239 | adhesin-like protein |
| Contig49_gene_240 | adhesin-like protein |
| Contig49_gene_246 | conserved hypothetical |
| Contig49_gene_248 | adhesin-like protein |
| Contig55_gene_2 | hypothetical protein |
| Contig55_gene_3 | hypothetical protein |
| Contig55_gene_7 | adhesin-like protein |
| Contig55_gene_13 | hypothetical secreted protein |
| Contig55_gene_23 | conserved hypothetical secreted protein |
| Contig55_gene_40 | hypothetical secreted protein |
| Contig55_gene_45 | conserved hypothetical protein |

FIG. 7B-1

**ORFs for cell surface proteins identified from *M. ruminantium*: Nucleotide sequences.**

| ORF | SEQ ID No. | Nucleotide sequence |
|---|---|---|
| Contig40_gene_34 | 737 | atggtccttgccttaagcataatcctactcagttcaattgcagcagcatctgcagaggattattctttaaccaatgccaaaatagatatggtaat ccaggatgacggattagtctttgtggatgaggcaatcacctaccattttataagaccatgaatggcgtctataggtacattccaatcaataact ttaacatggaagatttgctgtagacgttgatggcgcatattatgaactggagggtaatgatgacgactctcaaatagaggctaaggtctatctc tataaggataaggataaaaccgaaaagatcgaccctggtacagatgttacagtccattataagtactacatgagcgatctccttgatgtaaaggg agacaatgcagtattgaactattatctattgggagaagattgggaggttgacttagaggagattgaagcaaacgtccatttccctgaaaagaagg agcttgattacgagcttgttccaagcggcagtgctgaaggcaagtggtctggagacacattgaccattactggagagaatattaatgctggagat ggtcttgcattaatcgttgaaatcccattagatgagttcgcttcaggcttttcaaatgctgtccacaatgacactgatgatgatgatgacataga taatgatatcgataatgataaggatgatttaaaggacttgacaaaggctaagcagatttaa |
| Contig40_gene_35 | 738 | atgagtacttttattttagtcataataatacttggtattattttaataatcgcaggaataatcgtagctctctataatggccttgtgactgcaag aaacaaggtaaagaatgcatgggctcaaattgatgtccaattaaacagaagagcagatttaattcctaacttagtagaaactgtaaaaggctatg ccggtcatgaaaaatctgtatttgaagatgtcactgctgcaagggcaggattgatgaatgcaaacggagttaaggaaatcggtgaagctaacaac caattaacaaacaccttaaagaccttatttgcagttgctgaaaactatcctgagcttaaagccaatgaaaacttcaaggaattgcaagctcaatt agctgaaagcgaagacaagattgcatattcaagacagttctataatgacactgtattgatgtacaataacaaatgccaaaccttcccaagcaatt tgattgcaggcctcttcggattcaaggaagctgacttctttgaagctgcaggtgaagctagatctgtacctaaagtcgaattctaa |
| Contig40_gene_39 | 739 | atggataataaaaaaatatttgttattgtagctttggctcttttagctatcgttgcagtaggatctgttagcgctcttgatttaggtttccttgg aggaaatgacgatcaagacactgctgctgaagatagcgatgccaagacaactactattaaaggaattgaatttaacattccagacggatatgtta aagcagaaaattacaccttagatggtgaaacaagatcaagcggaagtatagactataaggtatatcaagaaggttatgaaaaaggcgctaccgat gcaatccttttcttaattggagattatccaactgacttaactgacgatatgcttgaacaaatgaatttaggtgaaccaaagaccattaacggtca tgacggttacataaccacttccaacgaaggcggagacacattcactgtattcttctatgcagaagatggtgacttagtcactgttactgtaacag acgacacccttcttgaagaaattattaaatag |
| Contig40_gene_40 | 740 | atgaacaataaaaaaatatttgccattgcagctttagccattatagctatcgtagcagtaggatcagtcagtgcttttgatttaaatttctttgg aggagatgacaagcaaaccactactcttggaggaattgaattcaatatcccagagggatatgaaatagtagataactacactatagtaaatgaaa ctctacatgatggtgatgatgaatacattgtaaacagccagtattatgaaaacgatgatggggattcactagagctctatacttcagattatcag gatgatatggaagactatattttaaaaatactgactaaaggggatgaaaaaccattaacggtcgaaaaggttatataaattctgaagacggatt tacaatgttcagttttgtggatgatggtaatttaggttttgttactgtttcagatgaaagcatacttgaggaggtagttaaataa |
| Contig40_gene_41 | 741 | atgaatgctaaaaactaactattctagcagccttagctattctcgctatcgttgcagtaggctcagtaagtgcttttgacttaaatttccttgg aggagacgacagctcaaccactactgtaggaggaattgaattcaatatcccagagggatatgagataaatgatacatacactatagaaaatcaaa ctagaaccagcagcggaggcaatgaatacattgtaaatcaggaaggctatggaaactccgacggtgaggaactattgttcttagttggacattat gatactgatatcaccaatgaaatgctttccgcaatgaaagttggtgatgaaaaaccattaacggccaagaaggttttataacttccgatgatgt atacactgtattctcttttgctaaagatggtgaattggttacagtaaccgtttcagatgaaagtgcccttgaaagcataatcaaatag |

FIG. 7B-2

| | | |
|---|---|---|
| Contig40_gene_51 | 742 | atgattgctgtgttttattaacatttcaactgttagtgcaattgatgatggaaatctaactgcttcagttaatcattagatgctccca ttcagatcagtctgccattatttcacagtctgaatctcgaaacaaattaaatgcaaataattctagagttttctagtggagttatgatt gtgtagaaactatgaattgtctaattgagaattgtctcttagatctgtaaatctagagattcttaaatctgataaacatcttaaatctgatcta aattctattgattcagatgagtattctcttagatcaagaataaaaatcttttaagttccaatgctctaggagcaggcacaagtactcttgcgattgcaa tgagaacttggagattcttagatcaagaggttcaacaatcagtgcccacaaacttatcgagacacagctcattatccagatcaa ccatgataaacgtgctctgctacaaagtgcacgattcgatgcagattcatattctattctattagaagatgcatcaccacgtcaataa accatagtcacacatcatgaatcaagtaccaactgttccgtattatttcttggaaatgatcctcaataatattcacaaatgaagaaaacagatataagccagatgaagcagatcatagaagc aactgttattctccatacagtaacatcaagtacttctcacttcatcaacaatgaagcaagcgaaccgaacaatgttacggtgctgcattgcatatgtggta acctgtgggttgctgtaaacatcaagtatattttcacaaactgcaatttcacaaatgaaagacagatatggaagtaccgcatatgtggta gcagaatgcactgtgaaaaactgcaatttcatcaacaatgaagcaagcgaaccgaacaatgttacggtgctgcattgcagatagggcttc atcctcagtccatcagtctgcttaaaatgaaggatatgtggtaaattgcaccttcataaacatattgcttatcaccaccatagct |
| Contig40_gene_54 | 743 | atgattattgccataatcttcatgtataatagggtccgcaataagagatcaactcctgcaacctttgcattatgggtggttgttggatggtggt cttattcttttgcttttcgccctaaaatagtgatccctaaattggcataagttctccaagtctattatgatcagaggattttg cagtaatcgcatatgctgattagattttttatattaaaatcgacaatcagatatgactgatttggttaggaaatgtctataagaaaat gaaatacaattgatgaagaaaatgatgaatag |
| Contig40_gene_63 | 744 | atgaataaggttcaattgtcctccataatcttagtataatcgcttagtcaatgctttggctgtagtcgaaatgatgatattttaaatat taatgtcactgacacccagatagtaagtgttaattgatgatcttaaacctttgatttactttctcagaggcatgatcattaatgatgggt taagctctgatgatgaaactgcaggttccaactcttaaacgactcagattttgattcatcagatgattatcagaaaggatagttgga gattctaaagagatcactaaactcaggataattccaaagatgatttcaaacagacagttctaaactagaatatcagaatatatatatgggaaataacaga ttcttcataattcaagctactttgacctactacaaagaatattaacattccccctatccaagatgggccattaggagaaccataaatgtccaaggaagcaatgctcaaatctcaaattcaaggtcatatgtctgaaatgtct ctgaaagatattctcaatctgatctttccaatttcaagttgtaaacaagaaagagtcgggtcttcccaatcattctttctatatatcttcaaatagcttagtatggcaaatctcagagga agccccgtgatatatcacagcagcaacagcgttgattctaacaatcttgatgtagaacaattgtctccaacatctctatgagaaactacatcaggattatcaacaat agtcatgataatctgacaatcaaaacaaccgatgaagcacgattatgtgaaactacatagactatcaaacaaatcaatcaatcagtatttatgccctgataatatcaataatgagacatcaactgaaactacatagactatcaaaacataattatttcac tagtcgaacggtacatatgattcctactgcattgctattgtaattgcaaattacaagtctattgcatgcaactgccctttcagcaactgacaatgtattgtaat |
| Contig40_gene_70 | 745 | atgagaaagaaataattctatattgctattatgcaactctcagttattccaactgcctttcagcaactgacaatgtattgtaat aacttacggcgaaactacatacaattacaatatagtcatttgcttgtgataattacttttgcaagcaaggatattacttgcaagatgatgtcatgcgcttggtg gtgaagtgattactgcagctgacgtaaatgcacagttgaagtggacactcctgaatggcaattccattacaacaaatcctccaatgtatgcctctgccttaagtcagcggg gatatgaccccaaacaatgttcttagtaaggacactcctgtaactgctactggagcagcagatcaaatttatacagaagcttgccattcaacataccaattgggaatctacagagatcctgtgccttgcaggaatcatcatgaactgttaatgaggaagctctgaa aattacaagcggacatgtctatgtaagcaagcagcaacgatcaaatttatacagaagcttgccattacagagatcctgtgccttgcaggaatcatcatgaactgttaatgaggaagctctgaa atgttgaaattccagaaattggtgatgatgatgtaaaggaagaggttcaagaagaggttaaaaggaacctttgtaaaacctggcaattgttgacaataataaatgactacag gaattatccaaattgtggatgatgtaaaggaagaggttcaagaacacttgaaaaccttgcagataccattcaacagctccaagaagttcagatgatgcaaaacgct cacaacctataatatcaacatttccgatagcgacattgaaagaagcgacattgaaaaaccttgcagataccattcaacagctccaagaagttcagatgatgcaaaacgct ataaggaacaattgatgatgctgtgttaacaataccacatcagattctccattgatgtattctcaatgctattagtattttaagtatttcagt taa |
| Contig40_gene_72 | 746 | atgaataaaaaagatttaattattataactatttttatagcattcactcattaacacttgttttatttaaatgataatctctcagcagc agacaatgctccaaaggtccaaaggatatagcaactaactcgtgggtcgcttcaatgctcttgactactattgactatatatatatcaattttaaatcagt |

FIG. 7B-3

| | |
|---|---|
| Contig40_gene_75 | 747 | atgtaaataggctaagctacgctcatttaaaaggaaacaattttcctaatatcagcttgataagcattccacaaagtttaacagaacctt<br>ttggatggattcagttcgttcctttacaataaatggaatcaatctgaataagaaaaccatctcatgtaactgattctatgcaaagaagaatggcgt<br>aaagcatttgtctttgcaacagaggatga |
| Contig40_gene_87 | 748 | atgatggtcattctactaataacactccttctgttcctatcctctcactaacaattgattattcaaatgatgtcataaactctataagcacaa<br>gaatgaactgtcaaaaataactgattctgttctgctactatagcggaaaggttctaaaaaggtggtcttgcttgatttcaatcaagatt<br>tttctgttcgattaccaacaatgcaaaaggagattgcaaatatgctgatttgaattgtcagataataaccacaaagagatatctagcgaatat<br>gattatatagtctaaatacaaatattcagttttcaaaggtttcaataagatttttagttgattgaatggatgaggataccgactaatcaggctctc<br>taagttaaattaa |
| Contig40_gene_88 | 749 | ttgatatctttatcaagcgtttcagctataaatacaaatgattcatctattcaagataatgatggagtttatccattcaagactcaattgatgaaat<br>ttcccaatttgatgaatcagaacaattaaatatcaataaggattccaccagaatccaatttaatcaagaattatctaatgattctaaagaca<br>tatctgcagattccaatcaagactcaagtctttgaaattggatttgagaattatgatttcaaatacaacaaagagctcttattcaaatgccctaaaggactca<br>aatgtcataaatgttacaggaagcacatttcaagatattcaagatgctatagataggcaaatgatgggacatccttatctcaagtcataca<br>attccatgggaatggacgcatcagcatcaataagcgcatgtcacattaatcaatattcacttgactatggggaaatattgacaataatggcaat<br>acttaaagtccagaatatatattgatggaacaaactgcaattgtaaactgctccttaaggggaatcatgcttggctgggggagccatttccaatc<br>ggagggccatatatttgatggaacaaactgcaattgtaaactgctccttaaggggaatcatgcttggctgggggagccatttccaatc<br>aaacaattccaaattgatgacctttatgtggtgctgcaaatttgtagagaacaatggcccaaattgggcggaattaccacatgggatcgatcaattgcc<br>ttgtttcaaattgcagcttttcataataacaatgccacagggagggccagtgcaagtttaaaccattttgacgtttccatagcc<br>ttggaaaattccacttttgccaaaattctgggggccatcatgcgcagttcaagtttaaaaccattttgacgtttcctatgcc<br>catagataactatgccaaaattctgggggcgccatgcgcagttcaagtttaaaaccattttgacgtttcctatgcc |
| Contig40_gene_105 | 750 | ttggtatctttatcaagcgtttcagctgcatgattaattcaagactatgaagattaactattcatatgatgattaatcattca<br>agactcttttaattgaagattaattcaagatgtttctctaatacagagttaaaaactcaagattcatcttattgacaatctaaaagagactataatc<br>aaacagaatcaatagatgacaccattaaccgttaaggagaattcaatttatcaagattaactttaagtctccaagaagaaatataaggattccaatttaaaaagc<br>tcaagactgaaatagatgacaccataaccgttaaggagaataacattttaagtgccttgagaacaaatttatatcactgagtttgatgctccctaccatagtgccttaccataagtggcagttctcaattcg<br>agcgaaaatatgtttaagggagataattattatgccttgagcatctttcaatatcactgcagataatgttacaagcatatattcaattcaattacaat<br>gcagccaatatataaatttaatgcactacatagttcccgtatttcccgtatttcaatatcactgcagataatgttacaagcaaatattcaattcaattaccaat<br>ggctacgtagtaggtgaaccgagaggagtgtcaatttacttgttcaatttacttggtcaatttactttggttgcaattacttatttatttttgatacgtaatttttggtatttcgaataatgctggt<br>ctctatgatggcgagcattattgaaggaggtgcagcttgacgacctctctgagtttgctcagtttcgaataccaactctcaaaataccaatctaaaaaatgtactttgattcccacttttctaaataatgatgctccagaggatgggg<br>ggcatggccaatggtgcagcttgacgacctctcgtttgtagtgctaaaatgggtatgaacttatttcttcttattgtttcttaaaaataattctgcag<br>tgggtcagtataactctataacatggtatgaaccttatttcttcttattgtttccttaaaaataattctgcag |
| | | atgaatattaatttaaaaaaaatcacattcttatgttttggttttctaatcggtttgatctcattcaattcaatcagcgctaatgattagg<br>cactgtattggaggataatgataataacggattaaatgactaaatgatgattttataaatcagatgattcagaattcagatagtaataaaag<br>aagcaattcttaatttaaaagttctaattgcaggatgaatctacatctcttgattctaattctgtagttctaattctaattctaatagttccgtt<br>gcttctagttctaatagttctgcaagttctaattctgcaagttctactagttctgcaagttctaattctactaattctactaatatttctgtaagttc<br>taattctactaattctaatagtctgcaagttctaaactgattaaaacgattatcctcaagaggaaagtgccttaatgagttcttaaatgcaatcaaaaca<br>ataactccagttgcatccaaactacaataaattatcctcaaactatctcacttaaataatctacttaacatattacaatagatggtaggaatcattc<br>actactaaggcacaattgtttcaaacatgtttaagaccttgtcattacaacttgtctttacaaactatcacatctgaataagaatt |

FIG. 7B-4

| | | |
|---|---|---|
| | | taaggcaatacttaactctgagaattgactgtcctcaattgccaattcaatgatttcatatcttacaaacgctcagctatctataacagc<br>aaaagcttaccgttcaaggactaagttaataacaattatgtcaataacgcggagggccatctatagcacaggaaccctgactataaacaa<br>ttcctcattcaacaaaatcatgcagcaaaatgtggagccatctattccactttaaacctaatcctaaacc |
| Contig40_<br>gene_119 | 751 | |
| Contig40_<br>gene_141 | 752 | atgaataatcaaaataagtattcttgcatagtttttagctgaggcatgagcagaagaatgggtcaggataaggtcatgattatttacaataa<br>acctatgatttacacatactgaaggctaaaccataagataaatgatgctgtaattgtttaaataatgcagaaaggatttcaatttatagaa<br>atcttctaaatcaatatgcagacatgatatagaagaaaattttgattatgattgagcttcattgaggatgagtcaagtcaaaagccctatt<br>tcagggtcatgactgattaaagaataaaacagattatgcactagtatgcctttgcgactctccattatatagtggagaatatatagaaag<br>catgttttgggattcttgatgaaatcctttagcagatgccataatcccttttcatattaagtcaaataaggataagttcaaggacaatgaggagt<br>ttaactttaaaatgcagatgaaatgtcttagagatgaagatacagaattcagagcctttgcattcaattatataaaaggacaatctgaataat<br>ataaaatctctttagatgatgacagcttgtatgtgaaatctctttatcaggctcttaaaagccctgttttttattgaagtggataataaggtttt<br>atttgatgatgacttaaaatctaaataacaagaggatattgataatttaaagttaaaatag |
| Contig40_<br>gene_155 | 753 | atggtttttcgataagttgaaaatgcacttgaatcaggaaataaatctcatgataagagggaatctcaaaagaatctgataagcgattcagataa<br>tccaagagagattctcttcagataataaaaataggaattctcttccagataataacaaatagaaattcttcagataacaataatgttcgaaatt<br>tcaaatatctgatgatctaatccatagcgccaaaaggatattgttctggattgcgatattgttctagctgatagtgaaattgaatcttacaa<br>agaggaatagatatcggcggagtaatataaccctgatgggaatgacatgtggtgatgaagaaataaggcgaaatattaaggtttcatc<br>taaaaccttgccattaaaaattctagaattgaaattgatatagtgacttgattcaatcatagatgtgttttcaaaaggcggttgcattat<br>ccaattgcagctttttttaaaaattccaatgagtccataggatattttggcgataatctggttttgtataggaagcataatacgaaatatgggggag<br>ctgaccattcaccattgccaattgccatataagaaacaactcttccagggacaatctttccaggggagcaatcttttaatgaaggttgctcaagcttctcaagattggaacccttaatatctcgattcaat<br>tttgaataataatctctctcttttagagacgggggcaatcttttaagaggacaatcttaagacaatttgctcaagctcctttgataaaatagcttccttgataaatagctgaggccgcaaatcagctaat<br>ataaacgggaggtgcaatccacagattcaatcctgttttaaaggatatgcattccagatttgaaatatagtaaaagatcagattgaaaagggaaaatc<br>gacattcaaacagattcaatcttgttttaaaggatatgcattccagatttgctccattaaataatgatgagaaaagtttttacttcc<br>ctttgatattgataataaggaggtataatcgaatttgctccattaaataatgatgagaaaagtttttacttcc |
| Contig40_<br>gene_156 | 754 | gtggaagttgaagggataaaatgaattcaaggaatttgaagaattaataaatagcggagtaaaggagattctctaaatgaagataagtttt<br>ggaggataagacacaagcgcctattgaaatcaagacagatgcgttggtcattgatggaaaaaaccatatcatcgatgaaataacaagcttcaa<br>tattatatataaaagcctctaaatcacttcaaaaacatcatatttaaaaacgattccagaggactctcagaggacttagcggtgccataactaactattcc<br>aatgacttaaggtagaacactgcactgccattcatagataactctacagaaaatctcatagaggactccagaggactgactgtgagcttgtatggggagccatctacaatggagaaaactc<br>taaattgactgtgaaaagtccatttaaggaaaatgattcagactttggaggggccattttttattgattcagattcaacagtaagataaata<br>atcctgtatttgagctcaacatctctgaattcgatgaggagccattacaataaggagaattgatcataggacaaatcatattcaatcagaac<br>atggcctttaaggaggagccatcttaatgaaacagttgactaaaacagttctcattttgactaaaaacaataaagcaagcgatgaaatgacat<br>acagacagaaatgaggatattccatatcaaactctctttgtgagttttataaataatgataactattga |

FIG. 7B-5

| | | |
|---|---|---|
| Contig40_gene_157 | 755 | gattgcaatttgaagataatgggtggtgagcgcttatgattcaagcagcagtgaatcgattcaaaataaaaatggcattataaccatgacaattg<br>ctgctttaatacagagagtccattccatcgagctttgattttgtttaatcaatagttccagattttatcatcatccgaaaatcttgaaa<br>ttcaaggttcgattttcaatcgagctttgtaggattattatatgggaagaaacaataccaataaaagtggaattagatgaaagtactgatagc<br>tcagatattggtgattttaatcaatgagtataagaagacatacaatctcgatacaaagaagttggcttcatcttaaaaagaatattattgaatc<br>cattaatgatttgatttcggataacttaattagaggatttcaattagcgatattaattatctgactata |
| Contig40_gene_158 | 756 | atgttatattatcgtgagcaggatgggccgattggagttggatcaaatttggaagcagaatacatatattgacgatttccatttaatatctt<br>gaagctctcttaagctatttgaaacaggtgatgaacagtcgttcgtcgaattcaatgcagaagatgttttatcttcaagttctcttccgatg<br>tcagagttgtgagagagtgatatatgaaagactattgattttgcaaatgattttatctgtgaaattgagaaagatggcttatgggcttt<br>tttccatccgaagaacaagtgatgaagactattatgaattgtggtgatttaatcgtcaaaatcaggacagaactattagataaggatctaataa<br>taaatgattgatataatttccacaatcttaa |
| Contig40_gene_161 | 757 | atggggattatatgaatacggattatctctaaggaatttgaagagttgaatcacactacagaaagcctatttgattttggaatctctggctttt<br>aatcatttaaagcagaacaatctgaccagctgagtgagctaagcaatcctgatgatatcttatatctaagtcagacttccggtgtaagg<br>aaaattacactgaattttagtaatttaaaaatgaaaagtgcttatcctacagaatttatgtccgcccaatttgatgggcagctgttttttc<br>aagaggcagatctaattactaaactgtctactgcattcattgtgctttcctatgaataaactggacatctccagactgatctcttaaa<br>gaatatgttttgccaattgcctttcattgaatatgcataattttgagaattggacactccacatctttgggaatgtttgttgcct<br>gctgcagcttaaagccatagatggatttagaatggaatggactttgagcctgcagaatatggactggaatcatgtttgagtcctgcatgtcctgaa<br>gacatttcattcctatctgactggacatgtcatgcaatgtgaaaacatcttttgaatgtttaggatgctataagcttaaaggatgcaagctgtt<br>gaattggaaatttaagaatctcaaaatcaggataggatgctaaaacctattgacgacactctatttgatgacgattcatatgcaggggtcttccaagctgtgatgtacgccccagactgtcc<br>atagcagtaggatatagcaagagatttagagaagattctgaaaagatttcagaagcttggaaagggcgctctttaaa<br>tccaaacttaaatgacacagagatttagagaagattttcagaagcaaggattgtgaaaggcctatgcaa |
| Contig40_gene_163 | 758 | atggaagatagaaaagcaaaattatcgttatgtcgttgtagtccttgcttttatctgcagcagcacagtcttctctctgactgcgcgtct<br>ttctgattgattcgtatcaaatgtaaaacactaatgaggatgccaataacaatggctataagaacagcagcgaagacaatattattctgactctg<br>acggacaatattcagttccgactcctatgacaattcaaatgaggctctgattttagatggctcttttcaagttcgacaattcagaa<br>tcaaactactattccaagctctgatgaagaacctgattttcttgcaagtctcataaggaattcataggtggcagttcaacacagacagttatta<br>tgactcctcctgattcaaactactactactgaggacacatcaaatgatatcttggaaatgattctcatatgatttaaatgaactctttacaa<br>aacagacaataagcttaatcagtgtttaattaa |
| Contig40_gene_163 | 758 | atgaacatactaatcaatgaactgagctatcggaatcggaatatcatgattcacaaggtgcaaatgtatctttcttgcaaggga<br>agagactgcaaatgcaatgaataagaaacggaattaaaagaaacaggcatatcaatcactattcattggttccagaatcattaagtctacacag<br>attacaaggatattccagatatttgacttttgtccttgtatcaagcaaaacaatagctaatgacgatataagcagaaagctaaacgaacac<br>agtccatcttaaaagaggatgctaaaataatcatatttcaaaacggcttttgcaaatgacgaaccatacttaagatttctttccaaaggaacaggt<br>ctactgtgcaaggatgtcattacaggttcattgacacgccgagtacatcagcgagtcactgtccatacagaagatacatacttgttctttc<br>aaaggatgatgacggcgagttcctatggctaaaatgcttataactgctcaatcatttcaaagatgacaatcatcaaagattcaggaatgttgaaaactgaa<br>gaactggataagttcctatgggctaaaatatgcttaattgatgaagctttatgaatttgaagtaatcaaggcatcaggatacaggaccaattggacagccag<br>aggagtatagggaagtcttcattcaagcttgttccagacacttatcacaagttcttccacattacaagacatttccaaaggcaaaagaca<br>gaatcgatacattaaatgaaaggtcattgaactggaaagtgtaagttgtgtaagtgtgaaataagcaaatttatatattataaaac<br>aatagagtctgaattttaa |

FIG. 7B-6

| | | |
|---|---|---|
| Contig40_gene_164 | 1375 | atgataataagtcactacaatctgtgttatctgttcttttgatagttctttttttatggattgttccctgattgacaaacagcaatgataacagtga caataatctaattattccacattagaactcagacttctcattttacaatagatattgaaaacgcacttattaagcgagaaggcaaatctaaaatggtgg attccattattccacattagaatcctatgagaatttacgattcaggctatgaggcctatgagatagaacttgacaatggctcttggtatata gtcagtctgtataaggtggattataaatactccatcgcgattggtatataagtagtgatgatgaggagaattgagaattttaagctttttaactagcattttcc tagcaaaggagagtattatgctacttttattaacattccaagctctgacgatcctccacttttgagatcctccacttttgagatccttaactagcattttcc attataatcattaa |
| Contig40_gene_165 | 759 | atgtctgtgttggtaaactgtaataacaactattattacttagtaactactgcattgttgtcgcaggttagcatgaacgatgcaat tcaaaattaatgactctgtaatggtcctgagacgcacttactgtatttacttacttgtgttattgtaaccattcttgcagttgttgtaa ccattatacttgctagaatagcagctaaaatggcgctaaaatggcgtagaattagaagaataa |
| Contig40_gene_169 | 760 | ttgaaatcagatagtaaacgggctaaattgccatattctctcaatcctgccttgggactgagcaatgttcagctgtatggactggaga cttgataagcggttcacttccgttaatcaatgagaaacagataagttgattgcttggacaatgacaatttctctccagcaagttgaatacagttt atgaagaaaaaaggttgtagaagtagttaatgacacatctgatgcaaacgatactgattccactccgaacatgcagattccaatacgaaagt gatgatacatccaaattcaaacaattcaaactaataacaataatcaaaacagcaatgcaatcaaaataacaatgccgagcctag ctctgaggatctgcaggtcagacagaaacagaggaatag |
| Contig40_gene_179 | 761 | atgattaatgaataatgacaagcagaaggttataactgcctttggcataatctctatttttgcagctgcttcagtccgtttgtagtcttgcc tatcttaggagttaa |
| Contig40_gene_187 | 762 | atgttaataagagatgtgttttagcataagcttattgctgttatctttgcatctatgtgcatagtttcagcagatgactctgagaggaag ctttaaggaattgctaaattagtgtccggcgataa |
| Contig40_gene_203 | 763 | atgaaaacaaatcttaaaaaacatcatattgcactgctgatggcactcatattttaattttatcgattggagccatctctgcaaatgatttaac atcagcagattcaaatgtagaatgtaaatatgaataatgatttaaacacaaatttggatagcaatgatgatataatcgccaattcaaaacagcaattcaattgatg ctgaaattgatgaagcaaatattcaaatgtcaaggagcagatgccaaggaaaagttaaagaaagcaattcattaatagaaacagcaattgaaaacgaaaatactgaa ggcaatacaaatagaagatgaaaattcaagcccttcaaataaatagcaaatgaaaaatgaaaaatatctaccaagctaccagaaacacag tttaacaatctatctaaaggactcaatctaaaatagtgaatcttgcatctgaaaaataaatatcctacaatgcaatatcctacaatgcaatatccaagcagcgaagattatgaatcatca attcaaagggctctgccctttcaacataagcgttccctatgaacaaaagatcaattcaattatttaaagcattatccaaatacaaaagccaatgaaggaaacatttcaaaaagctataaccactatagaatt gttgataagaacaatccattaaaaaatcctgaaaattcctatccagtttcagtgagatgcaaactatcaatcagaagcgaagatgaaagg ttagcttaaacattaattaaaaagcagcttacagttcaacagttgacgtttacaatttgacgtatgagcttctcagcagatgatgtcataactgaaggctctgcg atttgatgtataaattaaaagcagcttacagttcaacagttacacagatcatacagtcatacacagttctattaaaagatgacgaagg caaagcaatccatccgcaaaagttgccttgcctcaagatcaatgagtaagctccacaaaaacaacagacaagaacg |
| Contig40_gene_221 | 764 | ttgctctattgttagtgcaaacgatttgcaaacgattcaattgcattgacgattccattgacggagacagcagtaaatctaaattctattgaaattgaagacattcaagttga tctgtagaatgcagatgattagaaacagtcattaaatattgaatgaaaatgtcctaaggtatgatggaaatcagatgggaatccgattccgcaatgagaaatgtaaa ctcttcatcagttgcatgaaaatgaatcgatgtctcttcttctcaatttccaaatgaaggttgctactaattagaattgataacagtgctgat aggaaaaatgtcaagatttggcagttggtactgagactcggactgacaaagaaaatatgttccttatgcttatgatgctgaaaacactcaagtctatgacga attgctgaaggctttagagtgtatgtcagcatatgtcagccatactggccatacttcacaaggacatactgcaaggacatactgaaagtagaatcgggacttgaaagtcg gtgaagaaagtatttaaaatcgttacaaggtattacaaggcagttaacaaggcagttacagcagttacaagagcagttatggtgaaaagtgaagatacgatataatcgat ccggatgaatgttacgaggagaagaaatttgatgtgaagatgatgaagattttaacaagtaacatcatttgaaaaagttatacatcaaagaacattcaaaaagcagcgaagatcgat aggaaatccgatattttacttcttgtcttttaggtttacagttttgacagtttaggttttaaatactagaaaaaaatag |

FIG 7B-7

| | | |
|---|---|---|
| Contig40_gene_228 | 765 | atgaattccaaggaaatatctgttttatttcttatttaatattatcattagcatatatctctgcttcatttgcttatactggaactggatt<br>ttctcatgacattccattttcaaatactcaagccagtcagcaccatcgatgtattgatatccaaatacaatcagattgccatagcgaatcaaag<br>gaatatgtacttatgtgcagatgggacaccatcgatgttgaaggtgtcgtttggagagttcgttttgtagtgtcaatactccagagaacgtc<br>acagcatatatctgctccaagcgttttgttcaaagttctgtctgtagtagaacctgatgttgaataaggaagtcagcctgatgtagatgactctaagagaacgatagata<br>tggaagaacattggcggtggtcattgtagatgcaagaacctccactacaagctcatcctatgcttctgagatcatgtacattcctccaa<br>gtgagttctatccatatgactggttctacagtcgttctacagtcctctcgagactccacaagtcagctctcttcaaatagcgaggttcttattca<br>tcaagcagtttttacaagcggttctacaagtgactttcaatagcaggtcgatgcgataagtcaggttatgctccttgtaaggcatgtcaacctga<br>gaagatctcgataagaataggtgactttcaatagcaggtctgatgcgataagtcaggttatgctccttgtaaggcatgtcaacctga |
| Contig40_gene_231 | 766 | atgaagaaaatttaagcttaaaaatatttaatttatcattaatctttcctttgtattaagcataggatcttcattgcaacagaagattt<br>aaatacaacaggagataacaatctaatagatcgatccagcagacacattactctgatgaaaaagagataagctatcaaaagccattaatgt<br>ctgatgaaaactctaattcacagtattaggatccgatggtaaaagttatagttccaataatagtaaatcagagagttctttctatcatacgtcct<br>aacgaatctctattacagtattaggagggttaattgtcaagatttgcaagatgcaattgattatgctcagataattatacaatatctcaattg<br>taatatgttgggtgaaggaaaaccgattattgtattaaaaaattagaactattcatggccataaagagcttatgattcttataagttaaggcatat<br>ttttctgcatttgtcgtctgataatgtgccctgcttaactcaggagttcttttgatatgtgcctccttctcaaacatggacttatgttgattaaaagt<br>gatagtaaaacttggctgctataatacatcgatttgactcgcaatttaaatataagattgattatgctaatgatattgggg<br>ttgggctcctgctataaatgcttgaaacatggacattaataataacatttatgtcttatctcatcatttttgtcttgggaaaaaagattgagcat<br>aagttaagcgtatcagcagaatctggcgagaaggttggtaaaatctgaatgatgacgatctcctaatgtcattatgcaatattgaaggaatgtgtatttct<br>atgtgtggcctaaatgttttgcctaattgaatgaatgttaaaaatgctcactcatcatattgtgaaggcaaaaaga |
| Contig40_gene_232 | 767 | atgaaaaggaatatttattttattattttaatcagtatgagtttgtagtgcagcaaatgatgctgatgtctctta<br>tattgatgatgatgtttctgataatagtttttatttagaatatttagaaatggcattcgatatgatgatattgatatgatcgata<br>tgcttgaaaatgaaatcaaggagatggattgattgtcagatataatgatggatttctgtttccttgattaacataaatcattttgatgatagagcaaatcaattat<br>aatgagtattatgaagacggttatttctcttattgagaactatactctccttcgggttatgggatggtgtaattacactatttaaagatg<br>aaatccttaagtgaagaattctttaggatgcgatgcgaaaatcaggctatttgtttacgatgatataatagagagttttgtcagttcagttcggatataattaatattat<br>attattatttgcctcaaccgctctaggatgcgtgatgtgaacgctaactaaaagttcgtcatcaggttcaataaaagttctatgcttagacgatctaagaaaagttgtatatccttcc<br>ctgatgaagaattctaggatgcgtgatggcctggagaaagatagcgcaaaagtgcaatcaaaagtgcaatcaaaagtctcatagtccaagtcttatgatttgttaactcctagtgaaag<br>agtagtcaatcctgaaaaggaggaaggaggatcctccaaaagtgcaatcaaaagtgccaatggcctttagagtcacatctcttaaaactaacatcataccttcc<br>atcaggaaatactgctaattgctaattggcttttgcaaataatttgaagaaatgtgatgagtcctaataagatcttatgtgtggccctataaaatgaatcaagatcatataatctaatct<br>ccctcaatgtgatttctctagcatatctctattcgttgagtggccctataaatgaatcagataagatcatattaattctaact<br>gttaatgtctttagcatatctctattcgttgagtggccctataaatgaatcagatcatataatctaact |
| Contig40_gene_248 | 768 | atgaaaaaatgaaatgccagtatattatctcttaattgcatctgtattagctacttatgcattaatatttaatccagctgattgatagt<br>ctatgctatagctattgtatgcataccatttttagttcttttcatttgttctattaaccatgtctaaccatgtcttaaccaataaaagaagaagaaagaa<br>gagaagaaccattttacaggttattaa |
| Contig40_gene_251 | 769 | atgcctaaaattgcaaaattatggaataagctagcagaatctaacagaacattcctagctgtcttgctgtaatttttaggtctgtttcattgccgg<br>attccttaatcccatggggatctgaattgaatacagatcaaatctacactcgtccgcacctcaaagtcagcagtcgagtccgccatacg<br>ataggggagagggtttttagtctccaggcataacagagccccaatatcctgaaatgcagagatcttggctgataaactcatatgct<br>ccaatagcagagatgcctcaaggaaatcccatactttgaacaagtatcgttcatctccagtgtcttattgatgaaatcctttattac<br>agaggtttcgataacatccttgaatcctccattctagtgcattcatatcgcttcatgtgcttgcaatcggttcatgctcatcatgcttgcaatgatagagacaa |

FIG. 7B-8

| | | |
|---|---|---|
| | | aggatgaaagggatatttgctgaagatgtaaaagagccattgccagttctgacagactagccaatgaggttgaagaagcaatagaaaggctcgt gaaaacaagccaaaaaggagtttaggtga |
| Contig40_gene_252 | 770 | atgtttaatctggctattttggttttatttaggtttggcattagctatttttggaagcctgcaactgtatgggtcctggagtaaaggatccagt tattagaacaataaacacagaagttgcatccgtaggagttgcatttcattaattttacttgttatatttctacattgctctttgacattgattgca ctacaatcattgttaccttaatcttgtttagagctattctcgcttagaagatagggctagtgatgtataa |
| Contig40_gene_260 | 771 | ttgttcgctatagtaagcctatctgcagtcagcgcaagcgatgattttcaagttccttgctgatgactgcactctgatattcttgctattga cgatattgcacaaaaggacagttctcataaactgatggatgaagaggacattagtgttgaatttgaaattgatgatgggatgatgatactagct atgattcctactatgacgattctccagtgatgactggtcaaacatgaggattacgaccctgaattaattagtgaagatgctatattaactaaa atagaagtcttgaatgtcccatatgtgatgacaacatttcattcagatgataatggtgttgtagtatacaggccttccaataacctgatgttaa ttaggccttcaggattcctatgttatgatgtctattcattcttcacagatgaggatggtgttgatgacatgtattaaggttttcttgtcagttctgttaaggtgag atttctctattgtcatagatttttatgaggattgtgtgtgtttaatgattgattgatacatgtattaaggttttcttggtcagttctgttaaggaagt ccaactgttccagcttccaataaagattacaaaaacaggcacttattataatgataacagtattcaaagttttccaaggaattgcaaactatgcccttaaat cttatcaaatcaaaaaatcaatccacatttcaaatgtaagaagccacagtgaagactaattccaaagttccaaggaattgcaaactatgccctaaat ttgcacctgaaactattcgttacagccctacttgcattgtcaaccacttatgctctgaacagtatttccaaatcaaattgacaattccaagacaaaaagc gctccaggcacattaagcctactatttggtttcctgcattgtcaacactgattaagcagtattaagacagtgatcattaag cattggtggagttaagcttaacttgaagtatatactgtaaagtataagacagttacagtaacaaccggat |
| Contig40_gene_261 | 772 | ttggaagagaatccaattgattttaaggataattcaatcaattctaaagcctaaaggatagcgattacgagcatgcctctgatgagttgtctca agacttatacaatagaatcataaatgcaaagaaaatgaaataatattaacgagcctgaacctataagatacacaagtccatcttacaaaaaa acataactctgcaaggaactgcgacccaagagaagtgattatagacgttgagcaattggaagtgtcttttcataaatgataaatgtcaca gctcaatttttacaatttaactataacactgtctttgaatataaccaatgggtggagctatccaattatgaaatgaaaccaatagagttattatataaaca tatcttcataaatacactgctttgaatataaccaatgggtggagctatccaattatgaaatgaaaccaatagagttattatataaaca actcattattttattggaaaccatcagatcatgatgggagtccgttacaacatgcatgtgagatttccgatatctataattctgtattcattaat aattcagctgtaagggatgcgcgagcaatccgtggctaagcgttatggctagacagatgcatattttctaaacaacactgcaggaacaaatgcggtgctgtaa tggtttccggaagcgctattatagctggctggaacatgcattttctaaacacaccgagaaacaggaggttcctctatatcagcagcctatgttt gatgcaaaacgtcataaattgacaaacgatttggagacgaggaccctagcaggccctgatgtgttgacccta attattattctccctaatttcaacataacgattggggagacgaggaccctagcaggccctgatgtgttgaccta |
| Contig40_gene_269 | 773 | atgaaaagaagatataaagtttatttctattggccatcttaactatcttaagcattcagctagcgaattggcttagatgacaa taatgcaatagatgagaatgatggattttaaaattaagcaagacataatgtctgaaaagataatctctgataatgagatgcagattcaaataatg gaatgatgtgaatacagactcatccgatgaagtaaatgaggataatgtaatagaacaaaatacagacactgatacagttgatacgaagaa caatcatcagtagacactagattattcaatccaagattctgttaaaaggaaacgattaacattgttctaaagacatcgacaacaa tcctcttgccaatcagacaatcaaattcaacataaatgacaaacagtacaaagaactacggaactgcgaattgcaaattaaagattaact taagcccaaagactcacactttctttatagagtatgacgatgcgatgaataatccgacaattggtattttgactaaaagtgataaagcca gttcaaaacaaattaagcgtaaagtcaacaattgtgtataaaaacataacaagaacaactgacaagaacctcaacagcaagcaataaggcacttgcaaa ccagaaataaaaattggattgccaagaaacataacaagaacaactgacaagaacctcccaacagcaagcaaataacctgaatataatttaaatccaaaa catacagcataaactctagctacgacggcaagcaaaatgcgcaagctgaatataatttaaatccaaaa tccacatactatggaaggtggaattgcttaaggagtgaaactcatcacaaaggtaaaactgtcttgaaaacgaattgttcattttgga |

FIG. 7B-9

| | | |
|---|---|---|
| | | acatcagatatacgatgaagtttacaatatcatgaagcagaagactcaatgcattattcatataatgtctata |
| Contig40_gene_296 | 774 | atgctctttcagtaattgctactgtatctgctacttgtaacgtaatcgttattactgatcctagtggagaagatcctaacgtgctgcagcagg<br>aagtatgtccttgcaaatacacagttccagtcttcatcatgtcaagatgatgatacgccatgctgcctttcaggggtgaagtaatggta<br>cagaaagaactcattattgcagcgcttgcagctatgcagcatgagcactccagcatctgccgcttgcaagtgattaaggt<br>atccgtcttgttattggaggccctcaatgggtgcagctcaatgtgctcaaggttcaatgtccttatcttgttgtcgacgatgcgaaccattaa<br>gtcaccaccacaggagtgttcaattgctcaagtgcagttaatatagaaaagctcattcacttgagaacagtgcagtaacctatgtatg<br>gtacgcagaaagagtccgaagagagttcaggtgaaaatacggtggggtcagtaaatacggttatcctgcacttatattgtcgtaaggccatg<br>aaagagttgccgagattcagtgatgagaactattccaaatcctgtaaaaatgtgatgggctacagtttccagatgtgccgatca<br>ggtaaacaccaccggttatccgatggcagtgaactcagtgagaaaatctgctacagaagagagtcgtcaagttaagacatcacagttcttaagattctgttctgtt<br>acgtctgcatgcatgtgcagtagattagagactcagacattacagagagtcgtcaagctcagtgcagtcagtagagccaagcgactttaa<br>tccgtctttaagcagtgtgatagattagagactcagacattacagagagtcgtcaagctcagtcagtagagccaagcgacttaa<br>tgcaggttcacttaacaagttattaacaatgtttaatcgttgttgtgactatgtagagcaagcgacttaa |
| Contig40_gene_297 | 775 | atgtctattaaaattagaagagacacacttaatatatattattggcttttatttaattctatgcgtagattaattatctatgctttatgc<br>atccctgctcaagtcgaagaagtcgatgtacctattgcagttattatcgttcagttaaggaacgacatagttcctattgacaatagataatgttg<br>aaaatcaggtttaagaagaagcagttatattgatgagacatctccagtgagacctctaacggagacctgcctgtgactgaagccgagcaaatgca<br>gagaagtttgtaaaaagtcaacattccagtaccactatcgctccaattgcagtcaggatcgacgttaatgtaaacaagcaaactggtatcgtaac<br>cgttactgttatttgaagattcctcaactattaatattacagaaaacagtaccacatctactgatttcacagaaaacgaaccatcaaaagtgttt<br>ataattatagcttagcaggttag |
| Contig40_gene_306 | 776 | atgaaagcagtcattcctgcagcagttcctcgcagcagggcttggaacaagattcctcctgctactaagctcaaccaaagagatgttgccgtttatgacaagcc<br>gaccattcaatatgtaatagaagagtctgtaaattccggtgtagatgatattcctaatcgtaactcgtaactggtaaagatcaatttgaagaccatt<br>ttgacagttcctttcgaattgaacaccattgaacacaaggagagattcctaaaggaaattgaatatattgcaattcagtttgtcatgttagg<br>catttttataagacagaaaaagcaaaaggtcttggagatgctattatattgtcttgcacatctgatgacatctatggaaaaatctgttatgccttgaagaggttc<br>ggataccattacaaagagatcaagttaagtcagtgctatatggtgtattaataggcgtgaagataggatggttatccgtgaagaggttc<br>cgatgaaaaggttgaaagttaaatttggcttctattatgggaagatagggaagatctcaagaagcttgatgagattagacgattgcagtcagagtcgattagaggacggttc<br>agagtagcaccaagtaatttggcttctattatgggaaagatctgaaattgctaaccttatgcagcttatgattatagattgaggtacagttaagagaccatacgatagaccatattgatt<br>agaaatccaattgactgatgctaagccagttctgatgagattacgcaagatgcaagatgaacaaatcattaagagagttcattaagaagagattatttaa |
| Contig40_gene_310 | 777 | Atgaattgtagtgtatatgaagatatagtgaaatattacacgacatattaacttcaaatctcaatgagcttaattcagatttgcttatgg<br>tgattcagattctgaagaaatcttagatgaacctctcaaaagcttaaaacagttctgatactcgatatcgattacaccattactctgcctt<br>ataatgctaaggaaatgatgttaattgagctatacaggtgatctctcaattgtagtaacatcatttataatgtcaat<br>tcaagtgcaacactgatgaagtttcaatgagaattcatatgttagaatcttataggacaacatcaacttatataatgcaaa<br>ttacactggtctgtgtaatcatagatagtagtatggagttctccttaagatgcatcatcaatgaagttaggatgcttaataa<br>tccagtgggaataatgtaatctcaattttacaaatatggcaaataagtgccagctgtcatctcagctgtcatcacgatgggcagcaattat<br>cttagtgaaacgattgcaatcgataattgcagttttaaattgcagtttaattagtggttataattgggttataatatgggttataatccagaagagagcattgatt |

FIG. 7B-10

| | | |
|---|---|---|
| Contig40_gene_317 | 778 | aagggaaataatattgtaattaacaattcatatttcttaataattcagctacccgctgaagttgatgacattccatgagaggagataacct<br>atttggcagatggatatggcggagcagccttttagttggaaaaatgtaaaaataatcaattccctttgatagtgcttccatgcacaa<br>ggggagcattgtattataagtctgcatatgattgttcaatatcaatcaaccttttaaattcattttctgttggaaggaggcgtaatcta<br>tttagttcagaatattgatggctaatgatagatttcttgtaattttataaacaacactgcagacgattggatg<br>atgattaaaactgatgatgtattggttattggtgctggacctgctggttcttcagctgctggtttgcagctaaaggcggctagatgttattcttat<br>ggataagaaatccgaaatccggaaataggcgctcctaaaagatgctgaaggtgtatccaaaaagactttgataagttagacctgaaatgatcctcatt<br>gggttaccccaagaaattgcagggtcagattagtcgctcctgacgaactgatgtgccttgatgaagatgttattgcttgactctgaagcagga<br>tatatcctagagagaagaagtctttgataagcatatggctatggaagcaggagagaagagctcaaattaaaatcaaaaccaagctaaaggctt<br>gaaaagagaagaagatggaagcttcactgtaacttgcaagcatccatggtgaatccttgacattaatgctaaaataatatcggtgcagacggtc<br>ctgaaagccatgttgcaagatgggctggcttgaagatggcttgacatacaccaaacctaaacacatggaagctgaagttcagtttgaatgtgtaacgcaaaa<br>atggaaaagcaatgttcctgaattcctccagatatggctgaaagcgtagctccctggaagcgtacttctggctttcctcaagcagagatgacattgtaaatgc<br>aggactgctatcattccagatgtaggggagaccctagtaggcggctcgttaaggaatacttagttgatgctgtaaacaactgtgatgctattaagagacgctc<br>agcctgtttgaattgaatgtaggggagaccctagtaggcggctcgttaaggaatactgtagttgatgctgtaaacaactgttatgctactaaagacgctc<br>caagtaaaccattgactggtgaggatcaccaatggtatgaggtgcggaagattgctggtgaagtggctgctgaagctattaaagcaggga<br>ctgctctaaagactcctaaaagtagaagtatgaagattagtaaagaagaaatggtcatgaaatgcaaaataca |
| Contig40_gene_342 | 779 | ttgagttctaatagtttaagttctaatgaattcaatccaatcaattaaatttcaatcaattctaattctattctaattctaattcta<br>tcctaatcaaaaagccaattcaaaagttctcgtctgattttgctcaatgtaaaaacttaaaagtaaacgaactgaagaaaaaatattttataa<br>agcttgtgatggcaacgaaatccctataccttatgttgatcttatttcaattacatagattctcaattgaatctgttgggtaccgttcgaact<br>gatgaaaatggaatcgcttatatttttatggattcgttctacagtatcctgctcatatcctgtccatactcttgtttatgcttcattgaaggtgatgaaatcataatcc<br>ttccagcactttatctttctacagtatccgttcgtattaagacactgaaatcagctcattacagtcatatgctatctttggagagaaacttcattta<br>agattacaagttgcggggagcctgtatccaatcagaaggttcttataagctggtttcttataagcattgataataagaattatactgcaacaacagattcagaggtatt<br>gcaaagtaaaactaccaaatcagcaaagaccttattcaatatcctgtaatttttcaaatcgtgtatattactcagttacctaaggagctgatgaa<br>tattcctgtttaaaagggctttccaccgagattattgtgatggaaggaataataataaacaactaattccaaagtgcagcttccataaatattgat<br>agattctatcaaatcgcaccctaagattaatattattgtaaaagctctgctcagctaagatctgctatgttgaatcc<br>ttggaaaggggagaatacaaaaggttttgatgtaaaagcttcttgattcagctaagatctcactgcggaggat |
| Contig40_gene_344 | 780 | atgggatttgtattaatatcctctgatctgtattgattgatgaagcaagttcttcaagtgacttactcagattcagatttcaaatgatta<br>tttagtagcaaactctggagtgattcttgctagctagtcaagtgcatccagtagtctcaagtgctcagatgattcagatctttctaacaatgctagtt<br>caagtaatgttaattgaaaatgaagttaagtactaaaacaccactctaaaggcagtgaagctccgtctataggggcaatccatattatgttacttaac<br>tcatctctcttcaagctagtaaaatctagaaaggttttgcagaagtgacttttaacatcctggcaaaattacatcctggcaaacacgattcaagtgcttc<br>tgataatgtaaggttttaagcaaaggaagtatacacatagcttgcaggcactgaaaactatgcttcatcaagctatcctgtagcttg<br>ccattaacattaattagccactaaaatcaatacaggtggatcaacgttaaaaaaggaattatccaccgttataccgacccggatttcagtgacctgacctgatgaaatggaaa<br>gcattatccagtcagaaggtgacctttaaatatcttgactgctcatcctgctgctctatgcttaaggaaaatagctattcattaccttggtgcaatcaatt<br>tggctgcaggtaagaaattacctttgacctagcggaacctcaatcgttaagggaaataggtcctacagttatcagcaactgttactgttcaaaa<br>ggaatacaagcataaagctagcagatatcaggcaagtcctacagcagaaccacaacctcaatgtgttgtggcttcaattg<br>ccaaaagtcgccataaagataccaggtggatcaaggttcttgctctatcaaggttccatggctcggagcggcaaggattggcaa |

FIG. 7B-11

| | | |
|---|---|---|
| Contig40_gene_346 | 781 | atggaggataatctttgaaaaatagaaaactaatttgataagtatcttccttgttagtctgcttgcaatttctgctgtaagcgcaaatgagga<br>tgtggataatggacttatcgactttcagatgattcatcttcagtcagtcagctgaagtctcgattctgccattggatcagattctatcttgcagtcag<br>ctgaagtctctgattcactatagatcagactctgaattggaactggaagacgattatttagaacctaaagaaaagaatgttctttcaatggatgagaatgc<br>gatgataaaatataattatattgtgtggtatgatggtgatgagattggtttcccttgattttgtagatgattcaatgactattcatcactaattaaccactgat<br>atggtttctataattatattgtgtggtatgatggtgatgagattggtttcccttgattttgtagatgattcaatgactattcatcactaattaaccactgat<br>ccatacgattaaacagttatgacactccattgacgtgtgatgtgatgaatatctcgtctttgtgtatgcttttgtatgatgggattttgtggccacctta<br>gataatgggactgtagttatataatgttccatatgaggttgatgaattatctcgtctttgtgtatggcttttgtgtatgggattttgtggccacctta<br>tgaaattgggaaagttacacaatctgcgcagtgaattgggcacttgtaagcgtcagcacttatatcagaggaccctctaaacgactttagactttatgctctgtgt<br>ctgtatgtgacacttatgaaagtccaattgcgcacagtgtttacaagcgattccaatcaatatgtcggaacatatgtgagaatgaaaga<br>gcaatcatcacaaagtcagctatgcgcacttatgatgtgaagtcatatatgacggctattcattcatcttcagattctagcgccattga<br>gttctatgacgaccatcatacagaccctgattcacttgtgatgaaagatagattatatgtatgtagatagta |
| Contig40_gene_349 | 782 | atgaacagaaataaaataattgttttgcttgtattatgatagcagtgtgtggctttacaatgggcagttgtgcagccagcagcactacaataaa<br>agtaggcaattacaaggatgttggaaaggagataggatttcaacattcaatgtgcctaagatgcacagtattaaagaggttatgctgtaa<br>tattctatcacgcaagaatgtgacgatttcaggccacatacctatgtattgtctaaagataaagtatattataagaataaaaggcaaaatc<br>gtaacaagtcttctacagtctaagaatctcagcggactcagcataacttccactaaacaggtaagtggttacactccttataagatggatgtaag<br>ttataggaagatgactaatgctgagaaaagaaatttgtggcagtttagtttattag |
| Contig40_gene_352 | 783 | atgaaaaatcagttttaaaattctaattgctttagcttaattttattggctgtatcaattgtttcatctaatgatctctctgattctaatgt<br>ttcaagtgattaactgttgattcagatctctataagctctgatgatacaggatctagcgatcaaagttcagatgattcaaatcaggatgatgtat<br>ctcagataagactaatgatataaaaactgtctgattcctgattccagtcagtcagattcatcaaagatactcaagatactgatgataatacagatatggt<br>tctgataaaatgtaatttgattatcacaaaaaggcaatgagaaagtggagatactgagagtactggacaatagaggtaaaaactcttt<br>aaacactgcagaaaaacatctctgttgatgagttcctccctcaaaactttgagtttaagtctgctaaggcaagcaagcaagcaaatatgcagttgaga<br>tagcaaattgggacattggaaatttaaagaaaaatgaatctgctacctagtgattaaggctcaagcattaaaggctgaaatttcaccaatgtg<br>gcaaatctcactacagattccgataatatcaatgaaagtccttagcgtcaaggcagatgtggaagtgcttccgagaataaaagaatgagac<br>tcctgtaggacctaagaagaacaagataatattctacagtcaagattcataaattaaaaatcagacaaataataacaatatgactc<br>caatagattttaagaaatctggaaattcattgttttgctgttataatagctgcttttggctgtttcttgaatatttttaggacgaagaagaataaat<br>tag |
| Contig40_gene_359 | 784 | gtggatttgtctgattcttgttgtgtgatactctttattcagatggttctgatgtattatttaggtggatctgatgtatattagtcttagcgatga<br>aaataattccaagtccagttccaatacatatgtaatgatttaaatgattatatatatatccagatttactttaacttctcatataactgaatggaggc<br>caaattccaagtccagttccaatcagttcaatcagtaatgatttaatcctcaatccgttaactctcatataactgaatggaggc<br>agctttgaagatattcaatgcgtgtgatgggatgatataatcctcaatgcgcactttacactactgcttcagttattgt<br>aataaataagacattaactttcatcaatgcgaagaaagctgttttgatgcatcaaaatgctgtcaaaaacatatcaaagattttcttgttgaagcagatgggtga<br>acttaagcatcaacttcagttgattaatcagtgaaacaagaaagtgataagtatgcgcctcctattcttgaaggatctatggaatgaaaagcga<br>actatcgttaattgcagttttattaacaatagcgtgatggggagctaatggggcttaggagaaatttaactcaataatcagagttcatcaata<br>tccatttaaaacagttattctggagcaattctatttcgaaggtctttcagctatgtggatttataaattcattaacaactctgcagattctgt<br>accatgaagaaaggtggagcaattcatcttaaggagaaatttaccatcaataatttcattaacaactctgcagattctgt<br>ggcgccttgcagcttgcgctatgaataggcaagtgatttaactcattaattggcaactctgcaaataatggaggtccatttcatgtgcgg<br>ttctaatgattgattagcaattccactttcattaataattcagctgatcaaaaggaggatcaatttattta |

FIG. 7B-12

| | | |
|---|---|---|
| Contig40_gene_411 | 785 | atgaaaagaatatattttttaattgcaataataactaattgcagttgttgcagttagtgatgtataaatagccctatgatatatcaataacaa<br>tatgaaggaattgaacactgcgatattaccgaaggagacacgattaattctgctatcaatatatcaataatgagacttattagtgaactg<br>acaacatccaaattgcaaagacaaattaatgatgctgatgagagagcttcaaatattgagcaatataaatctagctaacgagagcatttat<br>cttgattatttatattgattaaagagaagtttccattaaaagacaagccagcagtgaacttattgctttacaatattatacaacaatga<br>tttcagctctgaaattcatatgctgccaatcagcaaattcattaatgaatcagctaagtttacagatgaaagaaaccaaattgttgaaaaca<br>atcctgatctatttaaaagacaggaataatctga |
| Contig40_gene_431 | 786 | atgttgattgcttactggcttatctgcttgtgcagcagttgacgctgaccattaactgataatcaacttaatccaactattttttatcttga<br>ttttaatcatgcgctttaaatgatgtttaaaaagaaatttgatctctttgatgtgttccaacattgatagctagaccttacaacgatg<br>gagaaaatgtctctgtaagctttttatagtttaaatcctaccattgatgtgataacttaaatgatgagattatagattatacattgaggttatg<br>gaagatcctaagccaatataactacattaaaggatgaataaggaacatatgctctgagtatggtcagatgatgtcaagattaatgtgattc<br>tgtaattggagaggatgaaattccagttatttttacaactgcaaactcttcagcaaactcttcagagtatgccctatctgtaaaagggttgctgatatagatggagattca<br>agagtcatatatcttgtcagtgacaataagaaggttactgcgagtattattatgtggaatataaggaatcactacatgggttaatattga<br>tgatattgatgtgtgatattgacattatgaattaa |
| Contig40_gene_448 | 787 | atgagcgaaataatagaactttgattacaatagaatcggcgcttttattataattgccatattattaatagccctgtttttaccattcag<br>taattggcagttgacaatgatgaaatagcagtaatcaccataagcgacacaatcacctatgagacaatagcacttctgccatacaagcaaaa<br>aggaaattgaaagcgaacttcagacttaactttcagaagaaatctccataaccaattgtaagctatattgagataaaggattgtgatgaagcttgctaaatagcaag<br>tgccactgattatatttcgcaagctaaaagtatctaaaaaacaaataaaaacaaaagctgaaaaatcgctgaaaatcggctctaaaagccagtgaggaatcggcctatgttgcgagactgttgcgaactgtgcacatgcaaaaata<br>caggagtctttaatgaaaagtatctaaaaaacaaataaaaacaaaagctgaaaaatcgctgaaaatcggctctaaaagccaatcaataagaaaagccaatcaataagaaaagcagctaaattgcaaatgcaacta<br>taatgaaatgaagctaaaaaactaggattgatgataaactcacttatcagcaagagctaaattgtaggtaagatatttaacctttaagagttaattaaaatc<br>attatacagtaatcacttacttgtttaggtgaaaatgataatttaacctttaagagttaattaaaatc<br>taa |
| Contig40_gene_466 | 788 | atggaaagatatttaaaattgttacaatcatcatcattgattgtcattgctatacttggctgttttcatctattctgatgacattctgaaaa<br>gattggtgaaaataacttgtggtgtgtataaggttacatatggttataaggttacatatgccatatgtttcaaaggccttgcatttgcatatcctgatgtgaagttgtaatatattgttaat<br>caaggaaaagcttcatcaatatgcttgtctcttcaaagacatcgtttacaaggccagtttcaacccgcttacaggttgggttgcggacacatga<br>gtaacagaatccgagacttacgaacatgacagccgtgcaatggaagctaatgttaaggttacaaatctttagtcatatgttaatatgttaaaaggacttt<br>tgatgttgtaatcatttgaacatgacatgaccatgagccatgccatggtagcatatcaagactaaactccatcttaagcttaaagtgataagcca<br>ctaaaaggttactaagtattggcttcatcattacactaaaggtaatggaatttccgaagtttatgagatctaagtaagctaagtcttataagtcttatcagttagttaatgc<br>attgttgatgctgccaaggattcgtttatgagattcctgaagttgatgtaagtaagtaagtcattttataagtcttatcagttagttaatgc<br>tacttataaccgattgaaaaataa |
| Contig40_gene_483 | 789 | atgataagaaacaatcattatagctgcagtagctattctcgttattgctgaattgccgtttgcattggaggcggcggaagcagcgatag<br>cgatccgacccacttgacagtagctacacacagcaatatggcacaatatggcagaacctgaagcaggtttcaacccgctacaggttgggttgcggacacatga<br>actataaccattgtacaaagctgtctcttcaaagacatagcagaacaagatgagacatagctcaagcttcaaccaactatttcaattagtctgac<br>ggtttaaaatgactgtaaagttagaagtgacgtcaaattctcagataactccaattttgacgcaaaagacgtagcattttacattccaactgc<br>aaaagacactgaaactgattagattagattaaccaatcttaagaaagttaacagctaaggatgacaagactgcgtatttgaattgaagaaccaagat<br>ccacattcatctatgactaaggtatggtatcgaacgctacctacggcaaagactactacggcaaaccacccaatcggtaccggacctat |

FIG. 7B-13

| | | |
|---|---|---|
| Contig40_gene_501 | 790 | gtattgaccactgggataaagtcaacaagctatcttttaaggcaaatgacaactggtatggtgacaaacccttacttcactcaataatcaccatgtt<br>attccctgaagaagctacctggctcagagtagctaggtaggcacaagtcgtcaagttgacattgcctcctgttgcaacctctgcacttaacgaatctgtagacg<br>gatacaactttgttgaaaagtctgcaagtaggcacaagtatctccttgcatatctgaagatactggaaaacagccagcagtgcaaag<br>atcggtaacaatgtaactgctgacaagtccatcagagaagcattgaacataggtgcaacctgtgataaatctgtgaagagtattctgtgtca<br>cgcttcacctgaatatccagcgtagatacagagaagctttgcaaaccctaagctaaagtaaagatggtgatg |
| Contig40_gene_553 | 791 | atgaaattaaataatctttcattatcagcataatttctatattctatcaattagtgcaataagtgcagaaaatactgataatgcactctc<br>aacagatacacactcaaatgacaatgtactctcaacagattcacgatcaaatgaataatcacgagaacacacttaacagatacac<br>actcaaatgagaatgcactcacacagaccactcaacaagagaacacattcttataaggattcagaaaagtctcttcatcagatgcttt<br>aataagaccatttatgtaaataaaacggaagcgatgaagcgaagcaattcctaacgctacactaaaaaagtccatcacaact<br>tgatgactctgacaatgctgtcatctcactactcggtccagcaattcaaatggcaattacacagtgaaatactctgcttgagataaactttagccataagagatc<br>atgacggatccttagcattattgagattcaatgaggaactgttttgatgggaaactaaatccataatatatcaatcagtgaggat<br>tcaatagtgacctttaataatacactatgcaacaaatctgtgcactttatgttgataaacatagccttaacagtaatgaactcaaattttagaaata<br>catattcacggaaaactatgcaacaaatctgcgatatctattttcacaaaactcagaaatactttagtcaaagaaatactttagaatctgacaactgtt<br>gggcaaacaatgtcagatatccctgcatataacaatatagccaacattactttagtcgataatactttcatcaactgtaattatacag<br>gcctatagccatccgtatccctgcatataacaatatagccaacattactttagtcgataatactttcatcaactgtaattatacag |
| Contig40_gene_636 | 792 | atgaagaaaaaaatagcaattatattttaggaattgcaattcgattcttagtcatcggcgcatccagcgcaggtttcttagactttttaggtgg<br>cgatggaactgctactagtctgatgacaatactttattgtcggtttgacaactcgactgactacccatccatagcgatctaagaacgggaatatg<br>taggatttgacttagacttgactggtctttgacttctctagtcaagaagtatgtgaagcagagatttaccatccagcagaacagccaatagcgactgttagtaaaacagccaatagcgcgaa<br>ttgactctgttcaattgactgactgtattgaacggattttacccgtattaacagttagctgacaccttaaagacttaactcaagttgctgaacaccatattctctgctttag<br>gcaagttgttgttgaagggacaacaaaccttagctgacaccttatattgtgacaccttaaagacttaactcaagttgctgactataacagattcatctgcttttag<br>cagctcttgaaggggacaacaaaccttagctgacaccttgtatattgtgacaccttaaagacttaactcaagttgctgactataacagttcatctgtttag<br>ggtgcatgtgatgctgtgctagctattgatattgtgttcaagaaggaaatgaccaatcagccaaaagtccaataacaatttattgtgatgaagaaat<br>ctcatctgaacaataacctgcacaaaagtacgacacctacggagttcctgtgttcctgcgctcttattcaaaaataa<br>ctgtagaaaaaactcgcacaaaagtacgacacctacggagttcctgtgttcctgcgctcttattcaaaaataa |
| Contig40_gene_721 | 793 | atgaatttcaataataccagatcgatgatcaccattgtaataataatagcgcaactattgcaacatccatgacactccgtagtgttgcagctgaagacgcaacagttgatccata<br>cactttcacaatcaacatgatccactctatgcaacatccgtagcactcggatgtgcttgttttgcagctgaagacgcaacagttgatccata<br>ccggtgtcagcgatgatatagaagcagcaaacaaattttcacgagaaaacattgcttaaagaagaatcatgaactattaatgcaatg<br>gacatcaccctttcaggcattctctgctgatgttgatgaaccaccatttagcagccagattcggcttttttgatttttcaagtgatga<br>tgctggttccgtgaaaatactgatgatgttgtttgtttgtttcaacagcaattccacccattttggatataaggaaaatgtgaatatacag<br>gatttgacattgaactgctaaagaggttgctcgaagaaacaactgacattcaagccagcgactcctggaacactaaagatttgaa<br>ttggacagcaatgaagtagactgcatctgagtgaattataccatcaatgaccttgaaggcaagaccctttgaagttcaacagggaagctccattctaa<br>aagcttgtcatcgttagagggatagcacttaagagaaattgcaagattgaacagatgtaagcatgtgatgcatataccattggaatgaatcgga<br>acacatcgaaagaaatgagactttaaagagaaaactggaagatctctagttaaggataggtagcagccttaagaggagaaaattgaactcatcagaattccaa<br>gtctgtgatgtgataatcatagacacggctcttgaagaatcgaacactaaaggataaggtcaaaagacattgaatgatcctatctcctgaataa<br>tgagaaatatggttgttgcatttgaaagggaacactaacagtgaccatgatgcggtcaaaagactaaggataaggtcaaaagacattgaatcctatctcctgaataa<br>aaagatagctcaaagtacagcaaatacgaattccagatggttgtaatctatcctgaataa |

FIG. 7B-14

| | | |
|---|---|---|
| Contig40_gene_730 | 794 | gtgggcataaccttacagcaatatcacagggcattagtgtggaactactttcagaaacctttaggaaactacccttagccaattcataccttacagctatcagataagcttcattatcgttatcctctcacatcctacttacacatattggtaggtgagatcgtacctaaaagaatggcattgaatgaccctgaaggatatgcattgagcactgcaaagtttcatgcagataagctcaatataatatgcaagcctattgtaaagctcctgacagcttcacaaatcttgccttaaggatttgttgcccatcaccaaaagaggatgtcgttactgaagaggaagtcaagctcctatcgaagagggcattgaagacgagaacaatagccgaagacctagaacatcatcaaaaggatagagattagaggtttagaggtagatatgccttgaacaagatcatctggctagacctagaagatgagattgaaattaacaaggctaaatcattgcaaggagaagagtgttgacattagaccatacagctgacgagttgatgacttcatagttcaagctctcaatgtcaatgactacctcattgtgtgttgatgaatttggatggaagcgtcctgaaaaatatgcttcaatcacacttaaacgaccttcttgaaggattgtaggaaacagagacattccaggaaatcgatgaagaggaccactacagaagcgttgagaatgttaggactcatcacattggctaatagacgcagattctctatagaagacttaaagaccttgaaatcgaaaagcgaaaagaaagccatacttggctaatagacgcagattctctatagaagacttaaagaccattaaaatcgaaaagcgaaaacgaaaaaagccatacttggctaatagacgcaggacaacgcctattgggattccttcacatgcaggtaaaatccctgaaaccggtgaaatattccatgcgatacacaaccattgcaggattccatccttcacatgcaggtaaaatccctgaaaccggtgaaatattccatg |
| Contig40_gene_732 | 795 | atggattctaaaaactgatttagtgactgcattgcttgtctttttagctattgtttccatagctcagttagtgcatggactgtgttgtgaacagctgtagactagttccacagcaaagctaccatttgcaggacatattcaatatatccgacggatacttcaatatatacctgacggatatcaaaaaatgagtcatatgttggataatgaaactaccaactcaaatgggctattttttattcaactgcagagagctattaaggtgcagatgataatttatattcagtagcagactacagttatcctgttatgaagctaatctaaccactgccaacttctaaaagtctgattggagataaagaaaccatcaatgtcatgaaggtttaattgcagaaaatgaattgcttaaagttcatgcttaaagttcatcgcttttctaaagtctgaagatgagattgtataactgtaatacttcagatgataattatttgaacaaataatcctgaggcatga |
| Contig40_gene_733 | 796 | atgaatgtgaataagaaaatatttttacttgtaatctttataatatctatttcaatagctggagtatattgtgcagacatccatcaggatagcgatttaaccgcaattctaagcaatgaaacagatagtggtttaacacagatagtggttaacagatgaaacagatagcttggctgctgctcgttcaattgtcctccaattagatgaaatgaatccaataactgctacagacgtgattccaactatacagcagatgtattattgaaaagtcaatgccatgaaagcctgcaatagcaatatgacaatgacacaatatgcttgaataaggtgctgataataggattagccgatgatgcactgattgccagataaatccagagatgaagcaatgaaatcctgaaatcctgaatatcactactgcaaagatgattacagcatcagaaagcttccaacaccatctaactcaaaaggacattaaacaaaagaagtatggaagggtcatgttgtaattaaggctctaatgaacttgcaacacctacaaagctcaagacgcagataaaataggcattaaacgttggagaatacatatccatcccaaataattatgagctttccagaagaggatgtctcactgagctgagccagataaaatagagctattaaaccgtatattgttgaacaatgaaaggttccagaaataactactgaatatgctgttgaagtagatagaagctccaacaaatgctactttgacagttgaggttactcttcaatatgctaacagattgctaattctcaatatgttgacatagaagactttatagtgtatccaatgtccaaactataagccttctaatgaagctcaaaatcttaaacaagagatccaagtattacagtcaagatgtagtagccttattgctcaagctgcttttatagtcattgctcagcaagtgcagcagatgcagcagacctttaaaatcaatgatgcttgctttaacagtcatgatgcttttatagcagctc |
| Contig40_gene_749 | 797 | atgatactggcactatttgttttatagtccattggctcagcaagtgcagcagatgcagcagacctttaaaatcaatgatgcttgcttttaaacagtcactgtctgattaatgccatttttacaatgaagacaaaacaatgcttacaagaccaacaatgtacattaatatctgattatgatgagattcttagcgaagcatatctgaaaaacagcagctatcgcatagtttcaggaggaaacaaacaatacatataacatataactgtttttgacagctataacgatcatgatcatcctatattaccaaggatatgttgccttagactgtgagtattggagtattggagtattgatggcaaaaacaatataatcagaacaaatgtgatactcagaaacatgatcatctgcagactgtgagtattgatggcaaaaacaatataatcagaacaaatgtgatactcagaaacatgatcatctgcagtcatttgctgacatgttatgtgatcaattaatgaattcaatcagaacaataatatagagccaatagcaatagcctataataaaaacaatagagccaatagcaatagcctataataaaaaacaatagagccaatagcaatagcctataataaaaacaagagatcca |
| Contig40_gene_750 | 798 | Atgatctcactgcttcttatttcaattcttgctataagcgcagcaagtgctgcagtgacatgtgtagacgcagtattgacctagcaagttcagaaattagtgaagtaagtgtagatgtgtagaagctacaagctacagataaaaatgttttatctgatgcagatgaagtttcagtagttacacaaaactcctttacaatgaaaatgcaactattgatatcagcgtcaacgcactttagctgatgacaacgcactttagctgatgacaacgcactttagctgatgacacctcagtaggaaaaaatatttcattgaagcggttgaagcagtagtacataatggttaaatctatcagcaggaatacatgttattccagcaagttatgttatgcggatgcttaaaagagctataacgtaatcagcaggaatacatgttattccagcaagttatgttatgcggatgcaaaaagctataacgtaatcagcaggaatacatgttattccagcaagttatgttatgtggaggaagttcatttcattgaagcagtagtacataatggaaaacatgttatgatcaattaatgaattcaatcagaacaataatatagagccaatagcaatagcctataataaaaaacaatagagccaatagcaatagcctataataaaaacaagagatccaacttcctcattggaggcagatccacccctcaacattactaagtcactcctctcgtaagcgttagtgattgttaactgtaaaagtggagattata |

FIG. 7B-15

| | | |
|---|---|---|
| | | taaccattccatttaatgtaactgatgacaaaggtaaagcaatccctggagatgtcattgtaacaatagtctgggaaaatgatgtaataagcaaacatattaaactaaacgacaatagctctgcaggatttaatattgctgatattattggaatatttggcggaaacagcacaggtaacggaacaggaactggaataggtgacttattcaacagaaacggaaccaacggaactggaaacggaaccggaataggtgacttattcaacagaaacggaaccaacggaactggaaacggaaccggaataggtgacttattcaacagaaacggaaccaacggaactggaaacggaacaggcatcccaggtattggcggaaacagcacaggtaacggaactggaaacggaaccggagacttcgatattgcaagcattctcgcaatgttaatgggaggaggcaataataccggcgctaaatttgcatatgtctttgaaaaaggagtctataatgtaagcgttgaatacttaagcaacagaaactacaatggagcca |
| Contig40_ gene_762 | 799 | atggaagaaaaaattgctttagctgcttgcagtggtatgagtccaaatggtttggttgcaagagttgcagttcatgatttggctattgacgatcatgagattttatctatttgtatgggttcaacttctgcaaatgtggaaggatttacaagagttcttgataaatatcctattttagcaatcaacggttgtgaaggcaactgtgttggtaaaatcttaaaggaaaagggtgttgatattgtaggagaacttaatgttggagatattttagcagaaactgaatacaaggctaatgatgctgcaaggttagatgatgaaggagaaatctgtgtaaagattgtaaaggacattatagaggataaaattaatgaattaagtgaataa |
| Contig40_ gene_766 | 1376 | atgttaaaaactaaattatgcggaattagtttaaaaatccattaatgcttgctgcaggtgttttgggaagccatgcatcttctcttaattggatttaaattctggtgcaggtgcagttgtatcaaagtccttctcaaaggaaccaaacgaaggatacaaaaatccaaccactgtagctgttgagggaggtatcataaacgctatcggactttcaagccctggcgttgatgcattcatagaggaattggaatctgtaaatagaatcaaaggcagatcaatcgcttcaatctatggagcaactcctgatgaattttcatatgttgcaggcaagattgaaagtttggttgacatgattgagatgaacatatcctgtcctcatgcaatggaaggatatggggcttccatcggtcaaaatcctgatttaacaagagaatttgtctctgcagtaaaggatactgtcagcgttcctgttcttgcaaaattaaccccaaatgtaacaaatatttctgaaatagctattgctgctgaagaaggggagctgatggtttgaccttaatcaattcattaggccctggaatgaaaatagatattataactggaaatcctattttggccaataagtttggtggaatgagcggccctgcaattaagcctattgctgttagatgtgtttatgacgcttatgaggcaacagacattcctattgtaggtgttggaggcattcgcaactacactgatgttgtagagttcttgtatgcaggtgccagtgcagttcaaataggaacatccattatgtatgaaggtcctgaaatatttggcagaatccgcaaatga |
| Contig40_ gene_769 | 1377 | atggaaattgtattatgtgtaacaggcagtgtagctgcagtggaaactgttaagttagctcgtgaatttaagcgtcaaggccattcagtcaaggcatttatgacccaagaggctacaaagatcattcatccaaatgctttagagtttgcaacaggtcaagaggttgttctagagctcactggaaagattgagcatgttaaatattctcaagcagacctaattttagttgctccagccactgcaaatacaataagtaaattcgcttatagaatttcagataatcctgtaaacacccttctgataactgcctatggccatgacactcctatcgtatttgttccatctatgcatgattcaatgtatgatgcagtgagtgagaatgtggcaaagctaaaggaagagggaattgttttcttaaatcctcgcttggatgagggcaaggcaaaattcccagctattggggatattgttcttgaatccattcgcactgttaatcttgatagggttaaaaagaatttaactgacgattctttagatgaaagcgaaattgaagatttaaatatggaaatgctttctaaaattgcaggattaaatgttttgataagtttaggtggaacatttgaagagatagatcctattaggggaatatccaataggtcctctggtaagatgggtcttgaattggctaaagaggcttataggcttggagctaatttaaaaatccttgctgcacatcatgaagtggagattcctaaggtctttgatgtgattgatgcaaaatccagtagcgttatgagcgaaaagacaattgaattggttccagattttgatgtattcattgccactgctgcagtttcagactttgctcctattgttaaggaggattataagatttcttcatcattaaatctttccttagagttcgaacctgttgccaagattattcatcagataaagaagattaatccagacatattttagttggatttaaggcagagtataatattccagaggaaagaatga |
| Contig40_ gene_776 | 1378 | atgttaagtatggctagtgtatgtgctagtgatgttaatgatacatacataaatcaaaatgatttaaaaatcgataatcaagataattgtattaattatgaaaaagtagtttatacagaggaaaacttagaaaataatttaatttcaactgaagattctttggaggatagcaattctattgaaccgtctgattcatttaaacaaaaaaattcccttaatgaaggaaattccgatgaacgtttaaatccagaaatagatgttgctttgaattcaatccatgttaacgaaactgctgaagtcaatgttacagttagaaatgctagcggatatgttttagtctcagtggatgatcaatcttttaataaagaccttactgattatcaggctagattcaatattaccggacttggctttggaaatcacaatattgcagtctattatggaggggacgataactatcttccaggatttaaattggaaactatctctgttgaaaagtaccaaacccaaataagcgagattgaaatcggtgaagtttattatggggaagatgccattattgaagtcagcgttcccaatggtgttgaaggggatatcacaatcaaaatcaatgacactctccaaacagtgattactgaagccattcatgatggaatggcattatt |

FIG. 7B-16

| | | |
|---|---|---|
| | | ttcagtttctgttgctgtaggcagcta ttctcttgatgccacatataatgaaatgattattatgaaaacgatactgcatctgccgaatttg aagttaaaaagcagatccgaatttaagcgttgtatcattgaatgcactgtttatgcacaatactgcttcaatcaatgaagagatt catgacgagtttgtaaacattactgttggagatgagaaatatgaggactgtcctattgaagattatgttgatagcattacaggggagttct ctcaaattttcctccttaccgcattctcatagaatatgggg caatgagaatttcgaaagcgctatgatcgaag |
| Contig40_gene_787 | 1379 | atggtagttgcaacaataatctttgcatccagctta ttcgacgcgtccttaaatgatttaaaaacttaattcagccggaataagtttggtttatac tgctattgggactcagctgctccaaacatgttgtatcattagttgttatttgagaggattcgatactttaggagaatcattgatcttagtta ctgcagtgcttgtcgtattgcttatctttggaaaagtaagatttgtgataaagtcagatatgcagattatgttgatagcagattctaatttaacc catgaagcagattagaaattggcgattctgtattagaacttgatggtgctgatttaaatgaaggagagatgatgaataa |
| Contig40_gene_815 | 1380 | atgatattggcaatattgcttgccgttggaatgacacttactgcagtaagtgcagtaagtgcagttggagtttaacttctccagcgaagaaaactc cgacggaggatcaataaacattgaaaatggaaaattgacaatacaaagtattgaatttaccattcctgacggatatgaaatgatgaatcatcaa agaaagtagctgaagacgctgaagatttgatgcaaaaccttactgcgcaaatatgcgaccaagtcgtaagtggtaaagtcgttatatacgaagaaataaata acagatgggattctgaaaaccttactcaacattcacttatattgaagatggtaaagttcgcaaagttgttatacgaagaaataaata tggcgataatactccaacattcacttatattgaagatggtaaagtccctaagtcgttaaataaatgcccctaatgatgaatcattgaatcagtaatgggaa aataa |
| Contig40_gene_824 | 1381 | atgaataagcgaatattctatatatagcactgattttttattattccctgctttctctttctgcagtcagtgctaatgaagacatttcaagtga caatctcatctttgatgagaatgttatgatgagaaatcattttcaagataagaatatcatatctgataatgattattgacgatg tcattccagttgaaaatgctaatgataatgcaattttagctgaaagaacttatttagatgatgaagaactatattagatgagaataagtgaggat aataaaaatgataagaccaaactctccgatccaaacacatatctctttaccgcgtgaatcaacaatagtggagctagtgtaataatatt aactgacaattatcagtataccgagggggatgaatcattcattcatgtatcatgatcagtcgcagcataacaatacttttagagatgcatatgcgaagagat taagtggttcaggcgttgccgtattatggtggtgctatctttatgtggtcaaacagcatagtccaacagtagaatattccgacttcaccgcaacatggcaaaatgtgtgagctgtctatt agtaatcgtcaaattatgggtgctatcgtattggtgggttcaaacagcgatagaatattccgacttcaccgcaacaatggcaaaatgtgtgagctgtctatt tggtgcgcgctatcgtattggtgggttcaaacagcgatagaatattccgacttcaccgcaacaatggcaaaatgtgtgagctgtctatt tgtatggtaataacaccaaggcgatatattgtaacttcaccagcacttcaccaacaatggtgctgtttatacctacgatcagatatc acagtcgattctgtaacttctcaccacaatgtgtgctatctcatgtgctatcatgtgctacctgccaacgactgtgagactgtgaacactccag cttgccaacaacactgcaaacaatgtgtgctatctcatgtgctatcatgtgctacctgccaacgactgtgaacatt |
| Contig40_gene_828 | 1382 | atgaaatataataacactagagatattcttttattctttattgtctcataattcctcaagtctcacttatcaagttctactcaagtctctacttatgcaggggatgtttgatgatttatcgga tgctggtaattacactagagatattttagatagcaatcagcttgtgatggggataaatctaaaacatgctgttctgtaaagatctgttctatg atgaatatttatattcttgttcaaagcaattcagctgttatagcatatcagattcatcagattcatcagattcaatcagatcttgtctaatacatcttagtttc gataaatatatatgatgtttaatgttatagcagatattatttaaatcttgagaagttattcagacagatgaacttaacttatgaggcgatttg taacttaattttaaacttaataaaaacgatatcttcaaatgttcaatagaacgtttaaaaatgatttcaaaatctcttttgatgcatgtgaacatttgtaatcttagcaattatgagcgcgattg gatcaaacttattaaccggaagtcttaattagtgataatacagaagaatcttttgatgcatgtgaacatctgtacgctcttgcgattcatcggc aacacatttaatatttttatataagaaagcggaaacaaaaatcaatgacgaggatgaaatcatgaactgtcatgaactgcatttttcta atgtcaaattcaataataagaagcggaaacaaaaatcaatgacgaggatgaaatcatgaactgtcatgaactgcatttcaattcaatgaaaatttcttta cagtgggtaagctccaatgtgatgcagttcaagctccagtccttcattgaattcattgaatttggttagaaactcaattgaattgactataagaaga acctactgaaacatccattcaagctccagtccttcattgaattcattgaatttggttagaaactcaattgaattgactataagaaga |

| | | |
|---|---|---|
| | | caagcttagaaacgatgcattccatcatcactgagtttccaacgaaaactatgtatatgatgcaattgtctctaac<br>ttgaccattgaatcagacctgctaacatatctgccgtttgattggtgttcaagcttcttcacaacagg<br>cataacggatatcctatgctttgatagcttgtatataacgcattcttgcaaacaatacaatcaagacaatagttcctgtcagcgaagcga<br>tgagctcaaagatatcgatgaggacaatccgacaatcaaacaacaattcaaacaaatacaattagcctaaggatgccattac<br>aatactgtcgttgacaatgacataactgttgaaaactcctatgagtctctgttatggcttccatatcaaactataatgtcattgcaaa<br>caatacaataaggcaacctctgaaactcctcatttggtgttatggttttatatcactgaaactacaatc |
| Contig40_<br>gene_836 | 1387 | atgatttaaaagcaatccctctatttgctttattgatttatttatctcggctcttcaagcgcagcttcaagtgatcttagttc<br>agtcctgccgataatgaaacttggaattgataagtttgactcaaatgaggattaacagttaacgaatacaaactatattgaagcgaa<br>ataatttggaaattgattataatctaaagaatctgttaatgcaacaaatgataaaagaaaactgttgattacaatgaagatatt<br>tcagttgaaagaataatctaagtcttctaaattgagttctgttcgtttataaaacaacaataagactctaactactcttaataaagtggaaa<br>catcctatctaatgtaaacctggagatacattagattttcaggttcattcaacaatagctaaatagatattccattgactgttacaa<br>gcagtgacggtgctcaattcattgattgcagcttcaagttcaataagggctctgaataaggtgtattcaacaacaatctattttcctgcgttcaaaatcctatgctctttg<br>ttacaagtccgcttatctatttgattctgtcagcaatatgaatgtattcaacaacaatcatttgttgtaggatgtgggacatccttctgccttgtcttgg<br>ctttagcaatgctaagctattcctctgcatatcacaacaatgtgatagtcaacgattccagactacagttcactcactatatgttggacacaattagc<br>ctggagcaaataacttaatgaaaataactaatctttaacaacatacctttcaacagaattcacaaggaataatcacaatacgttcacagtcgagaattatgtgacagtttgatgaaatggaaccactcc<br>tctccatctctttgctatgcgataccagtgatggaagcggtaataatcacttcacaatacatacaattatgaatcaaggtctaca |
| Contig40_<br>gene_837 | 1388 | atgaagcttaaaaagtttcagtcatttagcgtcattgatgatacaggcacagtatctgtagacgattctgtagagacactacgga taatgatg<br>tgtagctgctgagtcgctgtctgtagatgatcacggtgcccttgaagatgggagagtgtgagctatgaaacgacacttctattccacatacttcaaagacgat<br>ttaaaaacagttcgagtgctgagtgctgttgccctgaagatggtggctatacccttaaatagtaacaatgctactaaagacattcagatatcgttctga<br>ggtactgcaactgatgaattaagtgcaaaggatggtgaaggattcattaacaagtgacctattcaagtgtttagtagttatgtgaagtaaaataactactgaa<br>tattaatattactgcaaaaacaataccaaatcgatcctaattcagtgttattgaagtaggagacatattctgataggagcataticgagatatactatttacggctaaaaatatatatagga<br>gcgagatagtgccttcatagtatctaggcaatgcgttttcatctgtattatctgactgcgatctgtgcaagttatttctcaaccctcaagatattttataatctg<br>gcaatacattgatgtatctccagtctatgtcaagcaatagcccagattctgattgtattctgtctgcaagtgtctgacgattgcaatagttgtaggaaccttaca<br>gcaagtcagttaagtgctaatgcaataagatagcttaattccaaaccaattagctatattagttcaaacctgatctccaattatgtgctattaatttgattttatc<br>ttctccaataatgttactactgatgcaataacattattaaacagtgacttaatgatgttatgtatcacta |
| Contig40_<br>gene_841 | 1389 | Atgatttaatatcctttaattttagtattcttgtaagtgctaatgctattcaaggcgatttaagtga<br>tattgatattcttttactattgatgacgattcattctgatattcattagatgtttctagtgattaaaagaaaacagttgtcttgatg<br>aaatcgatttggataaggaatctaaccaattagatactaacaaaatattaagtctagactctaattattgattcaaaccaattagaa<br>tctgatcaattgagtcaaccatgttcactactaacaattagattctagttactcaatatcaattataccagtctccaatcaactta<br>tcaaatacttgattgaagaatgctatgtgaagacatcgtagtgctatagacctgtactcagccaaatatatctaaaaact<br>tcatatttactattccatgccatataacagctccatataacagtctatgtattgattaagttgaaaacatgacgtctgacgcgt<br>tcaagtgtctcaaacctatacataagaaaacagcgtcctgagtgttcctgatactactccaattattcaaacatattttgaaacagcttacagtctatgcaatga<br>catttatttgtacagggctaacgaaacgtcagtatccttcttgagactctcactacaatacaatatactacaatatagatgtaacagactca<br>gctatatgaacttcatgaaactgcagttcaatactcatactgaaatctcatgaagactcatactgaaatcatactgaaatcagtgaagatag |

FIG. 7B-19

| | | |
|---|---|---|
| | | cggtttatcaaaccctcggcatggccttatggaatacatctgatggagattataacattgctctcaataata |
| Contig40_gene_847 | 1390 | atggacaactccaatatattaaatctcagtaattatagtattatgtattgcagcaggagtaactgcatatgtataagtgaggtgataatgcagt<br>cttcagtgatttaactgatttcaccatctagtactagtcgattctggagatactgaaataactactgaaacaattctgaaacgggcggaa<br>taaccgcagtcaaactaatgtgctaccaacactggctgccagcgcaagcgtgttcttgaaatactaaccaagtcctgacaaaataagcagccca<br>ggttctgatcatctggctctgccgaagttcctctgaagatgcggagaaatactaacccaagtcctgacaaaataagcagccca<br>agctaaaaaacatagcagctggccaattgccgaagaagccgcttatatcagcagcgtatcagcagcgtatcagcctatgtctgttatattcta<br>atgcagaaggtactaatgtaggttacattactgtatcacgtggagcaattatgaagtgccgaggcgcaacttaa |
| Contig40_gene_848 | 1391 | atggataattcaagcattcttatatcgtaatcatcgtttatgtattgcagcaggagtaactgcctatgacttacaaatgacacagcaatactgt<br>atttaatgaccctctctgatttactcctgacgaatctggagatacccgtatagaaacataccacagaggaaacgaaattcaggtagtgaa<br>taactgcaggaacaacagactctgaagtggaactgttcaagcgcactgttaccggctcaagcagttcaagctcaagttcaagt<br>tcaagttcatcaagtagttctaatactcagcaaaagcttgaaactcagtcagtgcaacatatcaattctgcgcaacaagtgcaacactg<br>aaactcaggatgcctgagacatatgttacagtgcaacaatattgtctgcggatattatgtctgttttaaaagatgatgctggaaacactg<br>gttatgcgcatatcgttctgaacacagtcttggagcaacaagtcttgaggatcctggagcaacaagtaactaagagcctaatgaagtgaagacgattat<br>aagaaaatgaaacttccaatatttactgaataa |
| Contig40_gene_867 | 1392 | atgagaaaggaaatttaattgcaatcattgcaatcatatattatgtggagtgtattgcagctagcacaatatgcagtagcgcggatattgc<br>tactttagtttgaatgtcaattgatctcgaggatagggaagcttaatcgttgactctgaagatatcactgcttcaaaggctctattataattctt<br>cggcttctgatgagaatgtgtttttgttaaaaattaagcaattcaattgtaaataagactggagaactgaagctgggaagactcttga<br>gatgatgcagactttatggattaattctgcagttctgttctgttctgttaaattcaaatgaaatgtagaattatctgatgttgaaatagagacattctaa<br>aggatccaatgagtatttgtaacaaatgctgttttctgattctaattcaaatcttcatcctcttctgcagccctattgttgattccactgaac<br>gtcatgatgatgatgagagtgatgctgaagagctggtgaagaggccttgtgacgatgatgatgatgatgatcagacatctcaaa<br>tgtccgaatcaccacacagtgccttagcgatggaaatcaatcatctatgcctgccgcgattggaaaactgcaccttgggaaagattattgcttcagatgttgaaatcaatacagatg<br>gccaaagctgtgcggctctcttgcaacagacagaggcgaaggtgaagtccatgtgaaaactcatcaaattccgaaggctgtgccatgtccagattgcctgcatagaaggggaa<br>agaggctctccaatcatctattcaacagaaacattcaacagttctgcaggtgtctgtggttctctgcaggtgcaggaggaaataggagaagtaataggagaatatg |
| Contig40_gene_872 | 1393 | atgttgatatcaattgtacttatctctccattgcttaggtgcagtaagtgcagctgcagacgtcgctgcagatgatgctgccagcaac<br>tgtagatgaagttcaaaacagttcaaacaattgataatacaaatgatgatatcatatgatgatatcatatgtctatgtactggcgactcag<br>ctgattctaaggcaaaaaccacttccctttagtcagtaaatgcagtaaacgaaggggaaactttgtctttacacaattgctgtatgtctttcc<br>agtccttcaatgtttgtcaggtgtctttattataatatgatctgtatcatcttaccaatgctaacaat<br>cattggtggcggtgcgaccattgcacgatattgacgggataatcaagcaagaatattcaatatcccgaaggagttagcgttaccattatggttgtaactctca<br>taaacggtgctgccgatgaaggtgcagtgcagttatttataactccggcaagttaacttaatgaatgttactaagtaatgacaacagcagcagtcaagtct<br>ggtggtggtatttataatggcggtgaagttctgtaaccatagtaaccttcagtgaattagcaagatttaacgttaccaacaaacctaagaacatgttcacagaggaactg<br>tgagcagcattactccaatgagttctgtaaccatagtaaccatagatgtaaccacacagtgtaaccaacctcgtttattgctaacagtgttcc |

FIG. 7B-20

| | | |
|---|---|---|
| | | tacggtggtgcaatttactctggtgagacgacttctgcaaatttattagtaagcggatctaccttgaagacaacttttgcattcaatgtggagc<br>tattgatatagttgaacttcctataccatatctgattccacattcaaaacaataatgttaaaggaactggta |
| Contig40_<br>gene_900 | 1394 | atgaaagaaattgctatttatctcatcctattcatataattgttctcttattgccgcacaacacttaaatgtagttgtctcaggtagtatgaacctgt<br>tatgtatagaggagatattgtagtacttcaaaaagctaatttatttgaataacatgaatcgacccctcacgatgttcaagtgttgggatatagttg<br>tttataatgccgcttgtatgacagccctatctggtgactccagagcagattacagatagagtcattacaattaatgccaaccattgtaattcctaaaat<br>aataacaataaatcgaccccttatggtgactccagagcagattacagatagagtcattacaattaatgccaaccattgtaattcctaaaat<br>agatatatcacttttatgggttaaaggtcttta |
| Contig40_<br>gene_906 | 1395 | ttgtttgaagcaggtatgattgcttcttcctactgtttgcctgactgtgctgccttgtttgggcttggtactgtgttaacagatattgcagtgaat<br>gttcgatgatttaggaacagatcatccagttatgcaaagccgaaaatcaattaaactcgagtattactcatgggcttaactttataggatttag,<br>gtgctagtgaaggacttgcaagaggggttcctataaagaaatgctaagatttcaactgtttatttggcttatgtgaaaatagtgaattcatgaaaa<br>acaataatgatgagtcattaggtaaggaaatgctaagatttcaactgtttatttggcttatgtgtgaaaatagtgaattcatgaaaa<br>ttcaatcaatggtggttaa |
| Contig40_<br>gene_909 | 800 | atgaaaaactggaaaataattggattaatattaatcatcctcttctgctgtcgtttcagtttagcgctgttgatgactcttcatctgatac<br>cacatcaatcagtgcagatgccctaatatacagaagatgaacctacgactcaaagaagaggttcgagcctatatagatgaatatcacacag<br>ttccttccaactacattaccaaaagtgaggcaaggctctcggatgcatggacaaagtatgcacctgaaaagtacatagagga<br>gacatattctcaatcgtcaatctcctataggccatgaataaccgagctaattacaagaggatgcgataacactcttgagctgacagcagaggccctaa<br>aagaatagtcttctctacagacgactatgaggtttactatacaggagccactatgcaagctttgagcacttgactta |
| Contig40_<br>gene_917 | 801 | ttggttcagaatactaatctaagcaataatacagctgtcttcaatgaaagcagaatgagaactctgtatlgtgttgttcattagacgttgttgg<br>taacaattgtcaaatcatcaacgtcactcgataacaacaatgcttatcgtggtgatccactttcattcgtggtaatgacactgtcattagaa<br>attccactttcgacataacaatgctaccttagaggtggtgattgaacattgctggtgaaggatgtaccatattcaatgtagtgttttcaaat<br>aacgctctggtgaaaacggtgagctatccacgtaattgctgacggtaccgattcaagaaaacattactgtgacaataacactgctgaacgtgg<br>tgaggcgcattcgttgaaggtaacgacatcattatcgataataatgtcatggctgtactttcaatgaaacaaagctatttcaatgaaagtaaacctgacgaat<br>caggtattgaggtgctttggataatcaaagtcatggctgtaactacctgcaccttagaggtggcggttgaacattgcaggtgagaa<br>ttcattcgtggtgacaacaccgttgacattccaatacctgtagactcacctttagaggtggcggttgaacattgcaggtgagaa<br>ctgtaccatccacaacaacgtttgacattccgcgaacgtgtggagctgttttgtggtcattgcacaacactcatgttgacaatgttaattcatt<br>gctatttcaatgagagcaggccagatgactggttccacttcattcgtggtgacaacactcatgttgaaactgtaccttgg<br>caataacactgcttatcgtgtggagttccacttcattcgtggtgacaacactcatgttgaaaactgtaccttgg |
| Contig40_<br>gene_930 | 802 | Atgagaataaaagattttcatttttacttatcgcatgctattgcttgctgcagtttcagcaaatgatctgataatcttgaagt<br>tgatgatggaaatgttgtatctactgataccgtaatcaatgatgtgccatgagtgatacttcagttgataagattgcctgaatgtagatcga<br>cacaatctaatactacagagatactaattaatgaaataacaaatattgattttaagcattgatatgattacacaaatgaa<br>cagttctgatcatgaagattcatatcaggctgatagtaatcaagaggattccattccacttcactcagatcaagatgaacattatgttaagtgaaaac<br>ttccatgcttaaagcggacgcgatcagattattattatacatcctgccggtagcctacagcacagacaagaactcgcgatgatcttgatagta<br>tgaattccgccttgaattttatttacttcagtgaacacacactattgtggttatgatggattatataagatactactataacaat<br>acagatgagacaacttaagcaacttgattatgagcaactccaagtcgatgaagggcaagtccacatttaacctgacacttcagacttcagattatcgaagtc |

FIG. 7B-21

| | | |
|---|---|---|
| | | tttatatattggcctttacaggagaaacataactatagatgattgaagttttactgattcacaatacggctctctttaatgacgatgggtataca<br>aataccatacagtattgagattcattaattccactacagttttgttgaaaactgtattgacaatgacgatacctatcaatgcaactgat<br>tcaagtgatgttgttattaaaattgtaatgttccaatagtaatcgttcaaatgtattaatgttttgaattccagcttttactgttcagattc<br>aaatttatccaagattagagatagctatattcaagttttaagctaatcaacaaccatctgtaaca |
| Contig40_<br>gene_964 | 803 | atgagtattaaacgaatattacttacgagtttaatgctattttataataatatttcaattcgtttgtaagtgcaaatgaaaatgtaacaaatga<br>cgtaagtacgaatgaactatcaacacaaactgtatcaacaaaactgtgaaatataactactagtgaaagctagatctagactctggagaaacc<br>gggtttgatgagatcaaatcgaattcgacagagagtcatcatcatccaattggaccttgaggatgcacttaaataacgatgaaattgaa<br>agtgatgtgtttaactaaaaatgaacaaactgcaagcaaataaaactagtcttgacattaatatgagtagagtacagcccaaga<br>tgtactgacgcaatgctacgaattccagtcagtggagtacactctatctgatagtgaacctactgaaggaggccatgccagagttt<br>ataataatgacactgatagtttccgtaatatcgtaagaaacgatgaatagtagacattcaaatgttcgcgtagtgtgtgtagcgtagacaat<br>ccaaatcaatatgctacattcaaccaaatactgtgatagtactttcattggccttcatggcgtgtttggatgtaatgaactagata<br>ttacctgattccgttttaattaactaacaagttacttttgaaaattaaactgtacaagtagattcttttagtttaacagcgggtatttgacag<br>attgtgtttttaataatctggagtcctatcagcaccctcttcttcgtaactggagcttacaatgatggtggtaagccaatagtactaactaattgt<br>aacttcaccaattccaaacaaacttacaggggtgacggccctgggagtgtactgatggtactgattgtgcggtcagtttggtgtagtattcggtgctgaat<br>gtatggatgtaacttcataactgcaataacagcactgctactcacggtgtgttttgtcttttcagacgaatggataa |
| Contig40_<br>gene_975 | 804 | atggataaggtaggaattataggacaggcaggtagtctaggtacagcttagctcaaacagtggctaatatgtagatacagtttatctgcacttaag<br>aagagaagaattagctaaaataaattcaactggataaaacagcgaatactatccaaacataactaaaaaacaatatcatagcccactactg<br>acatgaacgacttgattgattgtgacaacagcaaaagttattgaatatccctcattgaaatcaatggtcgcttgatagaagaatacttttgatgaaacctt<br>cgtagccttgtcaggcccttaatttgcatctgaaattgtcttgaacctttgcaaccgatcaaacattgcttcaagaagcagtgaaagccataa<br>aggtcaagaaagtcctatccacaccagaattcaagtaaaatcattgatgattgtaggcctttgagatatgtggagtcatcaagaatatcaat<br>gcaatagcaaacgtatctgtaaggaatgaacataaatggcaagtggaatatgcgtcttgacaaagggctttgaagatactggtaggattat<br>agaagcatttggtgaaaatctcatgccaaagaatatcaacagcaagcgaatactgtggattcggagccttgtctaacctcaacttcaagtgaaagcagaaccaca<br>cccttgaatgctctatgccaaagaatactaccacgtgtgttgtttaaactttaaggtaaaactcaatcatgcctaaaggac<br>atctgtaataataccaatactaacagtgtgttgttgtaatgtatatgtaattgttaaacagattccgcctaaaatagcttaaagacct<br>atgaacaatattgaggagtga |
| Contig40_<br>gene_976 | 805 | atgatgagtgaagattcaatttgcttactataaaatctttacagatttacaaactgaaataaacaatactgcaaatggcggaattaatctt<br>agaaggatattacaagtatatagacaattagacagtaattttttacagaaagttgtattagtaataaaacataaccattttggaaatgggt<br>gtgtcattgatgaaataatacttcaagttaatgcaaattaatgaaattactagctaaattctattgcttattcattctaaactccacaaatgtttatgg<br>caaatactggaactatggaagggttagtattacaaacatctcaagcacatttctatttaataacaattgtatattttaacaattggtgagctatctttcataata<br>tagtgtatatagcaaaactgtagcttgaaaattgtacgttatgtcacagtgcacagtcttcaagtaactcttcagataacctgaggtcacacatggtcgtcagtaactacttgatgaatg<br>acaaacaattatacttactctctactagaaaattgctcctttcaacagcacatgagagcaataacaagtgaggagcaataacaatagaggagcataatagcaaattaacactgta<br>ttgtttcaataattgttcatttgaaaaataaaacaggaacatcttcaacatacaatgaagggtcaattttatttgataattaaaatgatataagcggtcatctaatgtaaat<br>gtttcaataaaataaaacaggaacatcttcaacatacaatgaaggggtcaattttatttgataattaaaatgatataagcggtcatctaatgtaaat<br>atattaaatacttcatttagtaataatcgctcttcaagatggaggagcatatatcaaggacagcatgatatcttcaaactcttc<br>attcaataataactgcactagatatggaggagcataagaaattatcaaggacagcatgatatcttcaaactcttc |

FIG. 7B-22

| | | |
|---|---|---|
| Contig40_gene_982 | 806 | ttgatctgtagcatacaggcctgctcggcctcatgcactgcagtcgactgcatgtgtaggcctgatgtcagtgcagacggttcaacaatcattgcaagatg<br>caacgaccatcaggagttttgggaaaccatatcacagtgacccaagggtagagaacaagtcaagccgtcttatgctgtatgcgaagatggaa<br>gcgtaaaaacagagcttccggcaacaacttacaaatacacagccaccatatgaacagcacaaaagcatga |
| Contig40_gene_996 | 807 | atgaaaaatatcaagaattatacttatattattgcttttgtattttgaaatagagactgttcagctcatcatataccatagtaaatgctgaagt<br>tccaaaccctcaggaattatgggatatgcagttacacactgttagtcattcttcagcctgaaaatgtaggcggattgcttattaaggatccag<br>ataacattaacgttacaaataaatatgatctggccacagaactggctaactgcatgcaatgcaatgcagaggtggatggagtcaatgtgaaaatatgacaatcact<br>acaagtgcagatactgtgaagagccattcaatgcaactgtaactgcagttcaattaagcatataccataaatgctatgaagcggattggacactatcaatattgaatcca<br>cggacagcctgattataagattgtagcttcagttcagttaagcacataccataaatgctatgaagcggattggacactatcaatattgaatcca<br>tattaaggtatatgactcaaatgacgtaagaacgtaagctattccggttatgattcaggacctggcagtcatccagtggcagttcaagctgcagtcatgacagcggagcatcttcttcatctgg<br>tctgactcttccagttcagtggttccagttatgatagcggtgcttcttcagttctgttctgttctgtttctgttctgaagtggagtgtagtgattaatctat<br>taagtcctatatttcattatttaa |
| Contig40_gene_1008 | 808 | atgattttaattattttcactattcctattcattactcgctatcgtgcgcaagcgcatctgaagacataactgatacaattgaagcacctgc<br>tgctgatgaagtagtaacagttgatagtgaaatccaagaatagaaacggttgataataaccttgaagaatagaaaccgatacaaataattg<br>aagagtggaagctgctgacgatgaagtcataaatgaaaaaatcgtccaagacggttgcttggcttttagcatcaatcttaagtggagcaaactcttaaacctactggaggaaag<br>gaagaaaagttcaaatcgctaatgatgaacaaactcttaagtggagcaaactcttaagtggagacaactcttaaacctaactga<br>ctcaagcttaatttgagcaaaactcttaagtggagcaaactcttaagtggagcaaactcttaagtggagcaaactcttaaacctactga<br>gcgaactcttaagtggagatagcttcaccctaactgacagctccaactgagagagacaactcaactgagagagacttacccttaattt<br>gaaagcacaaccctattaggtagagacagcctaacagtcaactgacagagacagcctaactgagagagacagctcaactgacagaccttcttaacg<br>gagacagcttaacctcaactgacagacagcctattaggagataacttaacactcaatatgcaagccttttaggtgcgaaagcacaaccatcaac<br>tggacagaactgttagtgacaattgacaaatctcttaacagcaatcttgagaaaaacttaacaaacaaac |
| Contig40_gene_1021 | 809 | atgaaattatatataaaaaatagcataatttcattttatttaattttatcgattggagcagctggacagctgtagaaaatgattattctaatgc<br>cgatttagatatttctaatgatttttgttttaagtgataattctaatgaaatttaatagattcttctggctcttttagatgattcttctgttgtcct<br>tagtttcagaaggttcttctaatgattgattgattcatatttcatattattctagaaaaagctttgtcttcaaatgaattggctctctgattgaa<br>gactctgtctattgactcaactactattgaagataaggcctagaagaaaaagctttgtcttcaaatgaattggctgaaggcacaaagacatatac<br>agacctgctaaaggatataaagagtgcttaagactgcttaactaaatacgactcattaactatatacgactattgacaaagtcttaaaaaag<br>gaatcgtattaaccttgatgaagactatgagcttacaatcaatgaaacggccatattatagatgaaatgaattgctgttgttgttaactttt<br>gaaaatggtgaatttgtcataaataacctagcttcaaaactgtaagatatcctctaatcttaactagctgtgatttcactacaaattatgt<br>cacttttcaaacaattatgacaagagctctgtgcatgcatgtataatcttgacaactcttattttcacagcagtcatgataatttatagataact<br>atgcgcttcaggatcagcctatgcgaatgcagtgtaatagaagactgtttgtttagaaacaccgtatccaattactcaactcagtatatgcgattatat<br>atctatgatggatgagaactctcatttttactactcatctccaattctccaattctccttactaatctaatctaatgctgctatgatgaaaaccaaattactcaactcagtatatgcgattatat<br>aatagaaatctccaactctcatttttactactctaatctattccaattctccacaggaggaggaggaggagccattggagtaaggaatg |

FIG. 7B-23

| | | |
|---|---|---|
| Contig40_gene_102_5 | 810 | ttgcagtgatttgataatcctatttcacttggaactgttgcagcaagtgaaatatagttattgatgagtctctgattcaattagttat<br>agaccatgcaagatctaagatgatattattattcaagaagcgattggatgattcttattatctatgatgatgcaaagctctatcgatttgacgaataacgtctcttaa<br>caactatctaattcagatgatgataaacagcttaaaacttctaatttagaagatgaaaaacagctgaaagtgtaaataaaggagataagcttcttaa<br>agattcaaatgacaatgtcgatttgttttattaatatgatgtaaagacatcattgaccaacaagcaataaccgtgcaggaagcgaagttccat<br>ggattataactgtttcctctccaatggaaaatgaattggactgttggtgactcttctaaaatgcaagcttgacaatattgacaagattgaa<br>acaatggaacattcgatccgaaaatgaattggactgttggtgactcttctaaaatgcaagcttgacaatattgacaagattgaa<br>aagagatggtacatataaacaagcttatgctactacagagacaagtgatgaaagagaggaattcagcataatgttcattatgctagtatgtttgatacggac<br>gttcatcaaagatcacttctaacattacagagacaagtgatgaaagagaggaattcagcataatgttcattatgctagtatgtttgatacggac<br>tttatatatagatagataaattgaaattattcaatgctcagaatatagattatcattctcttccaaaaacatcggtggagcat |
| Contig40_gene_102_6 | 811 | atggtctcagtgatggaacatttctgcagttagctattgcaaatgaatgcgctaagtgacttaacgatggagataagtgatgataaatagctattga<br>tagttctctgcttcagaaggggatgattttagctattgagtgcttcttcagatttgatagtaatgaattctatgatgagtg<br>taattaattctaattctattaattctgattcctattaattctgatctcttaaccctaatcctaatattgatgataata<br>aataaccataaagatagctttaaagctgtacaggcctcaaaaccgaacattacagagctttaaactaagataaacaagcaagcaaagg<br>ctcaacaatctatctggataagaattaccctctataatgatgactttaaagcaaatatgaataqtgataaacaaqtctatcacaatcqatqaa<br>aaggccatgtcattgacggttaaagaaatcaaatcttattgcttcatcaatgatqcttqattqtcttaaqaacataatattqaaaqqqc<br>gacgggacqaqaatqqaqctataaatctcctccttqtatctttttqqaaatqaqqaqcqcctttattcqattattccqataattcctcttcattqqtqttqttt<br>tgtatttttatccqcaqcqattactctccttqtatctttttqqaaatqaqqaqcqcctttattcqattattccqataattcctcttcattqqtqttqttt<br>qtqattattctcqcttqtcaactqtcaataqcqcqqtqqtqcttttaqcqatqcaatqqccataattcctcttcattaactqta<br>ttcaactqtacttcaqcqctaaqqctaqqcqqtqqtqcttttaqcqatqqccataattcctcttcattaactqta<br>tqacacttccaqcqctaaqqctaaqqatqqcqqtqqtqcttttaqcqatqqccataattcctcttcattaactqta |
| Contig40_gene_102_9 | 812 | atgagaaacctaaagatattatattatgaagactgatttatttgattattctatagaacgtgattcttctatagttcacctatagcagctgc<br>agatagctttgatttgatttgatattccagaggctatcatatagagaatgcaagcagtgattttgtactattggaqaatqqaqactattatqcattt<br>caattccattatgacaattccacagagaagactctgatgatatgctatcaggagctcgatatgctgaaaggcacaggtgctatgcttagaaatgqtqtcaattat<br>accaaqqqqatttttatatagagaggaagaacccttattatcaqqaqttccaaatqqaattttqtacttttqaaaatqtaqaqatcttqtqt<br>qattqattaaaqqaccttaqtaqtatqqatttqaataataqtcctataqtqcattqttqataqtaqttttaaqtqqtaaqttattaa |
| Contig40_gene_103_6 | 813 | atgaataataaaaagatatttgtgcggattagcagctcgacttgtttctaatggatcagttgctgcagttgatqtqqcattcttaqcqq<br>agcccaaccaaattcagcattgacggcatcgactccaagaccgagctactccacaggatatgcagttactgacaactatacaaqaqtqaatqatacaqaca<br>ctgctggaagctcagctataggttacccaagaqccaataaqactcttaccaaaatqqtqtqqacqqatatqcaaccaaqqqqattatactacattcaa<br>atgagtgaggatatcatctccaaagaggccaaataaqactcttaccaaaatqcaqatttqcttqaqqatatqtqqtaatcaqacaqatqactqa<br>ttatctgttgatggatcttgtgacaatctttgtgacaatctcttaccaaatqcaqatttqcttqaqqatatqtqqtaatcaqacaqatqactqa |
| Contig40_gene_103_7 | 814 | atgtccgaagatattgaatcaatgacaataatggtgctttgatagcagacgttaacttttgctgatgacaataataatqcttaaaqctqaatc<br>caactctgctagtcagatgacgcttcaatagatgaatctgctaatccactccagatcttgtagatacagataatqqattaaaccaatccatca<br>ctaaagccactatctactataccaaaccaatcgcctcactgttacaaaaacaatctgataacagctctaacatqcctqaqacqatttacqacatt<br>ggagacactatctactataccaaaccaatctagaagaaaqcataqcaatatcaqtqttqtqaaaacttcctqatqatqat<br>atgggaatatattggtttgctgatgacaggagaaaaatgagaqaaaatqaqaqcaatqtattcaattacaaaqcattaqaqcctqaacataqca<br>tccttctcaaqatacqtatqacaqqaaaatactaacacattaacacaqqcactttacattaacaacaatcaatqtaaqctccaactcaacaaqctcaaqaqttctta |

FIG. 7B-24

| | |
|---|---|
| Contig40_gene_103_8 | 815 | tccgaagaagtgactgttatgtctccaaattaacaattacaaagtgccaatgatccaatcgttaccatcgttgagaatagcaaacttacaat caacgttaccaataacggaataagcattaagtaattgcgtatctatgagatcctgaagaatcattattcctaaatgagttcactaacataa gtggaaattggactctttttgcaaatcgtgtggagattacgttttagcttggacagctgatataagtgaatctgctgctataatagtatct tttttaacaacagaaattggaaattcaccatagtctatagcaactatcgaatcctcaagtagaggcaaatgccactgtcacagttgttcc aagaattgaaaagactgtcaatgcactgaattgatatgggagagtctgttgaatacaatgtttacatcgaca |
| Contig40_gene_103_8 | 815 | atggacttaataattcaaatatcttgatgattcatagtggtcgtgtgcaagaaataaatctagactcagacataatctcagaggacaaaga agcaaaaatattcagatggaattaaactgaacatagacaatctcagtcatcaatgaaatgccatatcattaacgcaagaaaaacaagaa tattctattccacagcccaaaaacatcacaatagattaaaaaatgaaaaacaataccaataggagagccatatacaacctaaag gcaaaataaaatcatagaagccacaataaagaaacccaatcaaaatatgccgatccataaagcaatatacaatgacgaaggagaatgaaataataaa gtccacattcacaaaaacaatgccaatcaaatgaggggcaatccaactatcaaagcagatgagcatagaaaatgatcaaagactttggt acaccgcaaagcaaggaggaagcatccacaaactaaagcaccatcctaagcatgaaaaacaccacattaagaaaacgatgcaaaagacttggt ggagccatattcaacgatgccaatgatcataaatcaccgaaagcaataggtaaaaatcacgaaaccacagctgaacaattaagcataataatcct tgagaaataatcataaaaactccaatcatatgagtacgtggcgcaatacaaaaaataaattctcgatgagaaatattcatcaaagactccataatcaccgaaaca atatcaaacaaagtgaggattttctcaaacaataaaaaatacaaaattacgacttccaccatcgaaaacaatgaatctgacaatatccatga aatagactcattttagacatggattga |
| Contig40_gene_103_9 | 816 | atgagcaaaagtttagagacctttgaattattgataaatgcgacgatgagatagtttgattcagacattgtttttaggagatggtgaagg cctatttcttaggagaaggcattaattgatagtgatgatactgcatcgtgatgatatgcattcaattgatgcatgtgatcatgtggaaagtgagatatttt attcttcaggagaacttacaattcatcatcttgaaactattctgctgatgatgaaactatgacacatagagaaagtgaattgccctataaactccac agttaaggagaataaaggaattcggtgagcaatcaataattggacgcttgaagattgtaaactgtgaataagctcaaatgaggcac gttttggtgagcaatcctaataatgatggagcaattagagataagcagcgattctcttttaaagacaacaagcagataaggagagagttatctat atcaagatggtgactttccgttcggttgaaaaacaactcttgagaaaacaagccatctgctgatgcgcggagtattctataatgaaaattgtgatat agcgttattgaatccaaattaaatgacaatcaggcagatcctattgtgaatcaattatgagcagagctcagattgttacagtggcagaagaatcttctaattat ggcgggccatatacacttatgatgagtggatgatgagatgcattgcagatctagattgatataggagcagaatgtgtggagctatctatagcga aagtgcatctgggatgtttctaattcagatttaattcaaataagctaaaaactctgcgcggtgctatattat |
| Contig40_gene_104_2 | 817 | atggattttagagaggaattaaataatatctgatgatgaagaaataataaattaaaatcaactaaaatttaaatcaactgaaaacaactaaaatcaactgaaaaacaaaagacaaaaa agaagacaacaacttaaaaccaatcgataacaaatcgataacaacaataagaagacaacaaccttaaaacaatcgataacaatcgataaccaaaatgaaa ataaagacctaaaagagaagaaaaactccaacagaaactgatgaagaacgaatgcaaaaacctaaagaaacatagaccatccaaaaagattt aagaactaaacaccacaaacctgacagcatttctatctaatatatatatcagtgaggagctgtctgagaggagcatataaaagatgaacaacatcaccgattgaa agagagaaagaagacaaaagacattcctatctatcagtgaagacctgtctgagagagcatatatcaaacatatatataagacctggaaggaatgc gcctatcatcagccaaggattacaagcaagtaggaatcatgtttgaatcaatgtttcagactcaagctggcaagtcgcgacgtctaaggtatctgatgtctc acatggacacttccaatcgatgaccgcccatcttattaagctgcaatcattaaggaccttatcaatgctgctcaagtcctgattgacgtaatcggacttga tgtgagcatgtttgcaggctgcaatcattaaggaccttagcaactttatcgacactcatgggacctaaatgaagtcactaaggaatggaacaagaaag acagatgcaattcagactgtagacactcaatggatcactgtatataaatggcatcataagcaaggaatcacttaaaagattggaatgactttcaagaa cttaactgacatttcagccttcagcctagccttaagcctttaagcctaggagccatgacaatgtctcctttgggaatggataagt ... |

(continues)

FIG. 7B-25

| | | |
|---|---|---|
| Contig40_gene_104 | 818 | atggcagaaatgaccataagagaactccattatagaaataacagtgcaaggaatgagagggcgatcctcaatgatgatgaaatctttttattgaaaa gacgactttaagaataatctgcatttactgccggagcaataagcaatggaggatatgttcctaaaggatgtttcaatgaagtaacattg cagttacagggctgcctcatcaatgagggagatgcgaagatgagagacagcttataataaaaacattgccatagtgaaaagaggaatg aacggcgaacatgatgtcgcggagcagtcggtaattcagataatcttttgctgaaaaacacttccttcattaataactcatcacctttggaag tgcaatatacaatttaggcattgatattccaaaattaaaatattttatgtaaaataaaatagaagactgcagattttgaaacaatagctcccata taagcggtgagatctcataatgagataggtgaaatatcaatagatgattccaaattcaaaacgaaactgcaaaagaggatcagtcatatacaat gacagttatctgacaatcacatcagacagcgcagttattgaaagttggggaaattggaatcttaagcattgaaaaggaaaatcgccaataatatcagcgatt ataccactgtctataatcatgaaaggattgcaacattacaggaactattttgaaaacaatcactctaaaaagaaggatcctaactgccgagaaaaaatataa aataatagtccaatatgtcttaaaagaaataatccaaaagaataagactgtcagcattttaattgaaaatgagttaatttttagctatttgatg aaacttttattttccgtaggcaaagttttttttatcttgaatgaaaatgagttaatttttagctatttgatg |
| Contig40_gene_105 | 819 | atgggattttatagataaattaaaaaaagaataggcagaaaataagaaaaaagctctaaaagagataccaaaaggcactgattgaagag gaaatctccacctattgacaagcatcttttgatggtagcgatcgcctattgttgagctcttgaaaatgacataatgtcctaggacgagccagtcg tccatagtatcttaagaaaaataagtgacgatcgctattgacgacctgattgagctctttgaaccttcacctcgacgtgacgcaatccta aagataaaaacatgcctcaagagaagactaattgaaatataaatgatgaaaggaaattgagagcagataatacgatattcaaatgagaaaatgcaaaattgactctatg gttcaccaaagagcaactaattgaaagagctttctcattgatatcgtatgcctatcaaggtatgaaaagcatacgagacaagttgtgaaagatttaaaaacgat acaagataaatgatgagaagatgcctgaatccagcagaagcccgagctttaagtctaaagtagccaatacataaacaatgacaaggaactaaagaa atacatcctatccaaaatgattgaacaacagcttgagatgcccttgaatagagtcatgagcgatgaatcaatgacgatagccttttagtgacctgatgcatataatgagactgatga tgcccataaagaagaataactacttgaagttcgcaaaatcagctcaacaagtcaatagagtcatagtgttcatgagcgatgataagaccctattgaatatttgcttgaatattacaatctg gattatgacagatactacttcgagattgaaatgccttcataataacagttttaaaagcgaagcgttaaaaggagaagcgttaaggagtcgtcaatgaccctaatg |
| Contig40_gene_107 | 820 | gtgccttttaaggttgcagtgcgtagtgcttatctcaatgtgcttcacttcaaaaagtccaagtacgacgagctgataggagcagtaggaacctattttcagtgaagtaaaat ccaaaactatacaatctattcaaatgagttcacttcaaaaagtccaagtacgacgagctgataggagcagtaggaacctattttcaatgaatcaggaataaaat actccttgacatatttgtaaacgacaaaaagtccaaaccaagtacgacgactgatatgcgaatatgcaggattaggacatatgtttaaataattac atcctattaagtctggagacagttcaaggtagtgtctcaaggcagtagtgcagccaattcagttcctatcaggcatgtcgtcttatccatggacactacaa atccctgtaagcgctgatggaagcactgattgattattgaatatgcaagcactgttattcagcgtaaggctgcaacagagtaatataatctgtaggacca ggaggaaagtcacttcaccatcaacaagcagctacaatcaaaactgttaaaaactaatcaatgaggtgttggcacaggaagaacaagaatcctatatc acataacaagatgagccacagtggctgtcaattgcaatttccaagtcgatgagcagtcgatgcagtctataatgctatcagctcgatcaggcggtgtaaaactcacgatgaaggacagcgtta atataagtgccagtgcacgttcatattgcattcgttggagacatattcttggagacaataacatgcagctcattgaagttgcaatca tgaaggctcatcaccttgcaatagcattcttggagacaataacatgcagctcattgaagttgcaatca |
| Contig40_gene_107 | 821 | atggagaaaactatgaaatctaaactttttatacttctatctcattatcagtttcagcagttcatcagttcgcaagtgaactcaagc tgatgcatcaaatatagataatgattatcaaacaacatgaatttgatcctactctcgatctcgcaatgatgaatcaaaccaggattaaatctga aaaacaataatgaacatatttaaaagaagagaagaacacaaacccccagaatagagatgaaacatgcttacaacttatatcagaatcaat caatcagatgatgagctaaacctcacacatgcttaaccctcaataaaagctatgacaatgccagcttatacaaatgtattacggccattaat ttcagtgaataagaccaattttacaatcaatgacgtcatcgacgaaatggccatatgaaatgtgattgatttgaaacaataagg |

FIG. 7B-26

| | |
|---|---|
| | gagaaattgtaattaatgacttgacatttaagaatttcaaccaaacagtttacaaatttacgaaagcttacattaaacaatgtcaacttaca<br>gagagctttgaatcacttgaaagcattatattgtaagcaaggcgtcttgaatgtaaataattgcagttttttattcaaaccgcaaagaatat<br>cataagcggatccagtcaaatataaccgtaaacattcaatctttctgaaatgcaattatgaaagagcaattcagccaacagatggcagc<br>tggtcatccacaattccagattgaaaattcactttcaagaacgtgcaataacttgatttcaaggatatacctagatctagaaaactcaagt<br>ttcaataatatacattccaatttaagtgcggagcaatacttcctgcctaacgacgggagcaattcact<br>atcagacctatgataatcaaaaactgcagattgaaaacattcctgcctaacgacgggagcaattcact |
| Contig40_<br>gene_108<br>4 | 822 | atggataaaagattttatagttagcttatctgctagctatttcacaataggggctgttggcgttctgatgtatcagagctgacagcaaa<br>tgatttagatgataatgcttatctctaaatgatgtgaagatttgcttgctgagatgaatctggtgaatctgcaaggaatcttattttaata<br>atgataataactaatataatgaaaataggtaaatgcgaatataactctgattatgtgctggtgataatgatgcatctaaagacaaggtcctatct<br>gataatgtttcgattatctatgccactacccttagcgtctgtgatgacactccaaagcagtatctctaccgccactgtcagcttaaa<br>tgatttgagtggcaatcctgttgctgaagcagcgttccgtcagtgtcagtgtcatagtgtgggcagagtattccggcgatgaagttatgcatcaccacacagatggtacat<br>gccctcttcacttgataactatctgtctgtaggcagtcataagttgggcagagatctgttgtttcatatatacaggcactgcaggaaggggctatacttcgt<br>accacattcaatgtactgactcatataaatcagcctatacaatataagcgtacaattttcccttatgctgagctagggagaatattcaaatgacactgtaggtgatcgagatttgaacccctca<br>tacagtaagctgactcatataaatcagcctatacaatataagcgtacaattttcccttatgctgagctagggagaatattcaaatgacactgtaggtgatcgagatttgaacccctca<br>agcaaggcgaaatcgagggatgttattcaattcagcctataaatcagcctatacaatataagcgtacaattttcccttatgctgagctagggagaatattcaaatgacactgtaggtgatcgagatttgaacccctca<br>aatgccaccaaatacttcaatgtcttgcctaagacaatatgagctgtagccctatggagcgtcaatgtccagcgtcaatattcaatgatcctctgatgctcaagtggaacaca<br>agctaatgcatatgtcttattggaaagacaatatgagcgtacaatttccatcagcgttg |
| Contig40_<br>gene_108<br>8 | 823 | atgtgaaaatgactaaaaagaatcttttttaatagtttaatactagtctttttaatactcttaacaattggtgctgcagcgcagctgatgattatc<br>tgcatcatcagatctgacagttgaagatctgaagatcctgaaggagccatagctgagaagccatagctacgcgcttctgattaatgagaatcctgattaatgaaaataatgagattcga<br>ttgctgataaggggcttagtgctactctctcaaatgaactgcaatgaacctgaatatcgaaatcagaatacaaatgataaagctattctgaagag<br>gataattccattattctaagacaaggcaagtctcttcgtgaaaatgaaacacccgtttatttgactataaatgctccaaatatctattatgg<br>tgaaaccgctaatgtaactgtttctgcaagtatgggcgtggccttagccaacagtagcattatctgcttgtagcatcctttgtgaacatccttagcgatagtgt<br>atattttaattttgatgacgtattgctcaaaagaattatactgtttgcaagtactatgttttaaccagccgacagtcaataagagatataactatccaagtatctcttagccaagtactacaagtttta<br>ccttatcttctgcaagtgcttcaaaagcttaaccttggaaacagtctttgcaataaccagccttttgccaataactatccaagtatctcttagccaagtactcttagccagatgtccttat<br>agcttatgtcactcttcatgtaacctatggaaccagccttttgccaataactatccaagtatctcttagccagtcaccagtgttccaatcctcagcttgataaggtgatgatga<br>tcgtagaggatgatgcaatcaagtgactatcttcagttccaatttgcttaccaaaaaggaactgttcaatagctaagccagtcaacacttgctcacactgttttcagcatactcagttgatatgctcctattat<br>ccatctgcaagcgcttcaaaagcttcaagttcaaagttccaaaaaggaactgctatcatcgtgcgtgtccaatcctcagcttgataaggtgatgatga<br>gcttcgtttcactcctgcgcaattcaaacggatttatgttatgctaattcctattccattcattatggttgatg |
| Contig40_<br>gene_108<br>9 | 824 | atggtgattatgaataataaaagcttttttattgttagtttgattatactaactatttgcaataggcgctgtcagtgcagctgatgatgcct<br>ggccacatcagatgagataacagtggatgattcgtcagtagccgttttctacggctctgcagatgccagatatttatgaaactaatgagatatag<br>ttgctgactatcaaagtgattctatctcaaatgtgattgatgataatatacaagcgtgatgataatactaagcgtgatgataatacaagactccttctctgctaaggacaat<br>cttcttctgatgatgatgacgatcctggtgctgtaaatgatgatgatgaggatgacgatgaaagactacccttgatgatatctcagtgtctat<br>cacaaatgaatatgacgtaaccgcaggatcggttatagtttccattcgtccagatgttgaagaaggaggatgcattgaaggatatt<br>ttgtcgtttgtcttgatgacgatgatgagatattcttagctccttcaatcatcactcctgatgactactcctgatgatgattacttactt<br>gcttcagttagagattacagaagctgcaatgtggggattatgtggtacgtgtttctatgttaggatcgtgatgtgaaccctttatcgataatgatgag<br>tttgacactagtgctatctataccgtttactgctttagtgcccagaaggcacagtcacttaacttaatcgtccctcgagggatgaggagatgtagagacatct<br>agatgatacaatatgattttgatgggattgtattgcaagagattacactcaattttatgtcaagagaaggacacagtcacttaacttaatcgtccctcgagggatgaggagatgtagagacattca<br>tttaccaggaaattgaagatgctgatgatgaaatcaattaattatgggattagatatatggattgaacactatagatgccggcaacta |

FIG. 7B-27

| | | |
|---|---|---|
| | | tgaggtaacaatcactctgaaatggcactctcatttgtgaggatgataagaattatgatcctatagaaa |
| Contig40_gene_109_3 | 825 | atgaagtttaataaaaataggggcatatctgccatatcaataattttaattctatttttaagtatttctatgcgatctgctatagaaataagtc agatgatgctgatatgattctggagactttatccgttgtgaagtcagcacatctgattgctacggcgagactcctaatcagcgctgatcatccg gtgctgattcaagtgatgaaattataatcaacgaaacaattgcagatgaaaagacagacatcgcagctcaatccttgctgatgtgagaagaa aaccttcatgtttgaagtctctaatgatgttttcacacctgataacgattatgagttcatgtctctatgtgaggatttttaatcaatcggagata tttggatatatatcttaatgatgaactaacatatctgatttttaccgttgatagtagtcaaaagaatttcttctattagcttaagtgtctagagtgcg gattaaataagataacttcatatatgatgaaggatgatgtttataataatcgcctaatcaacaaaaagaatttacattatggagaaatcctgaa tttgtcatgataccttcattacgatacataccataacattaaatgcaattattcttctagagtatatcgaaggaatatgatgaatatgggatactatga tgaggataatgagggcgatattgaacctatcgatgaaccattaattcgatgatgccatcaaaaccactgaaactatttgattagatgtcttaatgaagctcc gattatagctatgctccatacaactcatctctaacattataagatgtcaatgtcataaccgattttatcattaatgatacctactttattccgga taagggtttcgattctcagtttatctgttgataatgccactgagacatataatgagataaagaatttaagctta |
| Contig40_gene_109_6 | 826 | atgcaatgtatctgcttctgatattagtgcagatgattctgtatctttagatgatgcagatcgaagcactgattctatagtgt tgactctgtaaacacatattctgcagattcagattcatctcttcaatgaagataaaagacaattatcaccctttccaatctaaaggatgataata agatttcaaaaatcaattatgaactttaatgacacacgtctcttttatggagatgatgtcataataaacgcaaatcttacagatatggacgaaacata atcgatgagttttccaagttacagttttatgatgttgcccctaagtttgcaggcaatgggatgaaatatgcttcctgcaatgaattttacaagcttgtga ctttaaggaaaattcatatcttgccattctaattctaatgatgaaggatctgatgaattcaactaatgtccttacaaatggaatgaagtgaccattga gacgaatatataacgacacagctgacattttacctttaggtctgtttagttaaatataacgctctaatatataaggctcagaaacatgataatgtataaacgatgacgaatctatgttccatttgaagataagacgatggcaatat tg atagcagagtggatgtggaaatttacgaataactactgttcattaaagacgattatgtcgtgaatggaga ggcaataattgttatttatcaatccaaattgcgtgcaggcgttacatatttcataagggctgattatgaaggaa |
| Contig40_gene_109_7 | 827 | gtgtttatttgaaatttgaaattaaaagaagttttaatattcattcaatattgcaatattgatcttatctattggaatggcatctgcttctga agaaatttctgattctgtttcaactgatatagcatctgaagatgttacaagcgaaattcaaacagataagttagaaatactagatgaag actcttcttttagatgatgctgagttgctgattagaaaaagatacaggcgataaaagtcaaaaagcaaagaaaaagattaataatactctctaccaaaat atgagtaccacccgctgagttcaattgatgaatatgatgcagaactggggaatacttttagtgatgaagacgacagcctgtagttgg cgaattgattcaaattgcatctgctattggttcaacgtagaagatcttggagcccaacttcaaatcaacttcaacctgttcttattcag gtcctatacctttgctctatctgctattggttgaagataccctatgaatcttccttgaagttgcagtaattgttgctgctaaaagatgact ttaactgttccttcaaagctataaggcatctgctaggtaaggataccaaaaccattaactgctacctaaaggataataaggtaagtaagcaa acagatcagctcagtcactgaaacgtaagacataacagtgcaaagaaccgattccaaaggtgtagctgctgttaaagtaagcttaaaataaagcaa cttacagcttcacagcaaatttgctggagacaagtcattgttgcggttactaagctgttcgggttaagttactattaaataa |

FIG. 7B-28

| | | |
|---|---|---|
| Contig40_gene_108 | 828 | atgcaagcaattattccagttcaaagcaatttttctaattttagtgacaaatatgaagaaaagtgatttaaacgtatattcatgtttagttct<br>tcttacttgcttgattggtcagtaagtgctgtcagtgatacgtttcagtcgtgaagacgtttcagtcgtgaagatgctgtagcacagatgctgtagcagttgacaatcactgaag<br>atgcaagtgaccctacagataagtacgtcagcgagccagtctccaatgatgttcaagcaacacaagcaagaactaaacaagaaccgct<br>accaagtctacaaatgtcttgaaagatgcacatccactaacattatgtgcgactactggtagcgatgagcgtagcgtagcgtagcgtacaatctac<br>tgctgtagctagtcttgctaaagcagttgagattgtaaatgctaaagctgtacagatttactattaatgttcaaacgtgactatatatta<br>gcaaaatcgaaagtcctgcagctaaaacgtaaatcttattgtgaaagcaacaagaaggagcgattcttcacgcttctgatacatatgtatcaac<br>gtttacgaagataacattcatggactattgactatctgtatttcaataagcgttcaaaaaacgtgctattcataactccactgaacaagacaa<br>tatagacagtgtttcaataaaacactgttctcggtacttcatctggtacagtacagcaacatatcacttacatatgtgaagtcagtacttgataat<br>tctccaatgtcttctatagagactgtttcggtacttcatctcgtagtacagcaacatatcaagttctgtttatctatgccgaccagctcaaaccaatgttac<br>attgaaatacggttctctatggtcctatggtcctatgctgaaaatacgtgcaatcgaacagcaattctaagtctgttatctatgccgaccagctcaaaccaatgttac<br>tttaagaattccgaattgtgacaatcggtgctatggtgttcattgatcgaagctaaaggagcatttaaag |
| Contig40_gene_109 | 829 | atgaactttaaaaaaactttaatgattcattaatcttattatttgtcttatcagtaggatttagcacagcaagcgctatagactctgataatct<br>attagatgaaaataataatatattaatgttaattatattgattctgataattcagattctatttttaattctgacaattcaaatgtctaaatcaa<br>ataatttaataattaaaataatttctataaaataagaattaaaatgaattaaatgaatctctaattctaaattctaaatttagagtgtgattcttcaatcaatgaa<br>aatttagattagaaaaatatgactctagaaacagcagttgcaaacatatcaaagtctgtctcacttgctgagaaggatacaccatccacatccagcg<br>tgaaatgatggttgactctagaaacagcagttgcaaacatatcaaagtctgtctcacttgctgagaaggatacaccatccacatccagcg<br>gtacttatgaacaaacaagtccacactaaaaagacataagcttaacactgtacaatagacaatacactgttctctctaattacactgtttatctaccactactactgtacatttggatcagta<br>gcctttacatacactttcagacactcagaacactcagaacactcaaaagacaataagcttacatttaaaaatatatattttcttcaaccactccaaatccaagcacttatcagattttggatcagta<br>catgctgaggcgcgatttgcaaatagaacaatcagaacaactgtacattggattgaccggctcaatagaaaccggcttatcagttgcccaatctaagtaagta<br>caggaagatacaacaccaattcattgaaatatcaatgaaccaggctgctgttgttgttaataataaacgaggctatatgcagattaacaatgcaa<br>gttgagaattgtaccttcaaatatcaatgaaccaggtgctgttgttgttaataataaacgaggctatatgcagattaacaatgcaa<br>ctgtgttttaataataaccggcaatttgaatgctgttgttgttaataataaacgaggtatatgcagattaaaaatt |
| Contig40_gene_110 | 830 | atgtttctaataggtgcagcaagtgcagcagatgatgctgttactcttgaaggggatgctgcagctgttgattcaattagtgaagctgagc<br>tcctataactactacggttagtgaagatgctagcacaaaaggattcctctgatgctgttgccactgtttaaaagacgaggaatcaataacaaaactgttgaagcaaggcacaattc<br>tggaactaaagaatgtacgcttaagtgaaactgctcgtttaacacaatgaatcaatataatattctattggtgaagcaaggaggcacaattc<br>aatgcaataatgacggcttaagtgaaactgctctgttgccactgtttaaaagacgaatcaatataatattctattggtgaagcaaggaggcacaattc<br>cttgatttcaaacggtgtgattatcacattgaacaaatcaacacaatatgcaatataatttctattggtgaagcaaggaggcacaattc<br>ttcatgtctccggcgattatgactgtgcacaattctgactagcaaaccgatgtaatttgaaaactgactaaaccacactctctacaagt<br>gctgccataaggattcctacaacctccattcaagttgacactgactagcagaaccgatgtaatttgaaaactcagatgactcttctccataatccatgttctgtttgaaaag<br>ttccaatgaaaaaacctccattcaagtgacattgacactgagaaccgtttcaataaaccgcataagcggtttaaaactcagatgactcttccataatccatgttctgtttgaaaag<br>gtccggttagttggataatgtgaaataagaggctcttatgctgcctcctgtcttcaatgcataatgtctatgcgacccttattggagcatacctttt<br>taagcagcgctgatcctgatgtgacactagttccgataactgccttaagcttcatatgcaagcatatttccagtggagtaa |
| Contig40_gene_110_4 | 831 | atgaaaattaaaagagttttgtcattttatgctcattattactattgtcaagtgttgcagctagtgatataaatgataacaccat<br>aagtgatggtgacaatctaatcaaagagcagatgggactttattaagcctttgaagatgataaataataaagaattaaatgaagtcagata<br>aaaattttactagtccaagatctgataatgataataataatccagatcagataaaatctgataatctgataatgataataatcaagaatctgataatgataataat<br>ctagaatctgatgagggcttattagtgatacaagatctgatgattaaataaaaaagcagacagcgtagttttgttagctcaaaatacggagataa<br>cgctgctcctataaaattaacactagcacctaatatataaagaataaacagctacctgagaaagaacaactacactgcctaaaggaagaataa |

FIG. 7B-29

| | |
|---|---|
| | acaactacctgaagaaaagcaataacaatgccataaaagaggaataagcaagtatatcttgaaaatagctataaggccttacaaaagaata<br>acaactatctagaggaaaacaatttcagcaccctaataaaagaaacaactatctagaggaaaacaactaccctccatcgagatggaat<br>taaagctatcttcaatcaaacaattacagctctcttcaagatgtccttagcagtgtaataagcaagaataatcatctaaaaagaatcag<br>agccaattgacgatggaactttaccgcttgcagtataaaatcaattctgcccaaatggcgctacaatagcctagataaggattatagctat<br>gatgaagattcagcacaagaggcattgaaatcaagaaagcattacaatcaatgaaacgacaccataaacgactgtccgcatcaaggat<br>ctttctcattcatttgattgactggatgaaacaataagtcacattaaacatatagtattcgccaatggaaaga |
| Contig40_<br>gene_110<br>6 832 | gtgactgttttcagttttttataagtgcttcatttgcttttgtcaatgttctaagcaatgcagataacgatctgtgcaaacttacaatagtcataa<br>ggatatttcctctccaaatgtgattataagcatcctggtgaactcctatttatggggctgtgtgaaatcaaaatattcaaaccgatggcata<br>tttgcgagaaataa |
| Contig40_<br>gene_115<br>8 833 | atgaaggtcttaaagatagcaattatcatgcttattttaatcatatctctggagcggttcagcaacagagaattttaataatgattaagtga<br>taatggactaaacgataacacattaagcgacaacagcttaagtgacacacacttaagtgataaaagcttaagcgaaagca<br>caatcatccaaaatgatcatgataatttaaaagatacaaatcagttgaaataatcctgcgaagacattacagactta<br>caaatgaaaataataaatgcaagtgaccttttagaattgacagacaatagacggagacaatcaatggcatttccaatcaacgaactctctaa<br>agcaatttcgtaattaacgaaatgccatacaaaggagccatacaaaggaccatcctacaaagacgccctattactcaaccaggctctgagcttgagacaaacaatgtaacctttcatcaac<br>atctcaatataataatgcaacctctacaaaggacagcgccctattactcaaccaggctctgagcttgagacaaacaatgtaacctttcatcaac<br>gacagctcagacaaaagtaatatttgcatttggagcaaaatatacaagcaataatgataagttatagactgacatcctcaatgatgagt<br>aataactcatcctgtgaataactatcaacaacatttgaaagctccaagcattgactggcttcgtcaacagtttggaaatt<br>cctcaatctacgttttaaacacaacatttgcaaatacgctacagcaataccacctccaaatcagagactatagtaattccatgattct<br>aaattcattaatctctatgcaaaatcttactgcaggagcaatagatattcagatagtattcttgacatattcttgacataatggttgcacattcattaatgt<br>gagttcacaaaaatgagggcaatattcctgacatattcttaatatgcaagacgtaccaataatgatt |
| Contig40_<br>gene_117<br>6 834 | atgaatttaaaacaaagaagcttatcaatctgatagcaaactatatgatgaaggaagaagggccataacaaatgacgatgatgaaaattat<br>tacagatatagacacgattatcaatccaagacaaactatatgatgaaggaagaagaggccataacaaatgacgatgatgaaaattat<br>actatgaaattgcaaataatccaaggacaaactatatgatgaaggaagaagaggccataacaaatgacgatgatgaaaattat<br>agaattgatgaatctatgcagtatacaatacaccgtctgaaaatgaactatctttgttgaaggagaaagaataacaaataatatttaattt<br>tacagatcaagactatgagcctgtcgttccaattattatggctccgagagactgtgttatttcttttatggtgaagtacagatgcgacatatatcatccatttgaagcaa<br>ccgggctcaccgactatgtcgttccaattatttgcctccaggagatgcagaaggaaaccaattagataatccggaattctctatcagaaccaactacaa<br>ataagatgaaggaagaactcaattagatgtaacttttgaagatgcagaaaacttacaggaatgcagaaaactgatatattgaaacttgaagttgcaagcattgacagcgttccaaaatacaactaagcttaa<br>tggatgaattcaataacaacatcatctttgaaaacctcaaaagcaacctatgaccaagcaactatgactcttcaatcatcctcaatccag<br>ggcaaatacaacacatcatcttgaaaacctcaaaagcaactatgaccaagcaactatgactcttcaatcatcctcaatccag<br>cataacaaagcagtcaactcacgtcaagcaactatgaccaagcaactatgaccaatccag |
| Contig40_<br>gene_119<br>8 835 | atgggaaaattaaattaattttattctagtttagtcttagtttagtcttagcttgtcaggtgctgcagttgctgtgatgcgcctgattccttttgatgg<br>ctcttaaatcttatacctgttctgattctagtgtaagtcatcagttcatcagtctgattgtgaaatggacttgttcagttg<br>acttaacaaatctgaggatattccttcaaagaaacttcagatgatgaaattgattattatcagttcaagtatatgacgattctttgattgatga<br>ttgtatttctgcaatgcactgagcatgcattaagaggctgattgacaatcaatgatcatcatgatgatcatttttgacggagcagctgcatta<br>ctgcgaatatcttaaggatgaaggattgacagattcagatattcaaaagaaatattgagaatgatatctctacttatgacttataccagcgata<br>gccagagcttctcaaaattggagattttatgaactccaacaactgtaatatttgatgaaatgaactgagtagaatcgagggctat<br>gagtctccagagcaattcttaagtgaactgagaagagtataatggcaaataa |

FIG. 7B-30

| | | |
|---|---|---|
| Contig40_gene_121_5 | 836 | atggattctaagaaatattaatgattgctgtagttgctttaatagcaattgttgctgtaagttcatgtctctgcaggtttccttgacttttagg aggacaacgctactgacgacagttaaatgaaagaagttaatttagctgcagcagcaagtcaagtcgacttacaaactcaaattgaaaacggtttagaaaca caatgtttgaagcaaatatcctggatgtaaaagtaactccaacttacgcttcaagtggtgacttacgacaatgacaccaaccttcaattcttagaaaataa gacgtattcatgtcgtcttccaacaaacaaatgaacgcttagctgatgaagttaatcgacaatgtaaaagtgaaagtacaccattgctattggtgaccag agttgttttatcgtacctaaagattcagacttaaacatcacatcctggtattgcgatcatgtaaaagatgtgaaagtaccatgtctaaattctcttaggaactgatgta aatctgtacctgcaggacaatatgctaaagaagcattaaccaacctcggtattgtattgtaactgatgatggcttgaatctaaattctcttaggaactgatgta actgctgtattgaaccaagtagctcaagatctgctgaatgtgtattgtatgctatgatgattaagagcgctaaagatgcagcaagcattccttg tgaagctcctgaaaactcttaaacacttcagttattatcctgtaactgagtttaagatgtgagtcaagatgagatcaagagcaaacacaagttcataa aattcttacaaaccaagaagctaaagacaaatttgttgaatacgatttaccattcacgaataa |
| Contig40_gene_123_8 | 837 | atgaagttaaatcaagtatttgtatttttactcataatatgtatcctattcagtatttcaacagttcagcgaatgataatgatatgatgtat aaatcaaatctgcaaatgatgcaaataaatcaagatataaatcaagatttgcaattaaatgaagcatatcaatcaatcagatctaaaccaaatt tgcaggcaaataatcaagaaaatgatttgctcaataaacactgaaagcatctgaagaataagcacccttataggcataataaaaccaatcgaagatacg ttcaatatagaaaacgactataaatacactgaaagcgataaccacctttataagcataataaaaccaatcagctaagcgaaataacca tgtcatttgatgatcaataaagctgaggatttgaatttttaaaggaatcactaaataatgtcaatttcactaacaatcacaataaattggcatttgattgatactcaacg attacaccatagttaatgaagacggaagcattaacatatcagttacaatacagtaaagaaaatatcagttctctataaataactgtaatttgtattcagag ggaatgatatcagtttcaatgagcattctccaacgagaaaaggatgaaggccatattatgccaataggttcgaattgtatatagataactgcagct gctaagaattacaaatttctccgcccctatggagagcaataaatttcaaaggagaaacaccttgtcattaaaaattcaaaattcaagacttgaatgccgaa ttgaaaattttcactgccccctatggaagcaattttgcaaagtatttccaaaaacaaataaaaggtcgccctatattccggtgaagacatgctttttgagaattgtga ataactgcaggagcaattttcaactcataacgagctaactggtgcaatctgagttcgattctgggcttg atttccaatgtctcatcaactattattctttcattatttctttatgatgcattgttaatggcctagcatacaagtctgtgagctgtgtgaaggttc |
| Contig40_gene_124_7 | 838 | atgaattattccattattctttcattatgatgcattgttaatggctagcatacaagtctgtgagctgtgtgaaggttc aatccttatgtgtcctatgtaatgtga |
| Contig40_gene_125_4 | 839 | atgaagttaattcaagagtttaggatttatctctattattgttcttacaattcttgttcaagtgtgggcagcagaatataaattaac agaaaagatttaataatcctttaaaataggtattccagaaggtacagactccagcaagatgcatattcaaattcaattctgctaatgtta actttgcaatgaagtttttgacaatatactgatgtgttcttcgtattgtacttacttaagactcttcttctgattcaaatcttatttccgatgtgatgtgattgatgattctcagaattgaaataataatattatgatggtactaattatgatgctgaatg gaatgctccagatgccagcacatctttccgatgatgagtcgagcttatcgtgagcttacataagaattactacacagattcgtcctcgtcttggctctgatgatgtgatcattatgatgtctgattcc attccaaatatccatcttccgatgatgagtcgagcttatcgtgagcttacataagaattactacagattcgtcctcgtcttgccaaaatgaatctatgttctgattcc gatggtcagaatgtttccataagttgcagactattctcttttgcttaaagaatcctaaaaagatcaattgattatttgttgaatgatttagatc catgaattcatttgttgaagaataaagcaatattgatgcttaaagcaacagcaataatacgtatccaca tattaaagcaaatgcagactctgctgtcctttcaaatag |
| Contig40_gene_126_4 | 840 | ttgtcaaatattgaaactgatgattcatttattgtgaaattcaaatatcaagcgatattaatcaagcgatataattcattaatgaattcacagcatc aaatcaaatcaacgacgattaagcactaatatagcaatttaatgatggcttaagcaacaaggcgacaaaagccaattatctgatccaatcaatatacgtatccacaa acggcagtgacgattcaggagacggaagtgaaagtgaataaacatgcagtatccaaggcagatgattcaatcatatac ctatccagcggaacttacaatggagagaataacaaaacataagaaaaagcttaagcactagagagattccactatcaatcgacgg tgaagacaaggcacagctattcatcatgaaatcagcgacaaattaagcttaacgacttatttaacaaatgcatataaggacgcaacctaa gcgactatggaggagccatatgaaatgaaggcggacactctaactcaatcaactctacaatcaaaactcttatgaaactctattgaggagcc |

FIG. 7B-31

| | | |
|---|---|---|
| | | atctacaacaattaggaagattgaccatcataaactcaagcatttaaacaatagcgcaatacaatatggaggagccatctatacacttgagt gacaaacatccagaactcagttttcgagaaacaaccctaacagctgaaaaagtgtgggagcaagcatagcagcaggagcaataacctca acaatacagattcctcaataatcatgcgatatattcagcagcagcgcttctcagcttagaaacatgtttataaacaacaactgcagtttcataaac cagaccacaaactacttgcaccccagggcaatcacagcaggcaatcacgaaacatgtttataaacaacagccttctcaattgcagtaagattctatgc aggagcaatacttgcaccctccaagcggacaccatgtcgtaacagaggtctacaatacaatcttgactataaca |
| Contig40_gene_1270 | 841 | atgaaaagaaaactacacaattatattggttattttaattgctcttatgcatgcgtgttgaataacttttattgcttcaccatcatctattc tacagatgggaatacaccacaatccactgatatggcaaattgttgttgtaaacttccaatgactgatgaggaactcaaaatatgttccgatcagtataag ccactatcgtttatatgctgcacctgaaaaatggttgttttgaagtcaagacgtaattatgaagagttattgcttctgagcctaattttgtttattgaaggtat gataaattccagttatcgtggatgtttgacctatcaactgttgaagtcaagacgtaattatgaagagttgttgaagtggagagacggagaagtttgaagtcaagacgtaattatgaagagttgttgttcactctctgtagtgctgtaactgacaatacaaatg ttacaaagatagacaatacgatagagttcttagcaagcttttagtgctgaagataaagcaaatgagttaattgctttaatgataagtatttg tctcaagttcaatccactgcaagcagcattccagattctgaagccaaaaactgtttattatgcttctgtggatggattatccacttatgcaag tggcgcttcacatgtcaattgattttctcgttgttggaggcaaaaacgtagcagacactgaagttaaggatagcggaagtgaattgacttgttcca ttgaacaggtaatgtcttggaatcctgattgttattatgccacagtgaggactttataaaggttatataagttcaaatgggctagcgta aggcagttaaggaccatagagtatattcatccagataaatattccaatatagatatggttgagctactaaagagttttata |
| Contig40_gene_1274 | 842 | atgaagaataaagagtttaatataatattgtttcttttattattactgattacaataatagcataggatctgttgttgcaacgataatgaagaaattaa tatggataatataatattgatataatatgaggatatcgctatatattgataatgtcgataactccaatataacaatccaactg acataagaatagacaattcaaacctaaaatcaagcaagactagattcaaattcaaattaatctaatcagattaggaagacgaattagaacaa agcaatgcaaatccaatctaaaatcaagacagctatcctccacatcactgtagacgctcagatgaaaacaaatgtctaatcaaccatttca aagcgctatagacagttggaacatgctggagatacaatcatgcccttcaaatacaaaaggctctggtgcacatgcactggaatattctacataagcctgaagctagc taataagcgagattcctaaaggattcaatctacagtcagcgacgcgtcaagcaaaaacaatcacaataacaacaacaaaaaaatacaacaaggtcagttatcatagaaggcagagagaatagaaataat caactgtacaatcaatacagttacagctttcaagcaataacattaacactacaacagcatattataagctgactgcctaattaaggattcaa acattggaataaacattacaggttcacactacacaaatccataacagctacaactgcatagcggaataacaacgcatagcggaatagacctctactctgagattatgtatacatcctaaacaa aacaacgatacaactactattcaatcaaattctaaagctcaagcagactgaatatgttaactcaatatcaccaaag cttcattggtcacaatccaatcaaattctaaagctcaagcggagctgaatatgttaactcaatatcaccaaag |
| Contig40_gene_1296 | 843 | atgagaagcactatcctgttaagtgcaagtactgcaagtcgcggaaagccgttccaccaagtcctcacaacagcagatgtactgttcagacagttgcagacgg aatgcccttga |
| Contig40_gene_1331 | 844 | gtgcttctcattgcttctataggatggttgaggcgatactgatggcattggttgttgattgggaggacttggcaatatccgttcgcaagtctcctag aagctttatatgtttgaaggatgagtagtcttcctgaatggaacgaactgtctgtgattgaaggaagaagcatgaaaggtatgctg tcataagagatcttcttcctgagttgcctccatggaagaactttccgtcatagacaggagaagccacagagactctacaaacttatcaaatca gtttatgatggagactatgatgacagtccaagcttgaaggtccaccagcagtcggtcctcagaaggagattccattggaagaggcagagta tcctttga |

FIG. 7B-32

| | | |
|---|---|---|
| Contig40_gene_1350 | 845 | atgaataaaaaattatcttatccctccttttagtattattagtagctatttctgtctctgcagttgcagcagcagatgctgatgtcacatatat<br>aaacgatgctgagatgtagacgatgttgcagacgaaaaagttgctcctcttacagctagtgctgatgcacaagacatccaaactaagcttgata<br>atgctaaacctggagacacaattgaattagaaaacaagacatatgacgttgataacaattaatgaactgaagctggaactgctttgaaggaattaccttcat<br>gacactgtcattaagctgacggtgcatccaagtggtagcggagcactcttcattgcaaatgaagctgtatcaattagctatgaaaacgtactgtagacaactgtaaat<br>cattaacactgacggctacggctacagctagcgcacaaaactagggagaacaagtacaggatatcaggatatcagatatcagataccacaacaactacagtataccccgccaaatcaagcaactagtgagagagctaactgtaacttgagatagagcaacttgtagtcctgtagcattactgtgaagcaacactcaagcaacactcaattgtgataactcagatttcaggtacgtttgaagatgttgaagacattgcgacttcatcgtgatataaaatgtttaaattcgttcgtcctataagacaatataagaatacagttcaattcgtgctttatcaaacagctatactacttaaatcaaaatcgacagagtatctctattcctctaatgtcaagtttctgtgaacaaatagtgcctgtatttactatatcaagagaggatctgaagttcgattttcttaatctgcctcagttcctgacagcagacagcagacattatagcagacaagtactactccacatcaaagcagcaagtactacacctgacaatttcgtcagtttcagcagcagacattatagcagacaagaacagatacatgcgcccagtttcaggcacctgaaccgcagggcta |
| Contig40_gene_1351 | 846 | atgtcgttatccattgttctggttatagatggtggattttattcatctctggttataggagtgattatatagttataggatgtttataagataagagctttcatctataagataatattctatacttggttagttagaggatgatatctatagatatggtgattttcattgatttgcaattctatgagaagagttaagagctttatgaataagacgatatccaaagccacaagctgacaaagctaccagtaattgctagccagctacagctactgctttacatttccagcacaagtttcctaataattgagaatggactcaaaatctttaatcaaagatgtttattaattaactccagataacgatactgtgggataggatatctcagcggacagatagataagagctttacagaagctatgatactggataacttgacacattcaggttcactgacagtatctcgtgaacatttcaatttgcttacaaaggatttaataactcttgaaaagctgactataaccgttatcactgccattgacatttcaaatctgcgcgcattgacattataacaattaacaataactccatgacaacaatgtggaatatcaaaaaaagataacttccatctaagaacaagtacgacaaggttagcacaaggttagcataactataggtgcatactacttaaaatcagaaaatcaagttcactgataaacttcaaaaagagattcaccaagacattgatggtgaacagaaatcttcttagatggagtaagacttttctaatgttcagcagacaaatctcttcagatggagtagccgatactaaatcaattccgttcaatctgcacatttcctcagtttcagcagcaaagacattattaaaaccttttatcatactcttgatgattcgtcttgatatcgcctttttcatctgtagccgtacagagtcctgttgcttgatatgttcatcaacaagtactaacttctcttctctgcatacctgtttgtgtgcagcagacagcagtacagtcatcagccacaaccttcgtttaagagactaagtctgtcacctactctgcgactactagtagcacatgcttatcttatctgcattgatatctatagtcattgctataagtcaagtattgacacactcgtttaagaagttcttgtgtttaattcgcagcgacaattgtgcatatctgcgcgcatttgacactatataaaatcagatcagcagaaatcttatctgcattagattaagtccataaggtaacctcggttttcctggcttcagcggtactattcagcgagtttcagcacattctatttgaaagtagcaacttccagcaagcagtatcacgggacaatcaccgcaattcactagcataaccataagccggactagcttctcttttgcattgatgatcctacatggtttcgcatccaagtaccacatttctgcattgatgaagccaaagcagtcataaccgcatcagtttcacactcttttgctatagcagttttaactagccttatgcagcttttagttacctacttgacctctataaggctcagtagtgttttcaaattcattaatcattaagaaactctccgcgtctcttctggagtgtgccgcccaaccgatattccagagaggatactaacaatagtcgtgttccagttgcagtgttttcttactactagcagcagcatcaataaccagcactagatggagacttcgcagaagcgtttggctatacgtactgaacgttacagttgactgatagtactcgaaatccgcagtaaatactccgttctactacgcatactctgtacgatttctaagtttactccaagaactattgtagatccaagcatccaagcaacttctcgctttcactccagaggaggcgcatattcaaaagaaaaggttcatacttggagcggatgagagtgcgcgaacgtcagcaagcagagcagatcaagtataaccttggtactataacgacacacactgatgatgataggggtcatactattttgataacagcagcactattattctgaacactgaaaagaacgattggctcactgcagtgaccttaatacctactgctcaacgcgcttttatagcctgcgcgaacgctcagcgaagcacaggcttactatgtgcaagatccagactactgatgaagtctatcaccactctgttaagaatatcctaatctctattaattaattacagaaaaaagatgccttttcaagagctgactactaactcagtctacggacaagtaacacttggctctctatacctctagcatttattatcatagatcgataagcttcagtttactacaactgcaggtggattcgcatacactgccagcaagaatcagactatcagcaactctgaaactaagattggaattgatctctaaaactactaatgcaaacaaattcagcgagagttgaagccaacccacagaaagctctccgtgcaagccctaatgggttctcgctctactatctaagattctaacgcagagaactctgtcaataaatattttcattgaagaattaacaactgatataatcaatggtgaactgacatttcagttgtttcactctttctcaaaactttcaaaagtgactgagcacaatcgtaaaaccgaaccaagatttattagtaactgcatgtacagtgtagggatgtttaaagatagatgggagattaattatttggagattccagatagttagcaagatatacaaatattaatcagtaagaatccagccccatttttgtcaaattaactacattttgctcaaattattgagaaacaatccaatcaatgtttctcaagagccttactattcaaatgaatcgccattaagactaacatcccagcatggggaaatatctgaccgtcgcacaagcaagaaaattctgttcatcgaaggaagaaaatcatcaaacataatcaaacatattcttaccttatgggatgaataaacttcttccaatgctcggtcttctaaattaaacaggcactgagggaaatttgtcgtattctgagcactattgcttacaatcttttagagaaccaagcacacgatctgttcttctcgatactagcaagcttaagttacacacttccacttatctttcacagattcccgaatcccgacactcacactgagccacttcacttggtatcttgcacaccctcatctctccattatatgctcctccctcaaactcacagacatctaatcagctataagcgcccacttcaaaataattcgctctaatagatggggccattcagtgaggtttttcctccactgctatagcattctcgaacccaagttcagagtatgcagacagttcttaattttcatcctactggagtactctctacatatttttgttgtcagcttcggctagcagttcttggatactgtggccaatcttcaccaaaatcaatcaatttaagctatagcgatatctcgatcagccaccttctatcaaagttgcagccgttgcaagccttgaaagggtaaaattgatatctacctactacaattacaaggaactcgaaatcatgtccgtgaagtagttcactgagcgtatatctaggagcttacacaatatggtgagcaattagtaccaatgagccataagtctgagtgacatatttagatggctcacacatgactacaccggcaacgtgaaacagtaagtttgtataacggaggtcaagatacaccctcaggtggtaatatgatgctgagcacgtgttcaaactttcgatctctttaagtcgaccaaatattaagatactggtcttgaaatcggaacgtgggcaacaagtataaagttttcctctccacctaaatgatgagtttctcccccacatagacagtactctaagcacgttcaactacctctacagtgaacagactctggagacacagcagcatgtcatctagttctgcaaacagccactggctccctgttcaagcatcgaaccaatttacaaggacaacaactgacacaagactgtagtacctagataatgtgttcagggtatcaaataatggctttcattaggttcgttcatacttcgcgacaactatacccagcgcttcagccgcagtctaagttttcaccgattgactccgcgcagcagaagcggtgacctcaggctcagctagagaccaactctgtgcgaactctcccattctgtaatattctttaatatcgtcataattctagaaatgatgaagatggtcattgtttggtaaaagaacaatcacgaaatagattgcatatgtcacagaggagaaccaagcagagagaaggaccgacaaagacatatagcaataaagtagtcccatattctgaggtttaaggactctaagtcttaccgacctctggtttggctttaagtgtttcggagacagcagacatcaaaacatagggaagaattgacggttgctttggttttagtagctagcagacaactgactgagctgtatctctaattagctttgcttcctatacttgagatcttttacagcatgtatataacgataatttaatataccagacacgcttttcttatacttaactgtcttagatcgtctaaggttagaaagatcgcagaggttgaaaatagccaagatttaggagagctctaggcactaacctgattgctctattgcttatcattaatgtgcaagcccaaagagagctatctttaaaactccttaccagttgcttatcttatgatagattactaagccttagaaatgccatctctctatactctttaatatcagaaatcattggaccgaaatttcctatacgtgcatttttatcctatattcttctagtggtgaagattggccatggcttttacagggcattagaaccatgagattgacgtatactggagaaccgaatgaagtggaatagctcagcaagacttagaggaagacgtggagttcagaagagatgagtaagtctggccacagaaacgcaataaaaccccctagggaagtacctagccgatactgtgtccgaaactcttccaagactcaacatggttagttcatataggatccatgaggaaggagagctgactaccccagactgttccatctaaatatatagcctccccggaacagaccattaagataagagctattatctcttaaactggtatagagaggaagcaactcaagaagcccaagccaactgagagaatccattatccctctattcgaagttgcatcttcaaaggctagtagcgtgagaagacagtgatattcccagactgaacagcgatagaatcccaacaatcgacagacaataagaaagcgcaggcaacggttatcagggcatctctctgcagcactagtaactcctcagttaaaaactgttcgaagaagccatatgagagtattttcaaccctaccttctagcctgtaaagcctggaaaatcaaacaacccgcccaatctagagatacttaaacagcgacagtagcagcttcttcaacattcgcatgcgagcatgctcattgctgtcgtaactgtctttctgcgacaatgtcagcacaagaaacagcaggggaagactacctagctgattacgacatagatagaactgagcagctcccctgtcaggagaaagcagaagcatctgttcactgttcgtcaggcctcacataaggccaagatacctaaatatgaagaatcaatatctaaactactaggtgatgaaagctatg |
| Contig40_gene_1355 | 847 | atgaacaataaaaagattatatgtctttttctattggtctctgcagtttcagcagcagacaattatagcagacaa<br>tcaagattcaattcctccaatgcaaatgcctccaatgaatgttgctacagaagacattagcaaactcttttcagatggag<br>tcagcaccggcgaaacaattggattgtaaaccatcaacagatgctacaagagatgaaaaagcgatgcaataaacctcgataataca<br>agcctggagacagtctcctttaactgatctcatttataatagaggagaaagaggcagttgctagctgatcagtttgaattcagccttacaattcaatgttatatagagccttacaattcaatgttacatttatg<br>atacaatcagaacaatcagaacattggtgctcaaatatcaatgatgatatcggaggtccaaaagaataaacaattaccaaatataagcaaactgtacaatc<br>taaatgaaatgaaaatccagaacagtgttgctcgcacaacttatatcttgcaatatatccgatagttagacagtaggccaaacaggttcaaggcggacc<br>ttgcctataaatccagagcaatatcaatgatactgttcttttaatatactggacaaggttaaaaaagacgaccttcaagccttttattcaaaggcgacc<br>ctatctgttccaggcacaacaagctaatcctgtaatcaacaggacaattcagacattttgatattaaaatcagatattcaagacactcaagccttttattcaaaggcgacc<br>atagatcaaaatgtcaatctgtaatcctgtaatcaacaggacaattcagacattcagacattttgatattaaaatcagatactcaagccgatactgatcaagccgatacttatgaagtgaaattgaatagc<br>aaggtaaaatttaaccttagcttactcagtttgtgcagttaactgaaagctatg |
| Contig40_gene_1362 | 848 | gtgaataacagtgctgataacggtgcatctatttctgcatcttctatttcaaataatcatcatatatttcctgaacaatga<br>tgccgttgcaatctattttgtgacgaatgattccgctccttcttgtttctctgattacaacagcctgattacaactgttgttgaaataatgcactgatatagcgccaa<br>caagcaataatactactggaaaaaaatactgaagaagaagcaataatcagatttgaaaagaagccttctttcgccaaattaacttaacgtgagacaactattatttt<br>aaattatatgcttatgcctcctctgtgagtaggtatatgagaatatgacagcagccgtttgaaagagaataacttaacagtgactcaactactactactactactactacta<br>caatactaccccagcacgtcactgagaaactgggacagaagagtgcgcaatgcgtaacagcactacactacactacaatcaagaagctctaca |

FIG. 7B-33

| | | |
|---|---|---|
| | | ctacaagattaaaaatctcagatgaacaacattccgtgacttgaacaatctcataaccgcaacgataatgacactatatttgataatgat ttcatctataactcactttttgacagtaaatttaaaaatggataataatattaatcgacctttgacaattgttgaaattataccatagatgc taccggaatggcaagaatattccgtactattcaagcagatgatgtagaaatcaataacattacattcgctaatgctaaaatagacgcaatggtggtg ctatctattggtattccggcgctagagtattgttctgattgcagtttgtaataataattcagctaagatgtatggagctgctatctattggaat ggtgctaatggtaatgtttctgattgcagtttttgtgaacaattctgctaagaaatatgtggtgctatctattggcacggtgccaatggagt tgtttctgattgcagttttgtgaacaattctgctaagaaatatgtggtgctatctttgaacgctgccaatg |
| Contig40_gene_136_3 | 849 | atgccggatcaactattcgagcattaaagtaactgctccggtgtaacaattaaaacctaaccattaaaaacgccaatgtaactacagatga tctaggcaatacagatgatgagggcgtcgcgattgacttgactttgaaaagtccggtaccattgaatattgtaattttattataactctgcaaacgctg ccggtgcagtatactttataaagataacagcaaagcaaataaattgtaattcagctataaccaaggtatactctggtgtgcagtttgcttt gaggaaagtggtactaaattgtacttttgtcaataacaccgctcaaggtattttcatggctggtgcaattgctttaatacaaatggtgcga agtaatgcgataaatgtaactttaccaataataaggctcatgactctggagttcaatggcaatgttatgatttatgggaaattgcagtttgataag taaattgtactttcactaataatagggtgtgcgtcaagatttatgagctacaagatatcaaattgcagtttgtctaaaaactcagcttttcacggagtgcagttcctt tgatgcggcgctatctattggaatgcgcagttcagcgcgtggaatgggcaattgaaaatgtctttatacctccgggatgtaagaaattgtaattcactga ttgaggaagatggcgaagtaacaaatgtaaatttactgagacatggtgtcttttactagcagacgttgcatttgtttacagcggatgtactgtagaa aattccaatttttattaggcgaagtggatggcgtagtggcggcggaattgtcttttatacctccgggatgtaagaaattgtaattcactga taatgaggctgataagcaagtgtgtgcagttactttacttttaatgagcaggtactgtagaaattctaatttcacca |
| Contig40_gene_136_4 | 850 | atgaaaatccaaagagtatatatatatattaacttacttgttctcttgtctgcaagcgcagcagacgatcttacagatgatat tattagtgctgatgagaatgaagaactattttagatgaaacagtcattgatgacgttcaaatgcaaatgataaactatgaagaacttatta aagcaaatgatgaaaatttgtatatgcctgaaatga |
| Contig40_gene_136_7 | 851 | atgaaacttaaagtagatagatcaagataaatgtttaggtgtggagtagttgttatcgcatgtcctgtaaacgcttccatcagtccgaaaacgctgg aggacacggttccaaaaacggtccaaactattatgatggttgaaaacgattattaaattattcagtgtggacaaatgtgataaatgtggtacttt gccaaatgttctgtcctgtccaactgtatatgttagaataq |
| Contig45_gene_8 | 852 | atgaatcgaagatcaaagttaataatgcgatttaatagttatcataataggtattgccgttatctttcttttcggcagtatgtttggtgtgaaaa attatcatcagtgataaagacatttagtttgtgcaattgacgaaagtgagcctgaccaggaatgggggcagttgatatggcctttagtac atatgaatgatgaagatactactaatatactccgattatccgcatgaatgtccatccgtctatagccgaacggaagtatcaggctatg ggtgcagggaaaaactgctcttgcacgattgctctattggaagacaaacagtgcatgcaatatcagccagtatcttaagaagattcttaatataatac aattattcctgtcagtgcagtttgattctcatcaggaagacagagcagaagaatacctgaatgaccagaggagactctgtaatgttaatgtcattgatg caagcggctaaagaccctgataaaaaggatagatgattaagtgctgctgaagcgaataatacacgcgaatattgcaatgtatcctgaaggtc tttatgaattgctcgcttctaaagcttcaagccatgtttgggtaa |
| Contig45_gene_20 | 853 | atgaaaagatcaaaaaatttaattatagcaattctgttgtaatcttttggattactattgcaattgcaggatacttcgttggtggtcctga cttgtcacaagaaaatataaaaccatttagtcttagctgcgctgataaatacgagcaacctaatggtgttgtatatgcatacctagttcgtttag aaatggtagtttagctaatactacactcctgttatccgtgaatgtatcaccttcaacatcagctcctgaaaccttcaggcaatatgctg ctcagattgtctgtgaacggagttgaagacggagtatgcaatgttggcattccataccggcgttgaagctgatcgtgtgt agtccttttatgacgaggaggtaacataatttatggacatatgatttcagaccattgagattgatgaagacaacctaagcgcaactgacatca ttcgtgaaaacgataattatgcaggttatggggtaacgaagtgcagaagtctaggacgcagatgctgttatgtattggttaaagcg gttccaaacaagatcctgctaaaagagagcgccatgttgcatgcagtttgcagcttgagtagagtactactagaatattgtaatgactcctaa |

FIG. 7B-34

| | | |
|---|---|---|
| | | aggttctttcactcgtttgcttgctacaaaggattggaaagctttgcatag |
| Contig45_gene_21 | 854 | atgaagaatacaagatagcaattatagagggagggccagcaggaatgatagctgcaataagagccgcagaaatattaggcccaaatgcagtatg cattctagagaagaatgaaagcttagaagaaaaagcttcttcttttaacaggaggaggccgttgcaacataacaacactcactcttgccatcttgaagagaaagaccttttaactattacaataaaacaaaaactcctaagcactcattatacacactccacagacaagcaagctacttgccatcttgaagagaaagaccttgaatttcaccaagagaagagacaataaaaggtcttccagacagcagaagatgccaagatacttgaagactgaacatttagaggaatatcttgaagagttagggtagatgtgtataacaatactccaataaatgctcaagacatagagcatgaattaaatgaaagatggaaccggtatttgaaatagaaaatgaaaagatatcattaaatgcatcaaagattatagtatctcaggagggcatcacctatccaaatacacaggttccgatggagatggatataaaatagcatctcacatgaatcatacaattacagacatcaagccgggacttgtctcattcaatattgatgactttctgctttagcaccttctgtacacctcactttagagtgttgaagtctcattaaggataagaaaaagatatctgtaaaaggggatatcttgatgcacaagtaacctaaagacagaatgaaatagaggaattgaattgtttgtccaacagattgcttgaaaatccgatttactcagataaggagagaatataaaaaccagataaaacaaagacagccgaagaatgaaactcttttacaacaggattacaatcgactttactccagagagagagataaaaggacagataaacaaggacagccgaagaatgaaagatgggcaataaagaactatatgaagaactaaagaaatgaaacagtgaagtgaagtgaaggtgaggacattcaaagactatttgatgattataatcttaatagcttttattgtgtcttgcattagagtttcagttatatggagggagtgataactctcaaactgaatctgaagtgtgcactatgttaatgtgacaaaaaacattactgaataataatgaaagcgggaatcttattgaaaccgaagatgcacacatatagaatttcttcttacagcgacaatgtaactgaagtgaaaacgttacagcctataattcttcaacagatgcagggaatttgttttaa |
| Contig45_gene_30 | 855 | atgcaaatgaagtgaagtgagcaacattaaagactatttgatgattataatcttaatagcttttattgtgtcttgcattagagtttcagttataatggaggggatgataactctcaaactgaatctgaagtgtgcactatgttaatgtgacaaaaaacattactgaataataatgaaagcgggaatcttattgaaaccgaagatgcacacatatagaatttcttcttacagcgacaatgtaactgaagtgaaaacgttacagcctataattcttcaacagatgcagggaatttgttttaa |
| Contig45_gene_35 | 856 | atggatataaatcaaagcaggcattgcacttgcaataatcgttttagtggctgtcattggctttcattcattaatgaagcaataatgttgtaaatcaactgtctccgcttactgaagttttgactattccatgaaacctatgacaacttggatgattctaaaaggaatattccttaatcagaacatcagcagtgcaaacgtcaaacgtaaagactataaggacatcaccatgatatattgatgtataacgatgaaaatcctagataagcatcagcagcactataaagcactaaagacggttcattcaattaaaatcactcaaaggctcaaaggctcgaaggagaaccctgatgaattttattataatgtgacaaggctactgaaatataa |
| Contig45_gene_36 | 857 | atgtttaaagtaagcaaaagcatattaatcgtttgttagtatcccttttcctattagttcacaagctagcgctgcagactctaagcttaag ataagagatattaattcagttgatgaaactacaatcttgatgccagttatcttgactcctccaagttatcttgactcctccaagttcatgcattcagattcct ctctaaactctaatgcttagatgctagaagaagcgagattattgaagagagaagctaaaagacaccgaaggttgtagtgatggctagcagcaagatccaaggatgagcgaccccgc atccctttgcaactgcattaaacaggcttggcttaaacctttagctctgcagttgaagttgaaatccaatcctaaagactttagctgactcaaagactagactgaaactccatagtccattg atattgatggagcagaacactggactgtagtaagcaaagtaactgacaaagaaaagtgtctttagctgactcaacaagggaaacatcaatatgag cattgatgaattcaactccctctttagcggaaaggaacaatccctattatctgaattgaacaaccaatgttcaaatgttcatgttcaaatgttataacttatatccaacaaaaaaca ttaaggtttagatcaatccaatgtctaagaccaaagtctaagccatattgaagttccaagaagtctagaaagttaaacacgaatggagatacggctta atcaacacctattcatggtgcaagtacctatctcacaatacaagtacaaataccatcaaaaaaccaatacaagtgaggtaaaaggaaaga |

FIG. 7B-35

| | | |
|---|---|---|
| Contig45_gene_60 | 858 | atggtatgatatgaaagaagaaggtttattttaatattattatattctattgatttagcagctatagcaatcatagaacattttcaag<br>cttcagtgatgttccggatatgattggaagtgatgaccatcgttgccgttacagggatgatgttcggtcgtaagatgccggagtcc<br>tagattccggacaagccattcaggaatgttgaaaatgttacaaagtctgcagacatttgcttgtaaacttgaaaaccggctacatattcc<br>accaatccagtgaaagggacgttccttaaaggcagacctaaatatgtgcatctgcttgctgaggcaatgagattgcattgcatctcagga<br>caataaccatgcattgattatggggatgaaggattgaacgacagcatcaaaaaccttaaggatgcaggaatctatgtgatagagctgaaaca<br>atctcctggcatctaaacctgtagtcatagaaaaggagatagaaaagtaactgttttaaactatgatgcggataacttgcagaatat<br>gcaagcatcatgcctccggcaactgcaaactcatcaggattctgcgcatatgacagcgagcttgcaagaaaacaagtggctgagctcgcgagaa<br>cgaatccagcatagtcattgccatatgcaattgaaaacgagtatagcagaagagcctaatgagtatcagataaacatgtccatgactgattg<br>acacggtgcgatattgtgataggttccatgccagcaaccaatggtcttatttccttaacttgatcttcatgtgacaattgtacagtgactctctatccgac<br>ttcatattcgatcagtcaattgcctcaattcatgatgctgattcagctaaggcattatgcagagttgtatcctc<br>tgtgatagttgctacttgctctcaattgcctcaattcatgatgctgattcagctaaggcattatgcagagttgtatcctc |
| Contig45_gene_64 | 859 | atgaaattacagttgcggtgtaggatatgtaggcttcacttgctgtctgctcaaaaacatgattgttacagctattacaacaaccga<br>atcaaagcagaatgctaaatcagttccataagtcccattcaggacgatgagataaagattcttaaggaggttcgtgaaggagagaaccc<br>ttaatctccataacaactgataaggctgcgtatcgaaggctcgttgttatcatagccactcctacaaactatgacgatgtaggcaat<br>ttcttgacacctctgtcgttgaggacgctatcgaatggaccctaaggtaaatcctgatgtcctatgtcataaagtcaacaatacctgtagg<br>atatacagaatctgtccgtagaagtatgaattagaaacatcatctcagccggaattcctcagcgagtcgtgagtcaagagctctcatgacaacctcc<br>atccaagcagaattgttgtaggctgtgatgacgaccagatgaaagaggcaagtcgaagtcgaagcgctcagctgaagcgctagaagaagag<br>aaagagcaaactctcttgaacagcaaccctcaatagcttgacaacaccctcgcaagctgcttgccctaagactgcttgccagccaagcgctgtttgacgagagtgtgcatgaccctc<br>tgtaagggttagctacttcaatgagcttgacacattgacacacttcgcctacacgatatctgaagctatcaagctgcttgacgagccctc<br>gtatcgaggccattacaacccatcgttgtcattctaattcagttgaagtaacacagctcttcaggatatttcaagaatccaagacagttgg<br>cctcaaaccatgattgaagcagtcgttgtcattcaattcagttgacaataccaagagtgtgataaagata<br>ggtctatagacttaacaatgaagagtaacagtgacaattccgtgcatctgcaatacaagatgtgatgaaaagta |
| Contig45_gene_89 | 860 | atgaatttgatgaaaattacagttgcggagtggatatgtaggcttctatttctattgctattctgtttgccagaaacatgatgtaaccgcaattac<br>aactactgaataaaagcagaaaaacttcacacaactactgttaacaattctaacaattctcatagaatgatgaggtttttaaggagactcgtgatgaa<br>aaggaaattaaacttcacacaactactgttgaagtaaagaatctgcatataaatcgatctcaagtcaatcagatccagatgtttgatggtcattaagcagaaatggcagatgatgatgat<br>gtcaaccattttttgacacaaagactctgtctcgttcgtgaagtaaagtgcgatcgtgaaaatgacagatgtgcagcgctgcttattctccgaacccagatgttaaggcagtttgatggtcattaagtcaacaat<br>acctgtgggatacagcagtctgttcgtgaaaatgactgtgtgagcaacagaatgtgtgacaacatcatatttccgcgaattcctccgtagtcaaaggcacttatg<br>atatgtccatccaagagatctgattctccaaagaatgttgtgtcgatgaagcaagaatgattcctatccttctaatagcgaccctttgcactcttcgtgagactttgagccttctttgaagtgtgaga<br>ttgaagaaaaagatctgattctccaaagaatgtcgatgatgaatactgacaccttcgacaccttcctcttgctgagagcaagaagagcttttccaaaacac<br>ctatcttgcattaaggtaagcacactaattgaacttcaatgaacttaaccctggcgaaattacatcgcaagtcttccgcgaccatttcaaataatccaaa<br>tgaccagaatcggagagaatccggaagagcctaattggaacatgaaaacaacaacaagcaacagcaagaattcatcgcgacagtgcagattattcaaataatccaaa<br>aacagttgcatataggcttattatgaaaagcaacagcgataacttccgcgcatccgccatacaggatgtta |
| Contig45_gene_91 | 861 | atggagataagatataaaatttattaaaagttttactatttttctgttttactcatcagttgcgattgcctcagcagtcagtgatttaga<br>tgaaggtaattctgcaaattctgttgatataggtgattttatcattatctgacaatatgatgagtcgcagataattgtaaaatttgaaa<br>ctattgaggtgctcatatcttcagtgaaaaaacactgtttaaagacgtttcatatgacttttcaacaccttatagatgaaaatactttgaagat<br>tccaaactgctatttgataatcttgctgatgagatattattgaacttaatgtacttattttgaacgggtctgatataaaagattacaaaga<br>tttaacaatcagcgaaatcttgaaaactcttaattgatgctaaaaacaaatcaggtattttttatgttaactaacgtaacttacaaaact |

FIG. 7B-36

| | | |
|---|---|---|
| Contig45_gene_93 | 862 | taaaattttataattcatagttcctgaatatgaagtgcggttcggttcatttttttaagtaataagttctgtgattaatgtactt<br>gctgtggagtttatggtactatgcattgattacttttggtctactggagtgtagtatattggccaagccaatgctctgtgattaattgtactt<br>tataaataatactgctaatgcagatgcggtgcaattcattgtggagtggcgtctgtgattaattgtacattattataataatactgcaa<br>aagagttagggggtgccatctatatttgcgcggtgccgtggatgcgggcgctcattattcaaatgtttatgatgctatgtagataattgctattt<br>attaacaatactgctgtgaaggtgctggattgctatttatgcggagcggttttaatattaattttgtacttttatttaa |
| | | atgaagataagatataaaattattaaaagttttttactattttcttgttttactcatcagttgcctcagcagtcagtgatttaga<br>tgaagtaattctgcaaatatgttgataatgtgattatcatggtgattctgacaatatgatgagttctgcaaataattgtaaaaatttgaaa<br>ctattgaggagtctcatacattagtgagaaaagcactgttaaagacgttcatatggactttcaacacctatagatggaaatacttttgaggat<br>atccaaatagccattgatgctcaagatgggacacaataccaactaaacggcacttatctggaaatgcacttatcttggaatgcccaataattttcaaaaaa<br>cttaactattggagtgcggcgaaacaatttggatgctaatcggtagtatctatgcattatcaattcgtcttctgaaaaattgtcttgaaagatt<br>taacattttgttaatgggtctgattcacagttgatttgagggagaataatgtgataatttaaaatattgctcaataattaattgttccttttgaa<br>aagtgttatgggataaaattctgccgttatctgttaaatgatctgtttaaactctcttttaaattatactgcggatatgctatccattctaattcaagcaccattgttaag<br>tattatggttctgaggatgttttcaatagtttctttgaaacatatattatgaaacaattattgattccctagttgattgctatcaatattgttgacttatgtaagaattca<br>catgtgattttttattcaatagttgttcaaggcacatagttgttcaaaggcacatattgtactttcattaaaattgtactttcattgaaactttctaaattattaacagaatttctgttctgccattac<br>tcaatcagtgattgtatgttcaagtgaagttgatgttataaaattgtacttcattgtactttcattagatctcattagaacaattatgtactcttcattagatctcattagaacaattatgtactttcattgaaacatattatgtactttcattgaaacatattatgaaacaattattgattccctagttgttgcttatgtaagaattca<br>ctgtgatgaagttgatgttataaaattgtacttcattagatctatagtagcataaattggatcttcattagagacaattatgtactttcattgaaacatattatgatccctagttgatccttatcaattcaagcaccattgttaag |
| Contig45_gene_100 | 863 | atgcaacgttcattatttgataaagttaaaacatccttatgatgcttccatccttttggattggtaaacgcttggattattatctatctcgg<br>acgaagaattcaacatcaaatggacagtgagctgaattgtctatgaattgtctatgcaatcctaaacatcttaaccttcagttg<br>caatcactgcattttctttaggatcattttatgtctcttataagcattgtcgctctgtaatgtccgctctgtaatgttccgctctgtaatgtccgctctgtaatatcaagatgttgatgag<br>gaatatgttcgtcctctgttgaaagcggttcactgttgaaagcggttcacttgactttatgaaatcaagaatggtccaattcaacgaaggaagcttctcctaa<br>ggaagagaaagttaaatataatcctcctatgagaagaatccttcctatgagaagaatcaatgaggatcgacaagaatcaagtcgacaagttgacaagttgaaatca<br>aggaaatgaaaaggaattcaatgagaagaatcaatgagaagatcaatgagattggaaaaagaatcctcaatcgaatcttatgaccgattc<br>atgtttatcataaagattcagagagacctttcaattccaaagattggaaaaagaatcagaacattgagaaaatgatgaattaaggagagtgagttgatcattaatgacaactg<br>cgatgcagagtaagaaagaaagatcaagaatcctcttgaggatatggacatggacatctgaccagtcattaagcattatgaataa<br>agactggttcagaatgaaatcaagaatctgcatcaagaatctcgttgaggatatggacatctgaccagtcattaagcattatgaataa |
| Contig45_gene_106 | 864 | atgaaatttaagattcacatattcactcttcatttcattaatagaagttgtgcagcgaggcagcttctgcagctgactctgatat<br>tgcagcggatgacagctcagtgatattgttgaaatagaagtatagaataaaagaaagccatatctctgtgatgatctctactgctcag<br>aagatctaagtggtgataaatacaagtgcatcaggcactgatgcgctacagtgagatgcactgatgctacagtggaactgagacactgga<br>aatgctacaagtgtaaatgcactgaaatgtactgaatctgatagcactttactgatagcactgtactgataccaccaattctcaagtactga<br>cgttcctgtaaccaatgcaaccatcattcctgtaagcacttcctgattatcaataatgtgaaacttcacattcaagtagtgacaatgcaaccg<br>gagagcctttgcaaatcaaaagattctgtaagcggagtatatttcttacattaataacggacatcatcatccatacacaggatttcact<br>accaacagcaacgtttgcttgtcattgcaaacaaagaacttaaataagaacttgacacttggtatgtatatcacgcgtcttgatgt<br>gggcaaatacgacctacttcagcgaatgaagttggaaacagtaaaaatacaccaaacttaagatttgtcaacattaaagcttgtcaacattaagttaaagtacgtattcacatagc<br>ttaaggcaagcaacttcaaacttcagcaagtactgattaacaacccctatatacaaacctttcaggtcaagtactgtacattcaatgcagaaa<br>agcctcaagttacttcagcagaagtactgattaaacagttcaggatatacaaacctataaaaacctttcaggtcaagtactgtatataacctgaacct<br>tttggccggcacatatcctgttagaatcgtcaataatgattcaaatctaaaggctaagcactgtaagccgcaatg |

FIG. 7B-37

| | | |
|---|---|---|
| Contig45_gene_116 | 865 | atgaattctaaaaagatagcaattgttctgtttcattgctttcattgcaattgtaggctctgcatcagctttaacttattggcgacc<br>tactactgactttgacaattcatgtcagtacctttacagggatgtaagcagaaacaataagcaccaatgactcctatccgactggg<br>tggactcctatgagggatgaggaattcaatgtgaggagtcttgcattaaggagctcattcttaactgacctatatgaattgcaggt<br>atgcagctcctgaagtgaataatgtctacatctgtgaggcagatgtggataattcagccttttattagaggcattactcattgacctt<br>tgaatccagtgtaataatgtctacatctgtgaggcagatgtggataattcagccttttattagaggcattactcattgacctt<br>actgtgatgcagtctctgaatgactaaagatgatttaaacaattgcaggattatatagaacaggcaaaacaggaaatattcctgaaactgctga<br>atatgatctctgaatgactaaagatgatttaaacaattgcaggattatatagaacaggcaaaacaggaaatattcctgaaactgctga<br>aggatag |
| Contig45_gene_142 | 866 | ttgtcaaacagtaatacagtagctctgataatgcatcagatgatgcttcaggatctgaaatagtatcaggaattaacgaagagcttgaatcaaa<br>taatttattaactgaagatttaagcgtagacgatgtaattttacaaactagcttttatacaagttatgcagttaaatctgcaaaatctcctactg<br>tattaacttcaaaaactctacagtggtaaaaggagataaattatacatttactaaaagacagttccaatcatgcatttccggcgaaaagta<br>atatttaaatttcaattcatcttatacaagaactaccgattcaaatgaatgccgcacttgacattaaacttaactcaaacaaatatgcttt<br>tcagcaatatatgatgcagcgataattatagcgcttcagaaaagacttacttaactgttgctaaagtcaataaaagaagcattgactcaagct<br>caagtgttgtaagggagaagaacctatacactatttaaaggataaaaacaacatgccctttcaaataaagaagataagcattaccatctctga<br>aaaacatataccgttactacagacaaaaatgcagagcaagctaaaataaataagttaaagacagaacttactcaacaaaatccaagtacttcagttgctgg<br>agataaaacatataactcccagtctttatccaaaaacagtgacgaaatgcactctcaggcaaaagtcatgcaaattgaaattcgacaaaatctactttaaccta<br>gtcaatatatttatgcatatctaaaagacagtagcctggaagtgcctgaaataatacaagactgtgaaaaatcccagtaaaagcttgaaaaatgcagttgaaaatcccagtaaaagcttcgcaggatcaacatcctactc<br>aaaacagacaaaaacgaagctcactattacctcttatgttgaaaaaccaagattacagttgaaaattcaacagtga |
| Contig45_gene_159 | 867 | atggatgaatgtaaacttgtattaatcggttgattaatgtagttgcagctggttgtcagctggtgttcatcatcatggaaagctgcaatatccatgaaaaggaaatgatcaatgagaa<br>gtttggcataagctaaaagtagttgcagctggttgtcagctggtgttcatcatcatggaaagctgcagctggtgcttatcagctagctcaagctaagacta<br>aagaggaaactgcaaattagcaaacatatcctgaatatgaaagcgacatctcttgacatcttagatgcagttgactatgcgtactcatt<br>gaagcaactccaaccaatattgtagatgcagagcctgcaaaatcctgaaagcattgaaggcattgcacttgaagtttgaaagctgagctttgaacctcaaataa<br>gggacaccttgcactttctataaggaaaacattgaagctgtgaagctgcaagctgtgaacctatagaaaagaattaaacgtacaaccaattatatcttcaaga<br>ctataatcaacctatgtcaggaaacattgaaactgtgaagctgcaagctgtgaacctatagaaaagaattaaacgtacaaccaattatatcttcaaga<br>atgacaacgaaggcatgaagtagtaatcttggctaattcttgtttatgtcaagttgattgtgaagtgcaactatgatgtcaactatgatcagatgattcagatgttt<br>tgatgcagcatgtaaggtagtaatcttggctaattcttgtttatgtcaagttgattgtgaagtgcaactatgatgtcaactatgatcagatgattcagatgttt<br>cattagaggcatgcaatcatctggccaagaagaggctattatgtcaagttgtacctgaaactcagctcctgcagatcatcactgcagttgaaacattgaagttgaagtatctccagactt<br>gttaagaaaaacagtccattttgcaatagacggtaccttgcaatgttgacctgattagcctgcaacctgcagatcatcactgattctccagactt<br>tgcaggttcctggaaccgcttcagcacgctcattgattactatataaagaataagtaa |
| Contig47_gene_98 | 868 | Atgggtttcctgataatgttaaaaaattttgattctgtgaaataaagaggtactgaaatgtactgaaaatagataagttga<br>atctgttgaaagtaaagtaattatgttaatttaatgaaaaagatgaacaacaaaattcagaggacctcattaatgatgaaatacttgatg<br>aatcaacatccaatgaagaatccagacatgcattaaattcacatatctaaattaaatcttgataacctagttatgattataaccatagtggagttaagaagattatttgatcaataagtcgatattgttat<br>ggtaatgaggatgaggaatccagacatgcattaaattcacatatctaaattaaatcttgataacctagttatgattataggtaatgatacacaatagatgctcttagagc<br>aagcgaaatattttaattgtgatgctaggaaataattgtataaaaacattacattaaagaatggttttctcatcaggctgggcaataaataatc<br>aggagagttaacaataataacttcaattaaataatgaaggaaatacttgaaggaaatactttaattcttggtaagctaagcaaatccacctcaaagagaacat<br>tctgtaattgctaaaaataaggcagaaatatcttcaattaacgaggggaattaactctaaatcttaatcattaataaccagatagacaaagacaaatt<br>tggaattggcaataagcaatactaataacgaggggaattaactctaaatcttaatcattaataaccagatagacaaagacaaatt |

FIG. 7B-38

| | | |
|---|---|---|
| | | ttgttaataaagccaggacagtatttgttaataaagccattaaagcacgacgtgatgcagttatatcaaatggggttatttaagataagtgat<br>tctgaaatttaagtaatgaatcaaagtatataataatttaaacatagagttctcaagaatatataatactatttaaggctaatgagtcacaata<br>tatcatatataatgataattatgaggataatgattatctagtttaggtattttaattgtaaattatagaaa |
| Contig47_<br>gene_7 | 869 | |
| Contig47_<br>gene_8 | 870 | atgatgaggaaacaatatttggagttatatttatcgttttttattttattcagcatttcaacgtttcagcaaacgatgctcaagtgacatgct<br>taatgatgcaagtgatgtggaattaaatcaagacttgaatgctcagcctatttcatcaaattgctatgataataatcagaatttaaagctcaac<br>ctatttcagattgctctgatgagctacagaaatctgatgatgattaaagctttaaagctttcgaaggggatcaacaagtttcaaacagcttgaagat<br>ttaaataaaagcgacgcgaattaatctaactcacagctataaacattga |
| Contig47_<br>gene_13 | 871 | gtgataatgaaatattaatatattatagtagcagcaaatcaaatttccaatgaagcaaacattaccatcaatgatttgac<br>tttcacaaatttcaataaatccctattgtaatcagtgacagcaattgaccttaataacgttaacttttactaattgttcctcaaatcttcat<br>tgattgcgataatgtttcctagcaatttgactataaacaactgtaattccatttcaaattcattgcaaattatctcgacgaccattaacaaa<br>ttagagatttataattcaaatttgatgggacaaatgttagatctgctattaagaataggcaactagtcattgaaaattcagctt<br>tgagaatttcacagggttcatgaagcataataaactacaaggagactatttctcatttaaaactccaattcatcaattccaattccaaact<br>tcactgaggagcaattcattgtaaatatttcatcttccagacaatgaggtgcaatccaagttgaagatgaggttcttagcggttatttaaacatttcctattccaattttcc<br>aattgcacatttttataatctttcatctcacagactggcctactccatgaccaatcaaagattgaaggctctaatttttactgccaatgaaggaagt<br>caaatgcagggcattatgctcatgatgctagctgcctattctcaacttttgacaatgaagagtatcag<br>tgcaaatgcaatctatgctcatgatgctagctgcctattctccaattcaacttttgacaatgaagagtatcag |
| Contig47_<br>gene_57 | 872 | atgaataaacaacaaaacgtatttgcttgatattattaacaatcattcttttatcgtagttgctgtcagcgatgcattgaaaatcctctgataa<br>ttctgcaagcgattcatccgagatccgatgattccagtaattccatattccacagtggctcgacagtgacgatgatgatgatgacaata<br>atgataagacgacaaaaacgataatgataaagacgataaagatgatgacgattga |
| Contig47_<br>gene_60 | 873 | atgttgaataaaaaaataataataattttatttaacattattttaatattgtctattcttcagcaagtgcatctgcagattcaacagatgaacaat<br>cttatcagatgattctgcaggcttatcaattcttagacaattctaataatctttattttagatgataatcaattttaattagctaattcaatt<br>cagataattccataactttaatctagatgattcaattcagataaattcaactttatctagatgaagattttagacaataaatcaatgaaaat<br>ataaaaacactaaacatctaaaggagaataaatttcatcaatgttctcctttccaacctttcaaacctttcatatttctatcaaggcttcagcaggaga<br>tacaataatcttagaaaaatcgatgaaatatgattctgctatgatagtcaattcaggaggaattgaagtcaatccatccacaatcgcgaa<br>acaaccattatcgatgggaatggagagggccagaatattctattggcttcagacaatattgtcttaaagaacatcaagttataaacgtttc<br>aatagtcaagggggagcaatctatgcaaaggaacaaatgtcaaaattcataatctcgcaggatatggaggagcagcatataactgattcctcca<br>atctatgttgaagaaatgcttcacaggcaatgtgccaatattgaagggagagcgtttacattggaggctcaagcaatatacactgtattttt<br>ttcttgaagatctgattcacaggcaatgtgccaatattggccaatattggccaatattttatccagctaaagaagcccatgactccaagtgaggatgttcctttgatgatcaga<br>gatgaaaccttgcagataaggtgctcaattttagattctacagatatgattcctacgattacaattcacagata<br>tttaaattctacagatattgattagattctacagatatgattcctacgattacaattcacagata<br>Atgggagtattagctagtgttgctggaggcatatttttttgaaggcaggcatgttgctacttgtacaggtgttgcttctgtaggtttgctttt<br>aatgggtgtaggtacaatttgcactgcttatgctctgttattggcatgacagacacggcaattttctatctaatctaatctgataaaatt<br>tcggttcgatttgctttcaatgagtttaaatctcattggggaggtatagtcagctgctgcaaatctacattaaggactgtaggaggtaaa<br>tcggttcgatttgctttcaatgagtttaaatctcattggggaggtatagtcagctgctgcaaatctacattaaggactgtaggaggtaaa |

FIG. 7B-39

| | | |
|---|---|---|
| | | aaaagttgaaaatggtgcattcagtaactgtggagaatacttaatagaacaagaatttggaacaacagtaattgaaaatataagaaaatcattaagagtttttatcaattga |
| Contig47_gene_62 | 874 | gtgttttcagtgagtttaaataaacttaagattggtagagttttatttgtcttttatttagttttatttcttgttcaattaattgtgttttttgcagttgatgatttagctttcaatgatacatattattctgatttagattctgttaatggggattattcaggttttcttagtgaaggagactttaatggaggctcttctgtggttgttgatggtgaaattgactcctctccaattgccaataataaaagaattcttcatttgcccttactagcaaaaaggattcatcttcaccttctatttccacatcatcaaaaaacaataaaaacaataaaaacacttcttctttaaaggaaacaagaccgccgccccatcttcacaacgtgtatttatgaccgcgacatagtgtctgatgaagatgtaatcggacctggtcatgaaaacttggactggattaacctaacacatgtcgacgacagcctattttcagataattcaaaggaagatggagcaaaaggcagcaagattgccaccaccattgtcgcaagcaacctagttaaatattatctcaatgccagccaactaaatgtcggcttgaaagactccaacggcaattacctctccggaaaaacaatcaatttcacagtaggcagcgcttcatacatacgcaccaccaactcatcaggcagatgctccctaacaatcaacctaatgcctggcgtctatactttcacaatcagattcctaggagactcctcatattccccaagcagcaaaaatgtcaacgtcacagtcctaaagatgcccacaagcatcacagcaagcaacctggtgaaatactatcacaattcaagcagcctaatcgccacattaaaggacacacatggcaacccccctatccaacatgacagtaacattcaaaatgggatcaaacaactataaccgcaccaccaacacaaacggaaaagccacactagcactaaatatgatcccaggaaacttctccgtaaaaataagct |
| Contig47_gene_4 | 875 | atgggaggtgaaataataaataatgaaaaattaaagttaattttaattttaaccttaatttttcaatattaattatgaatacagtcaatgcaagtgacaatggtatcattgcagaatacgctgatatctccacaattccaaatgatgaaaaggtttctatcaatgaaaatgactatgatacaaattattatgagttacctgataaaaaattagatcatttagaatcaaatgataatcaaaatcatttagaaatgaatgataaaaaactaaatgatggaaactcaaataatgattttaactatatacaagagttgatcaatagtcataaagatggagattcaatattcttagaagacaaaacatatataggcaatggaagtccaattatcataaataaaaacctaaatatttatggatatggctataaaaatttatccgatcttgacataaaaacaatactggacggaaactccaaatcaaacatatttatcattaataagggaattcaattaaatctttatggattaagccttatcaatggaaatacaagttatgaggatggaggagccatctataacaatggactattgagtatagatagctgttcaatttcaaacaataatgctggcggaggagcagtatactcctctgaaggctcagaaattgaaatatacaacagtctctttgaaaacaatagcggacttcttggaggagccttggatttggaaaatgcaaatgcaataatatccaagtccacattcaaaggcaacagatgcaatggagacggaggagccatttacaataatattggaaagctaactatctctaattccaccttttcctttaacaagggagctcgtggcggtgttatctacaataatcatggaaccctatcaatatacgattgtgagatgttcttaaactctgcaagccaattaggaggtactgttaaaaattggggaagctgtgaaatatacaattccacaatcaaaaacaatactgcagacatgtacggaggaggat |
| Contig47_gene_125 | 876 | atggataagaaaatgattgtttcagtggcttttcttttattgattttggcagtggctttagtctctgtatttgatgaaagcaatagctctgaaagtaaagtaaacttaatcgtttattctgaaggcccaaagtccttatctgaacttgtcaatgaaattaagacccaagactattatgaaggatatgacaatgagacagttgcctggatggagtccttaggaaataagaaattttattatggtgacggaataatagttattatgagcgcaactgatgcaagcaagcttccttccttatatgtcaccgatgtagagcttttttgagcattttgaatgtaacgttttggaaaaacgttctttaggaaatgtagagtatcctaaggatgtcctgtatgtcaagaatgtaaaatacatcggcgaggaatatggtaacttttcaggggcttaa |
| Contig47_gene_140 | 877 | atgaaaatctcaagaataattgtattattaatgattctaatcttcactgcaggaatggtttatgcagtagatttaagtgaatttaaacttaatttaagttttaaattctcctccccttaa |
| Contig47_gene_146 | 878 | atggattctaaaaaaatattagttattttaggtttaactgttttagctattttttttagctagttcagttagtgctggtgacttgatttctactggggttataatccagattcacttattatacttgaaggagccgattttaacattccagatggatttgaaagaattgaggataaatccattgcaaatcagacaagaaattcaggagtcttttcatccattttaaatagggaagtttatgggaatcctaaaggtgaggagatagtaatttctgttgtggattttgataattttgatgcaaatctgccaattcttagcatgatttgcaaaggctgccaaaagaaggaattgcttggctatccaggttttattggctctgatggaaactccactaagttttcttatgtatttgataataaggtggtgtctatatccgctccaaatgaggatttgattaatcaggttctagtggttgaggatgcatag |

FIG. 7B-40

| | | |
|---|---|---|
| Contig47_gene_160 | 879 | atgaaaccatatgtaattctcataggaagcgcttcaggatagaagaaatccacagttgcagctgacttgcagaaacattaaacattaagcactt<br>ggtgaaaccgattttataagaagaagtagttagaggaatcatagaagaagaatatgctcagcctcactcatcatcctacatcaatgcatattcca<br>gccttagaaatcaggaaaattacaaaaaccaagcagagcttatcaatgcagattgaagcatgcatcatttgtgcttccagcagtagaaagg<br>gtaatcgataggcaataaaggaccatgatgactattactagaggagcttcattaataccggcttcattgtgacatagaacagttacagacaa<br>ggcatcggtctttttctcatattaagctccgatgaggagaccaagaaccgattgtaaaagagcatgaaaagagcataagaaggaggaaagc<br>agctagactacttaaggaagaacagaataatcctacattaatgaaacctgtgaaacatatctgaaaacacagttgatgaattgataaggtaggaga<br>gaatcaacccgtcaagaagatgctatcctacattaatgaaacctgtgaaacatatctgaaaacacagttgatgaattgataaggtaggaga<br>aatcatattagacagatacagcggaagcataaagaacctgataagttccagagaaaaagaagaactaaagaacttatagtttaactgactataga<br>agataaggaatatgataagtttgcaataataatgaaacaattgaaaaaattaaaaattgacctgataaggaagtttgctcttaagagaagatatgtaa<br>gcatatcgcatttgcaatataatgaaacaattgaaaaaattaaaaattgacctgataaggaagtttgctcttaagagaagatatgtaa |
| Contig47_gene_197 | 880 | atgttaatatcagtcttggagtgattgtaattatcattatgtagttgcagctgcttggatttagcgtgtttcatctagtttgactgg<br>tggaatttcctctggtactcaatatgagttagcaacctttaaaatccaattgctctagttagaagcccaatcaatataaccggaactaaga<br>tttatgcaatgcaaaaacattacctttagaaagagagttgtaaatgctcaagtggtaattaaggttcaaaatgattggatagtgttgaaagt<br>gcattggcatccgtccgctgcttcagaagttgataaaagaataacaacaatcaaagaagattaaaaatagctcagcaggcttataatagttt<br>atctgttaaataa |
| Contig47_gene_208 | 881 | atgcaaccagaacaaacaaactatatgcaggtgtattccttccatggggtcgttcttaatagccctgtcagttttccccctaaacgtttc<br>ttgcggttttattattgatataagatctccctgagaagaaattggcatttgtctttgtctttttaaatttttctctaaatga |
| Contig47_gene_253 | 882 | atggaattaagtaaagtgacaaatattaatcgtagtagggattatctgtcttgcattgcagtattatctcttacattgcatctgaga<br>cccagatgattagaaaaatcagcagagatgcaaacgttgcgaagatgttgagctccgataatgaagctccattccagactacctatg<br>agccttagaaaaaatatggtaggcgtattgattctaggcgcgctgataacactattgttgcatgggtataggttatgcattgaaaaga<br>tctgaataa |
| Contig47_gene_269 | 883 | atgaaagtagcagcaattaggtgctgctgttacagaactcacgcagctagtgaattacaattttctagagcttgaagtagcagacgcaac<br>cgttaagaacaactcaatgacccactcactgtagtagaagaggttagaattagcagtgacgaagttgtagtagctgacc<br>ctgtatttgacggcgaattcactgtagtagaagaatcgcagctcaacagctgaaaccctgaagactgtatgcct<br>gcaatcagagcaaaagtaggagaattagctagcagcaaccagctaacgtgctatccactcactcacccctgaagacttaggaatgaa<br>atgtactactgacgaccgtgaagacgtgcaatctgacctgtacctccgatgtaccatcccgattaaacaaatcttgaagacttaggcaaaaac<br>gtaaacgtagctcctaccaccaggtgcagtacctacccaggtcagtacagttctacattgcaaaggattttgacaaggcatcgacac<br>cttaaagacttaggtgcaaagcaagaggttccgcattcacctaactgctaacatctcaaatcttagtgcaccagcaggattcgtcgatatgtttccgcagtaactg<br>caattacctacgctgtcttcttatcctacagacactgttgaaggcattgacaaaatgatgtctttaaacctgcattattagtactgctgactcaat<br>gaactccgttgcaccaattatctgaattctcatatcttagaaatcttagaaaaagatccaatag |
| Contig47_gene_304 | 884 | ttgtcagtttattctgattctgttttagcagtttcaacggttgcagtagcgaatgatgatgtaattggatgatggtagttcttctaa<br>ttcagattttaattagttcttctcttcattgattctctttctctgatgatgttttcctctagttctgtttctagttctgatcacttg<br>atgaaataatttgtctgataattgtctgataattgtcctgatgagtctgttggtgctgataattgtctcctcttctgatgag<br>tctgttggtgctgataaattgtctgatgatgatcatcttctgaagaattgcctaaaactgaaacagtcattaaagacagaccc<br>aataattataattatgctttagttaagagattaaccatttaatctaacagattctgcggactgctttatccataagacttgactgtcaagg<br>tcagtgcttaaataagactcctaatctgactaccaattctaaggacaggctatcttaagctaagcctctgttgatcatatgatgttttt |

FIG. 7B-41

| | | |
|---|---|---|
| Contig47_gene_306 | 885 | atttcttttactgggatgaaagctatgctccatccaatgcaagttctaaataactatcaaaagtcctcaacaaagattaaattgagcaatat<br>tcacggatatttgactatttcaaattatgtaagtgtcacattactgattctgctgaaagcctataaaagcaaatcagtaacaattcaagtta<br>ataaggcaaaatataatgtcaaaacagacagcaaagcattgtcaaagtcaagttgcaaataagattgaactactctgtaatgctaaattc<br>agtggagataagaattattacgcctcttcaaattgacaataactaaaatgaagttatattaaggctccatctgtaaagtatta<br>tatgacaaacagctctgctccttattgacaattaacctgactaacgtcaaggcagtccacttgcaaaaaga |
| Contig47_gene_309 | 886 | atgaataagaaactaaaatctaaaataatcctttatatttattggcttaataatcattattgcaggaatagcctttgtatttgatgattattctcc<br>tgcaagtgcagatgctaattctcttattaatgaacatcagaggtttcagtaagtaaataacaatgatgttcctagatgtcctgaaatg<br>atagcgctgtcatatttttatcctggtgcaaagatagaatacactgcatatctgccttttattaatcatctgtctgcagatggtgtagattgcttt<br>ttagttgaaatgccttttaattagcattcttggaacaaacagtgcagataataataatgctcctataattattctaattgtatat<br>tggaggacattccttaggagagaatggttctgtgctttccattatgatcaataagtcattatgataagtcttaaatcaaaggagtgatactccttgcagcttatcctg<br>cagatagtttagaagatgtttcactgatgtgataaaagtggaaatcatgccagtttgcttcttatgcaatcaaactgagatggatgagcactattc<br>ccagcaattcactgactgaatatgtgataaaagtggaaatcatgccagtttgcttcttatgcaatcaaactgagatgagtagcactattc<br>cgcataccagcaagacaagaaaatgaaaccattaaagatattctttttatacatcaatggttcttaa |
| Contig47_gene_348 | 887 | atgaaactaaaactcttataatcatttgtgcaactgtaatattggctgtgttgtaatagtttatctgcttttatttatgtcaacatggcaatga<br>aactcatataagttctaatattgcagatacttacaaaatggcgatgaaatcgttgtcaagctgtgtggataagtaagcctttgtaaata<br>agaccattagcttaaacttaaagatgaaaatatgtattttccgcaggattatacgaccgttagctatgatcttcttacaatgacaaagtgaagtatattataat<br>gtcaatttgactgaaggaaaatatgtatttccgcagatatcagttctgctcatcaagttaaataagtctgttgaagttaa<br>aaaagatgttaaactgcaaatccaagttctacagatagtctatctagtctataagtctacctccgagggccaatatgagcctgaatctatgagcctattggtct<br>gacgttatgacgaagacgaaatctcaatattctaccttacgactaaaatcgctaaaaccaagacctacacgattgcaggaagactatgagactg<br>gcaatgtccaatcagtgaagaagaattggttaa |
| Contig47_gene_349 | 888 | atgattattataaaattattctaatgaacctactgatgaagcaaagtagattcaagtttatatgatgctcaattaattggagaaaacgattagg<br>aactgtacaccttcatgtacagtctcttgataaggatgggattgaattattcatatatcataacataatgttatagagaacttgatgaggca<br>gggcttattgtacagttctcttgataaggatgggattgaattattcatatatcataacataatgttatagagaacttgatgaggca<br>actgaaggtcgtatggatgccagctcctggaacttatgcagccaatttctgagaataagcaattctctattcctccaggcttgatgaagaatctagtaatatatgatgtat<br>caataggggtctaagatagatgaatttggttttatatgtcctgaatataacaagtcctgaattattacagttcctgttcaaaagagtgaattcct<br>tgcttcttaagatagccagagcttgttttatattccagctcatcagtcaacagtcacgccctctatataacttaccttagagcaggaactcctac<br>acactagtttatgacctattcctatggagacattctacaacctatgattgattgataaattggttgtgtgttgataattgagtttaaat<br>ttga |

FIG. 7B-42

| | | |
|---|---|---|
| Contig47_gene_353 | 889 | atggaattgaatgatgaataatatatttaaagttgcactgattactgcattggtcggaatgattgggatgctagctttgcctcttatattgaacc<br>aaggagataacaatcaatgaatttacaagaaacaatattggtgagacagtttctgtcctgtgttgtagagtcggttaaattatcctcaagcg<br>gaagctcctgcttctggagctaaatgacggaacaggtaaaataaatgtcattgttttcgaatcggttttagtggagcttaaagtgctgaaac<br>gacttaaatgatttaaagtcataatataaaagttgtaggcagcatacagaatataagtcttctatggaattgattttagctaattccaattc<br>aattaaattgaatcttag |
| Contig47_gene_356 | 890 | atgaaaaattattcgacataaagacaaagtagcagttgtaaccggtgtgctcttccggattaggttggcaaattgcacaagcttacgcaagcca<br>agtgctaaattagcttcttattcgcaagaagagaaagattacaagaaaacgtaaaagaaatcgaagacaaatttggtactgaagtaatgtacg<br>ctgttacagatgtcggagattatgacagcattaccgcatccgttcaaaagtaatggacgcatatggaagaattgacattctgtaaacgcagcg<br>ggtatgggtaacaacaaatgttgtagaccaatccaacgaagataggcaagacacatccacatcgacttaacaggtgtatactacatgtgtaa<br>agctgtttgagaaatcatgattgaacaagaatacggtaaaatcatcaacacggttccatccacagtagagttatcttcctgcgagtatca<br>gcgcatactccctgcgaaaacgcgaattaactgttgactcctatataaaacttagctgtagaatggctaaatacaacattacgtaaacgcatcggc<br>cctgcagtattcgaaaccgaattaactgttgactcctatataaaacttagctgtagaatggctaaatacaacattacgtaaacgcatcggc<br>taaacctggtgaattagacgacttgcaatctactactgcatccagcttctgtaccggttcaattaatctgtgtttgacggtgatgga<br>ctgctatataa |
| Contig47_gene_375 | 891 | ttgactttcaacaacctagaataaacattaaagattgcatggtaatattgtagtgtttacagtatgtcttttatctatttagctgtagtgc<br>agctccaagcccagatttttatgctctgggtataa |
| Contig47_gene_380 | 892 | atgataagcatctctgcaatagtgctgcagattgactcatcaatagctactgacgattcaaacaagataatcaatgataataacaatcagacat<br>tgtattagaagaaaatgaccctcaacaaatatagctttagaagacaagaattataaaattgaaagccacagcttaagaaagccagcca<br>atttaccgattaaatatctaataaatgaggatgaaaccccatacattaacactacaatcacttagaccgtgactacatcggcgtgagaa<br>ggcataagaatcgatcgtccctaatcattcacaggagtagatcagattatgtggcgcaattatgtgggagatcagattgacgaattgaaggtacagctgaccaacaatagctaaagat<br>tgttaccctaaaaacatcatttcacaggagtagatcagattatgtggcgcaattatgtgggagatcagattgacgaattgaaggtacagctgaccaacaatagctaaagat<br>acttttacttacaacacagccactaaatatggcggtgccgttctgggagaaatggagaggcctggaaaatggcggagcgagaggtgtgcagt<br>ggaattataataaactctaatttcatctccaataaagcgaatgtaggaaaatcgtccgcgtgccgtgcctttctggcgtgagataacggaaccataagc<br>ttactggtatgccaataatgcaataacaccactcactgccaatagtgcagcatatggtgtaccagtgatgcatcagagaggagcatatttttgtcatgcgaaatgg<br>ataactgtgagtttaatataatactgaacagtgcaaaacgtgaaagcgaaacgtgaaagcggaggaggcagcaa |
| Contig47_gene_381 | 893 | atgaaattcaaaaaataatattttattctgctaatagctcttatttgcataatcagtgctctgcagttgctgcatctgatgcaaatgaccctat<br>tagccaagacaataatcaagactagtttagaagaacaaatcaggatcttcgataactaagactaaagaaatagtgaatcaagcaccaata<br>agaaattagctagaagacaaaagtattctaaggaaacaagtcttaaagatgaagaaacagactcattccaccatctaat<br>aatctaataaacatagacaacccacatcttacaccattagcctaaattgcgattatgtcctcttgaagagactgcaactactcatgacactga<br>aatattaagttcctcaaatccatgaccatcttaaggatgaggaagcctgcgattgactgaatccaaaaacatataaggccgat<br>taatgttgaaaattccaattacgatacactgaccatccattgaagtgataaaaccaaattatagaagatctccattcttgctcttaaatcagacataaac<br>aataacagcaatagtgaaatcacattagatacgaatctagataagcatgaagaaaaatacacagtcatcaatgacactgaagactgaaaatgaataatcaccatgcagagcgat<br>cttaaagctgaatgaaaacgcattacaataaacggattgatgaaggagacgaatcttcataatcactgcagacaatcttcagacaatatcaacgtca<br>atttttgcaaatgaaatctgacaaggaggagcacatcctatggctttgggaaataacaaatctaacacgttattatatgacaatgacaaaggaagaagatgacggccaccataaactcaatatggca<br>acatctggagagagcatctttgggaaataccatcaaatctaacacgttattatatgacaatgacaaaggaagaaagaagatgacggcaccataaaactcattt<br>cattgaaacgaagccaagcccaaaggagggagccaatgtttttccataccggcgagccaccataaaagatgttgca |

FIG. 7B-43

| | | |
|---|---|---|
| Contig47_gene_382 | 894 | ttgtacatctcagagatagagattaatcaaaacattatctgaagcaataaaatatatctaaacacattcccctaaagcaatataca cgataactggtttgaaacactcgctgactatgaggtgccatatgactgaaggctgcacaaattgatattcctaaatgaaaagcaaccagg tctcactggagaatccgatcagctttgaaatcacattacccctatcctcttcaataagaatacaaagaaaataagcaactatgatgataaag cttccattcaatctaacagcacatgcagagcatggaatcattaaatccgacagtaattctttaggaaaacaacaatatatgaaacagaaatcat caatgttgagagaataatcggaaatattgcaaatatagattcagaaattgaaatggagttttagtcactgacgaccacattctatgact tgaaccaactcatcaacaacaagcctaatcattaatgaaacgattacaatcaatcatgatgatatagactttgaattaaagaggga atcaatgtcaaccgcagcctattttccctatatcaacggaaatggatatgaggacaccttacgacagtgacggaggccatatcctcaataaatgagacaatgt cacaataaataatattccctatcacaaacaacagcggatataataatggagggcgccattctctggaaggagacaatgaaaggagctgacgga ccctgatttcaaagcaattcacaaacaacagcgcattcgaatggagggagtgccatcacctaa caaaaaacaaacagcgcattcgaatggagggagtgccatcacctaa |
| Contig47_gene_383 | 895 | atgatctgctatgcagataatctaagcatgcatgatcaacaatacaatgaaagcaacattgcatccgacgacaatgagccattctctggaagg agaataggaagaataataacacacattcaaaaacaactacgccctctgaagaaggagggctatcagcataagaggagatagagagataa taaacaacacattcacaaacaacgcatctacagaggaggagcatcagcataataactagtgagcataataacaacatccaca aacaacagcggatatagcggaggaggaataacttgtctatggaaataatgtaagcataacaatacaatgcataaagcacattgcatccaacga tggagagcactttacgtcagcatgattatgcaatgaacctaaacacaatcgccaacaatcgaatcatggggagcaatctactatgaggagcaatctact gggatagatataaggaataataagctaaacaatagataagtgaaatctatttcgacaatgcagaatcattttcaagcgaatattggttggaaacaa cttaactataacatcatcttaaacaataagataaagtgaaatctatttcgacaatgcagaatcattcaacgaagcaataattggttggaaacaa tgcaagcaattataattgaatccaaacactagcttgaaagctccaaatcttaattatattcctatgacgaattcctatgacgaattgatgaatatgacaattcc caaatccaaaaatagtgaatgcttgaaagctccaaatcttaattatattcctatgacgaattcctatgacgaatatgacaattcc ctaataacagacaccaaccagctaaactaagaggagcaataagaagtgatagaagtcgtatagcagcataaatctaacaacaggagag agaagggaagagatacaattaagaggagcaataagaagtgatacagcataaatctaacaacaggagag |
| Contig47_gene_391 | 896 | atggataaaaaaatgacagtttattggttgccctattttgccctctctgtgtaggctcatatctaatcttgaacctgccagcataagcta tcatgaggtcaatctcactgacctgcgttgcaacgaagtccgtcaaagtcccgataagtatcttcatatacagacaacttaaacattcactactatt ccgattatgaaaacgatcttaacatacaagttttatgatgtgctccgaatctcgtctcaaggcatctgaaatgcatctgagaatcttaaaaag gaagttttagtgtacggaaaaggaagtgcaggcaatctcacttattataaaaacaataatgccggaacttacacaatgtatgttgaagatagaat gtcacataattatatttgcttccgctaaggacttaacaattctactagttctactattctactgcataatgtatattcactagtttgtgtaatgaaactg atattgatagtttgactcaagctatgcttaa |
| Contig49_gene_3 | 897 | atggataagaaggacatcataatcatataatactcgttctcataatcatcactattggcctttcataatcatcaagtaactgaccaagg cactgacctatatcgcactgtaaagtatctcctagcttttcgctgatgttccactctcaagcaacacttacaaggaaaacgtcagcgaaaaca tgtatatttgtaaacgactaccaaaacgacattcaaaatctcattcaatgaatctctaagtgcctctcaagacctcgaggacggctaccaa tatctcaagagagaggaattcataaaagtcggtgcaggagatcatgagagagaggagatcatcaatagaataccaataaggatgatgatgctagcta tattcattctttcacctaacaacagacaattaagttcgttaactcatgacaatatcgtaactcaatcactgctcgcatatctcagcgcaagt attga |
| Contig49_gene_4 | 898 | Atgacatctgagattatgatttaaccactgcagtggtttagcgcgcacaagtgcagttacaataagcgatataaaacttatgatggagc aaataaattatttttaccttagcaataaccttccaatgggagcattaatatcttgcagattttgtagatattccaataagaacaatcatta aggaatttagaagaaagattgtatgaaaagaggatttaagccttatagaatataaaagatgaattgcaaaaatattgcatcagataatttccaaa tcaagtgtcactttaagtttctgatttttgattattttgatttattttgatggtctttaggcgattaattttaaagatgagttcaatcaaagattgaattttatgaattttaaaat tggtttaaaagatgaactttctgatttgatttggtctttaaagatgagttcaatcacagattgatttgatgaagataaat |

FIG. 7B-44

| | | |
|---|---|---|
| Contig49_gene_12 | 899 | ttagtttagcacttccagatgattgcaatggtttggatgaagaagatttatatcgatttaaaaaaattgtttatctgtaatatgttttaatg cctttattggcatagcaatctggcttggatcaataggggatgaggaagttattcaattcattcaaaggcattaaaggaattttgtatgatgaagaatt tcttttaaggatgttgaattgatcaataggggatgaggaagttatatcaagttagtcaagatgatgtaataaatacctttttaaatt ctattgattcaaaaaccgaaaggcattggaagatttcttatttagaaaattttaaaaattttattaattaatatatgtattaaatctaat gaggatattagtgaggagaatgaaaattcttattagaaacatatctgatatggaatttctgatgaaaagttagaaatattttattgttt tatagaatgtttgaaagcaaaacagaagaaaaccaattttagactttcaattctgtttgccaaaagagaattaa |
| Contig49_gene_25 | 900 | atgggctttaagagattaaaaagactttttcatcagataatgataatgaaagaatgaagaaaaaaataaatctggtgaagaaacttt ttatgaggaatctgatgaaaaagcttttttatacagaagaatatgatagtggcttatttgaaatattgtatgattctttaacaatggtt ctgatgatgactatctttgatgatgttgacttaaaagaggattttaaatggtctgataattatctttaaataatgttttgagaggattca tttggttctgatgattgaccttaaataaccaacgtcctcaaatagaaacttcaattattattataatcttaatataatcttaatcaatga aatcaatctgactcagacattgtctttgatagcaataacacacctacctgaaggatcaattgatatgataatcttacaattgacg gcaatggacgtacaattgacgctcaaaagaatcacgcatcttaatgtttaggagaaacatagattcaacaaacatcaccttcaaaacgcc tattctaacgaggatgagggggccataagcataggcaattattccatctgcacaattaaagatctgttttcaagcaaaacaaggccgatcgagagagaga tgatggaggagccatatcaatggagaaaattccaattaaaatataactctgtttcaagtctttgagggcaatctacactcatcattcaaaagtg gaaattgcctattctgtctttaaaacaataccatatctctcttgaatataatgtcctctcttgatgtgacatgattatcgaagagtccct ttttatagataatgcttcaatgtctgaaggggcaatgactctctgttttacttttaaacagcgttgtgctcaaagtttgataatattaactacgc |
| Contig49_gene_29 | 901 | atgagtaaaaagatccttttcctaactttgatgatgatgatttgattgattaataaaatgctcaaagtttgataatattaactacgc taatgatgattgacagtgattaagtaacagatgatgatgaaaaagctgaacaatgcctgaaatctcctgaaatcaaaatgcttaagcaataaga aacaaccaatactgttaagtaacagatatgaaaaaagctacaaaaagctaacaatgctgcaaaagcaagcaatactaaaagc acaagcaaaagcacaactaaccataaaaaatgctacaaaaagctaaaacactcaaaacagctagcagtagctagcactagaa agccactcaaaacaactacccataaaaaaataccaactcagactctcogagcatcagcagcagccagcagcactctctctctcaagtcaatagctaaagctaa accaaatacaatcagcagcaataaccatacagcaaactcagcagcgactagtgaaatcagtaaacgaactataataaaactgaatagtacaagtagctaagaa attaagagatacgttaatcacaattacagcaatcatagcacaaagctgactgctgtaaatcagttgcatcatctcaaaaggcaataccacgtaaccaattgattttggtattta gcaatgttcttagaccaattacccaatataacaaagcggcaactcataagacgcaaattaacttacctagttcttaaagtgacaaatacaacaatgcataactgcaaatgaaacaatgaaagcaaaagattgac agcagtaaaaggtaaacagtaccagcactaaaaacaacaaacaagtacgaaaacagtgctagaaccacaacccag tactaaaaagaccaatcctactgcactacaacaataacaaaagctagtcgaaagcacttagattcaa | atgatagcggggtatctgcaagtgatctgataatgatgcatcgatcgatacataatgatgatgatttctattaactctagtatcagatgtctggtaa tgatcaaatatctaatgaagccattcagttcaaatagcttagtgctaatgatgtcttatgtccgaatctgaaaagataagctctaaaa taaagacttcaaataattaagtgctcaaacagcacacaaaaccactactaaggccgctaaactactaaaactggcactagtctacaa ccatctagcaccagtatatctttagcaagcacatataaaactgtcatcacagattcgtcatcacagattccaaaggacaagacgtcaaattggctgtaaatcctgttgaaggtctggaagcttagtagttg cttcatatgctgaaattatcctcttcagtattccaaattaaagaatatatacaagtcaaaagtgatacaagttttcaaaagtatcaggtgctgcaacgtctaacggttgcaagcact tccgttactatgcctactccctagttgtttacattaaaagataaaagacctagcaataatgagggcctatccgcaaaaatgctttaatgtcacagttaatttgacggaa agtaagctattcagaactacggtccaaggtgaccaagcaccattaaggctaccagattccggtaagcttgtctattcagcaaaactctgtgaatatgcc caggcaatctgaaatcttcaaggtgaccaagcgaccagaacttaagccaaaactcaaaagtaaacagtaccaagcattaaatcaaaacaacaaccag cattccataacagtcagtttaaaaataattttaaacacagactctctctgcaaaagatttagtcaagactagcgactctaaaagtcaac

FIG. 7B-45

| | | |
|---|---|---|
| | | aacaaagactacaagttcaaaggaacaatcagcgttcctatcaattctgtcgggatgtcactgtaagccttt |
| Contig49_gene_40 | 902 | ttgcttgccattccagcaggatttgcagcagatattgaatcaaatagccacaataattagatgattcaaatacagtaattttgaaattaatgc<br>aaattcaaagatacaaacttagaagtaattaaatactgcaattagaaatgaatcaaataatactaattgatatgaattcaaataagg<br>caagattagcaatgcaatgccagtgcttgaaacactaggttgaaaacgatcaaacaatccaagcctagaa<br>tattcaagcaattcactctcagcaatcttgatgctagtgctgtcaaatataatcccatctagtgatacaagtaacgatgctccaacaggtaggtgacgg<br>taacgtaaacatatactactttgatctcttgtatgctagtgctgtcaaacggagtataacaacctagatgctacaataaataaataattataagcttt<br>ttgtagaaaactccataatatctttgcaaacggagtataacaacctagatgctacaataaataaataattataagctttattggtcagactct<br>tcaagaacaataataagctacgcttcaactgcattatcacaacaatatcctaaacttgaaaacatcacattgaaagattaaacattcaaa<br>taggaaacctaactgctagaaacaccattttcatagtggaaaagatattggatagatcttacaacaatattttcgagggcaatatata<br>caccccaaagaaaattacaactcaaaacttcataaacaacactgccgaaagtttgaggagccattgcctctgaaaatatccttaacaacaatataag<br>aacgtgactgtagaaaactccagcttcataaacaacactgccgaaagtttgaggagccattgcctctgaaaatatccttaacaacaatataag<br>aaatgtcgaattcatccatgacgtttcactaaacgatgcaggggagactattcatatcattcacccaattaa |
| Contig49_gene_43 | 903 | atgagattaagatattttgcaataattagttaattctttaatatttttagttccagttagtttgcaagtgaaactaatctgattcaataga<br>attaaatgattagctgattcttctactgaaatagatgattctactgattaaatcaagattaagttctaatcaagattaagttctaatcaga<br>attctgattctaatttaagcaatgaacaagaattatattctaataaacttagtgaaaactctctagattcacaagtcaagtcaaatgattta<br>tcaaactccttatatttgtcttcaaatggagtaaggctagctgattgaattcaagcttgcccagttcaataacagtcctaacgattcaaatac<br>gatctatgtaaactcatcctatatttgttctgatgagtttggaactcaatctaatcaacaataactgtttttaaaatccataaatataataggagaaagtctt<br>ctgatttaaataatgtctatattgcaaatgggttttataataaatccatcagttaaggaagctctgtagagctcaatattcaacttacattcaggaatgg<br>ctatgcaaataaggagggcaatatatatgtggataaatcttcctaaacattattggaagcctttttgattcaaaacaataaggtggtagcagcatacaac<br>atagtctctgaaggttttggaggtgcaatctataatgcaggctttttaagctctataacgactgtcttcttaattctaagttctataataactcaatagacataag<br>aacatatcaaaatcatcatatgtgctggaggagcaataatcgcagtgcaagattgtcacaatattcaact |
| Contig49_gene_44 | 904 | atgtttattggcttattattaatagtctattaatagtctattaatcatccctataagttttgctgtgatgcagacagttattctgcatattctgtgattctat<br>tagtttagagtgatgataatctttattagaatcaaatacagtttaaggattcaaaattcattacaatctattgatgatgttgattg<br>gaaataggactttagatgatacaagttattctgaaatacaagtttcaactaattcagaggattaacaatccctgattcaactaattca<br>gaagatttaactaatctgagaagtctgcaaatacagactcatcgtcaaatacaataacaataacaaagagtctaaatgaccaaataacaaacat<br>aaaagcttaattatgatgagtacgcagcagaatgaaggtttaaacatcagcttaaaactacagcttgcaattcagactcaatacaatat<br>tcgtaaatgcatcctatacaggttcaacagaacaaatgtgtatatagcttaaaaggggtttacacagtaacacagaagaataaccatcaaacaaaatctaatctcattggattg<br>tcctctgatacaagaacaaatgtgtatatagcttaaaagggtttacacagtaacacagaagaataaccatcaaacaaaatctaatctcattggattg<br>ggattcctaaatacaaatacactttagttgattgcaatggtgcattctttattagtcctgacggtctttatactacagtatatgccattgctaa<br>acatattcaatccacatttacaaatggacgctattccagtgaggggcaatatacattaactttgtaaatgttatttt<br>aaaataaccgagcggaagcttcctcctaatttatggtcgatgtagaaaggggagccctatataacaataaggatttgttcgaatctacaactgcttatt<br>tgaaataacactgcaaacgatactcagatgcatgtgaggcgcaatataacgatatggtgagatgacaa |

FIG. 7B-46

| | | |
|---|---|---|
| Contig49_gene_81 | 905 | atggcatatttgataagtcagtctttgaatctagtaaaactttaaatatttagatgattaattcatagcgggctgaatgagattgt<br>tttgatgatatcagcttaagtaaaatgaaaaacaagtattctaacggcattgaaatagaaattgataatctgttattgatgaaatg<br>gccatgcaatagatgcccaagaaaatgttctatctttttatgcactgttaaaaatatcgtagtaaagaatattcatttaaaaatgaatccat<br>tccaatggaggtgcaatagaaaatcgtgggaattaactatatatgattccacattgaaatatccatccttgagggcagttttaa<br>cgacggccctaaactagcttgatagctaaatccacaatcactgaaacatagccaaagaggcggagcaatttataataatgatgcgagttt<br>atattcagaatccatgattaacgaaaatgtctctagttttcatcagtattctgcggagcaatttataataaggcgagttgactattgaaaa<br>tcaacactcattagaaaccatgcaagtttggcggagcaatagaaatattggtcagttaaacataatcgattccacaattagcaataatgaatc<br>cagtggtgatggcggtgcaattttttaatgataatgctagcttactgattctgtcctaaacaaaacgaattggtcggccaataggaaaggggagct<br>gaggggcgatataataatggaggcaatctcaatattgcaggttcatcacttgcaatcattccataacttttttgggggagcgatataatgatgagg<br>atataatatgggggcaatctcaatattgcaggttcatcacttgcaatcattccataacttttttgggggagcgatataatgatgagg<br>caagatattgcagaatccaaattcaatgaaaattcctctaacaggaatgcggggcaatatataatgaag |
| Contig49_gene_96 | 906 | ttgctaattggacttgtcatctgtgcaggtgtcttttattttcaattaactatgcaactcccacatatctgatattcaatgcaactgaagtcaa<br>tgagggagctcatttacagggtattgaatgatgcttatgatgttccggtggtaaataagacaataacctatcataagcaggatatgaaatgg<br>gaccattggtgatgttcaaacggatgacacggagagtttgttatagaaaatgcccaatacctgccgatgccgtgaagacaattattatggt<br>gcattcaccttgcagggatgcaaatatcaaggatgttccttgatgaaatataactgtaattcaaagaataa |
| Contig49_gene_128 | 907 | gtggttttagttgctgttgtagtgattggctctactgcattcctattaatttatgataaactgtgaaactgaaatacactacatataatttatccaaaac<br>atgcatgatgattttgccatctggagacaataagtactgaaaatccactgttaatgaagcaattcgtcaatcaaacgtgatttaactg<br>tttattctataatagtgaagaactgtctgtataacgagaaatgtactatagcgcggtagaacatctcatatcagcgtgaatcaagcgctcatacagct<br>gttgcaaacagaactgtctgtataacgagaaatgtactatagcgcggtagaacatctcatatcagcgtgaaatctcatcagtagcacctgctactacatcatcac<br>aaatgatgttgagatattgaacatctcatatcgagcgcttcaaatcaagcgtgaaattacttatttcctaaatgagacgactactacacatcagtgtca<br>ataatcaagcataaatgtcactgcgtacggctcaaatgaactgatcaagtgcatctcacagctactccaatgtttcaagctctaattcc<br>caatctacaggcaatgatgatattattggtctgacaagatcaggatatatattaaggagtataccgacagcaatggcatacagcatagaccg<br>taggaacggacctaatgaggcttatgatccaaacacccaaagcattactgatggtgtagaggatacagcagcttataataatcaagacttaattt<br>aa |
| Contig49_gene_152 | 908 | atggataaaaaaactctagcaattattgctattatcgttatagctctcttgtagctgtctgtagctgttggtgcttacttgcaaccagcggtgatcaagtgacaa<br>tgtagtaagaatcgtcacttgcatcagaccatgacaccgcactttcgttgcaaagagaagaagttgtttgaagatcaaggtctcactgttg<br>aactaactcaattaacaatgtggagacttaatgactgctatgcaagtggagatattgatattggtatgcaggtatcaccctgtaatgtct<br>tccatttccaagagttcctgtaaaagttgtatccggtgctcaaattgaaggaagcgtatgtgccaataagaacagcggcatcactaccgt<br>tgcagacttaaaaggcaagactgtagcaaccctggtgaagcaacaattcaaaacatgctttaacctctgcttaacacaagcaggcgtatcca<br>ctgattcagttgaattcacaaccatgaaagctgtcaaatgactgacgcttaaagcgacgcaagttgacgcaatgatcattgggagccatat<br>tcctcaattgcagttaagaatggtgacggctgactcattagacaaggtattgaaacagttctgaaatcattccaggacaccatgctgttgttgtgtagctaggga<br>agacttcatcaaggacaccgtgactactcattagacaaggtattgaaacagttgaaagctcatgaagaagctacataatcactaatgaaaacctgcagaagcgg<br>ctaagatgttacctgaagacatcgtaccagatcaagagttacaagctaaagtctacgataccgtttcattctgtttagatgctgagtac<br>aaacaaaggtcatgactttcatgtctcttgaagtgcaattaggtcttttaaaacaacctttaactaggtctttttaaaacaacctttaactgaagaacaatctttgcagacttatag |

FIG. 7B-47

| | |
|---|---|
| Contig49_gene_167 | 909 | atgaataataagacattatttattcattgtttattcatatgtcttttattaccatactatggtatcagctgcagatgctgattccaatttaat
tgataattcagtaattgaacaaatatcaattcacaagcaattacacacatcgatgcaagtattgatcacagttcaaatgcaatcaata
ctaatattaattctgatatattgtttctaataacaataacaaatgatccaataatgattgatataatattctagtaactgatatcaattagg
tcaagtaagaatatattcaagctaccaataaaaatatatttaagtgcaaatgcactactgctgatgaactgtatgatgcttatctcgatgtaactata
taaaaataataaaattcaaatgataaaaattcatttagataaaaattataaattcgaattggcactgatattaataatactgatctgcttccgat
tcattgaccaagatacaaccgtaccattactgtggaaatcatactcgatggagaccacttgctagaatattctaatatatactgatctgcttccgat
aataaggccattactataatgttgaaatcatactcgatggagaccacttgctagaatatttaatattaatactgatctgcttccgat
tgttgttttaaatagcatccatttcattcaattgtacagctactggtagtgtgcattatgtttatgtgatattatacagtcacagttgcagctaattac
cctaaattatattactgcaatcacaactgcagtgatgtgtgcatatcgataacatatttaatgattatacagtcacagtagtggatgcccgatacaattc
ctatacctatatataacaacactgcagtgatgtgtgcatacggaaacagtttccaccttaacaagttaacttcattaaca
tgcaagtgaaatggtggtgcaatgtatgcatacggaaacagtttccaccttaacaagttaacttcattaaca |
| Contig49_gene_168 | 910 | ttgttcaaggttgaaccagctccatcaaatgtgactgtcgaagcggtaaatatcacttatcttgataatgagactcactgtcactgttccaat
cactaatgcaagcggtacagttgcagttgtaattaagaataatcgaaagaaccgtaaagcaacatgcaaacctaccaatattacag
taggggattagctgtgttggcgaatatatgtgactgtagaatacaacagcaagcaatgcaagtacctattccatgta
gataaggctaatattcctgatgtcaaccagatagtaactatcaggcatagtgttgttccaacaatatcacatataatgatgaaactactactgtaac
cgttgatgttcctaatgctactggaaatgtaactatcagaatcaacggatgtgttgaattgacacaagatgtaattgaataacattactgaagatggctcacat
ctgtaacattcaatgttcctggccttgttgtagtgcgaatataatgtaactgtagtgtacacagatgatgctaactataatgacgtcaatgctct
gcattgttcaaggttgaaccagctgcttccaatgtagttcccaatgtcaagtataaatgtaacctgacacaactacattacaggtgaagacaatagccgatgcatctgcctattc
cgtaactaatgctacagacctgtcagtaggcgaatatattcctgatgtcaaccagtatagtaactatacactgatgtccaacaatatcacataacaattgaaactatcac
catgtggataaggctatattcctagtgtcctaatgctacacaggtaatgtaaccattaagattaacgaactgatgttgaattgacta
tgtaaccgttgatgttcctaatgctacacaggtaatgtaaccattaagattaacgaactgatgttgaattgacta |
| Contig49_gene_172 | 911 | atgataaaaacagacaataaaggacagatagcagtcgaactgctcctctttttaagcttcataagcatcatagccttacaacatcat
aagcgatgcaaatgagtgaacaatagccatgcgtgctgcagcaagaaacggagcattcgaaggagctcctcaaacgactgcaatctatccaaa
ggacacctttgacaactattcaaaggacaagaggaaagaaggcctattcaatatga |
| Contig49_gene_175 | 912 | atgttaaatagaaaggctttgattttcattgattttaaatgcattttcagtgcttttaaatgcaatttaatgactagttctaatgctgttctaatgtctgttcatgtc
cactgttaaatgctagatattgcattgaagatattgcgattaaatgcatttcagtgcttttaaatgcaatttaatgactagttctaatgctgttctaatgtctgttcatgtc
tagatgatgattctaataattatcatctgaaaatatgattcttcatctgatgatgaaaacaagatgattgattagaggttctgattcagat
tcaattaaagacaatctcaattctcaaattctcaaagacaaaatcagcctagtatatatattaaggaaatcaggcctttaaacctaattca
gatctctgcaaaactaagcctcaatacgtcaacggtaaacatatgctcaattgacagataataacatatgggaaaggcctcattcttgccttaaactaattca
tatgatgcgaagatagaatttatggggatgatgattcaaacatctcttttctgtaaaggtcttaaggctcttaacaagcttactaacaagttcctgttgaaggcatacgga
tacaaagacttctccacatgttttattcatcacagaaaaactataaggatgatgccaaaagactatataaggatgccaccttaaagaagaacctaaaa
ttcagttcaatgtcatatgattttacacatatggtcatcaattgtaaagatgatgccaaaagactatataaggatgccaccttaaagaagaacctaaaa
ctaggctcatgtcatatgattttacacatatggtcatcaattgtaaagatgatgccaaaagactatataaggaaaacacaaaatgaaaatgaaggctcaattaagat
atccgctcctgagagatggatgctcatcatcatatatcatgattgattgtcttgcctatgtgattgattgacattgaaagcgctgtgctttta |
| Contig49_gene_180 | 913 | atggataataaagcgataattgaattgattgtcattgattgattgtcttgcctatgtgattgacatttaacgaaatgctccaat
ttcattgaatgtaactgaaatatgaactgaaatataacacaatacagataacagcgtagacactacagacatgccacctgtatccacagaagaaccaaatg |

FIG. 7B-48

| | | |
|---|---|---|
| Contig49_gene_181 | 914 | atctgaagttaaggacattgctaagaatgtctctgaaagtatacagagcagcaaataaggcagttgccgattctgagacaccttgcataaacag<br>actttcacagtttcagaaacgaaaccggtcaaaatgagggcatgaacctgatgtgatgtattatactgaaaatgatggtcctataaa<br>agttcaaaagatagattag |
| Contig49_gene_182 | 915 | atggattcgagcgatttaataagaatataggcactaatttaacacagattcaaacaacaattagacagtaatttaaactc<br>taatttaacagcaattaaacagcaatatagataatccaccaagattagacttaagcactaaaaatttcaaagccctaagctcaa<br>atgatgatctcttattccaatcttaacaaatctaaacttttatacagactattctgatgatgtaactacacatctagcgggaatctatgcattggtgcat<br>ggcatcagatttggtcattgaaaacaaccaattctatatagactattctgatgatgtaactacacatctagcgggaatctatgcattggtgcat<br>ccaataataatatagaaataacagaatatccattccatctcattcaaggtctctaagcaatacatcaaaacattacattatgggatagactctct<br>tcatattcctcaaatgcctattctaaagataatgcgaaggaaatgacatatcatcaaatacaatagatatcatttctgactattatgcaaatgc<br>aattacattgtcctgtcagttgacaccactctgaatcaaacagcctccattaaaatcagttcattgttttatgtatgttgcagagtatt<br>ttgactttgaaatgttgaatccatcaaataacttaatttacaaaaaacactattgaagctagctcaaatatgtatatgcattcaattc<br>tttaatgtatttgatgttaatattaaggaaaatacaatcaaaaccaattccaacgtagttatgggataagtgcatatgagtctataatcatga<br>tataggatataacaatctttttgtaaatgaacattcatgaacgtttcaatgttttatccaataatgacgttaacatactctctgggagattatgcaatcaggttcgatgcaagc<br>atatgggatatcattatgagataatgatcttgcactaatgatttacgtatttttgacatctatgttgatt<br>tcagcagaataataaatgtttttaaaaataagtttctaataagtatccagaagtatcaggaaagtatgcagttcaatgcagttaacgtaatgtgactgtttc<br>tgaaacaatcattattatgagataatgatcttgcactaatgatttacgtatttttgacatctatgttgatt |
| Contig49_gene_183 | 916 | atgagttattttaataaggacatatatcttgcatgtgaatatttattaattgtctctcatcgaacttgctatgggttcagcaagtgccagttc<br>tgctaatttagatgattttagcaatcttagcatctgtcatgtgactnnnnnnnnnnnnnnnnnnnnnnnnnnnnnnnnnnnnnnnnnn<br>nnnnnnnnnnnnnnnnnnnnnnnnctaattcatataatgattttaagtgttgcttgaatctgatgctaattcatataatgattcagcacc<br>tattttgaatctgattctaattcatgacattcaattaaatgatcaattagtaagcaacctataaaacttttaaaagaatatgataagaatggtatttttcttt<br>caatattctgctcctaatgcatttaatgattaagcaagactacgatctattctttgaagggttgataattctatcaattgacattaaggatttgacct<br>tagatgtaatgatttcaataatgattaagcaagactacgatctattctttgaagggttgataattctatcaattgacattaaggatttgacct<br>acaatatgttttgaaagaaccttttctaagtaagtaaagaagtaagtcatagccatagcttcatagggcatttatataaggattgcatttgaaaatctcttttataataatgtctat<br>ttctggggtaataagcacaatattgatggtgaaggtttgcataggtcatagggcaattttataataagggcaatctgacttgcaacactgctttataataatgtctat<br>ttgtcaatgggtttgactttcatctgcgagccattttcatctgcgaggcgagctagagaaatgaggattcctgacaattgaaaactcttcattcattaaaa<br>tctgaagatgcatatcagcatgtgtctctgcctagcggcgagctagagaaatgaggattcctgacaattgaaaactcttcattcattaaaa<br>tagtgtggttctgtttttaatcaatatgcagagagcatttgcaatcatgaaactaactataaaca |
| Contig49_gene_184 | 917 | atgaaaaacaaggcaatgtttttaatatctgcattattgatagcagttattctatctccagtgctgtaagtgctgcagatgctgtattgctgc<br>agatattgatgacattgacgattcaatcgaagttctcgtagatctctctgcagacacgaggatataagctatacgacgtctctttaata<br>caagcaaggataagaatacattacttcctcaaatattgtagagaggagatggttcatgtagtagacagttgaaaccactggtgatggt<br>agtcaatcaagccatatgaagcccatataagacataagaaagagcatttgatgctctgtggtgtactatctattggcaagcggtgtataacaccac<br>caatgataggagttttttcattggcttgattggtaacttctctattgtgctgcgatgacattaattgatttattatctc<br>tttcaaataatttataaacgttagaaatgctagaaatctctttgtctaatgtgaagctatacgttctggaactactgcaattagtggagcc<br>aacataactataggaggactccgattgccaattctttattattacggcagcaccgatttgctttaggtggcggtgacaacactataagaaa<br>ttgtgtgtttaacattccgctgaagctgtatgggttcaggtgttgcaatttaaatgaaatgcaaatgtatattgacaattgtctat<br>ttaagaataataccacactaacgaggttcaggttcaggttcattctgttatgccacattcatcaatcaatcaagttgacttaacaattgtaatgttacagaatgt<br>cctgcttctctatgcttcctatttgaatctgtattaacaattcatattttctataataatgatgacacgtttaaacagattaattg<br>tgccgttttctattcaaccgatccaggtaatctaactactgtttgaaatttgaaaacaatacaggagtcg |

FIG. 7B-49

| | | |
|---|---|---|
| Contig49_gene_194 | 918 | atgaaatttaacaagagttaattgcaatttttgtaatttgattgttgcttcagttccatatctgtcattgcagcggaagatgcagaagatga caatcctatcataatggtgctgtaatgaatgaacaggaacctgatcgtgtgaagatgatgacaatcctatcatcgtgtgctgtaatgaatc cacaggaacctgaatctgaggatgatgacatctgagcagatgttcaaataaagtagctcttagcaacatcctgaaatccattagtagttcaacagatgattctcaagca gcagttcatcttcaagcagatagtcagacagatagttcaaatcagagttcttagcaacatcctactgaaatccattagtagttttattaatgtccctttccat cattgacttgtacttaagagttagaaaatag |
| Contig49_gene_208 | 919 | atggataaaaaattattatcggtgcagttgttgcacttcttgttataattgttggtgctgtcctcatggaggaggcactactgaaagagg tcctgagaaatcgtagttgcagcttacagtcaggagagaaccagagagctgtttcgatccaattgcagttgaacttatatgctgagccac tcattcaaagtaccttattgaaaatgaccctaacgtacttacgcaaaagattggctacagactatgagattagcgatgattataagacatac actgtagacttaagaaaagatgtcaaattcactgacggttctgacttgactgtgaagatgtagcattcacatacaacgcagctaaagaatctgg cgcaagcttagacttatccgtttagataaggctgaagctcaagtgattacaaaagtcaaattcaccttaaacaaatcagattccacttcttag ataagtgcttacattgtattgttccttccgattcttataacaacgaatcatatggtaaacaccatcggttctgaccatacaaattcgta caatggacaaagtcaacaagttatcttagaagaaaacctgattactagtcgtatatcgtagctgtacctgatacagaaactgtatatactgaaaagtctacaagaag aacgaagctgcttcaacttagctaaaaacgagaagctgatatcgtagctgtacctgatacagaatctttgctgaaggacattaaacgttacaa tgtacttacaagacaccatcgacgttcgtggtgtatcttttacctagtgcaatcagaaaagcattgaactctcttttaactctccagatgacaactacaatcggt aacaatgtacctgcgatattgcaatcagaaaagcattgaactactcttttacctagtgtattaacagaagcagcaattgaagacgtgacgttg tccttcctatgacgtattgctcaccattacccatggctaacaagaagcagcaattgaagacgtgacgttg |
| Contig49_gene_226 | 920 | gtggaagtgataatatgtaaatataaaactgttgcattagctgtgttatagcaatcatagttgttttattggctatattgctgtttccaatgt agtgatttagctcagatgatactgaaggggaattcctggagttgatagctgcttatgagtttatgagttgttttccaatgatatatc ctgaagctcttttgacctctttgaccctgaaggcgtactctcggtttataataacgaccaggctgctgcccatatattgggacaatatatgatacaatcgtcagtacaca tataatgtgatcctcatattctgttgttataaacgaccaggctgctgcccatatattgggacaatatattgatacaatcgtcagtacaca ttgggtcgaaggcattccgtggagatgccgttggaatgagcataacctctgtaatcctttgccataattcagacatttttaatgggaaata ttaagataatgttcatctaa |
| Contig49_gene_239 | 921 | atgaataaaagcaaaaaactatgattatgctgattatgaccatgccagcgtaagtcgaacttgaagacat tcaagtcacagcatccaatgcacatcagatgcgttattgcatctgaagcaaatagtgcatatcctgataatgccattatcacatccgaaaagg aaaatgcgatgagaattgaagaatgaagatgtgaacgcatttaacgcgatataagatgaaaataccaactatccaactaatgaaatatccatctgtag aatatcgatgatgaagacgataaactctgaggtgcagaacatcagacaagatgaaaaaaactcggagatgtacaatcaaatccatccaacatcctatctgtagg agactaccattcctttgaggaagcttacaaagggcagatgcgagagaactatcaatcaagcgatgcgagaagacactatatgcggttgaccgctaggcttgacaaattcccttgagcag gaggatcaaccctaagcttacaaagggcagatgcgagaagacactatatgccggttgaccgtaggcttgaccgcatcttttacataagc tccctcaacaaccccagccaatcatcctgaacgacatcaaagacgacgcgaaccggcatatcaaataaccgcgaaccggcgcaaccggcgatttctcaaaaatcataagatcctcaacaatgaaatgaactgaacatgctaaccac agccatatactacaaccgaggaggagcatcttttgacgcatctgtccgtgctcttctcagacaacacgtcagacactataggaatggacatgctaaccac cagtcaacgagcgatgagcccatttgactgctatcggtctgcttgtctcttcagcaacacgtcagacactataggaatggacatgctaaccac gcagtctatgcaaacgcaatttggcaaggatattggcaaagtaattcaatactacagttctctagtgtcgatgtaattcccc |
| Contig49_gene_240 | 922 | atgacaacaactgcattcgacttcgagatagagaggaagaataggaagaatacttctacttccagcttcttgacgaatacgaatcagtagcagg caagaacgtttcaatcggattcagcgagatcagcgaagatataaccgtacaagcaacgaccgatggcgaaagctgcagatcaacctaaatattccg gatactacacatttgcagtaaacttcggcgagacgataaatgcgcagcattcgatgttgccgcaatcaacgtaaccatccagaccctaag ctgaccacagcagcagacatacaaggcaagcgccaagaacgccaagcttactgcaacatttcaagcttataaggaacttcgattccaagcaa gaagattacttaccattaccaagcagcaaagacgcaagaagactacactgcaaagcaagaagcaaaagaagctgtaaggtaaggtaggtacgtcgctcagtaagtaaggaagaa |

FIG. 7B-50

| | | |
|---|---|---|
| | | cctataagtttacagctcattgcaggagacaggacatacaagaaagtcactaatctgcaaagctgaccataaaatag |
| Contig49_gene_246 | 923 | atgaataacactactaaatattaattggagttcttatcgtaggctgctgtcagtaatgtttgtatcagcaactgcaataatga<br>tgtatctgacggaaactcttttatggacaagtacaaaatactgcaaatcatgtgaagaatgttgcttccaatgacattaaaagtgcagcaaca<br>tcataggtggaggatctgaattctcaaaggaagacaaatggtatttcaaataaattatactgatgaaatttccgccaatatgataca<br>aaaacaggaaaagcttataggttcaggcttaatgaagatcaatcaatcctttgcaatgacgatgatttaatttagaataa |
| Contig49_gene_248 | 924 | atgggttcaaaaaatttcaatatctggatgaattgattcacagcagtgcaaatgagattatttgattcagatattgtattagatttgatga<br>agaatctgaatatgatgatgaaactgatgttgatgatcaaactattgatgaaatgggcatgtcattgatgccaagatgggctgtgca<br>gattaaaaaatcatgcgaaaacatcacattaagaatctttgctttaaaatttcaaatccaagtttccaatatcaaatcaatctgtgatttg<br>atatttgagaattgcagattcattcacaatcaaggtacaacatctataatatttggaaacatatgctaaagaatgttgttttatagaaatta<br>cttatcaagtcctcttcaggatattcagtatgcatcataatgcaaggattccaaggcattcgttagcgattctcattttatcaaaatgagg<br>ttaactatccccattatggcttttaaatgacgggcttattgaactaactgaactcttaaagacaataaaatgtatattcgttatgattttgcagaatt<br>tgtgtgattttaaccgaaaggggaattgctgtgataactgcaaattaaagacaattccacttttgaaaatgaaaacagaatcctttgttcaattaaaatatg<br>gcatttgccgtatatctgattgaagttcaagattcaagttcgccaataaaatctgtatataatgaggagtcattgcaaacagcggacctttgtaaaatagcttcatgcaa<br>tattgatgaagatcatattgaacatgatgattcctatcattgatgaaaaggactttaatttattaaagg |
| Contig55_gene_2 | 925 | atgaaacagaaaattaattattgtaattcttttagtttagtttataaattgtaataagattcttctgtgcattttatacacattcgtacgaggag<br>caatgatttagctccgtggagcaagttcctcctgtgagctgtccaaatctcacagctaatctcacagctacaagtaaaaatgtctactactgataactactactaacacagttgatg<br>ctcctttaaataatggcgtttatgatctgatccatagacagtctcgtcatagatagtttccatgttgagtggatctaactcctataatggtgctctaac<br>acctataatgcggttcaaatactaataatgcggttctaacaccaatatggtagttctttctgattctggatacggtatctgttctttctagccagtccagttc<br>tcctgattctgtaatggtgttcatcagattctgtgtaatggtgtctgctcctgattctgtggggcggttcatccagtggttcctg<br>aacctgcagccagtggcaatggctcttcaaattaa |
| Contig55_gene_3 | 926 | atgttttgtttatattattgttcatttattgttatagagagatctctattcgtatttgctattgttgtttcaaatggcggaggcaataattctct<br>ctcttggacaattattacaattgcaagttcctctgcaagtttcggcaaaatattgttggcttttttaattccg<br>gcgattcttcagattccaagttcaagcaattccaagtgtttcagttctagtcagtccctgcgtagttcaagttcttctagt<br>tctagttctagtcagtcagtccagtctgattcagttctcaagttctagtcctgctgcaagttcgttcagttcaagttcctgctcaaagttctagctaacctcagtccagttc<br>tggttctagctctgatgatcagctctggaggcagcgttgttgaatctgcgcgacattatatgtgacctgctggagctgatgttgtaa |
| Contig55_gene_7 | 927 | atggctttgcttatttcttgcaatgtatgtgtctgcaagcaatgcaagtgattatattgatgattaaccatttcagacatttgatgattcactaga<br>tcttgtatctacatcaaattcagatattttattcttctgatagtgatgatggttgttaggtggtcagtgatgcttctggtgatgttctggtt<br>ctgatgtatcaagcaatgaatcaaataatcagcaatcaatcagctccttggattctaataatcaatcggtttagattctgtaattcaa<br>ttattagattcacagtcaatgtcaatcagtccaattgaatcagatcagtattccaagttcgtcagaaatgctgatagttcagatatc<br>agttcttcctaaaactgtgttagaggaattctctcaatattacttaagagataagctagcacctttattattctataaaagtacttgaaatt<br>cctcaatggtaaaacttatataaaaccacaaatgcttaagatcagtctagcttaccttacagcgactcctaagcaagactccaaccagcattcaaactcaggcagtc<br>gcctttgttgtgatgagcttatataagcttacattaaagatgctaaaggaaaggcttatcccgcaagaaatcagcattgcattcaaactatggaaaga<br>aatagtcaggggcaaattacaaactacaaatctaactggccaagtcaacctaacaattcaaatggccaattcaaatggccaagtacaatctaaactataggtaaatgacctataagttgcagga |

FIG. 7B-51

| | | |
|---|---|---|
| | | gattccaattatctctcaagttcaggctctgtaagcattaaggtcaagatggcacttccataatcgttccgatcaagcatcgtcaagggaaa<br>gtcctatacagtcaccctaaagaatgccaatggtgctgtttttgtctaatcaaaagatagcctttacttaagcg |
| Contig55_<br>gene_13 | 928 | atgaacaataaatactttttaggaataattatataataattgcagtttagcagtgatattgcttttcactagattatcaaacaaattattt<br>gaatgaagttcaatgatctgtaaatactacagtagttcattaatcaatgaaaatagttcattcaaacaaatgtcttcaaacaaatgtccaattgacaatat<br>ctgccgaacagtcattcccaatgcagttgagaaattaaaacacaccctgcttatgaaggctacgatgaagatacactaaaatgcta<br>gaaacctttaatgaagcattatgtttacatcaaagattattttgtagttatgataaaatgatgcagaaaatctacctacaagctttgttaa<br>tgatgcatttatttatgactcacatgcgatataattgaaaaacgttccttaggaaggatttaaaagtataatatatgttaaaaatgtta<br>aatttgaaaatcaaagdatagtgctatgatttttaa |
| Contig55_<br>gene_23 | 929 | atgctttaaatgataaatctgaactactaaaatcattatctatttattttgctaatagttcaagtttaattcagtttatgcaaa<br>ttcagataattttgatagtgctaaaagttcagatttcaattttcagtgattctaatttcagtgattctattttatagaaatatgattgttcgattctattt<br>taattaatgtccattctaataaaaggattctaattagttctatttgaagactctatttgtagttcctattatctctctagcactattatcagc<br>tctgcattgtagttctaattcagaagattttttgaccacaagcaatctaagtgctagctataagacaatcacaaaagaattcacagctaaactcactgatttaaacaaa<br>ttcagcaagtgcaaaactgttattttgaccacaagcaatctaagtgctagctataagacaatcacaaaagaattcacagctaaactcactgatttaaacaaa<br>atccaattgcagtgcaaaatataatcagcactcaaattgaaggagatagcaattattcatctgctgttgttaaaactccattaacaatcagcaaaaa<br>ctgctccgggaaatataatcagcactcaaattgaaggagatagcaattattcatctgctgttgttaaaactccattaacaatcagcaaaaa<br>gaagcttcaatatcaagctctgactgtcaaagaacatattataggacaagcgataagatggcttcaagtaaagataacgcttagtgagcctgccaataaatcttataattgga<br>ataaaaggtggcttcaagcttcagcaagaacattaaaagaattctgttcttatgaataatattccaaaat<br>aatatattataacctcatctgtatatgataatggaaacattaaaagaattctgttcttatgaataatattccaaaat<br>tctctctgtctaaaatgggaacaaaggaaacattaaaagaattctgttcttatgaataatattccaaaat |
| Contig55_<br>gene_40 | 930 | atgaaaaaataattcttgaacatgtatcttattctgttgattagtgtcgcatatgcaggaactgtcgatatattcacagcccctccccatt<br>gcaaccattagcacagtggtttcgagatgacaaggccataatattcaaattttgagtttactgaaaaacctgttttgaaa<br>atgataccgactatgtttgtagaaaagtatgaaggaaacaatgtcttattttatatgccgatgataatgactgcggtatttagagattgtt<br>gaaaaggatgcaaaaaatatcgnaaaatttccctgggactccctaa |
| Contig55_<br>gene_45 | 931 | atgaaaattaattaaaagagttattttgggaattatttgatttgcatttcctcagcaagtatcattcagcatatagtattgattc<br>tatggaaattcaaggaggatgcattcaacaggaagcggattggaagataagacttatgcaaccattatgtgggaagaatacactggagcag<br>atgttcttatacagattatttattccgtgacggtcacagttaaacctgagattaaactctatatggttccaaaaacgttgatcttttaggtgcattgaa<br>gttcctagtgcaaatgcattaaatattatccagacctgcctgagattaatctatatgttctctatgttctatcatcaagttcctattcaagttcctcatcaaggttgaatctgattgatcaaggatgtatc<br>cttatcaatccatagcggagaacaaactttgagacttttatgtctcagttcatcatcaagttcctattcaagttcctgtgaaacagtaacactgaaaattccatgctccc<br>ggctgtgatagcgttgatagtaagatgaagcttcaaataaggttattctcaagtcgtgatgaggcaataagtaggggttattccccttgtgggcg<br>ttgtagccctaa |

FIG. 7C-1

FIG 7C ORFs for cell surface proteins identified from *M. ruminantium* Amino acid sequences

| ORF | SEQ ID No. | Amino acid sequence |
|---|---|---|
| Contig40_gene_34 | 45 | mvlalsiillssiaaasaedysltnakidmviqddglvfvdeaityhfyktmngvyryipinnfnmedfavdvdgayyelegndddsqieakvylykdkdktekidpgtdvtvhykyymsdlldvkgdnavlnyyllgedwevdleeieanvhfpekkeldyelvpsgsaegkwsgdtltitgeninagdglaliveipldefasgfsnavhndtddddidndidndkddlkdltkakqi |
| Contig40_gene_35 | 46 | mstfilviiilgiiliiagiivalynglvtarnkvknawaqidvqlnrradlipnlvetvkgyagheksvfedvtaaraglmnangvkeigeannqltntlktlfavaenypelkanenfkelqaqlaesedkiaysrqfyndtvlmynnkcqtfpsnliaglfgfkeadffeaagearsvpkvef |
| Contig40_gene_39 | 47 | mdnkkifvivalallaivavgsvsaldlgflggnddqdtaaedsdakttikgiefnipdgyvkaenytldgetrssgsidykvyqegyekgatdailfligdyptdltddmleqmnlgepktinghdgyittsneggdtftvffyaedgdlvtvtvtddtlleeiik |
| Contig40_gene_40 | 48 | mnnkkifaiaalaiiaivavgsvsafdlnffggddkqtttlggiefnipegyeivdnytivnetlhdgddeyivnsqyyenddgdslelytsdyqddmedyilkiltkgdektingrkgyinsedgftmfsfvddgnlgfvtvsdesileevvk |
| Contig40_gene_41 | 49 | mnakkltilaalailaivavgsvsafdlnflggddsstttvggiefnipegyeindtytienqtrtssggneyivnqegygnsdgeellflvghydtditnemlsamkvgdektingqegfitsddvytvfsfakdgelvtvtvsdesalesiik |
| Contig40_gene_51 | 50 | miccvlltfstvsaidmdgnltasvnhldgshsdqsafisqsessktnlnannnlrvssgdydcvetmnelsnldskdskdnnlskdktslksdlnsidsdeyslksslssinsskkssyedgdneyenledsldsknknslssnalgagtstfgdlqtminnaqegstinldgktfigngsfitikkaitinggsatnlarfdarnlsyifkisasnvhikncyfsystncsvyffgngssidnchfdynykhlwvavnikyfsltncnftngktdmgstayvvadnatvkncnfinneasgteqcygaalqigasssginegyvvnctfinnrvitthsyshagalcfrpgikvynstfinnycnrmggattlhsdgeimnctfinnsageyggaistglmadnisvnitgctfinnyapmggailikgnnvkvtnstfkenkarendggavyilgndalilnstfqsnyaknvgagilingsyvtvlnssfarnnasygagiyvigsnanlfssnftnhnvkngsvyikgigayvyncnfasntgengaalyiegsnttlilsnftnnnvtkdggaiyvvgsnaklmasnflynnaipsesdiksglggavyikgnsntidsssfkyntarngsaiytdgknmnlsndnfdrnqawsyvldsvikpsssyfnrsdilinltliggnnianaiyntasvndiyfynvsyisskgkkvttsneihpvngasnsqngallyqddrednqlvnvivykdpnskstslsainkndiilnktfttgilgnvslnlsssvgkaiapgnyllyakhteddyykeidednqfeilplvdvavdivsskdiveynrtnkftvkvinngpnnatdvqvsavlpkglilvssspsvgtynsstgiwtignlnsgvnqtlaintranttgavnypvsvssyekdtneannkdnqsikipecdllidiassnhspkysdivnwtvtvknngpddaskvvvslgnlsgneliyqkstnanfnistqtlelsklasg |
| Contig40_gene_54 | 51 | miiaiifmynrvrnkrstpatfalwvvvwmvvlffafapkisdplagffgfsrgldlliiagfaviayagfrfyikidnlnqnmtdlvreiairneiqldeende |

FIG. 7C-2

| | | |
|---|---|---|
| Contig40_gene_63 | 52 | mnkvqlssilalvlilflslavvsanddilninvtdtqsdvidnsngisdyfssdngiinddglssddetagsqlindseddlssddla kdsdledsketsktqdnsqknedsktrlsdssiiritdssyssyfdlskdgairegtikdgdtlligrivsgkifsitkninilpisdgd tmsnclirliegssgtslsnlrivnrnekvgsfylcgihiinsaghdivnltinnsqmkcygiimsnasnnriinstiitgataipmt gssnnlfygnyietyntnmiyycmygngdfypredlekshdniiannyftsrngtydsycysvclmaeaggsgtviantfnntfrpit vstpdtlvinntilnvggeagiivdgnnvtimnnistkrlegfqwnkegdvvgiftygsntrrlignsidtvgtngirssgdatfisgn tintessacinltksnavvednalngigssavriytsklventtirnnnissdsegivlkgkidyslvcgniieisnpedaiivgkytn rnplvpqhyaifnntingivvnltdiseierndtdsglnntntsdsgnngtgntgntnitdvngtdingtdvngtnitdingtdvngt nvtdvngtdvngtdvngtdingtgnatipvnitklstsitvynttvlrgdyldaylkdqygnpisgvsidfhfkdkvyakttdsegkas lhfdaipdnytmnisftgnnylssnitidisvipvsyylnesnfyeyfgedgylkgdyeyadliffqgdfrnkrivlnqplriisdsav lydsiikiesdkvvvdgftivnrnpgnkqdnhrfailldyvrdvsvinnkikldsydsgygiylsetqdstvsnnsidvkadkltfgil lydskdnliqdniikvngtddphqyestiqvdtsisvddyeaegmiipevyktygiilfyssndigynvinatsglkkyytavkestn sivgvdlyydcsnynkvhhnnvvsakdpylyglgvlgaetgkrdq |
| Contig40_gene_70 | 53 | mrkeiisilviaiiaisviptafsatdngivitygettynnqnyksivdnyfaskgygssnvqgevitaadvnaissgisgktynsnqi vscalvdmtqnneitvevdnsittitpqmyasalksagitsghvyvstpvtatgesalagimncyeevtdveipenvkqaandqiytea aivenddvsseelsklvddvkeevqeknitdhdtivtiindysttyninisdsdienladtiqqlqevqddansykeqlddavnntts gfsidgilnailsifnfs |
| Contig40_gene_72 | 54 | mnkkrfklllttifiafalintcfilndnlsaadnapkgysnyyirgvcfnvpdsyklvdegwddvnrlsyahfkkgnnflnisldkhst kfnknlldgfssftinginlnkktishvtgfyakngvkafclcnrg |
| Contig40_gene_75 | 55 | mmvillitllsvpilsltidysndvinsistknelskitdsidfcyysgkgskkvvlldfnqdfsvrftnngqkgiayadlelsdnnhk eisseydyiglntniqfskgfnkilvewdedtglirlskln |
| Contig40_gene_87 | 56 | mislssvsaintndssiqdngdlsiqdsideisqfdeseqlnkinkdspesnfnqelsndskdisadsnqdlmgfenydfkyntkssys nalkdsnvinvtgstfqdiqdaidrandgdilylksyffhgngtaisinkpltiigsyeannkshyldaylksrilyidsddvtllnih fdyggnidnngnggaiyldgtncaivncsfkgnhawlggaifqsnnsndlyvggckfvennaqigagittcgfnclvsncsfennsavt agaimtdtqkngdmtffrlenstfinnnatgggainfdgyyqsvvnckfidnyaknsggaiygslkpfdvslcqfynnyantggairg tanynvsdcrfinnsahhagavflhsysnvidsyfennyaeanggaictdsntvgviikgstlignnattgsaimmvssriencnfs gnigksegaiysihdcnishcifdsnqaekggafyiyrgmnsnidncrfinnsanssgaiywyvnkgkisnsyfeenqarygsaiycs nveadsgfiitdcdfinnhpkedgsntkggaiylydqlkciivanstfeynyasrggaiyvegdvnlianstfkynkadifslsayndn anlivtlrgyenymnaiyaektvdfhnvtywdgefvtgdypikrnleaginiildcrgnghslnvtkmtnsmgevifdemrtlpsgtya yqvsvpdnsyytakklkpdifnvpylcenilgidvadisydqypvvnitanytgnytvyianssydvtftdqvergrvlgynititde dvvkgekliviphlfdikdgyagyvqlraidqenvelvyiqnrtsfnvykaasaleaegavavngsdielnymagngtvtiesikkdgs llengtdynftvnddkiiitgldaghyianltllivddyhnsssidvsidvliktsidvadsisiaetesslinatlspeeaglInyqsd netvavidndgritgilkgnatifvsyagnedyspsnatvkinvy |

FIG. 7C-3

| | | |
|---|---|---|
| Contig40_gene_88 | 57 | mvslssvsaasdliqydyedltiqnsyddliiqdsfnedliqdssnteIktqdssidnlketinqtesiddtltnqdlsslqdsskenik dsnlkssrlgksitvkgntfqsiqsaidgaeagdtiilsenmfkgdnyyglgegiynksitimgssfgsqyiilnalhssrifnita dnvtisniqftngyvvgepggaiywfgngkiinsyfslncanssmewdieggaiyfglkfkngyienclfkynsaydggalytcsqnt tiskctfdsnfgisnnaggmangaalsfsakdvyvidstflnndapegwggavviykhgyepyffncsfknnsaafggaicwltdggtf lnctfennhatggdaiphggaiykigrngniinstftrnyattgsaiylnaylnidnctftdnqadsegaiyiitdnvtirnclfdkn yaynygaaifswdhdnikvensrfienharneggaiyflgkncqiygclfegnrvsnfysfggavfmeisgedtsildcsfknnsalyk ggalyisygssekiaiinssfednsasnggaiqadwnlsliianssfednsasyggaiqvfgsvdlianssfednsasyggaihvfrsig lianstfknnyansleinqskesygrvtfkgkenyinaiytedysInfenvtywdgsfvtgspiksdceagikirivlrggvsagpv vlnitkitnikgevfneynglspgiyyyeayhpkdsyysesekisgmitvpkkatdntlaislddsiygedlkvnvntdvgeyriyi ansnydaiftdddvakgnv.iaydltvnenelkgnkwtilknslnvkngygayigfadledgenyinihnrtsfnvykaessidanetia iegdgaevnytiengtasidnirrgsaileegtdynftvtpdkiilitgldmgnytvklktivdsnynpstkevficilgrtaidvqesv aiekdksyllsptlipedagtlryisndesivkvdskgnltaise |
| Contig40_gene_105 | 58 | mninlkkitficlvlviglisfnsisandlgtvlednngilndlnddfinsdvnsdsinkeaisnlkslnsqdestsssdsnnsass nsnssvassnssasnsasnssstsnsansnssvssnstnsnssassnstnsnantnnsssdasktqtiklssqee salnefinaikttttkgtivlkndvlnqtisInnnitidgrnhsissldvtnmfktfakitlknivftnyheienlrailnsgeltvln cqfngfsyltngsalynskkltvggtkfnnyvnnsggaiystgtlinnssfnknhagkngaiystlnlilngsvfsnnsanesgga lyskgsglnikysrfnnnsaslnggalyssnstvisysnfvsnfveaydkasnggaafiyygskiaysnftsnhcktltnssqkksi qsmggalfyyggnhtlsfsnfknsvendggavriaknvgkftlnkcnftnnnasyedgaislatpnitisnsifknnfanedggaid tfslgsykvnvliknclfnsntafkaagaiylgvntvgsivnsnftsnkatvagafyiesisvsisncifssnkadnvskktiynkgk vvhsggavfvkngstvtiknsifksnkatsgaithgkmvidkcnftsnatngalygggktstirnsifyknsatktgalfine gnvnmkssmivsntaksysvystvsitlnnnwgntlsikdkspktlgltnvkvstwlhlkirakttklakgkttltidlrynnndkl vstafnnpltltvsegtlsskkvnlkngkatvfkfktnsktavvkvkllgktarctiktk |
| Contig40_gene_119 | 59 | mnnqnkysclvlagmsrrmgqdkgsmiiynkpmiihilerlnhkindavivlnnaerisiyrnlnqyadndieenfdyelsfiedev kskgpisgvmtglkniktdyalvlpcdspfiisgeyiesmfgildenpladalipfhiksnkdkfkdneefnfknademslemkiqnsep lhsiykkdnlnniksllddslyvksfirslkspvfievdnkvlfdddfknlnkgedidnlkfkk |
| Contig40_gene_141 | 60 | mgffdklknalesgnkshdkresqkneaisdnprgdslsdnknrnslpdnqnrnssdnnvrnfkyIddlihsgqkdivldcdivlads eiesykrgidiggsnitldgnghvvdgrnkaeifkvssknlaiknlriengyseldsiidvfskgehIsncsffknsneshrifgdnl vcigsiirnmgeltihhchirnnssrgggtikntgtinisciseynlsedgaifneglkIsdsrfefnhsnkrgaihnefnge tiienssfdknggrksandisnrfnlvlkdmhscikidnewtvfiekgsfdidnkggiiefaplnndekstfflkelldgndsqidlm hdikldiandeqlyfpdginfnrdnlifngnghtidalrmrniftlagndiifrnvnlengfsklsngaaismkegflkiyevefrdna aynggaisikdasvsidssifrhnaanaikfetggaiynengslsiidtlfisnslwgeggailnksgalsInncdftdnrsvkngn disnydsIrickcsfescdkannsndsgeitnsnlgskinnsnsdsgeisifnnlsklydsnfnhsilinkglIkidkdfpiksagik nsgklkaynfndkqiegidinnedggklvfvidgvevlntveisqkwieikifisstfkdmhserdylitevfpelskwckerrillte vdlrwgitredsrsgnsinilqyidkcrpfficflgqrrgripekgerkvteetfinfpkvsnlvghlsvtemeiehattlpIfklle ndfdnehakralflrenpfedvlspaqrdiylnrkpeddekslqlkdlirekciffdysciwdenmelylesssskgglitdftcngrp lseviiaevkkqienefpdykpvktdcifIddamlqnleimsishdfvgkkeidyinefiesdnerllIvkgaegigkntllsrvhal lnekgisslmrisnataksnssnlslsigseiglfngeealykg |

FIG. 7C-4

| Contig40_gene_155 | 61 | mevegdkmnfkefeelinsgvkeislnedisledktqapielktdglvidgknhiidgnnklpilyikasnitlkniifkngfsedysg aitnysndlkvehcqfidnstenagdlyggaiyngensklveksifkendsdfggaifidsdstvkinnsvfelnisefdggaiynkg eliidksifnqnmafkggaifnenslitindshfknnkasdgndigtenedisisnslcefinndny |
|---|---|---|
| Contig40_gene_156 | 62 | mnftefeellggeakeislyedvilesdedyrrgielkrdglvidgkghvidamerakafhiggdnitiknlkfknavshkgnggaie nvgkelsiknshffnncslgplggaicsfedmnindcifesntsvrsdggaiyletffkpnvtvimkncsfknnyadggfkdfgsnag aifnknanlylfdcnfednqvvsaydsssesignkngiitmdnccfntreshsifnlgfllinssrfyhhpenleiqgsifnrgfvgll ygerngykveldgkvldssdigdlineykktynldtkevgfifkkniiesindlssdnfnlednfnlgdinlsdykddeylmdllknkid liysgdfedsdesi |
| Contig40_gene_157 | 63 | mlyyrgagwadwdldnfgsrisyiddfpfnilkallsyfetgdeqsvefnaegwfytfkfssdvrvgerviyestidfandficeieer mglwaffpsrrtsdedyyelvdlivkirtelldkdlinkwidiisqs |
| Contig40_gene_158 | 64 | mgdymntdylkefeelnhtteeslfdlgisgliililkdgtnltswselsnpddilylsadfrckenytefsnfknakvlilqnyvrpnfg vgslffkeadlitklstwhslvafyginwdisstdslknmfanclsleyayfedwdtshirnfwgmfvaccslkaidgmenwdlssaen mesmfescmslediisfisdwdmsnvenifemfrdcyslkdasclnwkfknlknqdnlfancrklesfpswyddefingfgirnglnlid ddsffykiaggfdpqdifiavgyirdeeclkrllrdssvhfyarraallnpnlndteileefadskdyverayaienpfntnigiirrl anndkshlvrfkaenklkelksegleiiedyprefkqafeghdreraslvlsqwrgydstdanfilakvisdsdeeiefsetfeayii smeekpqdpslfnwfsstavecmekrvdedigfsqlfnnmykshmnstdyatafldffqdilendrveklnilrglvdswtdcpddan mhcayvilnikkiskdelediakakvcipeninsypklmafmnavleadk |
| Contig40_gene_161 | 65 | medrkakfivyvvcllaficsstvfsmtgglsdwivsnvntnedannngyidssegqyysdsdgqyyssdsydnsnggsgfldglfs ssdnsesnyyssdeepdflarlirefiggssttdsyydsscsnyyedtsngydlgngfsydlnelftktdnklnglfn |
| Contig40_gene_163 | 66 | mniilingtgaigiglgasmisgganvsffareetanairkngikrtgifnhysfgpesfkvytdykdipdnefdflvssktianddis rklnehksilkedakiiifgngfandepylrffpkeqvycarvitgfkrperyisevtvhtepillgslqkddgefidsrpvsiiskm indsgipsetteeldkflwakmlyncslnplgailngnygklmeneysvkimnelideifevikasgyrtnwdspeeyrevfysklvpd tynhrsstlqdiskrqkteidtlngkvielgekygvdvsvnktiyniiktiesef |
| Contig40_gene_164 | 67 | miivtticvlilivlfygfpgltnsndnsdnrliignshftidiengtylsgegksmvdsnystlesyenftisgyeayeield ngswyivslykvdyntpssdwvynsdvdedgnayiffnskgeyygyfinipsssdpstfenlsfltsifhynh |
| Contig40_gene_165 | 68 | msdvgktvttiiltlvttafglvaglawndaiqklidsvmgpgdaltglftyavivtilavvtiilariaakmgvelee |
| Contig40_gene_169 | 69 | mksdkrakfaiffsiailalglsniaavwtgdlisgslpvinetdklialdndnfspaslntvyeekkvvevndtsdandtstpnna dsntesddtsnsnnnnnrqnsngngrqntnpnnaepssgsaggtetee |
| Contig40_gene_179 | 70 | mingimdkqkvitafgiilflaaafspfvvlpilgv |
| Contig40_gene_187 | 71 | mfnkkmvlaisllavifasmcivsaddsgegsfkelaklvsgr |

FIG. 7C-5

| | | |
|---|---|---|
| Contig40_gene_203 | 72 | mktnlkkttiilalmaillilsigaisandltsadsnvdmnndlntnldsndiiansnsnsidaeideanysnqradakeklkesnsli enetegntqiedensspsnktdtsisietnsiergsdltiylkdingtgianeklsiqiinktytrttdskgsalfkinlasgkypia isyngsedyesssddfnisvspmktkinmlsnsivngrkltielldknnnplkykkisiilnkklynlttgkdgkvslninlnpgkfpi qitfsgdanyhtvskssaidvyklkssftvpktsiikgkylvvylkdsegkaipsakvafkingvsstkttdkngrisqkiglkvgnyt vqlnyngdkshlkkvqsfkirscnsktkftvanytvvrgkylsvylkdsenanlankkvtftylkksytkttdsngkaslkmteagttt vnlqfkgtgpylkssanvkikvlknttadiiaknqtrhlngsstiryyvkltdnngnpienetielkvrcnnittgsgnkitkktivls sdhiinksedkklnemakilrakgykvivsgignpyhvsdvrdysnvcvfslvggvdsgmfvdmshsyyknylkkyknqfvlgcvapp vylnlgnmtwlkrahdddyspksfkglyypgkyfntvtkldyvygdgaeelvnnflnyakkgksidlggsvpkttttykltttdkngnay vdlqvgtytisssilgnnykvdtqtskvnvik |
| Contig40_gene_221 | 73 | msivsandlnsiddsieadnlnsieiediqvdsvesddleksnidekvlsdgesdgdsgnetetlssgdennesdvssnpnegvatnle ldndadkenvkigelvtwtleaknygpydaentqvydelpegleyvshtvtkgefnpetgiwkigdlkvgekeylkivtkavttgekvn kanltsdtdiidpdecyeeeidveddddnhfekvihskqlprvgnpiflliiislltvlglntrkk |
| Contig40_gene_228 | 74 | mnskgkylvlflililsfsiisasfaytgtgfshdipfskyssqsnsdilnkynntdchseikgictyvadgdtidvegvgrvrfvgvn tpergvtayicskrfvqkfclnkevsldvddskrndrygrtlavvivdgknlnemllkeglaeimyippsefypydwssdsttsssyts gsssnsggsysssfftsgstvsapyvgsanshkfhystckwgkkisdknrvtfnsrsdaisgqyapckacqp |
| Contig40_gene_231 | 75 | mkknlslknililslilffvlsigssfatedinttgdnnliddnamadtlsdekeisyqkplmsdensnsngsdeekvissnnskses fliirpnessitvlggnfqdlqdaidyasdnytiyliccnmlgegkpiivnksvviegnghtldanyssrifcilsdnvvlknleliiqy qraydsyklrpydsknfdnapaltqeffdysvpplnstddieygwpaikwlgnngtlidsailnnkidyandigegkavswlgtggri intfmvsneyhhffvpwgivgyqkseqkvldtsphqvvygniegnvyfldvalnvlpnldvknvtsyyqegkkisfnlnhgnasfvne sleisilskkynytfnvfsdengnfefnlpknlsvgsynlivgfndgknnissnttvkinkatvsvsapdfkaqyysgakytlklinak tkkpisqmkvnlnvyngekvktytvktmnkgiatfdkftlpsviydagkhkvtisvdksydiskkeftvqiskaktdiklsktsfkykk sdnlkisiknqikktaisglklkvkvytgkkykytltkdkngmvkintkilskgshkigitsedkrylvsktttsikva |
| Contig40_gene_232 | 76 | mkrniyfiillvtlfliismsvvsaandadvsyiddeivsdeylelsdsemgisdidyddiesdmleneikenglsdnndvlksnlpene fkesnyneyyedimnsnsqkyqefinflinnksfefrenslsedqgyflyatknytirlwdgvnytilkddyyfastaeksgyfvnesfy ddiiyyheynyyldeeflgwlmwnanykvfvsgsiedkvdissvvnpekggspksgnlpssydlrdgyfvtpvkdgntancwafatm aaleshllktentsytlspqwdfsennlknvmsslgrngtdklvmssgqynfnsnymhavtivgwddnypknnfliqsegmgngafii gvkfipnrqnyldndyikesvlengavyismwdsffekndayyfyngsgynfnsnymhavtivgwddnypknnfliqsegmgngafii knswgtnagngnqyyyyvsyydqmlgfdntyagfaftnvenvtnydynynynplgftnvfpvnstsakfanqwaalksgtlksfglyvvsp sictanlivngisigntsylssagfhtlifngaayvnvgtfrveitlqhigsshtyipleerienysnvvsgynqsflwlrkngvdq wvdlktevdnaniclhvyteciegllethvrsnnlvtyfntsslnatlvdgsgnpianklyfkllnvtynrttdsngkvslpihlnpg sykflisflgdsiyhksnrlvnvkvnkmhtninqnvstvhqgeylglildsngkalsqqkvafcllsvtynrttdsagkaklilirlnp rkytftlkffgtagyyacnktfnltvlsaksgqsyemgiddydgknideniiiinnetfessdvvnndimynndtqyniinedkgyyn nhsndinfelldndqnyiysdlnllellnndqndicfdlnlleyidfdktdyndnlynlehymkdsltenedlyicenklnihdlnq ikiggi |
| Contig40_gene_248 | 77 | mkkmemasyilliasvlailyalifnpadwivyalaivcipflvlsfglltmskpikeeeerreepftgy |
| Contig40_gene_251 | 78 | mpkiaklwnkladpkniprlfavilglliagflipmglntdqiytrpapqsqmdaglplapydrgevlespgiteaqypenaenlgw insymtpiaemlkgispyfgtsicssppglideilyytrgfdtilessilmmafliaswlainftmdrtkderdiaedvkraiassdrl |

FIG. 7C-6

| | | |
|---|---|---|
| | | aneveesnrkarekqakkefr |
| Contig40_gene_252 | 79 | |
| Contig40_gene_260 | 80 | mfnlaiwvylglalaifgslatvwgpgvkdpvirtintevasvgvslillcynstlalltliattiivtlilfraisrleeigadv |
| Contig40_gene_261 | 81 | mfaivslsavsasddfsssladdsdsdilaiddiagkdsshklmdeedisvefeiddgddtsydsyyddspgddwsnyedydpelise dailtkievlnvpshygddnisfrlidlntglpipdvnlglqdsydydvysfftdedgvvvypipvkvgdfsivigfyedmmvneldd mvcnftklnvsiptvpasikiktgtyyndtvlkvslvssvkevlsnqkinltfsngkkatvvktnskgianyalkfapgnysvtaalvs dgiveankssiknikiikapgtlsptalsttyasgkyfqiklltnsktkkaigvklnlkvytgkykytvtvttgsngiakfsastlsvg thkvivtvkdtkyvsassktsssikiskasraisapkvtakykssstfkvtvknkaskkilsgvqvslkvytgkkfktynvktnskgvas fntksltkanhkvivnikasanynaasatsyinik |
| Contig40_gene_261 | 81 | meenpidfkdnsinskalkdsdyehasdelsqdlynriinakeneiiliepgtykihkvhltknitlggtgdpreviidgeqlgsvffi ndinvtaqfynltiinglsdnfgggicietgntyvdncifinntalnitnggaisnygnetnrsylfinnslfignhadhdggavttcy aisdiynsvfinnsavrdggairvsvygygnvgdcifignhadewagayyswagnssidrciflnntagtnggavmvsgslnltnsliv nntggetggsfyiqqpmfdaktvinvnnniitnnsspligkeifvkwnatqllfpnfnnndwgedptgpdvvdpnnvsdriipertkri tviydklnwglldrytdvldddyygkssssdskansdtktnssglkfdtenktnddskeeggsilnnsngfallnhnnssssnstagggl ekkdnstfvspkdyqkmvelfednpsaskstdiryfavlafillvflvglarkrk |
| Contig40_gene_269 | 82 | mkrrykvlflailtiisinaisaseigldddnnaidendgfkikqdimsekiisdnedadsnnandvntdssdevnednvieqntdtdt vdedeedpiipvdtrlfnpdsvikgndlnivlkdidnnplangtikfninndkqyqrttdktgtaklkinlspkthtffieydgcdeyyp tnlvfdlkvikpvqtklsvkstivyknnklmvylktsdnkalanqkikiglpkktytrttdknglaslninlnpktysinlsydgkgky lptskkikihvfenellgstyygkvellkgignssskviayvvglhvlehqihdevynimkqtsmhysynvykitltkksgnyntdr mrgqilaknyivphvnkqkynlvvdvhsttgvyykksyfihvpqnrhkpslnlankaikiintldkqskivywspdsqtsppylltlpim kagtptfvfetltsepvsrskyranilinavdklfg |
| Contig40_gene_296 | 83 | mlfsviatvsatcnvivitdpsgedpngaaagmsfannmfqssfimskddgyamlsggegngternyaiiaalaamghgatpasaaal asgfkgirlviggpsmgaaiggdynaylvvvddagtikvthhtgvvqlpggskgaiihlrnsagnpmygtaervrretavnigkmird gypatyivgkamkevaedsgekyggavnlvssistgdmfvpdqvnttgypmdenyskscekcgwatgfpdaerynvcpycgseltvns atdvlidsitvskdsvsvvysgsdrglsdditrevvkasvkkygynastiagslnkginngllivgvdyvepsdlnvkpdvravgvyynp lpngrsspawnlpinsmvltilgtligtaigfvlimlvifrtrllksfkdrvs |
| Contig40_gene_297 | 84 | mfikirrdtlihlllafilllcgrlliyvayassaqveegvpiagiivkgndivpidniryvenslgregsyidgdilktsirelpvt eaeanaekfvkrstipgttlapiagadvnvnkqtgivtvviedfstinitgnsttstdftenepsksvynyslag |
| Contig40_gene_306 | 85 | mkavipaaglgtrflpatkaqpkemlpvydkptiqyvieesvnsgvddilivtgkkrsiedhfdrsfelehhlktkgkedflkeieyi sdladihfirqkkqkglgdaiycakkhvgndpfvvmlgdtitkdtvpctkqlidiyekyeksvialeevpdekveryglilggeeiedsi ykidklvekpplrvapsnlaimgryvltpdifdcienvepgyggeiqltdalskldeiygqvfkgesydignridwlktslrfaledds arddilefikeeii |

FIG. 7C-7

| | | |
|---|---|---|
| Contig40_gene_310 | 86 | mncsvyedyseniitadinsnnelnsdfaygdsdseeildepsqklktgsdnsdfkdiqnlidnakendvielsgtytgdslivvnks<br>ltlksssatldgeflnelmainapnvildninfinanytglsvnnnyvtiqncnfdgcingelgcaliihgnnvnlnsnftnnvank<br>sschhtdgaaiyligndcqidncsfinnwgynfetsssggaiwikgnnivinnsyffnnsataevgwtfhgeeityladgyggaaflvg<br>knvkiinslfdsslshaqggalyyksaydcsiinstflnsfsvgegvylygnidglmidscnfinntadgldgvlvkytdlgsvlya<br>skfaenvvitnssllnnkgtsavyflgnnlnisnsiiennnlstaviymngsmndnfwsknfdsadefkndcfiirdnesqvpdtwfnl<br>vcdgldslkakgvvydynmsfvlkdasldnhaskisltnnlpryhinlknsaknkinpnelvivdnqadftydyiesakdsidvyddynn<br>lilskkvlsgityindsgndtkdlqcaidsassgslislsnktyvldtilinkdihisgeenttvmlsnssdyifkisncsaanysdyg<br>iaisninfildngdivalaeavngsslsidvasikitdnsftsregvvresitileledsqravlaptrnisisnnsleigmnpfdfnv<br>ksvingsdvrvdvggnlaskkasqiickdmvtkaiasnvdsrsgeyfnvslkdsqgkplqnkfvqigfngavynrttnesgelrlqinl<br>aykgvytfaisylgddecngsfevakitvnpqsplmannakyvsstktlsasfksmkgspisgktikfvdgktysgktnsngiasv<br>kvslnkkgtykftakfagdntfaavtksakvvis |
| Contig40_gene_317 | 87 | miktdvlvigagpagssaarfaakggvdvilmdkkseigapkrcaegvskktfdkldlemdphwvtqeiagvrlvapdgtdvwldedvi<br>dlpeagyilerkvfdkhmameagreegaqikiktcqakglkreedgsftvtcesmgetfdinakiiigadgpeshvarwaglkaytkpkhm<br>eagvqfemcnakmeksnvlefyfgsvapggyfwlfpkgddivnaglaiipdmagdksayeylvdavnncyatkdaqvelnvggdpvgg<br>lvkemygdnimlcgdaasqvnpltggitngmunggrfagevaeaikagdcskdflkkyedlvkeemghemqkytkvcdylwtlddddl<br>nsiahafqdmeft |
| Contig40_gene_342 | 88 | mssnslssnelnsnglnsnglnsnsisnsnsnrqkansdsrllilndknlkvngteekyfiklvdgngnpipyvdlifnidssiefv<br>ggtvrtdengiayifmdfsypgpytvyasfegdnhnpsstlsstvsvykdteisslqsygylgenfsfkitscgepvsngkvlisidn<br>knytattdsegiakvklpnqgktysiscnfsnrvyyygsslsknipvykraftqpncyallrkstftvtlkgadgkilsnrtlrfivdg<br>keynkttnskgaasinidlergeyrinyyfntdgvygpvsnytdlnvdpsgqykrllnvkssasakiyltggyatvtslikstaksi<br>tkkyktnfekavaiynyvrdnldqyyyntrkgatktlktksgnccdhanlvalcrasgiparysnskycvfgsglrsghwaqiyvg<br>gtwysadatssrntlghienwdtktnkkdynfrnlpf |
| Contig40_gene_344 | 89 | mgfvlissvsaidideasssdlsdssisndylvansgddsvasssassiaaddsdlsnnassnvnfenevlstnnnedteseivkd<br>sknqlssssslqastktkttlkgsgssvyrgnpyyvtltdsngkvlasqkvtfnilgknytrttdskgvasininlakgkyniaclyagt<br>enyasskisvaltvnlmstkintggstvkkgnaysvtldgngkalssqkvtlnilgknytrttdskgvasiainlaagkkftltasya<br>gsanylsskvsatvtvqkgdtsikpsgtsivkgnysftlvdgsgkglanqkvaikisgksysrttnsngvasiainlaagkkysivcs<br>yagssnykassstvslsvtnpstnsktfsiakieaaatnlkayvnknkavpttvsvggtnlkisefsylmskaivnlnsnntnaitlps<br>giyngasasnslnatvykagyvdlskrvynyidknkvpaaygtvynangaslgnagfnlytfafakildfhktnkylpnycsfdssvfk<br>asngsssnsssstnssssnsssgsnssgsgsstpavtvkatslkaastsvirgddysvtltdssgnalangkitfalssssytrtt<br>nskgvasltlnlaggkysittsyagtsaykaskltnvtisnsssrfflndietaaenvktyvtknkalpntvtvagtqltlsqfsyvm<br>akaihninasnnyislksvassnstgdyldttvyraqymnltnrvisfvesdkitptfatvynsngksvgkaefklytfafakilafy<br>ktnnylptyctfqssaigvvpdvatnvtinskinanmnqfkvglneknktvsnlsaylvgtgqstittniknvaaqltkglnstakala<br>iynfvrddisysyysdsrkgadgtlssgsgncvdqaslvvalcraagiparyshaggctfssglvtghvwaqilvdgvwysadatsvrn<br>slgnivwntnsyhsmkqyaavpf |

FIG. 7C-8

| Contig40_gene_346 | 90 | mednllknrklililsiflvsllaisavsanedvdnglidsddsilqsaevsdstiesdsieledkgnvlkssd nasfelddknnigsadseleddylepkeknvlsmdenawfynyivwydgddgdwsldfvddlknpenitirlnsydtpfdgvdlavin dydysitklttddngtvvynvpyevdelsvfvgfwydgdfvatygnwesyticavnwgtwyrdpskrtydfyvsvsdmdtyespigaqv vftsdsnqyvgtidenceraiipkvsygtydvkviydgycilnlsdssaiefyddhhtdpdslgderidmyvdssgvvyldlcydgslk vpdnstyepygddnpsgggsgnqsggtvangtftslqslfnraaanstisltrdyvyddgfdikgivinkdltingnahtldalgksri fyvnnstvkfnnilfangnatlggaiyngsavnclfinntagdggaiyygsalvcdfinnsasrnggaiysggavncsfinnsanlgga aiydslfavnstfvgntlassnptgsattdvsvvsfnpittyipsppsmtgsigwgavldftrpviytdynetfylltnftlqqdgf nnygnvqltgrdlvfkslypysgnysmaliisggiftptylgendtyeahfklnglslglhmvyayvdfgypeyysyriggymdrva ydrtaeiifpilinktveisssnlnkyygtgkytvtltdggnpiananlnvslagktypltnangqasmdinltpgtyeavctydgv sqrsniivrstinlqnltgiyqakvnatflnaagsplantkvsfrvgsktysattnanglatanvdlaagtydviainpvnneqktsk ltiskakssislssttsnndkvtltaslspstasgnvtfnlnknkynytakissgkasqtitglnegnytanayysgdsnlnsssastkvvv kiviptkiiyknmttgpvaksdgrignyfcvklvdgsnnaltgip |
| Contig40_gene_349 | 91 | mnrnkilvllvlliavgftmgpacaasttikvgnykdvgkgdristfnvpkdqaylkgvyafyhgkngddfrphtyvlskikvyyk nkkgkivtrsstaknlsglsilstkqvsgytpykmdvsyrkmtnaekkkicgslvy |
| Contig40_gene_352 | 92 | mkksvfkilialalillavsivssndlsdsnvssdltvdsdsissddtgssdtssddsnqddvsqdktndkklsdsqsdsskdtqdtdd nntdngsdkcnlliittkgnekvkvgctvewtievknslntaenisvdefipqnfefksakaskgnyaveianwcignlkenesatlvik aqalkagnftnvanlttcdsningkvlsakadvelsenknetpvgpkknkdnnstvkkiihkliknqtnntmtpidfkksgnslfav iiaalavlgifIgrrrin |
| Contig40_gene_359 | 93 | mdlsdsccdtlisdgsdgiilggsdcislsdennninfdlncnpdfnldydsnypnlnlssnsnskssntygndftlsrfksvltss ynlnggsfediqsainhaadgddiilngtftttgsvivinktltiigspnavldakniskiflveadgvnlknltfingksrnesdngp yqgtvnwqgsngtivncsfinnsgdeksygasilwkgsvgkisdsifknsysganggaifalgenltinnsefinnhgkeggaiyfggs samwiinsifinnsadsggalaacamnrqvinskfignsanngsiswcgsnglisnstfinnsadqkggsilftgtnnlvkgsvfins saniggainslnrlnyindlrfennaslgedcygdlefkrfstsiasedmvtsaidanldgrngeyfnvslkdeygnplinkdikigf ngrlynrttdsngqaslqinlkysmvytfaiciflgnddfygsftvskitvtkqpnlevnnfkykstkskvikatlkssrnpiqgkt isftvnnkvytaktdskgiasvnvslsskktyaftvkyagddtyssvsksanilvy |
| Contig40_gene_411 | 94 | mkkniflaililiavvavsgcinspmdninnmkeIntditegdtdynsainyinnkdfisgtdniqiakdkfndadeklsnieqykss lnesiyldylylikeevsikrqasdelyialqyytnndfssgnsyaqsanslmnqakvlqdernqivennpdlfkkagii |
| Contig40_gene_431 | 95 | mlialglsavaavadpltdnglnptifyldfnhgalndgfkkefdlfeyvpfdsvdlyndgenvsvfyslnptidvdnlndeiid ytfevmedpkanittlkdgirnicseygaddvkinvdsvigedeipvifttegdsmlptiksgdkvlvnkshnihvgnlvsansseygp ickrvadidgdsvylvsdnkkvtreyyddyveykgittwniddiidgviidimn |
| Contig40_gene_448 | 96 | msennrtlitigigafiliiailllialvlpfsnlavdndeiavitisdtitygdnstsahtskkeieselndaysnpkikgivididsg ggslvasdeisdllikkspkpivsyiqdkgfdeayqiasatdyifasssslggiglsyintdrysdekvtgvfnekylknnktksnskv ksandlanaqkmvdqdytlfikkiaenrnltadyvaelahgkkyngneaklglideigsksqsiekaaklsnatnytvtitypepqkkl teilgendifnikeliki |
| Contig40_gene_466 | 97 | mgkifkivtlilivlalailgvfiysdghsekigennlgvvykvtyghsndpnvtigivsgmhsreklhqyvlpyvskaflhpdvki vnyivnvtkdpedftkgrangeslvhdyvvkdkkefdvviighdhepgygeayyiatpvmdnasvklakkvtkdigfnhytrnksgp ttstsilkvdkpivdagtrvfvyeipevdgkvnafyksqlvnatynrlkk |

FIG. 7C-9

| | | |
|---|---|---|
| Contig40_gene_483 | 98 | mdkktiiiaavailviagiavfafgggssdsdpthltvathsnmaepeagfnpltgwgchmnynplvqsclfktdkngdivpdlatn ysisadglkwtvkvrddvkfsdnstfdakdvaftfntakdtetdldltnlkkvtakddktvvfeleeprstfiydlryvgivpeeydna tygehpigtgpyvldhwdkgqqaifkandnwygdkpyftqitmlfpeeatwlelaksgqvdiapvatsalnesvdgynfveksagragg islpyledtgktspagakignnvtadksirealnigvnrdkiceevfsghaspeytsvdtrsfanpnakvkdgdvakakqilkeggwed tdgdgivekdgvkasfdlyyppdyldrgslatvfaegakdlgivnlgadwdtiyanmyssasvmqtspdpyksiyqqynskeaddf ymnpnlynntasdmlmeqamhsndfkladslwagsalvnggwgpagdapwvwlanynynyfvkedidmgdqpdglgndflinvvdwtr tnsta |
| Contig40_gene_501 | 99 | meinldhkdhdgslsiigdsnggtvfdgenlnpliisisedsivtlinitfthgknnmgsairssgnltidnciftenyatnlaalyvd khsplvtmnskflenrakqcadiyfsqnseiillnnlfegstaeysyayspsvslqtgkslvkgntfknltgayykgalyiayngini anitdntfincnytgtdgailffqnaylknnkfidchsstaflysntefnaylsfedaeidgttfflkanvtddmqnkvknakvifyln genvgsassdnngvamisikkllengeyvisgtqsyseinpfgvnvknatarvnydhsslevwvstdgddgsngsednpfktlrkald ygtasavnltvhvkngiyngddnrdlsystlgkitivgesysnvvidgenitksifafsstldvtlinitlincpstlinaytlsmmdn ivinsgtiraqtgnngvtidnlrvingtdqaitgynlrltnsrfencdglthtgliwlstnnnkvtylenntffnntiagsaggaayy iqsdlisinntfdsnwitesrgenvayaggrhiisindkfinnevpkyvaqyrsigneeceiivenitfinnkasgngagiattgaivk ggkfinnsasnggaiylnhdntssycqmsledvifennsatcgkdifiegssgnniftylnnltivandlnvtsldsnltvsvfhps gaigggeisfyldgeyigkstlvnqnasleyvgfknntiyeftsiyeyaslndtydigivstkipyalenielyvsdgsgddengngs isnpfksiskalseqyqksntitvhilegtytgslnsnlripttvnilligegaaktiisdsssdyfitalkgkcelrisqmtlnraar dtqsaiyieeesnvaidnvtfiggqnyggaintagnlsirnsyfhdngyadrtlranayyggaicndgtliidntifesdhagrlsei anqgtlymnskvidsinaysinmdlvaigayggkgeitiensq |
| Contig40_gene_553 | 100 | mkkkiaiilgiallaflvigassagfldflggdgtatnddntfivgfdaefppygykddngeyvgfdldlagevcdrnnwtlvkqpidw dakdseldsgsidciwngftingreddytwsepyidnkqvvvvktdsginsladldgkivetqkdssalaalegdnktladtfkdltqv adyntafmdletgacdavaidigvaqyqisqkgsdqykmldeeisseqygigfkkgndqlkdqvqktldemfedgtveklaqkydtygv pgaliqk |
| Contig40_gene_636 | 101 | mkkkilliialvfiasvgivaaedatvdpytftipddytiatsddttcamqkdathaisfatgvsddieaakqnfisgqktllkees mnyndmditlqafsadvdgttiicl |
| Contig40_gene_721 | 102 | mkrsiifltiilslflvigyasaglfdfsssdagsgentddvfvvgfnsqfppfgykengeytgfdielakevarrnnwtfkpvppiidw ntkrfeldsnevdciwseftidgreddytwsqpyfnntklvivrgdsdindlddlgktlevggssilntieknetlkrkfakieqvd gydtafmdlesgvcdviiidsglgrylvsekhndtkilngtisnekygvafekgntelrdkvqktldemyadgtvekiaqkyskygipd gviype |
| Contig40_gene_730 | 103 | mgitftaiitgalggtfseplgnylsqfipysyqisfiiivilltsyftilvgeivpkrmalndpegyalstakfmqissiickpivkl ldsstnlalrivgpspkedvvteeevkllieegiedgtiaeeeediikrvfrlddqkvdmimtprneiiwldledeieinkakiiaskr sifpvadaelddfigvvqakdllskifegedvdiranvksplvvpenmlsmdllkefkenreyvhmvlvvdefgsvvglitlndllegi vgdipgideeddpkaverkdhtwlidgrfsiedfkdlfeiekempnevedgyttiagfilshagkipetgeifhedkftfeivdmdgnh idkilvtineedsdkldlesked |
| Contig40_gene_732 | 104 | mdskklilvtalaflaivsiasvsawdlfgtadetsstakttiaghdfnipdgyqknesyvldnettnsngaifystaesyykgaddii yiqvadysypgyeanlttaqllksglgdketinghegliaenefdglkvhaffyaedgdcitvitsddnlfeqiipea |

FIG. 7C-10

| Contig40_gene_733 | 105 | mnvnkkifllvifiisisiagvycadihgdsdltailsnetdsgltaimsnetdsfgccsivlqldqnesimcyrrdsnytadvfiekv
nwhgkpaikqyktdnkyfnhviitnqgwiiglgddgidseicenitakmitkdysisedyltqeikkkygrghvvikapngnygf
atptklktgtlnvgeyisipnnyelsrrgyvsldepdkieaminlsrtdlygddrreiitydvhlngnnnttdiyisnedgsligkdyt
gcvdnvifnnvtiegkdipiapnykslgsmsfevdknlsltdlafivvgvlviallfvlllrlirfiktrrsrsaprrtretprs
srgsapsrtrespsrtrretprpnlrnarrrdteedrrrndlrrnvlqnivedkrrseprrnvrntrnnrgrrgqrgrqtkrpp
tlyrke |
| Contig40_gene_749 | 106 | milalfcfivigsasaadfkindgfnssldysfynedqnmyiniwdyddeilseaylenssyrivsgenntynfvdsyndmdhvis
yitkgyvaldcgvleiaevdgkkqiilvskegtnvdslktcydelmkfnqnnniepiadai |
| Contig40_gene_750 | 107 | misllisilaisaasaaddmvdadidlasseisevsvddvqatdknvlsdadevsvvtqntpynenatidisvngtladdstiklfid
gedkgdlnlsaegkasyvipastldvgkyfieavvhngtssfggrstlnitkvtpivsvsdvtvksgdyitipfnvtddkgkaipgdvi
vtiwendviskhkiklndnssagfniadiigifggnstgngtgtgigdlfnrngtngtgngtgigdlfnrngtngtgigdlfnrn
gtngtgngtgipgiggnstgngtgngtgdfdiasilamlmggnntgakfayvfekgvynvsveylsnrnyngaindtaklititpledv
linatietaknmsdnttvsilltdgyekpiaggeinvflngedkgkvtaneegkasiafsnllkgdyellinyketnktfdffvnverm
gtvieyedmnttsvnekvdgrigefyqvtlkdnegkalanrfvqigfngkiynrttddkgqtklqinlfytgdytfavcylgddaynas
fivakikvskqtpkittkdatykadaktknikvtlksakdnaikdkkisvtvngktytaktdekgvatvnvlskkgtysftakyagds
gyaqvstkgiltlk |
| Contig40_gene_762 | 108 | meekialaacsgmspnglvarvavhdlaiddheilsicmgstsanvegftrvldkypilaingcegncvgkilkekgvdivgelnvgdi
laeteykandaarlddegeicvkvkdiiedkinelse |
| Contig40_gene_766 | 109 | mlktklcgislknplmlaagvlgshasslnwilnsgagavvsksfskepnegyknpttvaveggiinaigisspgvdafieelesvnri
kgrsiasiygatpdefsyvagkieslvdmiemniscphamegygasigqnpdltrefvsavkdtvspvlakltpnvtniseiaiaaee
ggadgltlinslgpgmkidiiitgnpilankfggmsgpaikpiavrcvydayeatdipivgvgirnytdvveflyagasavqigtsimy
egpeifgrirk |
| Contig40_gene_769 | 110 | meivlcvtgsvaavetvklarefkrqghsvkafmtqeatkiihpnalefatggevvleltgkiehvkysqadlilvapatantiskfay
risdnpvntllitayghdtpivfvpsmhdsmydavsenvaklkeegivflnprldegkakfpaigdivlesirtvnldrvkknltdds1
deseieldnmemlskiaginvlislggtfeeidpirgisnrssgkmglelakeayrlganlkilaahheveipkvfdvidaksssvmse
ktielvpdfdvfiataavsdfapivkedykisssslnlslefepvakiihqikkinpdiflvgfkaeynipeermiqcaktqmqdagtdl
vvandvykkgcefgsdsnevilvsdeikkvglnskseiaksifkeianki |
| Contig40_gene_776 | 111 | mlsmasvcasdvndtyingndlkidngdncinyekvvyteenlennlistedsledsnsiepsdsfkqknslnegnsderlnpeidval
nsihvnetaevnvtvrnasgyvlvsvddqsfnkdltdyqarfnitglgfgnhniavyygddnylpgfkletisvekyqtqiseieige
vyygedailevsvpngvegditikindtlqtvlteaihdgmalfsvsglavgsyslldatyngndyyendtasaefevkkadpnlsvvsf
ectvydnatilasineeihdefvnitvgdekyedcpiedygmiaftgvlsnfssyrilieyggnefesamieafvtpkkittygldi
iaqnisinddeiisvvpdhvddvvwdggsyrncsfennvavfnvtglgegvytvtatvndtefdhknftsiftvskvlpsigisin
eteiyvgdnvkiivslpidvsensvivfddrelsqkpvdgnatfyidclsygnksvpaiyygdekyrtavesinftvnkvpsflnvave
nsisdnevinfslandasgnitvivndetyivavsggkgtltvpklnggvysvnasyngdgkylpslnnsesfkvlvnsgqmelider
nntvsvylwdgatgnlsvkidgkvynatvvdgfaqvisnasygahayvlyednesdlklesvvdfvpkylspiginssilkvgdig
yinvtvpmgasgnisleidgksyliaidngiaefevenltagdktifvkysgdkvysqnstseslvfkgessthcsiedisvgdvaqi
kitgpsdvlgtviviingseytasisngegilnvynlqngdydielsylenskylsseyrdnlsvskiqtaisssnivcqynyegylnv
slkdikgnpiscaelsiddgvknlvsdvngqvkiptkdldandysvlisfagdekylpsnatvnvtvnkdipqiiasnliadyksddy |

FIG. 7C-11

| | | |
|---|---|---|
| | | lligledsqsnplagfdlsialngidgdydvystdsngivkvpik |
| Contig40_gene_787 | 112 | mvvatiifassifdalygfknliqpgislvytaigtqlapnmvtlvvfdwrgfdtlgeslilvtavlvvllifgkgkildknvnadngt adsnltheadleigdsdleldgadlnegdde |
| Contig40_gene_815 | 113 | milaillavgmtltavsaedswsfnifsseensdggsinfengkltiggieftipdgyemdesskkvaedaedfdakysackftkgddei vvnvfftdgdfenlsannadqvektlndikglyeenkygdntptftyiedgkvvkinapndeiiesvmgk |
| Contig40_gene_824 | 114 | mnkriflyialififiislsfsavsanedissdnllidenvydekillddvqdkniisdndyddvipvenandnailagndeelildenn seisednkndktklsdpntysftrlnqainsgasvinltdnyqytegdesfihgimisrsitingngmtisgsgvarifevftsnviin nitfrdayaegdsnrqnycgaifmygsdsivqhckfinnnannaggaivlvgsnsrveysdftgnnqgngavylygnntkaiycnft snnasekggavytygsditvefcnftnnsaylegaaidwegergtvkhssfanntanngaiswytangtvehsnfinnrmatfggai wwygekgtvkhsnftnnsgrnggaiqwskndgtvensnftnntailagavrwadngtikysrfinnhgysagaidyhltyanisgclf inntsdyranvyedlfesksysnfmnrillnngneinfntsegfnadynwfgdnslnyldkpniysntwlflqpivnhdsvflgesce itfrlysydgtevheydnalvypikltlnsnygnvndtvgleekaiftpqtlgytsvdvyaegsyigsvpinvyvpsfsdlnrtingne dsiitlnkhyifdpetdaafingviinrtvtiingftiingsnnarifqvtasnvainnvtfangyangstdedkdggaihwsgangni enstfynnhatgaggaiiwqaqygnvstclfinntaddganvyhnnypsdshsnfnnnimlyrngnnevhftvyngsnadynwfghnssn yncattglgdiwlfinatanpdtilisnsseisyklyayngreigeydnhllypiltl1sstngivndnvaleekviftpqnlgtatv takaagtdiqtisikvfeasfsdlnrtingnegfeiildknyayipeidaafinginithtvtingngntingldkarifqvtapnvti dnitfingyanddggainwgpngiiinsefinnhatsagaairw |
| Contig40_gene_828 | 115 | mkynkkifllllcliipqaiyagdvddlsdagnytrdnsplitsstygsstygsdggyddkneniyildkvsdgdksktccskdlsl dnacsmdksscsksnsacskgissdkdssnlsntylvsennyndfnvdidlndklsdldlnndlslnkdltlnlnsnndmdylnleevi qtdgtltyegdldqtylndeslnqdvqndslnkndlksplsdentfnifilsdntgnnlfdavaceildnsnfsnvkfnirsgnqina msedeiyelmapcdafiggwvssnvdavltslinnhpelsnkklfllileptgninssssslnlvrnstidykkifngisnddlinyfk atkrgnnfesigeyidnegssfnsifnnlvlykdindkanlknellyilyllghgcsyesanftgvqasgifrdrwysfdeyvltffne srnrtigilestmyiqsqldlvneiterleskgynvipiycpagnaeqlnimvkywtsacsnisgflenpqdfdiyvdgiismvaygv ggenftnatkffedanvpifravhseyitneqwelspvglsttksdkwwhvtiaesqgifdatyvggvdsyisnrtgailltfvpvhen ielltdrvdawwdlkytpnednknisivynyppqknigasyldaitsvynmlytlkdegyyltdlpnnvseledmmiacginvanwap geveklanrsgvallpvdeylewfdsliddivkqitegpvayigqmvrravlinytdevetmvndwynqikallpengtvaatnildkl vnslklyanassdgdenaslyydeflryydefkslnvsglngweapgnimlvnrngtdyfvipgltfgnvfigpepqrgweadienly hctavapthqylaayyymqtrqsnamvfvgrhathewlpgkevllsyndygsivvgkvpqvyfyitdglaeaiqakrrgfavlishlds pksythlygnltvlatlleeydnnhiiiesdsdkdnqaitygvik |

FIG. 7C-12

| | | |
|---|---|---|
| Contig40_gene_829 | 116 | msfgavsaadlntvqsgevsggvdiassnpgvengeltyeipdsveniqyaglfvdsytagssnlvygseanititkngeseqiaserl vasvgsadgevyvindhttkcfadymmtynltdrlqdakgnititvnatpiegytfynkigllvftyddgdgdqfhywvnagsswvk tdsgetskatfklgnvnydptvatidnfalssqdgvytfngkemdesivtetgvyyyihhkfdildkiknmtntlvytpgegsysfrnv lsvvklvktvpvyakvnisseyddivfsgtenllkvgitnngtgsasylldlyadgkkvnssqislaagreavislidntirpsaadtv sgadnkkinytvvvsdkntgevldessifpnllyngylgkglaypaekissfknitvngmilesslgdstyldasmtgktdswtidlpd gafftdafvypynldngnvpmftstfngaavnpiasyrdqpnigenakngyllvydvgelikagvnsfalskeagiagvpstliaf ynltdsdlltsafifngadllsneynslgrdvssdnilsigafdglvsaklhvfaadcqagegdltvngksyknvwagtnrsvgdyvvd lgkstnasnevsfistasnilalqqlavvqynvpsvkaslvseysnavfagtnnvlslnitnngkfdsiytvdffyvdgkkqnsteislk sgankglyliddtirpidastvngadnpkvnytvviidkeksmvldeititpsllyngnigkdlaypaenitsfrnitvsggvivdtld dstyinsqatnrtdiwnvnadgvftdafvypynwdktngympvwnarfngvavsplvsyrdqsnigffgkngyglvvydvskliks gentftlekeagitavypstlmafynatssnslktiyiyngadllanennflnrtvasdshldissfkevisaklyvfsagaqkgegni ifnnktykdvwngtvnsvqsfiidlgkspsvsndvsfvstgstim |
| Contig40_gene_830 | 117 | mpvwnttfngvtvtpvahyrdqsnmgtygkygyglivydvsdlivagentftlekengttavypstlvafynmpesstyvttylyngad llsnannflgrlvasnstldidsfdnivgadllvfaasaqagegslvingdlvadiwngssnsvdayaidlgknpkasnevsfvatgst ilalqqfivveynvpsaeaslvseysnvafagtnnvlqfnltnngalntsyivdfyidgkkvnstqialnsgesfgqyfiddtirpvda stvngaanakvnytvlvsckdtglildcevtltpsvlyngnlgkdlahppeeivlfdtitvngdviidtlddstylgakttgrtdewnlt vpsdadfevaylyvaynwcktasgmpewnttfngvnvtpvahyrdqsnmgtygkygyglyiydvsdlikaglntftlkengttavyps tlvalynvnesnvlttvslfngadllsnannflnrtvasnnvleldftvfdeilssqlyvfaasaqagegnlivnnetftnvwngtsns vdayivdlgndpslsndvsfvatgstilaleqfvvvkskyqtssdiqklidaaepgstldlgdnvfqdvanvvidknltikggsimgka getifvipaksangpdevritgvdfivedanvivqatadngssptsidtpnirisdnfidmidgsvvpesvtvlkldsergvlaptgel kvtdnaiaagikpfefdvtgvsngsdtnipegnnipakqasvihyqdmettavnskiegrvgkyfevnltdtngnplankfvqigfngv vynrttnetgvklqinlgykgtytfaisylgddyyngsfvvskikvstqntklttaaktykasaktktltatlkssvynkpingkkvt ftvngksysattnakgvatvkvslstkktysftakfagddmytkssvtgkvtik |
| Contig40_gene_834 | 118 | mnsnktyavlglllllllsigaisaedsiddmsltdinsadnsninqinaidnsidtststdssidtdnsietnldssiedknstdakntl ssnslastykitekdyltyfdkdgnilsgklksgdtidlsgtfskkafviniplititssdgtaklllnsninlvsgaggsmvsnlnmnts vektpalsavnrvtkvsfvnntvlstatgsyallntvnnsdvlfntfqttcfvegwghpsalvlsgsnynnissnnvivndsngiyltg ylqggsmgdstqgsntynyiynntvhsvrgvewakdkdgnkplpssfcygigvmgayneiientvynmyrgisatqtgnkvvnnlsni hgtwysggtnddgadytlyvttnsivkdnsisdskigdstaaihaaantnvtnnvlsniegtgvliegnnvvcnknsllgltndgliak gnvsnidisgnniinasetavslvktsrslaphditvsentifttkenpisyeeaystnitvennrikeasngtdpstegngtyyiids nfynyfdntgylkstikendilifvgpieskdkiyinnkvnitgidavfkdttiivlddgvvidgitinnpneakndrewgiqvngakd vtikncnitiydafsayavylidssdcklinnleakgdyltsavllyntnntvlsgnslktigtgqnytflnescldgcldgcl dgcldgcldgcldgcldgcadgcadgcldgagvnhiisgifrtyglfmvyssnnnvtdnkvdvssalekgyatyiestnaiggifihh nsnniiksnnitlngndpfmygagvvggnsnhtdyvssnngfesnainvkspyyaigillgynsskstlksnkislsannysyniasy kssentvdgtvtvlkdtivtstnitaqsnspivlnltvldednktvtvgsllayvnntlvnstslkgqstslgigaypkgtydlvvlyv nggiyrvgagacqfnvsdvintgngtkdiqnaldnakdgatvdlg |

FIG. 7C-13

| | | |
|---|---|---|
| Contig40_gene_835 | 119 | minkriislslliilvfliiglsavsaedsskaadldlnsssvsnidlssnsvaiesnsniasesssnivldnkssdttdiqtdsdss<br>sddnlnhdsnskiksdnskkvhtitesnyslyfdsngylnnslvssndtinlsgnfsskyfrfsipltitslendaflrnspiiitgvs<br>nenyvydaivsnitiesdlanisavwvigssnikvlnnniffttghngypialdsfvyncilanntiktivpvseamsskdidedngtnn<br>sdnsswqhsgislrdahyntvvdnditvensygvylcygasisnynviannttiratsetpsfwcygvyitgnynliygndfyhlyggvh<br>ssypynsivsnnfydidgldddnygaggdfgiyggnntliannsiynaklynagilvgtnsevygnyiqinssgegirigdkeggsyskv<br>ynntvdfldgkgiclygepnstlvydnilnsissidsldlsaeskgsglgigiyshyqsrakrpynistcnntiytsndyaidisqsst<br>kaytcygnlvfgkgiiypmevvypdygegnvyevsednfytyfdssnklsdkvkdgdslifvgefspkgkitlnkevnlfgygallkn<br>ttvfinapncrvhnftivnngideynlwgvyfeadnasivgnnisildkntsygiylcdsydnnvsdntiscqgdnlvfslltyeayd<br>tlfennkilaigtdelyppyeticidqvhsiselsktygvildsssrnqfihndievtstlegfhvpynpsvnliliglyiyyasnynni<br>sennvyvhghdpflygvgssgddtsksvtyacenifshnnitvegdyfvmgmilrhnskdtivdsnhfrlnsnnytygitleisegakv<br>tnnvlnstgnagiyamelyasnnndiksneiyasasyssvalyassnnnvthnviktygnkvqepaqgpehpdsvdlfntgislqkfss<br>gnnisdniietdgdaavdfdetstgntvgnnelsstkggnaavn |
| Contig40_gene_836 | 120 | mdfkkaiplfalllilfiigsssaassdlsspadnenleidsfdsnedltvntntnyiesgnnleidyksnskesvnatndikeetv<br>dynedisveknnlkssklssvykitesnysynfnksgnilsnvnpgdtldfsgsfnnkdfkidiplvtssdgaqfidcsfknkgsdg<br>snisnlninssrlqspliyldsvsnmnvfnnnlfscasksyalcfsnvsysayhntlqttafvvgwghpsafvlagannlnissnnvi<br>vndsngiyfttyvgdtisanlinennyifnntvhsvrgvewavdengttplpssfcyaiqvmgsgnkllnntvynayrgisasgsnsvv<br>agnvvydikgnyysgntkddggdyginvgpnsiventtiynshfnknsgvaisvgsnttvrynnitningtgadlsknfiefshnridn<br>vsdngirvkgqygntnisdnfinstdssitlIrsskdkypsrinienndfytdvspiyylegyigkltakdntlngssisdisidvpss<br>setkvsinstkidfnesvlimptvsaygisleglvdiivnsqkiatvpigsnytftpteagsfsinanftgneeykpsesavliltvtp<br>kettsiiispstvelndtvvispfvryngtllegfvdilldgekldtveigsdysyvpnssgsfyisasfsggngyasvsdmlltv<br>nessiedpddptnltvssilispntvevndtvlispfvrcngtllegIvdilildgekldsvvigsdyayvpstagtfnisasyaggng<br>yepsvsdivvltvnekqiidngtdngtdngtdngtdntgtqlgdgtdevgdvkisnltfnnynkdaivineiaydltvennk<br>ypidldvdgnytliidslnnkdilipsgfniniigkegsgtinngtiqlgdgtdevgdvkisnltfnnynkdaivineiaydltvennk<br>iiinteaspgnlyfsvyginakgyvfsvyginakgyvdslavrdndiflngsapyly |
| Contig40_gene_837 | 121 | mklkkfsvilavllvailaigavsaesvsdtdvaavaavddtagtvsvddsiddvsvdttdndvknlsaavaledgesvsyeindtsys<br>tyfkddgtatdelsemggytlnigtlnkdiqiisgsdinitakdgegfiinngtliilggdefpgsiivsgltftntnkdaiqvldyttd<br>vsiydnnmniigisslssdpnfsvygvsangfisglyienntmsvegdalsygievgaysdgayalsnpqdilisgntidvstsgamae<br>pmylsdvwdvtvvnnfvtaesvnapaygiqvadsamwasymdpnydgdlsspnnvlidgntfilnsdfmiyygittinygwdgiemesya<br>lplnitvsnnnvyanskkgvmgiaggiynltvidntviaiggsaeglytgdllgntyalyidydgnyaedtyvvvkdndvftnvtke<br>yafnndyervifennedlktfviddetysiffnddgtsdvledmedytlmigplnnkdivldsgseivilgldegyinngtivldgvsd<br>vyvsdlvfvnvnkdafyigdesneivivdnaivlvgkaaestnpyfslyaisangyvtglnitdnsiyitgdapysygislsayaaefn<br>peditiynntiemslsegssmaeaiyldcpsdatieennitietvgntfaygiqvadtlpaayeyasyrgeltspelvtikgntlniss<br>eymiygitvlsegalvngsgdlalcqfelflnvsentiyadstkgviglagkvynitmnnndlyvtggdasdvfsyddlgvgtyavgik<br>yngdsedgnyyadvfenniftnvsaeyindetvldeyvffnnfipldlgivleadkdaleigdlinytitvvnngpnaasdvyvsfels<br>dilllvtapeeydaefellnvsdlavgqekvnivaqvidggyllstayvdcyeddtymdnntasldmiavpividdsnyanyfnengy<br>lkddviatgtvvlfgnltnkdlfinapllisdckdtklvnttial |

FIG. 7C-14

| | | |
|---|---|---|
| Contig40_gene_841 | 122 | milislilvilsiscvsanditndaiqgdlsdiqysftidddlsnsdnsldvssdlkenscldeididkesnqttkilssnqldsnll dsnqlesdqlssnqldssllnsnqlnlsntytvsqstyskyfdkngyvktsvvapydtidlsgniisknfiftipchitsnnakltnc mikfenmtadgrssvsnlyirnsvewcpgvflegstnvdvygndiyctgangnpvrviysnysnifgnklelyftgymnlswkragill gdshynnifsndvtikdsnpiyllttygfeksnhntiynntvrssaisedsglsnpsawaygihlmgdynialntihnvyrgidsegsf nilagniifnltggyfegndgteggdygihasydnivanntifnskltgsaiylmpntaygnivynisghnglefnyyadnckvynni idvpvespiyvfgrmnnllienniltsvdsssilvkkgsnskyptdvtirnnlimgysktfnqspidysqiksdaniisfnnsiavynd tyfnyfaeignvrdysdwidlnntinysdsynynalvfvgnfssitdnittktdyiiplkdivnsrisdvyrnvpyneyksmmetlneiy tdivfngpspvdlrgvdsggnssdsnqtpmdgnqsmnessdngsdnstnssldnlddevkdsyenlidninstenasdvyvindanyal yfnedgsfrddfpiefgntlrfanltnkmfkidiplkiisdsedssllncfislegessntiisnlkfeldnlssnidfisikdgvsnv liynntfkldidssdslidsplsddaslsairlygsdyisrnifienniidfksnfgqlygiylsnkmdylnsktnpsgfiirnnvfsi dsnglinaiysdsdvknlllennlfnlssngnledsllygldlvkvdnltminnqfsinstylacginssdssgfnlsnnqfsvdsayl ayglnlkntnnfnlhnndfyidsgsfahaldlddccnfniannli |
| Contig40_gene_847 | 123 | mcdnsniiisviivlciaagvtaygisegdnavfsdltgfspsstdsgdtgigntttgnnsgggitagqtnvatntggssggssggss gsgsgsgsgsggssgsgsggnggntnpspspskisaaqakniaagaiaeeegayissvsdtgsayvcyisnaegtnvgyitvsyggaiie gaggap |
| Contig40_gene_848 | 124 | mcdnssilisviivlciaagvtayglndsntvfndlsgftpdesgdtgigntttgngnsggsgitagtdsggtgssgtgtssssss ssssssssntqqkawkpkvspekakalatsaarnsgwpgaycysatynsggyyvcllkddagntyahigsgtgrflegswskg vtkepneveddykenetsnite |
| Contig40_gene_867 | 125 | mrkeiliaaiailillcggvfaasnmqiadiatfslnaidledrgslivdseditaskgyynssasdenvvlvknyslrlsnsivnktg dtgssgddadfyginsavlvnsngsvelsdveietnskgsngvfvtnavsdsnsnssssgspivdsterhdgksdaeepggvppekpv edgpsvvggsggkgalsdgnqsmpapgassvdeqssadisnvritthgdksrgldatfggkiiasdveintdgqscaalatdrgeg evhvkncilntgvdeksgrgspiiystgnitadnsegcahvsqiaciegknsiasncefsagagnrednqeyvdlqqvfiyqsmsgd advgtslfdanccvlsieedseyyktapmfhvtntkaivklastelnfgsgvllnvsgqsqwgtvgsnqgelefdasdeildqdvfvds isslnmslastsfigavnpdddfgetnlvidsdsdwtldgdshlsslenngdidynghtlyvdgkaytespfk |
| Contig40_gene_872 | 126 | mlisivlislialqavsaaddavaaddavapatvdevqtidntitnddisyestdlivndtgdsadskakttlsanavnegetlsftql aadvsssspsmlsqayykdpstdtafengiltlngltliggatidgdnqarifnipegvsvtimqvtlingaadegaalynsgkltlm nakvndntavksggialynnggevlvtssefdgndltdrtvnqyggaalysnggsvtidtnvtnnlknivhrgctgtytgdlssaavts nnadltvtnsrfiansgsyggaiysgestsanllvsgstfednfafnggaidivgtsytisdstfknnnvkgtgstnsnyasggaicvq dannpglisgcdfeansgvvggavncentmvldctftdntansansetfngktnnrggfagaiynegtitisdcefddnagregirvk naeisdssftntridtcqnsnvlltnntynnpdrdvqaasgtqvtvdvadgdipnantapyivgdltftdlqalidsgssgirltgnvi ktaeeettfadglnvdktvtiyqaegkviqansqkifnvaegktltlrnatlqqsgetaitnygtvylyladnngftdcgdvlidnhqr ttetqltttqlnnliglvnggtvyigeskitkaededekeaykngividkdlsilgsyntyykyvktsinanndqriftvaeqkslslky invtnqaadegaqvvvsedatliadtanfikntavtkggalysegtvdltnvniknntisktdgvmaddnggaalynnqgtatldkvnv tcdnqktvyigdimdgvvvskgattitnsyfannsgrwggaitqtgtdqtltvedtifeentaifgaaifdnsplvvkdckfynnsaigp gspgtsnsggaailvmddtasadisgsefinntadcggavslagvgsdssiddctfidntayadggavyfwtesasvtvtdsefisnta pygqaienegglgdlivdgceftentaslrggalissgdtsvsnsk |
| Contig40_gene_900 | 127 | mkeiaylyliliivliaaghlnvvsqsmepvmyrqdlvvlqkanlfgihefdphdvqvgdivvynaawydspvihrvintaeingttc feikgdnnnksdpywvtpeqitdrvitingqplvipkigyitlwvkgl |

FIG. 7C-15

| | | |
|---|---|---|
| Contig40_gene_906 | 128 | mfeagmialptglpglaliglgtvltaygsgmfddlgtdhpgyakpenqlnfglsmglnfiglgaseglargvlykevqeklvtgfvps ikaygktimdeslgkgnakistviwayvensvilaiensingg. |
| Contig40_gene_909 | 129 | mknwkliglililillavvsvsgcigddsssddttsisadalnitedgtydskeevaayideyhklpsnyitkseakalgwhggsvekyap gkciggdifsnrqsilpigheykecdidtlgadsrgpkrivfstddyevytgdhyasfehlt |
| Contig40_gene_917 | 130 | mvqntnlsnntavfnesrnetsgiggaldvvgnncqiinvtsdnnayrggstfirgndtvirnsfdnnnatlrggglniagegctif nvdvsnnaagengggiyviadgtefrnitadnntaerggafvegndiiidngtfngnkaifneskpdesgiggaldikghgcnvtnvd sfnntayrggstfirgndtylenctldgnnatlrggglniagenctihnvdisnntaglmggiyviadgtvfrnitadnnsaerggav fvegndiiidnatfndnkaifnesrpddsglggaldikgdgcnvtnvnsfnntayrggstfirgdnthvenctlegnnatlrggglnia genctvynvdvsnntaglmggaiyvvangtefrnitannsaerggafiegnnvtidnatfnnnraifnetrpdesglggaldkdg cnvtnvstnntayrggstfirgddtyvanctldgnnatlrggglniagdrciiddvdsnnnaglmggiyvvsngtefrnitadnnt aerggsafingtgitirdgelnnnraiynesrpdesgiggfidvgdnilvdsvhsnnnsayrggstfirgsnvtvqncldnntatvr ggglniggdgckvinvsvsnndagedgavvyigdslfdnvnstnntaqrggssfiagnnvtvincnldnntasnrgggldvngsgc vfenvtlsnchadkeggavvyrgdnvtfnnvtsenntaergssfvagdnckvincdlnnnatwrggldvtgtnclfenvtlsnchs decdgavyisgddnrfvnvtsnntavvnyggstyiggtsnsvenctisnniayngggifiegedskftnnnitfnkaiatdedhdfnim gggvfilgnsnftnnnissnhakdnggvqiffgpdtfmdkiyafnntaenggfanllycdnlnvtnstfysnhatgdisldrgegga fhmsyatnidvqgnfsyntatngsaiysdgsdirvhdssffdnqa |
| Contig40_gene_930 | 131 | mrnkkififtlmivmllslaavsandldnlevddgnvvstdtvindvpmestssdkialnvdstgnttellneneiitnnstlsidln esitneissdhedsyqadsnqedsyftsdgniyvkvktsmlkadgdqiyyihpagsptatgtrddpldsmnsalnftsdgthtivvmd giykdtyydynntdvdtnlsnliiksdegasphfnlstsdyrrslywaftgenitidglkftdsqygsfnedgvkyhtvlrfinstnv lvencvfdndgylinatdssdvviknncnvsnsnrsnvfnvlnssftvqdsnlskirdsyitnssfklinnticnnvnsnlftvknssld iinntfkdsnyssyvfriynnetyanftgnnftnltgtdyllqvnyvndnttvsfvnnslkdvslglniryssnltmdgnsfdnlsl ssrpsysgistsysnvsftnnnftnsdsyilygyvnatiennftdnipsyyglraegnshdikennftnnkgncsiiqhysgnati hgnhfynnslngcghvinvtstsgseiykndfvnnsadngtvylygssnvhdnnftnnsvtglggaiysyfyninttikenvfdgnna sfggaiyyenypsynnkreivnntfinnsadfggaiysnksinniddndfinnsaqiggaifvdylyindfrynntnntisnnlfaen naqsggavvlysqnstvegnrfisnnasrygggalitsgnnsiivnntfanntaqlyggaigtndskiidnkfennsayqagailtins thnndfvgneatrgpaivyiddfnytaltyytyncsecncsncsgcsdceccvttivdpetgdeikilncsncdgcnctcenstvteh nitllynntgididedvyayhengllrvakenngmyylydnvnvtsaenytywayciegnnsypwlgngtlgvhvddlyfvrnslddsy vgdylkilisyfyhnldedkinvkeyiyiftdtdyrsnndrliqk |
| Contig40_gene_964 | 132 | msikrllltslmlfilifsisfvsanenvtndvstnelstqtvsndittsesisdtsldsgenrgldeiksnsteesssnldledgtl nndeiesddcltkngkeatlqanklsldinmsrgtaqdvldaivrissqggtlylnggtytegharvynndtdsfrnivrndgivdi snvrvvggsvdnpnqyatfqpntrdstslafsgyvwdgngntryypdsgfnltnvtfenlnctgrffsfnsgyltdcvfnnlesyqhlf fvtgayndggkpivltncnftnskqtyrgdgpgdgtdgtqfgvvfgaemygcnfintstathgafclsdewisaacvpsklvdcnfi nitsrwfavyihgnysnttrfitepqvvencsfinctatgefggalgishnnviinntefihnvggksaimvgginnthdgflgvntq gnnitiynctfedniakieggssahstdppfttyptgyygavvygnhtkiidstfnntaddscgaaiyirgdnttvvnsefynhtse ngtiylvgndckikdslfhdndadstgacifvegnraeigntfvnntapnggcvfiigdhtlvdndtkfiitnatngagiyvngsntm ilntsfinntavngsgafiyghdtdvngsyfegndatnggavfiegnindisnntflrnnatnggavyidgnhtkvnynnfteneaip isedqetglggaifirgndtnttantflhnkarngsalytdgtnfylhndhflenqawsyllittadpaeslykeqdieinvlyragdn iinaihnrnkpnethfmnvtyshsefgnittspadqyvepvqvensregellyqdrenyqqielrvehengdlalprtpfrtniygn |

FIG. 7C-16

| | | |
|---|---|---|
| | | vnttlnksslrkglyvvgaehiedwnykfimnstsfrildtmdimvnktsdkeeyfqdeiaewelifhntdngtdaenvtmtdhlpnvf elmnlsymfytpteaitnatlylnnntlrygvynsssqqwvygda |
| Contig40_gene_975 | 133 | mdkvgiigagslgtalagtvannvdtvylhlrreelaktinstgynseyypntklknniiattdmndlidckiiflsipssafrstlen lkevisedtilvttakgieypslksmgrlieeyfdenfvalsgpnfaseivlnlatvsniasrssenaikvkkvlstpefkvkiiddvv gleicgvikninaiangicegmninenaryavltkgfedtgriieafggkistaseycgfgdlvltstssesrnhtlgmlyggrlivde kasgivfegknsimaikdicnnttnsvvnfvydvivkqippkiafkdlwnniee |
| Contig40_gene_976 | 134 | mmsedsilltiksftdlqteinntanggililegyykynsnldsnflqkgvlvnknitifgngcvidgnntsslmeinannntvkiydl nfinghqntwnygrvsitnsiayfnncsflnstngyygsvyiaktsqahfnncifnnnyakfggaifnnnimyckncsfennsaqsggs lcingenngventnnytylencsfsdnsstahgaviycdewskgcfnncsfeknsattsggaitidganidinncsfnknktgtsstyn ggaiwiikndisgasnvnlntsfnnsasqdggailyngtcvlkisnssfnnntatryggsirnyqgtataylcgflkssdatygtit kngcygp |
| Contig40_gene_982 | 135 | micsiqacsasctavyvgpdvsadgstiiarcndhqgvwgnhitvtprvenkssrlmavcedgsvktelpattykytatpymnstka |
| Contig40_gene_996 | 136 | mkisriilillfvvffeiglfssytivnaevpnpqelwdmqvntvssffspenvgllikdpdninvtnkydlatelaevaevdgvnv enmtittsadtdeepfnatvtafgystpkgnsgsivisgqpdykivasvqikhtingyeadldtiniesilkvydsndaknvsygyds gpsgasqsysyssdsssndnayissdsssgssssydsgassssgsysggssydsgassgsgssgsgsgdvvinllspifsfi |
| Contig40_gene_1008 | 137 | mililisflislllaigaasaseditdtieapaadevvtvdseiqeietvdnnleeietdtnnieeveaaddevinetaeteikdeteit detiiseekvqiandekivqdglilgfsinltdllgesssInlskllsgdnlnlnskllsgdnlnwsellsgdsftlnwtdllggd sltvnwtdllggestlinwtdllgrdsltvnwtdllgedflnltdllgrdsltvnwtdllggdsltvnwtdllngdsltfnwtdllgd nltlnmssllggestlinwtdllgdnltfnmssllgedflnlmtsllgedfklnltnifgdnltaifgenlitnkleelfgddftlnmtd ifgedlalnmsdifgddsifnlsnilgestlinwtdllgesstlniskilgestlinltdlfgesstlinwtellggsltlnwtellgg dsftlnwtdllgnstlinwtdllgrdsltvnwtdllggdsftlnwtdllggetlinwtkilgndtslidnitslidispfvdnltta vkdlinkflkeektvsvinyedmttafdskidgrigkyfvvkltddkgkalsdkfvqigfngriynrtsdengtvklqinlgykgdyt faicflgdektngsfavakitvkkqkakltgtaasykasaknkyisatfkttagspiagkkitftinkktytaktdakgvakvvsitn kgtyaftakyagddtyatitsaskkltik |

FIG. 7C-17

| | | |
|---|---|---|
| Contig40_gene_102_1 | 138 | mklyknsiiillililsigaaavendysnadldisndfvlsdnsneilidssglddsssalvsegssngldsyysndlvndslss rssviedscsidsttiedkaleks1ssnelaegtktytdlkdiksaknvlnlkydylydstldkslkkgivltfdedyeltingnghi idgngiaggfnfengefvinnlsfqnckisslltscdfttnyvtfsnnydkssgacvyldnsyfysshdnfidnyapsgsaiygecsv idvydglfesqkpidwsfiygwdeteiyiedclfrntvsnystavygdyileisnshftnlfskftggaigvrnasltveksefnnvss lrnggvlyadmnvdeeksseetiikdssfvnsksdfggavlqlgklkiyrsnftentanyygga1ytsnvsfytskskfsnnvanemk gsaiyfdngdlkiensnvlsnpscegaiyiydsfynisgstfsnndva1hsffdrtrtvknsktgksttvksslnntwggdrnklnnv eypyfvsnlgqdii1npvkinatikdkyfnlvdglvtpvkdqgdsgacwafggaalesailkatgvs1disenniqsaglryslygk psltegydytalayylswlgpnnssideydqfgkispqlfsednyhildvifldpantssikdglikygalsasangadsdndffne ktyaqycnddeasanhiisivgwddnysknnflltpkngawivknswgsdwgkngyyisyydeslrscyavay1nntlrynklyqy d1tnyddfddgdydgviysnkftsngddliaavgtyfeyeddyvisvyvngkkaygqkgtsafvgyntiklnkyiavnkgetftvais ssampyvddtrihlpkgssfltvdgeqid1sqrgqiacikvytfndtkitrdqstyygsdkk1aieselegttisltdsncks1gsakv vdgvaqfd1vlgpgtyfytssyagekiinsfkvfstiggvsnkni |
| Contig40_gene_102_5 | 139 | maviliilfslgtvaasenividessdsnlvidhakdny1fngpikdnylsssisdnylskgv1ddsylsrsdlddsylsmddgkgsi dltnhqlsnsddkqlktsnledekqlesvnkgdkl1kdsndnvdlfinmdvktsltnkqynragsevpwiitvsslngtsyntqvrdv lsen1qylshnatmgtfdpengiwtvgdlessknaslltiltrlkrdgtyinkayattdsndvnllnnflliisirtgsskitsnitetsd eregiqhnvhyasmvdtdfiyryeedsseddgneeggsegnshtktrslgnklklfnaqnidyhslskniggalgfgynsnggflnsk diyealfvydytripilivfaaflvvlasivgydkvkssk |
| Contig40_gene_102_6 | 140 | mvlvigtisavsanecanditmeisddniaidsssalegddlaidssssdlsnenninsmdsvinsnsinsdsinsdsinpnp niddeinnhkdsflkavqasktgftelqtkinkaskgstiyldknylynddfkgkygivinksitidgkghvidglkksnlifindas nvvfkniifrkgcdgdengainligsdhiefnncsfnynygdrgavflsgsdysfvnckfnenigenggaliladsdysrlvnciffgn easdgavfitysdysyffnctsegnsvdytgafyldysdnssfidcvfdtssakdgafylgdchnssfincsywnnqvdygavcy ldncydssfiscnftgnsgsnpeldetpsigggvfyiseshglyfthcnfseneakndggalyasdsdvhidssvfeencalcggalya mnsdlfldsslfessvgdrggsifanksnvysknssfigyeiedeyvipasgayhlmegniggaiyslqsvlnissnkfnnnfglits ggdiysqysmiyiddccfsnsfsngfggslfnndyvqitdssfencssrdnggiysinsilncsdsdftncysyfggsicslntdl sinnnfykssaeygggsiyflygtldingslfsnsygqyggsiylrspqtiknitnnqflfsqgirgpriyidqyygeisngnvytd eyeekglfsdygmgisfesneglvplihyypsneslpsfydprggdseddyededddsdiavkdqiggnncwafsgiatleaclekvt geefgfsegnaknlmaissiyglnidtnnggydtmflaylaswlgpiyeeydtynplssisidlpsvfhildidflaprknsldndeyk raimngavsvtfdwvenkvsngfhsvsligwddydddidslgnyakgawifknswgyewdggfgylsykqklseeiapymhaytfsf kendigytdiygydfsglsdflilnstnayyknkfiaedneflya |
| Contig40_gene_102_9 | 141 | mrnpkdyimktdyliilmallisivspiaaadsfdfdipegyhienasddfvllenedysisisimdnstdrktlmdmlerhrcydf rngvnytkgdfyieekpyyqefqmgilyfcengrdlvvidykpplgmdlnnspidgildsfkwvsy |
| Contig40_gene_103_6 | 142 | mnnkkifvaglailaivlmgsvaavdmgiisgsptkfsidgidfnipqgyavtdnytrvndtdtagsssyrvtqatfennvhdaisvlv adydhdmsediisqrgnkttingvdgymqtggdyttfnylvcgnlvtitlnadlledilvgnqtdd |

FIG. 7C-18

| | | |
|---|---|---|
| Contig40_gene_103 7 | 143 | msedigindndnngaliadvnfaddnnnalkaesnsasqndasidesanptqdlvdtdnglnqsitksplksntgltvtktidnssnhmpv dgfydigdtiyytinitnnleesignisvvenfpdgliweyiwfaddnpnwknesnvfnytkalepehsillkirmtgnktgtyintin vssnltssqeflseevtvyapnltitkvandpivtigeianftinvtnngnrplsnlriyedpeeslflneftnisgnwdsfanrggdy gfsldqldigesaaiivsflttteignftnnvysnypnpqveanatvtvvpriektvnateidmgesveynvyidmtganklgiddfkik vtdilneyfdldkdsissnwkynrdekafeymlsdipesfefnfavyitergnytntvslkigdlpevsaesdvthvrisdaniaetal dstvnlqeqavfivnltntgdktfnpyelvvnddydedaltylsheditgkwienietdslsftlnstlevgesasfklyfntskvgsy snyyinindkeddsivivlalmnksvnsreidagdsveynifinlsgyqgpvkvedlfndtfaldkdtisenwhydetenafifdlsd npdtlnlsfnvtinekgnytnlaklilssdypeitaeapecvcykpdmtvtktvndteiyigdtvkytvtidntgdrtltniivkdeld pafildessitegwtynkdnssftynnisvgesailefiveiskegkytnivnvsspgvankearseetvaktiptniclenvtadpd sfvriiinitadkglingtvnitfpdgtneaveltngigetvwyvpdnyasgnysvfayyegngtylesegqnievipyyteislsnv taypdsdveieinitagdaklingtvtvsfpdgtnktaeiingtgnvnwtvpddykgnysisasypggnyldsnatanieviakistq itadipnaypgeeidisvnvtadndvpfngnitvnlpdgsketve |
| Contig40_gene_103 8 | 144 | mdfnnfkyldelihsgakeinldsdiiledkeeqkysdgiknidnlviongnghiinakektrifystaqnitiknirlkngktntigg aiynlkgkikiieatikengskyggsiyndegemeikstftknnaksnggaihnykgkmsieesiinentakggaihnyrailsien ttlrkndakdfggaifndgnelkitestieentssggaiynmigeiliknstitkniakiggaihswnklsiisstlnknksyeygga ihnfdgeifikdsiitenisnkggigfsnnkykittstiennesdniheidsfldmd |
| Contig40_gene_103 9 | 145 | msksfrdlelliencddeivldsdivlgdgegplylegiinldsdviidgnghsidacgkvrifyssgeltiknisllngysdesgaiv vdggkmdiidsiisgnysaddgaihieegelalinstvkenkakefggainnwdslkivnceissnearfggailnndgnleisdslf kdnkadkggviynqdgdfsvektlfeknkasadgvfynencdisvieskIndnqadkggviynngvfiikdcelinnrandggsivny eaelnvmgsslsgnlsnyggaiytydgemsidesrfddnraecggaiysekciwdvsnsefnsnkaknsggaillkkskyevdnvsfrd nepddvsnf |
| Contig40_gene_104 2 | 146 | mdfreelnkilksddeennlkstenkikdkkednnlkpidnkikdkkednnlkpidnkipnenkepkekktpqktdeermqnrpketi dhlkrfkelnttdsifnispyqvliilkdgtnitdwkeiedkdilyisedlsgesyisnkyrdlegmrliiaqgitskvqfiesmfa dckslidvigletwdtsnllslenmfggcssltscdglryldvsnvndmtalfndcyrlndidslkewntsnltkmwsmfagckslkdl rpisnwntsnvtnmtslftecelsndingirswdssnlkdmgsllwgcksltdisalsnwntsnvrkmgrmfwncesltdisplkdwnv snvedmvymfvnckslkdltplsnwkpskvlimrsmfdgcssiesinglenwnlenvttvermfdrckslsdvsalkswnlsndviagg ifnecpnvkenplkkeikdknkplhhidlnikfldiygtgwclvklgdiysrasyitdvpydclssivnaikndenfhvdfngegwtfd veadneqcyfnfhgekhafdtmnkydlaiviyrnirdnlsswkgwthrcdisplinelcslineneaden |
| Contig40_gene_104 4 | 147 | maemtirnsiiennsarnggailndgnlfiektfknlaftagaisnggyvslkdvsmenniavtgaafinggdakiedsfiikniai gekrgmngehdvggavgnsdnlllkntsfinnsspfgsailynlgidipklkylckikiedcrfennshisgeihneigeisiddskfk netakrgsviyndsyltitscdfkdlkkivhnfnlmtihssnfesngsdsaviendgeigilsiekgkiannisdyttvynhgkdcnit gtifennhskkenchnicnrsnmvlkeiilkdktvslfnegiltaekkyknfifsvgkvfylgmenefnfsyldelihsnisdtisfde dislsdefdfyeggieldrdnmvidgkgktidasgrsriflvtgnnitlkniifknghafdnyfmsnneggaikvykgldlkienckf idnisskggainnkghltisnglfesnksneggaiynhqklsiidtcfkgneghiggaiynkedleivstkflknivkeslfkarfip ilqledesfggaifnkkrmvikgssfkknmgldctdgawggairtigdeevtliqtefignylkdsnfggaissyktpnlidctfsdny pndln |

FIG. 7C-19

| | | |
|---|---|---|
| Contig40_gene_105 4 | 148 | mgfidklkkgigrknkesskrdtqkdtglkrksppidkasfdgsdeeyklfesimsyrdepvvhsilrkisddrlliejgkshpflel rrdailkikhasredlielfdlnedrwgilrnaiaskftkeqlmeinderklreiirysneenanciydkindeellidivcltryes irdkfverfkndpevmrrclessrspelkskvaqyinndkelkkyilsqndwntveyalnemkdekianealyefahkgknqlnksie fmsddetllnialeynldydryyfeigmaldrinddsllvdlmhnetdetlrrlaakyikseealkefvndpnenvrkialratckns ldkfmdlfnndeiilddhfildggidgiyetitinrcdnvtidgknhklecinpkielrieannfsiknietnmlirlnegslnisnsiidk sieinegnltgenstfdrrikningsinltdcnidqifnesslskgciigsiknddscnidnctineflynngrckienskvesasrn ysnpydggaisnqnasmeltkcilakastdkngvirnigsinlydcifednkaglsggaifnegrltasrckfknnlvefprygsf sratgryhfikhgnsilnlafmdlifncqfitdkindapeiiaqfgkdsylniencqfstnkktsvdaieglnfnnakfkvsfddveei nlanegpeetgsinknlketsstneglkerrstnkglketssinkgeettvssknedidaesilenfkgfeylddlindgsseitldcn iqmheleqafyeggieiyednltidgqyhtidannlsrifihitgngiviknikfkngyyyqdyfdnskdggvlcithsasakiincef snnesrqsggvvknnsdsleiidsnfrdnkviyqkgciinnasltlrncsfknnfsnagscvfnsedsslkifdcefnnntsrkdfea ggvrfslevpssggaianegsl |
| Contig40_gene_107 3 | 149 | mplrvavayifendidyhvnqtdltclagfdqnytiysneftskydeligavgtyfnesgikysfdifvndkkvqtqngtseyagfirt ivlnnyipiksgdqfkvfksnsvpyqawsrvhylngtslvsadgstwtdfaplnktvclkvytlndttkladandmiieygedsyfsv raatennisvgpgeevtftinnnttvktndegvakikiseapgtykitssynnqsyennitiisrertstrilyqnmstvavnskvdg rigkyfevnltddegqplnnmpvqigfngavynrttnatgvklqinlgyegsytfaiaflgdnkyagsfevailkvskqapkitapak tykasaktktitatflsdkghgvkgkkinfvingktytgttndkgvasvkvslnkkgtytctakfagdgmykatstnfkvkii |
| Contig40_gene_107 4 | 150 | mektmkskIfilliliisilIisisssvaselqadasnidndyqtnmefdpicndesnqdnlknnnehilkeentnppeiedetcftt lyqeinqsddelnlthdyifnksydnaslyqmyygplisvnktnftingnghiidgnemgaefdfennkgeivindltfknfnqtvlqi ygkltlnnvnftesfeslesiifvskgvlnvnncsfysnrakniisgsqsnitvnnsifsgngnyeraisanrwqlvihnsrfenftfk ngaiidfkgyyldlenssfnnihsnlsggailgkyfpayikvanktqylpsdpmiikncrfenisclndggaihfdfdsgsqriaqsln iidcsnftncsskygygaisilgglnleksnllnnyasfeggaiysswtninitdssiknnkaeknagaiyfdkgnlsiksdiinnsal eespttanaiyahdvaadfsdstfdngiavyadfashsnftnvnknddiflmdnhnyivsvetpgiklnltnneiivdslpskfnsqd wgwttpgkvqgdnddcwafatiasietglgkstgvlynlsqnyvqkylqlkyyevgdlrnsltgfitsglgyalswygvlptdaayddrg miadsdmnvprihvqdamfiytgenntidqlkkaiikygavtvqywayregeeilsegedisimet |
| Contig40_gene_108 4 | 151 | mdkkifivsfillaiftigavgasdvseltandiddnalsindgedllagdesgesgkesyfnndnmyndenrvnannldygagdndas kdkvlsdnvsdyiyattlsvsvddtpqsqyptatvslndlsgnpvaeasvsvsvdgddymtvitttdgtcplsldnylsvgshkvgaey sgdgtygpssasttfnvleeyssylntdlifiytgtgreggytsvtgkIthinqpisnatislyvdddfysnlttdkggeiegmlfnisv grhelrgeyvgdrgfepsnatkyfnvlpkdsvssniqmtlnasdaqvtganayvllerqyggpmedatisisvddvfymnvttnalgy affdlsddlsvgshklsgeypgneytgsssasitfnilpvddssynftvteyanyldtnttvldisskyyvngsfnvsvvspngtlstf tqdcspdghnnwsmadfgidgigsyiisgsllifknetlthfdnqtfhaicirpiymesteannpldilvvynssdatkvsvngsglfeg rkitdgpivwnltdlniteIgdynisvmsydskgnlidrfdynltigpngddyklyakidpnsystddvavalycpnaswgndievhiy mgnpIevItffpdsvspteaasfkkytladlriensndyrveikdfalnqfpgisfnikvcysnmilvsgngsfeidfdgasvnatltd snqnpisnasvsalvngvesncttddngnllipfegnttvkltyidnngveikgtgkyvkesviknrtetkiiyqnmtttvnsnvdgr igkyfevslqdadgnpianktvfigfngkvynrttnstggvslqinlgyagkytfaiaflgddymgsfevalitvnkqtpkitasska yrpnskakslvatlksakgnaisgkkisftingktystttnakglatlnvslskkgtysctakyagdgmykatstkfsvkia |

FIG. 7C-20

| Contig40_gene_108 8 | 152 | mmkmtkknlflisilllilltigavsaaddlsassdltvedsgeaiatapeesvlinenngdsiackglsdpisnetaniaidekttnd kaiseednsiyskdkanvlrenetpviltinapnlyygetanvtsarygagplanssinlaldgaagenilifddgiaqknytglaag nhavvasfsgygpypsasasksfevltptvnieieandiyygerayvtlhvtygnqpfanntiqvsldgqsstsfiveddgniqvtysn lalgshtvsayfsgygpypsasaskdfkvsketavslsvsnpqldkgdelrftpsvisngfyvmansysimvdgmsnysywtengtyf lstsslssgnhtltvsyagdasflpssanatftvnsykatlsimmietelypgddcyifidlydsnthqsiaanitvsvgnnsylypir vnssfnlptdnlapgvynvtaffdgnglydpetavgtltvlskkettlslsisnpvlsigdelrfipsltgdgsyiwgasytikvdgmg nqtcrlvndtyflstsdfaignhaltvsyagngeympssatgyfevtpkkanlslnmlstelypgddcylyiyltdsnthqsiaaniti svgnnsypypirenssfnlptdnlapgvynvtafypgndlygpetavetltvmeenatiktetylsiimasgdkylgdnipfsvsrtps gvslfgdnyifsidgvesqdifyenfsyfivtenlslgnhnltayypgdemylpssasqnftlisrpksdvllsieandtfigedatli inmidelgnpidganvylymdnkefalplvngvaqfsysnlslgtylvsalfngteynpanasasfevlnanltvtkdnffqffnnng vlntnatdlkfvgefndlgitsikinkpvsivgenaniinipvivssddvslaniafayngsepliyannvanleiinnafsykspsdk syavnitksenvtiidnsfnvggnntyginidaigfeidsndiy |

| Contig40_gene_108 9 | 153 | mvimnnkklfivslilltigavsaaddglatsdeitvdssvavstasaaesdiyetngdivadyqsdsisnvtvdddntkdeiirs spakdnllddddpgavnddegdcdedylddisvsitneydvtdqdavivsifvpdveegedgiegyfvvcldddeiflgpfnhti tpddygtdvtftasdleiteaanywvrvfyvsdlaeplidndeedgynmifdgciardytqfyvivppdgrisifdtsaiytvyccppg segtvtltlrdeedvetsftqeiedadqenqlywdlldymglntidaagnyevtitlengtlicedcirimdpieipevsyinstdyha tlvalikipselddeellidgtvliqiddetvfektlsefvegespdpfwvypkihwsdeldtsvklyvlnnqlidldlepgtydvt vkldldgwdevssteevrlvesnvvidedigasleifdgediindnevriiaitvtgcksgrvnlavegcpewecpdelenegdiyyi nsgfdiesgehevvsyvlnddrsvsnsailnfivyprificgnggediynyfadedsaihiypkgddvstirivvtigdevvldstid dlglspkindwgetytvgpanfnkklefghyepvvayysdayelstedgelsfidiigmvhvaciededetpvlavcsdrdgqigvyi rqytedgdqelepkyfevekhgfimptidqlgdceggyhidvayaddewifgndlivnnsseyfvlygcdwlyteesvvyvwcpddaeg iisltnndgtinvdheitdedkgkyveftleelgisgpgwyeisvrvngneidhigfdvpspiympnynvylpeegyepdysmliakle lnselegnitinldgtivfnkdiedmeaikdgskwlytlytsdldeaeegmhdvtvtfndlneersiefInrttesdgnlsiimlggty cinwndviaeviaptnyngrlvlrlqgeimqswdcelhwvnwdnyn |

| Contig40_gene_109 3 | 154 | mkfknkrgisaisilllflsismasaieisaddadmdsgdlsvcevstsdcygetlisadasgadsdeiiinetiadektdyrssil adgekknlhvesvndvftpdndyefmlydedfnqiggyldiylndeltysdftvdssessislsglecglnkitfiydeddvynrlnq tkefyiygenpefvmiphydtitlngnyssrvylkeydewgyydednegciepiddkfnvyikenpgdeyelwedefeangtinfdd aikttgnylirvfngssdysyapynssniircvnvitdflindtyfipckgfgfsvylvdnatgdiidkefklmvyildtsnpvriv eeemvkgnktytfdcseipenitylfigcifdgcrdeyssackeyaleltdsrietsinanigdsvignsssfrvvqdeenwqqidat ldiylneeysqtvtayaylenevlienlkkgentlrivyngtdiyqnseksynftvsdkranievdvsniivgdvtkitvnltdedgni lnkefnvsiykgssyydedseliysqvytgsanislpdleicdyyvraefvdesfvysqaedseyfnvyskgsyidlgktywpdnddvv lnislrnyieeninengevlfqfngtdyplttcedgailnlgklpvgkyqifakfdgdgeyeasnltqlrivkatiinveacdvlkgqse tvnitftdgdgnpldvkmldiniwdtdgnwldygqlrnsieikniqtdyiiramlsdsygeigscydypssaygfirvlngtdptvitv tntanidlaidgdpkviitltdedgkaisgaklnaavgnmesilttdskgcavlaigandtakvtytdengagvsasivnnvinttvtei veknitvpvtanatidlaidgsdvvvslndldgnaiasaslcatvgttnstlttddkgqakvaigvnetakvtytdengasvsasivnn vinstvvinntvkrnatkiiynnmstvsvnsevcgrigeyfnvtl |

FIG. 7C-21

| | | |
|---|---|---|
| Contig40_gene_109_6 | 155 | mamvsasdisaddsvsldaadsdivstdsisvdsvntysadsaissnedkdnyhpsnlkdddnkiskinyelndtvfygddviinanlt dmdgniidef fqvtvydegnplqsnslkgkgtmivptvsltessyydvalsfagneeyascneftsfnvtfkensylaisnydsyskin stkinfliiydvddeyindtadiylngeyytsvltngnenevtienlqvgentvlvkyngsniykgsedsatimgyekdtsigidapdvl igndarikinltdedgnivngrvdveiyeyytgddesyvpfkddyvvngeailiviyqsklragvtyfiradyegnltyfrsvgsdyfdc fnrsteividgriasddkditleiglfdqrvmiaglvnltvfdnesnvvidtisvetsaddyvnvtigklpyghyminasfegneeye gceleanlhvfkatnltievrdqikgesqivnfslvssdgglnesasliiirnmendliydgliinftdgkasynldnleegliiladynn gmdivgpfetvydsaskfatvriikqlngtiefepvndsiivnlkidignpiaeaplsvdvngqvfelitddngqamldnipnnvtiev kytdnqlvasnkivvlvkeqikqraaskivcknmstvavatpdgrvgeyfnvtltdadgnplvnktvmigfngrvytrttnetgevnl qinlgykgsytfamcflgdedynasyevcvlkvsshqpkltgsaktykvsaktkaisatfktsngnvisgkslvfiidgklynaktnsk gvatvnvsiskkgtysctvrssddgmyaatstkfnvkiv |
| Contig40_gene_109_7 | 156 | mfilkfeikrslifisilailillisigmasaseeisdsvstdiasedvtseiqtdnveitnldedssldadlekdtgdkvkkakkrint kliyqnmsttavvneydrtgeyfnvtlvdeddkpvvgeliqigfngriynrttdsnggaqlqinlaysgpytfaicylgedtyessfe vavinvaakkmtltvpsksykasaktktltatlkdnkgnlikskqisftvngktysaktdskgvatvkvslstkktysftakfagdksf gavtktgkvtik |
| Contig40_gene_109_8 | 157 | mqaiipvkdnflilvtnmkksdfkrificlvlltcligavsaaedvsvddvstdavavdtitedasdptdistvsepvsndvqantsqe lnkepatkstnvlkdgtstniyvattgsdendgltqstavaslakaveivnatagtdftinvangdyniskiespaaknvnligeskeg ailhasdtyginvyedniawtienlticdfnststssaavrcfaidsvfninncifknigskngaiyitstgtrtisnvliedcfgtys ssssiihlygegpvtldnieirgsymdpsvgtatylrsviyadqatnvtlknsrivdnigamgslieakgafkvinttfegnylntss ngvnggtfmfysgtssnsasnidisqsvikdnvlaggsiglfncvygthnidhnvimnnkyangndvplgsfsgaaistddnywgtner pntkttewviltvdtpemafvgvseaipvnlntyktnnetgavegmpdvdfgvtyalnganpstvtvanggtinylatvdgnetltf stgdafsfdvkadiaslliyvdglngnatgpgdsehpyktiaqainvaadgkiiviksgtytenslliiannitlkadknaeviidanneg riftvqkdaiirdltlingkstgnngaislldsgllitlnnvkiynstaqsgaivslsgsqlsvsnsefidnnasnggaiyvagvaditn nkfisndpedggaiyvagvadiesneftsnhatnggaiyidsenngtikdntftsntadkgeaiyiknanvslsgntmgendsiyldga slkttltflggktiaaefggtlnltatltdedgnnirggivftangetiatidlstdaqlktqytvpndaagcditisgsyslngav isgkihpavphwfieggsgyetladaidgasagdilyydlpedytevisktinkaltiknngtgvtldgnlcrilsissasvnlenl ifingatatnglliylsgsasndlnisgctfkdskftttstytya |
| Contig40_gene_109_9 | 158 | mnfkklmislillfvlsvgfstasaidsdnlldennlnvryidsdnscsililsdnsndaksnnlilnnsinkkelndnsnsnlec dssinenldlennykineksagklkdntntiyvsvdgndendgltletavaniskavslagegytihissgtyeqnkstqlshafnige dgtiikrigtanaftytsdtktktisfkniifsttpnpsnpilsmaggadlqidnctftdaiagrngliryylgsstgkitntnfigltg stsasssyitalaqskvkvenctfaninepgflnslvyvnnetnltlvncvfnnitgnlnavvnnrgymikncsftdislsgnsprg iwssetisknsityinssvfinnsvntevvvnssviqaksptiveysafldndvvfiinndndtdvtanynwwgtnegpkncsvnres sassnpssseekislvsdgvtvdnwaimtvdletsgliagedypiiininkymnergeidssveygisgaeillssqigtfnsdfiiy nednqniiqrqakvytngavtvfykateegsdtlnissgyeeivynlefgqsieyndiyvskdgndnndglsnetsvltiaraleige nlnsniirihigsgsyhesgfelngtytvqdgvlqvkrttysfigygnvviddgqnkslftvrnnsvsyknirftnvdgatyggaingd nlyrtayidltinnctfddllhvkssggaiylnyvsgrisinntkfynlttnsswggaisaeeafdlarvkvtnsdfrdnyannapamy lrvsnvtvlnsnfinnsakyypgaihfynasaliencviannsakkdsaaikisegtndvgnkiliksciiennsardeispaiyvekg aldisyssvvndlsiatrtyysnlyglqggvaiannwwglsnpfgeneiggnyssllggvfngsnitvdswvilnavlndtgvlkvgn ivnisidfnhvnttrgeiellssggkipkeytlrlnatggivypny |

FIG. 7C-22

| | | |
|---|---|---|
| Contig40_gene_1100 | 159 | mfligaasaaddavtlegcaaavdsisedasapitttvsedasigttfsdsaiesdsiqsnddlelknvtdvkqkdssdalkdgestti fvstgndndnclgsletavatvekainitktgtdtftllisngdyniegitipvgkyisiigeskegtilhasgdygfdisygcnfenl tisdlnstsstsaairlimdnydinninncifknigsaygavhvysngktsisnvliedcfatksddssiihvsgkpvsldneirgsy mlppafpwstpylgaiiflssadpdvtlmnsrihdnngsiysiitskgkikinttisdnclnasyasifssgvnsntatditvtqsvi adnilannavglldarfgvfkvdhniiinnknangndlsvgdlsgassfsiddnywgtnvrpndktsewviltgdvaecafvgvcenik iflnsyvtesgeigvidgmptvelavgvalnqenpsavtikdgvgtisylasiageetlilstgdvfefnvsseigslifvdgsvetsg dgtqenpvktiaeeniaadgkiiliknqtykesnlivdkditikpydgadviidgdnqdriftvtstatisdlsltgnatgdggaiy lnggnltlsflnisnciasdnggaiataagsdlylsnsiftdnfaskgqsifigqeailmdfvahmdvlspdasfnaisintdspvs ivsnnfndngaikgqavyikdapvslsgnimddeiilylesgsvnsnlifmdgktltvepgadvnltatltddkgnlirggeltftangv avgdpidisgdnelripytlpsdsegdiliisgsyysfdnggtlvngtiepdipywfieggrgyktlnetvenavagdviygspgtyiang ifitkdltikanetgdiildgngsrvftikngatlslvnldlsnggseggfvyiyaeggnlnvinstlrdlnivgypesfeggaikty asstiniesshfeninssafapilsglgggvklsltikdssftdik |
| Contig40_gene_1104 | 160 | mkikksfvilclliclftiasvaasdindttisdgqnlikeadgdllsleddnnikelneesdknllvqesdndnnpesdkdllvqes dndnnlesdegllvqesdddlnkkadgslfssykgdnaapikintsylikeinnsylekdnytalkeeinnylkksnnnaikeeiskyl lknsyalqkeinnyleennfstlikeinnyleennypsiedgiksylqsnnysslqdvlsdviskiinsskkesepiddgftalqyk insapngatisldkdysydegfstrgieikksitingnghtinglsasriflihfgltgnnkvtlnnivfangktdlyggaifnygnlt vnkctfknnyaktcggainsvgemilknsnfknntaggdagavfsfkignstnifkdiykdkvidgmdfiidyilnininygwdsinn csfssnvakgrgggaiyaftikingctfnsnkagehgavfankniniskskftnnkapkyggavyfrchelsgsyvnktwvskmkyy tatikdsiftkntaskggaiyefnhtvsdkkrlkvskcnftdnkaslgrdvfsgscsnciyfyvkistksvtvkktaksftltatitng tkklknkkvtfkngktytktknsngvakvkigkavikklkkgktysvqitylkksakttvkvk |
| Contig40_gene_1106 | 161 | mtvsvflsasfafgnvlsnadngsvgtynshkdisspnmdykhpgeliygcggnqniqtdghicek |
| Contig40_gene_1158 | 162 | mkvlkiaiimlliliislgavsatenfnndlsdnglndntlsdnslnentlsdntlsdkslsestiiqndhdnlkdtnnndnnkalkdpa ktftdlqmeiinasdlleltddykynnetdniltlisksnfvingnghtidgdnqcgifqingtnitlknlniinanstkdsalllnpg seletnnvtfindssdkrvifafgakytsnndkfidctsindgvinsylgeitinngyfesskpldwafvnslgnssiyvlnttfantt skyataikgdretvihdskfinlyanltagaiglkrieeaeidnctfinvssqknggaiflidiysdsedvpimisrssfvncysefga ilslggkitleedfntngaffdggaiyssfsqltisqtifcdnnsvelddrgsfggaifsdisalilincsfsnnaqtggalytyds gyyianstfkdntnkesefddiftdfdgeiatlennsysgecsiclnneryesviavsgmnftlieneinvtnpprkfdlrewgwvtpv knggymgscwafgtvgaiessilrfiglemdisennmqdsllqyyrygtlgaeeggeynlgpsyalswfgvfpseydvydelgkisaii atddsihlqdavfvpplmnstdkdklkqsllkygalavsyyaetdepglnentssqyslkndsnhrvllvgwdddyskdnfymtpppdg awiiknswgeelgdkgyyyisyydasfatlvpsvgfpimntviynknyqydiggtleftdmgneyvnefealeddfiaavgtyfidagv dynieiyvndelkysqdgtspffgfhtiqldsyvpikegdefdvkitsdcipilesgrqhyienksaanlngewdltsdgkvcaikvy ttdedkkkessrintridcknmttavasedgrigeyfgvtlkdengtalankpikigfngrvydrttdengsaklqinlaykgtytfa igflgdeeylgafevakitvkvgtpkltapnksykvsaktkslta |

FIG. 7C-23

| | | |
|---|---|---|
| Contig40_gene_117 6 | 163 | mnfktkgslililsllfliligigmasasedintdidtdygsdsidvsdvslndeqiasedslpnyeianksdklydegeeeggitnd dddenyridgiyadytitpsengtifvegeriqiifnftdqdyepvsgdwfinfygestdvdiyhpfeatgltdyvvpiylppgdyif fyegvvfddfggiedegtqldvtfedaegnqldnpefsirtnynkkvyanltidysvaelenlvegdditakislmdefnnkmtekvnl eiyrngenydskkvnvveqnnniifenlgegnyslevasidsvpkytniitkavnftvksnydpdnyqiilnpedekklvgdsyemgv klinpseeaeegsidlylrngnfvktlelnydedyshhiveglglpnnatflyqirdgvnvsesvnliryetesiidlessdiiigdd akikaslyldgivkkpinenfklylknyvededevefvydeeftiksetitlsdleegtyyisavyngknykylateeestlevfpk etrvdavartysteenvivgieladlsgkaikgtvnvldnktsyqvnttddighpveidlgklgyglhnielnytgddsegwlpsynn aeflviypsfmsiedgdvtsgsdltvnisltgpdegingiltvriydntgkylingdfnttngvksieliknitkdyliiygryygldts kieigpsnhylsseaygfiiriaegksekteydleltkvndntviaslkdsdskpvanaeltvkvngveskaktdnngmanisfsgnssi kvsytdannttakasmeiiiinnvtekivngtvevpveiekivyvngtvevpvevekivyvipnrtdtafeyenmvttavasadgrtge yfnvrlidatgkplaykpkigfngvvydrttdadgraklqinlgykgdytfaigflgddnytgafevakitvklqkpqlstasktyka saktkltatfksehgntvsgkkisftvngktvsgttnskgiasv |
| Contig40_gene_119 8 | 164 | mgkfkfifilvlalflicgiaavvdapdsfdgsnlipvsdssvsgqsdssvngsdcengtcsvdlnksednssketsddeidydskyyd dslidglyfcndlehafkdakqhhknvmiifdgaaciyceylkdegltdsdiqkeinendillmtytsdspelsqkleiygtpttvifd engtelgriegyespeqflselkeyngk |
| Contig40_gene_121 5 | 165 | mdsskilmiavvaliaivavsscsagfldflggdnatddslngkevnlaaaaslknvyddelipmfeakypgvkvtptyassgdlqtqi engletdvfmsasnkqmnaladeglidndtnlqflenkvlivpkdsdinitsfddlkdvkgtiaigdpesvpagqyakealtnlgiwd aveskfslgtdvtavlnqvaqgsaecgivyatdaksnddvkvvceapenslntsviypvamikdakdadaakafleflqteakdkfve ygftihe |
| Contig40_gene_123 8 | 166 | mklkskyfvflliicilfsistvsandndmsingnlqndangdingdlqlneayqsdtnlnqnlqannqendllkasedktyndlyndi kncedtfniendykytesdnhtfisinktnlvingnnhvidgsnkaggfeflkeslniiiindltfincndytivnedgnislnnvnft nnhnklgilysegmisvfngaltinncnfdsnnntnliytnfaelritnsnfsngkgigspiyanrfelyidncsfenftapyggainf kgntfviknskfknlnaeitagaifakyfpktnkdppyipgedmlfencefsnvssthnggaiylnldsssegfaktihinncnitdas sdfggaiasqgeildfsnlniinchakiggaiysswadlslkdcniinnsadkdagaiyfdyskliidnsnftdnkvnnissgkesily andvdaeirnsifdngvavyanfasnskfenntstdlflwnntnylvsvenkgiklnltnntinvdklpskfgdrdwgwasplkfqgd nvacwafatagalecallkqtgvlynisenniqnlqlkyfsegdrrnsaigyaysglghslswygaitseddpyderqmysdvaetdkr ihvqdamiifggrndtrnlmkeaimkygavsiqymyapydtanytevdlqpghfvtligwddncppekvntkmaidetnippgpawl mkdsedsklgedgyvylsyydislsilskdfypvipqaagvayifentndyhvnyqtditglagfdenysyysnefvskydewigavgtyf nesgidysfdiyvngekahsqngtsefagfrtivldkvypikandtfkvifksnalpfqaysrqhyipnmsmisadgsnwidyadknrt vclkvytiesdkenissrastiidcknmtttavasadgrvgeyfvvtlkdqngtaltnkpikigfngrvydrvtdengsaklqinlayk gtytfaigflgdedylgafevakitvnlhspklsapnksykasak |
| Contig40_gene_124 7 | 167 | mnysiifififlmdalvlmasiqvcgacgkgsnplcvpmvm |
| Contig40_gene_125 4 | 168 | mkfnsrvlgilslifvltilvssvgaaeykltekdfnntfkigipegtdfqqdaysniaagnvnfamkvfdnignntdgvvsvlyfkds ssdsnlisdviddlnssgevveendrnyiivknnydaewnapdastssdefwsfigdlcssgsdmnfgdgdsnihlsddgvniedssanv sfsknqiyvsdsdgqnvsissegvkvsggssnetvdvnadvdsvmnsysefadyslclknpkkdqlilicgndldllkqmadsasfk |

FIG. 7C-24

| | | |
|---|---|---|
| Contig40_gene_1264 | 169 | msnietddsfisensissdindnslineftasnqindniaindglskgdcksqlsesksiyvstngsddsgdgsekspyqsikhavskad ddsilylssgtyngennqnisigkslsiygedstiidgedkaqlfimnssaklslnglliltnaykdgnlsdyggaiineggqltiinst iknsygnyyggaiynnlgrltiinssilnnsaigyggaiytlgvtniqnsvfekntltaekgvgasiaaggtitlnntdflnnhaiysa aallsignatinncsfingttnytagaisnhgmfinnslffncrvrfyagailappsghhvvtevyntifdynnagnhgavtnnfgda eitmincaitnnyiqknvfygdialddnatvqycwwggnnissyyysphsnnedpgqinasrwlmmtftssngnisadevntltvsikq yfdndtkeiyeynedinlpltvkffddnkktiatktlkngtasynyipvkgvnavyaqitneiieipvvqkkesnlstsnltkyyknes qleakitdgdnnplsnktisielIgktynkttnengivkqniglkpgqytaniifkdpeyknknitvqitvlknstsisaknlvkyykn ssqltvklldnnkkamkskkvkftigkntytrttnangaatfninlkvgtynvkvsfggddyykgssktvkvtvkttkmqakstkirkn snfvatfkdangkviknlkvkftlnkktyttkttnskgqatlkvsvklgsytliksqyastktygatvfntkikvvk |
| Contig40_gene_1270 | 170 | mekkttiilvililiiacgvgitlfaspssistdqnttitdmanrtvnisssvdrvvatsppmttivymlapeklvgvnfqwtdeelky vpdqykdkfpviggwfgsqdgnyeefiasepnlviegidegmgvdlstveergekfgslpvvavtdntnvtkidntieflgkllgaedk aneliafndkylsqvqstassipdsekksvyyasgedgistyasgashgqlislvggknvadtevkdsgseltvsieqvmswnpdviia tdedfynkvyndskwasvkavkdhrvylspqspfkwfdrppganiiigvpwtakviypdkysnidmvgatkefysnfyhyglsdeqake iltssqlkgsdl |
| Contig40_gene_1274 | 171 | mknkslililsllilliitiisigsvvatdneeinmdninidnneedianidnvdnvdnsninnptdiridnsnlnreteldsnlnksnqir edeleqsnaksnlkssklsstitvdgsdenqmsnptiqsaidsanagdtiiiltgksyvhchfivnkpltliseigtsmspcpsntkgsg ahgifyispeasgtvlkgfnltntygdydydygiilrgaenveiinctintvsdgdgirienatntkiadclikdsniginitgssktv tnnnitnnkvtgvnvginnndttihtnnitynqhsgidlysgdvyyilnnfighngnskssssgagiyvnsnitkveikgnflkqngqyg vlndyrvrnmdasrgaetleinnnnnylghteritvhieyskyaggpftydsendlyvvgdgngdwdigktvvylgyafyrdetvcgs tlfkapsttwgtevykleispisqvkkgvysvsivdvngivasdissiyvtfylnknntdaepqsgdiyktvlmengtatvnltdkefk esgnkitacfpglynvytinpyatfdvndsdipgsyrnttinatdmslvpnsgnkitarltdengnpvageslqfkisgistytrttd engeanlkvslsnpktytvninfkgsenynkssktiktvkkqtpkiessnidllpksgenftvtlkdannkaiankeisftlgkktyt rttdengqaslkinlantgkytittksektsqynevsksntititkgankvniessdktyipksgenftvtlkdansnpiaskeisftl gkktytrttnengqaslkinlantkkypittkyagddtyssasaentitiakaaaelttynrtyinksgqmfsakltdknnipleneki sftigkktynrttdadglayltinlaydknistkflgndqynaktntnsititdeietayidkglkndeigriideikpnydvkflgds yddvnlninktlliytdvnttlngksaspvfnlrgqnigvsffni |
| Contig40_gene_1296 | 172 | mrstillsastaesrspslttgrctvqtvadgmp |
| Contig40_gene_1331 | 173 | mllicfiglveailmalvdwediaisvrksprklynvlkdelglpewnelsvierrsmkkryavirdsfpelppweelsvidrrshkrl ykliksvydgcyddspslegppaavgpqkeipleeaeyp |
| Contig40_gene_1350 | 174 | mnkkiiislllvllvaisvsavaaadadvtyindaadvddvadekvapltasadaqdiqtkldnakpgdtielenktydvdttfnvtkq vtikgqdtvikasgasqgsgalfianeagtafegitfintdghknygeqvsgyaiqlaiengtvdnckfidwssgvygkgasfcsitn syfngsseqvtngqkkeygtkainlmgshditvtgctfegqvldaisiasnsgnnimtdntfidncyalyfggastqgcviannsfirc gycvddkgnvifkdlpiistqkaangyiiadntieanegsifmkaesgntahgypskigdinitgntitataganpegitfmyilsnsg plnpyapialvnnldagitpvtvwyadwdnengtvipaadkavtsiniaeiaaadgtvtvelvdvngapqagqtlsykiddgnateie tdengkavinvpidenataqtvavefagtndllaassaqvsfkntatkrtatqinannmsvvtlapntgdtndnyfnatlldaegnplvn |

FIG. 7C-25

| | | |
|---|---|---|
| | | kevkigfngkeytkttnengvaqlkinlgykggytfavaflgddeyeasfgvylinvaaqtpklttkaatykasaktksisatfkteqg sviankkisftvngktytgttnskgvatvkvsinkkgtysftakyagdntykavsasakltik |
| Contig40_gene_135_1 | 175 | mslsifvlviggfinkrillifvfliffisigsvvandldsnsvnqdnyisdvdsfdgsnsvlssnldssidkdnylnldsnnnlnl dsdknsvsgsdlnlnnadlinsvsgsdlnlnnadlinnsttndssnsnsnnlenltnlddskgasnqkpqkylipndssigsayiqki idnaapgsticftgsfykniylkidkalniiskgtvinssyriplvftisrggsgtnisgftanlansfveasdvsdisisknkiftkr kaivlenvfnskivrnsflrfetaidisksggltisnnitpdngynvgislkdiyrdkvsilnnnitghdrriestgiyfgpnaknvl iegniidewytgvdfpnsvnnvsilnntlnhngdgviingwinnftfnknvvtntgrvgvlfdydfygtkgdftleknfftqsgqldlr ntgdqavtigenfasrrcvrvamkngfsiktrqngnyyfsivdknsrgvsglpnfsatisingvsynvnfinsvayvevdgasgende vlldvgedkrklsdwgetqnlssemeyykkiyddliksmveetnndnqdmkkvedkngtgstpsggnggdgsisdgrssvssngdss pasagtsnvaassassagpsaagadtpesstvkslsldeetfrvagvgglvflicviglyyredimdmike |
| Contig40_gene_135_5 | 176 | mnnkkiimsflvlliaisvsavsaacliadnqdsissndnsineiatedisdkindksl sdgvstgnnwivkpstdgksdansiqka inldntkpgdslltdknftleksvslnkdltingniynqnnltdlfiidpkseggpknititnvtfyvngnenivlangenygttyi dlanikisnctilpinpdsnindtvlniksdrtvgtggstgfvlvsgnklngintlknndyvlkddfviqkadpilntalicpnmti ttydkntndtpsyyevklidqnvpvinrtiqigfngkiydrtsdengiakvkltlaytsvytfavyflgdesyasafdvstvtlikkn atitpktvsynvnaktktltatlkdknnkalankkvtftvngktytattnskgvasakislskkgtytftaqvlqgtisiiqfpkkgkl tlnplstnltvkkytfkkaatkkiqvtlksgktvlkskkltikvngktysgktntkgiatitikltkkgtytytanfagdntykaisks qkvvik |
| Contig40_gene_136_2 | 177 | mnrsadngaiyfnnqnfgqnltinhnifInndavaiyfvrndsasnadynwfgnnatncdiaptsnnmemntwlflnatsepegisld scciifklyayapsgvseydssrlkeinltvtpngrinttgaklgekvhytpesaecmltasienafyttrlkisdgttfrdlnnlin rncndtildndfiynslfdskfkngininrpltivgnnytidatgmarifriqaddveinnitfanakidgngqaiywysgargivsd csfvnnsakmygaaiywnqangnvsdcsfvnstvtdehggaiywhgangvvsdcsfvnnsakkyggaifwnaangvvsdcifvnnsaks ydggaivwneglngaisdcsfvnnsandggailwneaaggtvsncsfvnnsanksgaaiywdsgargvvsdcsfvnnsanrsgalywfa ndgvvsasifvnnsgdngvlyfnntnkrnlsindnifInndvvaiyfvnsdstsnadynwfgnnasnfdteplttnveistwlflnata dprpveilnssdisfklysynatgisdydnsqlgpvnltltatkgdvdsiaklgetviynptslgtgsvtakvenvaysieinniksnp nlsvesdeltygnniaialnyesaatgkvnitlkgkksdytfadldlnetislgilaadeyevieysrdeiytnasargtlkvnkans tltvsdiefdykdmgsgeisftnatgveakvinhdeaivfvrgntitvlnlsadsyilevttitdenhnevsknatitvrkvnstinvn divlyygesinlavttdgaigisadidgenvelnenivtipddlesgnhtltittvpndnhkeasktvnivdcrignitvvvdgveysi pavngtaittnmpeeieklkenitdltgleeaqtnatnlannltianqivdkliaqleeaqanatqtindlthqlneaqtnatkiand qtnanqivdnltgqlndagtnatkiandlenanqivddltrqlee |

FIG. 7C-26

| | | |
|---|---|---|
| Contig40_gene_136_3 | 178 | magstirafkvtasgvtikrlitiknanvttddigntddegaaidfeksgtieycnfiinnsanaagavyfykdnskaincnfsyngavys ggavcfeesgtienctfvnntavydilgggavcfngtgnaincnftnntaggyfswagaicfntngnainctftnnkahdsggaiely gngklencsfdknsandggavkiygatkisncnftenkaaelsgdggaiywnasagklencsfaknsafhggavsfeedgevtncnftd nlagdsgaiwftadgtvenstfikneawdeygggivfytsgdvrncnftdneadkggavyfngagtvensnftnnkagdggailfsed stvkncifvkncatdirsdryfercykyvfykngevtnssftennateggailfkgngkatdcnftnnsakfggaidfeshatvenssfn gnkassngsaiwmnraggivsssvfvnnrantgtiffrndnstshltindnifInnngvaiyfcknsdsntdynwfgnnatnydiapv annaeintwlfInttvnpcmisildsldiafklyaytpsevseydnirlkavdltltptngifnttktelgktvgyipesdgigtltas ienasyttlkitdgttffdldyiinannnntivldrdytynstfdynftdgividrpvtlilgnghtinaaemvriifhigadnvkikni tftnaisngygaiywgananlssclfennsavmagavafygstgsivsdcsfmnnsanngaimwgvsddsvvsdcsfmnnsaiqgg aiywssndgvvsdcsfvnnsavrnggaiywekinvmfpavfl |
| Contig40_gene_136_4 | 179 | mkiqrgiyiiltlvlfslsaasaaddltddiisadeneelildetviddvsnandnydeelikandekfyawk |
| Contig40_gene_136_7 | 180 | melkvdqqkclgcgvcviacpvnasispenagghgskttetimmvengfiklfsvdkcdkcgtcqmfcpteaiwle |
| Contig45_gene_8 | 181 | mnrrskliiailiviiigiavilfgsmfggekissgqdkdilvcaideseprpgmgavdmaflvhmndggitnytpiyphgmvhpsiaep eeyqamgagekllhdcfywedkqqcmqyakelleyntnyscdaviavnsgaidniisaagtlkyngeevnasgidfireeqntmgmtr gdsvmvivnalnqaakdpdkrdkminaavseytagniamypegsfmellaskglqamfg |
| Contig45_gene_20 | 182 | mkrskkliiailvvillgllllalagyfvggpdlsgenktilvlaadkyeqpnggcdmaylvrlengslanytpvypggmyhpsqsapgn lqcnmllhdclwngvedgmqyakeivafhtgveadavvvlydegvdnvldsirpieidgeptnlsatdiirendnyagykgnegvtgtm sradavmvlvkavskqakdpakksanlhaaldeytkgnivmtpkgsftrllatkglesfa |
| Contig45_gene_21 | 183 | mkeykiaigggpagmiaairaaeilgpnavcilekneslgkklllltggrcnitnntpihdqlnynknknflkhslytlpqdkllai feekdlefhgednkrvfpdsedahdildileeyleelgvdvynntpinagdiehelnermepvfeienekislnaskiivstggitypn tgsgdgykiashmnhtitdikpglvsfniddfllktlsgltlenvevsfkdkkkisvkgdilishfgltgpaiidisnrlleksdlt vlddklnlksrdeieelelftnritidftpdlteedikngitkdspkngkmaiknymkkylpnnfidyflmkidinpkktmanitkkdk nklaenlkrhvfeieslemdlakvtiggvkskeidaktleskyveglyfagevlevagptggynlqiafstgylaggeaanslkne |
| Contig45_gene_30 | 184 | maneggghlktllmliliafiegialgvsvimggddnsqtesegvhyvnvtkniteynesgnlietedgthiefssysdnvtegenvt aynsstdagnlf |
| Contig45_gene_35 | 185 | mdnkikagialaliivlavigfsfinesnnvvnqlspltesfdysmepmttwddskkeysfnqnissangkdykditidilmyndgksl dkhtstinstkdgsfnlkftqrlegepdefyynvtkatei |
| Contig45_gene_36 | 186 | mfkvskslivclvslfllvsqasaadsnglsirdinsvdenynldasyldslqdsngmhsdssinsngldksisngtssn lkdndldnndgeseiieeeakdtegvvmagdsyscgpaslatalnrlginlslsevsqhtntskdgtnmgslidaagynfsavgveiq skdlaensivhldidgaehwtvvskvteesvfladstrgninmsidefnslfsgkaillselnktnvsnksknikvldqsqclnvkg kgwvrvlvgyktewrglintyswvlrpkvinghvsysaweyvkvkhlswgkykvkvpiykykyiknqyevkgkk |
| Contig45_gene_60 | 187 | mwydmkrrfylilfillilaaiaiigtfssfsdvsgydlgsddlsiavtgdvmfgrkmpgvldsgaspfrnvenvtksadillvnfe npatystnpvkgdvplkadpkyvhllaeaneiviasqdnhaldydegindsiknlkdagiyviggnnlseaskpvviekgdrkvtv lnymdadnifaeyasimppatanssgfcaydselarkqvraearenessiviaymhygneysrspneyqinmshelidsgadivigshahv |

FIG. 7C-27

| | | |
|---|---|---|
| | | tggvemyhgkpifynlgnfifdqsnpathrsyflnldlhgdnctvtlyptvivgylpqfmdadsakallaelypqcdqlkvnddgtaql<br>tfklgnitdnstqsndvrly |
| Contig45_<br>gene_64 | 188 | mkitvagvgvglslavllaqkhdvtaittteskaemlnqfispiqddeierffkevregertlnlhtttdkaaaygdadlviiatptn<br>yddvgnffdtsavedaiewtlkvnpdvlmvikstipvgytesvrekygirnlifspeflreskalydnlhpsrivvgcdddqmeegqmf<br>adlllegareeekransleqdipilithlteseaiklfantylavrvsyfneldtyagtkgldtqmiidgvcmdprigghynnpsfgyg<br>gyclpkdtkqllanykdvpqtmieavvhsnsvrkefianqiisrnpktvgvyrltmksnsdnfrasaiqdvmksikaegipiliyeptl<br>ddgsefsrsevvndierfkresdiilanrldcdvlgdvaekvytrdlfrrd |
| Contig45_<br>gene_89 | 189 | mnlmkitvagvgvglslaillaqkhdvtaittteskaeklnqfispirddeierffketrdgkrklnlhtttdkesayknadlviiaa<br>ptnyddvnhffdtsavedaiewtlkvnpdvlmvikstipvgysesvrekygvknlifspeflreskalydmlhpsrilvgcdddqkeda<br>qmfvdlllegvrleekrsdspkqdipiliapfteveasklfqntylalrvsyfneldtfaqtkglntniiidcvcmdprigghynnpsf<br>gygyclpkdtkqllanckdvpqalieaivnsnavrkefiadqiisnnpktvgiyrllimksndnfrasaiqdvikmikaegikililye<br>pilddgseflksevvndldifkresdiilanrfdqdilgdvadkvytrdifgrd |
| Contig45_<br>gene_91 | 190 | meiryknllkvftiflvlliscgfasavsdldeqnsanivdngdlslsdnmmsesadncknletieeshtfseknlvkdvsyglstpid<br>gntfediqtaidnaadgdiielngtyfgngsdikitkdltisgnletildaknksgifyvnsnnvtlqnlkfynsivpeygsavhflsn<br>gsvinctfinntaggvgtidyfwstggvvylakgngsvinctfinntanadgaiycgvdggsvinctfinntakelggaiyiggghd<br>ggahysnvydcyvdncvfinntagegagiyyggglifnlyfy |
| Contig45_<br>gene_93 | 191 | mkiryknllkvftiflvlliscgfasavsdldeqnsanivdngdlslsdnmmsdsanncknletieeshtfseksvtkdvsyglstpid<br>gntfediqiaiddaqdgdtiqlngtylgngspilfsknltiggsgetildanglsgiinsssekivlkditfvngsgftvdlrenngdn<br>lkycsiincsfekcygdknsaviclngsgiildcdfhytnctiningsedvsilnssfnytgyaihsnsstivkacdfynsffetyy<br>entnkvyngnivdlcknssisdcmfkgtyyetiidsvdsntyqfstlhvcdevdvinctfirsitefsgsaiyhfgngsiinctfinn<br>saggshgtpsylytqdgvvyigsddclvinctfinchsntfggalyinarncyvinstfiknsayeggaiylaggdcyvinpvfsnnka<br>nhslyndindlnavsyendtsddnqtekiinpsielqyldnlliifkdiegkaisgesvsliinnktisvitdsngeakvplnetsmv<br>kafyvdanglnvsssmmikivektnyipikrnssfidcknmttsaitnskirdgeyfvvslkdangkplsnkpiqifngkaydrtne<br>ngsarlqinlayvgtytfavcflgddyyngsfvvakidvnacqkaslnapsktykasttkkaltatlkdakgrlvsgksisftingksyv<br>aktntngvatvkvslskkgtynftakldndktfkttassgklvik |
| Contig45_<br>gene_100 | 192 | mqrslfdkvktslwmlpsffglvnglgfiylgrknsnikwtiegivyeipwliailnifnlsvaitafslgsfmvlisivrsvmvney<br>qrlldeeyvvrpsvesgshgldkqikngqfnekeaspkeekvkynpydlsgidknydgrikfdkykaeikemekefneknndnvkelvek<br>rfsqsgityrdfmfiikdsedlfnsqaanaldmidlapeytetidaeirkkmetlrtiiekndelrdeliinmttetgsemeiknlfed<br>mghltssikhye |
| Contig45_<br>gene_106 | 193 | mkfknshillvslisifllsisaasaadsdiaaddssvdiveledinikeshylcddastgsedlsgdentsasgtddatggndtdat<br>ggddtgnatsvngtenvtdsngtnatngtnatnntkydgpvtnatiipvstsadyqygnftfkvvdnatgeplanqkisvsgvyfftfn<br>ngssisttkvfttnsngllviankninknidtlgmvynftaldvgkydltfsgndslkivvntlpitvnkvnaeikasnfkdevgtsk<br>kytfklvnkntgtviklaslkfgiklnssgyttynsttnlsgqvgynlnliagtypvrivnndsnlkastvsrnvltlkkvgvlsasnr<br>tilynsaptaiikltdkktgkavagavlkvrvyttskkysdlafytdnkgqvsfkaalslgkhkmiistldnnytassitryvtlkktt<br>gkisapkisatyksgklytiltlknakngnamygstlnirifvtsksyykytgmtdgngkvnintsslkpgtykvsvssgdsgftakaat<br>ggikitkiplkisptaykekynsgktfkikvtnkntnkiisgikvtvkvytsakkyktytvkvttnkgiaylkvtqkpgtyktvvslsna<br>yysasavtskitvtk |

FIG. 7C-28

| | | |
|---|---|---|
| Contig45_gene_116 | 194 | mnskkiaivlgiillsfaivgsasafnlfggpttdfdnkfmsgtftgdvsrnnistndslsdwvdsyedkernitynmscikggsfltd lyelqgmaapevrnfngedwkvyysqavpttdenktanessvinvyiceadvdnvtyminiaydnesidcdgslycgffkddiqplle sitlkdakkapqiydllnmtkddfkqlqdyieqvktgnipetaeg |
| Contig45_gene_142 | 195 | msnntdssdnasddasgseivsgineelesnnltedisvddvilqtsfytsyavksaksptvltfknstvvkgdklyiylkdssnhg isgekvifkfsnssytrttdsngmaaldiklnpkyafsaiydgsdnysasrkdftltvakvntkltssssvvrgrnlytylkdknnna lsnkkisitisgktytvttdkngraslklslktgtystkinfagdktynsqlskkikiytlktvmtipstsvvrgqyiyaylkdsdgn alsgqkvmkfdkiyfnlktdkngrvalkintrlgkipvkasfagstsyasksvtitsyvektkitvenstvkrgkyfyaylkdskd kgisnqkvkitlaninytkttdsngkvalkieenpgnytiklnfaktnsyyassklkinvlnnatakiiakdqtvlgeysvrltdmns nplanqtveitaatvnrsvgsglpitkktvvinsdniynkatdsqfiksigevlkskgykviinsnignpahctdamgaysdvcifcif ggvdsgmfvdmaaswyqnllkkydnevlgfthtqrnlatdtwlerahdddyspknftglsypgtylndydmdyvygrtatemannfik yavnglsiglnntvpcnvmeynvttgdngyatitdllpgdyavissyinktagyvadtvisiievk |
| Contig45_gene_159 | 196 | mdecklvligfgavggvaraismkkeminekfgislkvvaagdsssaicqdgldeellktkeetgklanypeygsdisgidildav dydvlieatptnivdaepakslltlkafadgkdvvtsnkghlalfykeiieakekagvdfkfeasvggampiinlcqetlascgissikg ilngttnyilsrmttegmtyentlaesqlgiaetdptqdvegidaackvvilansvlgidatyddvevrgisdvsleainlakeegyy vkligevsrkqlkvsprlvkknspfaidgtlnlanittladditvmgkgagsletasamltdliniiknk |
| Contig47_gene_98 | 197 | mgfldnvkkifdsgenkevkprngtgkidkvesveskniynfnekdeqqnsedlindeildestsnetrnftylnnlihsgvkeiil dsdivygnedeesrhgiklnldnlvidgngytidalraseificdarniviknitlkngfshqagainngeltiikssinnegklag gilnlgeltldesviaknkaehtggilnffgklsitkstlkenigignkaisnnggeltinksriinngidtknfvnkartvfvnkai karrdavisnggylrisdseilsneskyiilniefsrlyntifkanesqyilyndnyednglssigifnckfiennakasivyndgnlc sidnalfennashknsniitnksnltinnlkikdngknilnddyifirnlspqieskiigeglaenikdkpqeekfdfgyldkkihdn ktgeiileedirfenyemcyyeggieldmdnlvidgkghtiegakksriflitgkniklkniifkngflykdynlmnnqgalktnsn csltvenckflnnfsqdggaihsgknvdiiksiftsntvkmfggggainndgnlsirestftnnsaeryggaicnkgeislfdstltn niakvhifktsygkggaiynkgkltisnsslskntagisggaiynwkhneryepiitkgrgseamcyegeliitestlynntaeesdga iynegkmnitdcdinndsnnknt |
| Contig47_gene_7 | 198 | nmrktifgvifivfilfsistvsandaqvdmlndasdvelnqdlnaqpissncydnnqnlkaqpisdcsdelqksdddlklseggstsf kqlcedlnksdgefnlthsykh |
| Contig47_gene_8 | 199 | mingnmiidssksnfnfkfsneanitindltftnfnkslfvisdsqltfnnvnftncssnlsliaimfpsnltinncnfysnsfanyl dgpfnkleiynsnfdgtncldsaikenrgqlvienssenfftgvhgsiinykgdyfsiknskfinsnsnftggaiivkyfpiayeegds fvyrhsndmlienctfynlssssngaihldldsgsegivetlivkssnftdchskfggaisilggylnisysnfqnnsasfeggaiys swtnakiegsnftanegsqnagalyfdkgkltindckfidnkalkerertanaiyahdvaayfsnstfdnggvsyadfasdskienvd knddiflmdnhdyivsveskgikinltgneinvdslpshfdardwgwttsakiggdntdcwafasissletsfakasgvlynlsqnylq klqlkyfysgdckrnsltgfsysgpgyalswygvlpvdngyddrgmiadtdlederihvqdvlfidtgrddavellkwailkygavtvqr gingpygelptegddiaimshgthfisligwddnyfeleegdddplhkfawitkdslsgfstadytkfdaidnyaivpgraavayifen didyhvnygtcltglvgfdanynysnefvskydefigavgtyfnesgidysfdvylnsekmlsqsgvsefagfrtikldeyihikagd vfkvvfksnsipfgaysrqhyiegmslasadgeswsdlapinktvclkaytvkedkevspsrastkidcsnmtttavasadgrigeyfv vtlkdqngtviankpikigfngrvydrvtdengsakiqinlaykgtytfaigflgdenylgafevakitvnkgspklaspnksykltak tktlnaslksgngnpvsgkkitftvngktytatnskgvatvkvslnkkgtysftvkyagddtfaavttkakltik |
| Contig47 | 200 | mnkqnvfalilltiillsvvavsgcigkssdnsasdssgqsddssnsifhsgsdsddddndndnkddknddkddddd |

FIG. 7C-29

| | | |
|---|---|---|
| gene_13 | | |
| Contig47_gene_57 | 201 | mlnkkiiiiltfliliisissasasadstdetilsddsagllnldnsnnnlylddnqfnlansnsdnsnnfnlddsnsdnsnfyldedld nkinenikntktilkennssiasfsnlshilskasagdtliilendykydsaydsqyqgievnsitidgnnhyidgnearifylasdn ivlknikfingfnsqggaiyakgtnvnitdcifennlapdnggaiyvegnasiksvkfinnsagyggayindssilediiftgnvani eggavyiggssnitncifdgnladkgaaifipakespmtpsedvpfdesdlnstdmdldstdmddnstdynftdmddnstdynftdmdd nstdmddypdesdedfpdgdyvfpdwwegdefeydgiecinvfitnstfinsndfyrgaifsehdnnisidqclfenmssqyapalyc nvmvnilinntgfknlhargtgamafldnvyaivdncsfknisssknggaifydsnswghsspvslivinssflncssdyggaivlg ggfksksdssfinnsarygagavhvtycydilvydtvfynnrlnednsfggalfidsaekalinntrfvnnsndaiyayesrikinnsy fenndeylrsiytegiilgdnkyndtlvdlqydptyliigtgeglkldlinntidvttipssflaadwgwmspfknqdfsggcwcfst caaiesallkstqktyslsmqnmqklsteyskygnnhiveagstivalhyalswmgvfpeeydtfdmigklsrqistnetihiqdaaft yprsisydidqikqtimkygtvtsdfyavneapfnentsafycnetdgrdathavavvgwddnypasnflvtppdgawiiknsygee nychgyvysyydtvfnidggvaylfentenytknyqtdiggdiflvndsdsysyknsyqsigddyisavgtcfndadedytveiyvnn vlktsqsgkspfrgfhtiklenqiqvkigdnftvvmkthsvpivn |
| Contig47_gene_60 | 202 | mgvlasvaggiffeagmiatctgvglpvglalmgvgtictaygsglfgmtdtgnfysnltdenladfgfsmsinliiggysaaaakstl rtvggksvqisiskaafasdqrgayttfhtisskttyiqkvengafsncgeylieqefgttvienirkslrvfin |
| Contig47_gene_62 | 203 | mfsvsinklkigrvficlfilvfiscsincvfavddlafndtyysdldsvngdysgflsegdfnggssvvvdgeidsspiannkknssf altskkdssspsistssknnknnkntsslkenktaapssqrvfyvdrdivsdedvigpghenldwinlthvddslfsdnskedgakgski attivasnlvkyylnasqlnvglkdsngnylsgktinftvgsasyirttnssgrcsltinlmpgvytftirflgdssyspssknvntv lkmptsitasnlvkyyhnsssliatlkdthgnplsnmtvtfkmgsnnynyrttntngkatlalnmipgnfsvkistfhpryitssknvtv tvlsmptsisasnlnmtygdsylnatlkdahnnplsnkktihyklnntiynrttnnngqtsliininpgtyqfnlyfnenyqnsnkta tvtvngipnsiiasnlvayvnesptivatlkdannnplsnknltfnrtgltlniltnanggatynlngctnfnikitfnttgyafssk tvnvnikfwpstitangattyftdtvqlsaclkgenntplanknvkityanknitrttnsagnvyydfnenvgtynvnfsfkenyyqna sktvtvtvnkmptsitasnlnitydqgssliatlkdshgnpianktvnfkmetnnynrttdangratlalnmipatfnvnitfshpsyq tsskvtvtvnpisnsliasnlvayvnesptivatlkdannnplsnknltfnrtgltlniltnanggatynlngctnfnvkitfnttg yaitsktvsvnikfwpstitangattyftdtvqlsaclkgenntplanknikitygnknitrttnsagnvyydfnenvgtynvnfsfnq nyyqnasktvtvtvnkmptsitasnlnmtyqdgssliatlkdahgnpianktvnfkmetnsynrttdangratltlnmipatfnvnitf shpsyqtsskvtvtvneiatnlavsnlnmiymdgshlaatltdg |
| Contig47_gene_4 | 204 | mgeeiinneklkliliitlifsilimtvnasdngiiaeyadistipndekvsinendydtnyyelpdkklldhlesndnqhlemndkk lndgnsndfnyiqelinshkdgdsifledktyigngspiinknlniyygyknlsdldiktildgnsksnifiinkgiqlnlyglsl ingntsyedggaiynnglisidscsisnnnaggavyssegseieiynslfennsgliggaldlenanaiiskstfkgnrcngdggaiy nnigklitisnstfsfnkgargviynnhgtlsiydcemfinsasqlggtvknwgsceiynstiknntadmyggqlytfefkmtvndcli ennyadeggglfadadsrlivinstlinnnakigggidakqayltvnnssiinnnaksnggiyadkhpaeihntnikdnngnsggvf igdisakisdstlngnsgetggaifnkgkliiekstlnsneanyggaiynqknltvnkssfdsnkayeaagiynlgdfliessnftkqs vshkagvilsvngnikikdsifkqtsgadeggviftregnifidsslflnnalsygaaidnsaimtiqnslfsrnkafgagaidnggd ltvtnstftnnkvtnnggaidnngklymsgsvlvnntagnyggaiisrkdtnieycqildnsapegdglydsgdylisnnwgennpn fdellnfnidedfkwiemnftnstplmqkkvsnltislngkdknnnsfklenpdkipilkssiqvvsedskikynlnivngsaststdm klaktvnaildneivsldvlennnesddsedsdsndsnnpnnsndnsdnvtddsddsnksnnpnnhgsgnknndnnknyynkn glryskmknslnsidsnldndylnlkennenddsnsnkdmnysdktdlnnessnkeidenetklfdinysllilipiallilvlfa |

FIG. 7C-30

| | | |
|---|---|---|
| | | frrknkdd |
| Contig47_gene_125 | 205 | mdkkmivsvaflllilavalvsvfdesnsseskvnlivysegpkslselvneiktqdyyegydnetvawmeslgnkkfyygdgiivims<br>atdasklpslyvtdvelfehfecnvlekrslgnveypkdvlyvknvkyigeeygnfsga |
| Contig47_gene_140 | 206 | mkisriivllmiliftagmvyavdlsefklnlsfkfssp |
| Contig47_gene_146 | 207 | mdskkilvilgltvlaiflassvsagdlistggynpdsliilegadfnipdgferiedksianqtrnsgvfssilnrevygnpkgeeiv<br>isvvdfdnfdanlpilsmickgcqkkellgypfgigsdgnstkfsyvfdnkvvsisapnedlinqvlvveda |
| Contig47_gene_160 | 208 | mkpyviligsasgigkstvaaelaktlnikhlvetdfirevvrgiigkeyapalhssynayslrnqenyknqaelinagfeehasfv<br>lpavervidraikdhddiilegvhlipgfidieqftdkasvfffilssdeedhknrfvkrameirrggkqldyfkenriihdhlieqag<br>khnvpiiksyeiestvkkmlsyinetcetiylkntvdeldkvgeiildrysgsiknisypikgfkeplirkidvsseireydkfiknlnk<br>fpekkeelkelysltdyrayricainnetiekikndldkegllfkedm |
| Contig47_gene_197 | 209 | mlisvlgviviiimvaaayvgfsvvssltggissgtqydelatiksncssleaqfnitgtkiyamqnitlerefvnaqvelikvqnd<br>ldsvesalasgqpasevdckriqgskedlkiaqqaynslsvk |
| Contig47_gene_208 | 210 | matrtkqticrlysfhggrflialsvfplnvscglifdirsppekkfgivflnffsk |
| Contig47_gene_253 | 211 | melsksdkylivvgiifclalavlspyiasgdpgleksaecanvgedveapvmeapfpdytyeplekigeigvillgalitlivawgi<br>gyalkrse |
| Contig47_gene_269 | 212 | mkvailgagcyrthaasgitnfsracevadatgkenismthstiemgaellelagvdevvvadpvfdgeftvvedfdyaeviaahkagn<br>pedvmpairakvgelaetvpkpangaihfthpediqmkcttddreavadadwimtwlpeggmqpaiiekfadvikdgaivtsactiptp<br>glnqifedlqknvnvasyhpgavpemkgqvyiaegfadqaaidtlkdlgakargsaftlpanmvgpvcdmcsavtaityagllsyrdtv<br>tqilgapafaqmmanealtnvtklmadegidkmddalnpgallgtadsmnfgplseivptileslekrsk |
| Contig47_gene_304 | 213 | msvilliflavstvaaidvdtndnlddgsssnsdlissssldssssddvssgssevsssdesldgnnlsdgnvssssdesvgadnlsdgn<br>vsssdesvgadnlsddesssdalseelpktetvikadpinynyasvkgltinltdsaglalsnkltlvksalnktsnlttnskgqaif<br>klsasvgsydvfisftgdesyapsnasskitikksstkiklsnihgyltisnyvsvtlldsagkpiksksvtiqvnkakynvktdskgi<br>akvkvankigtysvnakfsgdknyyassnsskltitkmkvyikapsvkyymtnssapyltinltnvkgsplakkkvsvkigkktytlkt<br>nsgqiakfkftkkvssynckinfkatsnfygasvnskmtiqkmptslkapsvsinstnygkvlislkdgkgkalkntlvtvnvtelkkv<br>ftlktnasgvatfsfngektfnlkikyagnknyaassvskinvkqikvklsdvigasrvlidyvnrtkdlpsnvqynynftvtqlty<br>laskavkninnknygdivllsvpksykssgeiydtvykkdfvkiansvvgssynyknkeyvsysiykvpfkvysisfakvlnfygnnkk<br>lpnyslftladfakvkdngqynfylttdniagkksdlnmlkslaktlksmgynavivgigpdihnvayrygctgnnsvllacfggvdvg<br>cieewagdlgdlnghsfvnsyqgahvlglwftkpygasvslnkkvgiawdadygfplntpakymkshnisyietgtvanacklisegkm |

FIG. 7C-31

| | | ggpqlis |
|---|---|---|
| Contig47_gene_306 | 214 | mnkklkiilyillaliliiliagislwylmdyspasadanslingtsevsvskinngflfldgpgndsavifypgakieytaylpllinlsa dgvdcflvempfnlaffgtnsadeiinnasynysnwyigghslggvmasryahnhfdkikgvillaaypadslengvslsiygsndksl nkesyddakkympsnfteyvikggnhaqfasygnqtgdgvatisayqqenetikdillyings |
| Contig47_gene_309 | 215 | metknliiicatvilavvivlsafiyvnmgnethissniadtlqngdeivvklvdkdnkplvnktislnfkdengkgnavsydlltndk gevynvnltegkyvfsadyagetfigssslnksvevkkdvktanlsstdtttkaktktytdwqedyetgrydedgnpiyrsimstsgg qyepgiyecywsangpiserrig |
| Contig47_gene_348 | 216 | miiknysneptdeakvdsslydaqligendlgtvlhgpfqneesdikiayligmhpleskahralfdtvldkgdlnysyiyninvi geldeategrmdgllaqefvahhiidrgydffldihsnrgsrspgtyeisnflfapgfdeesskymnvllskidelvyyapeyrtspe fitvpvqksgiptlvyetysyepieltyelseklvdavdsldfd |
| Contig47_gene_349 | 217 | mlvlafaiiflgysislgnnqtagvklndsnkiyingsypaepipdakidtsgvnsvllgqnelgsvellgpfgnsdseikiaysigmh pweskvhkalfdtvlaknsslkycyiykinvtnyntddegrmdgllaqefvaphiingdydlfldihsnkgtvggtyeqtnfafavg qdekseafvkkildkmpelvyfpadqsppyitlpveqagtptvnyetfsyedinttydlidklvdvvdnlefk |
| Contig47_gene_353 | 218 | melndeilfkvalitalvgmigmlafasyiepkeitineitrnnigetvsvsgvvesvklsssgsscflelndgtgkinvivfesvlve lkdagndlndfkghnikvvgsiteykssmelilansnsikles |
| Contig47_gene_356 | 219 | mknyfdikdkvavvtgassglgwgiaqayasqgaklalfarreerlqenvkeiedkfgtevmyavtdvgdydsitasvqkvmdaygrid ilvnaagmgnnkmvvdgsneewarhihidltgvvymckavgeimieqeyqkiinigsihsrvifpgggisayssakgavmnltknlave wakynitvnaigpavfeteltvdsiemdgfmdliaaycpagrlgkpgeldglaiylasdassfctgglicvdggwtai |
| Contig47_gene_375 | 220 | mtfnnlrinikdcmvifvvftvlllsilavsaapspdfmlwv |
| Contig47_gene_380 | 221 | misisaisaaddssiatddsnkiindnnnqdivleengpstnialedknykiekpqlkenspgnftdlnylinedettrhnttitldrd yiggekgiridrplildgqghtlnasqnnrvfhitsenvtlkniiftgrsdyggalywqgdngkiincnftyntatkyggavfwgdde fegtadqtiakdgiiinsnfisnkanvgngeawengggegavywanngticnsyfhnnraggqgaitwkgndgiicnntnftans agdsggavfwrgdngtisnncefnnniaygrtsdgisrggaifchgengkisncsfmensakpesesgkggaiyaeyntfitdcifi rnsadyggaillifrtgdvyrnifinntalngntitlkgighstitnniilnktnalywnesdytieanwfgnnatqysepyeysqtwl flnatanpnpapfniptevkfklwlynkktkkiteydnsllptiqlslsqtkgsinketagldppinytanevgtgsitgkmewitdsi ffeivndpklevsvnpseidygdnitlhlgyedeatgtvnisfkgsthektieniplnktititesilpdeytvtvfysgdnqfsrask tadeklkinqknpnmtvtsyeiyvnctngvmfsikldkdatgkiiltgdigreinltegsikdgkriieiknngfdlgkynvtfsypgd eiyweyettalseikvietkiipqkeeivlliigdksinytinpsnavgdvtftsndtnvvkvngsdieaidkggatitikfsgskdy apsnatvniigremakltaenitvtynaegylkvalkdsknksisgailivdllinktnyttdsngeikvptkslaagnytasiefegn dkylpanttagvtiekdnpritsnnitnkyhtedylivslkdsasgpisgaeltvylngsetyktdgngqikiptkdllpniyvanisf |

FIG. 7C-32

| | | |
|---|---|---|
| | | agnenyteanasasinitkldtrlnatdtitkynvnkdmivtlkd |
| Contig47_gene_381 | 222 | mkfkylfillialiciisvsavaasdandpisqdnqglvleetnqdlsitktkeivesstnkeisledhkvishenkktslkdeetd sftnlnlinidnpnnhtislncdyvlleedctyidteilsssnlttshilrdegslpidlnpktykarlmvensndqsievikttnie gssfwlnqtinnnsneitldsnytfnssadsgfingiyinrslklngngitingldegrifilitadnvtitnvnfangksdkggail wlgkngnisncnftdnmatsggaifwgntnltdyysngqddgtiincnfigneaqkggamffhtggatikdgctfhnntgqeggalf wlnyggrienncnftfntakgsggaiycpqvelinncifqnntaqskieerimkggaiylqkggtvrdctfignialndesdglrfyk ggepftlkgmppfptaps |
| Contig47_gene_382 | 223 | myiseieinqniilntegnkiylnnspksnihdnwfgntllnydevpyegctnwiflngesnqvslenpisfeitftlssfnkntkkis nydarklpfnltahaehgilnpnsnllgkttiyeteinveriignianidsefeimeflvtdgttfydlnqlinnsnneinisgnyt yhddidfefkeginvnrsliingngftinglnssrifningdnvtinnisliingngyedtydsdggaiywkgadgtliqsnftnnsgyn ggailwegdngriiinghiiqknkqrirmeevpsp |
| Contig47_gene_383 | 224 | micyadnlsminntmesniasddngailwegeigriinntfknnyaseeggaisirgeigeiinntftnnnasyrggaisiiitsgei inntftnnsgysggilcygnnvsiinntmesniasydggalyvsmdyamiinntiknnasdngaiywdrykgiislntiannanh ggaiyyegyssnlnyniilnknseiyfdnvrtfngsnnwfgnnasnynlnpntsfeydnspnvtlsdwlflngtanpkivnafessqi lfklysydgiliseydnslitdtklnlsaergrfdktsasfnepinytaieggrdtirgaidksgysinltnrrvsskiamdtkeinys rnasiklnyndfaggnvtirlmgenneylfenmtlnktiflgvinrdsynvrieysgdrsfleenisesivnkagtkivptndtidlg igensxkvnytfyviddegqyitnpedignisfksdgsavevdsktgeintikegtanilirfggdenhldsnasvyvissnkirtkita enlttdykkddyiiarltdltgkpianaklivelngtnnyttnskgeikvptkgldsneyiakilyegdesyrfsnasvrlivnklnte itannittiynitkelvirlkdvngcpvsgveltvdingmnnyttddngaiveikglipnnytakitfegngnynkastesdieilki psilngtdmtvnykedkyltvslkdknkpihnasisvelegiknyttnsdggikvptsslpaknhtamirfegneiyeksnatakitv nkisgkltasnvtarygdnqnlvislkdsknplsgfkvsvdlngkknyttdssggikvstkdlvpdtykailvfagnenytgsnasas vrinrinttfkytnmntiafdsniegrigeyfrfqildedgkplsgkqvfigfngvkynrttnetgearlqinlkyvnhytfaiaflgd dyykgsfnvalinvteqipvlstsaktykssaktktltatlkssr |
| Contig47_gene_391 | 225 | mdkkmtvllvalfcllcvgsylifeparhisyhevnltdtcvakvpvtdkvssytdnlnihyysdyendlnitsfydvapesssqghlr mdnikkevlgtekgsagnltyyknnragtytmyvedrmshnyillsakdltiftnvysslearivnetcdidsldssya |
| Contig49_gene_3 | 226 | mdrkdiiiilvlliislialglhnhqvtdggtdlyrtvkvspsfsldvplssnltrenvsenmyivndyqndiqiisfnmknaskmdl iedgyqylkreesykfgaeeiikisnhtvwhnkddgsyiaffspnntednimlvthdnitmarilssary |
| Contig49_gene_4 | 227 | mtseimiltptavvlaadsavtisdiktydgankilfylsnkppmgaliynladfvdipietiikefrrkidgkedlslieikdefekyl hqiisksrstlsfqegldyfiefigeelsyvdfdefkigLkdelsdfdiglgldfkdevgsqidlyedkfslalpddcngldeedfisd lkklficnmflmpfigiaisgfekdemfpsfihfkinylydeefllrdvefgsigdeevilkalaqddvintflnsidskteraledff |

FIG. 7C-33

| | | |
|---|---|---|
| | | iefknflfnyieyciksnediseenenflenisdmefsdekvrnifigfieclkakqkkpildsisvlpkgelsnladsligitslrr<br>kiedevetvggpidvaiitkgdgfvwikchdsfdkdlnpqffdsn |
| Contig49_<br>gene_12 | 228 | mgfkrlkrlfssdndnemekneeknksgeetfyeesdekafyteyddsgfildnnsddsfnngsdddlslndglkedlngsddnlsInn<br>gfeedsfgsdcdltlnnqpssnrnfnylnnlihshqneinldsdivfdsqmdntyleginldmdnltidgngrtidaqkksrifnvlge<br>nirftnitfknaysnedggaisignyssvyfenchfisndagendggaisigensictikdsvfkqnkadsggaivnegtlkimssnfe<br>ynssqvfggaiythhskveiaysvfknnisssgggiyvlfdcdmlieeslfidnasmseggamaneyggkirineslfrnnhsliggal<br>cnkgspvddgknlvsvsdskfeynssienndtiystgvlklegntfnendrilasnnpeinskyveatediidlaksidysiagesnl<br>felldsdirnfnylenlirssggeiildsdiilgddedytdgirlsnenlridgnysidaksrsrifsisqcnitfenlrfknayseg<br>nggaiysvnsfltfkscsfennsdnggistenstnefktlstennrnefktllfedcsfennssrsggaistenndliliktclfdrn<br>esnlgaaiicqngkvrldncgfkeniasdgaaiyysslpigtyinddsvnfleindsvfeanrltgtnltvsiidcdcsisfnslsfkd<br>nkfdygdlinqkylenknsiilksskfigngggitasnlkviscefidnrsnafssqeyfydgsseiedctfknnhcaisshesslkikd<br>arfygndsaimnrgkayindsrfrdnsmaiensansymfasnlnlldnasgeshdminqghlsvidsdfincnktlnlicqednedav1<br>diegcsfktdskrpisinggsssilysrfeldqskiaifndsklnidalsfkdyegndlegkliynndylkskrdildkidssesait<br>kyayetlpadwkgfdylinlikesngevkldcdilindieedyyg |
| Contig49_<br>gene_25 | 229 | mrkkilfltlmilicftlnsvcaqsldninyandgfdsdemincdlhkdssqkslksnalsnkktntvkltdmkkaesndvkqtgaak<br>asntkstskstttktnatksnttkstatkttanssstkkatqntttintgtlaksssymayveknaklqepitiskkykspeylylvs<br>kavsnisktkveikdklitnysntdcksvngtinkteyvqvakktvsfieknhrapnwiasskgniprnglilvfskcldqynksgklp<br>ssiklndldlnkmkqkidsskkvnststkktntsstkktnstsakktnttstkktnptatstnnnkslvestldsiiksilnnienklnpt<br>nkvlsttgtkkntvtvnsskvnvqissssstvnvkisakdntnsgkntnsgsakktnttstkkidtnstkktnttstknnts<br>sakktnttstknntsakktntltsklksdykkgekifnwrdngigyekyrntkkgalktlqtrgncvdhahlivalsraaglparyvnannckfssgy<br>tnkaiktlantltsklksdykkgekifnwrdngigyekyrntkkgalktlqtrgncvdhahlivalsraaglparyvnannckfssgy<br>vsghvwaqvlvgntwvvadatsnrnkfgvvknwnvnsyklvgkyssisf |
| Contig49_<br>gene_29 | 230 | miagvsasdimdasdnpnndsinlvsgesgndqisneaisvsnslsanddsyspesekisskiktsnnlsasnstkttkaaaakttk<br>tgtslqpsstsiysgqylvitlkdknskalsgqkvliniskfkntyktktdskgqvklavnpvgsfklvvsyagnqnyssskysgtlkv<br>sksdtsltvastsvtmttplvvtlknkktnealsgkkikfvmdrvsysrttdakgqaklkvnmkyvfnvtvkfdgtgnlksskvtktik<br>ptkipvsfvysansvkyghsitvslknnlnnktlsgkkivvktsdskksstktttsskgtisvpinsvgdvtvslsyagdssykaasssk<br>kikglkdsskitsstgtipvgdsytvtlkdssgkalsnkkivftfdgksytkttnskggaslaiskgpgtysvnvsyggdsyhsgskls<br>knvktsnsmisianvikaattirahvdytnrfnksyvvtinglkyspdefaymmsqaivkinngqksgyvtfknltgdydskgssingn<br>lmkknyislantlissvnknnkipanistnlgkieanlyifglakalqfygeekylpkylilknsfikgssttvtqkakilnckeafn<br>atefekylktggksalnsaivakaksltkgltsckakanaifkyvrdkvsysysdskkgaaktyktksgnccdkanlivamcrsvgvy<br>aryshaqgctfssglvaghvwaqtycratqtwytadatssrnslgkinnwntkkysqaknyvlipf |

FIG. 7C-34

| | | |
|---|---|---|
| Contig49_gene_40 | 231 | mlaipagfaadiesnshnnlddsntvnfeinanskdtnlesnlntgnlemnsnntnldmnsnkarlamnsnasdletlgltrgefengs npsleyssnslsdnsnkyispssdkntygsnkvgdgnvnlyyfdasasddtgngslerpyktlknnrivensinylangvynldati nknnisfigadssrtiisyastafitnnilnfenitlkglniqnrgnltarntifiggkgywdrsynnifggaiytpqnenyttliinc sfinntadyggaiyacgnvtvenssfinntaerfggaiasentltnnirnvefihdvslndagglfisftqlngtdlhfyncsadfg ggitalysnvslnrfigkdnkarydggaiyqtfycslliensifannsanngglyvdnsnslkvtksnftqnnatekggaiyslwntla egnsisntrfnnsfsnnnaknysnfyegkdvnmrigsgnvtlyhrneteideipsyyslidlnqvtsiknqqsggncwayasiaalesa iikaggealdlseesmknlivlfsdygypwltnngngdfanayltswlgpvfeddnpgddrsylspvlnsrihvqniqylgrnnytdn drikeaimkygavatsyymdnsyynyrtsayycpsatssnhavaivgwndsysksnfkttpggdgawivknswdtnwgdngyfyvsyyd ilifplgsmdwghayvlndtiklkdknyqydisgltdyfynasstawyktkhtadedeylaavstyflttdytifikvngeelynqsgn seygyrtiylndfiplkagdvfetifknvsgetgipvsegsafnkvlydrngsfvsydginwldidydiywtynsdvygshyyvsaalc lksfsfineigtnltlefnysldnegdrispvniiahvineygfnldngvkfiingtetiadlingyaniswnftdienevyalfekt gylsssanetatlsekyvtldintllsedklititvdssrkinetl |
| Contig49_gene_43 | 232 | mrlryfaiislilliflvpvsfasetnldsielndladssteiddstdlnqdyssnqdlslnqnsdsnlsneqelysnklsensldsns qssndlsnslylssngvrladlnssfaqfntslndsntiyvnssyigsdefgtqsnpyktvlaginaattdlnnvyiangvynintit vlksiniigeslnvilnasnennilsvkgssvevsifnltfrngyankggaiyvdkssiniigslfdsniayvtsdngyggaiynnagf lklynttfknnkvvaaynivsegfggaiynelgemtvlnskfynnsidirniskssygagaifnragfvtifnssisnnsiytnyslg gaisiwasrnvyiinstindniisgsygfasvisnkgtlqienstisnnninassvenstiynlngnfnlinskmennkiktiktnll mcledqlivnssfnlanelkglnmtslpshydlreeglvtavknqssgacwafafysamesyllkvenisydfsennmkncmgdgsen stdwddgayvvalayllrwsgainetddpfnarskvsptnltrvkyltdalyipirlgaldndqiktailkygaifvpvysniikans ksgysdiqyicnhavaivgwddnysasnfkdtppgdgafiiknswgtsggegyyisyydasfaasietsaavatnvvnttgeyrnn yyydtfgntfetigynsdtiwfanqftaisdnplnafglytygdstytvnitvnnksvytssgkivgagfhtiklsryvpltkgdtfri ivklttpstlfplavetnysgftpraksdyngsfispdgktwydlrnssnnravkfyedmyfytlknasvclkaytafadelelnlssn spiyytgdtikilnltvtnrgdlasnssiavpldksysivsykisenngnksydihyngssfnmasgiwsipylenessvlilslkmns nndvnikvsanssscsvkdnvyanislkykipskfanipsintta |
| Contig49_gene_44 | 233 | mfiglllglllipisfagdadsysaysgdsisleddnsylesntvlkdsknslqsidddclignrtlddtsysdstnsedltnpdstn pdstnsedltnlessantdsssseiktitkslndqntniksInydeyadyinlnqlinydfaisdsntifvnasytgstengsqaspyk siysaynyafglssdtrtnvyiakgvytvtrrmtinknlnligedslntiidcngngaffisprrsyttvyspllnifnltfngryss ggaiyinestvnfvnvifknraeasyygsveggalynnkgfvriyncifenntandtsdacggaiyndmgemtimgsqfinntakgen aaggaiydfsgilvifnstisksslsnysmggglaswsshnlifiinstfdsneghgkyvfgsaiankaimmyienstfsnnlangtsd kngtffhlngvldfdnvnftnnrainpkedilicledqfiiseafsgediaeilsemelsqlpssydlrdynlvtsvkdqknsgscwaf stlaalesyllkyentsydlsennmknligayIgntdwydgnhymslayllrwsgpvnesgdpfndtshnsrftnivkqvedvlyv plrnyldidqikaailkygalyttlcsddsfdnnpdyycdvisisnhaitivgwndsyadnfavrppgdgafiiknswgpsegydgy wyvsyydktlagygdyaiaamaftsvanastyknnyqydtlgntfesigygcstawianqftalnnplaafglytygssylvnitvn gisrlvqegnvkgagyhtikiddvvellsgdifkiivklstpdsnypvaieskrsdyssransnpgesfisfdgqnwdqlyevgdilkf ymymnktfteqnicikaytigpsdvhlharanattytggdtveikitvsnegatvndlnismkwnssfflksftklngefdstkkiwh fdtfseggsstltlvftmrgnndvaslsydynysgfnpgdanttq |

FIG. 7C-35

| | | |
|---|---|---|
| Contig49_gene_81 | 234 | mgifdkvksafessknfkylddlihsglneivldddislskneknkysngieieidnlvidqgnghaidaqgngsiflctgknivvknih fkngihsnggaienrgeltimdstfdgnnaslggavfndgpklmiakstitgniakeggaiynndgevyisesminenvssfhqysgg aiynkgeltiekstllirnhasfggaignigglnildstisnnessgdgaifndnaslsisnsmieanvsdgleggaiynkegelnit gsvlkqnelvgqigkggaiynggnlniagsslcnhsinffgaiyndggkiniaeskfnenssnrnggaiynegevnirksskiknks dggvieningdfkifnceffsnesqniifnqdsleinytdfkdnrsksmllndgvksksmslvkgeingndvkdtlilnegnsltiset vfennlipngdaivnssnlliltnpkinddnqeirngnlllkrssldikgkingegkietddhsnedkfdfgyldslihgspdkeivld kdiklenyevdfyeggieldfddlliingngktidargksriftisgknitlkhitfknghsyknydnplnnnggairinananlittdc kfldnlsedygqviyngsgdlvltastmkgntaendggaifssgevkinkskfinnsgnnggaiaivnsndkasvtesifnenaadsk ggaiwfhnsnialadctfndnyatcgaaiygeiskgsisnstfkrnlssyawhdgklvtnknhaifidtgslndfnqdrdniincdf idnnnnlyaqkhdliksrldehlalwkrnl |
| Contig49_gene_96 | 235 | mliglvicagvfyfqfnyatptylifnatevneggsftgvlndaygfpvvnktityhkpgyemgtlvdvqtddtgefvienaqylpdag ednygaftfagdgkyqgcsfdgnitvipkk |
| Contig49_gene_128 | 236 | mvlavvvigstafllnydetvkytyynlsktcmmdlpsgdnyenttvneairqindtnrdltvlfynsednstvarvefetindfka tateqtvanrtvwyneengtymaflgnsvthdniliiltndveilehlissvkfiflnedgtvnstsdmvnnqsinvtggtasngtdasa statsnvsssnsqstgndgyywsgqdqdyikeytdsngiqhidrrngpneaydpntqrhytdgvedtaaynqdfn |
| Contig49_gene_152 | 237 | mdkktlaiiaiivialvavgayfatsggssdnvvrighlpsdhdtalfvakekklfedqgltveltqfnnggdlmtamasgdidigyag itpvmssisqgvpvkvvsgaqiegsaivanknsgittvadlkgktvatpgeatiqnmlltsaltqagvstdsvefttmkaaqmtdalka gqvdamiiwepyssiavkngdgvliensseiipghpcccvvaredfikdhrdsldkvlkaheeatkftnenpaeaakmlpedivpdqel qakviadtvfisgldaeykqkvmdfmalevglgllkgplteeqifadl |
| Contig49_gene_167 | 238 | mnnktlfiiglficllftipmvsaadadsnlidnsvigtninsqaittsdasidhssnanaintninsddivsnnnnnsiidindsdi esqkdgsskniikstnkntndnsnnetednilvtdinlgknnknsndknilsanaltadgtgttfgdlqyiidqdttgtitldknykfes gtddayldgitinkaitinggnhtidgdhlarifnintgsasdivvlnsihfingmadgsdnanggaiyigsptlnyitainctatg nggaiyahadgtniaanylylynntavnggalyvygndytvtvvdarynsasgnngamyaygnsfhlnkvnfinntaygedseggaiff ahnsddsivnnsyfannsanrdgaivwdqgahfgelynskfynntanhssgavrwsgengtidncsfidnkaygtnlepgfdfdggqq ilggnggaitwlgsvgiirnsnftdnyaeanggmflifadindpnsicndthiincnfisndaglnggaldwdgkayngsvsgskfyn ntaarsgaifwkgngiitgsdfkynsangthlvqpegfltpggnggaviitgsdvnitysnftnnsaarargavylqlnnntmvlns sfennsagtnngaldfytgaengkvinstflnntanrsggiywngekgvingsifydnkalnggtyvngsqitdggdggaiiwtgshg tlenstfknnnatnrggaiflekhnledpndycknitvlnctfeknsagtngaidwfegaengrilinstftenyarrsggavfwngvn gtisnstftlnevglegadtgtgetiptgdddggaikwtgangliensifrenkalegrggaiylennengtvnnctfelnsaftngga idwhegakngqlinstltnntagrsggavywnghngtingtnftdnkalgthhteggteggdggaiiwtgsygtielsnfhnnsarwrg gaiflqknvhegeehcynttvknsyfeenfagsnggaidwsagam |

FIG. 7C-36

| | | |
|---|---|---|
| Contig49_gene_168 | 239 | mfkvepassnvtveavnityldnetitvtvpitnasgtvvikingtqkdertvsgdnptynitvgglavgeynvtveysndpnynssna stlfhvdkanipdvnpdtgivvptnitynddetitvtvdvpnatgnvtiringtdveltknitedgsqsvtfnvpglvvgdynvtvey tddanyndvnasalfkvepaasnvtvvptnityldnetitisvnvtnatgtvvvkingtevntttftgedkptivvtvpdlavgeynvt veytddpnynnsdasalfhvdkanipdvnpdtgivvvptnitynedetitvtvdvpnatgnvtikingtdveltknitedgsqsvtfnv pglvvgdynvtveytddanyndvnasalfkvepaasnvavvptnityldnetitvtvdvpnatgmvtikingtgveltknitedgsqtv tfnvpgltageynvtavyhddvnynesnasalfnvksapvnltvtatnvtygdnvtvtatvpndatgnvtitigdytekkeitpgsnt veftvpdlevnnyvvyanyssdsnyesgivnapfhvdkapshvevdgidinytdletitvtvsdnnatgfvtitingtdieltkevsag qavfdvkdlvvgeynvtavyhsdrnylnstasdtfkvdksdvknmtispvnitygenetitvritdnnitgnitisvngteygpveldn gvavfnvpglivgdyevtasysgdsnynpasstettfvdkekpnvhvvsenidygknetitvivdgfnvtgnvtikingteiatkeind kgravfvvpglqageyevvaiyngddnhessegsdtftvatvtpnmdvetedidygdnetitvtlpkdakgsvnititdengtvvyege aqledgkatvdvpgitpgpynvtvkypgdrnynptnktvrfnvdkvvpdvdvdtvnidygdnetvtvtvnpdgvtptgsvnvtvrds dgkvvyegnvdlvagkatldvpdlgagdytvdvyggdsnyddst |
| Contig49_gene_172 | 240 | miktdnkqgitvelllllsftflsilaltnlisdanevnnshgcskktehskelpqtdwqsiqrtpltigrtrerkaysi |
| Contig49_gene_175 | 241 | mlnrkalifslivlfmlsisavsasdntfnegtglnediadlndfsdlnsnfnnglssnavhgldddsnnnlssenmisssdekqddl egsdsdsikdnlnsnsikcdqnnsnstadksntkiqtkisakdintyykeksslvlylkdnknqalsnktikislngktyaqltdklgk asfslyglkpnsydakiefygdddykksvrtvkvnvkkvdisintkdfstylnsniffsvkvlnkltkspvegiriqfnvyssqknykn yyalsdkdgiatlkknlklgsydvytyvkddgqkdyinyrntknkvsikisapgemgcssiyihvnenesavafrrdstyaadlyivaq kwhgrnavkqykltgtyffhaivtsdgwlvgtggadnptinkkieslaggmvssnniqnskintirkyerslgighfaivdpkgnyaiv wksgyvkqklkngqyidvpnsrgmfrkgsyksfskdtataalriaatdrfgvnrrditvfhykrstknyqtsaqvkayaandkgnlagr rtggksdnihykktyisrsklpgtpnkkllgthsfgkidtliktgtkvsapaltanqnqtkyfkvtvrnkktnktlrgvkislkvytgs kfksyavttnksgvanfntkalsagthnvtisqanhkyivsgskiviktvkknntvnstnssvvngsgvngssssnasvnnasepinn sttdnssenngsagnssssdssvgngtasdgyvngsssdssvgngtasdgsmgnsstsdgsagngsnfasvldvsaainsdsnvgnds qsnsktetklssmktdiltsfiklin |
| Contig49_gene_180 | 242 | mdnkaiigivialivivlacfayvtfrngnapislnvtenitnntdtsvdttdnatlvsqdpnndsevkdiaknvsesiseqnkavadsg dtlhqtftvsenetgqnegmepgtyvmyytendgpikvqkid |
| Contig49_gene_181 | 243 | mdssdlnknigtnlennfntdsnnnldsnlnsnfnsnlnsnidnstqeldlstknfkalss |
| Contig49_gene_182 | 244 | mdgsysnltnlnfytnatsensnyltpiyineasdlviennpiyidysdgcnynlagiyafgasnnilgnnrisiysrslsntskhyi ygidfssysnsnayskdnakgndissntidiisdyyanaitlscavdttlesnslhlksdfvgmvaeyfdfgnglnpsnnfnftknti eassnmvyaiqffnvfdvnikentiktnsngsygisayesynhdigynnlfvngndvsmigtnfdaigtghsgiyymrdshdlsihdnn vlsnyslggdyairfdassseninvfknnlssnngkylgndavngnvtvsennhyygdndlgtndlrifdlyvdlngndnkgdgsigkp fksiskalsylknltniygssasssttkvkgiihlgegkyngygtnlriyitgldveifgsgynktlidgvsshwffdisedssvsik nlslangvyryndgglihnkgnlylencifdnakmspssailyndgilnlknlmmtangylhynngfidglylnfigdslsederll ntdslsfiltayvhddngnpitggvirffiegkeilvnssliegklytfsslngiikisgyysnaytnlfvnigkvnssiisdtikv yvrnysaneksdgsfekpfksindaldalntclepvtitvlddetteqiddsrlnrnnvitiesinktnistnwtfksdanirlkglif dgyglvkdntyltidnclfnntpasaivstngsltllnsnftnnnvkdnhtfytgfstpvittslwdiqydydkggavdnsfsnltiln cnfafneayrnggaifnngsdlhisnssftsnlafsgfyenpraidfsnamdkdgdrnvaskggaifqylgeevvtdtgflnnttaggyg |

FIG. 7C-37

| | | |
|---|---|---|
| | | gafyssgiypyrndsssiiegipfivyetedglmdnfgnyadnllspqdiyfincnfdsnvapirggavycinnsqtqyiscnfgnnlv ytynmsqlfgglnknshrkwifedeldqvysifftavnnggaihd |
| Contig49_gene_183 | 245 | msyfnkghiwnilliclligtlamngsasassanlddfsnlacdxxxxxxxxxxxxxxxxxxxxxxxxxxxxxxxxxnsyndlsvgfesdans yndfstyfesdsnsydisdslvnsndrlvnsngliefnisapndiqlndkapiknslkeydervfyvsldgndfnnglsqensfksln kalenlhdankttiyvfegtflsensydlffegvgnsqmisiigsgvnktildgeglhrlfnvdnsinltrdltfvngfdfssggaiy nkgnltlvntcfynnnvysedayqhvsllsggaienegfltienssfiknsgvsfnqyayggaicnhgnltinnsifnnnsletyidl nensyfrkwnalqtggaiasfsdgalisntefsnhsisilnkypfvqktfmtfsaggavyiegnnhnfincsflsndadnggavyfkgn ntcfdycdfdnnsafmggaimtidynlneawmptlknltsnkysnlnisnsnnhfictdfgigyrispggaagyfkidnitidnss ftnngvlenctifvssrcggavflyggdskvnnssfvhnnvevggaimnygfdtnvsnskfinnsacysdggaifhsigdllidncdfd ynravknggsiqasydytnnylfeqkslynnsrfknsaaeyggaifdmgnavlyndlefinnsasyggaiynqfsntfrnstfvnnsa fsedysnggaiynygsnalyessifinnsadmeggaisnfgescvvqnntfnlnkafkggsvylsgqggrfqdnnvfssfaiyggglyn sninliclsnsfnncsanvsggaiynlvstlelysnsmndckaklsglgsgnyvftcanisylvisfanngsfnivdnkgvllvanisd nmgnpitggnftfilfnqtnqdidligssgssssnnsspsnlessiigvcdvveqqaflrydtylelgsrytisgtysyaaepvltqva nlnsvlstrmyfssnitddmvnfgegfnyeillldsndnyipnae |
| Contig49_gene_184 | 246 | mknkamflisalliavilslsavsaaddaiaadididdsievssvdlsadtedisytdvsfntskdkntlssniveegdgswyvdskv ettgdsgsspyktikeafdasggngtiylasgvynttndrsfslaldsgnnlsiigagsdetlidllslsnnfinvrngnnfylsnvk lirsgttaisganitiedsvfansyyyggapilslgggdntirncvfvnnsagswygsvailngnanvlfdnclfknntntnggsvfy ttssnikltinncnvtecpvafyasyfgnvvfmnsyfynndvtrlnnrycavfystdpgnltidyckfenntgvdsasiisayssnrpl nltvtnsefidnkmgknsygyytvfnniymgswggnlylkntgsfgnlsfvsissaninseinlivldnttydinaieinvigtltdd mgnpinmsgfdlyfndtlvgsqltfdsgvnnytfkealsgsylvkyvynstanftnfnqktsvmnisplenidvyvatdgsdetgdqte anpyatvekaldvastalnanvyikagtykyyryraidtangilnligydgdvtidmnnetafcnvsnrsnvfisnvdfvngysqylvd nygiinsfgnlilseckfsdnngyyyiisggstidsctfennkfqqqnsarilfnpayvnnvtfynitaigfsanslnqkydltienck fydnarilisngnvtirssefanlsnqraletqgvvvlsiddctfkdsdqsvylydyasttianisnskfinithenpvygnqqeiy lennevsdlaapvyyirsgvyirsgyvaspitilvlnnetieqesygatlkakvlddsenaisnsfvfdfndeqingklvydemvaksmgiydg tylvsasstnllnpilktgvliitplmnkelyvstggsdetggdtevnpyatlkkamdeavafnntihvaegvyaidtaleidtntaiv nivgsgentvfdmnneinfintisansiielkdltlanakspana |
| Contig49_gene_194 | 247 | mkfnkslaifvililvafssisviaaedaeddnpyhngavmneqepgsgeddnpyhngavmnpqepesedddnpyhhgalmnpqepgs tddsqaagssqadssnkvalskyptgnplvvllmslsiiglgtlrvrk |

FIG. 7C-38

| | | |
|---|---|---|
| Contig49_gene_208 | 248 | mdkkiiigavvallvliivgaavlmgggttergpqeivvaayshggepeagfdpiagwnyyaepliqstllkmtpngtyakdlatdyeis ddyktytvdlrkdvkftdgsdltaedvaftynaakesgasldlsaldkaeagdykvkftlnksdstfldkmayigivpsdsynnesyg enpigsgpykfvqwdkgqqvileknpdyygkqpeiekitilfaqneafnlakngeadivavpleygkekldgytmylqdtidvrgvsl psvpdtgelspddnytignnvtcdiairkalnyginrtalaegalnglgypsydgiahqlpwankeaaiedgdvayanktleeagwds dgdgireknqtkasfkiyysasaperqalavgaaeqakqfgieiepvgaewdeiypnefsqgvlwgystdpsdmygeyyssdfnpar vnnsavdkhmddafaesredsykdwsavswdgstgispkgdanwlwlgeikygyfvndrvdisndtallqphggdlfsnvydwtmtnat aek |
| Contig49_gene_226 | 249 | megdnmvniktvalaviaiivvllaifavsnvvilaqddteggipgvdmaalwslnggfqwiypgssfdpegrtlhniymlddpygevk timqytynvdphilviindqaaahifgdhildtirqhdwveghsrgdavgmsitsvnplpiipdilmgnikimfi |
| Contig49_gene_239 | 250 | mnkskktmimlimailvlltmasvsaseledigvtasngtsdaviaseansaypdnailitsekengdeniiatcdngkigyenddktiia tngngnigyeddnlitsdkelnaldkgkyqslsvgdyhsfeelqtilnqadggetielnydyslgaggstlkltkgltingnnhtl ygvgldrilyisslntqpiilndiifkdggkkdsytnletnwggaiyynptteggaiggepadfiinnctfenngavnggaifwngsl kiidsrffnneielgsggavyangnltaigcsfsnnrvrhgligmdmltttftdegywakviqyysfysvdvipptgaifcngtckin dssfdnnqageanemgtggaihsmnditvcnstftnnkaydqhggailcnrsgfiynstfrnnvanvggaiscfyylnaegstfsnng geigttwmdehsfdflidnfigsipiigdiyaqlnfldllgvesvdvltgqyfsvggalytgldcnvdkctfernhaaeggaiyser kvtaknsafssnkvfrgdsavselmssggknrdgaihaenattirnsefsgnsapskggavycahhlemsdssflyntayqnggalya dtigtisntkfsgnsvtkgsgdggatensqggaafskgdmsisdssfeqnmakhhggaaytdgkmtvknsnftvnsanggaiyasvmndevtnsifkk knsvfkrnsvdgdgtensqggaafskgdmsisdssfeqnmakhhggaaytdgkmtvknsnftvnsanggaiyasvmndevtnsifkk ntgtngdggaiyindkswpkfdscvfsdnkcvvkssvensqggaiyvrnddselkvtnsnftgnaagqggaifsgkvneitnsvfkng asksgaviyiepncnpkirqsvfeenvggdkggavylnskysyleltgcnftkntakeggggvyaqqmsakvssnrfisnkatdgkgggi yvrnyhitetvkryttefvdctftsntctdngglcmdstysvlk |
| Contig49_gene_240 | 251 | mtttafdfkiegrigkyfyfqlldeygnpvagknvsigfsgriynrtsnetgwaklqinlkysgyytfavnfggddeyaaafdvaainv tiqtpklttssktykasaktkkltatfksykgtpipskkittftingkkytaktnkkgvatvkvslskkgtykftasfagdrtykkvtks akltik |
| Contig49_gene_246 | 252 | mnnttkiligvlmgllivgaavmfvsataindvsdgnsfmgqvqntanhvknvasndiksgsniiggsefnsqegngyfyqinytdgn frqydtktgkligsfnedqsilgnddgfnle |
| Contig49_gene_248 | 253 | mgsknfqyldelihssaneiildsdivldfdeeseyddgikldvddltidgnghvidakdglcrlknhaknitfknlcfknfskfpis nqsgdlifencrfihnqgtiynyfgniwlknccfyrnylsrsssgysvciynakdskafvsdshfyqnevnyphygllnldglievkns ifhenkgedceicvifnrkgellvdnckfkdnknvycsydfaelivsilneagkvslsnstfenenrilgsiknmgicriidckfkdsl iynsqwyssvsrpdeldfgpylevedssfankydegviansglckiascnidgrsylnnddvlfidekdfnllkdniinsgeivfdydr dvpiyesfkghgksngtnsnleddldndksddgypplgalfr |
| Contig55_gene_2 | 254 | metenliiivillvliamagifcaflytfgtggndiapvepnltanqtnvtnvtnmtndtanattvdaplnngaygsssidsssnglsgsns ynggsntynggsntnnggsntnnggsssdsgnggsvapdsgnggsvapdsggggsvapdsgggssgggsepaasgessn |
| Contig55_gene_3 | 255 | mf-villfafiviggsysvfaivsnggnnslswdnitiagpsgnvsddgnnsddglligifnsgdssdsssnsntgssssqssspar sssssssssqsssssqsssssqssssqsssssssssssqsssssqsssssqsssssssssqsssssydsgsgsvvesghyydvnsgdeldw |

FIG. 7C-39

| | | |
|---|---|---|
| Contig55_gene_7 | 256 | mallilamscvsasnasdnlddltisdsnsldlvstsnsdllssdsgvssddssndasgdvlgsdvssnesnnqsqstldsnnqsqsgl dsdnstlldsqsnnqsnsessdsdssetviknatsisvssktvvrgnslnitlkdnastllsnktvtftfngktynkttnakgiaslt ltatpkkylvkiafvgdelyeassksvnvtlsktptsisnsgksivrgklykltlkdakgkalsgkkisisfngkkytkttnsngqvnl tinvngktykmtykfagdsnylsssgsvsikvkmgtsilgsgssivkgksytvtlknangavlsnqkiaftlsgktynrttnakggas lkiglssgktynltykyagnsyyggssgkvslfvktpttmknsgktivsgetykvtlkdadgkslankkvsitfnnktyakttnsngqa sltikgtfgrsyplsykfagdskygpssgslclrvkkatslkgsassivggksytvtlkdsnstplanqtivftldtkkynrttnakgg aslkiglaagktynlaykysgtsyyngssgsvklkvkfptsltnsgksvmngtgynivlkdsksnlvsnktisigfngktydeitdang tvtllidanvpktykmtykfagdsdygassgtvnltvkfknaftisqiisassslksyvlknkkvpatvsvngvslnltsftylmakat isinsnktsgsillvpvdsnytnngsrinanlykanyidlakkvissaeanklvpnsvstniglvshdlysfglakalvffnsdhylpn ylilssddvgekhstvipsnargnasqfkaglneaetltaagiakylvasghdatnseikalaaklvsgktslwdkanaiftfardnit ysyyadskkgaagtlssksgnccdhsnlivslcraanitarfshaqgctfssglvaghvwaqiyidgvwytadatsrrnslgnivnwnt nhyntlkqydhlsf |
| Contig55_gene_13 | 257 | mnnkyflgiiiliiavlavifafsldyqtnylngssngsvntnenssfnqsnnglqtnvqltisaeqsfpmekiaeeikthpayegyde dtlkwletfngsimftskdyfvvmdkndaenlptsfvndafiyddftcdiiekrslgkdlkdiiyvknvkfenqrivpmif |
| Contig55_gene_23 | 258 | mllndksellkslslflllivlltsfnsvyansdnfdsakssdllfsdsnnvyienidcsdsilinvysnkkdsnlgsyfvgsssdsyl kdsnsdsafvvsnedsyledsnlnhsknylssgslsasskskviltttsnlsasyktknftakltdlnknpiagaklsfvilsktyyrt tdkdglaslminlapgkynistkfegdsnyssavvknsitiskkklsissdlskkygdsnsfqvkitdngnpisdikvalklsaktyy rtsdknglvslpinlligkyiinssvydnkfyysntnsnniivssqnpynlsvlkwgtkgniknsvlmnnipksslthaiisacmngt pliqfgngsgkkvfinagvhghelssqaaafklinniynskkkingtvyivpvlcpkmtegnaryfnnvnlnsvankngtvsnklvnla lslkvdvlgdfhctrpngdpgknvamgtsspmassatlakyisktgyssllykkageeypgavedvcnlkgitsvtcealtphgkias gsvgksynmmiallkyygiti |
| Contig55_gene_40 | 259 | mkkiilgtcilfllisvayagtvdiftapsplqplqnsgfgdgqghniqifeftenlyktwfendtdyvvekyegnnglylyaddendc gileivekdgkkyixkfpwds |
| Contig55_gene_45 | 260 | mkinlkrvilgillliicissasiisaysidsmeiqggcistgsgledktyatiyvgeeytgadvliqiyysrdgsqlnpgnkvpktvd slgcievpsanafkyypdlaeinlydsdgylidsrdvslsihsgeqtfgdfygsssssssyssssssgdgstttyhsgtsnsy vgnsntgkfhapgcdsvdkmkpsnkvyfssrdeaisrgyspcgrcsp |

FIG. 8A-1

**ORFs encoding the biosynthesis of exopolysaccharides identified from *M. ruminantium*: annotation.**

| ORF | ORF Annotation |
|---|---|
| Contig40_gene_55 | glycosyl transferase GT2 family |
| Contig40_gene_106 | glycosyl transferase GT2 family |
| Contig40_gene_223 | glycosyl transferase GT4 family |
| Contig40_gene_233 | NAD dependent epimerase/dehydratase |
| Contig40_gene_257 | NAD dependent epimerase/dehydratase |
| Contig40_gene_303 | glycosyl transferase GT2 family |
| Contig40_gene_304 | NAD dependent epimerase/dehydratase |
| Contig40_gene_305 | hypothetical protein |
| Contig40_gene_306 | UDP-glucose pyrophosphorylase GalU |
| Contig40_gene_315 | UDP-glucose 4-epimerase GalE |
| Contig40_gene_366 | polysaccharide biosynthesis protein |
| Contig40_gene_367 | polysaccharide biosynthesis protein |
| Contig40_gene_368 | polysaccharide biosynthesis protein |
| Contig40_gene_369 | glycosyl transferase GT2 family |
| Contig40_gene_370 | nucleotidyl transferase |
| Contig40_gene_371 | glycosyl transferase |
| Contig40_gene_372 | glycosyl transferase |
| Contig40_gene_373 | UDP-galactopyranose mutase Glf |
| Contig40_gene_391 | glycosyl transferase GT2 family |
| Contig40_gene_450 | glycosyl transferase GT4 family |
| Contig40_gene_470 | UDP-N-acetylglucosamine 2-epimerase WecB |
| Contig40_gene_653 | CMP-N-acetylneuraminic acid synthetase NeuA |
| Contig40_gene_654 | hypothetical protein |
| Contig40_gene_655 | N-acetyl neuramic acid synthetase NeuB |
| Contig40_gene_656 | hypothetical protein |
| Contig40_gene_657 | polysaccharide biosynthesis protein |
| Contig40_gene_660 | glycosyl transferase GT4 family |
| Contig40_gene_908 | glycosyl transferase GT4 family |
| Contig40_gene_920 | polysaccharide biosynthesis protein |
| Contig40_gene_960 | glycosyl transferase GT2 family |
| Contig40_gene_967 | glycosyl transferase GT2 family/CDP- glycerol:poly(glycerophosphate) glycerophosphotransferase |
| Contig40_gene_969 | glycosyl transferase GT2 family/CDP- glycerol:poly(glycerophosphate) glycerophosphotransferase |
| Contig40_gene_970 | glycosyl transferase GT2 family |
| Contig40_gene_977 | nucleotidyl transferase |
| Contig40_gene_978 | CDP-glycerol:poly(glycerophosphate) glycerophosphotransferase |
| Contig40_gene_1113 | glycosyl transferase GT4 family |
| Contig40_gene_1115 | glycosyl transferase GT2 family |
| Contig40_gene_1120 | UDP-N-acetyl-D-mannosaminuronate dehydrogenase WecC |
| Contig40_gene_1121 | dTDP-4-dehydrorhamnose reductase RfbD |
| Contig40_gene_1122 | glucose-1-phosphate thymidylyltransferase RfbA |
| Contig40_gene_1123 | dTDP-4-dehydrorhamnose 3,5- epimerase RfbC |
| Contig40_gene_1124 | dTDP-glucose 4,6-dehydratase RfbB |
| Contig40_gene_1125 | glycosyl transferase GT2 family |
| Contig40_gene_1126 | glycosyl transferase GT2 family |
| Contig40_gene_1127 | exopolysaccharide biosynthesis polyprenyl |

FIG. 8A-2

|  | glycosylphosphotransferase |
|---|---|
| Contig45_gene_62 | glycosyl transferase GT2 family |
| Contig45_gene_64 | UDP-glucose/GDP-mannose dehydrogenase |
| Contig45_gene_71 | glycosyltransferase GT2 family |
| Contig45_gene_72 | hypothetical protein |
| Contig45_gene_73 | dTDP-glucose 4,6-dehydratase RfbB |
| Contig45_gene_74 | dTDP-4-dehydrorhamnose 3,5-epimerase RfbC |
| Contig45_gene_75 | glucose-1-phosphate thymidylyltransferase RfbA |
| Contig45_gene_76 | conserved hypothetical protein |
| Contig45_gene_77 | glycosyltransferase GT2 family |
| Contig45_gene_78 | conserved hypothetical protein |
| Contig45_gene_79 | glycosyltransferase GT2 family |
| Contig45_gene_80 | acetyltransferase |
| Contig45_gene_81 | glycosyltransferase |
| Contig45_gene_82 | glycosyltransferase GT2 family |
| Contig45_gene_83 | polysaccharide/polyol phosphate ABC transporter permease protein |
| Contig45_gene_84 | hypothetical protein |
| Contig45_gene_85 | polysaccharide/polyol phosphate ABC transporter ATP-binding protein |
| Contig45_gene_86 | glycosyltransferase GT2 family |
| Contig45_gene_87 | hypothetical protein |
| Contig45_gene_88 | glycosyl transferase GT2 family |
| Contig45_gene_89 | UDP-glucose/GDP-mannose dehydrogenase |
| Contig45_gene_94 | glycosyltransferase GT2 family/CDP-glycerol:poly(glycerophosphate) glycerophosphotransferase |
| Contig45_gene_95 | CDP-glycerol:poly(glycerophosphate) glycerophosphotransferase |
| Contig47_gene_70 | glycosyl transferase GT2 family |
| Contig47_gene_408 | oligosaccharyl transferase STT3 subunit |
| Contig49_gene_169 | glycosyl transferase GT4 family |

FIG. 8B-1

**ORFs encoding the biosynthesis of exopolysaccharides identified from *M. ruminantium*: nucleotide sequences**

| ORF | SEQ ID No. | Nucleotide sequence |
|---|---|---|
| Contig40_gene_55 | 932 | atgtcaaatgaaatttcacaaaacacagaaggaatattttagtggttcctgcatataatgaggagcgaaccgtatcccaaatcatagaatgcattgcagagaggggatacaatgtagttctagtcaatgacggctctgcagacagtaccctcgaattggcaacagaatccaaaagaaagtatcctgataagatatttgttgtctcccatgtaatcaacagaggcttgggagctgccttaaagactggaatgatggttgcacttaataagggagccaaatacataataacctttgatgcagacggccagcatgaaatcagcgatattccaaatgtctgcaagcctttgcaggatggagaggctgatgcagtaatcggttcaaggccttttgaggacatgcccttgtctaaaagctttgcaaaccttgttatgaatgcccttacattcatattctatggaaggaatgttaaggattcccaatcaggattgagagcctttacagctgaagctgcagagaagatcgatgtggtttcaacaggatatggagtctcatctgaattcattaaggaaatcagtgataagaatctcagattggctgaagtaacaatcacaacaatttacactccagagactcaacataaaggtacagatgcaattgttggcttaaagatattaggtaaaatggtgattgacttatttagaatctag |
| Contig40_gene_106 | 933 | ttgttaagaggtagaaacatgggaatgaagaatctaattttatccaagagcgatcaattcaatcattacaaagataaggcaaatcaattgaaaaaggaaaataaggaattaaagctaaaaatgaggaattggagtttaaaaacaatgagcttagtcctgaacttgaagagggaattagcctaatcattcctagctataagggagaaaatcatattcagcctcttttagagtccttggaaaagcaaacaatttcaaaagacctttttgaagtaatcttcatcgtcaatggagaaatggattccacaatagacatattaactgatttgcaaaatcaaatcctgacatgaacataataattagctatacaagcgaaggggagtgtccaatgcaagaaacattggaattcggattgcaaaaagggaatatataggatttcttgatgatgacgacttcatcagcgataattatctaaaagccctttatgaccatatagctccaaatagggttgtgctctctaatttcatcgacatcgatgaggaaactggagaagagatagggtctcgccttgtcccatattccatgaacagggaaggcatattcaatgatgttgttgtaaaactgactaacctttccatcataacaactgcaaagataattccagcattagccgttaagggaactgacttcaatccaaatctcaacaatggagttgacgtttcctattatgcaaggctatatccaaagaatcattttgaattttattttgtaagcaaggaagaaggagctgtctattatagaataaggcgaagcggttccatttcaagacaggaaacttcctatcaattcaatgtactggaccgattgaaggtcatcgatgacattaatgaaagctataaacaagttgataaaagcgatgaactctatgtccacttcctaaagatactctttgatgctcaaacatacttcattggattgtatttggatgaatatcctcaagatcgtgaaaaggtcattgaagaag |
| Contig40_gene_223 | 934 | atgaaaatattggtagtgcaggaatcagactggcttaagagaaaccctcatcagcagcaccatctaatggatcgcatggtgctacgtggacatgaagtaaaagttatcgattatccaatcgattggcctaaagaagactcaaaggacttatctttcatagggaagtccacgaaaatgtctctaaggtaaagccagaggcagacatagaggttatacgtccttccttcataaaggagccagggcttaactatgcctccctatacttcacacataaaaaggaaatcaaaaagcagatagatgagttcaagccagatatcatcatgagcctagggcttctaaatgcatacacaggttcaaagcttgctaagcagcatggcattccattcgtatactaccttattgatgtgctatatgcacttattccagagaaggcatttcagtcattcggcaagaaggtaaacatgaaagcgatagagaactcagaccttgtaatcactatcaatcaaaagcttaaagaactggcaatggaactaggttcaaaaccagaaactaccattttgattgatgctggaattgatttaaatgactttgaccctcagcttgatgattccaacataagaaatatgtataatataagtgaagatgacacagtcctattctttatgggttggatctatgaatttgcaggaatgaaggagcttgcaatggagcttggaaagaataaggaaaaatatcctcatatgaagattctaattgtaggggacggcgatgcctatgataggatggtggagataaaggaggagtatgatcttggtgaccaattgattctcactggaaagcagccttatgagaggatacctgaatttttagcctctgcagatttctgtcttcttccggcttatattgatgaggaaatcatgcaggatatcgttccaatcaagctttatgagtatttagctatggaaaaggttgttatagcaagtgagcttccgggcatttccaaggagtttggatatggaaatg |

FIG. 8B-2

| | |
|---|---|
| Contig40_gene_233 | 935 | atgtccaaatataacgaatatcaagataaaactattttagtaactggtggagcaggctgtgtaggcagcaacttaactagaaaattagcagagct<br>tggtgcagagaaagttgatcattttagataatatgtccctcgcatatgaagtgccaaccaacgaaaacgttgagcttattcaagggaca<br>tccttgatgatgagggagttaaagcgcgtatttaagatgaagcggactatgtattccatttggcagctcacttcgctaatcaaacagtggac<br>aatccggaaaccgacttgatggttaacgcataggcattctaaaggtgcttcaatatgcacagctcactggtgttgaaagattgtatactcatc<br>ctctggctggagtatatgggcttgactctagatgcttgaagagcatgacatatccattcctgcacacccatacaggttactaagc<br>ttcttggtgaattatataccaattattcctaattctctctattggtccatgacaaacaggcattgcctattacaggagacggaaccaaggga<br>ccaggaaaaatacagaaatgtaattcctatatgacatgccatttgtaaatgcaaggttcttatttaatgttattcgccaggggaagtt<br>ctgacctttgttggagatatcgtcaacggccttttgtcaatgggagttgaagaggaagcgataggtgaagcgataaacctaggtcagtaagg<br>atcacagagtaattgacatgcaaacaaggtcaaccaactcactgagttgaaatgaagagggcatcgcctatgttgcaagacgtaactggatgctaag<br>accaagcttatctcaattgataaggcaaagacattcttggttataagcctaccgtatcctttgatgatgttagaaagagttacggttg<br>gtttacagacaactggaagacattgaaagagatgctgaattttaa |
| Contig40_gene_257 | 936 | atgaaggataaaaacgttgtagtaacgggtaagcgtaagatgcttgaattagggatcctaaacatcgaatcacgagaactgacaatcacgagaactgatgacgcagacttag<br>cgacaatctatcaagcggtaagataaggactatgtcttccacttgcgaaaacaacaatatcaaaaagtgatctctcatcttcctgcagtctatgggaaaa<br>aaagatattaaaggataaagcgcgtattttaagctgcaaaacaacaatatcaaaaagtgatctctcatcttcctgcagtctatgggaaaa<br>aatattgacgctagcttaaagctcctctaaagagagcgaaaactttcctctggacagagcttgcaacattcaacctatcactcttaaagtcattcc<br>tccaaacatgcctcttaaagagagcgaaaactttccctgctccgtatttcaatgtctcggtcacaagaacagagacttattatgttaaggaaatagctaa<br>atgaatcctacgggattgattatgtagcatcctaacggagaagtccagttatttatgtgacggcgagcaaaacagagacttattatgttaaggaaatagctaa<br>agcaaatatctcctctagaatcagacatcagcagaatacctgagtcatcaatgttgccctggcagacaacattccttgcagacattagcaatttgataag<br>gcgacgttctagaatcagacatgatgtaaaataccttgatgaacttgaggaacaatgtgaaaactgaaaatgttatagcagatgaataa<br>attagtttcaagcagcatagtggctatatacctgatacaatgggaggaagcttttggctgattgagagcaaagactcaaagtatgtgatagaagttat |
| Contig40_gene_303 | 937 | atgcaagcatagtggctatatacctgcatacaatgaaggaaggaaggtgctgatgtgataaagagcaaagactcaaagtatgtgatagaagttat<br>tattgttaatgatggcagtgtttgaggctattactggctattactggctaagagtgctattgaagccggtgcagagctaatcatccgactaattaggaaaaggag<br>agcattaaaatcaggttttgaggctattactggctattactggctgaaccttgcaacatcgatggagcgcagcataatcctgatgattccaatt<br>attcttaagctatcattgaagatgagtgaccttgaacctttgaaatgcagcagatattgtagtcagaacactcctcgcctataggagagt<br>tgaacaagggttttagacattgccactaacatgtctcgaagaatcaaggttttggtatatagaggtgaatgcctagtggatgcagcaagcggtttaaaaatagttgaagtcct<br>gaattgcttaggttagatatatgtttgatggctctactaaagatccggtaacccatggttgttggttgtattgcttaaaataatgaaagataaagccgttag<br>ataacgtctgatatgtgtatgttgatggctctactaaagatccggtaacccatggttgttggttgtattgcttaaaataatgaaagataaagccgttag<br>gactttaaaaatag |
| Contig40_gene_304 | 938 | atggaaactcaaaggattatggtaactggcgaagtggaagtgattgttataggaacaaacctgtaaatgaacttagatctagaggacatgaagtattgtc<br>tgttgacctttgcatcatgaggatgaggctgatttgtattcagatcttacagtgattatgtaaggagacattgtaaggggagacattcgtaactatcgtcaaatgg<br>aacgcatcttcgatgacaatgacaaatttgactatgtttacatttgcagcagaatacgcagcagataaacggtgaaggatattatgaaaaccttt<br>tgggaaccaatgtaatcggttgaagaatatgatcgtcttcaagaaaacagcccataaaaggacacttagaatgattcattcctctctgctgaagtttatgg<br>tgactatgaaggaataatgaagtgaagaatgtaatgaaaacaggcaataaaggaagatgactatcaatcccaatggctg<br>gagagttatgtgcatgaactgtcaaccatgtttgaactgaaactgtttaaggttcgtcctgttaactgttatgtcctcatgaagcttactct<br>cctatataaggattcattccaatctttattcttatcagtgcactcatgtgattgctaggacacctcatttattcagttgcttattcatgtgattgcttaggacatataaagaattattgattatgt |

FIG. 8B-3

| | | |
|---|---|---|
| | | ggaagacactgcaaatacctttgcaaatattgtagataatttcattccaggtgaagtctataatgttgaagcaaacaggaatgggaatgacca<br>ttgaagagtattctgaccttgtgcttgaagctgtaggtagtgattcttagtgacactcctagtgacttcctgaagacttactacaaagttaag<br>accattgactttctaagctattcgtgattctgataactgaagacttctcctaagtctctcctaagaagaattaaaagaacagtcgaatgatgaaatg<br>gtattacagaattgaagattag |
| Contig40_<br>gene_305 | 939 | atgactaataaaagtcctgaagagagatagaagaattaaaggctcagtttctaaatatagaaagaaaccgtattcttaaagagagatgtgc<br>ctcctatgaagataggattgaacatttgctatagagcgaaaagagctgtctagagccatcacccaattcgaatcattgaattgagcttcgac<br>aatatgatttggagagctgattaataacacccgcaagttaaatcatagaatcgatatcttcaacagcgaggacaat<br>gagaattaaatgaattgattaataagctaacaaggaattggatgatgcaaattatgaaatatctcgattgactactgaatttcataagcttag<br>ggttcgcaaaaatcaaagaacctattttttagaaaatcgtttggatattgcatatccaaattggctcaatgaaatacacctaaatgaatttg<br>aggaacttggattctgggataggcttagagcgaacaaaaaacctgaaagttatgatgatattgacatttga |
| Contig40_<br>gene_306 | 940 | atgaaagcagtcattcctgcagcaggcttggaacaagattcctcctgctactaaagctcaaccaaaagatgttgccggttatgacaagcc<br>gaccattcaatatgtaatagaagagtctgtaaattccgttgtagatattctaatcgtaactgttgtaaggtaaaagtcaattgaagaccatt<br>ttgacagttccttcgaattggaacaccattgaaaccaaggaaatttcctaaggaaattgaatatttcagatttgcagatatt<br>catttttataagacagaaaaagcaaaagttcttgagatgctatatattgtgctaaaaagcatgtcggcaatgatcctttgttgtcatgttagg<br>ggataccattacaaggatacagttccgtgcacaagcaattgattgacatctatgaagagattcaatctatagagtttgcatatgaagaggttc<br>cggatgaaaaggttgaaagattggtatataatagcggtgagatatgtgagatttccttacacctgcaggtattatgcgcaggttatgagagtgcataaag<br>agagtagcaccaagtaatttgactgatgcctaagcaagcttggaagttatggcaagatatggagagtcatattaaggagagttagtgaagt<br>agaaatccaattgactagcttcctaaagttcatgaagtgacagtgcaagatgcaagagtgatatattgaattcattaaagaagagattatt<br>ggctaaagacttcctaaggttcatgaagtgacagtgcaagatgcaagagtgatatattgaattcattaaagaagagattattaa |
| Contig40_<br>gene_315 | 941 | atgatttaattactggtggagcaggctatattggctcccatattaataatttattaaataatccggttatgagactatgtttagacaattt<br>gtctaaaggacacaaaaagctgttaaatgggcagtcttgtaaatgacagtctttaagtgacagtgataatcagattaaagagatcttcaaaataatg<br>atatagaggcagtaatgcacttttgctgcttttcatctgtcgtgaaatcctgaatcgatcttgaagagagcctgaaagtatttaaaataattttgaaaataca<br>gctaatcttttaaggattatgaaggagtttagagtaagaaaattcatatttcctcaactgcaattgcttatatggtattcaaggagattcctat<br>aagcgaatcagctgcagtctctcgctacgttatttcaatgcagcaatccatgcagagtcaattgttgagaacctattaaggacgaatctgacttgagggttgaagaat<br>tgaaatatgtctcgctactgttatttcaatgcagcaggtgcagtttggattgtgatgactatgacactccagacggaacatgcataaggattatat<br>ttggtctttgatgcagcatttgcaatttggaagagaaacagcattccattttttgtgatgactatgagaggaatgacctgcaatatatataggattatat<br>tcatgttcaagacttgctgatgctcattcaaaggcatgacacttgtaaaaaggttacaggaaagttacaggaatagagagcctttaatgacaacatatatttaaccttgagacggca<br>atgatttcctgaaggagttcaaaaagcagattcattgacactgtaaaaggcagagagagagttgaatatttgaagagcgcaatatccactgtattaagtgaatatttat<br>gatatcttaattgacagatttaccaaaagcagaagaagtcttaaaatgaaacagagagtatccagatttgaagacatttgaatcgcttgaa<br>ttggcataagaaacttcacggataa |
| Contig40_<br>gene_366 | 942 | ttgaccgttccttcctccttattgtcaatgtgtcaagcagcatctgtttgtgaatgcaattgctgaatgcaattgataaggaaaggcagtaacaaaaatctatattatggc<br>agttatatttaacgtatgtcttaatttggttcttattccaatgtttagttatgatgagaggcaatatccactgtattaagtgaatatttat<br>tatcattttaa |
| Contig40_ | 943 | atgattattattccacttagcatagtttctctatgcaaggcttatcattgactcattactgcaaccaataactctctgtcatcaactct |

FIG. 8B-4

| gene_367 | tattcaaataattgtttga |
|---|---|
| Contig40_gene_368 | 944 | atgaatcaaattaaatccattttttaaaaatactggttggttatctgtttcacaagtgataacaagcatttgtgcattcctatggaccataatcat<br>agccgatacctgggagtatctgattatgcattgcattgctctcatttgcagttctttcactggcttcttcactgggcttatgggaatagtgatgattgggaataagca<br>catacatcactcgtgaaattgcgaaacataaagattagtaaggaaatatttaacacatatctttttattaagcttattagccattatctta<br>tttatttaagtgattgattttgtatgtcatggatactctcattaactataatagttacttgttttacaatagaacttatcttcatgtc<br>tatgactactttttaaatggagtttccaggccttgaaaagtaaaatcaagccataggagctatattaaatagcagtttttattaatag<br>gcattctaataacattaggttttgattggcgttatatccattgcctttgcctacactgttgcatattcaatatattttcatatatgtttta<br>tcatatgttaaaacattcagccgacctcattagaattgatacaaattcataaggaagtaatataatcaaatccattccttttgacttacaaa<br>cttctctattctatttattttcacaacattttttgtagtttaccaaagcgtaatgttgtcctatttggctggagattatgcaacaggactttataagtctgcatacaaca<br>taataaatgttttcacaacatttttgtaaaatatttgttgttaattatattcctatcagcataggcatttctcctatgcaagccagtggtgatcttat<br>gttagctatgagctttctgtaaaatatttgcctcaactccagtccaaatactatctgacagtttcattcctattgtca<br>ttacagcaaccaataccacttgcctcaactccagtccaaatactatctgacagtttcattcctattgtca |
| Contig40_gene_369 | 945 | atgctaatgtctataatctgtgttttataatgatgaagaggtttagaatcattaaaaacacaaaatgaagaatatgaatt<br>aatattaattgataatagaaatcatgaatttgttttataatgattttaattccgcagcttcagcctcaaattatgtgaaaaaaagcaaaaggagaaatattgcttttg<br>ttcatcaagatgtgaatttatgaaatatttatgaaaatcatgaaatttaactttaaaagatataaatactagaattgcttgagttcaagga<br>gtttctgagaaaactatgggagaattactacaatataacaagttgttcctgattccaaatcaacagtgtcagattatagtattacagataaccga<br>aaccaaaccctgacgaactattgcttataattccaagaggtattcgaaaatcaattttttcccataacattatatcatgtatctgaaggaggttcaatg<br>atgagcagattattgtttaaacattgaaaaagtttaaataaatatgattataatcgcatatacacaaattgttttattaagtcatgaacc<br>tctttagaatacttttaaacattgaaaaagttttaaataaatatgattataatcgcatatacacaaattgttttattaagtcatgaacc<br>gaataatcagttaagttggatatccttactattctgaaattttacatataagaatcccataactaatttttatcaaattttaactttctaa<br>aaaaatcttaaaataa |
| Contig40_gene_370 | 946 | atgcaaactgttgaatgattcttttgtgcggttttgaaaaaagactaggccagttactgaaaagtgccaaagcgttagtgaattaaaga<br>agattatgcaatacttgataaacaattatttgatttaaaaaatgctgaataaacgaggttatctattagcaggattttacacgaaaaaaatcc<br>agaacgctatggtgacgaatataaacaagttgtattagaaatggagatatagttgcagacattaacttaaaaagatgataaatgggaagatc<br>gaagcactggagaagataaacaagttgtattagaaatggagatatagttgcagacattaacctaaaaagatgataaatggcgaaagatc<br>agattacttttgttacaatgttgtcaccaaaatgacttcctaccaaggtattgtagacataagtggagataaaatcactgctttaaagaaaaac<br>cactattggattacactatataaacggagaatttacttcaccacagggtattgattgactctggagaatttaaaacagtgatatagaaaaacatta<br>ttcccagtgcttgctaagaaaacaaacaacaacagacctgggatactacaggaagatgatctcttttggatggcaatcgacacatcaaaagaattggaatctgt<br>tcaaaaggtatgaaacaaacaacagacctgggatactacaggaagatgatctcttttggatggcaatcgacacatcaaaagaattggaatctgt<br>aagaaggattcagactctcttccactatcacaatgataaggatgaaaccatgtacataatgtccggtgcagtatactcgagtttgaagacagg<br>aagaatacttgaaaaacgattccattcgtattaaacctgttgtccattcattattgcaactgaaaatacaacattacaacattacgttaa<br>tacaccattttttagatgataccaatcagagtaaagattattataactctgttaa |

FIG. 8B-5

| | | |
|---|---|---|
| Contig40_gene_371 | 947 | atgagtgaaagaaaaatttaagtaaaatttgttgatttcaagatagtctaaaagagaatgataattcttttatagacagtctaaaaagaa<br>ttttgatgtgaggtttgagttcagatgacccgattatctctgtgttatgcttatgcttagattatgactgtataagaatcatgtgga<br>ctattgaaaattatgttcctgacttcaatatctgtgattatgcattagcttatgtgatatcattgaattgggacagatatctcgttttccattt<br>ttcttaaatcgtcctgacttgaaaacgttagaaacattagaaaacaatagaaacaatcaagtcgttaaaactgacacaagcgttaaaactgatttttgcagttttgtagt<br>ttccaatgaatgggagacgattagaatccgtcgtctcatgaaacgtttgaatttgatgtaactcatcaatttcattttgctcttgaaaatgtctcaaaacagggc<br>ttgtgacctatcggcatggccttgataagaagttgatgctttgctgaggctgcattccaatctattgggagatccataattgaagaggaattcaacctaaatc<br>tatactactgaaaaaataattttgatgattttgactgtagaggaagccgtgacaaatatcttcaggattttgtttaatatctgcaatcagccttttagagaagcctaaatg<br>ctttataaattgtaatgatttgacttggacaaatcttcaggattttgtttaatatctgcaatcagcctttagagaaagctacccgt<br>aacctactttttagttgtgatttgacaaaactcaagagcatcagtacaaatgattaacagatttattataaaccttatttttcttaattaaggtagc<br>aggataggataatgaaggaaaaactcaagagcatcagtacaaatgattaacagatttattataaaccttatttttcttaattaaggtagc<br>acagaattacacattgaatttatcggaagaagatttatcacttcattagagactaa |
| Contig40_gene_372 | 948 | atgtcaagtgcaaatatccagattatgttgtatccatagtgaagaggatatcaaaatattgattctaacgacattacactctctttttgt<br>tggacgtgcaggcaggacaattaggctttgtaagtgacgatactgagatactggagtatactcttcctactgtgaactaacagac<br>tttactgatgtggaaaaaacagccctgcagacatatatgtcttgtcaattatagaagtacttgcaaactgagactgtgaaaaggtagaa<br>cgagaagatatatgaaaatgaaaacttcctgaatatgatattcttctgaagaggttatagccgaacaatgtctctgaatatctgtgatagttataaacgagtgtggaagaa<br>ttgaactatgctaaagactgtgacctctgtgaagaggttataggcgaacaatgtctctgaatatctgtgatagttataaacgagtgtggaagaa<br>aagatctactattacaacatgttcatagccctaaggagtcattgtgactggtattccattcttgcagagtagaaaaa<br>agagtgacatgacgtgatatgatgattatcaaaaagaaatctatgattcttaacagaacgtctcttgttttgatgtttgatggacaaacaaactt<br>gagagtaaagaatgtgaactaaaagtcaatgacttagcttacttggatcttaatgtccatatgtggattgtaaaagaaagattgtaagatgggcttatgtcc<br>atatttatatggcttgcttcataagatatgagacgttaa |
| Contig40_gene_373 | 949 | ttgccttgtaatagaaaaagaaagccatattggagcaatgttacacagaggaaaagcacaataatgtccataagtatggtgcatat<br>attccacaccaataagaggtatgaatttatcaatcaattgcggagtttaaccgctacacaactcacctgttgccaactacaaggcg<br>aattatacaacctccttcatatgaacacctctaccagatgtgggagtgaaaactccagaggaggcacatatacgcaaagatttaagcagcaaaa<br>gctgagccaaatattgatgagcctcaaaactgcacagatcctccatcctcattgtgaacaagcttcaccttgacaacaactattcaacg<br>cgaaaagcagtggggattgcacagatcctccatcctcattgtgaacaagcttcaccttgacaacaactattcaacg<br>acctctatcaaggaattccaatggctatgcagaaaggctgacgatagatgactactgcttgagagcttgaatacag<br>agccttgacttgagtttgagcacttgagaatgtcctgatatgagaactgcgtgattactaggaggatatcaagggtattataataatataacaagga<br>taattgagcataagcatttgagaatgcactggcagcaactactgagaaccattcaagggtattataataatataacaagga<br>tatcctatgaatgatgagagaaaccactagcgcgcacgttgattactaggagtatcaaggagctgattaatctatcttgcgaaggcttgg<br>gatgtataggtactttgacatgtgcaggtcgcagtgaggcattgagtaatactctctagaatag |
| Contig40_gene_391 | 950 | atgcgtttagaggttgtagataagtcagtcagttacaaaatatccatttcagattggtttatgattcaattaaagcataaagattgtcttcagagct<br>ttgtgacattttcaatataagaatggaccgttcctaaaccctgttctattctataaactggataagctatgcgtaagcagaaaatacaaaag<br>aggaaataaagatattttagagaagatttgataagtagaataagtatgggttgaagtataagaccacaaatta<br>ttattaaaaatcataa |

FIG. 8B-6

| | | |
|---|---|---|
| Contig40_gene_450 | 951 | atgaaaatagcaatggtagtcaattcccacccatatcggaggagttggagtacatatacacagcctagcaaagcaactaatcaggaaggcca<br>tgaagtatatgtgattacataccctcacaagacattaaggacattgacgaattcatgtcattggaacaaaaggaataaatatccaggctta<br>gaggattgatgtttgaattaatgccaaaaagaattaaaaagcttataaatgagaaaacattgatataatccacgccattacctattccct<br>gcaggatgggcagcgttaaggctgaaaatcaacaaataccaaaacctatgtgactgcacatgtcctgatcagatatcttgaatgtaaaaaca<br>aaaatttatgaggcccttataagaaagattaagattcattgaattcagtagacattgaaaatcaaaactacagagagaataaggataagtttaaa<br>atgttccaggcataaagagaaagattaagattcattgaattcagtagacattgaaaatcaaaactacagagagaataaggataagtttaaa<br>aggaactggttaatgaatacaatctagaccccaaataagccaatgcaaatcttgtaattgttggagaagttctgaattaggaaagttaaggaaaagaaaaatgtgaatctccttgt<br>tgaagccaaaagactaattaaaaccgatgcaaatcttgtaattgttggagaagttctgaattaggaaagttaaggaaaagaaaaatgtgaatctccttgt<br>ataaatcaatgacgtttacttacaggacgcattagcatgtggaaatgcagtcattggaagcatctatccaagctgtgacttgctgcttcctttagcgaa<br>agttcgacttgtttaattaatagaagcattagcatgtggaaatgcagtcattggaagcaatataggcggaataaagagataatcacagaagacgt<br>tggattattgattaatccaaatgatagccaagacctagcaattgcaatgcaattgataagatacttcaggatgaagaat |
| Contig40_gene_470 | 952 | atgaaaatagctattgtacttggaacaaggccgaaataatcaagatggcttctgttatgatgaaacagaggtcatgaattgttatt<br>aatccacacaggccagcattatgataaggaaatgtctgaaaactctcattgactgaaactacctaccccaaattataacattcatgtaggct<br>ccggctctcatggagctcagacaggcaagatgatgaagcaagatgaagaggttcttcttgatgaaagccagatatattgcttgttcaaggagat<br>acaaatgcagtgcttgcaggcgcacttgtcgagcagacatctgtcgcagacatctgtcaaattatactttgttccaacagaagaatcagcaatcaaccttgctatggaagga<br>tttccagaaaaagaatcttcataaccgtaatactgtagtgatgcttgctcaggaaacctaacaatgcataggctgaaaccgttgacgataaggaacgcct<br>gatgaaggccttcaggaattggaattgatattgacatatgaagcgacatgaacatgaacattataatcaagcctgatgttcctgcactgactttttgctttctcatatcagagcgtcctgaaacagtaac<br>aaccaatataattgaagctcttgaggaattcagggaggcaatcaatcaatcaagcctattgaaaatgcaaaatgcaagaaagatcttagatgatg<br>tctttgacagattaaacgatctccctcatgttcatataatcaagcctattgaaatgcaagaaagatcttagatgatg<br>ctaacagattccggcggaacatcctgtaggttccgataaggaagtgatactgcaagaaagatcttagatgatg<br>tgccgagggaacatcctgtaggttccgataaggaagtgatactgcaagaaagatcttagatgatg |
| Contig40_gene_653 | 953 | atgtataaagataataaatattagttgtaattcctgcaagaggaggatccaaaggaattccgctaaaaacatacgtttttttaggtaaaagcc<br>tctcattgcacacacaatagaaatgggaaagcatccaaatatgtggaaagctgatgagctagttgtgacaactgacgatgagaatcaagttcatcagcg<br>aaaattcgagcagaacaatcaaaaggatggaaagctagctgaaagactctatccaccttgatccggtaatcgatgccgcaattcaaaag<br>gaaggaaaaagcaatgaaaatatgtgttgtaattaccgtacacaatcataagtgttgtagacgacaggcacttaaggagacacttagtttagctattgaaaa<br>actattaaacccgacaatgaaaacaaagattatgacacaatcataagtcttccaaaggcataaggaaaccggaagcatatttgcaacaagaagagaa<br>aaagtatttccattatataaggaaaagggtaaaccgacaatatagtcttattgaagtatccaaacaggaaaccggaagcatatttgcaacaagaagagaa<br>tttgtaaaggaagatagccgtcttggagaagaaaatatagtcttattgaagtatccaaacaggaaaccggaagcatatttgcaacaagaagagaa<br>ggtagctgaaaaaatcctaaacagaagaaaatccaataaaaggcagatcctatggagaagtgcctcccacagaataggaaccggccatatttacagaggcctctcaa<br>tagcttcaaagcttgtaaaccacgaagtgattttcctctttgatgaggctcaggcttgaggtcaggaattaggaattaaaaacaacaactatccattc<br>ataaccctaattcacatactaaacaccaattcaaaatacaagcaaatacacaaagaccctttaggataatggattttatcagtaa<br>tatcataaatgacatactaaacaccaattcaaaatacaagaccctttaggataatggattttcatagtaa |

FIG. 8B-7

| | | |
|---|---|---|
| Contig40_gene_654 | 954 | atggaatcaaagacattacaaatattgaagagattacaagcaatgacgtatatccttagtaaatctactattccaagcaaactcttcaa<br>atcaaaagaataaacacaaacagccttgcaatcagctgtcttgacctaatcgacaaaaacagaataaaaatcacattcaatgagaatcgaat<br>caatcaaaatcagcaagaaccctctcttcttaagacaaaaggccaattgaaaagaaatgaactcatcaaaaaacatcaaatttacaatcaattca<br>aaagagatgaaaaaactggataaaagagaccaaatcatcttgaagatgtttaaggacatcacaaaaaccatgaatttgactaaaatccatgta<br>tgataagatcctaaagcaggatatagccaatcaaattgcaaaatacttcaaagattattccaatcccttgaaaggaaaccaatactcattgg<br>aaaactataagacctcatcaagcaggatggagagtttacctttaaggaaatgaaataagcaatgaatagccttgaaattcaaaagctctttaaaatca<br>gataagtcctatacagccagactacgattcagagttcagagttcagagttgacaaatatctgattttatgaagatgcctgaaattgacgactattatggaggcataatcat<br>tgaaaggcaatccagactagaaaaggagacggttcagtactgttgaaacagcaaatacttcgtcccagattcggataa<br>caacagcaagatagaaaaggagacggttcagtactgttgaaacagcaaatacttcgtcccagattcggataa |
| Contig40_gene_655 | 955 | atgaccatattcaatgaagaaccattcctaatagcgcaaataggcgtaaactactacgacattgcaaagagaaaatatatccaatgatgc<br>agctaaactaatggttaaggaggtcatgacgcagagcctaccatcacaatacgaactattcaagaagttcgactccttgagagcagaatagggaaatc<br>cagcatattgggacacaagaaacggaagagccctaccatcacaatacgaactattcaagaagttcgactccttgagagcagaatagggaaatc<br>gcagactactgcaaagaaatcggaatccctattcctatcaacacattcctatcaaaaaagatagccaaatagcacatatcatatccaccgagcatcaaccttg<br>aatatcatcagacccttacaaacatcccattcataaaaagatagcaatagagacataatcatatccaccgagcactgtgtgctctcc<br>atgagtaaaactagctataaagaaactcgaacatagaaaacgctaacgacaaatacaaaaaggagaagctgaatcgaatcatcaattatgaaatagaggatatcagactaacaatagatctcag<br>tatccaacagcaaatgaagatgcaaacctcatcttacaacagcctatcttgatttatgcgccactatccttgaaagcactcacattagatacacttcaggaa<br>gccagatgagaatatgctcatgaataggaccagaatccaagaaaaacaggccgactcattagaagttcaacaaaaacataggaatcctgaaagcactcacattagatacacttcaggaa<br>acgaccactacatgaaagatgaataggaccagaatcaagaaaaacaggccgactcattagaagttcaacaaaaacataggaatcctgaaagcactcacattagatacacttcaggaa<br>cctctccatgtgaaggagaatcaagaaaacaggccgactcattctccaagtgaactgcattgtctccaagtgaactgcaatagatagtgtggcaaaaagccaaaa<br>gcttacatataaaaggcctgaactggcattctccaagtgaactgcattgtctccaagtgaactgcaatagatagtgtggcaaaaagccaaaa |
| Contig40_gene_656 | 956 | atgacttttacgtaaagaaatatgccaacatatctgtctcttgaagagaaaatgaactgaaccacaagagattcaaggctgctatccatg<br>gcaattaatcagaatgtatctctactaaaaacagacgaaataaccagaaataaccagtaaccaagtcttttgagtcagtcaacagtcccagtctttcctagcgataaag<br>taaatacattcctcctttataaaaacagcatctctataccaagacatctctatcgctattgtctatgcgctattgtatgtttaatattcgaccatccaaga<br>aagtcatatctaaatgggaataccaagacatctctataccaagacatctctataccaagacatctctatcgcaattcctaataacaatgacttgaaacaatagaatc<br>cccatatctaacaatcattcagaagcagtgcaaataagagaaaataatgtcaaatacaatgaccgaatccttttaggctctttataaaca<br>aaccaaaatagaagaaaattgccatttacagatgagaaaagactttatgcaaacaataaaagagaattagagtctgcattcaaaatagaa<br>ataaatctattcaatattattgaagctcacataccttaattcaaataatgattaataaaaatatagagcttcttgaaagagaagcaaagca<br>agtctatctgttgtagcctatagtaccaaaaatacaatgctgataacaatacaatcaagaagattgaatattcctgataaatactaagt<br>gtccatccattaggatatagttaccaaaaatcttcaagcttcctaaacaaaagcaattctattcattcaaacaagtaccaaaaatcttcaagcttcctaaacaaaagcaattctattcattcacaaggagttattgaaaat<br>tttatgaagatggcagtaaaacagttgttctcgtctttcggtctttcatcgagcagtattcatcatgatgcagcaatatgataaaactagaacatacataga<br>tttatgaagatggcagtaaaacagttgttctcgtctttcggtctttcatcgagcagtattcatcatgatgcaagtcatcaaggagttattgaaaat |
| Contig40_gene_657 | 957 | Atgtgggctcagtaaacactacctgcactttgttccaaacatgccacctgtcttccatacaccagtcttccatacaccagtcttccatcagtgctcgtctgctgaaaa<br>ggataagaaaataagagattccttctatcgatagagctgacattcatatcaacagtcgtacctattgttcatccgtgctcgtctgctgaaaa<br>acctattgcgatgcgctcttaatgaagcatgcagtcagtattgtatcacaactcgaatatccttcttgcatgatgacctaatgctcata<br>acctacttagaccttcaggaaatgaaaagatattccctattccttgttcttcaagatgaaaagatattccctattccttgttcttcaagcagtatattccctattccttgttcttcaagcagtatatagggttttgtaagcatctacctacata<br>tgcaggatacaatatagaacagttgtctcggtctttcatcgagcagtattcatcatgatgcagtcatcaaggagttattgaaaat |

FIG. 8B-8

| | | |
|---|---|---|
| | | gattcagctttgaaaatggtcaaacctaaggaacagcttgccttgcccttccaaccattccaagcaatgtttcaagctggtagttgattca<br>agcgacaaatatgttattggaatccttttagggtcagtgcagtgggatgctattcaccagatatgcctaggaagcatatctcagtttcct<br>atctccattgcagttcttctctcactgtgccagcagctgtaggatgctactctctaagcattgttcacataataatactattcagctcaatga<br>aatactatctcttctctatgtaactccattgtctgtctaggtgcaatattcatggaatgtatgaataacaataatactattactagagaaaacac<br>ggaggttataatcctgttaaattatgataattgtagccatatccaacattgttttaaatctgattcttgtgccttatc<br>aatgatcctggtaaattatgataattgtagccatatccaacattgttttaaatctgattcttgtgccttatc |
| Contig40_<br>gene_660 | 958 | atgaatattttacatgtgctcattcttctatccatgtctgtctgctggaggtagttactcaaattgctttaaatcaagtaaa<br>agataataatgtgcatgtttacacatcagactcctgtaagcagcgattgaaatttgaagatgtcgttatgatgtagatgtgatggaattaaag<br>ttgattacttagaaatctgtcaaacagatttaaattagctaccatgttagacactccacttccgcttatttagaattagaaaagatataaaa<br>aatcatgacatcattcatattcacgacatatggcagactttagctatttagtaagccattatgtcgaaaaacaatattccatatattgttca<br>gcccatgatctgtacttccttcttccaaaggaaggattaaaaatggagtctctgaagacaagatttggattaagatactcataatgcatctt<br>gtgtatttgccctactgaagtggaaagagcaatacattaaaatggagtctctgaagacaagatttggattaagatagtccctttggaataaatatt<br>gaagagtatgagaatttgccagaaacctgaaagttccgttcaagttcaatattgctgatgggataagctattctgtttgttgaagaatcca<br>tgaaatcaaaggccttgatcatttgatgaaaggatgaagctgaaatgatgcctttaatcttttaattaaggataatagttagctattgtaggccagatg<br>atgccattttgacactttgaatgaaagagatagcaagcaggaataatctgaatctcaagtaattattacagaacctttgaagcaatgcttgcaagccatt<br>gaagctttagtgactttgactttgttgtaatgcctataaatcatgatcttaaagtacaagtgggcttgagcaatgcttgtgcaagccatt<br>ggtttaaccaaaaacaatcatatcatgattggttggttgtgagcattcctgtgatgatgaaa |
| Contig40_<br>gene_908 | 959 | gtggctaagaagtttgatattgtaacaggcagagattaggcagaggatgccgaattgcattgaatgttacaatgcttaccaaacgagg<br>aatggagtgtgagatagcattggatgaatccgcaccagtatattgtttaaaagaacaatatgaagttaaggttatcattccacaggctg<br>gaggccattctgccactctttaagacaactgtaaacgctgcaacagtttctgttaagctctcatttaaaacaagagcctaatcaaggaaagaaa<br>ttcgatctggtcttggaatcctggaggggagccatcatagtgctcttgctgcaaagataaccgaacctctgtaagcctttatcac<br>tcctttgacactaagatatgcggaaagattgaactcaacattagtcttgggataagaaaagccttgataagttaaatgaacattgcagtgaacttaagaag<br>taaagtcctttcttgcctgtaaatgcaacacattagtcttgggataacaacaattgtatctcatcagttccagcctattgaaaagactgccaggcaattga<br>aaaaaccagatgcaatggagtttgaccggtcaagcaacgattcaactggttcttatcctgtcttatgtgagatcctctagaagaggagtttataaagtatatgaaactaagataa<br>ccagttttcaaaatacagtgacagatttatagactgggtaaatatctttcarctgcaatacggacgctatcatgatgaaatcttgacaatttttgacaaatgacggccttatgctccatgaggccatg<br>tcaatgtaggcttttatagactgggtaaatatctttcarctgcaatacggacgctatcatgatgtttcaatatcaggaggctaccattgaatgtga<br>cttgaagacctgatggagccatatttgatgtggtggcaactatgactatgctaaaaatacagctacct |
| Contig40_<br>gene_920 | 960 | atgagcgaagtcaagcagttgcaaagttgcaaaggcagcgcaattatcctaataggaaacgttatctccgtgtaggaggatatatctaccg<br>cttttaatgcttccctttaggacctgccgcatatgaattctcggacttacaactccttccaaggatcttcaggttctcgtctgcttgag<br>ggcttccacctgcaattgcaaagtatgtatcgaatacaatgccctgatgagaagaaccttgctcgccaaactactatcacagcctgaagctcttctcc<br>atggtattcctaggcttttcttcggattcataatgtattcgtagcgcccaataattacaaactactatcacagcctgaagctcttctcc<br>attcaggctgtaggtctcatcactccttcagcgttatcgtttggaggatttccgtggagccttcggttatcaccctggtcgtattaggttcccgtt<br>atacaagagctatgaacagatattcatgattctaatggcacagcactgttcttcttgattatccacccttggtcgtattaggttccgttt<br>ttaggttttgtagcatctgcaatctctgcagtctacatctcaaaagatatatgggcaaaatacacttccgcaaaccagactttaagttttcc<br>attgaaggacgagctgaagctggctaagacactgattttcttctcgtaaccgttgcagccgttgctgaaatggtatctcacagtatct |

FIG. 8B-9

| | | |
|---|---|---|
| | | gcacacttcttatgggagccttcctcctgcagtcgcaatcggatactttacagcagcagacccctatcgcaaggcttccttagtcgtatcaaat<br>tccctgctacaacaatactgcctgcaacatctgaagcatatgcctgaaggaccaagtgctcctgaaaaatatgtgacagcaccataagta<br>tggaatgtcttgttattccaatgtgtgtaggaatagctactatcttcgcaagaggaataatgggacttgtatact |
| Contig40_<br>gene_960 | | |
| | 961 | gtggttatacccagcctttcaatgaagaagcgactgagtcaagtgtaactgtagtcgcaagtctcatatataagcgaagtcatagtgtgga<br>tgatgatcaactgataaaactgtagagagaagcgaggaagcgaaggcaggagcaactgtcataagccataaggcaaccaaggtaagggtagctatca<br>aacaggattaaaaattcccatgtgatatagtgccttatagatgcagatgtatccaattcactcctacaaagatagacaagataatcaag<br>cctattttggaagtaagtaacagacattacaaagaccacattgccgggaaagtggcgttacagagcttactgcaaaacctctttagttt<br>ctcttccctgaattgcattatgaacagccttaagcgtcaattgcagggaaagcgttctgcacttaataaatcaaattgaaaaggactatg<br>gtgtgatgttgcatagtattggatgctgatgttcatgaataagcatttgaagttgatattgagacattcaacatgacatgtcttcctt<br>gccgatttaaacaaaatggcaaacgaagtggttagaaccatcatttgacagggcagttgattagccgtgcactatgatgatcacccttgaaa<br>ttatatcagatgccatcatgggattgtccctatcattcttgactgtcattcatgattttcttttcattccattggttcatatccgttt<br>tagtggctcttgttgaattgcactgactatagccactttcctgtaatcgtatcaggcttatattcaaagtcaattcctattttaaggaaagggatacaagtacg<br>gcattaagtcattgtttaagatgcacttcaagagctttacttcaagaacttgtatattcccttcagatgactatcatcaaa<br>taatgatgcaggatatcagtggagcttacttcaagaacttgtatattcccttcagatgactatcatcaaa |
| Contig40_<br>gene_967 | | |
| | 962 | atgaaaacagaattagtgtcatcattccaattacaatgttcatgaattcctagaggattgcatagaatctgtcttgcacagactatcaatca<br>ttgggaccttgtagatgttatgattatcaaaggaatcttcaaatcatttttagtgatgacggctctacgagacagcggtgaattgctaagtcttatg<br>cagccaaatgaaaatgttgaatacagatatgaggaaaatcaaggattaggccatcgaagaaactacgatgcgaatttgctgaaaggactat<br>atcattttatagattcagatgacatcattcctccaagcatatgaaaggatgtatcgcttttggcgaacaaaaagagcttactcacattaaggaaa<br>atctgtatggcgattttaattcacaccactgctggctcggaacaagctatcaatttagcttttcaatagtctatgaaaactgctattttatggagagtgaggggatgg<br>gccctgagctattttatgacacaccactgctggctcggaacaagctatcaattttagcttttcaataagtctatgaaaactgctattttatggagagtgaggggatgg<br>tatgaagacattccagttccagtacaactccaatacaactacaagtgcatgatcatattcaaggaacaattcaagtatcataagaatcaggccttatgtcatggatttaacgaa<br>aatatccaataataactcataactacaagttcatgaggcttttatgtcatggatttaacgaa<br>atgtcaaggagaggaaattgcataggtaagaattcataatgtaaagaatcaagatttgatgatcttcatcaataagctaaaaagcatgcata<br>gacgagtctcaagaaatcattgaccttttgctgattatcgaccgtaacatagaccctaaatacttgatgagataaatgagattgaaaagct<br>caagtatgaatatttgtttgaaaggatttgacagactattgaaattgcttaattatgagcatgttaattctt |
| Contig40_<br>gene_969 | | |
| | 963 | Gtgatcattcccatttataatgtttacgaattcttagagagtgccttgaatccgtcgttaatcagccataaatgatgactgactgg<br>atatgaaaggatcttcaaatataactgatagatgaccggatctacagattccagcctataatcgcaaagaatatgcccaaaactacgaaaaca<br>ttgaataccaccatgaagtcaatcaaggattaggccatgcagaaactacgatgcgaatttgcagaagggactacataattttccttgattca<br>gatgaagctttctccaaatgcctatgatgataaaacagccataagaaacgatagcgatgcacattggagattctgagattaa<br>ttcaaaaaaatacaagatttcaaacattaataaatagcttcaatgaaaacataatttccagtttccgaggaatactctatgaggacataccgta<br>atacaaccgcttggaacaagcacacagttcaatgcctacgaaacacgtttcatgcctacgaaaaactgctactttatggaggaagaaaatccaaatcgattac<br>acaaacaccctgcaaattaaaaatctcgaagacagcgcttatgtcatgggctgtgtggaaagctaagaagctaaaacgaggtatgatgaaggc<br>tccgccatgtaaaacaatgcgcttaaaacaatggcttcataaccgacctcttatttttattagaagctaagaagcatgataaggaacagggatataaaata |

FIG. 8B-10

| | | |
|---|---|---|
| | | atgtcactaatccgagattacatccaaataacatagatgctgatgaattcaagtactgaatgagtatgaaagttaaaatatgaatatctgat<br>ggatgatgaaattgacaagatagttcaattgacttcaagctgaaatataaaggagacaaagtctatc |
| Contig40_<br>gene_970 | 964 | atgcaagatcctaagatttctgtaattattccaatatatataatacagaagagactatatcgaagagacattactgtctgtaattaatcaaacaatctt<br>tgatgagatagaggtcatcatagttgacgatggcagggcaggaatcacggaattatggcctaaagatgaaagcgatattgtcatgaaaatgtcttaagattgcattata<br>tttccatcaaaagaatgaaggggcaggaatcacggaattatggcctaaagatgaaagcgatattgtcatggaaatgtcttaagattgcattata<br>tatctgccaccaacagcatatgaaacacactatataatatgctataatgctataatggaattgtcatcatgagcttaaacgaaaggccttccatattat<br>caacgtatgggaagagagcctttataaaagttattcaataggaattcctgattaggaagaaataagaatcttccactattggagatcttggaaatgtgaaaagtacgaagttgaagagg<br>gggataccctgtaacaaataagttatatcttagctgattccaatctcattttcaaaagaaatcttccactattggagatcttggaaatgtgaaaagtacgaagttgaagagg<br>ccattttcactggaaagttatatcttagctgattccaatctcattttcaaaagaaatcttccactattggagatcttggaaatgtgaaaagtacgaagttgaagagg<br>cacacagcaggacaagagcctaagaacattagaagacctaagactttcaaatgctaatatgctaaaaatgtcaaaatctcttgaaaagttgaagagg<br>agataaggaattatgagtatcaaaatgctaaatataccagatgcgctgaaatatataccaggaagttgaagaagttcttttcaccatgataag<br>ttgtttgaagaggttctatgggatagttaaaataataccagatgcgctgaaatgagctatacaagaatcctgaaattccat<br>aataaggattatgagaatttccctgtttgcaccttgaaaatgagctatacaagaatcctgaaattccat |
| Contig40_<br>gene_977 | 965 | atgatcggtgtaatattagcagcaggaatggcacaagacttatgcccttactaacagcattgcttaaatcaatgaactac<br>cttgcttgaacgtatgattaaaactgcataaaatgcagacataagcaagtttatagtggtcgttgctataacaaggataaggtaatgacttat<br>gccccgaaatagctgaaaatatgatatagaaatcaagaccattgaaaacgaaaaatacgatgttacaaatacctctgtatcaacctatctgca<br>agcaaattcattgaagaaacgaccttgacgacttattctagtaacagagacagtgtagtagacgctgaaatcattacaaggctcgcagtttc<br>acaaaatacaggcatgataataaactccataggaaaagattagcattccaggagttgatcctcataggagagttcattgaatcctttaatgaagacaaga<br>caatagctaacgcaaattcaataggattttgaaaaaattaattgaagaggacccctcaaaactattatgactttgcttataagactaagtcttatcaa<br>gacgtagccaattcaataggattttgaaaaaattaattgaagaggacccctcaaaactattatgactttgcttataagactaagtcttatcaa<br>gaccattgactttgtattgacaaacgattaaaatggaccgaaatagatga |
| Contig40_<br>gene_978 | 966 | atggcagaagaagaaagcttaaaaactaatcaaagacatattatacatctcagcaaagcgcagcgctagagcgctactatatattgctc<br>atacattatcctgcaaatgaaaatgaaaaataattccatttgaatcaagcaatggcgaaactacacaggaaatccaaaatatatctatgaagaaatcg<br>tcagccaagccttgacaaggagtacacattgcgtagcggaacatggatattggactccagatgtgaacatcatttacttaaagaagaacaagaacaaaaccaaata<br>tttttaaattcctatattacacattgcgtagcggaacatggatattgactccagatgtgaaatcagaaggctttgactaccacg<br>catccaaacatgcatggaactccatcgcttgaaatagcttgcatagaacgttgcattgacatgggaaatcagaagggctttgactaccacg<br>aggagtttagaaaaacacatcatctcatcatatctggcaatatctcatcacaaaacgaatactcatcaaatatattcagaagggctttgactaccacg<br>gagatgcttgagataggatatcctagaaatgacatctcctggaagagacaatcagttcataccaaaggccaataagtttgcaacagaaatggacttcg<br>aaggacaagaaaatcattctatgccgatgattatgcctaattataaaatccattatttggtcaaggagatatgattggtccaagtacaatgat<br>ttcattatagaatgcgatggacagattggacattcaagagctttatctaatttcagacatgattaactgattattcctctgtaatgtttgatta<br>ttccatattaaaagaccatatgatcttctttgcatatgatcagatgattataaaacaatcttaggacttt |

FIG. 8B-11

| | | |
|---|---|---|
| Contig40_gene_111 3 | 967 | atgtctattaataagtcaaatctaatttaagcctaaaaataaactaaatcttattagtgcaattccaataaagcagatatcaatccaa actaataaggggacttcgattcactccatgacttagtgaatatagcatatgtcttgaaggcttcctacacttcacagactttgtttcaaatg agcttagatatttggttgaagatggcttcaatgtagttgtattctgctatatgatcctgcagacttgttgaattgattttgattgaagta attcgtttgatgagtcagatgcagtgaccctactggaaattggagcaattactattggactatagacatagtgcataccatttgtctatcc tccctgtacagaatatacatttccgtttgcatggatatccaaaagcccattctgcaaggaattcttacattgacaactatcacaagaatcatttgattgaaagg ataaattaataggttgatgagatatcaatattacaaggcaggctactgacttcttgattgagtcagcaattctacaagaagaggaatgtgagaaatattgt ggagtggataaggataagattcatatttgaaaagaaagaatttgatgtcttgatgagtgtgcagacatctagataatattcatctaaggggcgtttgacggtcctcaagag agcatttccgtttgttgaaaagcatatcaaaggcagatatattgcgtctccatgcagagagttgactacagagttcagcagcttcatgagaagaaagaatccttcattcaagcgctttgacgtcactaggt gtaaagagagttctttgataagcagcatatcagatagcgatttgtattgctatttgaattgcagatataaatattgcgataggatgaattcctacgtcatatttga ggcaatgcctatggagtgtgtgtgttgactacagaggtttcagcaatccctgaagttattgatgatgaagga |
| Contig40_gene_111 5 | 968 | atgaccaaaccaaaagtttccatgattttatcagcatatatgaagagattcatcgataaggccatatgcagtctaacaaaccaagccttaa agacatagaaataatcataataaacgatggatccaacgatccaccgataaaaaccaccagaaatcatagagaaatatgctgaagaagaccaagaatcactgtaa taaccaatcaaatattgggcttgagcaagcagataacaatgaggcaattgcccaaggagacataaggatcaaagatcaaggcgaaatcaaccatgctatcagatgataaattatgatgatgcaac tacagattagatgtcttgagatagcatacaatgaggcatacaagatacagagacataaccatgtatcagatgtataacatgattatgatgatgcaac aggacgaatatacgaaaacgactggtttaatcaaaccttgatgaaagctttgatgtatagtattacacctgagaaaacaaaagactttc tatttgacttatcagtaagttcatgccaaaagatcttaaggcagagagaattcaataataacagacatcattttattacagacaacatggttctatgatgactata gacatgccttctcttcttttatgtctatctttaaggcagatactgtgaagcggatgcctttatgcaagaatgctcttatgacataactgaagatgcataaaactgaaggtcgtaaggaacgttgttcaatctaataaaaa cacccatgtgtagatgcaaattatcgataaccatgtccaagataaatgtccaagataaatgtccaagataaatgtccaagatgggtgttcaatctaataaaaa agttcgacctttatcgcataacagataaagataacacagaatattacagattatcaggatcaaatatcagattatcttgataatctaggtccaaagaagaaaagttcttttagatgtaattaa gaagactatgagaagatataaaaaaataacagaataaaagacatccagaatattag gtatgacaattatgaggaattaaaaaaagaacaatccagatattag |
| Contig40_gene_112 0 | 969 | atgaaaattgtattgtggacaaggatatatcggattgccaactgcagcattattgctaaagtggctgtgaggttgttggcgtagacataaa taaggaaatcattgaaaagctaaaccaaggaatagcctatagaagagcctgaataagcgactcaatcaaaaatgcggtagaccaaggccatt atcatgcttcattaactcctgaggagcagacacattcatataacgttccaaccccatatttgcctgagatcttgctgtgactaagctat gtaatatccgcttgcaattcattctgaaatgaaggaaatgtcgttatcatcgaatcaacaatagctccaatgtctcaatgtctcacagatgaggt aatcaagcctatctcttgaaatgaagctatgtatggtgagaccatctgtactaaaaagctgaaagagtgtctatagaaccttgtaaaaggagaa aagagcttgtaaacaacaacagaataggtggaatcactgaaatgctcaaaatgcatgaaaacaccttcagagacgtcaacatgcacttgcgaatgagcttgctaa ataatagagactgaagcaaatgccagaattatcaaaatgcgttattgaacgtccctgactttcatctatgcaaagtaaatcaaggctcaaagacaatcaagactcagaagttaatatcaagcttcaaggatacaaataacagc gaggccactgccttgcaatcgatccatatttcatctatccaaagattcaaggcaaattcgagatatccaagaagacagccaaaaataatcaagcttcaaggatacaaataacagc atgccaggttttgtaatagagaattaccgggaaagttcattgaacgatattgtgagataattgcaggactaaagcgtatttggagtgctacaatgaagtgg aaatacagacgatgcaaggagaaagctgcattgagatgaattgcaggactgaaggctgcaggatgaagtgg |

FIG. 8B-13

| | | |
|---|---|---|
| | | ataacagagaattaggctggaaaccaaatacacatttgaaacaggaatagtggaaacaatccattggtatttgacaatcaagactgatgga aaggtaaaatccggcgaatatcaagatattgaaaagtgtactctaaaaagtag |
| Contig40_<br>gene_112<br>5 | 974 | atgaagtatcagtagtaacacctaactataatgtcttaaatttcttaaacgcctatttgaaccttagcttttcaaagtaggttcatagaaga<br>gatcatcatatcgataatcgatcatctgatgccagctgtgatcttatgaagaatacataacagtcctagctataagattgacataaactta<br>taaaaatgataaaaatcttggatttgctcctgcagtcaatcaggcattcgcttgctaatccgaactaatctattctgtaaacaatgatgta<br>gaacttgaattaatactataagaaacattaattcaatctatgaaagatccattgaagagggaaaaatccattctccattcagtcaagatgat<br>acagtaccataatagaagcctaattgatgatgcaggtgatgaatataatctacttgcatacataagaaactaggcgatgggagtccgattgaca<br>actacaatgaaaaaggagatattctcatcctgtcaggtgctgcaggtctcattgtatagaaaatccatttggagaaaataggtcttttgacgataat<br>ttctttgcttatgtagaggatatagatcttttcattcaggctataatgagttaagataaggcttgaaactaacctagagcctaaatcatctatcatta<br>tggaagtgctacaagcggaagcaggtataatgagttaaagataaggcttaagataaggcttctactcctctttaaggaaaagattggatgattattataagaattcccaattc<br>ctctaaagattgttaatttcatcttcatattcttggattttcataaatacctctctttttaaggaaaagattcggttcaatctattgggc<br>ggaataaaagagggcttaagaagaagagaataaagaataaaagaacccacttgaatgaaaaaactgaaaatattacttaagatagatgaagat<br>gattaagaacacatttggctacttttaaaaatag |
| Contig40_<br>gene_112<br>6 | 975 | atgagaatatagacttatcaattattgttgttaattataacacagggactatagattcttgttttagctgaacctactca<br>ttatacatatgaaatatcctttgtagacaacaaatcaacagatgacagccttgaaaaactcaagaatactttaaaagtgaaacagaacgaggaa<br>tattaaaatcattccaaaccatccaacgatggttttgcaaaggcaaatataatattgcaatagcaagcaagcaaaagggattcatctttttta<br>aactcagacaccttatgaagcaatccactatcgacaagtgcatgaattacaataacagacaaagcacgatgatagatcgcatagggctgtaa<br>ggttccctttgccatggaagtcttgacaaggcctgcaagcgcagcttccaaatcctgcaaactcctttatatgtttcatataatgtag<br>atagtgcaagaacgattataatctggatgatcttgatgatgttatgagatttatgagattgatgatgatttgcttgtaggcatttatgctttgtagaag<br>actacaatcgatgaagtaggcctttttgatgatgcttcttcatgtaatgaagcagcagcgaggatattgattggtgctaaaacaaagatatttatg<br>agtttatgggcaatgtatgtcttttataaaaagcactaatactaaaaaatataattcctttgtaaacattgcagtctatattggaatggagtt<br>ttgctaggttttaacttagttagaaatgcctcaggtcttga |
| Contig40_<br>gene_112<br>7 | 976 | Atgattaaagaaatcagagaattaaatgcaatactagtcatcatcatagacattattgtaattctatctcactaggccttgcatactttgtaag<br>attcagaaccacatattctcagtaggagctccctccattccatgacttactcacatgtttgcataattccctacttatatctat<br>tatactactctttggcttttaaagccattccgtaaccaatcatcaattttcaggatcatgctccctcttaagctatttgaagtctgacataatgcattc<br>atcatcctgttgctatttttgtcatcatcaatcagctaactttcaaggatcatgctccctcttaagctattgaattgattctcacaat<br>cgctgaaaggtattggtcgttcttgtcgttattgagaatgatgagaacaacctaacctgaaccgcaacatgctaaccgaaccaacgagacatgcctgg<br>cattcgagttgcacataagatcaactctaaaacctattggatacaatattgccgattttttaggaaagaaaatataggcaaacgattt<br>gaaggaaccaagtttatagcagctttgatgactgctcgtgtcctgtcaaagaccataagtttgacaggttgacattcggtcaagacaagccatcccctaagta<br>ttattaccatcaaacgaaatcgtgatgcatcgtgaggaaagaggaatcaaggcaaagcaaatcattccagactattcaaagttcaataagtctccaagc<br>cttcagttgacatgcttgatgacatgcctattcatcaatcatcgctatgttccattgatgatgccttcaattaagttcaagaagatagtctagat<br>tacttgtatccattgtagctattatatacacatctcaa-catgatttaactgcaattaagattgagttctccaggactctatctcttt |

FIG. 8B-13

| | | |
|---|---|---|
| | | ataacagagaattaggctgaaaccaaatacacatttgaaacaggaatagtggaacaatccattggtatttgacaatcaagactgatgga aaggtaaaatccggcgaatatcaagatattgaaaagtgtactctaaaaagtag |
| Contig40_gene_112_5 | 974 | atgaagtatcagtagtaacacctaactataatgtcttaaatcttaaacgcctatttgaaacttagctttcaagtagttcatagaaga gatcatcataatcgataatcgatcatctactgatgccagctgtgatcttatagaagaatacataacagtcctagctataagattgacataaactta taaaaatgataaaaatcttggatttgctcctgcagtcaatcaggcattcgttcgacattgcctaaatccgaactaatctattctgtaaacaatgtgta gaacttgaattaatactatagaaacattaattcaatctatggaaagatccattggaaagatggaaaatccattctccattcagtcaagatgat acagtaccataatagaagcctaattgatgatgcaggtgatgaatataatctacttgcatacataagaaactaggcgatgggagtccgattgaca actacaatgaaaaaaggagatattctcatcctgtcaggtgctgcattcattcaggctcaaataaatggttatagaaatcattttgagaaataggtcttttgacgataat ttctttgcttatgtagaggatatatagatctttcattcaggctataagtttaagataagtgttgctgcacgaatatgtttgatgattatgtaaaagaatttccaattc ctctaaagattgttaatttcatcttcataatttctttggattttttcataaatacctcttcttttaaggaaaggattcggttcaatctatttgggc gggtaaaagaagggcttaagagaagcaggtataagtgttaagaacaggaatagaaaagaccacctttgaatgaaaactgaaaaatttactttaagtaagaatggaagat gattaagaacacattttggctacttttaaaaaatag |
| Contig40_gene_112_6 | 975 | atgagaaatatagacttatcaattatttgttgttaattataacaagggactatagattcttgttttagctgaacctactca ttatacatatgaaatattcctttgtagacaacaatccaacagatgacacgccttgaaaaactcaagaatacttaaaagtgaaacagacgaggaa tattaaaaatcattccaaaccaatccaacgatgttttgcaaaggcaaatatattgcaatagacaagcacgatgatagatgcattaggctgtaa aactcagacacccttatgaagcaatccactatcgacaagtcgatgattacataacagacaaaggcacgatgatagatagcacctgatttgatctgcaa ggtttccctgccatggaagtcttgacaaggcctgcaaggcgcagcgcagcttccaaatcctgcaaactcctttataaattgtttcataatgtag atagtgacaagaacgattataatctggatgatcttgatgatgattgtttatgaggtattatgaggtagattgatgccttgatggcattgtcttgtgttagaagg actacaatcgatgaagtaggccttttgatgatgcttctcactataaggagcaagcagcaggagataatacatcaaaaagaaatccaaagatatttatg agtgtttataggcaatgtatgtcttttatataaaagcactatactaacattgtaacattcagtctatattgaattggagtt ttgctagtttttaacttagttagaaatgcctcaggtcttga |
| Contig40_gene_112_7 | 976 | Atgattaaagaaatcagagaatatcagacaatattaaatgcaatactagtcatcatagacattattgtaattcttatctcactaggccttgcatacttgtaag attcagacaccacctatattctcagtagggaggctcctccttccattcagtgactatttccacatcgtttgcataattcctactatattctat tatactactctttggtctttataagccattccgtaaccaatcatcatcaatattctcgtgctgaggacattgtaaagtctgacatatgcattc atcatcctggttgctatttgctatttgttcatcatcaatcagctaacttcaggatcatgctcctcttttaagcctatttgaatgattctccaat cgctgaaaggtattgtgtcgttctttgtcttgtattgagaatgatgagaacaaacaacctaaccgaaagaaacaacctgaagcatatgcttatcatcggagacaatgacttgg cattcgagttgcacataagatcaaatctaattgcacataaaacctatttggataccaatatttgccgattttaggaagaaagaaatataggcaaaacgattt gaaggaaccaagttatatatggcagctttgatgactttgcctcgtgttctaaagaccataagtttgacaggtggtcacaggtggtcacagtacttccctaagta ttaccatcaacgaaatcgttggatgcatgtgaggaagaggaatcaaggcagaaatcattccagactattcagaaaatcattccggctaagc cttcagttgacgtcttgatgacatgcctatcatcataatctccaa-catgattttaactgcaattaagattgagtcctcaggatctcatctt tactttgatccattgagctattataatcacatctccaa-catgattttaactgcaattaagattgagtcctcaggatctcatctt |

FIG. 8B-14

| | | |
|---|---|---|
| | | caagcaggaaggataggctataacggtaagccctt catgat gtataagt tcagaagcatgaaggt tcaggat g |
| Contig45_gene_62 | 977 | ttgggaggatttatcttggttgaaatatcaattgtaattccagttctataatgttgaaagtacttaaggaatgcttggatagcgctgtcaatca<br>acatt caaggatattgaaataatatgcataaatgatggctctacagacagt tcct tagatat tttaaaggaatatcaagagt ctgat gat agaa<br>ttatcattcaatcaggaaaatcaaggtcctgcgtcgcccgtaatcttgaat taataaatcaaggcaaat acgtatat ttct tggat tct<br>gacgat tat t tgaactgaat gcat tggaaaagct tacaatatctgt gaggaaaagt cat tggact t tgact t tgtact t ttcaagctgct taact t caa<br>tgacaaact ggaaaaaccttccaaacaaagtattataatatggcttcctaaatgataggatataggagataatgtat t tcatataaggat t tat<br>atgattgcgttttaatttgcagtgtctccaccagtctaagctatatagagagct tat tacagatatcgat tatccgaaggcatcatcttt<br>gaggtatgtat tctt t ttaaagaccctctaaagcaaaaagaat ctat tcctt gat gagt t tctatacaatcgccgcaggaggat gactc<br>cctacaagctcaggatctgatgat tat tatgtataaggagcttat taataagat tctccaaggcaat gat gtccataaaggagagt t t tcaatctaatc<br>tgaaggaggat tgtat tataaaagt tcaaggagcttat taataagat tctccaaggcaat gatgtccataaaggagagt t t tcaatctaatc<br>agagagattgcctaaagcataaggaagaaatcgtaggatatagcaaatgataagctaaggaagat ctaagt tcatat at gat ctgt gct<br>ttcttcagatgactataaggagttt cattatagatcagactt tatgataagaataaagat aaatgacttga |
| Contig45_gene_64 | 978 | atgaaattacagttgcgggtgtaggat atgtaggctttcactt gctgttctgctcgctcaaaaacatgatgttacagctattacaacaaccga<br>atcaaagcagaaatgctaaatcagttcaagtccccat tcaagacgat gagatagaaagat tctt taaggaggttcgt gaagagagaaccc<br>ttaatctccatacaacaactgataaggctgccgctataggct gccgat cct tgt tatcatagccactcctacaaactat gacgat gtag gcaat<br>ttctttgacacctctgctgttgaaggacgctatcgaat ggaccctt aaggtaaatcctgataggtcctcataaagtcaacaatacctgtagg<br>atatacagaatctgtccgtgagaagtatgaat tagaaacatcat cttcagccggaat tctt cgtgagt caaaggctctctatgacaacctcc<br>atcaagcagaat tgt tgtaggctgt gatgacgaccagatggaagag ggt cagatgtt tgcagat ctacttctt gaaggcgctagaagaggag<br>aaaagagcaaactctct tgaacaggacat t ccaat at t gct tacacacctaacagacct gccta agt actgctt gctaaggcctatcaagctgt ttgcaaacactt acctt gc<br>tgtaaggg ttagctact tcaatgagct t gacacat cc t cggat atgaggat act gct tgcct aggat acaaa cag ct g ttg acggagt gt catggcccctc<br>gtatcggaggccat tacaacaaccat gcct t gt tcat tctaat tcagt t agaaaggaaat t tat t gcaatcagat tat ttccaaggaat ccaaagacagt tgg<br>cctcaaaccat gat tgaagcagt t gt t cat tcaatgagtcatcgat tccgtgcat ctgcaat acagat gt gataagatata<br>ggt ctatagact tacaat gaa gagtaacag tgacaat tccgt gcat ctgcaat acagat gtgataagagta |
| Contig45_gene_71 | 979 | atgcatgaat aat aat tagtat tataat accaacataat tcttcaaaaacaat tgaaagaacaat t cattcat t t aacacaggat t t aa<br>aaat tatgagatggt t t t t gtagatgat gcatcaaatgat gat acagt aagt tgtatacaagaact tagcagat aaagt aaat tatcagc<br>ttatt gtaaataaaaacaataaaggt cctgcctat tgcagaaat agggagt at t t gct t ctagagaaagt at at t gt ctt gtt gat cgat<br>gatctaat t caat tt aaccatat t tcctcat tgcataat tat gt taaat cagacaat tt t gat t ccgcct t taca aaggaat aaaat aat aa<br>tcaggatgagct tatagat t taaagtggataaat at gt gct tgat tcat t t ggctcgtaaaaataaggaat t gt tagagccaagat t t ga<br>taaat ct t gaatgct tat gaaaat tccat t tcct t gt at t t at gt at t t at gat aaggaaatcat ct taaat at t cct agaat t cat gaa<br>gat tatagatagt gt gaggacactgat t tgcactgat t tgt gcaaat tgt ggcaat gt cgt t aat t gataaat act t at t t t t at ta<br>tcaagaggagat tct at tcagacaggt ct ct t tggataggttt gaat ctgtaaaactt t t gaagtctgat tccttat t t t aagaagat g<br>at t tgagagaaaagt tggt tcat tcagaatccct agat t tat t t tgcaatat gcaat at t gaat tct tctcacaat gat acaatagt gagatgt t |

FIG. 8B-15

| | | |
|---|---|---|
| | | tttaaaagatggatgttctgattattaacaagttaagtcagtttaaggtgtttgaaaaagagattggaagtttatcttaaggttagatt gtttttattgaatcatagattgtattataattgtgttaagtttaaggtttaaaatataatctataa |
| Contig45_gene_72 | 980 | gtgaatgatttaaaaaagttatatgtgttttgcttgcaatttaattgtattttatgtgtaggtattaactttcatataatgtttagacaccattaa tacttaactcatgttaatttagatttagttagtccaagcatggacaatgctaacgatgcaaatcatattaaaatcggcagtagttcattaccaaat taagcaaaattttaccgtgtaa |
| Contig45_gene_73 | 981 | atgacaaaatttagttactgccgtgcagttttatagtagtaactttataaaatatgcttgataagtatcctgattatgaaatagttaa tttagatgctttgacttactgtgaaacttgaaaatcttgaagatattgaagataatccgaattattccttgttaaggaaatatcatggatg aagtctttgatgttgttgtaagcagcgtagactacatagtcaattttgcagctacagtattcaattttgcagccttgaaagccatgtgaccgcagcatagaagatccgcagata ttcatcaaatccaatataatcgaacacagtattgcttgatgcagcctataaatcaaaaattcctacaagtatccacgacgagt atatggaagcctaggcctagcctgaaggatattcaccgaaacaactcctctccaggctaacagtccatattcagcttcaaaggcaggtcagacctca tggtaagagcatatggagaacatttcgaccttccaatcaacataacaagatgctcaaacaactatgcccatactatgcccagaaaactcatc cctctaatgattctgaaggacaggagctcctatatacgtgacggaaaaacataaggactggctacatgtctacgaccactg ctcagcaatcgcctagtcctccacaaacagaaccagagaagctaataggagaagtatacaatatgtgccacaacgaaaagcaaaacatagaatagtaaac tcattctcaaggaagaacttaacaacacaaatacacatttgaaacaggaatagtgaaacaatccactgtatctagacaatcaagactgatgga ataacagagataggctgaaacccaaatatcaagaatattatgaaaagatgtactctaaaaataa aaggtaaaatccggcgaatatcaagatattatgaaaagatgtactctaaaaataa |
| Contig45_gene_74 | 982 | atggcaagttaagattgttaaaagtgaaattgaagtgtatttacagttgaactgaacctaccgttttgaagatgaaaggctacttatgaaac ctacaatgagaatgacttaaggcagagggattgatttaaccttgttcaagacaatcaatcaaagtcatctaaagtgtcctagagtctcc atttccaatacacagcacagcacaagaaagctgttcgtgtaataaaagagaagtcttcgatgtgggatgttggatcttagaaagactcaccaca tatgaaaatggtaggggaaatactctctgaagaaacaactatttataccaaaaggattgcccatgcgcttttagtattatcaga tgaagcagaattgtatacaaatgcacagactctacaaagagatgatgaggagaatcaatgaacgatcaacagaataggaataagatggc cattgggaaatcttaaggaagaagataataattttatctgaaaaggacaaattatggaagccgatgaaagagactccaactgatttttga |
| Contig45_gene_75 | 983 | atgaaggaataagtattagctggaggttctgaacaagactgtatcaattacaaaagctgtatcaaaacagttattgccttttgtatgataagcc aatgattattatccaatttcgtttcttaatgcttgccggaattaagcttgccggaattaaacataattaatttctactccaaggatttgcctatgtataagaac tttaggtgatgagaagaatttagaataagctttcatatgaagataagcttttaggagataatactgtattcacggacatagattagtgaaatactgaaaagagctatgaaccttga agaagtgcagttattttggtattactcaactcaaaatccagaaagttttggcgtagtttgaattttgatgatgaaagttttatccgttgaag aaaaacctaaaaatccaaaatcaaaattatatcccaggactatcttaaaggaaaactatccaaaaagcatccaaaatgaagacaaagcgtttatgtagcatgtgcagaga tttagggtgaaaagaaactacctctgttaatgacgagtatctaaggatgacctgaaccatccaaaggaaaactatccaaaaagcataagcctc agataccggaactcatgacggctgcttgaaggcgcaattttatgatagaactatccaaaaagacaaagcgtttatgtagcatgtgcgaagaga tagcatttataatggttatattcctaaagagaacttctcgaattagccgaacctttaaaaaactatacgggcaatatctctaatctaaactg gcaaaaatgaaaaataa |

FIG. 8B-16

| | | |
|---|---|---|
| Contig45_gene_76 | 984 | atgaacagatttggaatgatttaatttacctttattttatgaattaaaccagaagtaattgttgaaatcggttgttgtttaaaggagaaatac<br>aaaaacattttagaatattgctattatctaataatcaaagttatcgatccaaatcctgattcttcttttgacccatatctttaaaaa<br>ataaatatggagataaattcgaatttttaaaggaattaagtttaaatggcttaattaatagaggattatgacgctgtccttattgatggagat<br>cataactggtatacagtttatatgagcttaaattaatccagaacttattccgaaatatttccgctaataatctttcatgatgtttcatg<br>gccatatgctagagagacctttattataatccaactttaataatgcagttttgagaatactcctaaaaatggagtcttaacagccatagagatttt<br>atgaattgggagatattggtttaaatccaactttaataatgcagttttgagaatactcctaaaaatggagtcttaacagccatagagatttt<br>ttagatgaaactaattttaaattttatcattcttctgtttaaatgcattctatgatttgtgtttgttcctagtcaatcatgtgatgaaaaaac<br>aatattgcaaatttttatgatagtgatgttataggctttagaaaaactcttatttaaaattaagattaaattaacacaggaacacattattaaaaata<br>agaatattgaaataaataacttaaaagatgaaatagataacttcttaaaataaaaaaatattgattaactgcataatttctaattagaaaagaa<br>ctagcaaactaaacaaccaaaacagaaaatagaaaactcttaaaaagaactagacaaactaacacaccaatatagacttaaaagaaaaactaatcatttc<br>aaccaataaccaaaaggaattagaaaagtattagaaagtctaaaagtgacaaaacctacctagagaacgaac |
| Contig45_gene_77 | 985 | atgacatataaagtaagtataattattccagtatcagcagagtttattattaggatactttaaaatctatagaaaatcaaacaatgga<br>ttttgagatattgaagttatttagttaatgattgttcaacagataataacagcgaaagtaatgaatatgctaaagaacatgagaatattg<br>ttccaataaatcttaaagaaaataacgtcaaccaggcattcaaccaggcattcaaacaacattgaattacctatgcaagcgcagactatcttatgttttagat<br>caggacgatacctttaaaagaaatgcatgtgaaacattataccaatataccgaaaatgttgatatgtatgtgtaaccacaatatcgt<br>aagcaatgaagatctaacattttgctttaacttgcattcgattggccgaagagatgaaatcaataagattgacgaaaaaaccaaattcctaa<br>caatggagttgcagcatgttcagcatgttctactggcagaaggaataattctgcttaaaatattaagaggaataattctgcttaaaattctcgttgtggattactccgaaggagttgggaagatatattc<br>ttctcaatcagggcattgttactggcagaaggaataattctgtgagttttacttaattactgtgaaaaaacataaaaacgacaattatacc<br>ccaagtcaatgcagaatatcttgatgaattctgtgagttttacttaattactgtgaaaaaacataaaaacgacaattatacc<br>atccttattcaatgcaggctgaacatgtcgaacatgtcctatccatcgttttgaagatactcttctatagaatcttttttgatacattgataaaagatgaatatcc<br>catgaattgtttaagaaagtgctgagaaaacattgtcgttttgaagtaataggaagaaaattgacaaggagtaaaat<br>tttcgaaaatagcattaatatatacagcgccattaaaagtaataggaagaaaattgacaaggagtaaaat |
| Contig45_gene_78 | 986 | atgagtataaaaaataaaattgagatatatctggctatgatgaaaatatgctttgcccatcttgcccattctgcccattctgcccattctgccctagctgcgctagctgttgcgctagctgttgcgctagctgttcgctagctgttcgctagctg<br>ggatattgaaaatgagatatatctggctatgatgaaaatatgctttgcccattctgccctagctgcgctagctgttgcgctagctgttcgctagctgttcgctagctg<br>taacaaaccaagtttagagctttcagaagatatgtcttgcccattctgccctagctgcgctagctgttatatgtttatatgtttatatgtttatatgttta<br>aataatgacaaatatctcagattatatcctgattgttcgctagctgttcgctagctgttcgctagctgttcgctagctgttcgctagctgttcgctagctg<br>agattgcctttaagcgaatatggaagaactgagatagtttctgtaaaaattttaatttatcaaaacagagtaacgataattagtct<br>tgcttagaataagtgtccaaggcaagaaagtcaatgtgtttcgtttttaccgtttttacctgcaatgatgtttgtataaaagactatataactattt<br>gataacgatgatatgtttaatgttcaaatcgtttttggttcccacagattaggaaacagtcaaaagattacagatgttgcaaaagataagcatta<br>tcaaatttcagctatctcaaagaaaaacaatacaatgtaattgatgatgatgactttgaaaaaatgaaggcatcgattagtctcaacttgca<br>atccagatatatattttatgtcttgccttatcttgccttatcttgaggatttcctaaaactatgaaaatcagtaatctccatccaacatattatgcatat<br>atcccatatgggaatttgtagagacaacttagacgattatcttaattcggatgaattgcatgaattttctgcagtaccga<br>agaatatctgattaattctactgaaaatctattgtcggatcaagtaatgtagtcttagcaggttctgctagga |

FIG. 8B-17

| | | |
|---|---|---|
| Contig45_gene_79 | 987 | atgggtgtagtaatgaaaagaacaatttaataaaagataacttctgtcgctaattactttgactagcattaaggaagttcaaatccaa
ttcttatttaattatgataattacctaaaaaaatatcctgatgtaaagaatctgaatgatccttaaacactatctattgcatgaattg
atgaagagccgtactaatttgatgaaaatattaatcatacagtttagttgaaattccgtttatttgatatgaatactgtgaaaa
aacaatctgaaattgattcctatagtaaagcattaatgcattaatgcttcttgaaaggatataagaaggatacaaccaagtataaaattaatgc
agaagaatattatgaagttcgtcctgatgttaaaggctgttaaaatcctttagttcattatttaaagtatgaagtatgaagtaacctcaa
tgactgaaaattttaaatcttaaagagtatcagctcgttaaaaattcaaattattattaattattatgaaaaaatcattgattta
agaaacgaaccgagcaattatcattatttgaggaatctgctgagcatattgaggaatcggatattgaggaatctggctgaaccctttagttcatttgattatcaaaaaggatataacctgcaatagttcaatgtgtgaaattcattttaa
gaaaatccgatattgaggaatctggctgaaccctttagttcatttgattatcaaaaaggatataacctgcaatagttcaatgtgtgaaattcattttaa
acctgaaagatattcttattttgaatttggttacaaaagagatataaactagcagaatttgatgggaagaatacttaaaagatatcctgaagt
ggttaattcattattgaatttggttacaaaagagatataaactagcagaatttgatgggaagaatacttaaaagatatcctgaagt
taaaaagcaggattttaatccttagttcattattgaagtatgtgtgaatagataaataggattaagaa |
| Contig45_gene_80 | 988 | atggaattttataaaataatatctcaattcgaaaaatgatagataaaatatagaaaatatagacatagattcaatgaaataatctgtaatttttaggttcta
agtaaaaataatatttatgttgcaacatattttaatattccacattattcctggaaaaatatactggcgatcttcaattccgtt
atctaggcgtaattctccattaacttatttaatgttgtattagttgttttattaggttaggttgtgtgattatttagggattgagtataagcttaccaattatatga
gctgaaatcaaatctatctgagataattgtattgttgagatgatgtaaaattagaacttcagataattaccaatttataattatga
aaacagtaggattaaccattcaaatagcgtatttatagggataatgttttattagttgaatcttcattattcaagaggagttaaaataggtt
ccggatcaataattagccatgtagttctgccacctgtagttttctaaagctcttttcaaattacatatgtattaggaatcctgaagaatattgaag
gaagatgttactttgtaaatgatttcaatttagacaagattatactattgaagagattaaaaactctcaatgaaaatgaaagtgactttga
ttttgtagaaaagaaacatatctttagacaagattatactattgaagagattaaaaactctcaatgaaaatgaaagtgactttga
ttttacagaacaagcataaaaccgttctcttcattgagtaa |
| Contig45_gene_81 | 989 | atgaaaagccaaaacaaaagcgcaaaagaatctgagagagaaaaacctaataatctaaaagtgattgtgtgaaaaatttatatgttt
acattctggagttacaggaggtactttctaacaataaagtttgatgaaaagaattgatgtttatttattgagtgctgaaa
ataagttcttaaattattagcttttccaataacaaattaaaattaataagaaaatatcatagaaatatatgaatcaatgtagaacaagagag
acagaacaaataataatcatgtctgtaaccatgtttgattgataacaatatgttgttaatattgttaattataacataga
tattgtccataagacatttgattaaccacatttattgataaatttaaacataccattatttgtttttatccctacatactact
tttattttttatgccaatttgacacatttattgataaatttaaacataccattatttgtttttatccctacatactact
atgattcattaagcgatataaattccaaagattttatatcagaatgagagttaatgttttaaaaatgttaattatataagtctttgaac
aacttccttttgtaaaaaattaaaaaacagatgttgaaataaacagatgttgaaataaaatctgtccagctaatcattaaacataatgaag
attttcccaaattaaaaaaacagatgttgaaataaaatctgtccagctaatcattaaacataatgaag
ggttcgcaattgattaaagaacagatgaattcaaagaggatgaattccataaccttttcatttttaggaaattgtcatgtgaattgaagaata
tggttttctcacgcacttgaaacagatgaattcaaagaggatgaattccataaccttttcatttttaggaaattgtcatgtgaattgaagaata
tggttttctcacgcacttgaagaagttgaagaattcattgttg |
| Contig45_gene_82 | 990 | Atgacaaaagttcagtaattattccaatataacgtgaaaaatatcttaaggaatgtttgattccgtctgttgccaatcattaaagatat
tcaaattatctgttaatgatgttcaactgttcaactcgtaaaacccttttaaatgttttgcataaaagacaaacgcataaaaataagca
ctgaaaacagaagggtcagcacgttaatactgcaaatctcattaaaagaagcccaaggagaatatagttttgttgatgcagatgattagt
gaaatgcttagaactcttctatatttccatgcaaatcaaaagattggatatgctttttttcaaatgattatattatgacaattcaaaaa
ttatgtttgaaactgaattatataatcatctgtgtttgaagaaatgcaatgatgaagagaatacaatttttaatttaacgatataaagaatttt |

FIG. 8B-18

| | | |
|---|---|---|
| | | tatttaaatacccagtttgtcctgttctaattatataaaagaattttagatcaaatgatcttatttcccagaaggcatgtttttgaa gacaatgccttttttacaattcttttattaaatccaactgtcttgatttttaaaaagcattatatatagaagacgccatgccgactccgt tactcaaacattgataaaggaagtttgatattgttaaggcaacaaataagtattagatgtgttttagaaaatgaccaatatctaattta aaaggaacttattaatcatacgttctccatgctgctgttgaatggtttaacaaatccctctagaacttaaagatgaattgtttataggttaattaaa agagatttagaggatttaataattcaaaagaagatttaagaacaattgaaagagagaatacttattaatattgatatttccgataagaacaa atattatttgattcttatctgaatataagctatcctcagcagattatgatatttcgataagaagatatt |
| Contig45_gene_83 | 991 | atggcactgattgagaaacgaactcttcttattggagaaaatcgtaaaaaagaattttgcagcaaatataagattcgatattaggatatt ttggagtattttaaaaccattattaatcatgatttttacttactaatcataattttcaaactatttgcggaagcattgaaaattatccagttact ttttatccgaccaaaactatttcttgatttttaattctgtcacatcagtatcagtgtcactaaggcaataaaacattaaaagaact gctgcaccaaacatatttttacgttagcaggagtcgtttcagaattttaaattttaattacttaataatattaattgtgtcatgattgt gaccagatcccccatttatatatttcagacatacaacattatgggcgttattacattaatcattatgatactgcaattctatccaatgaac ctgtttatgtgtttacttttacagacatacaacattatgggcgttattacattttggtatagccaattttctgctatgggaacaatacc ataatccctgaaccgttcacgaataatgatttaaatccaatttttggtatatttagtgttatatgtttcaagaaattttgagaaaagattactt tgaattttaa |
| Contig45_gene_84 | 992 | atgaatcaaaaagagatgaattaaatctaaacaaataacaaatataaacttgattcagaaattgataaatttaatcttaagaaaag agatcctcaaataaaatcagatttaatagctcagcaacgcatgcagcaacgcatgaaatgaaaattctcaaattgaaggagaatctgaggaaatta aagtactctccaaaagcataagaaataaggtaa |
| Contig45_gene_85 | 993 | atgcaaagaaaaataaaaaaataactaatgaaaaagagatagaaattcaaataagtatgagaatgaatgataaaaattgttcttgagaa tagcgctgttgttcagaaaacaaggataaaaatgatgaagctaaaaatcaaagccaaaaattctcaaattgaaggagaatctgaggaatta ttccagagcatgttttagaagagaaccaaaatccttaaattcttaattcttattaggagcagttgatgtttcaatcaatatgaagtggaaattgttgaagga ccaaacatgggaatcaaaagcctattcaaaatgccgaggtgaaatcggaatgatgaaatccgatcatcagaaat catcaattgaagtaaaataatgaacctataattaagaacgatcatcagatgtagatgagtccttgtcatcaataatccagaatatcatcagaaat accaagagaaaaatctaaatttcatgcttcaaagttattcacaggtatttatgaacctgattgaaaaaatcctaaatggtgc aggaaaagcacattgctaaatgttatcacgagttattcacaggtatttatgaacctgattgaaaaaatcctaaatggtgc taggtgcagttttgatttataattattctgaagagaaatatctactcaaatggagcagttgtttaggttgaagaagttttagaatcaaaa tttgatgaaatggtgaattgtgcaacttccagaacttcagatttagtatggaggtgcttgaagtaggagatgtgaactttcaga |
| Contig45_gene_86 | 994 | atgaattataaattagcattcattccagtataccaatgtagaaaatcattacctaacctcaattatttcacagtcaatatggtat tgaacctagaggtcatattagttgatgataactctacagataatagtgcaaatattataaaaaatgttagcaaatatgtaatttaag gaatatactgtgacattggaagtgggttctgtgcagacctcagaaaatattgttttaagctatgctacttcagagtatataatgtattagatct gatgattggttagaagaaactgcctgtgaagttttattatcacttaataatcatcattaatgaaaatgcagacatgttgtgggagtcaaacaagactaga caatgagggcaataaaatttttattatcacttagggttactacaattactgaatgagattacaatactcgaatgattacgaaacacacagg aaattatagacgatccgaattttaagttagtcgttacagattagataaaatccaaatatttttaggacgatgcaaatgtctggggaaaattttt aaaaagaccctaataacagaaaatgaactatcattccaggacatagttgctcaagattgcaagatccagtttttattaactccttttcgttgctga |

FIG. 8B-19

| | | |
|---|---|---|
| Contig45_gene_87 | 995 | aaaaattgtatttataaacgacataattgttcattataacaattacgttgcgatgatgataaatccgcttcctatgtaaaactaaaa<br>atctattggcagaatcaaagcatatgatttaatgatcatattagtaataaaaatttcaagaagaattttctacagatattattagtaggc<br>aaattaaattactggttaattcattttaatgattctaatattagcacatatgaaattaagcttcttttaaaaaatattctcattatttag<br>taattgttataaattaatacaaatctacgaaagatattaaaatattttaaagaaatagatgaggaaatt |
| | | atggataaaatagatatttacttatggatacaagataatgacgacataacctatgcagttagcccacctatcttaagtctttttatt<br>gtcgattatgatgtgattcttatactttatgaccatattgcaatgttcccaatgttgtattaggatgcaaacgaaattttagataaat<br>caaaatttttagatataaaggagttttaaaacatattccggcttcgcaacctttagatataaacgtctatatgaatggaggcacttgg<br>ctggatttgacctgctttaattaaaaggcttccgatgaagatatttaatcggttccagacacaggagacatctactccaatccaaataa |
| Contig45_gene_88 | 996 | tgcactgtttagatcccccaaagatcctctataaagacaataactgcgattattccgaaaaaagaggttcagatattaatcatgcagaaacag<br>gaacttacttcttaaaaactattgctagtgaatttccagaatattttaaagtgcttaaataccaatactaaaactctaaaactgaactggaac<br>gatgttggggattaattagaatcaccggaaatatttaaagttttcaccactttaaagacataatttaaatctgaacgattcatttatcatcctcttttaa<br>aaaatttgtagaatttccaaagatctgttttcaccactttaaagacataatttaaagatgctgcgattcatttatccatacctcttaa<br>tgaaatacaacatcactacccaaaacaattcaattgcagaatctaatagcagattggattattatcttatctaaataatttcaaagatcgtttcaaaat<br>gaatcaaattacaattcaatcatcatgttgaaaagcgaatcgccatgataaaattaaagaca |
| | | ttgttgatgcagatgagttcataatttctgataacgtcaaatcctcgcgaaatcattaaaaaattatgaaatgatacatcatcggatacgttagagcaat<br>gtggattacatatgttccaacataatgatgactataatataaattattcccaaagtaactcatgtacggatgaaagtttagagcaat<br>attataaggttattgtacctaaagtttaaatttgtaaattaaagattgctcatttccaattcgtgttgaaatggaatcataattaaattgcataattcaataga<br>aatgattagtaagaaaagtttaaattaaagattgctcatttccacttagatctatagcaatgcatatctaaagttcaattggtgcc<br>caataattgcataaaatttatataacttgtcttggggttccattggaaaatgctttgacaaaatttaagagagaatgatattcgcttg<br>atgattagaatttttgcaaaaaattatgcctggtatcgacatcagatgatattctaaaaaatcaaccaatcaatctagattttgcgat<br>aagatagaaataaagatatgattttgaatataattacctagaaatatttagaaaactatgcttatttgccgaagaaatcaggattattgatgtaa<br>aaaattaaaatctgttccaattttagatgactcccacgcaatattcatcctataattcattattgcttacatataggaaaatatgaccctgcgga<br>ttttttcaacggaatatattatttaaacacatgttgatgtgcaaattctgaatgaatccattcgttcactatattaaatgaaaaagaga<br>aatagaaaaattgcttcctcaaaatctgagaatttggggttcagtaa |
| Contig45_gene_89 | 997 | Atgaattgatgaaattacagttgcgggagtgggatatgtaggcttctattgtctatttgctgccagaaacatgatgtaaccgcattac<br>aactactgaatcaaggcagaaaaactaaccaatcataagtcccatcagagatgatgagattgagaggtttttaaggagactcgtgatgaa<br>aaaggaaattaaacctcacacactactgataaagaatctgcatataaaaatgcgatctgtcattatagcagcacgcaactatgatgat<br>gtcaaccattttttgacacatcggagctttgtgaagatgcatagaatgactctcaagtcaatccagatgttttgatgtcattaagtcaacaat<br>acctgtgggatatagcagtctgttgtgaagaatatgtgtcaaaaacatcatatttctctccgaattcctccgtgagtcaaggcacttatg<br>ttggaagaaaagagatctgattctccaagcagaataattgtgggatgcgatgacgacagatattcctattctaatagcacccttcacgaggtttgtagaccttcttttggaggtgtgaga<br>ctatcttgcattaagggtaagctactcaatgaacttgacacctttgccagacgaaaggtcttaacacaatataatcattgactgtgtgca<br>tggacccaagaatcggaggacattcataacaatccatcattcggatacggaggttattgtcttctcaaggatacaaacaattattagcaattgc |

FIG. 8B-20

| | | |
|---|---|---|
| | | aaggatgttccacaggccctaattgaggcaatagtcaattcaaatgctgtgcgaaggaattcatcgccgaccagattatttcaaatatccaaa<br>aacagttgcatatataggcttattatgaaagcacagcgataacttccgcgcatccgccatacaggatgtta |
| Contig45_<br>gene_94 | 998 | ttgggcttagattttcagttgtaatggcagcttacaatagcggagcatatatccaagagactcactactaatcaatcaaagcctgactt<br>taaggaaaacatccaagttattatcgtaaatgatgcaagcagtgacaatacagagtctgtatgccaagagtctgtgccaagtacatcaaaaactatcctaataaca<br>tcatactaatcaacaacagaatcaactcggcctgcccatacaacaagaaatgtgggcctccattatgcagaaggggagataatcaactttagac<br>agtgactacatatcaaagaagaccttgaacgttgtagattccttcttgaagacttgttcatgtggacatggcatcaatccaatcaagtt<br>tgtagggtccaagcgtggagaccatccattaaactaaatataaaagggcacaggggtcataatctcctaaatcctgatgccatacagctat<br>cctctgcatcagcattcttcagaagcgacattcttaaagctagccttttcaatcattccagtctcgctacgatgatctgtctgttttac<br>aatgacaacagtcctgtttcagattcattcctcaaactgcacttatttttatagaaaaccatcagtctctgaagatgctcttctaatcagatgctcct<br>tagaaaccctcttcttggaatactctcaaactgcacttatttttatagaagaagcaactgataacacttcctgacctttatgaaaggttccagattcattcaa<br>acaggtctatcttacatccagagtaaataactatatgtaaggcttattaacgatccctatggacctagaagaccttactcacctatgcaagct<br>aatctccattctattctatattggagacaaggtgtattcaatcaaagtccatcccatctatcctaaagtcac |
| Contig45_<br>gene_95 | 999 | ttgcgttatatcgcagatgagcttaaagtcgcaagacttcagatcgaaagccctatgaatttgaattcattccaaaggatgagttcattgtc<br>taatatgaagaaattagccacctccaagtacattttctaactgacaacttttcttgccttcatgagattcaataagaagacaagctca<br>ttcagctatgcatgaactggaattcaagaattcggctatgaccttcttgaggatgaacagaagaccatgctaagttcttccttagggattcc<br>atccaatcttatgtgcagctcacacaatgtgattgacatttatgccgcaatttgacattgacatagataagtctaaggttctctccttagggatcc<br>tcgaaatgactattactctccagagcatctggatgaggactatgtaagacaatgagggcgagttgaacagaggtatctaatctaggggta<br>aaagatagtcctatatatatgctcccacattagggagacccctaaatacaatgctgtgttaatattttgacattgaaaagttcattgatgagctc<br>gggatgattatatatttaacttacagataaataaggatgagcagaagccttttctaatctctaacattcttattacagacatattcctctattcgattacagaaag<br>ttataacatagttaacttacaggccaatcattcttgcatatgacttggttaggtaatcagagaggatttaatctatctaacttgaaggagttgcaga<br>gaagttccggcagaattgtaaaggataacagagaagttgttaggtaatcagagaagagattttaatctatctaacttgaaggagttgcaga<br>gtttcagttgattatttgatgcatatagcagcagaaacgtatttgattatgttttggaggaataa |
| Contig47_<br>gene_70 | 1000 | Atgaagcttagtattatcatcatacctacatacaatgaagaggaatatcttcctaaactgattgaaagcataagtcaagagtttacagattatga<br>agtcattgttgcagatgcagacagcaatgataacaccagagatagctgaagcttacgatgcattgtcgtagatggaggcttccagcaatcg<br>gaagaatagggggcgctcagttgctaaaggagaatctgctatttttagactctgaattgaccgaacattatcttgaaatgtcata<br>gagaatttgaagaggaagtttgggaattgcaataccccagatgacccctctccaaaagaaaaggacatctatcttcataactagccaa<br>ttggtttatgatagctgtagaaaacatcaagcacatggtgcaggatgctaggaaggagctccacgacgatgtggaggat<br>ttgatgaaaacctgacattgagaggaggaagactttatattgaaaagtggctgagaatatgcaataatgaaagtccttaagtcagttaaagatgctaaatagga<br>gtttccacaagaaggcttgaaggtaggaatattggacatgaaagtggtgcaggaatcagtcagaagatcatgattttaggggcaaaagaacaag<br>cgctgaagattaggattgaatttggacatgaaagtggtgcaggaatcagtcttgaagaatctgaaatagaacgccgtgc<br>aggaatcagttccaaaacttgaaagcagtcagatataagtcttcaaatagaagataactctccaagtcttgaagatagaacattgaaagt |

FIG. 8B-21

| | | |
|---|---|---|
| Contig47_gene_408 | 1001 | gaccactatccataactgctcttgacagcacagatatggagaggattgcagaaaagtccaaaaacagaaagcaaagttcatttaaaagaagct<br>caatgagtttaaggacaaggaatttgaaaccaaccagcttatcgaatatgaggatgaatcaggccatataaaac<br>atggaaaacaacaagtaaaaacaatttaaaatctgtggttatcatagctatattgcttattattgttttgggtcttaggctcaatctgtaga<br>tattggaggagttcctaatgaacttaaatcacactatgtagacgaaaacggtcttccttattcagtgaaatggactcatacttcaactacagga<br>tgaccgagaattatatgatcatggatactttggtgacactaagtaaacgtaccggttggatatgcattcatcattccctcagtaggca<br>gtaggtgattatcaaccgatgattgcttatgtgacttcgttcctacttctgtaattcctacttacatattcacaagaaggattacaaacgactagttgagcaattgcggcctcat<br>ttggactggggctattgtttcctcacttgctgtaattcctactacacacattcgcaggattttcgatacagatatgttcaacataacctgttattcttcata<br>tgattgtagtattaggtccaaactatattcacacacattcgcaggattttcgatacagatatgttcaacataacctgccttattcttcata<br>ctgtcttcttgttgaagcttttaaaaactgataagctatcatacagaatcatatctccttattagcagtagcttcaatagcgctctattccctttc<br>atgacaggttatatgtttattgttctgtaatggtctgtaatggtattggttatgattgtgttctttgtattatgcttctatttcaatattgagatttttagaac<br>cattaagaactatggaaataaactgaatggctgaattattgaaggtattaccggcctacagagggtttcacccttcaagcaggtgctgacgtatgcctaa<br>ttattagccgtcgagtaggtggaattattgaaggtattaccggcctacagaggtttcacccttcaagcaggtgctgacgtatgcctaa<br>cgtacttattctcgttgcgaaatgcaaattcctaatttagtgactgaggacttgtagttcattcctcgcta |
| Contig49_gene_169 | 1002 | atgtcaagtttaattcaattcaattcctacttgccttaattgttatcgcattgatatgtggattctttcatttataagtactcgttggttatgcc<br>ttggcttattggtaagcttgagcaggcaggacattcataagtcctccgtcccgttccattgtagctgagctgaaatggtggtattggta<br>taatattcgattcatcataggatcttcgccgaataatctcttccagtattgaccttccagcttgtgtttgtccttctgttgttctttctt<br>gttggaatcatcggcatggttgatgaccttattgtatttgtcctcaaggagaagctattccttctcttttggcaggcataccattatggtgggt<br>tgccctcctaatgtaggccttctataatgatcatgattccgatagcagtacaatacggtattcaatcaccccaaacatgcacttgcaggattgaatg<br>gaatagatcaggcctgggttatttcaatgaccttcacttataacaagtatccgccaagttttccaggggataccgtaccctatcattgggcgacaat<br>atgcttgaaccctcttctgcattcttattataacaagtatccgccaagttttccaggggataccgtaccctatcattgggcgacaat<br>cgctgcaattgcgttgttattggaaggtaaagctcatccgactcagctcattgtcctctaccgaacattatagtcagcgttaaagttctacagtgctg<br>gagttatgaaaggcagcagcagcacaatccgactcagctcattgtcctctaccgaacattatagtcagcgttaaagttctacagtgctg<br>gtattgagaaaagccgtgaatgcagcagcacaatccgactcagctgtcgatgatgatggggaataggcattattttttggtattctttgtatatattgttcactgct<br>gatgcctgggtaactcatgatcagacatttgcacagttttatacacttgaaagattatttctattatttgggct |

FIG. 8C-1

ORFs encoding the biosynthesis of exopolysaccharides identified from *M. ruminantium*: Amino acid sequences.

| ORF | SEQ ID No. | Amino acid sequences |
|---|---|---|
| Contig40_gene_55 | 261 | msneisqntegiflvvpayneertvsqiieciaergynvvlvndgsadstlelateskrkypdkifvvshvinrglgaalktgmmvalnkga kyiitfdadgqheisdipnvckplqdgeadavigsrpfedmplsksfanlvmnaltfifygrnvkdsqsglraftaeaaekidvvstgygvs sefikeisdknlrlaevittiytpetqhkgtdaivglkilgkmvidlfri |
| Contig40_gene_106 | 262 | mlrgrnmgmknllisksdqfnhykdkanqlkkenkelklkneelefknnelspeleegisliipsykgenhiqplleslekqtiskdlfevi flvngemdstidiltdfaksnpdmniiisytseggvsnarnigiriakreyigfldddfisdnylkalydhiapnrvvlsnfidideetge eigsrlvpysmnregifndvvvkltnlsiittakiipalavkgtdfnpnlnngvdvsyyarlypknhfefyfvskeegavyrirrsgsisr getsyqfnvldrlkviddinesykqvdksdelyvhflkilfdaqtyfiglyldeypqdrekvieevrkhnfeyfsyekleg |
| Contig40_gene_223 | 263 | mkilvvqesdwlkrnphqqhlmdrmvlrghevkvidypidwpkedskglifhrevhenvskvkpeadievirpsfikepglnyaslyfthk keikkqidefkpdiimslgllnaytgsklakqhgipfvyylidvlyalipekafqsfgkkvnmkaiensdlvitingklkelamelgskpet tilidagidlndfdpqlddsnirnmynisedtdtvlffmgwiyefagmkelamelgknkekyphmkilivqdgdaydrmveikeeydlgdqli ltgkqpyeripeflasadfcllpayideeimqdivpkiklyeylamekvviaselpgiskefgygngieyvqkaeevletaqrildegryeei skkgreyvksndweaitdkfienaleelik |
| Contig40_gene_233 | 264 | mskyneyqdktilvtggagcvgsnltrklaelgaekviildnmssayewnvptnenveliqgdilddeelkrvfkmkpdyvfhlaahfanqn svdnpetdlmvngilklqyaqltgverfvysssgcvvgldskmpfeehdisislhtpyqvtkllgelytnyfhnlydmpivnarffnv fgpgevpgkyrnvipnffywsmtkqalpitgdgtetrdwtfvgdivrngllsmgveeeaigeainlgsgkdhrvidmankvnqltgneegiay varrnwdaktklissidkakdligykptvsfddglervygwftdnwedierdaef |
| Contig40_gene_257 | 265 | mkdknvvtgglgfigshivdaliddnkvtiidnlssgkmeninpnhenltiikedlmdadlekilkdkdyvfhlaalasvpgsvaeplry nqmnidaslklfiacknnnikkvifsssssavygenpnmplkesenflpcspyaaqkascelylksfhesygldyvalryfnvfgprqdensp yaavipkfisailngespviygdgeqsrdfiyvkeiakanilsaesdyngvinvalgksmtinrlfeiisdvlesdidvkylderpgdikhs ladisnldkisfkpdedkfeeqlretvkwfisqme |
| Contig40_gene_303 | 266 | masivaiipayneealadviaktskyvdrviivndgsadrtadvraieagaelinhptnlgkgealksgfeaitddsiivtidgdgqhnpde ipiilkpliedgvdlvngsrylygheentpayrrvgqrvldiatnisagikvtdsqsgfrafspkarncfrfkdtgfgiesemlvdaaeagl kivevpitvrydvdgstkdpvthgvgvllkimkdkavrtfkk |
| Contig40_gene_304 | 267 | metqrimvtggsgfigtnlvnelrsrghevlsvdllhhedeadlysdsysdyvrgdirnyrqmerifddndkfdyvynlaaeygrwngegyy enlwetnviglknmirlqeklgfrmisfssaevygdyegimsedvmenrpikdtyqmndyaiskwagelmcmnsatmfgtetvrrpvncyg pheayspykgfipifiykalhglpysvhkghkriidyvedtantfanivdnfipgevynvgskqewemtieeysdlvleavgiddslvtytp aedfttkvktidfskairdlkhdpkvspkegikrtvewmkwyyried |
| Contig40_gene_305 | 268 | mtnkspeeieelkaqlskyrkenrilkercasyedriehfaierkelsraitqfesielelrqydleeliqntrklnhridilrrylqter edneklnelinkltkelddanyeisrltteffhklrvrknqrtyflenrldiaytklaqlkytlnefeelgfwdrlrgkkpesyddidi |
| Contig40_gene_306 | 269 | mkavipaagltrflpatkagpkemlpvydkptiqyvieesvnsgvddilivtgkgkrsiedhfdrsfelehhlktkgkedflkeieyisdl adihfiirqkkqkglgdaiycakkhvgndpfvvmlgdtitkdtvpctkqlidiyekyeksvialeevpdekveryglggeeiedsiykidkl vekpplrvapsnlaimgryvltpdifdcienvepgyggeiqltdalskldeiygqvfkgesydignridwlktslrfaleddsarddilefi keeii |

FIG. 8C-2

| | | |
|---|---|---|
| Contig40_gene_315 | 270 | milittggagyigshinklinksgyetivldnlskghkkavkwgslvnadisdsdklreifqnndieavmhfaafssvaesveepekyfknnf entanllrimkefrvrkfifsstaalygipkeipisesaelkpinpygesklmvenllkdesdfgglkyvslryfnaagadldceigedhnp eshliplvldaaigrrnsisifgddydtpdgtcirdyihvqdladahlkalqyleepfndsnifnlgngngfsvkevidtckkvtgidfevk vegrrpgdpdiliadskkaeevlkwkpeypdledivesawnwhkklhg |
| Contig40_gene_366 | 271 | mtvsflfvngaasvllnaidkekavtkiyimavifnvclnlvlipmfsydgeaistvlsvkyllsf |
| Contig40_gene_367 | 272 | miiiplsigiffyarlIidfIysnqyslastliqiiv |
| Contig40_gene_368 | 273 | mnqiksifkntgwlsvsqvitsicaflwtiiiarylgvsdygivsfavsftglmgivmdlgistyitreiakhkdlvrkyfnnififklila iilfilsglilyvmgyshltiivtlvftielifmsmttflngvfqafekvkyqaigailnssflligilitlgfdlgvisiafaytvaysiy fsymflsyvktfsrphledltnfireviiksipfglthffysiyfsidivmlsylagdyatglyksayniinvfttffvvyqsvifpvmskf fkesqnlikvsyelsvkylllliiipisgiffyarpvvdliysnqyslastpvqiliwtvsflfvngaavllnaidkektvtkiyliaaif nvclnliliiprfsydgaaiatvlseilititilyhiftdykpdlgllknviklivcgiilfvalylnlslwfaipvgfivylisflitks idddndryvirelinr |
| Contig40_gene_369 | 274 | mlmsiicvyndeevlekylleslktgneeyelilidnrnhefnsaasalnyggkkakgeillfvhqdvefyennlkdikyyfencqnlgiag vggvseenygrittnivsgipkstvsdysitditetqtldellliipkevfgkyqfdeetcydwhlygadyclnikqkgysvvlfpitlyhv seggsmsleyfktlkkvlnkykydvnriytncllshepnqlkldilyyseilhirnpitnlfsnfnflkkilk |
| Contig40_gene_370 | 275 | mqtvgmilcggfgkrlrpvtekvpklveikedyaildkqlfdfknaginevyllagfihekiqerygdeykgikinyviedepligtlnair lgmealgedkqvvirngdivadinlkmieygersdyfvtmfvtkmtspygivdisgdkitafekeplldyyinggiyftkglldfgefktg diektlfpvlakenklgyyreddlfwmaidtskelesvqkeyenktdkpwgyekvliytdkylltkelylkegfqtsfhyhndkdetmyimsg agyiefedrkeyfgkndsirikpgvvhsiiatentlhevstpflddtirvkdyytr |
| Contig40_gene_371 | 276 | msekkkikvkfvdfqdslkendnffidslkknfdvevsddppdylffgaygykhldydcirimwtienyvpdfnicdyalaydiiefgdrylr fpfflnrpeienvrktierkpidtsvktdfcsfvvsnewgddyrirlfhelskykkvdsggrslnniggpigmgldkkfefdvthkfsfale naqnrgyttekifdafaagcipiywgdpnieeefnpksfincndltveeavekikevdqndelyhamlneptflgdldkylqdfddflfnic naqplekayrdrimkgktqehqyklinrfyykpyfflikvaqklhiefigrkiyhfird |
| Contig40_gene_372 | 277 | mssqniqiyvvshseedikifseydiilpkkttallgsvyedydhwnyakdldlceevigeqcpeyldsykrvvegkdlyyynmfiapkeviapycdwvfpi rleredikifseydiilpkkttallgsvyedydhwnyakdldlceevigeqcpeyldsykrvvegkdlyyynmfiapkeviapycdwvfpi laevekrvdmtgydydyqkriygflterlfdvwmdkqnlrvkecelkvnglrlnvhmwivkrkivrwayvhiymgllhkdmrr |
| Contig40_gene_373 | 278 | mpcnrkreshiggnvyteekhninvhkygahifhtnnkevwnyingfaefnrytnspvanykgelynlpfnmntfyqmwgvktpeeakakik qqkaeanidepqnleeqaisligrdiyeklvkgytekqwgrdctdlpsfiikrlpvrftfdnnyfndlyqgipmggytkiiekmldgidvel ntdfledkdkwmamadrvlftgmideyydycfgeleyrgldfefetldmenyggnavinytdretpytriiehkhfenavsdktvitreypk awekgqeayypmnderntelfnryndladkegnvifggrlgmyryfdmwqvideaklklvksle |
| Contig40_gene_391 | 279 | mrlevvdksvtkninfrlvydsikayrlsselcdnfniknkdlfInpylInwislwlsrkntkeenkifleefdkIdktkkyglkylilkt tkllkiks |

FIG. 8C-3

| | | |
|---|---|---|
| Contig40_gene_450 | 280 | mkiamvgqfpphiggvghihslakqlireghevyvityphkdikdidgihvigtkginipglrglmfginakkelkklineenidiihghy lfpagwasvkagkstntktyvtahgsdifemykkqkfmrpfikkvlsdadivlavsnalkdeilkidvpgikekikihwnsvdiekykttee nkdkfkkelvneynldpnkpmilfvgniikrknvnllveakriktdanlivvgegselgklkekvnddkindvyftgarrdvediypscd llvlpsfsesfglvliealacgnavigsniggikeiitedvgllinpnsdqdlanaidkilqdeellnkfksnarnrakdfsktelpydelk |
| Contig40_gene_470 | 281 | mkiaivlgtrpeiikmasvmdeiengheliihtqqhydkemsenffidlkiptpnyihvgsghgaqtgkmmegieevlldekpdillv qgdtnavlagalvasklhipvghveaglrsfdetmpeeinrlaadicsklyfvpteesainlamegisrkrifitgntvvdacfrnleisks rdkdqydegiqeldidmdniltltmhraetvddkerltniieaieelsdmniifpihprtkktmenfnlfdrlndlphvhiikpvgylfdi lliskstiiltdsgglqeeaitldvpaltlrynterpetvtaggnilvgsdkevilenarkilddedfanrmksaknpygmgnaaelmikii eesdkndtlkmvapdevmasftrhmkavdeditvvdfeeknnslikiafqgedikypydelnlngliiiyedys |
| Contig40_gene_653 | 282 | mykdnkilvvipargskgiprknirflgkkpliahtiemgkaskyvdelvttdeeiikfisekfgaetikrdgklaedsipldpviydaa iqkegksnekydvvitvqptspllktktldlaieklinpdnenkdyctiisvvdcrhlswgydekekkyfplykervnrqylpkayketgsi fatrrefvkedsrlgeniglievskqesididnyedwvvaeriinkkkiiikadasheigtghiyrglsiasklvnhevifildeaqelgie ivknnnypfiithsnkgkgkeadekakeeiiekiveydpdiiindilntnskyktlrdngffivnfedvggvkyahlvfdalyehkiplk nlysghryyilkdefyyqsfkkidkevnriltfggtdpnnltektleailestkyneieiligysklkeeigekykdnerisiyenvkrm sehmhnadliftsagrtmyeiaslgvpciclcgnerelshifgniehgfinlgsrvskedlirtlentindyelriemnkrmgnvdlkhg fdnirklikkeyknwkaeqlnk |
| Contig40_gene_654 | 283 | meskditnieeiipsndvyplvnllfqsklfkskeintnslaisclidlidknrikitfneeieskisknpllktkgqlekeleImknikft inskemkldkrdqiilkmfkdinknhefdlksmydkilkgdiaikfakyfkdysksleretkyslenykdlikdgeftfkgneisnewkef ksslksdkslysqdaeiidkyliygrcleiekdvlkniekanpdydselyrflrhngadllklifdkalanskierkdgsvpvgnskyfvp qfg |
| Contig40_gene_655 | 284 | mtifneepfliaeigvnyydiakkenisnmdaaklmvkeahdagcnavkfqsykantiasknspaywdtneeptqsqyelfkkfdsfgeaey reiadyckeigilflstpfdfdsidyIddfmdvykisssdltnipfikkiankgkdiiistgastldevklaietienandkykgeagigi mhcvlsyptanedanlImiknikdlypnyeigysdhtkpdenmliitaylygatilekhytldktlqgndhyhgmdpddirkfnknielik tinggydkiplpcegesrkqarrsilakeeigegtiiitedmltykrpgtgispseidnvvgkkakitipedeliqydfle |
| Contig40_gene_656 | 285 | mtftvkeicqhiwsleekyelnhkeiggcypwqliirmylyyeitrktnvfesaqqssisladkvntflpfiknsilsnplsgkdtkdvlifd hprkvilngeyqdiysyflkdiliknksfetiespyinnhfrssankennvkyndrillgsfinktknrgklpftdeekdfietikrele safkieinlfniiedhilnfqydykkyielleIkrpkpkgvylvvayenkalvaackkknieileIqhgtispyhlgysypkntmlmntikei eyfpdkilsfgdywqnssfpiesdckiismgfpyfednsktfmkmadednkqilfisgvigkylselayelakelnekknkndlensen nesdlennytfiyklhpgeygtwrenyeylnkanefdnfkvidksepplyelfaksnyqigafstaiyeglafncktfildpvgveylddl idknivkvksseelinfiedednldlkeydkdyffknfdesifdeil |
| Contig40_gene_657 | 286 | mwaqvnttialvpnianlglpytmvrflsaekdkekirdsfypmisltfistvlicllflifghpiadalfngsmqvlyittaisffacmnl mlityfrtfqemkryslflvlqsyigvfvsiylytagynietvvlgiitgyaavfimmaflivrhlgfsfgkwsnlkeqlafalptipsnvs swvdssdkyvigillgsvavgcyspgyalgsillmflspfavllptilpehyekgdmaevdkylsysmkyyllltvpaavgmsvlskplly iittpeialggymvtpfvclgaifmgmygitnnilllileknttmilgkllwiivaisnivlnlilvppylniigaaiatllcymlafgvtaiasrk tmrlpfnrkelvkiliasaimgavvymmnpsgivnvlailvgvvvyfaiifvlkavtrkelgifkdlvk |

FIG. 8C-4

| | | |
|---|---|---|
| Contig40_gene_660 | 287 | mnilhvahffypclsaggvvnasygialnqvkdnnvhvytsdsckqrlkfedgrydvdvdgikvdyfrnlsnrfklatmldtplsayfrirk diknhdiihehrqtlailvshyarknnipyivqahgsvlpffqkeglknifdkafgfkilhnascvfaltevekegyikmgvsedkieiv plginieeyenlpepgkfrsrfniadgdkllifvgriheikgldllidafnllikdsssspiklaivgpddgyldtlneriaennlesqviit gplykrekhealvdcdlfvmpskyesfttsgleamacgkplvltknnhihdwvdgnvgiscdddeislkeamkkllfdddlsetfssngkkl ikekynwdminegilsiynrfi |
| Contig40_gene_908 | 288 | makkvliivtgrglggdagialnvynaltkrgmeceialdesapgilfkknmewnkviipqagghsatikttvnaatrsvkalfktrslik ekkfdlvlgilggaiigalaakitrtpsvsllitpldtkicgkigtptiilpennlflepnipdrmvksflpvndnislgdkkkaldklneh cselkkknpdamefdpskqtivfssgsslfektaqaidqfskysdrfnlvlcgdpleeefykyidetkiinvgfidwndllhladlavltn dglmlheamvcnlpvvilkrvkygryhdmvsifkgatiecdledldeaifdvvdnyddyakntatykeailsvgdniadiveksfk |
| Contig40_gene_920 | 289 | mseessskvakgsaililignvifrvggyiyrflmasllgpaaygilglittpfqgifqvlsaaglppaiakyvseynaldekdlarqtifts lkimvflglffgfimvfvaapiiltnyyhkpeallplqavglitpfsvivggfrgafqgvvkmeyilytraleqifmilmatalvilglstlg avlgsvlgfvasaisavyifkrymgkyippanpdfkfplkdelklaktliffsipvtvaalaemgiysictllmgaflpaaaigyftaadpi arlplvvsnslattilpatseeayalkdqvllekyvtapykygmffvipmcvgiaifargimglvyftnaaymngavslailvvgmtfysvyt isgsivqgignpripmyilligcvitlglgwyliplfgieggalattissfimmvpmfligfrmtkthapysflikvtvaslimaivsiivp nnvyglitgivvcpivyvimvillktlshedvaefrkyanklgpirkyankllfdidkhssd |
| Contig40_gene_960 | 290 | mvipafneeatvaqvvtvarklsyisevivvddgstdktveeaeragatvishkqnggkgvaiktgfknshgdivafidadvsnftptkidk iikpilegktditktkfaresgrvteltakpllsffpelnyeqplsggfagkrsalnkifekdygvdgvivldadvhgisilevdigdig hdmssladlnkmanevvrtiidravdygrvtmmdtlgnyirmaimglsliilglfmiffvpfiplvislvlavgialtiayilikvqrsip ilrkgdtstalksfvkmhfpvivsgliililmlstflsaatfndgrisveltsrnfvyspsddyhqtisvrgpytidsaienetdmvrippda lstlemsandtmiidgeyysvntsregevdvfrlskavrhdldlyprevipnsrlaevfngvivnhninfnnssevmegyvqfsispkatna tffnltldneslIssvgnfknds yytiayddilcaftgddikkgnvtfeyagkcgmivfedrnntsirnfidsdrdsfvklytl |
| Contig40_gene_967 | 291 | mktrisviipiynvhefledciesvlaqtinhwdlvddyqrnlqililvddgstdcsgeiaksyaakyenveyryeengigharnygcefae gdyiifidsddiippkayermyrialkndsdltigsvwrfnskltwasniheiafggtkelthikespelfydttawnklikfsfwkehgfq fpegilyedipvtmpmhylannvsivyencylwrvrdgisksitqttddlknvecrlyvmglvdkfnenvkeeelhrvknlkwiknd1mif inklksmdidesqeiidllldyidrnidpkyfdeineieklkyeylferdfdrllkllnyehvnfytlnihskgsdvviegdkdvfktssfi vndfikegkkakyiqkvnleeealevsgfvvipgleakefkdveysfylvnsenrkkialrheqiylgninsyrlrfgkkfsykaagytvfv pyeliednedflgenkliivfkqrgvthnifagnakknvrsrsenravligktymsigydknneiiinvskarhsydrieieddlcifgpy dgdvflhynksfispesnipfayddgngcyrldlnirsteggilydngeslvykdkellclysskgqcvissllldhnikinkfknfslvse isernneidivsrlhsldigdrqlksatlyffldknqssypiaeakiikdvsttqdshigdnayiddkdsedidsssIngentyelnfknm nnkiitenlyhgyfdllirydfgdlvfstpihllddfkallkkkvfhftiyrgnawtlrirakkwnwdgrpriytrayrifkhlpinkkr imfesmwgakyscnprylyeyidenhpdyeciwslndehipingngirvrrwtlkyfyylatskyfvdnvnfneryekrepqryvqtmhgtp 1ktlgldvpgdfptkaseerfiercsrwdyitvqseyvediarscfkfdkdflrygyprtsmlytmnneedinkikermnipldkkvilyap twrkknkveiml |

FIG. 8C-5

| | | |
|---|---|---|
| Contig40_gene_969 | 292 | miipiynvyefleeclesvvnqtindmeltdgyernlqililddgstdsspiiakeyaqnyenieyhhevnglgharnygcefaegdyiif<br>ldsddklspnayewmyktairndsdmtiggfwrfnskkykisninkiafngnkekthisespelfydttawnklikhsfwkknhgfpegil<br>yedipvtipmhflannvsivyencylwriregksksitqttteiknledrlyvmglvdkffdenvdderlrhvktmkwlktdllifirklrs<br>mdkeggykimslirdyiqmnidadefkylneyerlkyeylmddeidkivsilnfkaeniketkvyqknghimfnadkevfkqspfyidqyir<br>erynrkyigldieirddgflirgfmlipgldiknfkdrehrfhltnanshkkikidsedvetgnissfnirfgrgfsydaagykifipfskic<br>ddeffgenrisvdfklngiyqspflsyekkelcqnfflgyakkdirqktnmkaviykntyfliirytlkdeilliealplknyfkeirldenv<br>lkldsdhignlyiyyeadsineeekiafeydnedksyqidirklkkpgkilcdgensiykskelillldskyygclistlndyyldiyyfds<br>ltqvldirqnrdrididaklysnrfnetrstykadriktaklyfkddsskenyilsdgmidrqtgdikfsidfsnkeitknlyekihdlyve<br>yaydetsteeeaivnkevdeseydsvskeekennkiektenepypvegrnnkineesrfstelylfkgddktisksyyeykvvhdlkgflkl<br>kvlkrwpvyedtpgkrlkhsgisyklfsklpinkkrimfesiwggkyscnpryyeyidenyphyeciwsfkdehypikgngkcvrrsslky<br>lyylatskylinnvnfkkhfikrkgqveigtmhgtplktiglddappgefptkksqkdyikknknwdyltvqsdyvaeisrtcfkyekdflkfg<br>yprtdilytknn |
| Contig40_gene_970 | 293 | mgdpkisvviipiyntedyieetllsvinqtifdeieviivddestdnskyiiekyaldysniqvfhqkneggisrnyglsksksgeyihfld<br>sddylppttayetlynmalknesdivignvlrfalynvweeslyknayndfdediaimslnerpsilwdtlvtnklfnreflirknirfpnkk<br>isfqdipfslesyiladsisfskeifhywrlrsnqssvtgqdkslnikdrleilrivqnllekyeveeeirnyeyskwlnhdlkfflkrfn<br>yypkeyheelfeevygivkiipdalidslnsykkvlftmirnkdyenflfaplenelyknpeipsflndeyksyfdfekameeelniell<br>dfkndndnlyidfdgylnylspndnykiiaklvdendyenpllvnhlenkqiaipfyllkdkkragikviyefesfkktaylknrhksier<br>ekffidldlgknsylydlireknienylidididisfnskeftikakskksidkismeniisfekiaypiydlkyeenednnlkneengeytfk<br>fkipryydilksavkkwelncdeyfnsiklsetfeffetykikfvntrnkilieneifnpikmiyalnhentdklniktlkgensrlnkei<br>kktnekneilneenkliidknktlnkenklnkkieeyksrkvvkivdslkn |
| Contig40_gene_977 | 294 | migvilaagmgtrimpltkdipkallkinettllermikncinadiskfivvvgynkdkvidlcpeiaekydieiktienekydvtntsvst<br>ylaskfieendlddfilvngdnvvdpeiitrlavsqntgmiidnfkelneesfkliiddesfnedktiangkinsigkgldipsstgefigv<br>skvvsddvaqfnrilekliieedpqnyydfaykdlsliktidfvltnglkmdrnr |
| Contig40_gene_978 | 295 | maeekrsfkllkdilyisakrsaralyyigsyiipanekillfessngrnytgnpkyiyeeivsqgldkeykcvwsfmhpdkkipgnaiqa<br>krsffkflyytlrsgtwifdsrhlyylkknkktkyiqtwhgtplkklalmdyidmsgnqdieayheefrkntsawqylisqneyssnifrr<br>afdfgemleigyprndilvnkdnekdideiktrlnipkdkiilyaptwrdngfytkgqykfatemdfrlyeefsddyaliikfhylvke<br>nmdwskyndfiiecdadwdigelylisdmmitdyssvmfdysilkrpmiffayddyknnlrdfydmvedvpgpicqtneelvdfiknys<br>enayknftfgekyekwndkfnqfddgkasqkiinliker |
| Contig40_gene_111 3 | 296 | msinksksnlslknklkslfsgnsnksryqskllrgdfdslhdlniayvlkgfptlsqtfvsnelrylvedgfnvvfcymdpadlveldfd<br>levirfdesddptgkleqlldyeidivhthfvyppcteytfpvcdrlgipftvfahavdifkydvdkinrvdeiskspfckgiltlsnyhk<br>nhliergvdkdkihitrqatdyeieelekernvrnivsisrfvekkgidvlidvadilrdedyefsiygfgglekayqrqidelnldnisi<br>kgrldgpqevkevfdkadilaspcriaengdrdgiptvifeamaygvcvlttevsaipeviddgrngflvppdspeifadkireianlspee<br>rfeiakqaqvdvgctssvdetmktlfltwsl |
| Contig40_gene_111 5 | 297 | mtkpkvsmilsayneerfidkaicsltnqslkdieiilindgstdktpeiiekyaeedpritvinqsniglgasrnkgmaiaqgeyvgfldg<br>ddwyrldaleiaymeaksdktditmyqminyddatgriyendwfnlnnldesfdgivftpektkdfifdlsvsscqkiyrndfilksinasfp<br>egiyfedmpffffyyylkaerisiirhhfyyrrkhnasithvvdanyldtveagcelmrrfidngfyddykfdliaykingprmalmditeda |

FIG. 8C-6

| | | |
|---|---|---|
| | | keplfnlikedyekikneteyyqdyldnlgpkkkkfflldvikydnyeefkknnpey |
| Contig40_gene_112_0 | 298 | mkicivgqyiglptaalfaksgcevvgvdinkelieklnggiahieepgisdsiknavdqghyhasltpeeadtfiitvptpylpedlscd lsyvisacnsilpvlkkgnvviiestiapmstdevikpifenegyvigedlylahcpervlpgqimeelvnnnrivggiteectkkaadvyr tfvkgeiieteaktaelskcmentfrdvnialanelakicaeigvnaldviemankhprvnihspgpgvghclaidpyfiyakapetakii klardtnnsmpgfvientgkilskldkdaekisvfgvaykgntddarespafeiiaglkaagyevvihdphfdnpdyldfddaikdssmili lsdhnqfkdmdydsikrnmktkliifdtkniiksvpedvtlvnygnlykfih |
| Contig40_gene_112_1 | 299 | mriilitgaygmlgsdlrevlknhdliatgskdldidteercidfiakerpeivinaaaytavddcethydayavnalgprnlaiacnkidi plvhistdyvfdgtkritpliendklgpqsaygktklageefigentqkyfilrtawlygihggnfvktmldlakehdeitvndqigsptfs ldlamaicevldsdkygiylhltndgecswydfakeifrisdidvkvipvsteefprpaprphysvlsnvkwksagfvpmrdykealnqyisl ynffvkigki |
| Contig40_gene_112_2 | 300 | mkgivlaggsgtrlypitkavskqllplydckpmiyypisvlmlanikdilistprdlpmykdllgdgsnlgmsfsyaeqenpnglaeafii gedfigddnvalilgdnifghrfteilerardlddgavifgyftnkpeafgvvefdnewnvlsieekpehpksnyvvpglyfydndviela ksvkpsdrgeleitsvneeylnrgklkvellgrgmawldtgthdglleaanfietvqkrqslyiacleeiayskgyiskeellklaeplkkt aygdyltklaerki |
| Contig40_gene_112_3 | 301 | mgkfniiksieiegvftveptvfedergyfmetynendfkaegidltfvqdngsksskgvlrglhfqytqpgqklvrvikgevfdvgvdlrkd sptygkwmgeilseenkqlfipkgfahgflvlsdeaefvykctdfykgdeggiqwndpdigiewplgdlkeedlilsekdkllkpmkdtp tdfymede |
| Contig40_gene_112_4 | 302 | mtkilvtggagfigsnfikymldkypdyeivnldaltycgnlenlediednpnysfvkgnimdeglvdvvssvdyivnfaaeshvdrsied pqifiksniigtqvlldaaykyqikkflqvstdevygslgpegyftettplqanspysaskagadlmvraygetfdlpinitrcsnnygpyq fpekliplmisnaledkelpiygdgknirdwlhvydhcsaidlvlhkgkigevynigghnekqnieivklilkeldkpeslikfvkdrlghd rryaidstkiteelgwkpkytfetgivetihwyldngdwmekvksgegyqeyyekmyskk |
| Contig40_gene_112_5 | 303 | mkvsvvtpnynglkfinayfetlafgsrfieeiiiidnastdascdlieeyinspsykidiklikndknlgfapavngqirlakseliysvn ndvelefntietliqsmersieegknpfsiqskmiqytnrsliddagdeynllaytkklgdgspidnynekreifsscagaalyrksileki glfddnffayvedidlsfraqingyrnylepksiiyhygsatsgsrynefkirlaarnnvwmiyknfpiplkivnfifilgflfikylfflr kgfgsiylggvkeglrerkgiekthfewknwknyfkiewkmikntfgyfkk |
| Contig40_gene_112_6 | 304 | mrnidlsiivvnyntfkltrdtidsclaepthytyeifivdnkstddsleklqeyfksetergilkiipngsndgfakannialeqakgdfi lllnsdtlmkqstidkcmdyitdkghddidalgckvsladgsldkackrsfpnpansfyklfhinvdsdkndynldlddgiyeidclvga fmlvrrttidevglldaffmygedidwcyrikqagwkivfgqaeiihykgassedkntkkrnpkilyefyramyvfyckhytkkynflvn iavyigigvllvfnlvrnafrs |
| Contig40_gene_112_7 | 305 | mikenqrilnailvildiivilislglayfvrfkttifsvggslpfsdyfiftivcliptyillyyffglykpfrnqssifsgaedivksdi mafiilvailfiingpnfsriml1l1slfgmiltiaervlvvlvlrmmrtnnlnlkhmliigdndlafefahkinsktylgyniagflgrke nigkrfegtkfigsfddlprvlkthkfdrvviaiplkyyyhlneivdaceeegikaeiipdyykylpakpsvdmlddmpiiniryvpldaf nkfkkivsdyfvsivaiiitspimiltaialaikiespgpiifkqerigyngkpfmnykfrsmkvqddeeeksqwttkddprktrigtfirkws idelpqffnvlkrdmsvvgprperpyfveefkktipkymvkhqvrpgltglaqvngyrgntsikkrieydiryvenwslaldvkimfwtvfr rnknay |

FIG. 8C-7

| | | |
|---|---|---|
| Contig45_gene_62 | 306 | mggfilveisivipvynvekylrecldsavngtfkdieiicindgstdssldilkeyqesddriiifnqenqgpgaarnlginksgkyvyf ldsddylelnaleklyniceeksldfvlfkllnfndktgkTfgtkynmaflndrigdnvfsykdlydcvfnlavsppaklykrelitdidy pegiifednvfflktllkakriyflldeflynrrrddsltssgsddydiipsmnylfdicrdlddfellkeglyykfkelyirfskvndv hkeefnliredclkhkeeidediandklrkrskfiyesvlssddykefhyrirlydknkeindlkkenkslknenklkssnkklkkenkh fkstkaykvwkkyskikd |
| Contig45_gene_64 | 307 | mkitvagvgvglslavllaqkhdvtaittteskaemlnqfispiqddeierffkevregertlnlhttdkaaaygdadlviiatptnydd vgnffdtsavedaiewtlkvnpdvlmvikstipvgytesvrekygirnniifspeflreskalydnlhpsrivvgcdddqmeegmfadille gareeekransleqdipillthlteseaiklfantylavrvsyfneldtyaqtkgldtqmiidgvcmdprigghynnpsfgyggyclpkdtk qllanykdvpqtmieavvhsnsvrkefianqiisrnpktvgvyrltmksnsdnfrasaiqdvmksikaegipiiiyeptlddgsefsrsevv ndierfkresdiilanrldcdvlgdvaekvytrdlfrrd |
| Contig45_gene_71 | 308 | mheyeisiliptynssktiertihsiltqdfknyemvfvddasnddtvsciqetladkkvnyqlivnknkgpaycrnrgvfasrgkyivfv dsddliqfnhisslhnyvksdnfdsaftkgikinnqdelidfkvdkydglihiarknkgivrakdlinlelImkipfsfvlliydkeiiInn slefnedyrygedtdfalrylancgnvrvidkytyfyyqeedsisrqvsldrfesvklfesldsyfkeddlreklvhsripsrifignmnyff yngnsedvfkkmdvldlfnklrgfkvfekrdwkfylkvrlfllnhrlyyklwlrfknnl |
| Contig45_gene_72 | 309 | mndlkklyvllailiviyvginfsyngldtintlthvnldlgpsmdnandanhikigssftklskiftw |
| Contig45_gene_73 | 310 | mtkilvtggagfigsnfikymldkypdyeivnldaltycgnlenlediednpnysfvkgnimdeglvdvvssvdyivnfaaeshvdrsied pqifiksniqtqvlldaaykyqikkflqvstdevyglgpegyftettplqanspysaskagadlmvraygetfdlpinitrcsnnygpyq fpekliplmisnaledkelpiygdgknirdwlhvydhcsaidlvlhkgkigevynigghnekqnieivklliketnlnkpeslikfvkdrlghd rryaidsskiteelgwkpkytfetgivetihwyldnqdwmekvksgeyqeyyekmyskk |
| Contig45_gene_74 | 311 | mgkfkivkseiegvftveptvfedergyfmetynendfkaegidltfvqdnqskssskgvlrglhfqytqpggklvrvikgevfdvgvdlrkd sptygkwvgeilseenkkqlfipkgfahgflvlsdeaefvykctdfykgdeggiqwndpeigikwplgnlkeediilsekdklwpmketp tdf |
| Contig45_gene_75 | 312 | mgivlaggsgtrlypitkavskqllplydkpmiyypisvlmlagikeiliistprdlpmykellgdgenlgisfsyeaqenpnglaeafii gekfigddnvaliilgdnvfhghrfseilkramnleegavifgyytqnpesfgvvefddewnlsveekpknpksnyiipglyfydndvieia knvkpsfrgekeitsvndeylkrglkvellgrgmawldtgthdglleaanfietiqkrqsvvacleeiafingyipkellelaeplkkt nygqyliklakmkk |
| Contig45_gene_76 | 313 | mnrfwndlilplfyefkpeviveigcfkgentknileycyytnsklkvidpnpdssfdpislknygdkfeflkelslnglnliedydavli dgdhnwytvynelkliekrfdqnnfpliifhdvswpyarrdlyynpelipeefrhpknlamfpdknelgdiginptfnnavfentpkngvl taiedfldetnlnlsffclnafygfgvlfpsqscdektilgifysdsdvigllektylkirftqehiiknknieinnlkdmnslnkknidlt ginsnlekeldklnnttelekeldklnntnidlkeklliistnngkelekldldnlkddktylenelkdlnnttelekelnkvtndktnlki elnninntnielekivddlcnekslknkindleyangrtlktienlngdiysktyendslkednllltktnkdfledikninlnydleqk ilnleeeknsilssktwkfgapfrkisnifnkn |

FIG. 8C-8

| | | |
|---|---|---|
| Contig45_gene_77 | 314 | mtykvsiiipvynaaefiirdtlksienqtmdfedievilvndcstdntakvineyakehenivpinlkenngqpgiprnigityasadylm<br>fldqddtfkknacetlynkistenvdmvcgnhnivsngrsnicfndwaeedeikinkidenpnfltmgvaawskilrrefvldnnlkfteg<br>vgediffsirallaegiilllkntivvdylvrgeslshqvnaeyldefcefylnffnyceknikndnlyhplfngrlnhvlsmlffadlyfd<br>dlswvlikihelfkkvaekpfvfedtsyriffdtlikdeypfensiniysaiksnrerkfdkgvkyleqeaklyidngngfnekdsiianyk<br>iyefnevefnlenfknikrirfdpitwqfincviheiktnngdllyeainsinrrelyglnkeeqssnrnskenirykssddssaegiadif<br>lttdsqyllygdfnnlksikinfevnlidnnevskivenlienydh |
| Contig45_gene_78 | 315 | msiknkfslfnsssnnsdfenlinnyykkvledienedisgydrnikyyndlkdcelfsseyyitngglelseeyalahylnegykqsrnps<br>pefnndkylrlypdvrlaslnplahyvlygekegrrlplseyeeleneivsvknliyqnrvtdnlvllrdkvskgkkvnvvfvlpammfvyk<br>dlynyfdnddmfnvqivlvphrlgnsqkitdvakdkhygifsylkekqynvidgydfeknegidlvstcnpdiifyvlpymrifpktmkisn<br>lpsnilyayipygefvednlddlffnfgwneiawkifcsteeylinsteksivgssnvvlagsarmdslinfeesdedykwiyskeenkkri<br>iwaphhtlarpgmddslsystfdenfeffynyakdhpdiewvirphpllkevlsnintnmrvqgiadenfaddyffkweslpnarfheeidy<br>fdlfatadamitdcisfkaeylfankpglilnktgveldgyqgeitdawyncdgsdfekieefiedvvvggndylkekreeifnknfnvnlg<br>saskvifdyiknelt |
| Contig45_gene_79 | 316 | mgvvmkknnfnkkitfvanyfwtsikegsksnsyfnydnylkkypdvkesgmnpfkhyllhgideerstnfdeninsyslvensdlfdyeyy<br>ceknnlkfdsyskalmhylekgykkgynpsikfnaeeyyevrpdvkradvnplvhylkygkievtsmtenlnlkeyglvknslfdynyyme<br>knhldlrneteaiyhyleigykkgynpsnkfngeiyfkknpdieesgwnplvhylkyggkeertdkcdknlkeyslvkesglfdyqfykdky<br>dldlnsykrglihylefgykrgykpsrnfdgeeylkrypevkkagfnplvhylkygvneeriglirrisfkninknydveailenidndvtil<br>lnvedsnnlkecieniksttkdykiilihenlddedleyiksnndiellrrsphesfinalnnildnakndiiflknnirtfekwifkltva<br>aysddrigfvspisnystvslinieedekssefisniskrdyeesplpndscvfikkdvfkelkfdessneenwfatfidrglekgwksild<br>dstyvyqfnevepqqadeydystpyvlenrpsvkfinsdafnnsfqniheyaddnleeniqektrknilfamhyggveftvkdivnaikn<br>dyecyvlrafknkmklykvfndyfisikefnikypwtpkmihsdeykqiyfyilnynidileidhllhtfdlqelakkldipiiltlhdf<br>yyicpsyflldennkycggycgdqprncstrvtwidlpanivewknqweymkelfgmcdyiltadftkdmflehydslksdditiehgr<br>dlirydnnytvpniyqpikilipgvigphkgldfikelkgfdddnrleyhfigqvddelksmgiyhgpyeredfakwvfkikpsfigifsvc<br>aetyshltesicsgvppvlasnlgalktriesqgggwlvniddaeetyeqildisskeeykfvtenlkdirissseemgskykeiydkltk<br>kedk |
| Contig45_gene_80 | 317 | mefikyksqfekmidnkiligmpelidsnisfkgknnilccnniklenididfngnnsviflgsnlgvnshltifnnstlflgknntcgssis<br>isvaenqnlligdncivesdvkirtsdnypiynyensrinhsnsvfigdnvllgessfisrgvkigsgsiispcsflpplfkafsnsyvlgn<br>pgrilkedvyfvndsindytieeiknssinenesglfdfveketlsldkidnilkfnsedsldfiqklflqnkhknrffie |
| Contig45_gene_81 | 318 | mkkpktkaqkesrekkpnmlksdcmkkilyvlhsgvtggtfltnkdlmknvekefdvyllsaenkflkifsfsnnkliklirkyhrnyginve<br>teetetnniswsakdfhnswlsniyfeilvnynidivhrhliinhsfdlpqvaeklnipivlshdfylcpfytlldenynycagecshnk<br>kncycpmdslsdiinskefiisewrvnvlkmfnyinvfvttsffvkdlflsiysnediinnnfkviehgrdfpklkkqmfeipssnkpikilc<br>panhlnimkgsqlikrikeednknlieffhlgnchdgieeygfshgtferdefhkkveeikpsfvgifsiwpetfchtiteawscgipvigt<br>nigviqdrilnkggwlvdrnnpkkayeymaeifenkeeyleianniktmdlkdtkmmsieyiqiynnlleik |

FIG. 8C-9

| | | |
|---|---|---|
| Contig45_gene_82 | 319 | mtkvsviipiyngekylkecldsvccqslkdiqiicvndgstdktlsilngfaskdkrikiistenrggsarntalkeaqgeyisfvdadd wisenalellyfhaksdldmlffqminymdnsknyvetelynhlcfernaidedtifnfndikeflfkipvcpvsklykkefldsndlyfp egmffednaffynslfksnclgflkkhlyyrrhadsvtqtfdkrkfdivkatnkvldvflendqylifkkelinhtfsmllewfnksplei kdefyrlikrdfrgfnnlkedfknnlkeeyllifdisdknkyyldflseyklssadydifdkeryfhlnsqeyleyksnksnnykisvvipi ynnetfihrtlmsienqsfglenievimvndnskdntelvineysskyenfkaihikegtgspgtprniglyestdyviifldhddyfeida leklynaineedcdfvygtyasvdedlptkiiypnelhgyfkniygnprsiafpppsiwtklfkrsflienriifptilgedaifiskalfs adgidylwddlicyhtlnkksftknvsydylvqgfvseeylyniyndfesqsyelkenstipseksseniekmnlykirsegildfylnqfy rsdlndediyrifpilsdfvstri |
| Contig45_gene_83 | 320 | maliekneiflleeivkknfaakykdsilgifwsilkplliimilltiifsnlfggsienypvyflsgkiifdffnsatsvsmmslkgninil krtaapkhiftlagvseflnflitliiligvmivtrspfyilesmiaiipimsliimitgislilavlcvyfsdiqhlwgvitlmlmyasa ifypmniipepfhgimilnpifwviggfrilvlwgtipsrmmlnlvllsviilvfgiivfkfekkitlkf |
| Contig45_gene_84 | 321 | mnqkrdelnskqninldseneisssseinlkkrdpqnksdliaqqrmkakrelieryrnmseseaestlqkhkkir |
| Contig45_gene_85 | 322 | mqkknkitnekeieinsnkvrmddkncslensagvsenkdkndeaikigsqnsqiegeseeiipehvlerqnpkidnsdyeinsvsdtlp vieegeskpiqnaedeivkkelvdsvsdvvpvvgekeennepiikddssdvddvlssiipeyhqkssievnnvslsfniendkidnlkeyi irtlkrtkekkikfhalnnitfkiykgekvgiigyngagkstllnvitgiyepdegnvktygkisplslgagfdynysgreniylngavlg ydkkfleskfdeivefselqdfidlpiknyssgmlaklgfsiativepdilliidevlgvgdvnfqkkssnkikslmdggttvllvshsivqi reicdkaiwidkgelrefgevnevcdhylkdagnatknqvkdirfn |
| Contig45_gene_86 | 323 | mnykisilipvynvenyieksInsiiisqigienlevilvddnstdnsaniikkyvskydnfkgiycdigsfcgprniglsyatseyimy ldsddwleetacevlyntiinenadivcgsqtrldnegnrkfyyhlwttltdpnedyntrmkttgeliddpnfklvvtcldknpnilghan vwgkifkkdlitenelsfpedivaqdsvflinsffvaekivfindilvhynnlrcddddksasyvkttknlfgrikaydlmdniskkfskee ffyryllvgklnywfnsflmdsnistyeiklifkkyshlfsncykftnlrkdiknifkeidegnydiaastvsklqsksfsasenkikvsv iipiynnekflskcldsvingtlneieiciciddgssdnsieilngvylkdsrlkiisqenlgaatarngliakgeyiafldsddwlelna feklyenittnnsdlvlfnsiehkenanlkerihiknsipdynyytfnynykkdlvmngyldiwskmyrtsflkennigfsnhqifndiqf hiktmlnakkisycpefIynylrinhpslqnnlslgnesfilldeledylidnefynelksnfnirfklteleslteklenpyrneffkl iknnfkkmqlteygrkelppenyqffndvltydsffeyalknsekerqklsnaladsekdrqklsndlensgkerqklsdalvdsekerekl sdalessekereklsdalesseierqklsnalessekerqlsndlknsekeqelikkeftssnswkvteplrkirtlikk |
| Contig45_gene_87 | 324 | mdkneiftlwipdnddnnlsqlahlslksfllcdydvilytydhignvpngvcirdaneildkskifrykggfktysgfanlfrykrlyeyg gtwldldlliikrisdediiigsqtqediysnpnnalfrfppkdpliktildysekrgsdinhaetgtlilkllasefpeynqylkhfnys nivnwndvglespeiflkclntneiygfhlfntffkfvefpkdsffttlkdiilnsstseeyafnlmkynittqkyiginewdlsyln ifkdafsknefkytilidsqnlkkmeiyniiraifssyglesekdiqiiicgksdighdkikfkdnviflasdfqdmkyylndyifgehifp inkpvifkeeffknnftsdvehvlnnssnilvnlnresyklcllanidvfnldmdvlktlnmrikevdnsliydysfrdddvlkmlkvd gcdsksflnvkselsnlnikfsqktsyhyfsayknilnsnsydefilkehndklqclnafylnrinprydy |
| Contig45_gene_88 | 325 | mldadefiisdngqmprelikkinenyyylikwityvptnnddynikfipkrithvrdesleqyykvivpkkvvndfnvrvemqnhnlkfdn fnrnelvkkdlnlkiahfplrsieqciskvsigwpniiainlynlswgfhwkmlfdkikeendisldldleffaknyalvstsddiliknqpi nldfcdkieirydfeynylrnilenyayfaeeivsfkrklksvplidrfilklasdydvieksglfdvnwyckryspprnihpihylity |

FIG. 8C-10

| | | |
|---|---|---|
| Contig45_gene_89 | 326 | renmndpagffsteyyfkthvdvansgmnpfvhyikygkkenrkiassksenfgvq |
| | | mnlmkitvagvgyvglsiaillaqkhdvtaittteskaeklnqfispirddeierffketrdgkrklnlhtttdkesayknadlviiaaptn yddvnhffdtsavedaiewtlkvnpdvlmvikstipvgysesvrekygvkniifspeflreskalydmlhpsriivgcdddqkedaqmfvdl llegvrleekrsdspkqdipiliapfteveasklfqntylalrvsyfneldtfaqtkglntniiidcvcmdprigghynnpsfgyggyclpk dtkqllanckdvpqalieaivnsnavrkefiadqiisnnpktvgiyrlimksnsdnfrasaiqdvikmikaegikiiiyepilddgseflks evvndldifkresdiilanrfdqdilgdvadkvytrdifgrd |
| Contig45_gene_94 | 327 | mgrfsvvmaaynsgayiqetldslinqsldfkeniqviivndassdntesvcqeyiknypnniilinnrincgpahtrnvglhyaegeiin fldsddyiskktfervdsffedfvhvdmasipikfvgskrgdhplnykykgtgvinllnnpdaiqlssasaffrsdilkaslfnhsrsrydg svsvvyndnspvsdsipmifnenlsvsedallinqmllrnpllgilsnctyfyrkkatdntslisdsanhrsyftsrvnnymirlindsldl ygkvpefiqyvvmydlqwimeirqvdhlidledlthlydcklisilfyigdkvifnqrsipsilkshillikyfgwgylddktfnfkqidkky ydehgnlipyiekdqlsfiigklelnkiyldivdikniksinlnnnngtpdddkkddgknshdfylssqddedrqelylsgmitsffnsd fdiyaivsekdkssshilekeikvkkispqrdnlsnfnygynqcfevriplsektsrisfrmgfkslnevcnsigietlsedsfdyinhh dlafsgdllidynhtsrlsqvsnykiskdyliidngnhmivrkrslittikyelvtfasilgereegwrtgillralyfilypfyrnkriwi fmdlpytaddnglqlfksvrnmdklkledynklildidesllsrerhpykyelfegkdiglvglikvnvfssiknvfsrdsdddengkvkfikg gslgldkdyelednqdysdylnehfgfadvnedyldnqdiqvegssfeddiehsskfrrnvykagfvksfdakvdakyndslsnlenrfd krvsniktrtnadvrekvglsrdrddnfskgfspidfiygfdlskflsensfvylvnyilyriskillrpkrikridnrkikkyftleqst shfnnvrhmenqyiassnrdklrkllarekqsneynalkkigpvlayksikhriyalyaevivsshpdnnliypfygnfphvagivkaktvf lqhgvtkddvsf |
| Contig45_gene_95 | 328 | mryiadelkgrktsdgkpyefefipkdefslsnmkklatskyiifltdnffalafmrfnkktkliqlwhgtgifkkfgydlledeqkktmlkf snkitnlmvsshnvidiyarnfaidkskvlplgiprndyyspehldedyvrqlrgefeqrypnlrgkkivlyaptfredpkynavfnyfdie kfidelgddyilciklhprynkfadsanridldeltdtynivnfteykdeqklflisnilitdyssvmveytllnrpiiilfayldnylene rgfyfdyrkevpgrivkdtdelvvirekdfnlsnlkefaefqgfdyfdaysskrildyvlee |
| Contig47_gene_70 | 329 | mklsiiliptyneeeylpkliesirsqeftdyeyivadadsndntreiaeaygcivvdgglpaigrnrgaavakgeillfldsdleltehyle nvieefeeedlgiaitqmtplsqkkrdiylhnlanwfmiavenikphgagcygiisrkelhdecggfdenltfgedtdyiervaeisqfkvl rnakigvstrrleeeglytllkqygkstvndfrgkrtsaedlgyefghessskllesgvqesvpklessadissqiednsps ledeidieshypitaldstdmeriaeksknrkqssfkrrlnefkdkefetnelieyedesghikheavgldsrkifysicgegmghairs svilehltkhhdvyifsserayfklsekfdnvyeiggfntvyennvrtkktffkamkanptnlkegynvlykeckvkpniiisdfenyss mlskimniplisidnihmitgcdydypphhkadmltakavtksyilrpkrhiitsfffpplkhpkmtalyppvlrkeimdlesesgdhvlvy qtaessinlmdelkkldeefivygfnkdgtdenltyrafnedkiyedmrtakaiivnggftmiseaiylkkpiystpahknfeqilngfyve klgygeshedldvkkiekfldnldtyqmnlnkvekwdntailedidlsiemyakkny |

FIG. 8C-11

| Contig47_gene_408 | 330 | mekqqvktilksvviiailllivfglraqsvdiggvpnelkshyvdenglpyfsemdsyfnyrmtenymdhgyfgdtkvngtgwdmhsyfps gravgdyqpmiayvtsflygiinmfqemsllevafwtgaivsslaviptyiftrritndygaiaaslivvlgpnyishtfagffdtdmfnit lplffilffvealktdklsyriifsllavasialyslswtgymfyvavmvlvmivffvlcfyfnieilepfknygnklewlinqkelfatli vlvvgliglllavgvggiiegitgltggftlqagaadvwpnvlisvaemqipnlvtgglvgsflantggvvngvggivclfgvlivlytfvq rlfrlnsvkvkgdtakphkskrkatsvrteqkrfsvslkdigsfgstdeinkskrhtvlylslffwivssaiavtggtrfiqvlvvpmgic agifvgyavdyvknnvdndkvllliaviasililalpitqiaygldnamtiglvvlvillaisaiviyakksikdsdvsikkalvvlitlal vsptvcgafqttaatvpgssdpmwfamdyvkenstndtviiswwdfgylfqvaschptsfdggsqtgdraywvgksltsdyaqskgilqml attgsnasmllseytgsnvtavhaldetlgksrseaqkiltskynltndqakavvkqshpsnpnnvsfvlssdmigkagwwsyfgswnfdtl nstnyqymandyvpikqntqgnitilnesgiiyqavvngkngtnettaqmetiwdnnrskidlngteynplkasnliciensyltvnktl nkdgnytlyllgsgddytailmdnnlkdsvftrlfllggigqdtfelsnmqdgvsvwtlrdgssnsddagsq |
| Contig49_gene_169 | 331 | msslisiptlpliviialicgilsfistrlvmpwligkleqaeiigkdihkssrpivaemggigiilfgfiigifagiilfpvltfqlvvvliv vllvgiigmvddlivlsskekiflliflagiplwwvappnvgllymimipiavsitsnltnmlaglngiesglgvismsltisciilgkydv aiismtmlgtllaflyynkypakvfpgdtgtliigatiaaiafigrvkliafivlipniidaalkfysagvmerqqhnptqlnedgklvrpe qgfkslirlvlrkpvdektavmmiwgigiilfgilgiiivallmpgvthdqtfaqfihlkdyfyylg |

FIG. 9A-1

FIG. 9A. ORFs containing membrane-spanning domains identified from *M. ruminantium*: Annotation and position of membrane-spanning domains.

| ORF | ORF Annotation | Number | Topology * |
|---|---|---|---|
| contig40_gene_28 | hypothetical protein | 1 | o26-43i |
| contig40_gene_32 | MFS transporter | 14 | i7-29o39-58i70-89o99-121i128-150o155-177i190-209o213-235i256-278o288-305i317-335o339-361i382-404o424-446i |
| contig40_gene_33 | hypothetical protein | 4 | i7-29o249-271i421-443o447-469i |
| contig40_gene_36 | hypothetical protein | 4 | i7-29o247-269i423-445o450-472i |
| contig40_gene_37 | hypothetical protein | 4 | i7-26o239-261i417-439o444-466i |
| contig40_gene_42 | MFS transporter | 12 | i21-40o50-72i84-103o113-135i142-164o169-191i240-262o272-294i306-323o328-347i368-390o394-416i |
| contig40_gene_43 | Na+-dependent transporter SNF family | 13 | i13-32o42-64i85-107o142-164i177-199o219-241i254-276o291-313i320-342o357-379i386-408o430-452i457-479o |
| contig40_gene_47 | hypothetical protein | 2 | i13-32o38-60i |
| contig40_gene_60 | hypothetical protein | 7 | o20-42i55-72o76-93i100-122o142-159i164-186o190-207i |
| contig40_gene_62 | cobalt ABC transporter permease protein | 7 | o4-26i28-47o57-76i88-110o130-152i286-308o323-342i |
| contig40_gene_74 | hypothetical protein | 3 | o5-27i36-58o228-250i |
| contig40_gene_76 | type IV leader peptidase family protein | 6 | o4-23i28-47o52-71i83-105o120-142i259-281o |
| contig40_gene_127 | Na+-dependent transporter SNF family | 12 | i7-29o42-64i85-107o139-161i182-204o224-246i259-281o316-338i359-381o385-407i428-450o460-482i |
| contig40_gene_131 | diacylglycerol kinase DagK | 3 | i21-39o44-66i91-113o |
| contig40_gene_145 | hypothetical protein | 1 | i21-43o |
| contig40_gene_168 | ammonium transporter, Amt | 11 | o10-32i45-67o99-121i128-150o165-184i191-213o223-245i257-276o281-300i312-334o349-371i |
| contig40_gene_173 | hypothetical protein | 5 | o10-32i45-67o82-104i124-146o150 169i |
| contig40_gene_174 | hypothetical protein | 2 | i21-43o47-69i |
| contig40_gene_175 | Na+ dependent transporter SBF family | 8 | i12-34o38-60i73-95o100-122i129-151o166-185i197-216o226-248i |
| contig40_gene_176 | heavy metal-translocating | 5 | o308-330i508-530o545-567i851-873o878-897i |

FIG. 9A-2

| | | | |
|---|---|---|---|
| contig40_gene_183 | P-type ATPase | | |
| contig40_gene_188 | ferrous iron transport protein B FeoB | 10 | o319-34i353-375o390-412i433-455o465-487i494-513o555-577i584-603o623-645i652-674o |
| contig40_gene_215 | hypothetical protein | 3 | o5-39i51-73o100-119i |
| contig40_gene_218 | transporter MIP family | 6 | i12-34o54-73i99-121o141-163i175-197o217-239i |
| contig40_gene_220 | xanthine/uracil permease | 10 | i2-21o25-47i54-76o86-108i115-134o154-176i236-258o268-290i302-321o325-347i |
| contig40_gene_230 | hypothetical protein | 12 | o18-35i67-89o93-114i121-143o176-198i234-256o307-326i346-363o367-386i399-418o422-439i451-473o |
| contig40_gene_246 | hypothetical protein | 2 | o75-97i109-131o |
| contig40_gene_247 | hypothetical protein | 4 | o5-24i31-53o57-79i91-108o |
| contig40_gene_249 | NADH-ubiquinone oxidoreductase subunit | 7 | o5-24i65-87o124-146i158-180o205-227i234-256o266-285i |
| contig40_gene_250 | NADH-ubiquinone oxidoreductase subunit | 6 | o20-42i73-90o95-113i126-148o163-185i198-220o |
| contig40_gene_253 | hypothetical protein | 6 | o15-36i43-65o70-92i122-151o166-188i195-217o |
| contig40_gene_254 | hypothetical protein | 3 | o4-25i32-49o54-73i |
| contig40_gene_255 | hypothetical protein | 3 | o5-20i27-45o50-72i |
| contig40_gene_256 | hypothetical protein | 3 | i5-27o71-93i114-136o |
| contig40_gene_268 | hypothetical protein | 3 | i2-19o29-51i58-80o |
| contig40_gene_273 | hypothetical protein | 1 | o10-43i |
| contig40_gene_282 | ABC transporter permease protein | 6 | i30-48o58-77i84-106o111-129i136-158o193-215i |
| contig40_gene_284 | MatE efflux family protein | 4 | o20-39i249-271o303-325i337-359o |
| contig40_gene_287 | hypothetical protein | 12 | i21-43o53-75i95-117o137-159i166-188o194-216i258-280o285-307i320-342o362-384i397-415o419-441i |
| contig40_gene_290 | NADP-dependent alcohol dehydrogenase | 2 | o29-51i64-86o |
| contig40_gene_301 | ABC transporter permease protein | 1 | i167-189o |
| contig40_gene_326 | hypothetical protein | 6 | i21-43o53-75i96-118o128-150i163-185o215-234i |
| contig40_gene_338 | hypothetical protein | 6 | i12-34o49-71i97-119o164-186i211-233o238-260i |
| | hypothetical protein | 4 | o25-44i79-101o131-153i196-218o |

FIG. 9A-3

| | | | |
|---|---|---|---|
| contig40_gene_356 | YhgE/Pip-like protein | 6 | i28-50o450-47oi491-513o518-540i553-575o606-628i |
| contig40_gene_366 | polysaccharide biosynthesis protein | 1 | i28-47o |
| contig40_gene_368 | polysaccharide biosynthesis protein | 14 | i13-32o42-64i84-106o110-132i144-166o171-193i218-240o250-272i292-314o329-351i358-380o384-406i413-435o440-457i |
| contig40_gene_378 | acyltransferase | 8 | i13-30o45-64i84-106o121-143i150-169o179-198i210-227o242-264i |
| contig40_gene_379 | hypothetical protein | 2 | o15-37i50-72o |
| contig40_gene_387 | hypothetical protein | 6 | i20-42o52-74i105-127o132-154i175-197o207-229i |
| contig40_gene_401 | hypothetical protein | 1 | i211-233o |
| contig40_gene_428 | 2-polyprenylphenol 6-hydroxylase UbiB | 2 | i485-507o511-533i |
| contig40_gene_433 | Transposase | 1 | i49-68o |
| contig40_gene_465 | hypothetical protein | 4 | o5-27i59-81o101-123i144-166o |
| contig40_gene_471 | peptidase M50 family | 6 | i12-30o35-57i70-92o112-134i146-168o183-202i |
| contig40_gene_475 | ABC transporter permease protein | 3 | o217-239i271-293o308-330i |
| contig40_gene_481 | ABC transporter permease protein | 5 | i23-45o83-105i126-148o187-209i247-269o |
| contig40_gene_482 | ABC transporter permease protein | 6 | i12-34o105-127i148-170o185-207i246-268o296-318i |
| contig40_gene_487 | ABC transporter permease protein | 6 | i12-31o46-68i89-120o135-157i164-186o206-228i |
| contig40_gene_495 | protein export membrane protein SecF | 6 | i7-24o113-135i142-164o168-190i211-233o243-265i |
| contig40_gene_496 | protein export membrane protein SecD | 5 | i13-32o240-262i269-291o343-365i372-394o |
| contig40_gene_498 | hypothetical protein | 5 | o5-22i29-51o66-88i95-117o121-140i |
| contig40_gene_510 | MatE efflux family protein | 12 | i22-44o59-81i102-124o139-158i171-193o198-217i252-274o284-306i318-340o363-385i392-414o424-446i |
| contig40_gene_514 | hypothetical protein | 6 | i2-21o41-63i75-97o117-139i152-171o194-216i |
| contig40_gene_526 | MatE efflux family protein | 12 | i25-47o57-79i99-121o136-158i171-193o198-220i254-276o286-308i328-350o365-387i400-422o426-445i |
| contig40_gene_535 | amino acid carrier protein | 9 | o10-29i140-162o177-199i206-228o243-262i298-320o340-362i383-402o407-429i |

FIG. 9A-4

| | | | |
|---|---|---|---|
| contig40_gene_541 | AGCS family | 11 | i21-43o73-95i108-130o148-170i182-204o209-228i268-287o291-313i334-356o371-393i415-437o |
| contig40_gene_544 | MatE efflux family protein | 1 | i42-64o |
| contig40_gene_552 | methylthioribose-1-phosphate isomerase MtnA | 5 | o15-37i56-78o88-110i131-153o182-204i |
| contig40_gene_561 | ABC transporter permease protein to 166 | 1 | o10-32i |
| contig40_gene_562 | hypothetical protein | 12 | i30-52o57-79i106-128o138-160i173-195o229-248i268-290o313-335i394-416o421-440i447-466o493-515i |
| contig40_gene_565 | transporter SSS family | 9 | o10-32i52-74o89-111i118-140o155-172i196-218o228-250i330-352o362-384i |
| contig40_gene_570 | transporter sodium:dicarboxylate symporter family | 4 | i19-41o46-65i72-94o104-121i |
| contig40_gene_571 | hypothetical protein | 1 | o56-74i |
| contig40_gene_574 | hypothetical protein | 1 | o336-358i |
| contig40_gene_578 | hypothetical protein | 8 | i41-63o67-89i249-266o276-298i788-810o820-837i850-872o882-904i |
| contig40_gene_579 | cation-transporting P-type ATPase | 1 | o10-32i |
| contig40_gene_602 | hypothetical protein | 1 | i7-29o |
| contig40_gene_608 | 2-oxoglutarate ferredoxin oxidoreductase subunit gamma korC | 3 | i7-26o188-207i214-236o |
| contig40_gene_609 | sortase family protein | 1 | i259-281o |
| contig40_gene_610 | hypothetical protein | 8 | i12-34o39-58i70-92o97-119i131-153o157-179i184-206o211-233i |
| contig40_gene_616 | phosphatidylserine synthase PssA | 1 | i21-43o |
| contig40_gene_617 | transporter ExbD/Tol family | 3 | o15-37i125-146o161-183i |
| contig40_gene_635 | transporter MotA/TolQ/ExbB proton channel family | 5 | i21-43o48-70i93-115o120-139i146-168o |
| contig40_gene_638 | hypothetical protein | 7 | o44-63i68-90o100-131i271-293o298-320i609-631o635-652i |
| | heavy metal translocating P-type ATPase | | |

FIG. 9A-5

| contig40_gene_657 | polysaccharide biosynthesis protein | 12 | i41-63o73-95i108-13oo134-156i194-213o217-234i255-277o290-312i319-339o344-366i379-396o400-422i |
| --- | --- | --- | --- |
| contig40_gene_659 | hypothetical protein | 2 | i408-430o434-453i |
| contig40_gene_661 | hypothetical protein | 13 | o20-37i49-71o91-113i120-142o146-163i176-198o233-255i315-337o370-387i392-409o419-441i446-468o483-505i |
| contig40_gene_662 | UbiA prenyltransferase family protein | 9 | i5-27o32-51i82-99o104-121i128-150o154-176i205-227o232-254i267-289o |
| contig40_gene_666 | hypothetical protein | 2 | i7-27o37-59i |
| contig40_gene_668 | alpha-ribazole phosphatase CobZ | 1 | i378-400o |
| contig40_gene_677 | hypothetical protein | 1 | o358-380i |
| contig40_gene_693 | tetrahydromethanopterin S-methyltransferase subunit G MtrG | 1 | i50-72o |
| contig40_gene_694 | tetrahydromethanopterin S-methyltransferase subunit F MtrF | 1 | i41-63o |
| contig40_gene_695 | tetrahydromethanopterin S-methyltransferase subunit A MtrA | 1 | i222-244o |
| contig40_gene_696 | tetrahydromethanopterin S-methyltransferase subunit B MtrB | 1 | i83-105o |
| contig40_gene_697 | tetrahydromethanopterin S-methyltransferase subunit C MtrC | 6 | i7-26o36-58i65-86o101-120i127-149o174-208i |
| contig40_gene_698 | tetrahydromethanopterin S-methyltransferase subunit D MtrD | 6 | i5-27o37-59i66-88o133-155i162-184o210-232i |
| contig40_gene_699 | tetrahydromethanopterin S-methyltransferase subunit E MtrE | 6 | i61-83o87-109i130-152o167-189i231-253o258-277i |
| contig40_gene_713 | hypothetical protein | 11 | o38-60i72-89o99-121i133-155o159-178i198-217o222-244i257-279o283-305i321-338o342-361i |

FIG. 9A-6

| | | | |
|---|---|---|---|
| contig40_gene_722 | hypothetical protein | 5 | o13-35i42-64o69-91i100-119o123-145i |
| contig40_gene_727 | TraB family protein | 4 | i240-262o272-289i296-318o351-373i |
| contig40_gene_729 | CBS domain-containing protein | 1 | o5-27i |
| contig40_gene_731 | sodium/calcium exchanger protein | 9 | i21-43o58-80i93-111o116-133i153-175o185-207i220-242o252-271i280-297o |
| contig40_gene_740 | hypothetical protein | 1 | o10-27i |
| contig40_gene_747 | MFS transporter | 14 | i7 29o33-55i68-90o94-116i128-150o155 172i193-210o214-236i263-285o289-311i323-345o355-377i396-418o471-493i |
| contig40_gene_748 | 2-polyprenylphenol 6-hydroxylase UbiB | 2 | i476-495o505-527i |
| contig40_gene_764 | hypothetical protein | 7 | i28-50o88-110i117 136o172-194i199-221o226-248i269-291o |
| contig40_gene_770 | hypothetical protein | 1 | o4-22i |
| contig40_gene_771 | hypothetical protein | 1 | i104-126o |
| contig40_gene_780 | energy-converting hydrogenase B subunit O EhbO | 8 | o5-27i73-95o99-121i164-186o201-223i257-279o283-305i312-331o |
| contig40_gene_785 | energy-converting hydrogenase B subunit J EhbJ | 3 | o4-26i38-60o64-86i |
| contig40_gene_786 | energy-converting hydrogenase B subunit I EhbI | 4 | i27-49o53-72i85-107o142-164i |
| contig40_gene_788 | energy-converting hydrogenase B subunit G EhbG | 3 | o4-26i28-50o65-84i |
| contig40_gene_789 | energy-converting hydrogenase B subunit F EhbF | 13 | i25-47o85-102i109-128o132 154i166-188o203-225i246-265o270-292i305-327o331-353i365-387o402-424i452-474o |
| contig40_gene_790 | energy-converting hydrogenase B subunit E EhbE | 3 | o5-27i46-68o83-105i |
| contig40_gene_791 | energy-converting hydrogenase B subunit D | 3 | o4-19i26-45o49-71i |

FIG. 9A-7

| | | | |
|---|---|---|---|
| | EhbD | | |
| contig40_gene_792 | energy-converting hydrogenase B subunit C EhbC | 3 | o10-32i44-66o70-92i |
| contig40_gene_793 | energy-converting hydrogenase B subunit B EhbB | 3 | i5-27o37-59i66-85o |
| contig40_gene_794 | energy-converting hydrogenase B subunit A EhbA | 1 | i7-29o |
| contig40_gene_795 | hypothetical protein | 7 | i9-31o46-80i87-109o124-143i150-167o172-194i214-231o |
| contig40_gene_800 | potassium channel protein | 3 | i31-53o57-76i81-103o |
| contig40_gene_803 | hypothetical protein | 7 | i7 26o36-55i128-147o151-173i225-247o267-289i310-332o |
| contig40_gene_804 | potassium uptake protein TrkH family | 10 | i2-19o24-41i62-84o124 146i167-189o219-241i254-271o309-331i372-394o434-456i |
| contig40_gene_816 | 4Fe-4S binding domain-containing protein | 7 | i5-22o27-49i56-75o85-104i111-133o148 170i177-199o |
| contig40_gene_825 | hypothetical protein | 1 | i21-43o |
| contig40_gene_826 | MotA/TolQ/ExbB proton channel family protein | 3 | o24-46i133 155o165-187i |
| contig40_gene_827 | hypothetical protein | 7 | o5-24i31 50o60-82i102 124o134-156i168-190o200-222i |
| contig40_gene_832 | hypothetical protein | 1 | i21-43o |
| contig40_gene_833 | MotA/TolQ/ExbB proton channel family protein | 3 | o48 70i158-180o190-212i |
| contig40_gene_838 | hypothetical protein | 1 | i7-24o |
| contig40_gene_839 | hypothetical protein | 1 | o5-27i |
| contig40_gene_888 | restriction endonuclease | 3 | o323-345i352-37 1o381-398i |
| contig40_gene_890 | undecaprenyl-diphosphatase UppP | 7 | i7-29o39-61i94-116o120-139i192-211o221-243i255-273o |
| contig40_gene_905 | hypothetical protein | 7 | i26-48o53-75i95-117o121-140i161-183o193-215i228-250o |
| contig40_gene_912 | hypothetical protein | 11 | i9-26o31-49i65-87o91-108i121-143o153-175i182-204o219-241i262-281o296-315i322-344o |
| contig40_gene_920 | polysaccharide | 12 | i13-35o55-74i95 116o126-148i169-203o248-270i319-341o351-373i385-407o411- |

FIG. 9A-8

| | | |
|---|---|---|
| contig40_gene_926 | biosynthesis protein | 430i437-459o463-485i |
| contig40_gene_929 | hypothetical protein | 6 | i13-35o50-72i84-106o116-135i166-185o195-214i |
| contig40_gene_929 | hypothetical protein | 10 | i12-34o44-66i106-128o143-162i169-200o210-232i253-275o308-330i343-362o366-384i |
| contig40_gene_941 | hypothetical protein | 8 | o15-37i50-69o84-106i113-135o139-161i168-190o205-227i239-261o |
| contig40_gene_953 | peptidase C39 family | 2 | o277-299i475-494o |
| contig40_gene_957 | hypothetical protein | 1 | i84-106o |
| contig40_gene_958 | hypothetical protein | 1 | i218-240o |
| contig40_gene_960 | glycosyl transferase GT2 family | 3 | i222-244o249-271i295-317o |
| contig40_gene_962 | transporter permease family protein | 3 | o10-32i44-66o86-103i |
| contig40_gene_963 | transporter permease family protein | 9 | i19-41o46-68i75-97o101-120i133-155o165-187i194-216o254-276i296-318o |
| contig40_gene_966 | hypothetical protein | 10 | i12-29o44-63i76-98o108-127i140-158o163-182i195-217o230-252i287-304o314-336i |
| contig40_gene_971 | hypothetical protein | 5 | o41-63i76-98o108-127i148-170o180-202i |
| contig40_gene_983 | Na+-dependent transporter SNF family | 12 | i13-32o42-64i85-107o142-164i177-199o219-241i254-276o315-337i358-380o384-406i427-449o459-476i |
| contig40_gene_988 | hypothetical protein | 1 | i46-68o |
| contig40_gene_989 | hypothetical protein | 1 | i20-42o |
| contig40_gene_991 | ABC transporter permease protein | 8 | i17-39o258-280i301-323o343-365i420-442o633-655i686-708o723-745i |
| contig40_gene_993 | divalent cation transporter mgtE family | 12 | i12-34o54-73i78-100o130-152i165-187o202-224i231-253o263-285i298-320o340-362i383-405o420-442i |
| contig40_gene_1003 | cobalamin biosynthesis protein CobD | 6 | o20-42i49-71o81-103i169-191o226-245i306-328o |
| contig40_gene_1007 | ABC transporter permease protein | 8 | i13-35o250-272i303-325o340-362i419-441o623-645i680-702o717-739i |
| contig40_gene_1012 | Na+-dependent transporter SNF family | 12 | i7-29o42-64i85-107o140-162i174-196o220-242i255-277o315-337i358-380o385-407i427-449o459-481i |
| contig40_gene_1022 | hypothetical protein | 1 | i5-27o |

FIG. 9A-9

| | | | |
|---|---|---|---|
| contig40_gene_1023 | hypothetical protein | 3 | o200-222i227-249o259-281i |
| contig40_gene_1024 | hypothetical protein | 1 | i163-185o |
| contig40_gene_1050 | hypothetical protein | 6 | i20-42o60-77i90-112o122-144i156-173o183-205i |
| contig40_gene_1052 | MFS transporter | 13 | i13-35o45-65i78-97o102-124i137-159o163-182i202-221o225-244i270-292o297-319i332-354o365-387i408-430o |
| contig40_gene_1053 | hypothetical protein | 6 | i21-40o45-67i80-102o117-134i147-166o176-198i |
| contig40_gene_1056 | hypothetical protein | 4 | i19-41o46-68i73-95o99-121i |
| contig40_gene_1077 | SpoIIE family protein | 8 | i7-29o39-61i82-104o114-136i157-179o184-203i224-246o256-278i |
| contig40_gene_1080 | MatE efflux family protein | 12 | i5-27o32-54i67-89o109-131i144-166o170-189i230-252o256-278i299-321o331-353i365-387o391-413i |
| contig40_gene_1083 | hypothetical protein | 9 | o15-34i46-68o78-97i104-126o146-163i176-198o208-230i237-259o269-291i |
| contig40_gene_1095 | hypothetical protein | 1 | i5-27o |
| contig40_gene_1107 | hypothetical protein | 1 | o15-35i |
| contig40_gene_1109 | isoprenylcysteine carboxyl methyltransferase family protein | 5 | i20-42o47-69i90-112o117-139i176-198o |
| contig40_gene_1125 | glycosyl transferase GT2 family | 1 | o253-275i |
| contig40_gene_1126 | glycosyl transferase GT2 family | 1 | i273-292o |
| contig40_gene_1127 | exopolysaccharide biosynthesis polyprenyl | 5 | i7-29o49-71i92 111o115-137i286-307o |

FIG. 9A-10

| | glycosylphosphotransferase | | |
|---|---|---|---|
| contig40_gene_1130 | transporter | 10 | o5-24i37-56o66-88i101-123o128-150i163-185o195-217i224-246o251-273i285-304o |
| contig40_gene_1144 | peptidase M50 family | 6 | o4-21i61-83o103-125i175-197o306-328i360-382o |
| contig40_gene_1153 | MFS transporter | 14 | o10-32i44-66o76-95i100-122o137-159i164-183o198-215i217-239o259-281i288-310o325-342i349-366o395-417i429-451o |
| contig40_gene_1154 | MFS transporter | 14 | o10-32i44-66o76-95i102-124o134-156i163-185o195-217i222-241o261-283i288-310o325-342i349-366o395-417i429-451o |
| contig40_gene_1156 | transporter | 7 | i29-60o70-89i110-132o162-184i197-216o226-248i261-283o |
| contig40_gene_1161 | hypothetical protein | 2 | o27-49i56-74o |
| contig40_gene_1162 | hypothetical protein | 3 | o5-24i29-51o66-88i |
| contig40_gene_1165 | hypothetical protein | 6 | i9-31o46-68i80-102o107-126i133-150o160-182i |
| contig40_gene_1183 | hypothetical protein | 4 | i5-27o66-88i100-122o126-145i |
| contig40_gene_1188 | hypothetical protein | 2 | i27o292o307-329i |
| contig40_gene_1199 | cytochrome C-type biogenesis protein DsbD | 6 | i9-31o41-63i70-92o107-129i142-164o179-201i |
| contig40_gene_1202 | carbon starvation protein CstA | 12 | i33-55o59-77i105-122o137-156i163-184o204-223i244-266o286-308i339-358o362-381i388-407o417-439i |
| contig40_gene_1210 | hypothetical protein | 1 | o10-32i |
| contig40_gene_1212 | hydroxymethylpyrimidine transporter CytX | 12 | i7-29o39-62i75-97o112-134i141-163o178-200i213-232o247-269i289-306o310-332i344-363o368-390i |

FIG. 9A-11

| | | | |
|---|---|---|---|
| contig40_gene_1213 | phosphomethylpyrimidine kinase | 1 | i21-43o |
| contig40_gene_1214 | molybdate ABC transporter permease protein ModB | 5 | o15-33i46-68o83-105i133-155o195-217i |
| contig40_gene_1221 | heavy metal translocating P-type ATPase | 8 | i161-183o193-212i224-246o250-269i408-430o435-457i768-790o795-814i |
| contig40_gene_1222 | potassium uptake protein TrkH family | 9 | o22-44i56-78o116-135i168-190o210-232i253-270o305-327i370-392o429-451i |
| contig40_gene_1231 | MFS transporter | 13 | o28-45i57-76o81-103i116-138o142-164i177-194o204-226i255-277o282-304i317-339o343-361i374-396o401-423i |
| contig40_gene_1232 | MatE efflux family protein | 12 | i20-42o52-74i94-116o136-155i168-190o194-216i255-277o282-304i324-346o361-383i396-415o419-441i |
| contig40_gene_1239 | hypothetical protein | 10 | i20-42o57-79i91-113o128-150i162-184o199-216i229-251o266-288i309-327o337-356i |
| contig40_gene_1240 | hypothetical protein | 3 | i20-42o46-68i75-97o |
| contig40_gene_1242 | hypothetical protein | 6 | i20-42o57-79i105-127o131-153i182-204o209-231i |
| contig40_gene_1249 | CAAX amino terminal protease family protein | 8 | i21-43o48-70i83-105o131-153i166-183o188-207i212-234o244-266i |
| contig40_gene_1250 | CAAX amino terminal protease family protein | 7 | i20-42o47-64i85-107o131-153i165-187o207-229i236-258o |
| contig40_gene_1252 | hypothetical protein | 4 | i42-64o74-96i132-154o174-196i |
| contig40_gene_1253 | hypothetical protein | 6 | i22-44o71-93i123-145o155-177i209-231o246-268i |
| contig40_gene_1256 | hypothetical protein | 1 | o4-26i |
| contig40_gene_1257 | CAAX amino terminal protease family protein | 5 | i59-81o96-118i138-172o182-204i209-231o |

FIG. 9A-12

| | | |
|---|---|---|
| contig40_gene_1258 | peptidase M50 family | 6 | i12-29o34-56i77-99o112-134i141-163o178-200i |
| contig40_gene_1259 | preprotein translocase SecG subunit | 1 | o30-52i |
| contig40_gene_1267 | acyltransferase family protein | 11 | o4-26i39-61o81-99i106 128o133-155i162-181o185-203i215-234o244-266i287-309o319-341i |
| contig40_gene_1271 | ABC transporter permease protein | 8 | i12-34o67-89i102 119o123-145i152-174o203-225i246-268o311-333i |
| contig40_gene_1284 | hypothetical protein | 1 | i23-45o |
| contig40_gene_1299 | hypothetical protein | 1 | o20-37i |
| contig40_gene_1300 | hypothetical protein | 1 | o25-44i |
| contig40_gene_1304 | hypothetical protein | 3 | i37-59o69-91i132-154o |
| contig40_gene_1315 | hypothetical protein | 1 | i13-35o |
| contig40_gene_1327 | hypothetical protein | 1 | i164-186o |
| contig40_gene_1339 | phage tail tape measure protein | 5 | i96-118o180-202i209-231o321-343i356-378o |
| contig40_gene_1352 | hypothetical protein | 7 | o4-26i33-53o63-85i97 116o121-143i156 178o198-220i |
| contig40_gene_1353 | hypothetical protein | 3 | o20-42i128-150o165-184i |
| contig40_gene_1354 | hypothetical protein | 1 | i20-42o |
| contig40_gene_1356 | formate/nitrite transporter FdhC | 8 | i28-50o65-87i115-137o141 163i175 194o198-217i222-244o248-270i |

FIG. 9A-13

| | | | |
|---|---|---|---|
| contig40_gene_1378 | MatE efflux family protein | 11 | o31-53i66-88o108-130i137-159o169-188i216-238o253-275i296-318o333-355i362-384o389-411i |
| contig45_gene_1 | C4-dicarboxylate transporter/malic acid transport protein Tdt | 10 | i7-25o29-51i58-80o95-117i129-148o153-175i187-209o213-235i242-261o276-295i |
| contig45_gene_10 | major facilitator superfamily protein | 11 | o15-37i50-72o85-107i144-166o170-187i220-242o257-279i286-305o315-337i350-372o377-399i |
| contig45_gene_29 | conserved hypothetical protein | 2 | i324-343o363-397i |
| contig45_gene_38 | conserved hypothetical transmembrane protein | 6 | i21-40o50-72i92-111o121-143i173-195o199-221i |
| contig45_gene_52 | phospho-N-acetylmuramoyl pentapeptide-transferase MraY | 10 | o15-37i58-80o85-107i175-197o201-220i227-246o251-268i275-294o298-317i346-368o |
| contig45_gene_67 | conserved hypothetical transmembrane protein | 3 | o32-66i73-95o141-163i |
| contig45_gene_72 | hypothetical protein | 1 | i7-25o |
| contig45_gene_83 | polysaccharide/polyol phosphate ABC transporter permease protein | 7 | i27-49o69-91i104-126o141-163i170-189o199-221i228-245o |
| contig45_gene_96 | conserved hypothetical protein | 1 | i20-42o |
| contig45_gene_97 | conserved hypothetical transmembrane protein | 7 | o4-26i38-55o70-92i104-126o141-163i175-197o212-234i |
| contig45_gene_98 | biopolymer transport protein | 3 | o25-47i133-155o170-189i |
| contig45_gene_99 | ion transport protein | 6 | i2-20o25-47i68-90o121-143i150-172o177-199i |
| contig45_gene_114 | conserved hypothetical protein | 2 | o15-37i42-59o |
| contig45_gene_143 | conserved hypothetical transmembrane protein | 8 | i13-35o77 99i106-123o133 155i168 190o205-227i234-251o256-278i |
| contig45_gene_146 | heat shock protein HtpX | 4 | i12-34o38-57i150-172o182-204i |
| contig45_gene_150 | conserved hypothetical | 1 | i79-101o |

FIG. 9A-14

| | protein | | |
|---|---|---|---|
| contig47_gene_1 | transposase | 1 | i45-64o |
| contig47_gene_12 | hypothetical protein | 1 | i62-84o |
| contig47_gene_21 | hypothetical protein | 2 | o10-34i47-69o |
| contig47_gene_22 | hypothetical protein | 1 | i5-27o |
| contig47_gene_26 | hypothetical protein | 6 | i20-37o42-61i82-104o131-153i186-208o218-240i |
| contig47_gene_35 | hypothetical protein | 6 | i7-24o29-51i56-78o88-110i117-136o141-163i |
| contig47_gene_36 | 2-polyprenylphenol 6-hydroxylase UbiB | 1 | o507-529i |
| contig47_gene_37 | hypothetical protein | 7 | i28-45o49-67i87-109o129-151i158-175o180-202i207-229o |
| contig47_gene_41 | hypothetical protein | 1 | i46-68o |
| contig47_gene_46 | hypothetical protein | 1 | o29-51i |
| contig47_gene_58 | hypothetical protein | 13 | o27-49i70-89o104-125i130-152o167-189i201-223o238-256i269-286o291-313i326-343o348-370i396-418o433-450i |
| contig47_gene_65 | hypothetical protein | 1 | i26-45o |
| contig47_gene_67 | hypothetical protein | 5 | o26-48i50-72o82-99i104-123o128-145i |
| contig47_gene_68 | hypothetical protein | 7 | o18-40i52-74o78-100i112-134o149-171i184-206o221-243i |
| contig47_gene_69 | hypothetical protein | 8 | i9-28o48-65i88-110o115-137i144-163o168-190i211-233o283-305i |
| contig47_gene_79 | hypothetical protein | 1 | o20-42i |
| contig47_gene_80 | MotA/TolQ/ExbB proton channel family protein | 3 | o18-40i127-149o159 181i |
| contig47_gene_81 | hypothetical protein | 1 | o907-925i |
| contig47_gene_86 | V-type ATP synthase subunit C AtpC | 1 | i20-42o |
| contig47_gene_88 | V-type ATP synthase subunit K AtpK | 4 | i7-29o60-82i89-111o143-160i |
| contig47_gene_89 | V type ATP synthase subunit I AtpI | 7 | o383-405i418-440o469-491i507-529o533-555i567-589o599-621i |
| contig47_gene_91 | hypothetical protein | 4 | i5-24o28-50i57-76o81-98i |
| contig47_gene_92 | hypothetical protein | 1 | o47-69i |
| contig47_gene_99 | hypothetical protein | 10 | o10-32i53-75o81-103i136-158o168-190i202-224o291-313i320-342o352-374i387-409o |

FIG. 9A-15

| | | | |
|---|---|---|---|
| contig47_gene_100 | hypothetical protein | 1 | i12-31o |
| contig47_gene_103 | hypothetical protein | 2 | i21-43o48-67i |
| contig47_gene_116 | type II secretion system protein F | 5 | i42-64o68-89i213-235o250-272i284-306o |
| contig47_gene_123 | hypothetical protein | 4 | i9-31o41-63i76-95o105-127i |
| contig47_gene_125 | hypothetical protein | 2 | i20-42o47-69i |
| contig47_gene_127 | YhgE/Pip-like protein | 6 | i21-43o417-437i458-480o485-507i520-542o569-591i |
| contig47_gene_147 | hypothetical protein | 1 | i92-114o |
| contig47_gene_150 | Na+-dependent transporter SNF family | 7 | o26-48i61-83o122-144i165-187o191-213i234-256o266-286i |
| contig47_gene_151 | Na+-dependent transporter SNF family | 4 | i7-28o43-65i85-107o142 164i |
| contig47_gene_154 | hypothetical protein | 6 | i13-30o40-57i78-100o136-158i192-209o214-236i |
| contig47_gene_157 | hypothetical protein | 1 | i92-110o |
| contig47_gene_163 | transposase | 1 | o15-32i |
| contig47_gene_165 | transposase | 1 | i45-64o |
| contig47_gene_166 | 2-polyprenylphenol 6-hydroxylase UbiB | 2 | i114-136o146-168i |
| contig47_gene_172 | mechanosensitive ion channel protein | 3 | i12-34o61-80i85-104o |
| contig47_gene_174 | hypothetical protein | 4 | i54-73o77-99i193-212o227-249i |
| contig47_gene_179 | MatE efflux family protein | 12 | i21-43o53-75i95-117o132-154i167-189o194-216i256-278o282-304i324-346o361-383i395-417o422-444i |
| contig47_gene_181 | hypothetical protein | 6 | o4-23i36-58o63-85i106-128o132-154i167-189o |
| contig47_gene_185 | hypothetical protein. | 1 | i114-136o |
| contig47_gene_187 | hypothetical protein | 5 | o41-60i73-92o102-124i156-173o209-231i |
| contig47_gene_190 | hypothetical protein | 2 | i5-27o40-62i |
| contig47_gene_191 | band 7 family protein | 1 | o4-21i |
| contig47_gene_192 | hypothetical protein | 4 | i9-27o32-54i61-83o103-125i |
| contig47_gene_193 | hypothetical protein | 3 | o40-62i69-91o101-123i |
| contig47_gene_209 | hypothetical protein | 11 | o15-34i47-66o81-103i135-158o168-190i202-224o274-293i300-322o327-344i351-373o388-410i |

FIG. 9A-16

| | | | |
|---|---|---|---|
| contig47_gene_212 | transposase | 1 | i45-64o |
| contig47_gene_219 | hypothetical protein | 2 | o26-45i65-96o |
| contig47_gene_220 | hypothetical protein | 2 | i12-31o36-58i |
| contig47_gene_226 | hypothetical protein | 6 | i2-21o26-43i55-77o82-101i108-130o134-153i |
| contig47_gene_234 | MFS transporter | 11 | i7-29o44-66i73-90o94-116i135-157o161-182i203-225o240-262i269-303o327-349i356-378o |
| contig47_gene_235 | hypothetical protein | 2 | o15-49i70-92o |
| contig47_gene_246 | CAAX amino terminal protease family protein | 7 | o20-42i63-85o95-117i124-146o151-169i176-194o209-226i |
| contig47_gene_248 | hypothetical protein | 5 | o10-32i62-84o104-121i128-146o161-183i |
| contig47_gene_250 | hypothetical protein | 1 | o10-32i |
| contig47_gene_251 | hypothetical protein | 8 | i36-53o63-85i119-141o156-178i199-221o231-253i367-389o393-410i |
| contig47_gene_252 | cobalt ABC transporter permease protein CbiQ | 5 | i28-59o74-96i109-131o146-165i243-265o |
| contig47_gene_254 | cobalamin biosynthesis protein CbiM | 5 | i21-43o53-75i88-110o125-147i154-176o |
| contig47_gene_256 | ferrous iron transport protein B FeoB | 10 | i288-310o320-342i347-369o389-411i424-446o456-476i512-534o569-591i611-633o648-670i |
| contig47_gene_258 | hypothetical protein | 1 | o15-34i |
| contig47_gene_265 | hypothetical protein | 1 | o56-78i |
| contig47_gene_271 | type II secretion system protein F | 2 | o144-166i173-195o |
| contig47_gene_275 | hypothetical protein | 11 | i5-24o29-51i100-122o132-149i154-176o180-202i223-245o307-329i349-368o372-394i399-415o |
| contig47_gene_281 | serine phosphatase | 8 | i13-35o55-74i95-117o132-154i174-196o201-218i239-261o276-298i |
| contig47_gene_284 | acyltransferase | 10 | i12-34o49-71i92-114o129-148i161-183o187-209i222-241o246-268i281-300o315-337i |
| contig47_gene_286 | hypothetical protein | 5 | o15-37i58-77o112-134i173-190o195-217i |
| contig47_gene_287 | hypothetical protein | 7 | o5-27i63-85o90-107i114-131o136-153i165-187o222-244i |
| contig47_gene_294 | CDP-alcohol phosphatidyltransferase | 5 | o20-42i49-71o91-113i139-156o160-182i |
| contig47_gene_298 | hypothetical protein | 2 | i73-95o105-122i |

FIG. 9A-17

| | | | |
|---|---|---|---|
| contig47_gene_300 | hypothetical protein | 5 | o15-37i58-80o85-107i120-142o146-168i |
| contig47_gene_301 | hypothetical protein | 5 | i9-31o35-57i70-92o102-124i144-166o |
| contig47_gene_302 | hypothetical protein | 6 | i17-39o63-85i97-119o129-146i158-175o188-205i |
| contig47_gene_307 | hypothetical protein | 2 | i44-75o95-114i |
| contig47_gene_310 | hypothetical protein | 1 | i68-90o |
| contig47_gene_316 | protein translocase Sec61-gamma subunit | 1 | o35-57i |
| contig47_gene_328 | hypothetical protein | 5 | i21-43o76-98i110-132o137-159i180-202o |
| contig47_gene_331 | voltage gated chloride channel protein | 10 | o19-41i61-80o158-180i193-212o227-249i262-284o304-326i333-350o365-387i392-414o |
| contig47_gene_338 | hypothetical protein | 6 | i5-23o33-64i93-115o153-175i182-204o214-231i |
| contig47_gene_365 | transposase | 1 | i45-64o |
| contig47_gene_366 | cytidylyltransferase family protein | 7 | o6-23i36-53o57-79i92-111o116-138i155-177o187-209i |
| contig47_gene_371 | hypothetical protein | 5 | i17-36o73-95i102-124o128-147i168-190o |
| contig47_gene_385 | calcineurin-like phosphoesterase | 3 | o5-27i48-70o75-97i |
| contig47_gene_388 | hypothetical protein | 1 | i2-24o |
| contig47_gene_393 | Na+-dependent transporter SNF family | 12 | i13-35o45-67i88-110o146-168i181-203o223-245i258-280o319-341i362-384o388-410i431-453o463-485i |
| contig47_gene_394 | Na+-dependent transporter SNF family | 10 | i13-30o45-67i88-110o145-167i180-202o226-248i261-283o318-340i361-383o387-409i |
| contig47_gene_395 | transporter Na+/H+ antiporter family | 11 | i12-34o49-71i78-100o105-124i187-209o238-260i297-319o358-377i398-420o430-452i522-544o |
| contig47_gene_408 | oligosaccharyl transferase STT3 subunit | 13 | i9-31o125-144i153-175o180-197i204-226o230-252i273-295o345-367i426-443o447-469i481-503o507-529i542-564o |
| contig47_gene_420 | MFS transporter | 14 | i17-39o54-76i88-110o115-137i144-166o176-195i207-229o233-255i275-297o307-329i342-359o374-396i417-439o482-504i |
| contig47_gene_421 | hypothetical protein | 5 | o10-42i49-71i77-99i106-125o130-149i |
| contig47_gene_422 | hypothetical protein | 6 | i21-43o53-75i104-126o165-187i224-246o250-267i |
| contig47_gene_424 | hypothetical protein | 4 | i17-36o46-65i70-92o102-124i |
| contig47_gene_425 | hypothetical protein | 6 | i7-29o56-75i80-102o117-139i159-181o216-238i |

FIG. 9A-18

| | | |
|---|---|---|
| contig47_gene_428 | hypothetical protein | 8 | i7-29o49-68i88-105o109-128i149-17|o181-203i215-237o252-274i |



| | | | |
|---|---|---|---|
| contig47_gene_428 | hypothetical protein | 8 | i7-29o49-68i88-105o109-128i149-17|o181-203i215-237o252-274i |
| contig47_gene_431 | transporter small multidrug resistance (SMR) family | 3 | o30-49i56-78o83-105i |
| contig47_gene_433 | ABC transporter ATP-binding/permease protein | 11 | i13-35o55-77i124-146o150-172i237-259o274-293i365-383o403-422i484-503o508-525i601-623o |
| contig47_gene_438 | hypothetical protein | 8 | i7-29o49-68i88-105o109 128i149-17|o181-203i215-237o252-274i |
| contig49_gene_6 | conserved hypothetical protein | 2 | i43-65o85-107i |
| contig49_gene_9 | conserved hypothetical transmembrane protein | 6 | i13-32o42-64i91-113o133-151i158-177o187-209i |
| contig49_gene_22 | cobalt-zinc-cadmium resistance protein czcD | 5 | i30-52o56-78i91-113o128-150i187-209o |
| contig49_gene_28 | cation diffusion facilitator family transporter | 6 | i13-35o39-61i81-103o118-140i160-177o182-201i |
| contig49_gene_32 | conserved hypothetical protein | 1 | i20-42o |
| contig49_gene_33 | conserved hypothetical protein | 1 | o46-68i |
| contig49_gene_34 | conserved hypothetical protein | 2 | o5-27i32-54o |
| contig49_gene_39 | conserved hypothetical secreted protein | 3 | o10-32i35-52o67-89i |
| contig49_gene_41 | conserved hypothetical protein | 7 | i21-38o48-70i91-113o123-142i149-171o181-203i582-601o |
| contig49_gene_75 | preprotein translocase SecY subunit SecY | 7 | o15-37i44-66o94-116i147-169o212-231i270-289o293-312i |
| contig49_gene_77 | conserved hypothetical transmembrane protein | 5 | i7-29o39-61i112-134o138-160i173-192o |
| contig49_gene_83 | cobalt ABC transporter permease protein CbiQ | 3 | o5-27i40-62o77-96i |
| contig49_gene_84 | cobalt transport protein CbiN | 2 | i5-27o69-88i |
| contig49_gene_85 | cobalamin biosynthesis protein CbiM | 6 | i7-29o44-66i73-95o105 127i139-161o176-198i |

| | | | |
|---|---|---|---|
| contig49_gene_101 | conserved hypothetical transmembrane protein | 3 | i20-42o52-74i81-103o |
| contig49_gene_133 | conserved hypothetical protein | 1 | i98-115o |
| contig49_gene_153 | ABC transporter permease protein | 5 | o5-27i34-56o87-109i149-171o186-208i |
| contig49_gene_169 | glycosyl transferase GT4 family | 8 | o4-26i60-82o86-108i115-137o157-179i184-201o216-238i297-319o |
| contig49_gene_173 | conserved hypothetical protein | 1 | i7-29o |
| contig49_gene_191 | Sodium:dicarboxylate symporter family protein | 8 | i13-33o43-65i78-100o137-156i177-199o214-236i292-314o324-346i |
| contig49_gene_201 | heavy metal translocating P-type ATPase | 5 | i21-40o44-66i73-95o243-265i270-292o |
| contig49_gene_205 | ABC transporter permease protein | 5 | o24-43i83-105o131-153i195-217o251-268i |
| contig49_gene_206 | ABC transporter permease protein | 1 | o44-66i |
| contig49_gene_207 | ABC transporter permease protein | 3 | o73-95i116-138o158-177i |
| contig49_gene_217 | ABC transporter permease/ATP-binding protein | 6 | i21-43o63-85i134-156o166-185i246-268o283-305i |
| contig49_gene_218 | ABC transporter ATP-binding/permease protein | 5 | i38-60o75-97i158-175o179-198i276-298o |
| contig49_gene_225 | conserved hypothetical transmembrane protein | 8 | i7-29o49-68i81-115o130-152i203-225o245-267i288-307o311-333i |
| contig49_gene_227 | ATP-dependent protease La LonB | 1 | i229-251o |
| contig49_gene_231 | conserved hypothetical protein | 3 | i5-27o37-54i61-83o |
| contig49_gene_232 | conserved hypothetical transmembrane protein | 3 | i13-33o38-60i72-94o |
| contig49_gene_242 | hypothetical protein | 1 | o52-74i |
| contig49_gene_243 | conserved hypothetical | 5 | i66-88o103-125i138-160o170-192i213-230o |

FIG. 9A-20

| | | | |
|---|---|---|---|
| contig49_gene_247 | transmembrane protein | 11 | o18-40i47-69o91-113i126-145o160-182i191-213o247-269i314-333o348-367i380-402o412-434i |
| contig55_gene_5 | MATE efflux family protein | 5 | i13-35o45-67i69-91o101 123i287 309o |
| contig55_gene_10 | conserved hypothetical transmembrane protein | 1 | o45-62i |
| contig55_gene_14 | hypothetical protein | 10 | i5-27o37-54i67-89o93-115i122-141o145-167i179-201o216-238i243-265o270-287i |
| contig55_gene_27 | conserved hypothetical transmembrane protein | 4 | o4-23i30-52o62-84i97-116o |
| contig55_gene_29 | transposase | 1 | i45-64o |
| contig55_gene_41 | conserved hypothetical protein | 1 | o5-24i |
| contig55_gene_43 | ion transport protein | 4 | i9-31o41-63i138-157o192-214i |
| | | | * The topology is given as the position of the transmembrane helices separated by 'i' if the loop is on the inside or 'o' if it is on the outside. The example 'i7-29o44-66i87-109o' means that it starts on the inside, has a predicted TMH at position 7 to 29, the outside, then a TMH at position 44-66 etc. |

FIG. 9B-1

ORFs containing membrane-spanning domains identified from *M. ruminantium*: nucleotide sequences

| ORF | SEQ ID No. | Nucleotide sequence |
|---|---|---|
| Contig40_gene_28 | 1003 | atgaagttgaaataatgattataggatctgctgctttcaaacttcctatatcatcatgaggatgaaatcctattgtgcagtatgtagcata tattgcctcattgcttgtcataatttttagggtctctttaa |
| Contig40_gene_32 | 1004 | atgaaaaatcagtcatactcctgctgcagtatccttgtcactgcattcctgcaaacatctgtagctttgccctttaatagcaaggaa gcttgcaatgagca

FIG. 9B-2

| | | |
|---|---|---|
| | | acgttatatatggcattcttatcctcacgcctttaggcatatatctcaaatacggcagggagccaaaggtgtcaagtgatgccatatatgagcat gagcctccaacagatgactctccagcctttgtaaatgcaatgatgagtggattgagtaaggatgttggaaaggttgataagaaaggtttccaagc cacaataatggatctcattaacagagacaagcttggaatggaaatagcatatacaaataagaaaagacctgtgt |
| Contig40_ gene_37 | 1007 | atgaatcttaaacaaaaagcaattatcatgctcatactctcaatacttctaatgtctgccatttcagcaagcgactataaaggaagctatatgga ttatgtgcatatgaacgtaaacgaaaacggtttggttcacgtcaacgaaagctttacatatcaaatggtatctccagagtctgaaataagccttc ccctctatcatggcaccaatgcaagcattgaaaatatccatattagggtcaacgatctcttggttgcctatgacctcaagaaaggggacactcta gatgagctagtcatacatcctaagtcttcagattatgattatgactctgaaagcacaggcacatatcttcttgatgtggaagtcgaatatgatat tgaaaatgccgtaaaggtctataatgacgtaggggcattcacttaccaaatcaataaaacagattttaatggggtttctttaggaatggcccata taagaatcaagttcccaggcactcaggagcatgaatacttcataattcctaaagagggcgaaagcagtgcccaatgggatgaggaccattttcat atgaccaatagccagcctgcgaaagcaactgtcataattccattagatgaattggacgctgatgcaaaatatgctcagcatattgattctgacgg attggaagcgattaaaaacgactcattcgatttgaagtattccctaattcagatagtcaacatactgataaaaatctttgtaatcatcgcattca tccttccggttgcaatatacctgaaatacggaagggagccaaaagtgacccttgacagcatctatgagcatgagcctccaacagatgatcctcca ttctttgtaaatgcaataatgggcggaacctttagggacgtcggctagtggatacaaaggcattccaggcaacaatcatggacctgataaatag gggaaagctatctgttgaaactgaaatcaatgaaaagaacaagcaaaggacatatcttgtggcaaaatcaacag |
| Contig40_ gene_42 | 1008 | atgaatataacagaaaatcagtctgataatgatgaaaaaatattaacaaagtcattttgtcttattttggagctttgctctttacagcccttgt aatgtatgcattgatgtccactgtaacagagtatgccagctctatgggttccactgcaactattgcaggtcttgtatctggaatatatgtattcg gtgggctttgttcaagaatatattcagcaaatgcattggaaaagaaggattggaagaccttagccctaatattcctttcaattcacttttagca tgcatattgtacttctttgtcgacaatgtcgaattgcttattttagtcagattcatccatggccttggatttggagcttcagcaaatgcaatagt gactattgcaagttcaattcttcctaaaaaacgctttggagaggctttcggatactttatgcttggaaccactatcgctgtaggattaggtccat atatcagcggattcttctatgatatctggggctctttcggcagctttcttctagctactgtattctcattcatagcattggtctgtgtcttttc cttgatatagaaaggtatcatccagatgaaaagataaataatgaagatattttatctgatgctgaatcagtaggcacagaatctatagatgcaaa cccaatcaaaaaacaaaaggaaaaaagaagcttcattgaaaagatatttgaaatagatgctatccccgtctccctatttacagcattgactgcac ttggatatgtgtccatactctcattctataggctttatgcagtggaactggacctggttggcccattctcaattttctttttaatctattcagtc atcctagttgcatcaaggccaattgcaggtaagattcaggataaaaatggggataagatcatctgtgtaataggcatagttgcacagtcaatagg actcttccttatagcttatgctccatctgacataacaatttatatctgtgctgtatgtgcggctttaggttttg |
| Contig40_ gene_43 | 1009 | atgggagagaaagcacaatgggatagttccctttcatttatatttgctatgattggagcagctgtagggcttggaaacatatggcgtttcagcta tgtactatactctaacggaggaggatcattcttcattccttattttgtagcaatagcaatcatgggaattcctttttaatacttgaatatggtg ttggattcagctttaaggattcgttcacgaatatcttaaagaaaatagatggaaggcttgaaatagtagcctggatactgattctttttgtattt atagttgtaatttattatatggtcatactgagttgggatatggtatatctgctgaccagctttacatttggctggggagtggacactgcagctta ctttacaaatacagttggaggcagtgcagatttggcaaagggggaatctttttaattcctacaaccatatgcgtagtccttatgtggattgtat tatggtttatatcccatagggatgttgacaagggaataggaaaggtttcaaaagtattgatcccatccctttttgtcatcatgggaataatcgta ttctattcaatcacattgccaggacatatgataggaattgatgcattgcttcgtcctaactggagaatgcttcttgatgtcaatatctggcttgc agcatttgcacagatcatcttctcattaagcatggggcaggcaatcgcccttacatatgcaagctatcttccagagtcctcaaggctcactgaca atgtattgatagttgtcgcctcaaattcattgtttgaaatattcacagcatttggagtcttttccatattgggatacatgtcattgaattctgga atggccttaaacaaattggttacagaaggaacagggcttgtatttattgttttcccaatgatattcaatgtcatgggtacggtaggaagagtatt ggcacctctcttgttttagcaattctatttgctggaatcacttccgctttaggcttcttcgagcctatgctaa |

FIG. 9B-3

| | | |
|---|---|---|
| Contig40_<br>gene_47 | 1010 | atgaagaaataagaaatgaactgacctgcttatcttgaagatatcatgttttgtttggcagttcttattttcctgctcgatacctatctg<br>cggagatgggaagagatcatcgctatctttgaagcatatcggatttattccaatagatatcctcattgtacgattggttcttgaagagatca<br>tggaagaaaagagcatgaagccattgaatataggctaacactgatgattttgagagatagaacatgctcttatggtacattcttctctgagattgaaatgattaattgcagaatta<br>agcaaggccaatgtaaataaggctaacactgtgatgtttaaaggctattaaagctcatgaacgataagattatgataataaactaaagaattgaa<br>aacaatcctgtagactttaaggccaataccaacctaacttgctgaggaaagagaagatgaattctcatcacttctgctcgattatgcacttgttgaaacagagaat<br>ttagtaaactcttatccataaccctaacttgctgaggaaagatgaattctcatcacttctgctcgattatgcacttgttgaaacagagaat<br>agaaggtgaattaactgacataaaggatgctgattcaatcacttgaatgtgatagaaaggtattccaaattggtttatgaatggt<br>ttattatttaaaataacttaataagcattatcctatatgatatctcttgctatacgtacccaatccgttgatagcgaagcagatgttcatgtga<br>ctgaataa |
| Contig40_<br>gene_60 | 1011 | atgatagaggaattagtaactacatgtctatacggaaagcggagcttcagcagctctccaatattacataacaattctagtctttacaat<br>cttgtcccttataggcataatatatttgtctttaagatgtataagcagtcaaagcctacagtgaacaatcgttctaattgcgtttaacag<br>ctattgcaactgtggacgtcttattctaatgtcaatacctgctgtaaacctgcatcattgtaataataatggggggtgtcttggcaag<br>gaggaaggttccctgtaggtgccctacagcattgtttcaggcatattcatggaatgcatattcatggcttcagatgcttgcttgggg<br>acttatggagcaagtgcaggatactggcttcaaggttgacagctttgccattcagatgccattactccaatcattgcatgtactatattcatggcatgttaacactatagcgct<br>ggataactgatatttcagctatctctcttcaggaaccgcattgcagattactccaatcattgcatgtacattaacgtttcacctatgacttg<br>actcacggagtaactaatgcagtgcttttagtcgtattgtattgactgttttaagaagatgtttacaagagctaagattaaatatctgtctaatcc<br>aagctcaagtgatgaaagcattgacttaactaattaa |
| Contig40_<br>gene_62 | 1012 | atgaacttacagctattcatccaggcgtatattgcttactattttgcttcatttttagcgatccttatttgtatt<br>gagttttttagctttgattcttattctttctgaatcggacaggggcacatagatatctttcaacgattcttcatcacctatgaagcaattgcatat<br>tgattataattctaatctccctcctgaatcggacaggggcacatagatatctttcaacgattcttcatcacctatgaagcaattgcatat<br>gggatattgatgtcattgcacttcatcaatgataattgtaatgcattaaggtcattttccatcaggatgctcagttcctatcaggagatgcttatatctttc<br>taaaagcttcaatcatccaatgataattgtaatgcattaaggtcattttccatcaggagatgcttatatctttc<br>atctgaagccaatgggtagaatcagatagagagattgattttaaatgatgattcttgaagacaatcttctgaggaaaataatcttcagat<br>gaaataattcaaaagaagattcagactctcaatggttccaatccaatcaagcctgatagatcatgactgaaagtcctgatagatgaataacagctcatggtccttg<br>caagagatacaataaaagtcctcaaagttccaatccaatcaagcctgatagatcatgactgaaagtcctgatagatcacagctcatggtccttg<br>aagagtccatgttacagccaagtcaataatgcacagtacacgattgatatcacaagtcagcctttacacaagttcgagcttgcagac<br>atcatattccttgcaatcaatcatatgtcacagtcacattaacatttattttgcattatagtatttttattcacttaaatccttcaataga<br>ctctcattcagcagtttaccatttaacatttattttgcattatagtatttttattcacttaatctatc |
| Contig40_<br>gene_74 | 1013 | atgatgatttaatctctgaataatatatctattcattatatatatggtcttgccttcaatggtattctctcacctatgttgg<br>aaggcgtgaaataatttccattattgccataggatttgttctcggtgctattgcgatacttcttcattatatcctatgtatcaggacagtccct<br>atgtattggcaatctccaggattgtttacaatggagaagtgagataataaacctgaacattccatgcacatccaatcagtgatgtcactgaa<br>aagattctaaatcaaaatgggtcaattcagtaagcactaatgattgagcttacacaaaagctcgataaatagaacgaaaacatatattga<br>tagctatcttaagaatgattctcagatagagcgctatagcataggaaccaataataatttccgttgacctaagaagacgatgcaagctcaacagcca<br>cattgggatcccttgttacttgcttcccaatactgttggagttgagctcgaatttgccttgtcacattaagttaatgtaatgcaaatcag<br>gttctggatatcaagaaatattaaggacaatcattatactatagtctcagtagaaggccctgttcaggataccattcattatttctatgatca<br>tctgctccagattatgttgtaatgtgcattacagcataggtgttgctattggtcaggcatatatgttgcagagcctttaaccaagtttg |

FIG. 9B-4

| | | |
|---|---|---|
| Contig40_gene_76 | 1014 | taagagcctttagaagagggggataa<br>atgtctggcttcattgtattcttacactcttattggctaactattatgatctgaagtatggattattccaaataagttaagtgttttcct<br>tatgacattttggattctaataaatgtattgatttaattgtcctaataatcgattgtacgcaatatttatgtatcttattaattataattt<br>ttattatctcatttgtcctatgactactcctttgggagttggagctgaagctattctgttcaataggtttcactccctttatagat<br>attctgaatcatttctatactggcagcatcttaaatatcttttcattcaatagccagatatcttcatcctagatctttcaatactgataaa<br>ttcaatcttattgtcatttccggttattctctattactgcttgtttataagttgctaggaaaacagctgaactgatattattgcttttcca<br>atatgaaattgctcataaaggaactgtcaacaaagacagtatttataaactgacctgaaggagggaatgattgtagaggattattattcaatagc<br>ttggagctatttaacttgatggaagagctgactggaatgaagagtgctacaatctaaaagcaagtcaatttaatagaactttccaatttaaatca<br>gtcatcttcaatggcaggtctgacaaggatgacattaaactaatcaattttgcatatatgaaacttttaatcttcgttgtttaatttcaacaataatctaa<br>aatggagttccttttgttccctctttgactgtaggatatttggtattctgtggtttggtgtttatttcaacaataatctaa |
| Contig40_gene_127 | 1015 | atgagtgataaaatgaatgggcagcaatctatcattgttcttcgatggtagttctgtcgtgtcgactggaaacatatgagataccgta<br>tgtattatacagcaacgtggaggggcattcctttccaaagccattcgcaagattagctcccatatctgttgccatatcccatatcgttgccatactattagatgggaatcctccattttaatattgaatatggcg<br>ttggatataatttcaaatcatccttccaaagccattcgcaagattagctccaaagcagaatactaggatgctcttcctacctcagtattc<br>atcatcatgatatactattcatgcaagcgaatcctgcagcgaatcggatgggaataacaaactttattccagtcattgatattaagcttcttaaggatgggagcagatccaaacacatt<br>ctttgcaagcacattcctccatacataagcgaatctgcaagcgaatcctgcagcgaatcagttcttgcctttgtctttataatcatgattgtatt<br>tcgtttggtacattccatgaccttgctgcgcaatgattgattgaagaggtgagcaagatcctttcacggattgaacttgcttttagacttcaacatgat<br>gtattgtttttcattgacctggcagataaattctctcccttgcagcgcaatgattgattgaagaggtgagcaagatcctttcacggattgaacttgcttttagacttcaacatgat<br>ggcgcattcggccagataaattctctcccttagcctgaatgagcattctgtgttgtagcatatctacagtcttaaacgtattggacaatgcatatgt<br>caataccagcgtgcagaccttgtaactcaagtacagattctatctgtttgtagcatatctacagtcttaaacgtattggacaatgcatatgt<br>ggaacagcggtgcagaccttgtaactcaagtacagattctatctgtttgtagcatatctacagtcttaaacgtattggacaatgcatatgt<br>aatcggaccttattcttcataacagtctatctgcagggcttacaagcatcctatcaactattgagccattgt |
| Contig40_gene_131 | 1016 | atgatagacagttttagatatgcattaaatgaattgcagtttctgagtttctcttataaagatgagaagaaacctgaaaatccaaatgattgttatgatgcttgt<br>tataatagccggatttctttaaagatacagaacagaatggataatctctatttgcacttgctaataagtgctgaatgataaaca<br>ctgccattgaaaatgctatagactacaccagagaaatgactgttgataaggacaatgactgttgataaggacaatgactgttagccagagatgctaaggatgtctctgcaggagct<br>gtctgtaattgcatctgcatctgcgattgttgattaattattttattccgaaagttctcttattgcttaa |
| Contig40_gene_145 | 1017 | gtgatttgagagaaaagcccttaaagatgtccttgagatagcatttgcctctttgttttttctgctaattgaaataggatttgcattgtttgt<br>cagttttattcattggagtatttattgatagtagtagggaataggatgatagaagctatgtttga |
| Contig40_gene_168 | 1018 | atggtagtactagtgcaggagatactgcatggtgctcattgcaacaatccttgttctttcttaatgagcatccctgaagtagctttcttttatag<br>tggtttaacaaaacgtaaaaatgtcttaaatacaatgtttcttgactttattgcatttccatagcaagcatataggttgtatatggatacc<br>catttgcctttgagatgtcagtataagcggtttgatagctcaacctgcattcttcatgagcggaatcctgaagaatcttacaggaacc<br>atccctacaatattgttattgtgttccaattaaccttgccggtcttacagcggccctatccaggtcaatgctgggaaggatgaaggtctc<br>agcatgatagtcttcatcattgctgggtcacccctgtttatgtaccgattgccactggtatgggaggagatcctatgcagatggatgtt<br>ccctggactttgcaggaggtacagttgtacatattcagttctcggtgcagattccttggttcggatgggccctgtctcggaagaagaagacacttcc<br>ttttgccacacaaactttaggatatcctgtatcaaacgttgcagctgcaacagcacttatcactgggttggtaattatgatattctcagctaa<br>cggacttgcagcatcagcttgtttgactcaccggtggagtgctgactgtgatcagcaggattgtttgattcgtttgcagcagcagcattgtcatt<br>caaccatgtagggcaatcagcatcaccggtggagtgctgactgtgatcagcaggattgtttgattcgtttgcagcagcagcattgtcatt |

FIG. 9B-5

| | | |
|---|---|---|
| Contig40_gene_173 | 1019 | ggttttgtaaccacattcgtatcctactttgcaatctattacttaaagacaagattcggctacgacgatgctttggatgtatttggagttcacgg tctttcaggtgttttggggagccactaattgcaaccgtatatttgcagttccagcagtcggagtgcagcaggtttgc |
| Contig40_gene_174 | 1020 | atgaacatcttaaatctgccactaatatcagtcattgaagccctatcctaggaaatggaatctcattcttgcctcattatcctagctgtgtagtcaatga caagagagcctataaatcagtcattgtcatgaatgagattaagctcctcatgtttcatcagcctcttcctcatgactggcatacaatgc tcattgcagcggcaagaaaactatcttgtcatgaatgagattaagctccagattggccataatataacagctggaatatcttatcatatgtccc ctaattaatacaatggccttatcggacttcttcattgatatatgctgttttacttcattgaatctatgctgttttatcatgtcaactattatcttaagacaatcaaatgat aaagtggcattcattgtaaatgtattgtaaagctaactcttttagtaaagctaatcaaggatgaaaaagaggggcaatatagactctcagccaataattaa taatcggattcatatctttagtaaagctaatcaaggatgaaaaagaggggcaataatagactctcagccaataattaa |
| Contig40_gene_175 | 1021 | atgtctgatgatgaattatatagaagagctaaagaagtgatgaaaaaattggatttttataagcatttatatagctatattgtgtaaacat acttctttttgccataaatgcaatcacatcctcgcaaatgtgttcttattggtaactatcttttgggaataggcattgtaattcacttt taaaacatttgtcttgactggaaaactgaagacaaccgagaggaaatgattcaaaaggaaatgattcaaaagaaatgaaaatgaaaatgaaaaataa |
| Contig40_gene_176 | 1022 | atgaaagacttttaagctagtgaaaatattcttataatcatcataatcatcattgcaattgcagttgcttcttccaggctcattcgattg ggttatggagagtttatggtatcaacatcataatctctacttgaataatcctttgaatggtaccacttgaagatagagaatttttg taaacgtattcaaaaggcattgacagttgccttgtcctgtggacaagcagttgccgatccggtgtctggtcggtccgcttgtcaattgggttgccagcctattc gcctcaatgagcgcattgacagttgccttgtcctgtggacaagcagttgccggtgtctcagtcctccagtgtcagtcctttatcacattccttgcaaagggga tcttgcacttcagtatccctgacttgatatgtcattcaattgttcagatttgcttgatagatgcttctccaatagcatttgatgtcctgaattacaagttccagacttc cattcaatcctgtggatatgtcattgctgcagtctatctgcctgagcgatcgtgtgcagtcgtggtgcaatactccaggatagcttcatgaatatcgttcagtagtgtcaatccaggccattct tgtgaggagcttaaggatataattgcagcaataagagcttgcagcgatcgtgtgcagtccgatcggttgatgacaaatatgcttgtttgtgatattgatagatctctgaatgaaa gaaagcagatgtgaccatagcaataagagcttgcctgcaagactgtgtcacaagccttgcacaagctctactgacctggtttataccttccctt gcaactgttccaggagccttgtatcagtatgcaaaactttgcaggttccatacttgcatatatttttagaaaatattccactgatgaggaata g |
| Contig40_gene_176 | 1022 | ttgaacgaagagcattacaataagcagctattaaggattatcaagaaagcactgttgatttaagtgtttatgtcatagagaagagattatga tgaagatgttgatataagtttgtgatgtcctgattgtgccgatgaagctgcccatatcacgaccatgaccatgatcatcaccatcatcatg accatgaccataaccatgaacacagtcatgaagctcatgagcattcttatagtcatgacgacatgcacagtcatgatagccagccacgagcat gggatgagcagcatagcagcacagaacatagtcatgagtctgaggatcttgtggatgcggttgcatgtcggtgcatgatgatgaacatgagcatgtgccatgatgattagagaacatagtcatgaacatgacc atagtcagcaccatcatgagcatgaacatgaacatcatagcatcatgagcatcatgagcacgatgcagccatcatcatgagcacgatgagcacgacgaccatgaccatagtcagc ccatcatgatgaccatcatcatgagcatgacgacgaccatgacgatgatgacagcggaagactactcgcgatgtgagaggacacagcatatcatcaggagctatcatgagggttctcatttgtg catgtcctgactgtgcagatgtcagatgatgatattgttacagccatcagcatgtcaggtcacagctaggcacagaagcctaataatcaaagacactacaacagacctattcaa atcatgtttccagtggaatattgtttcacagcagccatatcctgctacagcatcgtgcatcgtaggcaaagcatcctgcatcgtcagcatcgtgcaagctatgcagccgaactactcaagactactatatctacatgcttgg agcacttatagcaggctatgaagtcatgtgagaggccagcaatcctgcatcatcatgctcaccatccttgtcaagcgtcacactgtcggtcctg |
| Contig40_gene_183 | 1023 | atgagtgaagtattactcctaatggtggggctaaatattcaaataaaaacaaaagccctgccagcaagaaagcaatgattcctactataa aatgtcctttgataggaagtcccaatgtaggcaaaagctgacattcaatatagctatgttttcaattatcctgaa ccactgtggatatcgatgaggcaattcacatattaacaacaagaacagttcacatataacagaccctccaggggcttcattatgatctacaacaataacc |

FIG. 9B-6

| | | |
|---|---|---|
| | | gaagaggaacgtgtagccaagctattggtattggacaaacgctttgacttgatggttcatgttgtggatgcaagaacatagaaagtcaataga<br>ccttacgttgcagcttatagatgccgaaaggaagttatcctgtattgaacatgatggttgaactgatggtgagaactgggtgcaactgtagatgcc<br>cgtcattgtcccatgagctggaattccagttgcttactgcagctgcccaaaaccgaggattggatgactgaagcatacaatcgtaaactat<br>gattcaatagaagatcaaatcttaagcgagtctaagacattgttgatgtcttaagacattgttgatgtcgattatgaaggtcaattgaaatagcaatctctgagattcaaag<br>aaatatcaaaggggaattactctatccaagtttcaaaagcgtttcaaaagcaaaatcgaccagcctgtcagtatccgactaagttgctcttgcagactat<br>aggattgggataatctatccgagtcatgttgctgtgctcaaacaatagacagctaaacattcaggatacccaggatacccgacagcctggagaaaagctaagcagaatcatgatcca<br>gcaaaacatataaagtcaagtttacaacaatagacagctaaacattcaggatacccgacagcctggagaaaagctaagcagaatcatgatcca<br>tccattctatggtcttatcatctgcctgtgttttgttcttggcctttatcttattgtaggagttcttggtg |
| Contig40_<br>gene_188 | 1024 | atgattgtgaatcctgtcattatctagcgtagttgttatttcattacacctccatatattgaatttactgatatttgtattttaat<br>tccggcaatagcctttgattgttcctaatgatgcaattaaaaatagtagagcaataggtgctcttactttatttttagtcattatttgtagcatatt<br>ttgcaattagtgaatgttagggcctatgatgtgatgttcttacaaatatgatgtcaacgttaattaacctctactcctagtacaagtgatatcagt<br>gcttgctctaatgctatttgatgtattgattgattatgcattcaatatttgtggagcattgtcttaaacgaacaagtagtagttgatga<br>tgttgatgatgaagatgcattttaa |
| Contig40_<br>gene_215 | 1025 | atggcttcttgtaatatagggaaaaaaattcatagcagagcttataggtaccttttcctagtgttcttcgtaccggagctgctgttgtaactttt<br>actattctgatagcgtaactccaggtaactgcatggaaagctgcatcggtgctcggggtcttgagattgctgatagctattgcattggtttaa<br>ctgtaatgcatgtatctactactacatgtgctacccaagtaattgagcatgtttaggacatggatatctcctgcttgattgccgaatgtataggtagtagttcttcctatgcttg<br>gcaattgacagtatctactacatgtgctacccaagtaattgagcatgtttaggacatggatatctcctgcttgattgccgaatgtataggtagtagttcttcctatgcttg<br>aattggaggattaggtgctgttgatgaaaaggcagaaccctgattgcacgtacccttggtcttctacttggtgacacccttgcttgcggaaccaattctgggatttcttccc<br>ttgtaatggggcttgctgttgcttcaatcaaccctgattgcacgtacccttggtcttctacttggtgacacccttgcttgcggaaccaattctgggatttcttccc<br>gcattcaccggtgctgcttcaatcaaccctgattgcacgtacccttggtcttctacttggtgacacccttgcttgcggaaccaattctgggatttcttccc<br>gatttacttgattggtcctatagtaggtgcagtcctgcagtcgtcctggcagcaatattatatgatactagctagctaaggcaatgatgcattgcattgccacaac<br>ctttctttgaagaatag |
| Contig40_<br>gene_218 | 1026 | gtgtatctgggaagctcattgcattcattgcacctatggttgccgatatgcgcggaaaatcaagtatctctcagcattgatggttgt<br>agtttggtctatgttgcaattgcaattatcatcaggccggtcaccaccgcggtaaagcaataagctattgcctcctgtaattgtaggtcctatga<br>ttatggttattggcttgttgcccctaccgctattcaggaaataagagactgatcagctgatcaggtccaatcaatcatattgtgctctt<br>gcagcattcctgaccactgctgttaatagcaatccgtgaaaagagtattgaagttatatccttcctcattgtattattgtagcatatgtcgt<br>tgcagcttattagtatggtgttgacttttcagattctttcagcaagcctcttgaagttccagagttctatgccgttataactacagct<br>tcaatcctacagctcttcttacaatagttccgattgctcttgtaacaatgttaggacccaagttgttggacccaagtatttaggggaaatcattgga<br>cgtgactagttcaggaccctgattgaacaagacccttgttgaggtcttgtgacgttcttgcagcgctcctcggtggccagctaacac<br>cacttacggtgaaaacacttctgttgtaggtcttacaagagttgcatcaatctatgttatcggtcttactgcagtttgcagttatctttgcat<br>tctccggacacttgctgcacttctgccatgccacctctgctagttcaacctgttatcgagttgctatctgccttcttacgattcattgcagtaaatggt<br>gtaaagctcttgattcaagaggaagttgattccaacataacaaaaacattgttgtagcagctaccatgttggtttagttaggtggagctac<br>cttgccgttgctcaaggtgacttatctgtcaattcctgatgcctcttgctatgtgtaatcc |
| Contig40_<br>gene_220 | 1027 | gtgtatatcaaagcttttttaatgattgaacttgaccaagaagtgcattgacttgactgttttttcaattctctatacagt<br>ccacctaatcgatgtaaactataccctttaacttttaaatcagcaccctattgctcattttaattaacgttagtctatgctgaatgcaggccata<br>tagagaactattcctatggaatgttcctaacaccctgtatcattcctgacatcactcttctcttcttagaatggaatagtggacaagatagcaata |

FIG. 9B-7

| | | |
|---|---|---|
| | | atgatcgttagcggagtcataagcatcctcgtgattgtacctactattaaaaccaagttcaatggtctactccttttcggctg<br>catcctatttgcaagcttccacatagtcctcacatctgggcgtggggaggcatagacattccagtatgcgcttcagcatcattccttat<br>tcatggtattggcagttgacaaaaacctaaatactactaccacttcaatattcctgattatatcaataatatgcattatc<br>ataatacctatattgttcttatactactactaaacatgactcttcatcctgtggattggcataagcgataggatgagcttaagatagt<br>tattaagaactatataaaagcgaagagtttaatacattgtaatatctgatatatctgattatagctgttgtcttattatactgtttgtgaagtgatat<br>ggtcatatggagctaatctgacattcctgacacaatctcacttttctctcaagagtctctaaacggattcaacagtgcaaaagcgagaagtcattttactat<br>aacgataagaagttctatataagaaatctctcacttttctctcatcctcaaatcagccaagagtttcattgatcattcctgcaatcatagcaat<br>cggaacagtgttcaacttctcaaacatatcagaagaagaaataacccatggtgagagattacaagacac |
| Contig40_<br>gene_230 | 1028 | atggcagctataatatgtccaagatgtgaaaaatgaatgatggaagcttagattctgcatctatgtgaacttacttgatgattataatga<br>agaagacaacaatgacaatctcttttataagatcaatgaacaatgaccaatgatgggagacctgcaagaaacaagtgtcagataaatgaaatgccag<br>ataatctccaaaaacctaaacataggcttgccatatctttaggatacctgtttgcaatattaggcgactataggattgtcttgcaatttat<br>ctaattacaagaaaagataagaatgccagaaggcatgactaatccaattggtattctcttaataagaatatgcttaataggtgttttaatctt<br>aaatgacaattgatataaatatgtttagatcctttcaatatgactcgcatgaataataactcaattactataattccagccaaatgaatg<br>ttagcggtctaatatctcaagttttatttgctttttaa |
| Contig40_<br>gene_246 | 1029 | atggaagaattatattatatgatttatatagtttttatagtagatcaattcttggcctattattaagctataagaagcatatgaacctttt<br>tataatctgaaattgatgtttttaaccttagtttagctatagtcgtagtgttttattattaaccatgcctgattgattggttagttctg<br>taattcttctcaccatagcattcttctgcattgtctttgcaatagaagaaggccaggatatgtgagaaactgtagaagctaaattttggtt<br>gcagtaattgtctgatttaacatctgagtcatatttaaattag |
| Contig40_<br>gene_247 | 1030 | atgaatctaatgctcagatttcaatgctagtagtagtcagtagtcttttcctttgcaggtagtcttttattaggttccatagaaagtcatggcgagagt<br>ccaattaaggccaggaccctccactattatcaatatcctattgcagctttcattcattgaaatttcttcttaaggaacaagctccctaaaactgcttcaatgc<br>catttatgtgggaattacagtaatcctagcagattcctactcgagtaattgttgtcgttgcgttgcaaggttccttaatgataataattc<br>gttatctatgcaatccataagatttgtagagcataatgcaggatccatcagttccctcacggttaagctaagctgtgtaagggctgtattctc<br>agcgcaggagaattgcctctcttgcagtaattgctgttgctgctaactgaaccatgatattggtgaataatacaatatcaagcag<br>caaacggtccttgcatttaaaatccctcttgaaacccgacattcggtatgcttagaggtatatataatgttttcagatcaatcgcttgtatatctt<br>aaggaaaggaaatcattacaggatttgaaacggagtggtgggatacctataggagatgatttgatatgtgattacaggatttatca<br>gctatgctctcttccactcctatgttaaaatccaaaccattcctgtaatgctccaaatatccagttattcgcttgttgttcaattatcatgattatt<br>atgctacaactcctatgttaaaatccaaaccattctgtaatgctccaaatatccagttattcgcttgttgttcaattatcatgattatt<br>atttaa |
| Contig40_<br>gene_249 | 1031 | atgcttatagagaacttaggtgagacttttaggaacaatccctcttggagatattgttctatacttaaccgctccatatattcctgtttgt<br>tactatacttctatttacagctctaatagcaatcagtcgtactgaaacacaagttgaagctatgtttggctcacttgatgagaataaggttgcag<br>tgggactgaaggagtttaagcatcagagatttctagcgataatatgtggtatagcaacagcgggagctatgattacaggggaccttttaacttc<br>acctattatgccttgattggtattgtcataattggtatcgtttcagctgtaaagcaagtgaagtcacttatcagtcatgatt<br>gattgccatgatgtgtgattgccattgttgttgtggagcagctataatattggcagctacaggtaccttaagctgtttgagcttgcaagcattc<br>cagcaaatcctatgtgatgatttgtgacactgttatgcaattggagctgtgcggtagaagcggtatagctccattcttgcaagcaagcagag<br>atgtttagaactccaggatctccatgttcatttacttaagttcattgattattcacttaagtgtgtccttatagttagatttcctatagttagatttcaltacctattgactatatt<br>gtaa |

FIG. 9B-8

| | | |
|---|---|---|
| Contig40_gene_250 | 1032 | atggtagcaagcgtaatccctcaagttgttccgctttcctatagctcaatgtataccacagcctatatgtggtttgattgtagctttattgg<br>cttgattggagtggcaatggacattccagatccttattcttattctaacagatatagttggatggctatgctatcgtcgtagctgcagttg<br>gaactgacttgtctgaagcattgatccttccagtctggtagttgaatggcagagatcatggcaatttcagagatatgtatatctcgtgagatg<br>agaaggctgataaagatacctccatttcctgtctgtttacggcggtacgtgcgtagtccctgcagtgcagtatatgcgatgcagcttatag<br>aatcggatacggcatattcctgtctgttttacggcggtaggagcaatacaggtatttcctgtgttatggatatcggttcatattcttcatcctccgca<br>tgccatatttgttcttgatggcgtaggagcaatacaggtatttcctgtgttatggataatcggttcatattcttcatcctccgca<br>tactggcttttaagcctattccttgcagcttttaagactttattaaaggttgcttcaaagatcgattgattgaatacttatgagagagaata<br>tggaagaaaataa |
| Contig40_gene_253 | 1033 | atgttggaatttataatatagaaacaatatcaatggcctaatgattataggtgccattggagttgttcttcttaaaaaccattgataaaat<br>tattatggttcagttctgaagcaggtctgttttagctatcgttagctttaaatacctgatggcctcctaactgcagttctcgatccat<br>tatccatcattgtattcttacttgcttcttaattaaaatcaataaagtgcgaagtctaaattagaggactattccacttagacaagcttaatata<br>agcactgaaaatctagaagaaaaatcattagataaaactctgaaggaggcaaataa |
| Contig40_gene_254 | 1034 | atgtatatagaaatcataggagttattacaatttaatgcttaagagcagtaataactaaaaacagagcagaaaagttacttacataaatgt<br>aataggtttctgtatctgtcatcattgcttctatcattgcattaaatcacacattggcttttgtattagctgcagctttcttcattcctctacaatcg<br>gttcaaatgcaattgcttatagcttaaggatttgaagatgagataagctatgataagctatgataagctatgataagctatgtatgaagaaggatgaagaaaagtaa |
| Contig40_gene_255 | 1035 | atggaatatgatcattggaataatattagctgcagtatctctgatttaatttttgtagttgttgacacatttgctgaggcttgctgaggctccagg<br>agttaaggtgcagagaccttgtgctattcaatcaaggaaaggagatttgctgaggttcttccaaggaaacatttatgttctcag<br>atgcttcagcaggaaccttgatagcaggaatagcaggagtctatgtcttaggaattgaccatgaccatgaccactattgaattcattctcatttgtcatttgtctatattgaaac<br>aggctatgtgcagatcaggatgtgattgcaatattacaattcaaggaattcatcatcctacaagttccagattgcttgaaagattgctaagtcct<br>gatgttcattgcgaatggtgattgcaatattacaattcaaggaattcatcatcctacaagttccagattgcttgaaagattgctaagtcct<br>ttggcaggtatactaaatatgaataa |
| Contig40_gene_256 | 1036 | gtggctatagtagttgcagtcattatgctttgcctaagattgccacttcttcccgaaaggccaatcaggttctcttgactactagcgcact<br>gtttccaaccctatttttgctataggaatattgcaatattgcaatatttcattaaatgttttattgacgtctcatcttaagcgtgattg<br>tcggattagcttccgctctcttttgtaaagtatgattgactacatattcccaaagcctccaaatgcgaagacggggggaatgtctaa |
| Contig40_gene_268 | 1037 | atggaaatcgatgaattaattacttacttactcatcattgcagttgttgcgatttgcatttaataaaaatattttcatgctcttgcctatcttgtaat<br>attgctgtagcctatgctaatgtttattatattactgaaaacaatgcataa |
| Contig40_gene_273 | 1038 | gtgaaaaaataatagaaaaagcattacgaatactacattaaatcctaatgatttcttcctattgaagagattaaatcattaatgcagctttattt<br>ttgctcaataactgcttatttacatgcttattacatatgcatcatgaacttcttttttaacaatttggaataagcgggaattgatcttatcaattcattaa<br>tagacatatcttatcagtattctcagtgacaatatatgcgctctacaagaggcaagataattagcatatcctttgctattgtatcc<br>atatcctatatcctcttggaggatcattaattagtatgggatttcatccgcatcctatctattaagcattatctatcacagaattctcttaacaatagtcttag<br>gtttatagattatacagaaagatggcaagttacaaatgcaatggatatcgcgcttaggagacagcgaaggaggagtcttg<br>aaaacaaatcctataggcttggggaggatatatattcaggagtcgctacagccacattagcgtgatgcatcatcataagaatctagaagaa<br>atttaggaatatggaaactaagataagtcttgaacggataattgtaatctggaacggataattgtgaacctcaaaaggagaatgaagaat<br>aa |
| Contig40_ | 1039 | atgtcatttttaacattaatattaaaaatcctttaggagcaaagccgagccatactcaatcataggattggaatcggtatagccacaat |

FIG. 9B-9

| | | |
|---|---|---|
| gene_282 | | catcgcattggagcaattaccgacggaatgattgcaagtgcagatgacacactgcatgccggaggatgtgatttacagtaagcggaagatag<br>agagcacatcatcacaaatggctacatccggtacgacaacaattcccatattttgctgttgtgaaagattgcatctgaaatgaagaggagatatagcccatgtaacggtgtaaaagatgct<br>ataggaatgtatatgaccgtcctattgacaacaacactaccgagatagtgattctatgagtcatggaatctatgaggaatctaggtttccgacttgac<br>aattacagaaggacggatgtataaaaacgacactaacgagatagtgttggaatcttgaaagattgcatctgaaatgaagagaggagttggagacacaa<br>tcacacttgatgacaaggaattcaagattgtggaatctatgagtcaggtaacaccttcaggacgaagggatttacagccattaaaaactcc<br>caaaaactctcaaaggatgaaggcaaagatcagttccatctatatccaaggtaaatgatggagaggatgttgataagtcagagatagaatcaccga<br>caaatatggagacaatctgacaacaatagctcattatccgactggaaatgactaagaacatgatagacatgttgaacggagcaagcttagcca<br>tatccctcttgcaatcataattggagctgtcgaatcataaacactatgcttacaagtgtattgaaaggacaaggagcttgtgtcttaaag<br>gcagttgatggtctgacgaaaagattctattaatgattgtaggtgaatcaatagtcattacaatgttgccgcataatcggtcattgtagg<br>agtcattggagtggaactcctgcagcgtctaagtaatgcagcttctaaaaggctctaaacccctgtatattcagttgacatat |
| Contig40_<br>gene_284 | 1040 | atgcaaaccaataacaataaaaacatcgaatcaatcatagagacccctaaaaaggccataaatagattgacctatcccacaatcctttccatgctttaat<br>gtttgcaaataacttaatagacagcatgtgggttagcgcacgcaaattcacttactttcagtcctcagatcatgtctccattgtatctgtga<br>ttattgctttggaagtggagtggagtgggagtagcgcgcaaattcacttcactgttgtctctcattcccgttgtctaagcgttatgagtctaacaatgctgca<br>atccatagtattatataagctctttatcgtttatcgttcaatcatcattcgttctctcattattcttctatcaagcatcataatcattacttctttgatcctattcattatttcttatttttaattgg<br>gtctgtttgatattggatgcaatggactatgtgatagggccacagtgccttagtgtttaatgcaatcctgctttagtgctataattgtatctggtaaagaggatacattcat<br>cagaagggacattagaaggccacagtgccatagtgccttagtgccacacttgctcacacttgtcacacttgctcttacgtactctattcacgcaattcttcattatttattttgg<br>ggagtcaaaggggctgctatcgctacagtattgtcacacttgtcacacttgtctatgtgttatgtctctggtaaagagggataggcattatct<br>aaaattgagttttgagtactctgctttaattatctttacttattgccgggatctttttgtactgggtctttttcactgtgttgtggcgattgtgtcaattc<br>ctattgtagctatctgcttcattcatgctttcctaagcttcatgaatctctcaataacagttgcaggcatagctttcggcatagctagcttgaaatgtgggcgagcttcactgtgttgtgctgaacatctattctaataactctttcttgatttcttcttgcctatccga |
| Contig40_<br>gene_287 | 1041 | atgtttggtaaagataaaaagagaactctaatgaaaagtgttgtatgaaggcaaccaaatttgatagttattcaaagagcatattcattgc<br>agtgattttacttggattctatttttcctctattcaactgaattcaatatattgaaacatgcaagtctatatgataaatcaaccaaattgc<br>cattgactcgctatttttgcaattgcagtcttttgcagtcttttgaaaaggcagttattcataaataatgcaagttgtataaataagattcccatatatcataaataagctttaacactattcaggatgtaagtcg<br>ttctcaagcattttaggaaaagcattcatgcttttgagaatagaggacaactcatctaagtgcaactcatctatatgcgatgcttaagcctaactc<br>aataacagttatataagttcattataatcgtatggagatcttgtaagaatcttgtgttgatgttctccgattggttaagaagagaaaacgaaattcatcatatgacctaac<br>tgatgaaaggttcattaatccagaggaaataatcctaattataagagaagcaattagtgttgatgtccgattgatgttccgattaacaattcattttgctatgatatgaaatacgacgat<br>gaaagctaagaattccagaggaaataatcctaattataagcagaatcctaattataatcgcaacaactatgatgtttgctatgattattgaatctgctataa<br>tataacaggaactctaattataaggaccccctcaaggcaatagggcgtattcaaaaggaatgcaaatcaatacagagacgatt<br>tcaaagatccaaaagagccctcaaggcaatagggcgtattcaaaaggaatgcaaatcaatacagagacgatt |
| Contig40_<br>gene_290 | 1042 | atgcaactttaaaggattttgcaatgaaaagactcatcggttgggtagaaaaaagaagtaccctgaatgtggacctatggacgctattat<br>taaccaacttgtgtatctccatgtacttccgatattcacacagtatggaaggtgcaatggtatggtgacagagacatgatcttagtcacgaag<br>ctgttggtgaagtaggtaagttgaagtggtagcatggtcaaactcaaacctggcgaccgtgtaattgttccagctcaccctgactggacgat<br>gaagcagctcaaagaggattcccttcacaaccacccgaccctcggttgttgaagttctcaactcaaagacgggtattcggtggtgaaagatt |

FIG. 9B-10

| | | |
|---|---|---|
| | | ccacgtaaacatggctgacgcaaacttaacctcatccctgacgattatccgacgaaggtgcatgtatgttaacgacatgtggtccactgta |
| | | tgatgggatccgaaaaacgctaacattccattgcgctgcaggtaactgtttgttattggtactgttggtcagtagtctttctgctattgga |
| | | tgtttagttgcaggtagattattcgctgcaggaactacccgtcctattctgaagttgctaaaaatacgtgcaaccgactaatcaactacaa |
| | | aaacggacctatcgatgaacaagtaagagaactacgatggtgcaggtgtagactgtagttattgcaggtgtaacttgcagacacatggg |
| | | ctgaagcaattaaatctgcaaaagcagaggaactgatatccaatgtaaactacttaagtggtgctgacaatgtattaatccacgtagaatgg |
| | | ggttgcggtatgtcaaacatcaacattaccacaacgattatgtcctggtggagcagtaagaactgaaagactgctgatcttgcattatgcggcag |
| | | acaagaccctgaattattagttacccacacaattcaaggtcttgaaaaaatcgaagatgcattgctcttgatga |
| Contig40_gene_301 | 1043 | ttgctaaagcagatcattaggaaaaatttacaagcaaatataagattctgtttaggcatactttggagttttcaatccttaatcacaat |
| | | ggccctattgacagcgattttttcatcagtctttgcaagaaacattgaaaatttccctgtttacttcttaacaggccgttgcgttattgattttt |
| | | tcaatagcggaactaaaatagctattgacctcactaaaaagaacagcggttcttattgtcaagatatgtatttgttgcattggga |
| | | ggaatcttttctgaattcattaacttccataagccatcctattagtgaggtgatagtgctattttgtgtaactactgttcccatttatatgctat |
| | | tttctcagtcattccatagatatttccagcttattatagctcaattcatctgatttaggagttggactgacactttccatatcagacattgaat |
| | | atttatatagatatttatgtgtatttatgctgtgatcttcagaggttgttcatgtatgaagattccacaacctatcagacagtatatgaa |
| | | ttaaatccgatttatgtgtattatgttattgagtaatcataaattccagaaccagaatttaagaaataccaaaacaaaagttgatgctaaccttttaac |
| | | ttcaatagtaatcttttatatttggagtaatcatatttaagaaatacaaaacagaattacattagagttataa |
| Contig40_gene_326 | 1044 | atgggatatttaacagattttattttaaggaagcttttggtttatcctctcagcaatatagttacattatttcttggatattgctaacaataag |
| | | caagtttccaaatgttctatcaagtttggagtagatgtcgattttcagttcagttaatatcttttcagttgattttcttttgttagttcattattca |
| | | tgacgcgctattcattggtaatttaagaatgcagttgacttcaatgtcatcaacatttttgctttgacattgacattgactgaggagttgacgcaatacttaa |
| | | aaggtagtggtattgaaatactttactatatattcctacaataattacaattttttgtttgctttattgactgaggagttgacgaatatattgcaa |
| | | tatcttagttttacggtgaaaatcaggagctttatcacagaagaattgtatgaatgcaattcctcaggaatatattgcaa |
| | | ctttcctactactagcttattcattactgacttgcaattgtttcaattatattttatcacacattggctttacaacattggccttgcagattagct |
| | | aaatatgacagcttcaatgaagaataaacttcaaggcaataactcaagcaatcatcaacgacattaagcaatcggttgggaacttatattctatgtatattat |
| | | atgttcctatcatatttcttgtatatcctttgcatatcccattgttatggcgttcagcttcatgtactaaagcagaattaattgcttaattgctttttgctc |
| | | catttatttcttgtaacagtgcacttggttttattgtatactaagcagaaggataataatggatag |
| Contig40_gene_338 | 1045 | atggaagactttaaatattacaagaataagattaaagaggagattaaactagcatttgctcataataatactttttaatcgttctgtctcttat |
| | | ttcattattcctatgtttgttaggatatttctattccgatcagataactccataacattcagcctatggttgatacctttgaggaaaacattagaa |
| | | atggaactgtgacttttatccaacaaagtccctatttgcaaataatgttgaagtgctatattcataggctatatcgccttgggctattta |
| | | gaattgtcgtttagcaacaaatggattatttattgcaacacgagagtttgttgattctatcattgtcgaacgctatgtctttcaactcttcctcatgg |
| | | aatatttgagattctgcagatttcagcaatcattattgcaacaacgaggatttgattctatcattgtgctgaacttgtgctatatgttaaatgcatcctg |
| | | attactcctatactgattcatatttgatcctttagcgatgctaaaataactgtgggacaaagattttaaatcctcttttaaaaagcatgagtat |
| | | agaattaaggaatctttatatttgctttgcgatctgtaattcttttattgcagcattcattgggcaaatattaccattccttttgcata |
| | | ttggatttgctcctgttttgggataagcctgattaa |
| Contig40_gene_356 | 1046 | atggctaagagaaatttagtgaagcttaggcaagatagtcacactttaaaaaagatttactgtattaccaaatccagtgtgcc |
| | | tattgtattgctttgctatttatattttaccttcttttatgtcttttatatacaatccagcatgtgggatccatacgataatacagaaatattg |
| | | agattgcagttgcaaacttgttgataatgaaccactttgaagaagaatcattaaatgtggtaatgaagtagagatgagctgagggaatgat |
| | | gatttctattatgggtctttgtaaatgaaacggaactgcagagggttaaaaatgaacctattattccggaataattccaaagaattcag |

FIG. 9B-11

| | | |
|---|---|---|
| | 1047 | taaaagcattaagtcaatcactactgatgaccctcattctgctgaattggaatatattgtcaatagaaatccaatcctatggcatctaagttaa<br>gcgattccgctgcaaaggcggtctataataagatcaatgctaagatcgtttattaatgtggcctattcaaagttaggcgagcttcag<br>tctgcattgtctcaaggtgcaggtcagatgtcatcggtgctgctgtccaattgtcttccgatccgctcagtcaattctggcgcttctcaagtgaa<br>gtcaggctcaaatcaggtgaaatccgctgcaaatcaagttcaatcaggtggtgctgaagttcatcaggcagtcagtcccatgcat<br>ctgaggtcaagtcagggcaaatcaggtctctcaaggctcttccagatacaaagttcatcccagcagattcaagcagttcctctcaagtgca<br>agttctgctaagcagttggattcctcgttgatgttgacaaattgccagtggtgatgacttgaagcatgttgaaacagttccaagcaattggctaa<br>tgcaagttccaatctggcgggatcttcaagtcaactgcaaacggttctgtccagcttgcaaatggctctgtcc |
| Contig40_<br>gene_366 | 1047 | |
| Contig40_<br>gene_368 | 1048 | ttgaccgttcctcctatttgtcaatggagcagcatctgtttgctgaattgataaggaaaaggcagtaacaaaatctatattatggc<br>agttatatttaacgtatgtcttaattggttcttattccaatgtttagttgatgatgagaggcaatatccactgtattaagtgtgaatatttat<br>tatcatttaa |
| | 1048 | atgaatcaaattaaatccattttaaaaatactggttggttatctgttcacaagtgataacaagcattgtgcattcctatggaccataatcat<br>agccgatacctgggagtatctgattatgccaattctactccactgcctattgtcactgcctatggaatagtgatgatgatgattggaataagca<br>catatcactcgtgaaattgcgaaacataaagattagtaagactctccattagtaggaaatatttaactaacaatatcttttattaagctatactatctta<br>tttatttaagtgattgattgtgtatgtcatggaacctttgaaaagtaaaatatcaagccatagctaaatatcaagaactatcttattaatag<br>tatgactactttttaataacattaggtgtttgatttggcgttccagtccacccttttgggcgtatctcactgactattaataccattcaaatattttcatatatgtttta<br>gcattctaataacattaggtgtttgatttggcgttccagtccacccttttgggcgtatctcactgactattaataccattcaaatattttcatatatgtttta<br>tcatatgttaaaacattcagccgacctcattggaagttaggaattggatacaaatttcataaggaagtaataataatccaaacggacttaatcgcatacaaca<br>ctccctctatttctatttttgtcacaacattttttgtagttgtaccaagctaatattcctgttatgagcaaattcctcaaggagcaaatctaatcaaa<br>gttagctatgagcttctgtaaaatatttgttgttaattattattcctaatcagcatagcagtttcattatctgacagtttcattcctattgtca<br>ttacagcaaccaatcactgcctcaactccagtccaataactactatctgacagtttcattcctattgtca |
| Contig40_<br>gene_378 | 1049 | atgaccatagaagtccaagagaatattatattagatgaagttcgctcacttgcaatcatgctcgtagtcgttggcattggcaaggctgttttc<br>atataactacaatagttgctgtctgcagcggagtattcccataactcgtatgaagcagcgttccctcctctctcttacagtaagcggatctcttcttt<br>taactagaaaaatgaggtaaaagtttttagaaaagcgattcaaaacgttatgtctgcctcttctctctggataataatatatatagttgcc<br>gggctgcattgcatggcattgcatgaccttacatcgaatatggtgtaacactgcattggttgtggagacattcggcactgttctggttatttg<br>gtcacttattggaggtttatcttatatacacattcgattcttgactatcacaagaagaagtttagtattcagataagaagaagtttgctatcgatgctggttatagtcggaat<br>taatactactggctccctattaatcaagcgatgttcgtggaggcttcagatcttacttctcccagttctgga<br>ctggacacttgcaaaatccatctatcttaaaaggcttgaagactttgcaagaccaccaccaaatggataaagaaaagtcaagaaattga<br>tagggcatttcattgcattaagtatgcaagcaccaaatggataaagaaaagtcaagaaattga |
| Contig40_<br>gene_379 | 1050 | atgcaagaattgaattaggagaaccaaattagtgaagttgattgttcattgtcatcagcttgaatcttcatcagcttctcacattattctt<br>tagagatatattatgataatgattttagctccaataagaaaaacatgcactgttttgcttcctgtaagctcaataatcataaataggat<br>taagttggctttaaatacgtaatgacaagatccatgtaagaatagctagtgggttaaatag |
| Contig40_<br>gene_387 | 1051 | atgaaatcggagaaattattactgattcttaaagtatcctattaataacattaaagcttaataattacatagtcctcggtatcgttgcagg<br>tcttgtactcgtattaaccggcgttggcgtcggagcaggtcgaatagcgcagccactggaattgttggaattattgaattatta<br>tattccttcctatatactttatattcttaggatacgaattagatgttataaactttggtattgaaagaagatgacgcctcgaatcgacttc |

FIG. 9B-12

| | | |
|---|---|---|
| | | gctagacaaataactaatgtgtattaaatgtacattacttgctcatttacatgttaatccaactatcattatgataattttatcatacctcaa<br>tcaaacttagttttaattgtaggaataatattttatcatagcagcattcgctttattaatggtcaatgcagttagctcacacagacagct<br>tagttgaagcattaaatattccagaagcaattaaagatattacaaaagtgggaattataaaataatagcagtattccttattttagttatcta<br>ggccttgtcgtatcattcatttcagagctagttagttttagtgtattgtattaggcgatgtaggcacatatatggagctatttatctgtattttcacaatcta<br>cctagccttgtagtcttcagagctagttagtgattattatactcagatgcagtttaa |
| Contig40_<br>gene_401 | 1052 | atggcgcaaatcaaatgccagactgtgtgccaagacgtgtgccaagaacaagaagatacaaataaattctgtaaaaattgtggagctaatctatcaaatgtaaaagc<br>agaagaagtaaaattagacctagacgctgcgctctgcctccaactgaagagaaatagactttaaacactgctcaactgctgaagagaaaattagatacagatgctt<br>ctgaagtaagaaaactcctaaagctcctgtgaaaataaaagatatgcagcaaatgtgacatgtgacaaaatgtgacatgatgaaaagttctgtcaaga<br>tgcggacaatccacagcatccatagttccatatgaagccaagactgaaagcaagttgaaaataatgacaaaacctgtccatcctgtggaactaa<br>agtaactacagaaaagttctgtccaaattgcggatgtaggcacacaacagttcaaacacaaaacgctcaacagaaatattgtagaa<br>attgtggaaatccgattgatcctaaagctgaaatatgtccaaaatgtgcgtaagacaattgactgttgttaaaaaagaaccttatttctcttt<br>atctatcacttatattcccagcctggcaattctataacatgcttgtatgctttacgtatgcttacggtatgtacgatcataaggatgcaatgcgtatccatcgt<br>tttaacaatttttgtaattggagtcttattatacatgcttgtatgctttacgtatgcttacggtatgtacgatacaattgctttaaataatg<br>gagtgtatgttgaagataaaactcttctaa |
| Contig40_<br>gene_428 | 1053 | atgcaaagaaagacattatcacgtttgatgaaattcttaggaaattgtaaaattcttaggaaatatgatataagtttaggccaaaccaccgtaatag<br>gataagccattagaagtggatcagaaaataagaattattaaaggaagacttccagaaagatagagagattgacattgacattgcaagagctggaacca<br>catttatcaaattggccaattgttaagcacaaggcctgattgtgttgagagaataccagcgaagaactttcacagctccatgcagtgatgataatcct<br>cctattgactttgaggaaattaaggtaattatcgaagaggatcttggagaggaaatctaaaagatttttttacagagtttccgatcagccttgc<br>tacagcttcaatcgctcaagtccatgagctaaactgcataggaaaggtagcgtttaaggtacaaaaaaccaatgttcaagaaatcgttg<br>aaactgacttgaatataatgaaattccttgctaatgaacagacagattcaataccaccttaagcatcttaatcttccgcgtcgttaaggaa<br>tttgacagtccattcataaggaaatggattttgacaatgaagtcttgacaatgaagactgactgaatatgtttgatgggtcaaatatctgaagttatctgagggatg<br>tgttccaactattttatccagatactactactcattgcagataggatggtcgtgcttatttaaacaaattctcttgacgattttcatgcagaccctcat<br>atccaaatatataatatttcattacagatgacaattccatatgttctatgtttcattgatttggaatgatgggagttccttgatgaaacttcagacaagatttggc<br>cctgaaatatttcattacagatgacaattccatatgttctatgtttcattgatttggaatgatgggagttccttgatgaaacttcagacaagatttggc<br>tgaattgatgatttgtttctcaaatcgtgacattgatggctaatcaatcagttaattatatgaatattctaa |
| Contig40_<br>gene_433 | 1054 | atgagcatagattaaattttagataataaagacccaattatatttgttgaaagaaatattaaatttgattctagaaaatccaaagtat<br>attagcatcctatgatttaaaaactaaatagaacataaattaacttactttaatatttatatttatatttatatagtgttcttggaattgacattccattca<br>ttttaacgagcttaaatccaaaaagaacttcgcaaatacttaaacagaatccagatctgaagtttgactgcagtcaagttttataaatttttcagaa<br>ataacctgaaaaacttatataaatgtttaaacagaatcttaaactcaagaaatatggtcaaaggagagaaaaagacttcattgtcgatgc<br>gactcagttgactggatatcaattccgcagaataaaagagcaagaacatcatccatggaatcccaaatccaatgaagtttcaatgaagttatttctcta<br>aaggctattatattggattttaaagcgactgtgtgatggattacgattctatgattcctgttcatttaatccatttctggagctccaaatgat<br>gcaggacttttgaagagattttagaaaaccttcaaaaagacgaataatcagaaaagaggagtacattaatctttgataaggatattacggcta<br>taaaactaccaaatggaattgcaagtataaaatcgttcctttcatttttccgaaagaaaattcaacgacaagacttgatgatatttaa<br>cctatccattagccgtattttaacaaaacaaagaaaatatggaagaaaatatacaacaaattaaaaaggaattattagaaaattagat<br>tcatgggagaatttaaaccaataagggcaaatcgaagatttttttcaaattattgaaacaaggcttgaatatgagagaaatccacaaatata<br>ctccaaaatcagttga |

FIG. 9B-13

| | | |
|---|---|---|
| Contig40_gene_465 | 1055 | atgcattagaacttatgaatttattgattccatcttagagctgtttattttatgctacctgcttatgtggctaactaagtggtctgcttt<br>tgagggggaactccaattgatgcggagcgaattaccgagatgggaatagaatatgaaacggagtaacatgaaaggttgcattaatgaa<br>ccattattggaactctgttggtgtggtcttatattaggattcttaatggcatatgatcgcgcttatcggtgatgcagtgaagtttcataaaaggag<br>gtttatggaagcctattctctggtcttatattaggattcttaatgcattcggcgcttaatgcattcggtgatgcagtgaagtttcataaaaggag<br>aatgaatcttcaaagtgccagcctgctccgataatgatcaattagattttgttcttggagccctatatttagctcttttagttgtagaataa<br>gttggagcttttttattataattgtctgcttagtattttacttcatttaagtagtaatactatacatatttgcttgaattaaggatgtttgg<br>tattaa |
| Contig40_gene_471 | 1056 | atgtttgaatttacaaaaaacgaattaagagatttagtgattgtgattgcatttatcgtgcttgctttgcaatagcaaatgtcaaattcgattt<br>gcatgcattcatttcaattctacctattgtaatgtttggagtaggagtgggattcatttcatgagctggacacaaatatgtggcaaataat<br>acggttacaaagcggaattaaattatgcctataggattattaattgcacttattacatcacttatagatgggtatttgcactgcctgtgaa<br>gccaagattacagcagcagagaatattgatgaagagaccactgaaagatgcaatcgctgaccgatgctaatatcgcttgattgctattat<br>agtaatagcagctataacatatccattaaaaagctcattacacttttgaattaattaactagtcagcactgttgctctctgtaaacgcat<br>ttttagctacattttaacattgcctttctatacatattgggctgaaaatatgatttaatgcttatagaagttaa<br>gctgcaatcatgatgttatcatctatgtttatagggctgaaaatatgatttaatgcttatagaagttaa |
| Contig40_gene_475 | 1057 | ttgggcttattacaacaggtatgaacagtccgttcaaacaacaatgaacgaaggtgctgcagataactgtaaccaatataacctcaattgg<br>tgcaggactattgatccagtctgtgatgagttaagaacataatcctctacaagcttttatgaatataatcggcagaccttgacctgaaggaata<br>ttgttgatatgcctcatcgaacgatatgtcttcatggaagaaggcactaagcagctcaagcattgcaagcaatatgcaaatgaatataactgtctattggagataa<br>aaagcataaatggaagctttttgaagaggaagaaatttgaaattgaaatgtaaagtaaccggtgacgctaagcagtagtgggtttttgaaacctgt<br>tatttccgcttagaggaagtgctgaaggaaatgtctgtatagtcaagacagatgaagaggtaaacgacactgttgtggcagatcgatagag<br>gataaatatgaatctgacaacaataacagcgaaggatgtctcagatgctgatcgtaaataacaatgtcatgtctgttttaacaatccttcagttagtctacagcagtgacgaatagggctcagcattcgt<br>ttccgctcttgcaattattgtaggtcataagaagctaaagatgaattcatgtggagagaatcagtcaagatcaagaacaattggtcaagagtatctgtaggctaggctcagcattcgt<br>ctgtaggatggaaaagcagaaagattctaaagatgaatatattatgggatacagatcagattttgcttttaacaatcttcagtatgtaggctcagcattcgt<br>attctcattgcagagtcggttgatgaggagtctaaagattatgcggatatttgcagcactttcatcatgcattgaataac<br>cattgtgttgattgattgaggaattatctgctatagcgcaagtaaattagctcctacagaagcattga |
| Contig40_gene_481 | 1058 | atgttaagaagaaaactaatgataagagcaatgttatataccgtcaaatcttaagacaaagacacttgtaattattgactgtcagcatt<br>gattatcataagcattttcgtatgcggatatttcataaggacatcctacaagcacatccgcttcagctaatcagatgcctccctgaacacctttcctcctgaacacctttcctcctgaacacctttcctcctgaacacctttcctcctgaacacctttcctgaacacctttcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcctcctgaacacctttcct |
| Contig40_gene_482 | 1059 | atgaataaacaaaaaatagcaaatatttggttggaatagtacgatttgtcgtattaatgattgcgtatgcagttgcaatatgtattatt<br>agatttataccctattgaccagtttaatgcttatttgttgatgtcgcagtaactgacgtgcagtaactgaagctcaaagagagcaatttacaagcaataatcagtaatacaaagttaa |

FIG. 9B-14

| | | |
|---|---|---|
| Contig40_gene_487 | 1060 | atgttccattgcctgagaagatttccattggcttatgatttgcttcaagaaatctggaactcttaatctaccgtagaccagttatgat<br>gttattattgacaaattcatgcttctcttgcattgatgacaatatcctgatttatcatcggttttgcttttgggtggtatgctatcga<br>taaaacaaaggttcctggattgataaggcagtgaagtctactgttatgccatccaatccgctccatcctttggtggtatgcttatcga<br>tggtattctctgtttatctggatggttcccaatagatcgagttcctgctcctattgcaatgtataccgaaatgaattggttcctatcctga<br>agcggttcttcctacgctgacattaagcctgtaggtctgtcctgtcaatgtataccgaaatgaattggttcagttcctatcctga<br>ctatgtattgtttgcaaagtccagagggaaaaggcggcactgatggtgaacagttcatctcatacccctgaataggacagactgcagcgggt<br>aattcttatcattcagtgagctcttcgagagggttcgtcatgtgaacagttcatctcatacccctgaataggacagactgcagcgggt<br>cttcaaaacgacgttccactatttttaggaattgtggtcataagtgcaatattttgtatttgtaggtaacttgcttgcagatattcttattactt<br>catagatccaagaattaagagaatgagttcaatgattaa |
| Contig40_gene_495 | 1061 | atggaatttttaaaattaaaagatcaaaaatatttttattaagcgttcttctatggctgtgcttccagccctctgatgtacatagcaacatttgc<br>tttgatgaagtccaggccttgacgctctatttgaccgtctattgaccatgtaaacatgtatatgtctgtattgttgctgtcttatctttgcttgcaatcattatgg<br>catatctcttgaaggaataacataacatacctttaaagatgatgcttaccattccaattcaagggaaagttcctgctgtcttgttttctc<br>ttgttccttcttttgcttttgtctgtcggttcctcgtgcctctcgtgattttgttgctgcggactaagcggattactgtaaa<br>cttgcaattaacagcttgcacagctcttatttgcaaatctattgctctttttgacatctctccgtttgtattattcattgttgtttacaa<br>atatggtgcctatggtgcggagctagtcaagagataagcagatagaataagacgtttcctatagttccaatatgtgccctagtatgt<br>ccttatttattgcatctgcgagagataagcagatagaataagacgtttcctatagttccaatatgtgccctatgtcctggtatgt<br>catttcttatcttactttactcaaaaagacgttcctctttag |
| Contig40_gene_496 | 1062 | atggaaaatcataaagcttaattgccataccatataatctacttactctctctaatgaatagacaaggagttga<br>acttaaggagatcacttgcctgaactgcaactgcacgttgaccaatgacctgaaatgcaaagtcaattaactaaagaattgaatacaaaca<br>acataaagtgacagcaagtgggcgaaaataagttactgtagaactgttactgtagaactgaaaataatgttaattcaagtacatttcaaaggccatagatggaaag<br>gcaaggtgatcagcagtagatatgaaggtcctgtttatctgaagagcaatggacaaatatatcgctatgctattcgatttcattttatttat<br>ggcagttactgttttaattgtattttagagagcctgtcacttcagtagagctatattatcagcttattgggtagcgattatgatacctaattgcttcttggagta<br>tgtccattcttcacataccctgtcaattgcatctgtaggtcattattaatgcttatggcacactagtttgagcatgccctgtgcagctatcgctgcaat<br>agacttcttaaagaaggagaagaagaactgttgatgaagacagctagaaacgctatgcacacaggtttgacatgccctgtgcagctatcgctgcaat<br>gggaattctttacatagtcactgtaattatcatgcctgaagcaactaccttagacttagagttggaagagacatgtcaaaaagcaagatatagtgctcct<br>ttctttcaacctggcttatgaacctgaaactctaaaagaagaagaagagatgcaagtcaaatcattaagacagttaaaagtccaaggtgatga<br>aggttagtcttaaatccaaatctgaagacctcttcaaagactcttctaatctaaagactcttcaatgacatagacagtt<br>ttctaaagattctgaatctgaagactcttcaaagactcttctaatctaaagactcttcaatgacatagacagtt |
| | | atggctagtaatttatccaaattcttcaaggatagacaagtaatcatcctaattatttgcctcataatcagtatcataagcttccttgg<br>agtagaacaaggacttgacctaaaggcgtctccatccaattgcaatcctgtaacactcctgtaaacgactcgtacaatgaaagtggtcacctg<br>tactggacaaagggcttaacttatgcttgatggtaaccgatgaaagtccgtcaaggcagatgggacgatggctgtgctgaaagagc<br>cccgaagaggtggagcggctgattggtgaagatctggagacgatttttgaagcaaaataagacagtcagtcagaaatttgcagagcttgcaaagggaa<br>agacgctcctgtttgttggagagtcggaagtggtaatgtatcttgacgaaggaggatgttgacagcgaagaaagcagaatgtgcttgcgggagagcttgcaaagggaa<br>aaggcggacatgaagttggtaatgtatcttgacgaagatgtgccgaagatgttgaaacagcaaaagcagattgaagcaataaagacaggatgaagttcactgcacttcc<br>actgaagttcaggtcagttggtgccaatacagttcccagagtaggtcagcagttggcacaggatgtcagtttgcacaaggagtcagcagttcagttcagttcagttcatgaatcc<br>gtaaagattcacactgtaggttccaatacagttcccagagtaggtcagcagttggcacaggatgcattgattgcacaaggagttcagcagttcttgcaatcc |

FIG. 9B-15

| | | |
|---|---|---|
| Contig40_gene_498 | 1063 | ttgtatttcagcagttgtatatcagatatagaagagccttcctagctatccctatactcattacacattatctgagataatcattatccta<br>gggtcgcttcaataatccattgaaccacgacgatgaaaacaccaggcatagaagaaccaggtttgattgcatctgtaggtactgggtagacgaccagtcatcat<br>tacggatgagtgctgcaccacgacgatgaaaacaccaggcatagaagaacaagaactcaaatgaatgcaaga |
| Contig40_gene_510 | 1064 | atgtgggagatggtttgcttgcagccttatctcattttatcttgtcattttatcatcttgttaccaagtcaactccaggaatgtgatgcctt<br>tgaacattgatgataactctatatactctgttgtgctgaatgcatctgttgattgtgggattgtgagcttgcttatattttgcattcctgccgttgaaggtcagt<br>ctcatgttaattgacatctgtttgtgctgaatgcatctgttgattgtgggattgtgagcttgcttatattttgcattcctgccgttgaaggtcagt<br>tctgcttcaattgttgcaaatattgactgtgccattgtcttgtattcgttggggcgattcttgttatggtgagaataacacttaagcagcttgg<br>cggcatatttattgtgctgttgattatttttgattaataatatggttaa |
| Contig40_gene_510 | 1064 | ttgcaagagcaaacagaagaacatagatttaatcgtaaacatccaaagagcaattaacaagctgcacttcaatcattcgacaacttctt<br>catgtttaaacaatatcatagatggaatatggttgctgattagaatcatcatcatcatcatcatgatcatcatcatcatcatcatcatcat<br>ccatgtcggtttgcaaacgattggagcaggtgccaacagcaccaatcgtacaagtgtatcgtgctgaactacaagggctgaaacagc<br>gccatccattcgatgatgtaagcataattgtcacaatcttgcaacatcgtcatttgtgtttaaatcctccctccttatgctgatggtgc<br>cgtgaaatcatagagagaaactcaaattatgtatatatacctctgttgagcatatctatcttttacctgcaatgatgctgcaatattcc<br>gttctgaagggaaatcaataggcttccaatctgtccaacatcttgatgctaatgaatattatcatcatagatccctatcttatatgtcctgta<br>tgggagtcaaggtgctgcatttgcaactgttcttcgtgctgaaccttgcaacacttcaaatccatcatgatgttcttatagatccctatcttatatgtcctgaa<br>cctaaaaatcaagctaagcgaatataagacctataagaatattaagaggaatcttatgtagtggaattcgcaacaagttcgccaagaacatgtaagttata<br>tctcttttgtcctatcctcattagttgtattgtcaagcactcaataatacatatgtcaattttctttttgtattgccagagc<br>attggagtctctccaatcattgttcatcagaatttcatcataacatatgtcaattttctttttgtattgccagagc<br>tcaaatttacagtgcgattctaggaatattcatcataacatatgtcaattttctttttgtattgccagagc |
| Contig40_gene_514 | 1065 | atgtttataggtcttttggctccggctattgtgtctcacgtttcattatgctgtcaggctcaggctcatctgcttaagaaaggacttaagaataaaat<br>gatcggcttttataaggtaaaatgctaggctgaattgtgattggctgtgattgtatttgcgattgtaatagtctgtccattttgcttcacttcttt<br>ttggacagccaattgaccagtttcccttactgaagtttccttacagttgttgaattgctgagcattatcacaattacacttgcttct<br>ataattgagaagtgggatgggaaaggatacttgggttaggattcaatgctgaactatatgaactggttttggaatccatgattttggagtgctatg<br>gtcttctgcgcattttccctttaatctttattttcaggaacctatcaggcagaggacttatgtgattaccttttcttcgttatttttgtcagcg<br>gaatccctatgggattttgtcattactggtctattctggtctattctgaaagtgccaaatgtcctatttgatcatagaaagttccaatgtcctgaaaggatat<br>gtctcttgaaaccgctcatgttggaagactgcttgaataacaatagcagcagcagcaataa |
| Contig40_gene_526 | 1066 | atgaagagtccaaaactagatttgaaggagttgaatcaatcttaggagacctaagaaagccatatgaaattatcaattccattaatttc<br>actattcacaagcctcctatagtgtcatagatgccgttgggtgtctctcttggtgccgatgcattggctggtgtgctttgtaagtccaa<br>tattcattgcctaatgagatttgggacaggagcaaccctgcaatatccaaatacattggaggggataagaaaatgtca<br>gacaatggtgcagtcatgcaatactatagattgtcatcaatgatatgagctatgctgtatgctgtatcttatccaattcattatacg<br>aatggggcatcaaatactatagattgatttgctcaatgtattgtcaatgctatttgcctctatcttaaatattgatctatattattattat<br>gggtccttagaagtgaggagtgaggagtaaggaggagcagctattgcaacctcattcccttttgtttgtaaacctcctgtttattggttacattaaaaa<br>ggacacttattggcctattttaaggcctctttttcagcactctttttccctctctaacagatgtgctgcatcaactgtcaacagatgctgtgctcagttgagc<br>ttgttaacaatgccctctttgcatgtgctgcatcaacagatgctgtgcagttgagc<br>ttgttaacaatgccctctttgcagccactctttttcccctctcttactgtgcatcaacagatgctgtgcagttattcacgagatggagg |

FIG. 9B-16

| | | |
|---|---|---|
| Contig40_gene_535 | 1067 | gttgttacaattgcaacaactcctatgctgctgtaggaactgctttgatttcagtggtagctgccaattatgggctagaagatatgaggacat<br>ttacttgccataggtattcaatgaagattcggttctatttgcttcatttggcttcatttattgcagcgatagttgtctatgtat<br>gtggctggtttaaatctgattgatagtgtaatgtccataagaattctaattatcgttatgcaattgcaggactctactttacttttaaaacaag<br>aggagtccagataagattatttttagagtcaagggtaggaacaggcaatatcataggagctcccactgcattatgtctgggagtcccggcaatgcttg<br>tctccacagcttcaagggtgttaggaacaggcaatatcataggagctcccactgcattatgtctgggagtccccgcatgcttctgatgtgggtg<br>atgtgtatcatcggagcatcatctgcattcataagcataaattggctctgctctttttgcgtattctcctgctacatatgcgtaggattcaatatgc<br>tgcatattatatagacatgtgtcttcataagacatgaataatcgttctatcatccaagcacacttgttcggttagtgcattgatttcatcatatgttt<br>tttgctccttaaccttgctacttggaggggaaaagattgccagttatgttctgtactgttttctttaatcgaggcaggtgttcagcccctaacgcttcagcttctgcagatgta<br>caggatcatgtatgttgtttcaacattcaaaacgtcagatgtactcactatgttgccactggacacctcttcttgtacagcctctgcattgatgctgtccac<br>tccacccctgcaaaacaggattgctcagacactatctgtatatattgacacctcttcttgtacagcctctgcattgatgctgtccac<br>tggagtggtaaggatgcgcggtttccggtgctccatatgccaaaacgccattcatctgtctttgatgga |
| Contig40_gene_541 | 1068 | atgaatgttttagaagtttatagatatctaagcgatagagcagtaatgcctaataaggcactcttcctattctttattctcttcaaataaggcactcttgccttatt<br>tcttcctctgctgttgacttttagttcagctgcttcaaaccagcctgttggttacaaccatctgcagtaataatgctgttcttgtcttgatcttcag<br>tgtccttagttgactttttagttcagctgcttcaaaccagcctgttggttacaaccatctgcagtaataatgctgttcttgtcttgatcttcag<br>gatgagccagagaaggcatgtgacgcttacagcgcttgacgatgtctcttgtcagaatatttcgcagatagagccgatgtctcagcaatatttcgacagatatttcgacagtctctcagcaatatttcgtcttgcaattttaat<br>gcattttaatcaatctctctttgtcagatagagccgatgtcttacacaaccttccatctatgctatagtttgtctgtgacattttaatgcatttgctgcagtcat<br>tcattgcactctacactctctttgtcagatagagccgatgtcttacacaaccttccatctatgactaagcaggaaatgcacttacagcaaataaccttaatggcaggctgctgcagtcat<br>gtcattggaaatgccactctcttcaggaaagtgtatgaaatacatatcagaaagacacttaagcataagttcttaaccataagcagctcgacggctgcgaaggtcttga<br>atgtgggaattccttgtaggatatgcaattggatcaatggatgtatttttcagttcttcccaggattctcaagatttctcgaataaacctgctgcgaggctctctctgctg<br>gctgcaaactctgtaggatgagcaggccaagttctataagaagatactattataaccttttatctcattgg<br>tggtcataatgactatgagcaggccaagttctataagaagatactattataaccttttatctcattgg |
| Contig40_gene_544 | 1069 | atgagaacattgaatggaaggaagacaataataaagcttatagatcaaattaaagcttactgaattgacttatgtctgcagcaattacaa<br>gcaagttgattacagcaattaaagatgcagttgcagttcgtggagcccctcgcaatcggtctctgcgcttgtatgcacttgctcagcttgccg<br>gagaagacatgaaaaggttgcagttgagatgaaggatcacgtcactgtcagtgaggacattaacacaaacctgtcaattgatgaggagactgctgctgcgcagagcttatgtgatgacgaga<br>aacatgttcctatcattgagacaggagaagttacactctctgaggagacattaacacaaacctgtcaattgatgaacagcaagcttcgctcgcttcaatcaggaaaga<br>cactgtctacctgatgttgagacgaggaggtatcctcatgcattgagacaggagcaagcttgaaccgcctgtgaattgatgaacagcaagcttcgctcgcttcaatcaggaaaga<br>acattcagatgttgcaagcggatatctcatgtcaatagagaaaatagataagttgtaataaggggcagacaggtggccatgatgaataagcaaa<br>attccagatgttgcaagcggatatctcatgtcaatagaaagatatttgacattccgttttatgtgagagcaagatctgccgcaccaatcagcacattgataagaaatca<br>gcatctttgatacagaaatagttccaaaggaccttataaacaggtcattaacaggtaaccggtaagttcgattgaatattgaataaggaatcaaca<br>cctgcattgatatagttccaaaggaccttataacaggtcattaacaggtaaccgtagcttagtttcgattgaatattgaataaatttaaaga<br>gcttttctaa |
| Contig40_ | 1070 | atgttattaagtaaaatttagaagaattattatgggtatggaacctccattgaaatattccttctcattgttttccattccacttgg |

FIG. 9B-17

| | | |
|---|---|---|
| gene_552 | | tttggcagtggctgctgaagaatgagcagcttcaagccacttcaatgtttatgaaggcttatattcctatcatgagagaactccattgatgc<br>tgcagctgattgttgtattcttgtcagagatcttcgtgaggaatcgaatcctccaaacgacaatgaagctgcacagtgacactgcttccacc<br>atcaactatgcgcttacttctgcagagatcttcctgagaatcgaatcctccaaacgacaatgaagctgcacagtattggatatac<br>cagagttcaaacattcttatatcatcttgctcaagtgttacagtgtttacagtggagatagtcttcctcatcaattacaaatgaggtaatcactcttgtaaagaca<br>cttcacttccttgtcttgttgcaattcaatgcgcttgtgcaattattatgaacgcttgaaaagagattgattattacgatacatag<br>ggtggattctattatgtattcaatgcgcttgtgcaattattatgaacgcttgaaaagagattgattattacgatacatag |
| Contig40_<br>gene_561 | 1071 | atgatggttttggaatagaagatcctttggat=tgggagtttatgttttactcattggaatgacattggttgttgcctacggcgcattaaa<br>ctgaataatgaggattaa |
| Contig40_<br>gene_562 | 1072 | atggtaggttacgtaggttacctagcatggaaagaacaaattcctcgaagactttttggttgcagtagagaaactcaccatacattggc<br>attaagttacgggctacttttatctctacgggcagctattgtcggttttggagggtgcaggtaaatatgtaggttatactatggcttgcat<br>tcttaaatattcttgtaggatattcattgcattgtattctcggtaaaagaactcgtaagatggtaagaatcttaactcctcaaccttcct<br>gagttttaggccgcagattcgatagtaaattcatacataacttttagtggagtttcatctctgtcatgctgtcgtaattttgtgatatgtcttt<br>tatcggtcgcagaagatttatggaaagttcttaatgcttgacgcattgcaaagaacaatcatgttattcttgactcttacattttgtattcttggta<br>tcggcggtttgaaggtgttactgaagcaaactcggtttctgagcaaacatggctaacaacatgctcactacaacatgctgctcgtaagttccgt<br>tgggcgttactgaagcaaacccatctggtgactctcgtaaccagtccgtaacactgtcctctgttgagctgtcctcttatgctattagctcagcttcag<br>cttcctaaactgactgactgtaaaatccaataagtatacttctgctgagcaagaacccatctggtcatatctatgctattagctcagccacagctttgcag<br>taaggttcatgactgtaaaatccaataagtatactatcgaactccaaaatccaataactcagccgcactatcatcatgtgagatgctattagctgaaaatatgtgctattaacctctctataatagcgcacatagctcatcatcatgttagagctacggataaat<br>gtaggttcattatgtcactgtaaccagatccaatggtttctgtatatcatgaactccaaaatccaaatatgactccaaaccatagctcatcatgttattactattactactgtttatactcttactcactattgtctattcaatgcgcagcatttgcactgtaatgtctctggaattgttttagggcaatagcgtaatactatgctttgactttaatatcaaccgtgaaatctattctcaatagctagtcggttgcaccatgagtcgtatgtctgtatatgctagttcagcactactcatactgcgactagtacaaactcgtactgcacatgcccagtcgtcaaaatatgctgcaatgcattatttcagccagccaatgagaaaggtttggttgtcagtccctttagaaggcaatctttgaggtcgctttcaactcatgtgtacagctccatctgcactagcggtaaccaatggaatctatttcctaataaagcatactctcgaaaatccaagttcatgttttggaggcgtatgtccaagttacaatccaactacaactaatatgttacagtactaactcgaatctcaagcttaagtcttatgctgtttgtaacactactcctcttcacttgttcactccagctagttccatgtcgcatagtaccttctggttcttccttccctttcttttactactactacactcctcaatcttctttgcaccattccgagctcttgatgagttccggccttgcaacatcgttacttctacactacatattgaactataacttctctttacaaccagctacccgttagccacgattcgctgtgactgtcacctgtaggagtgatgcgtaagatactctggtggtcgaatttagctaatggccttaattctcttatgtctcgctaacggtatctgacttacttctagagggctttatagcatgattcatctcgctcggtaaatactcatgtctcggatttatctaggtcctagaaactctgtaaggtgtttaacgaactcgcccctgatcatggtcgctgagcaaatatgcactgcatgctccattgacatgaatcttttaaatttttacgatttcatttgcaatatgttcagcttttcgactttattcattaagcca<br>tttcaataaagatagacaattttctgataattgtcataacaatattcagcattcttttggaatatgttgcttattttattcattaagcca<br>ggcctgtattgattattgttgattttggcttatttgcttattttattgttgattattatttgcttttgaaggttgaattgaatgt<br>ctcattttga |
| Contig40_<br>gene_565 | 1073 | |
| Contig40_<br>gene_570 | 1074 | |
| Contig40_ | 1075 | atgaagatgaagtaatagatgttgaagattatgaagtaagagattagtagcaatagcaatagtagttagcgatgatgatgaaagaggataatgatactctaaaag |

FIG. 9B-18

| | | |
|---|---|---|
| gene_571 | | ttcaaatgatataattacacactacattagaactgcaaccattagcttatccaatgaaagttaattatactgcttagtgcaa<br>ttgttctcattgcaatattcttattgacattttgttaa |
| Contig40_<br>gene_574 | 1076 | ttggttcttattgccctatccttgctgaagagcacatgtgaagattgagaccaaattgagaacatcagcacaacgtttaggccacgatgaggacatgca<br>aatgctaaatgatatcaaacagcagattgcgacatagctgaataattcaaattgcctatgcctgtaacaattcaaatggcaaatcatagttgatgagaatgcctcaaaccctgagaagga<br>ctcgggcaatgaatgctgattgcgacatagctgaacatctatgtgaatgcaggctcactgactctacaagcataaacttcttaagaaggtcttatgacgacaattcatcagtacaatc<br>accaaaagataatctatgtgaatgcaggctcactgactctacaagcataaacttcttaagaaggtcttatgacgacaattctctatcaagcaatgcattggggaacagacaatg<br>ctttgcatccctcaaaacctgcagctcgtgacaatatctatatgacgatacattcgagatgaagcaagtcattcaaatgagtaatcagaaaactgac<br>gaaacctgaccattgcagctcgtgacaatatctatatgacgatacattcgagatgaagcaagtcattcaaatgagtaatcagaaaactgac<br>tcagattatataacagacacaagctgatccaaatacttagcagcgcatcctattgtgaagctatctgaaatgcagatattgtagtgattatatgaatgag<br>ctatgctcatacacaccacagcaattattacaaaggaacatattcattcaatgaataactgtaagctcatactgttaacttgcgctccttactcaagatgattt<br>agaatcctgcagaatactctgcattcaataagctataaggagctacaatcagttattatgactgtctataacttcaaatatcctattggacattc<br>catgaaaggctctcatatgaacttccctcaaaatgccagcttccctcaaaatgccagcttcaaatacaattcaaatatcctattggacattc<br>cgatgcagctcatatgaacttccctcaaaatgccagcttccctcaaaatgccagcttcaaatacaattcaaatatcctattggacattc |
| Contig40_<br>gene_578 | 1077 | ttgatagaggaaatcttaaaaacctacaataccaccaattgaagtttaaccaatcatgaagctaaagaaagattagaaaaatacggcctaataa<br>gattcaagacaggaaagcagacgggctgttaaaacttttttatcacaattgccgatgcattaaatttctcttataattgcagcgataatca<br>gctatctaattgtaaccattagatgctgttgtataggttattgttgataattaactacaattgcaattattcaagatgcgtgcagaa<br>aatgccatgcagaactaaaaagcctagtgagcaggaaagcccatgtaagaaggaggcaagacaaaatcatccctgctgaaaagcttacaat<br>tggagatatagtcctgattgaagaggttagaaaaatgctgattgtctcaagaagatgcagatcatatgccgcaatctgaggcaatcttgaagaacagagagtcaagcatctgctaa<br>ctggagagtctgaagaggttagaaaaatgctgattgtctcaatgaggcaatcttgaagaacagagagtcaagcatctgctaa<br>gaggaattaagaacaaagattgtctcaagaacagaaagatgaggagactccttgcctaaaaaagtgacaagcttgaaaaagaattgagcttatcca<br>cggaagattgccactagtgaatgcttaagaagatccaagattcttccaagattataatatcataagaagattgctgactgcagtttcctgctgtagctgca<br>ttcagtctgtattggattattcttataaggattccttaagaagatccaagattcttccaagattataatatcataagaagattgctgactgcagtttcctgctgtagctgca<br>attcctgaaggattacctgcggttaacattcatctgtacagataaagactggaacattaacagaaaatagaatgactg<br>agtcgaaacttaggttcatgtacattcatctgtacagataaagactggaacattaacagaaaatagaatgactg |
| Contig40_<br>gene_579 | 1078 | atgaattaatagcagatattgcaagtggtctcttttgatgagttagttatgattgaggatttattgttattgcattaatgactttaat<br>tggaaaggctcttctgcagatttctaa |
| Contig40_<br>gene_602 | 1079 | atgagaactgaagttcgtatagctggtttggaggtcaaggagttcaaggagttatcatggcaggaatcattatcggaaggcggcatccctttatgataat<br>taatgctgtacagaccagtcctatggtctgtgagctcgtgaggcgcttcaagaactgaaatcgttaagcgatgaagcgatgaaagattgactatccta<br>aagtgacagtccagtatctcttgtagcctatgcctatgtccatgaagcctaatcaaatatatggtgactgaaggacgaaggtgttctaatcattgac<br>cctgacatgcatcgttgaagaggaaattgttgattttgtaaagagcacagatcaagctctacagagcccagctacaagacagcaacagagaga<br>tgttggccttaggattgtgccaaatattgtgatgataggtctattgaaaggtctattgaaggtcactaatgtggttctgttgatgctgctaaaaagctattt<br>tggatagtgtgccaaaggcacagagaggataaaaatattcaagcattcaagcaggtatgcttaatttaa |
| Contig40_<br>gene_608 | 1080 | atgatttgaaaatataaaaattgctacaatcattattacaattattgctacaatcattattcatttatatcattggcctatgcctgactgaagtaaactactctc<br>ttacaagaatgttgtgaacatgatgatattaatgctgtctgtagtaattattccatccattgggttttgagaagataaacaatgttccatct<br>ctcaaggggtttatattgatcagatgtctaatcttccaaccaaggagatgtggttcttattggacataggacattgcaggatctccttcttg<br>agattgacagttgaagaagtttgaagaaggagatattgtaactctcgatggcctgagataggtgagataaactatacagtcaaatcttctaagatagttcc |

FIG. 9B-19

| | | |
|---|---|---|
| Contig40_gene_609 | 1081 | agccagctatggtctgtatttaaatgaaagccatatggaagggatattcacaatcaggaaattatctaatcacttgccatcctctggttctt cagctgaaaggcttattgttgttggagaattgaattctacaagtctaatcaatgaaactgctttggagaaaatccacatgcatcatgggcatgg tataactttaggattccttgcttttaggattgattgtttcattttcattttatcctgaagaggaaagaatattttagcagttgtgattataat aactattttagtttattttctgcttattcccaattcttctcagattttggcagatcaatagatggctgaatagtatgatgggtgttaatt aa |
| Contig40_gene_610 | 1082 | atgtctaatcgatttaattccttaagaaaggaattctaaggttaaaaatatatctccaaaaattaaagaaattcaaatcgaaagaagaataa ttctaagaataaaaggtctaaatcaactattgaatatatagttcctgaaatctcccattacgtaagaattcgactgattagactctgattctg gattttcaattctgattattggatgattcgcctgaggtgtctcttagacaaagatatgcaaaatatatttttggagatgattaagtgatagaaactttaagatcc cctgcgatgactcatatgattggatggagtcgataaagatatgcaaaagatatgttaaataatgaattggaagaaataggaattttcataaaagtaggaattatg cagagattcgagctatatgggagattaagataatgtgtgctatttagataataatgtgaaaattataaaaatgatctttattggatgaaagttattctgatttcttttaa aaggattggaataatgctaaagtatatgctatttgaatggtgatgcttattaagtggcttattagagttttctgatttttatgataaagattattagatgatctaatttt taagacagtcactcaaagaaagcttcctaaatcaatggtattaaaagcaaattgcttaattttaaagtgcattttaaagatgtgcctttgaataaggatgaca attccaagagccgctttgaaaaaatgtttttatctgatattgtttggcatcatctatgttttatttcttgtataccaaccattcaa gatgaatttaaatttgaaatgcaaagtcaagatataaagaagattgatatttttcaattttataagttgatatttaatgtatgcgacgaaggatt |
| | | atgagattaaaaagtgttgaatggatatctttagcagtatctgatgtctcattgaattcttaaacatgacattgattcttagctatttaat ggttattgataacaattaatatgcaagtctatttcatatcaagtctgtcatcctctcagttgtttttgactctgtagatgatgggtttctagaaaacttaatc gtgtgatccgttaggattggtatgaatatcttagaatagattcttagcagacattgtatccttgttgcagctcctatgctatattactccatagtg tcaagcatttcatctctggccggataatcaattcgtgataagctcttgataacctatatgatgggatatccaaggctgacagatacaatgtgat agctgataaaatcaatatatggggatttgtaggcctcattttatgataagcacaatcagatatccaagtggattattaaactattatcttattgtctt ttgctgttgcagctgtctgatcttattgttgattttgccaatacaagtattattgacatgatgacattgaccttgaagcatatggataaagccagtgatagaaccgatgataaggtaagcaatgttaggaga ttaccgaaagcaaggtcagcagttctgttgtctgttactaatgtaaaggacgtctttaagaacatgaaagataccatcaatcaatcaatcaatcatcaatccaatgaagttg gatgttggtcttaaagaagatgctgaagagaacaaagaacagaaagttaaagagaacagaaatagtgaaagaagtagaataa |
| Contig40_gene_616 | 1083 | atgcaattgacattaagcgtcataagaagctagacaggagaaaagctagacaggagaaatcaaactcaaactgaaatcaaaactgttcctttcattgacatttatttacattgct tatattttagtggttacaagtacctttggagctgctacagttgctgctacagttgatgataatgttcaggttctgaagcgaatatgacgcactactggtg atgggagttattattgattcctgttgccggttgcaggttggcagaagtgctactggtgtgcagaaagttactgtagtgtggtgatgatgtcctgagatgtgagatgtcctgagatttaaggaaatgcaattggt gtcatgcaagatccttgaccaggagatgttcagattaaaacgagtgaacatgcgataattattaagcgcctccaagtatgagtccgcaaga acgggttccacacgccagtag |
| Contig40_gene_617 | 1084 | atgattatagaaatgctaactgatcgatgatttaatatgattattagtggaatgctgctcaaaagcggagaagttatcacctataaattctcttgcttggtat ctatgtctttttaatatccattagaaaatatttttacttaggaagaataagtaaaattgatgctagatatgctacagattagtgggacaattacctcttcta tggaacaggggcgagctattgaagcctgaaacatcagtcactataagaaccctgttcaagattcatgtctgaagcattgaagattggctat aagaataaggacagaagttgaagaaagttgaagagacagattttttattgtcaattaagtaagataacaaatggatcagtcagtgctttaaagaccattat tggcttgctcatttggtctaattcgtactgtgctgtattaagtgtatttggatgaatttaaaagaatttggatggtgctactgtgatttggatgtgtgaatccagatcaagaatgtgcaatgg |

FIG. 9B-20

| | | |
|---|---|---|
| Contig40_gene_635 | 1085 | ctgaagtgtattacattgctcttattactacaattgctgttgactgtagctattattcttatgcctttgtacacttatattaaggtttgatt<br>gatgatgaaatggataaaatcgaattggcaactaaaatgactaattggagttatgcagttattaagattcgtgttatgaaaaattgcctgtgt<br>ggttgaagctcttcaagaggcagatgtatcgcaagtgttaaggagattacagatcctattccaatattcagatttcattcaagcctagtatgc<br>ttgaaaagagtataagcaatatcatttagagaagcaataagtgatgtaaagtctgaaattactgaaagtaagttgagacaatag |
| | 1085 | ttggcttcttattccaaacctaaatgattgggtttgcttatatagcgctaaggagtttaaaataattgattattgaaggtgtgatta<br>cgagattcctggttttattatttctataagcataggacatattgatagatcttgagtgttcttgcaacaataggcttattggaatgctgtttcct<br>ttgttaggtcactctatgctctactataagcataggacatattgatagatgacgatgccgaaagtcggataagcactgaaaagtccatcacttca<br>tttgggttatctttctgtatatatctttttaaatgggctgttgtgatatatgtcgattaaagaaacgttcgcaatgcaatgtatggaagg<br>tgcttttcttgaatttttatgctctatttttatcaccccagaataagcttatcattcacttgattattggtatga<br>ttctatctgtcattagaacatttatgtctacttgaaagtgaaaatgtgagaacaatcttcagatgatagttcctgagttcaaggatataagactca<br>gctcaaaatcctattgaaaacacacataatcaattcttatagtgaagaacaatcttgtaatctctaagaagaagctagctatgca<br>agttgaggatttgaaagacgcttttaagacgcttcataagagtttcatagaacattctattctcaggcagattccacttaaccatgattaatctgctccagaatacagcgaa<br>gattcaagtcagttgtaaatgagttcatagaacattctattctcaggcagattccacttaaccatgattaatctgctccagaatacagcgaa<br>agagtagatgagaccataaaaaataaggactgattgtgatcattgctgtgagatgaataatctttagaagaacttattcttaatgatgg<br>acttccagagaagtcagatgagaatactgaattatttgaaaatgcataattgattaatctgttgacg |
| Contig40_gene_638 | 1086 | atgggaattaagagaatttttcctaataatatttcatagagaaatcgcatttattcattgctattgctattctccataatgctattgccttagacctttaggtgtag<br>tctatggaattaagagaatcagtcttatttggatagcaatcaattatattctgcgcattccaatctcttaaggaagcgcaataggtcttcactgaattgac<br>ataaggcagatgttcttgtgcaattgcaatcatatctcaatactcatggggaattgtttgcagcaggggtgattgcagtcagtcatcatgcaat<br>cggcgctatctgaagtatacagttctaaacaagagcgatcagtcgatcttattgaagttgagacatattgaagtgttcctgagagactgttcca<br>actaacaagtccaatgaattcataagtgcgagacatcaatagatcagtcagtagttgactgggaatcctcgtagataaactcggagagactgttccgaaggaggaagt<br>gttgatgaaaatcataagtgcgagacatcaatagatcagtcagtagttgactgggaatcctcgtagataactcctcaaagattgattaattggtag<br>atttagcgaacaatcaatcttatgtcagagattgtaagactgcagataaaatggcaactctcattgttgtcattgtcattatctgtcttgca<br>aattccaaatgatgcaaatgtaaagactgcagataaaatggcaactctcgccttgctgtctgtcaactccaactgcaattatggc<br>atctattgaaaccaagcaaaaggaaatcctggaaagagaaagaataaccatcgaaaagttgctaagtgg |
| Contig40_gene_657 | 1087 | atgtgggctcaagtaaacactacctcgcactgttccaaacatagcaaccctagtcttccatacaccatgtacgatcctgctgctgaaaa<br>ggataagaaaaaataagagattccttctatccaatgataagcctgacattcatcaacagtgatcatctgccattgttttaatattggac<br>accctatcgcagatgcgctcttaatgaacgcatgcagtattgtacatcacaactgcaatatcctcttgcatgcatgaacctaatgctcata<br>acctacttagaaccttccagaaaatgaaaagataattccctattcctgtctcttcaaagctaagaaggttttttgtaagcatctacctacata<br>tgcaggatacaatatagaaaacagttgttctggtcttcggtcatgcagcagtattcatcatgatgcattcccaatcttcaggtagtcttg<br>gattcagcttgcaaaatggcaaaaccttaaaggagacgttgccttctcccctccaaccattccagagatgcctttaggagcatttgcaagatgtttcaagctggtagttgattca<br>agcgacaaatatgttattggaatcctttaggtgcgtgcagtgcattgaaaaaggagaatgcgagggtactctctaagcactgcattacataataacaacccagagattgctctt<br>atctccattgcagttcttccaacgattcttccagacattcttccagacattatgaaaaaggagaatgcgagggtactctctaagcactgcattacataataacaacccagagattgctctt<br>aatactactctttctcactgtgccagcagtcgtgggaggagcgtactccttagctctctaagcactgcttacataataacaacccagagattgctctt<br>ggaggttatatgtaactccattgtctgtctaggtgcaatatcatggaatgtatgaatcgtatgagaataattacatacttatactagagaaaacac |

FIG. 9B-21

| | | |
|---|---|---|
| Contig40_gene_659 | 1088 | aatgatccttggtaaattatgataattgtagccatatccaacattgttttaaatctgattcttgtgccttatc<br>atgaaggttgtagtatgtgagaactgtgtgtgcaaatatcaattaatgatgatgataattgcattgaatgttccaattgttctgaag<br>tttaaaagaacttgaaagcttttcagatgaagagatttcctaaacaatctgatgaatcatctggatctgattcagttctgttatgtataaatt<br>gtggtttaaaattccagagtctgaattgaaaagatgacatatccaagtctccaagttctgatagttctgatagtgtattatgaaactgttttcttatgttcaatctgatgacatcattcc<br>gaagaatctcaagagtctcaaatctctcaagactctcaagttctgatacatcattcctattcatgcagaatccgattccaacccatattacgaagaacttatag<br>tattcatgccgaccctaattatcttctgattctgatacatcattcctattcatgcagaatccgattccaacccatattacgaagaacttatag<br>aatctgatgaaattatgcaaatcaatacgaagatgatgatcaatactatgtaagcaatgaaatgcaaatcagcttagatgagcttattatacttcaga<br>tatgaagacgaatatgaactgatgaactgatgaaattattcctcatgctgaaaaaagatatatgaagattcacagattcaggatttgcatatggtc<br>ctaatgaaaataccagagagatgagtctgcagaaactcctgttgtttaacaaggcaagtcctatctgaagaggatcaaaggctatttgacaggttca<br>atagacataccagaggatgagtctgcagaaactcctgttgtttaacaaggcaagtcctatctgaagaggatcaaaggctatttgacaggttca<br>aaccaaatgtatttgacagccctgaagaatatgaggcattcaaggctacttaaggcagccagatacaaatattatgtaggat |
| Contig40_gene_661 | 1089 | atgatgttttctaatatttccaagtattaaatattgaaagaaaagattattatgcctattccttttatggtctatagcgcaataataactgt<br>cctttaatcaattccaatgaaaagtattgaatatattgttcagatgtctatatcttttatatcttcctgtattgccgaatggctata<br>acaacacttatctatctccttgattttgtctgtgaacttcattttcttattagactcggttttgtgatgaagttccattat<br>gctgttactggtgtatttcaatctttgaaagctttaggaattttaaatattcaatctcttttaagcctgccggagagt<br>gcttttacaagcttttcattgagagctgttggtgggcaaatgaactttagactgcctgctgtaggatctgctgctcactgcctcttttgggcgattcatttt<br>taatccttgcagttgatgagagtccaaaatattactcaaacatgattgtttgctttggctttcattaatctccgataaagaagcttttcaagtct<br>attccattgtttttgctctattacttattgaagagttcagatgagttcagatatctctatgatttgctctgctgttctgtgctttcattcagtgatttat<br>aagtacattttttaaaaactgaagagttcagatatctctatgatttgctctgctgttctgtgctttcattcagtgatttat<br>attatgggctgaacttcatttctagagcaggaaggcacattcgcttcaggttcaaaggttattcccaaaagtgatttccaagagaattcattccaacccttaccggcaagctatct<br>tattctacttccatgactttctattctattgataattgaatttcactggtatttatagattttcaataagaacaaat |
| Contig40_gene_662 | 1090 | tgcttatttgattctatttctattttatatgaattcatcactggtatttagattttcaataagaacaaat<br>atgaaccccatatttagaaattattaggccggaaatgcagttcagttatggcagccatatcggttgtcttaatgatgattgtaggccattattacgactt<br>gccaatcattctttgtgcagttcgtcttgtttgcactgcgctggaaatacaatcaatgattgtattcgattaatagatagaatcaata<br>agccaaacagaacaaataccttcaggaagaatcagtctgaagaatgcaagaaaactattcctaacctctcttttgcaatcgaatcatcctaagcttt<br>gtgattgattatatgataattccaatgcctcatatggcctttctgtaattgtcgttccagcagttgtaatcatgtatcttatgcagaaactatcttatgcaagaacttaaggcaat<br>gcctttgattggaaacatcacagttgcaacctaacaggggttctgcttgttgcacttaatgcacgttaaggatatgagagttgaaggtgacaag<br>tattgttattttcaatttattggattgttgtgcactattattatgggaaaaaagattccttccatcgttcaatcatcatgcatgtcctatactgcgcttataggtgtcc<br>ctagaaggagcaaggaaaacatttccatttctaagtttttctatatgatttgtgataactaaagatagctatgctatatagggatatgaaggtgacaag<br>ggtcttatatattggaatcttaagtttcttatatatgatttctcaagaatctaaagatagctatgctaataagctttgtgctttttgttttaggttcatttgat<br>taatccccagaggaagtttgtgcaaagttctctaagaatctaaagatagctatgctaataagctttgtgctttttgttttaggttcatttgat<br>tggtttagcattttttgctgctcttaa |
| Contig40_gene_666 | 1091 | gtgagaaaaatggataaaagaataaatttgtatcaatcctctagatttaccctccttgtggctattttctattgataataataagatacagtt<br>tcatgcaaagattttagatttatatggcctttagcttagccatatttgctatatttgctattatcatcttatcatacaattaaaaggattgg<br>ttgagttcctattaaagttgttgttgaaactaatgttgataaggctttgatgggctattactggaagacgaagcaagcggaaatattccaaag |

FIG. 9B-22

| | | |
|---|---|---|
| | | agggttgttcttaatgcaaacgatatctttaaattagtcttaatcttgcaattgccaatcatttgatctcttgcctgtagacgttcttag |
| | | ggagtatataccagacattcctccagctaatcttatgagattgtatgagattctagagagataagtgatgatttaggtctc |
| | | aaaagttcttaaataaggccgatgttattaccgttctgatgagtaaaacatatttgagagagactatcctttgatgatgtactttg |
| | | gataatactttttgattacttctttttaggaattggtaatgataa |
| Contig40_gene_668 | 1092 | ttgtctaaaaaaataaggctaataaaaacaagaaaaagaaaagtgaccaaaccattcatgaattagagattggaaactgattaaaacga |
| | | agatgtctatacataaacatccagattctctgacattcagcgatcagcgatgaatagacataattgaaacatcatgattc |
| | | tctctaaagatattatgttagcttaatagatgcaatatgaagatgcgttgaactgatgtagcgttgaaattactgaagaatataagaaaac |
| | | aacaatatagaaggaggatacataagccaaagtttgataactccaattcatcatcatctgaaagattctacacagatgacataacatatcacgtaattct |
| | | taacgatttggagtccatgcattaagccctaagctgcattcagcccaatcgtcattcagcttttataagaccgcaacaagccaaaggcaaatctttgaatccttcacatg |
| | | ttctaatagaccatgcattaagccctaagctgcattcagcttttataagaccgcaacaagccaaaggcaaatctttgaatccttcacatg |
| | | ccctccatataacaatatcctaaacaatgaagatttcttggttcttgctttccaatctgcagagtgaatcaggattatataatgga |
| | | aataggattgacatcacaaatatggaatatgaagatgacaaactgaattctagattacttgttagcgaagcaattgtgaagatgggtcaccataagct |
| | | gcgaggacgcaataagaagatcaatctgaatattgaatatgaagatgacaaactgaattctagattacttgttagcgaagcaattgtgaagatgggtcaccataagct |
| | | atgaactttagaaaaacacagactgaggaagtgatccactgagctaaggaaaagcaaagagtctgagatcagttcagtgacagaaacattaatgc |
| | | attgattatgctgcaataccacagaactggaagtgattttagaaagcaaagagtctgagatagattttaaatgaaa |
| Contig40_gene_677 | 1093 | atgaatgttataatcaccctgatagagaagcagtcagttctactacttgttctgtttgtgaaaggcctgtcctgtcagattgtgctatgaagctgcagg |
| | | aaatgtctactgtaaagattgttaatgaattgtaacacaaagcataatgaaaaggcaagcaagctcctaagctcctaaagaggcagccgaacaa |
| | | taactgaagaagttcaagaagctgaaagagcagttgaagaagctgttgaaatcatcactcctgttcaacaagagaagttgaagag |
| | | attatccagaaactccgaaaaagctcctgaaaacttgagcctgaagttgaatacgaagaaacatatgtagaacatgaagacgtgt |
| | | ggaagacagctattatgaaatatgagcaggagcagtccaatgatcctgaaatatcgagaaaaaagaatcagaaagagaagcta |
| | | aagaggaagaggaaataattgagctaaggaccctgaagctaaggaagccacctgatgagaaccttattactaccggatgagatgaaagagaagaat |
| | | caacctagcaaagctccaagtaaggacctgaagctaaggaagccacctgatgagaaccttattactaccggatgagatgaaagagaagaat |
| | | ttacgaagctccaaaaactccaaaagacgttcaaaactccaccctagaaaaagaagaatcgaaaagaatttgaggaagaaattatgcaagaaagagaactcggaaaaaga |
| | | gctagaagcgaagaaactgaaagctgaaaactatcagaagcgaagaatactatagtgaaagcaagaatgaaagctaaagaaatcgttagatt |
| | | cagaagtctaaaagtctaaaaaaacaagaaactgactatgaatatgaaaacataacagaa |
| Contig40_gene_693 | 1094 | atgtctgaagaagaatcagtaccttcaaattgtctctaccgatgatgatgtacgagcagctgcaattaataatttgatgaagctgaagaaagtaga |
| | | attcgctgttggtgaatacttccaacgttggtgacaacaaacggtagaacggtataagtttataatttttatgtattattttaggtcttgtaatttaa |
| | | tagtatctattgaatttggttttggttggtaagtcaatgactactagcttactagtctaa |
| Contig40_gene_694 | 1095 | atgttagattttcaaacaaaccaaatactactgtgattagaaatgcttctaataatgtagaataccgtcaaagctcttaggtagagaagaag |
| | | attatttgctgcgtaatcagcaccagatttttctgaatggctattggtattgattagctctgcttagcagttgttattccactactagcta |
| | | aattatgtggtttatag |
| Contig40_gene_695 | 1096 | atgctgacaaaaccctgctgctgataactgctgctgagtaagtggagactacattgtaggggacctgaaagtcctgtgttgctgtaactaccttt |
| | | agcttcacaatgaagatattccagctgctgctggacgctattgctggaccttgtaagactggaaacttaggtattgaaaagtttgtcaa |
| | | acatatttcaaaccccaaacatcagattcttaatctcttgtggtgctgagttgcaaggtcacattactggtcaaagtatccaagcattacatgaa |
| | | aatggttgcgaccctgaaaagacatcactgctgctaccggtgctattcctttcgtagaaaacattcctatgaaggtgaagttagaagattcca |

FIG. 9B-23

| | | |
|---|---|---|
| | 1097 | acaacaagtagaacttgttgacttgatcgcacacgaagacggtggagcaatcactgcaaaagtaaagaagatcgaaagatcctggtctt<br>ttgaagaagatgctatggttgttatgaagtgaaagaagatgaaggagtagagtgaagagaattcgtcctatttccgctgaaactgatta<br>cttgaagcaagaatcagaaacattgacactcaagtaaaattagttggtgctgtacaaagaaatgcagtaactattcagaaaagtccaagg<br>tatcatgattgattaatattcacttagtaatcgttctttgttaatgcaccattagtgcataa |
| Contig40_<br>gene_696 | | |
| | 1098 | atgtattaccttaatacaatttattcctgaattaaactcttgatcctgaaaccggtctcctcggtgcagttagatgcagagttaatcat<br>tcttcaatggatgagataaatggagaaatcgaaggtaactcgaaagtcgaaagcggctgctgatgaattaatgaattccttagatccaattccgcaccattag<br>gttccttcccaggagagagaggtaacttgttattcaggaacattgaccaatatggttatgattattataggaatgttccttatcatgca<br>gcaatgcctatattaacagctatggggggtttatatg |
| Contig40_<br>gene_697 | | |
| | 1098 | ttgaccaagtcattgcatgttggtgcagtttgtcaattcttggggagttcttgctattcgtagtagcaagttacgttaggtactgg<br>tgtacctctattggttacatgtctttaggtataggtgtttaatcggtgcattagcaggtgtaggtataattcagcattaaattaaaaggattag<br>aaatgctcggaccaatacttgattagtatttgcaatgctcattgttatttagttgctaagagaagattgttggaatgatactctattgattt<br>gttatgaaagatgcacagctgaaatcgctggtgctgctgctcttctctcctgtctttgagctcctctcctgtcaattgcaggtgatactctattgattt<br>attattaaccgctgtttgtagctcctgattcattgctctcttttacatattagttactatgctatccaacaccattcgcaattcgcatgtttagac<br>ctaacgaagatcaagttagacactcctttaaatgtggtcatccactgcatcttaacatagattattactgatattctgcaatctcgctggaga<br>tacgcatggttcaatttttagttgttgacttatcgcgttacgtctcattttaaaatgttgttaaatgctcctacgaagctgcagcatctgt<br>taaatggtccgattatgcaaaagttgaggaataa |
| Contig40_<br>gene_698 | | |
| | 1099 | atggatcttttaatattttattattgttgtaatcgcaggtattattatggtggaggtgtacacttcattcctgtaggtgtgctcctgcagc<br>tatgctaccgctaccggtgtagaactggtaccgcaatgttagcagctggtcgcaggattaactaatcaccgcagctctatgaccggtc<br>aaccagtatggttaatcgtattagcaggtcagttggttccatgttaatgatggtatcaccatgctattgtaacttattatattttcgt<br>gttggtagtaccagcatctgtaaagcagcatcgcacccaattactggtggaaccaagaaatacaaaacccagtaccgaaggacacgg<br>tattcctaccgtctgttacataagtgtatcatcgtgttgctgtgtggggattagtcactggcaattaatgaatttgcta<br>ctgcaaacttaactggttgactactattgaagtttcgtagacccaaattcaaaagactccaactggaatcctcgcttgtgctgttctcttgtagc<br>tataacattgaggtactattgaagtttcgtagacccaaattcaaaagactccaactggaatcctcgcttgtgctgttctcttgtagc<br>tgctattttctgttttaatgatcaggaggtattaa |
| Contig40_<br>gene_699 | | |
| | 1100 | atggaccctattacattaggtgtagtcgcattgatggtcgcagcagcaaccattgcaggtgctcgagagacttcagagatctgacatcggttcaca<br>aagtaacccctaactctcaggttcagctcgctcgtccacaaatggacacttcacaccgtatgataaataagcagctctcgggaaccagtagcatacg<br>gatgctgtggtatttccggtgctgctatttcggtgctgcaatttgcggtcaatccctatagtgcaattgcaattggcgacttgttctactgtgct<br>gcacttgttcacgcaattatacacgcagctcatgtcatgttttatagtcgggatggtcgtcaatcctaattatattgacacaccatttatatgacgtattaac<br>ccaatcctagccctacccattccaaaaattccatctcgctagttttatagcagctagttgggaatactattgtgtcaatcgatcatccacaggggatgttcattatgcagaa<br>gacaccattaccaaaaattcgactacggtggagctcctgtgaggtacccctgtagtagcgattcaaggggatatcgtaactaagctcctcgtgctaaaaactctat<br>agtgaataccaaaaattcgactacggtggagctcctgtagcgattcaaggggatatcgtaactaagctcctcgtgctaaaaactctat<br>cgatgtaggtaacttctgtgctaaatatggtggaccttttaaccgattctgttttgacttattgttttgacttctgattactgtgtat<br>tcggagctttaggaggacaaattgtaggtattgtcatcgttcatttttattaatcgctgctaattacttacttgaaaagtcacaagcaaaattc<br>ggaccatgaggaataa |
| Contig40_<br>gene_713 | 1101 | ttgacaataattcaaaaaggtagaattgattgaactcttctatgatttaatattcgtatatgcaatatcaaggcttacttcaattataagtga<br>acctgtcaatggaggaatagctccattcagtctatttgcatattatcacttccttgtcatttacaggcatggctgctcacttttactaactatg |

FIG. 9B-24

| | | |
|---|---|---|
| | | taaaccgttatgccaatggaagtggtatgaatatgtcattgcaatcataaacatgattgccgtaatctatatgcaaataccatatcctgact |
| | | tggaacaattattttgtattttaatgttccatgctgataatgtctctttacggttgtattttgtattctgttcatgccataaggaaaaatcatt |
| | | aagggagctgcaggtaattcaatcactactctgctgttgtatgttccattttatattatcacattctatttggcatatggatg |
| | | ttgtcattgctcaatgtccttgctctatcttgactgagcctttttcctaaggaaattcgataagtcaattatcaatttccct |
| | | catttgataagaacgattgaattgctgacaatcattacttttggtgaagctgttgtgggaataacacattcttaatgtaaacaacttgatt |
| | | tgttccaatacttgtattcctgattgtgtcataggcatgtttggatcatatgtcttcaaattcactctagtcgatcatcatagggaagagaa |
| | | gcctaagattgatgttcagtcattattcattgtaataagcattaatctggttactgttgccttgaattgattcacagcgggagataaactat |
| | | tggataccgagcctgatggtgataattccattcattgatgtctctttctatctgattgttttactctaaggaatatattatgatgcttagaattaag |
| | | aaaaaggacattgcattaatggttttgattagttaatgaagtattgctatttactatctgttggcagca |
| Contig40_gene_722 | 1102 | atgtttataatctttccattcattctttagcgctaacctaattccatcattattggaataagcgtattggtatattggtatattggcatattcctc |
| | | attcattacacatgaaatctccttggtgcctatctcagttatgcattatcacattctgtaatcttggattgtaatgtaatctttgattatgttcatatttgcaa |
| | | tcaatgcaattcctccttgctaggattgcaattcacattgtaatctgcattttatgctgattgctgtagtcgattccttcagatagcaat |
| | | gttgctagaaccggcgcttttattgtattttgtcctagtaatgattaatgtcaatgttgctgcagaaaccctatactaattacaat |
| | | tatttaggtgttatttaatagcacaaggaataatggattaataatatggcaatgaatata |
| Contig40_gene_727 | 1103 | atgagaagaatgtttaaaatcataggaactgcacacgtgtctcaaatagtgtgaagaagtaaaagaagctattttagaagacaaaccaga |
| | | agtagtcgctattgaattagatagagaagtagattagcattgaatgaaagaaatgcattgtagaagatgaccaaatccatattaccaaaa |
| | | tcataaaaaacaaagtagggggttttctagttacaaccatccttgtaccatccatatggaaacaaaattggagatgacctagcatcaagcctggc |
| | | tctgaaatgatcggcgcaattgcagctgaagagcaggttcagcagacaggttcagaatcgcattgattgacagagacataaacatcacttgcaaggttct |
| | | aaccatatgaacagtctgcaattgggaaaagcttaaattcattgatcatcgagcttcctcatcagatgatgaggaactgatgtagaggcat |
| | | tgaaggaacagtctgcaatgcgatgaggcaatggcaatagtaatctccaaggacgcatatagaagcattgttgaattgaaggatgcatat |
| | | cttgcaacagcatattgcacattccagaagactgattgatatgacaaggaacaggaaatcaacagatcaccttgataatcc |
| | | agaaacaataccgcctcatagcgaactgattgatatgaatccatagaagaagagacattgttcaattcattgttaataagcatgataatggattttta |
| | | ttgttgtatattttttcttgctcaggatcaaagctaaagctagcctcgaatagtaagctagctagcaaaaggtctcaacctactttatcacccctcttggcggcagctg |
| | | ggctcaattcttcaggacttgctgaagcaaagtttcagaagtttgagagatggagaaggtgagaacaggacattaataatataggaaaaatcgaaa |
| | | gtttcaggacttgctgaagcaaagtttcagaaggtgagaacaggacattaataatataggaaaaatcgaaa |
| Contig40_gene_729 | 1104 | atgaaatggactgcgatatcataattagtgaaatactaatcataatattaatcgtacttaacgactttctcccttgcagaatcgcagt |
| | | tgtctctgcaagaagaatcagaatgcaaaaaattgcagatga |
| Contig40_gene_731 | 1105 | gtgcttctaattaaagtgcagatgtctttgtagacgttgcaagtaatgttgcatacaactaaagatacaaccatatttgtaggactcacat |
| | | cgtcgcattggtacaagcgtcctgaagcagctgttcaattacctcgcagttgccggaacaaatgcgatttcccttggaaacgttgtaggta |
| | | gtaacatattcaacatattggcagttgttggtgtctctgcattgcttggaacattgacagttagtattgataaaagagatttcccattt |
| | | ttggttgtatcttcaataggccttcttcaatagccaccatatttggagagataagcagactcgcggtataatctttgataatcatcattgc |
| | | ttatgtctatgtcctgttcaagaggcaagacaaagacaagcaatgtctgaagaagtcgaagctctattgcaagctatattcggattaagcgatgta |
| | | acattgcataggtattgccggaatcatattggttccgattggttgtagactcatcaagctgtaacttctattactgcacttaaaaaggagacaatggtattgtaat |
| | | cttattggtcttacaatttgttgctatatggaacttcattgcctagcttgtgccagcgcaatactccccatagccactccaatagcacctgcaagtgtat |
| | | tggtaatgtgcttgatcaagcagtgatgcacataccaatagcacaccaaaatgaagtggataaaagaagtgcgttttagta |

FIG. 9B-25

| | | |
|---|---|---|
| | | gcattattattctctatatggcattgtcattttaagaaattaa |
| Contig40_gene_740 | 1106 | ttgatagtgatttgattgaaaaatagttaatagcttatcttgatagtgatgatttggaaaaatagttaatgattatagaat<br>tattaaaatacataagaattag |
| Contig40_gene_747 | 1107 | atgcccattaatcctagtggcttttgcatcattcattatagctctgatgctgcacattcatgaatgtatcaatatcccactgttattgacttaaa<br>cacagatgttgaacatacaaaccataatcagttttatccttgatacagcttcattgcctaatcagccaaaatgcaataatgctcttatcga<br>gaaagaaaagtattcctaactggcattgtctgacttagagcgcttaggagcattcattgcctaatcagccaaaatgcaataatgctcttatcga<br>tggtcactattgaagtattgcgcgtgagcaattgcattgatgacacctgctacacatatcaatcataagtgaacatatgacggccagatgctacaacagc<br>ccttgcaatccaagcgcaatcgtcggaattgcagcagctcatcggaccattgttgagctgttgtaaccacattcctatcctgagatatgat<br>ttgtattgaactattaattattctttatatattgcttgttcgtcttaaatgattttcaggaaagacaatcgattaagcatacggcctaat<br>acaggatccctttctctagccatagatttaataatttgactctttgaaaagaagaagcaaatgaaagatgcttatttgatgtaagcctctaa<br>cattgcgacataatcgtgctaatctgatttggactcttataactgcctcacacttgaatcgtatattctaatatcaatctaccttcagaca<br>aggataagaaatctatccgcgcacatgattgctagactagcatttgtcctattgcctcacacttgaatgctatattctatattctaatatcaatctaccttcagaca<br>gttctcaagctctctgcattcaatacaggatcgtcctattgcctcacttgtgtgatgcctcctttaagctatc<br>cagactaagccataaatgcaatatgcaaatatgcttattgcttaaagctatc |
| Contig40_gene_748 | 1108 | atgggaaataaaagaagaaaagctgcaagacaacgtttgatgagatcatcgcgttgcaaaagacaccacttagcaaagctattaacaaa<br>taacgaagacgatgaagctttgaagtttcagacctagttgcaatgaagagctagtcctgcattcatcaaattagtcagctttagcta<br>caaggcccgatatggtaggaaaatgatatatgtgaaagcattgaaagcttctgaagagctactctgaatcaatgaagaaccacagcaactccttgaagaatgagaaggtc<br>attgaaggagcttgaaagcatggaagttcagtagaagttcaaagctatctgaattcaatgaagaaccaacactgacttcaagattcgcatagggc<br>aacattaaggaagcggcatgagagtcgcagtaaagttcaaaagctgaattctatgacgaatcgtaccgatgtaaaggtaaagatcttgaataacc<br>tagctggaactgtagacaaacatgtatccggttcaagaacctataactaacttaaggatgttgaatacattaagatacctgaagtctatcctgatactg<br>gactatatggaagaagtaagaacatcataagcaagtaagcaagtagttcgacgatcgaagttacagaccttccagcaatgagatgaagcatcaacaatacagaattg<br>cagttcaaagctcataaacatggaagctcattgacgtacgaagcaagtagttcgacgatcgaagttacagaccttccatgcagacaatcagatcagatccagtaacctttgtaacaaggat<br>cccaatatgaaccctaaatcctaaagcaagtattgattgacgattcttccatgcagacacattcagatcagatcagatcagaataacactcttgtaacaaggat<br>gctaagctttgctacatcgacttggttgatgagtggtaaacgacattcatctcccccagaacactgacgagttca<br>aactcaccacattaatcaatctgatataatcatctcccccagaacactgacgagttca |
| Contig40_gene_764 | 1109 | atgtgtccttttagtgctgcatgatttgcatatgtttgacacctattgctaataagattcaaacaagattaaatatccttcgatttctatctttt<br>agcattgatccttgttcattgtaattcattgaatgatactgtcatttgcatatgttttatgaattacagtttgcagatgtattctttaattctagtg<br>atttggctggaatgatataaatgccctaaatgcctcgttggtaattgcagcttcaaggctttaaaagtgcagttaacacatatattggttct<br>ctatctactgttggaaagccttatcttatgtatggaagcacttaaatgtaaaagattctctatgtatcccaatagagcataagcttcttttg<br>atttaatctgtcaatttattacttactctgtgatgaggcctttattggtctcatttttgactgcgttataatgtgtcgtttgcgtgtagga<br>atagaactttctatgaaattgctaatgtatgcttgtttttttagcggcatacactgaagtaatcactcagcagtcttcaagcagttttgatttcgcaataagttgaattgatgcctctatattgggcggtgagga<br>gctttagccattacgcacatatttgtttagcgcaggatatatgcaggagatatttcaagcaggtcttactgtcttttgtgttcccgcccgccctattttgtctgttgatgtattgttagtgatgt<br>atatacgtcctgattacgcaagtaacactgcatgatatgccttcttgatactcagtagtcttcaggtcgttaagtcttaaagaaagttatttgaattgta<br>gggtttattttggtccattaattttaggagtttgtatgctgtattaagtcttaaagagatttaaaagaaggataaattggaactctgaga<br>tgaagaggagttctgatgatgatgtgatgatgaagatgaagtaaaaagaaattctgataatcttgatgaagttctgatg |

FIG. 9B-26

| | | |
|---|---|---|
| Contig40_<br>gene_770 | 1110 | atgaaaaagattattggtattattttataatagttatatggttattggaggttctttagtttataaaactataagactctcaaatactgt<br>agataagtcccaagagtctatagagataagcaaaaatgaattacaatgttaattccaggtgatggtggaagcgaatctgaatctaatacta<br>cagctatagcagctgcagacctgcttctaaagcttctaaagctttagtagtgttaatataaatattgaagaaatgtgtcaattgcaggtaccgaagg<br>tcgtatgaattcaataataattataccctcaagtaagactcttcttcttacgatattctatatgaagaaatgtgtcaattgcaggtaccgaagg<br>tatgaagcaggttatacctcaagtaagacggttttttaaaacagcataagccattggtttaagcaggggatgacctttatgttatcttat<br>gtactgcgccacagagcaagtttgcagaggaagaagcactttgactttataataatctaaattataataattcaacaaattag |
| Contig40_<br>gene_771 | 1111 | atgaagcttatgcagatttaaagaatcttgaaagagattataatgatgtctgatttccgaagagaatacatctatctttcaaaccagtatag<br>gcataagatcgatacaattgatactagcaatgataaggactatgcaaggcaaaaagaagttctcctcgccttattcaaaatatgaagatg<br>ctaattatcaaaaagtcgtgatgaggatgaacgttagttgaaaaatacatccacaatcctgaatctatatattaattctagagaagaaa<br>accaaaagcggaggaactagccgtggtatatattagcagttcttgctgcgttagcttgctgaaactagacttggatatatttag<br>cgaaaatacaatagtgatgtaggagatatactcctcaaactcttatctgcaacaattaatgacacagcttttcctgaagtaaaacagactataagtaca<br>atcgtacttcaaattatactaataatactccttgttatctcagcagtagcaaactcttattcaagcgattattctcagtggaagttcttataattcctatggcga<br>tcaggttattcaagtggaggctctgttattctcagcgaggttctggctattcaagtcggaggctctgttatttctagtggagttcttcttactc<br>tagtggagttctgctattccagtggtgtctgttcgtatcgattgattag |
| Contig40_<br>gene_780 | 1112 | atgtcttatgaaatatcacttatttcaatttttagaagtcgtttaacactgataatagcctattcatcggtgttttgattcctgaattgaaag<br>aaaatatgttcaggcaagaattcagcaagatggacctccgttacaacagctttgtttattggcatctataaagtcctgtataagtaatgccatat<br>tccagccaaattcaatgctccagattatataaggcaatgccagtcttcttgtttattgtagttttagctatattcttagtatattaatgccatat<br>aactatcaattcatgctgctaattcaagttccagttcaagttgattttcaagttgctattgtttcatccattgaagacatcagttcaa<br>atctgtatgtctgctaattaaggtctgtatttggtctatcatccattgtttcatttgttccggcagcattaagcaaaagcattattagcagat<br>aaagatccttaagatgattgtatttggtctatcatccagcccatgtgcccagtcacttggcagtagcttgtttcttgtgatatatgtcatttt<br>attgtcatacaagccaatgcagcatcatatattcacttcagattgcctgttataatgcatcatcagtgcattctctccaatatttactaataacagtatactccactatttt<br>gaataatccgttcatatattcacttcagattgcctgttataatgcatcatcagtgcatcccaatatttactaataacagtatatccactatttt<br>tgactagaggatttttaatatcttgatatgggagttttagctattgtgattgcttattctaa<br>gctgttattgtatctgctattgggagttttagctattgtgattgcttattctaa |
| Contig40_<br>gene_785 | 1113 | atgttttgtttcagctaatctcttaattggtccgatattatctctgttatattgattcgttctaggttctagaatccatctgatgagaaaaa<br>tagtttaagtttaccgcaagcaagaatcattgctgttataagttgcattaatagttcattaatgttgacaattccttactataatgatt<br>tgccaatagcaactacattttaggagctcattttaggagctcattttattcggccttttgatattcattggtagtgcattactggagacgagcagaagtcattaa |
| Contig40_<br>gene_786 | 1114 | atggctgaagataaagatttaaaaaccacaaagaaatctcaaattgaataagaaagcagtcctatattaaagatgaaagtaaagcagtcctatattaaaatcatggtcttgcctat<br>ttcattcattatagcttcttttagcagtttatttaggagtggtgatcatgtttatttaggagatataactccaggtggagcaggaaccttcaagttggagcatgattgcagag<br>caatcatattgtctgttgttgtttataactgtaaatgaagtccattaaatgaagtccattatctcataagattcattagcctttgaactgtcgagcttta<br>gcttatgtcttgcttgggttgtgcagggactttgcattgcacaggctcattgtgacagccattattcatggctttgttccacaggctat<br>tgcagcaattcaaattgccttttcaaatcctgattttaacaaatgctgaatgctgtcctttattttaaatatagcagtcggactaagttacttgtaggttaagtg<br>caattgtaattgcctttcccaatttaaaaaattagcggaagaataa |
| Contig40_<br>gene_788 | 1115 | atgaacaatgtttcaggagcaatggcagcagaattctaatattggttgtctaatacttgctgctttgttcttttagacatatcaatattgctgc<br>atgcatagttgtagttcattctagctgccaatattgtttcttacaaacatgcctcttgcaagataaagtcagaacaatccgattcattggaaa |

FIG. 9B-27

| | | |
|---|---|---|
| | | aatgtgttatttatgtactcattgttcttgaatcctattctgtaatttactgggggttgaaatatgtctga |
| Contig40_gene_789 | 1116 | atggtcgttattccaatattggctgctgttgccgccattgaagcgagacagtgaaggcttctccattattgtaggacttgc<br>aattcctataattgcaattcttgccgcctatacaggtatcgttaatttttgacaatatagaaagaattcatattcctaatgcctctaatctag<br>ttgaaccctgttgcaagctactttacctacttcacaatatcttcaatatgtatgtattcttgagataaccgctttgactcaagtgcttttattggtcctcaagcacagagacaatt<br>tctatctaacgatatcttcaatatgtatgtattcttaggtcaatgacttaaccgcttgactcaagtgcttttattggtcaagcacagagacaatt<br>atgaaatcgcattgaaatacctgatttaggttcaatgcggcgacgatctgtgatcctcaaggacttgtagacggcttgatgcctcttatattgcaagcacagacaatt<br>aattacagacattatatgcaacctttgcaatgcgcacgtccacactaaaaatcagcggtatacaggtaaggcaagaccttgatactcttgatttgttcaagatatgtagttcagtg<br>gctatattcagcaggattgcttgcattgtatgcaatgctgcaatttgctatatctcttatattcaagcataagcaagccataatggattcagcaataatacttcaagatttt<br>cagtattgtgcatgctcattcagcaatgtcgcaatgtcgcaatgctgacttgaaagaatgacttgacatgcttgactctttagcaaaattttagcagcaataattgcattttgctcactaaagctg<br>agtttgtattggaactcaaatgtccattgcaactgaactatcctagacgtgcagcgcagcaattgagctcatgatgcaaatgaaaattagtcattactg |
| Contig40_gene_790 | 1117 | atgattatggatattcaattagtcttccctattgctcaggcgctctcagccaatcttcattgcagcaatcttcattgacaatatcataaa<br>gaagataataggtattgcattattcgaagaggcgtaaatctcatcatctgcttgataccaaggctgacggttgtgaattacataaatcatctg<br>aatgcatgactgcagactgtttgtcatcgaattccgcctatcctagccatctgttgcagcattgttcttacaagcattgttaatcgtgcaagcatca<br>gctgtaatgctgcttagcaatgtgtcttatacagaagcatgaacatcaagcgcaacattaagcgaacataagcgaaatattgggggatgaaaatga |
| Contig40_gene_791 | 1118 | atgattgaatatattattatttgtcggttatagctcagtgcgttattcactagccttctccttaccgcactttacgaagactgtgcataaatcagccattctagtttgaat<br>atctgttctgttcttcattgcagtgctattccaccttgctgtctccgatgttgctcttgactcaagcattgcttgactcaagcattgcagtgctatcgctcgtcagtat<br>ttatcgctttgctgttttataaaacaaaggagggcttaa |
| Contig40_gene_792 | 1119 | atggcttagtctagagggtctagagggtatgaacttaataactattatccaatcaatttattaattattctgcacttatgtcgcacttatgcagctatgg<br>gatttaagaatgatataaagaacatgcctaatgtttgctaagatctttgtatgtgtcaagattcatatctgaatggaatgatagtgcgtgaataatagcatttattg<br>gattaggtcagcttatttgctctcttatctatattcctgctccgcttcatgcattgaagaatctgaattgaatctgaattggcagaacagatggta<br>ttaaataatcctgttctttcctaattttattaatgaacaagatgtcagaacaagatgtgaagaactcaagaaaataataagtgaggtgacgcaatgattga<br>agaacctgaagatctgttgatgtggcagaacaagatgtgaagaactcaagaaaatataagtgaggtgacgcaatgattga<br>aagaagaagcttctaatgaagatgtgataataaaactactgaagaagatgtcgagaactcaaataataagtgaggtgacgcaatgattga |
| Contig40_gene_793 | 1120 | atgataatggaactttatttggatttcagagtgttttttaaattgcattggtttttcttattgcatcatcatgaaatcatctgagaatcattacttacaaaac<br>tgtctctatgggctttatagggtactttcttcattgaaatgcattggttactccttgattcttgaaatctcgtcgttcatgctatgtgtggggcatagaattcttta<br>aggacattgctttggttttacttttattagagtgtgaacataagctttatgcaacattttaaggagggcttaa |
| Contig40_gene_794 | 1121 | atgttttatctagaatttattatgcaattgcttattggtagtgcttattttggagattatcaagctactatagatatgcctggtaggtatttatttt<br>taaaggagaccagtatgatcctattgtccattgtaccgaattaaaaaggccaatatctcaaactatcttagcaaacagcattacttaa<br>ctccaagggacttatctgttgatttagattcagaagtcaagttgattaaaggttgcagtttattgctccaagacgtaaggtatcattccttt<br>gagccttatataaagggatgttagaatag |
| Contig40_gene_795 | 1122 | atgtcatcttataaggacacacaatattgctttctctattcattgctttttatgacccttttgcaattgcacttgcagttatcggagc<br>aatatccctgacttgaccatgaattagcgaaaacatgttttaatcattattctcattgaatgatcttaagcatcttcttttattagttga<br>atctgccattattaggttgataattgcttattaggctcattttcctttatcctctcataagggcttcactcactctatttagagct<br>gtagtaataagcattgccattatttattgctatttgctattttggtctattttggaatgatcttctcttacttaattgaacactattactattccattaaa |

FIG. 9B-28

| | | |
|---|---|---|
| | | ctatgttatttagtcggaatttaatatttagctgtcctattcttgaataagcaattggcctctattcattcttttaatgcttttctta<br>tcactttggttatttgaatagtccctgtcttaagataacgtttatctctaatatctctgtgtttagtctattcagccatatgatt<br>ttagattcattagtccggctggaataagccattcagtcctttcagatagaaaatgctataaaaattaggattgcttttattgcttgat<br>aattgctctttatttgatttttatttccaaataattagatttctatcttaatcttctcccacacttattaa |
| Contig40_<br>gene_800 | 1123 | atgaaaatagaaatgtatggagaatcattagtgaatgaattaaaaatatatggagattaaagaaataaaaccgattaaaagaatcct<br>cgttattatcctaatatttgcttaggtctttaggtctcaacataacaattctatctattataacaatcataacca<br>tagccactgtaggatatggagacataatccctgtaaccctgaagaaaactgcacgacatcaggagtggaagacatatgaaagatggattgca<br>tacatattacaattatcattactcattgaagaaaacttgcacgacatcaggagtggaagacatatgaaaagagattggctaaatggaaga<br>ccattatattctatgtggttttggaagggtaggaaccgcagtttatgaagaaccgcagtttatgaaaagtcaaaagtaataattattgaaaagaatg<br>aagacaagctgaagacattgaagagtgaaaatgtaacaacaggaagcgatgtaggaaagacccttaagaagctcaatattgac<br>aagtcattaggggtgattgtaacaacaggaagcgatgtagacaatctattcattgttcttacaacaaggaaatgaataaggacgcttgattat<br>ttcaaggcaagcagtgcagctaataacttcagaacaagatatcaaaatctataaccaaagcatgctggacaataaggtcatatccctgagtaagcgaggaactgacattt<br>actttgctgcagtgcagctaataacatacataactcaaagcatgcattgattatcttgaaagggaattgaatacttaaaagcacaat<br>tgccatttgaaacatagaatatcattttccaggaattaagacaccagttgatgtgtatgaaccgttaatgagttc<br>cattgatatgttaaaacaatccagaagtccatgaatccatgatgtgtatgaaccgttaatgagttc |
| Contig40_<br>gene_803 | 1124 | atgaaaaacaagaaattgataattttttgttttgttttattgtttgcaatcatgccgcaatcatgcctatacttcatcgtatagatcaggttgtcgacgc<br>tctcaaatattctaaccttgttgttgttttattggcttgtcgttttactatttcctctacacgagatgcagattataaaca<br>agagtgcaggcatgaccttggaatctgaaattgctcctgtgttttagtaagcctgcgtaaacaacactccaagcgacgtggtggc<br>ggagagcctgttcgggcttatctttgagcaaaggaagtcattataagttcattataatttcagcgtctcttaccttgatagtcatatgtgttctttgtg<br>attccattgcttgtcattctagcaattctgacaattatagacaattatgcattgcttattgctctatgcgttataagcatgctagagcattgtgctaaggctaccgttattcagattcaagtgaattct<br>ttgtaggaatcactgcaatagttattctatgcgttatgcgttatgtctgaaaaaaagattgtggttcaaagttttcaatctacaatgaacgttgcaagtattacc<br>aaaagattctataaatattattctatgcgttatgcgttattggttgaaaaagattgtggttcaaagttttcaatctacaatgaacgcattgattaagga<br>taagaataattattattgcatgcctttatccttatcttattgcatccctgtttagctgctaaccttgtgtgaaaagcaatcattagcttgtgccacaa<br>aagtatccctataatattctattcaaggtcaggatgtttaatattgtatcactactcctttagctgctaaccttgtgtgaaaagcaatctcattgaatgactac<br>gtgatgattttattcattcaaggtcaggatgtttaatatattgaacttctatttgatgaaccttaacttgcagaaagcg<br>aattagtctgatctcctcatgaagtatgaacttctatttgatgaacttgcagaaagcg |
| Contig40_<br>gene_804 | 1125 | atgcaaggattaggagttgtattaatagtccaacctagttgcattaatatacgagagtacgaccctatgctcctttatgatcctgttt<br>tgtatcattgtcttaggaactgcttagaatatcaaagactataccaagcttaggcttaagcatgtgtactaatatcatccttgcat<br>ggctatggcctccctatcggagctcaatcatgtcctcattaggcatccatcttgtcgatgcatcttgaaaacatgtccgcatggacc<br>ggaagcggaatgactttttttgtaaacgttgaagtattgctaaatccatccttaaacggccagaaacatgctaagtggattaggaat<br>tgtaattatcttatcgagaattctattcgagcaggtactgcagcatccagattataaatcagaagctagaagaaatcaagcaaaca<br>tcaaacaccttaagaaaagctctagaaatctatttaattcatacagcagtggaaatattctttcatcttgcaaggcttcctatcttgat<br>gccataaacatcacattcacaagcatctcaactgaggaatgtccattaaagaatgcaatgtggattctaccaagaccagatagtctacctaat<br>cagcatgtttctaatgattttaggtgcaacaagcttacaatcattataagtggtgcaaaacatagtgtccctataggaaaagcactttaaagatgttcat<br>tccaattatgtattaccttaatcatgttctgtgtgcattttattagtgacaaataagatgttccacatgtcaacattgatacgtgtcccatgcatgtaccatttca<br>gcagtgacaaccacaggggcaaatgtggtttgatccaacgtgcttgcaacatgaacgggtccacattgatccacagtgaacgtgaaatgtaggtccgaatgaacaaattgttcgatcttat |

FIG. 9B-29

| | | |
|---|---|---|
| Contig40_gene_816 | 1126 | tggaggttcatcaggatccacaggaggtggattgaagctcattaggattattacagtgctttaaagaatgaact<br>atgaaaaatcatcaatcataggagcctgtctgttcatcggtcttgtcagttttttgaatatttgcagtttttgaataatagccatcctattattcattacattaatgatattttctacctattcaa<br>ttcacatacacataggagcctgtctgttcatcggtcttgtctatcaatcgtctattttgtacaatgtagatagcacaaatattcaaaatacgctagaaactttattcaattgg<br>ccatcggactatatatgctgttcttatctcgttgcaaagatcttaggaccattcctttttgccgtggatggtgttcatcagatcatgatcatgactgcaatgat<br>gaagctgcagtgatccactatctcgttgcaaagatcttaggaccattcctttttgccgtggatggtgttcatcagatcatgatcatgactgcaatgat<br>tcttgatctttgcctttataagactccaaacaaaaacctgaccatgaatgtgccaattaagcacagtgatgttttatctgtttatagcgggaaacattgttactacaca<br>taataggtgttgattgcttttatgatgaatgtcaacataggcttttaaagacaataggctttgcaataatacattgctataggttgtcctgatgttgatattgcaataatg<br>gttggaatcatcctgcatatgcttaaagacaacaaaggaaaattgtatcagttgcttaagctgtgccaagaatgtgcaatgatgctcttttctata<br>ctcttattaaagtaaagtacaaagttacagagtcatttatgctcaagctgtgccaagaatgtgcaatgatgctctttttctataa |
| Contig40_gene_825 | 1127 | atggcacgtcataaatctaataagcgttgaataaggtgaagaagaatccaatgtctggagcagcaaacctgtgatgctatgttagttat<br>tgcagtagtcatagtctattgtctttttagttctctttgaacatgcaggaatcgtttcaatgaagacgtctccgagagaagcaggaagtaa<br>tgcaacagatgcaacagtaactgactgaagggttcaggaattgaatgacactccagatgtaagtaagttcagtaaggctatacagag<br>atgggtaaggtctataaggactcatctactggtaagctgattatggttgagggctaa |
| Contig40_gene_826 | 1128 | atggtaacagttattcctggaagtgacttactactccgcattaactccgattaaagtttacagataccgtaatagtatttta$\text{}$taat<br>ttttgcagttgtacgctgtaattactgtaggggcttatctcagaatacacagttctgtaagaaatacagttcgttaaagtaatcaagatttaatat<br>acgcaatatctagaagtgagagtttacagatgttacagaagactccagagatgaagaagaattcaaagaatcaaaagaggttttaatcaatata<br>gcaagatctgagagttacaaagattgtcctacccttggttgatggtaccactactgttgtaggatgtcgatccgtgcagttgcatatgtgtctctaaggtcaga<br>gacagatcgttacaaagattgtcctaccttggttgatggtaccactactgttgtaggatgtcgatccgtgcagttgcatatgtgtctctaaggtcaga<br>tgcaacctttgtctaatgcgatcattgtagcttcgacactacttgtagctatgtaggatgctgatgaatgatag |
| Contig40_gene_827 | 1129 | atgtatgcaatttggaatattggcagcagttctgtatttgtatcaagttaggttggctgttggcttaaccctcaaagaagtatct<br>ggctactgtctgttattggatatggtcaggagtactcattcttcttccctccttttgctactgaaattactgagcttatctacacat<br>taactctctgttcttttattataatgctgttccctgttccatgctgtttcaattgtcagtatctttcggttcagtatctgttagtggctcctacagtcggttagg<br>tgctgtggatttaagcgtatatgtggcagcagctttggttttaactattatagttactaactttgcttcaagcatattcgttcgatatgttgata<br>agccttatccgattgtactggtaaacttcatgtttctcctggaactttgctgtcttgcttcaagcattgtcagcaatcatg<br>ataagtcaatggatccaatcagcatagttcaatgaagtttgctgctgcttgagtgtcttttagtagtttggcatgtatt<br>tcaagaaaaacaatattctaagctaa |
| Contig40_gene_832 | 1130 | atggctcgtcgttgcaatagacgttttgaaagtgaggaagaagatccatcagcagaaccgccaaccttgtagatgcaatgttggttattgc<br>tgtaggcctgcttgttttcctgtgctgttgcatgaacatgcaaagcgtctcttaatgagcagctactcaagaggaaagcagcaggtcatgg<br>tgtatgatcaggagatgactgaggttcaagaggtcaaatcttgaatgagactccagatacaagcaatgcaacaggtcaaggttatactgag<br>atgggtaaggtttataaggatccgtctacgggtctaattgattatgttcagaataatctgcttaa |
| Contig40_gene_833 | 1131 | atgacattagctattgaaatacattgattttgcagatgaagctatttatcaggagccaacaatgactattgccatctctcaaaataacaaa<br>cgcaactggctttccattttagatagttcactaactgctataacacaagcattacagataccgtaatcattctttactcatcttttagtat<br>tcgctgtagtaactttaggaagcttctatcagaataccttctgtaagaaagtaccttattaattaatcaaagaaatgattattcaatctat |

FIG. 9B-30

| | | |
|---|---|---|
| | | gatgcacagtctgctgaggaaattaaaatatagtaaatagttcagatatttcaaagttccacaaaagacaattctttgtgacttgctgacagtga<br>acatcttgtaagaatcaaggagacattagctcgtagattgattgataatgaagaggataagattactcaaaatcttcaaaaacagatattg<br>ttacaaggatagtcctacacttgattgatggaacacttatccaaatgggtcctcaggtcttgcagcattggcagggatgtgacaaccctt<br>gcaagcgcaatacattcattcaatacaactgttatcgtattggagcaggtgctgccgcttacttgcatcaaagattagaagacgatggtt<br>cggtgaatatcttgctaacttggatgcttgatgatggacaatattcaataaaaggatgataagctagaataa |
| Contig40_<br>gene_838 | 1132 | atggaaattattgattgctatcattatctagtgcagccattgtatttttaatctattatttcagactgtcaatggagcagttt<br>tgatatagatgatttaaaggatcatctccaccattctaaaaggaagcagccactgccacgttaatctgatgatgaagcggaagaaaaag<br>tttctgtaggtaaaaagattaaatatatacctttaaggacattgataaatcttattctaacactacagatgcattttccaaaagattagatgcattt<br>ttagatgaaagaagtgaagaattaatgcaaaattggtcttcagtaaccactgatgactggaaagttgaaaaacgttgcgttactgcttgtga<br>cagcattgatgacttagagagaggacgctgaaactataagaaaagaagcagatgaataa<br>aagattctgaacttctagaagaggacgctgaaactataagaaaagaagcagatgaataa |
| Contig40_<br>gene_839 | 1133 | atggctaatgaaattataccaagtgaaatttcattcttatttagtggtcatattgcttttgtagtcattatcattgcattgcaatgaaaaa<br>ggtacgccaatctgacaatacttcttttaaaattgatgaaaagaattgagcttactactgaaaagacttgaaaatggtgaaaataaacgtt<br>tgatgaaaatcctattcttcttacctagcgaacagcagctcaaatcagagattccactgctaaagtcatgagcgatgtaggctat<br>ttgcatagtgaaatcaatgaacgtttagcacgttgaagctcttgaagctcaaaccgaacttaaaaattagaaaaaatgcttgcagaaattgaagataaaga<br>gaaaaactcaataaggcaaataa |
| Contig40_<br>gene_888 | 1134 | gtggaaaagccacaattagttaatttatatgctaagtcgttgaagattctgcttaaagtctataagaacttccaacagaaccgt<br>agatatatatgcagtcttgccaacatcaatggcgatttgtatgttgttgcatgcaaaaactatgacaaggaatggaagttgaatcgatg<br>tcttaaggaaatgaagttatcggaaagaaactaaggcacaagaaactaaggcatcaaagtcagcgttgcacaagttcctccacaggcaaaaagatat<br>gctgaagagagaaaatcaaattgtagacagaacgatcttgtagcacgaaacgatctttgagcttagctaataataggaagactacggtaaatgaacgt<br>agacttagaaggaaagtcctgctaatagagtccatagaactccatatgcagcgtagcagcgtgactacatagacaatgtaaatgcaccc<br>aatatgatgccgactcaatagacgcgtatgatgactatataggctatatagacacctagcaatgatccactataatgatt<br>attgattgcaaacaatcgagaccatataatccaaaaataaacaataacaataatcaaggaagtctattctctagaataagcgactgaaagctta<br>gcagcttaaattgcaaaatttcatatctcaaggagacaatgcttatctaagtctccaagaaatgaaaggaagtcaagtgcgttaaaagaaatgattaa<br>cctcaagaaattctaatacaattgttcaatcattgttgcttatctgattgcattcatactttg<br>gccaatacttggaaatacaattgtttcaatcattgttgcttatctgattgcattcatactttg |
| Contig40_<br>gene_890 | 1135 | atgatatttacaagcaataatcattgacttgtccaagattaactgaatttctacctgtaagttctgtcatttaatatttattcaaca<br>agcattaggattaagcaatgttccactgcttgccttagtctatttgatgtcttattgcatgtaggaacccttgtagcagtattctctttagcgatatta<br>ttcaaatgattcaaggattctttctatagcctattggattaaggatgaaattcattccagaaatcagaaggaccctataagaagcttgca<br>tggcttacaatcattgccacatcagaatcagtctgtgagtgttgaggatctactgacattataggaaaatgttacagattcaggatttacagattgtacatacctgc<br>atcttgcttcttataacaggatgtctttttatatgtatccaaagaatgaacagtggaaaattgatgttcaaaacataaccatcaaagaagcat<br>tgcttatggatgcgacaggcaatagcagtattgccagttcacgttccgcaatccgcggacctagtattgccaggactagacaag<br>gaatttgctgccaaattcagcttatcatcatcatccagcaatcttagtgctgtagttcaattgcatttgaatgatcttaagcggaggcaatataga<br>gattggtcatgttttagttgattatgtagcagtcattttgggatgattctttggagatattatatag<br>acatattgcttactattgttgatagtaggagatcattgtttttggtttggagtattcttatag |

FIG. 9B-31

| | | |
|---|---|---|
| Contig40_gene_905 | 1136 | atgatgtaactattttatttaatatattaaatactaatacatttttattaaaccctaaagagagagttattcaaggatttattgtttattct<br>aatgagtgtttttcttattatttcctaatattttatattttatcattattacttagcaagcccttaattttattttccctttaatctctttgagcttttaatgc<br>tcttttaggataaactttcattacactaatttgattaatatttcattattacaattatttataatgttagttctgaaatcctgttttattgagttatgaggga<br>gttatagtaaacttattgtgcttaagttggagctttagttttttggttaagcatcgctatttcatcgtcctttttggcatttttttcatt<br>tgccttggcatgttattgcctctatggttttaatttcaggagagatatttttcttattcctttaatgaaaaagcaagtaatatctaaaaattcagacaagc<br>ttataggatactccctattggttttaatcattacttagtttatcatttggatgtgttcttttattttaattttgtccgatattggataagatttgccttttga<br>ttcaattttttagcattaggcttaataatcattactttttttactatctattttaatttattatctgcattctattattctttataaaatagttaa<br>tattagaacaaagaaaggcacttttattttatttactgaattaggcacttttatttttcatttctgcattctattattctttataaaatagttaa |
| Contig40_gene_912 | 1137 | atgttaaattaaataaaaaactatcattggtaatccttgtttattcttgcaatccttcatttgctaggaaatctttttccaataat<br>tggaggcctatacttcagttcagttcatttgccattgcagtgtattcttaggatcgctattcttaggaaagcgctgaaggcatagcaaataaaacttcacctcaa<br>agtacatactttcagttcagttcgtgtatctttaggatcgtctgcctatataatgatgaaagtcctaagatgagagaaactcttaagatgagagaaactcttaaagatgagagaaactcttaaagatgagagaaactcttaaagatgagagaaactcttaaagatgagagaaaatcccttcaattgtgtgggatcttc<br>gaacaatatccatagcctctgcaatagcgtctgctacagcccctgtacagtgctacagtcttggtcaatagtccaatcaattcaataacaatatttcttca<br>catttcggaggctctgacatagccgaattataatttccaatgctgtggtagaatcgttgtcaatgcttgtccaatcaattcaataacaatatttcttca<br>atgtcatgtcgatgcaatttcctcagtaactgcagctgcagctgcagatcacacttgcattatccaatgctcattcttatttagctcatcatcataacacagttgcagttttcttgtgtgatgcaagc<br>ataatgacacttcctcagtaactgcagctgcagctgcaataacacttgcattatccaatgctcattcttatttagctcatcatcataacacagttgcagttttcttgtgtgatgcaagc<br>attaaccagaacacttgcaatcattcctaacattcatgacttccaatgtatttccaatgctgctaacaacagcgatattgtaagcttgttataggc<br>tcagcttaaaagagcattccaatgtaaagaaaataagcaatctcaatgatcctgattgcatgcaatgcttaccattgtaagcttgatttacagcatt<br>agtggaaacattgctgcttgttgatagcgattaccatttgtaagcttgatttacagcatt |
| Contig40_gene_920 | 1138 | atgagcgaagagtcaagagttccaaagttgcaaaggcagcagcgcaattatcctaatagaaacgttatcttcgtgtaggaggatatctaccg<br>ctttttaatgctccctttaggacctgccgcatatgaattctcgactacaactccttccaaggatcttcaggtctctgtctgctgcag<br>ggcttccacctgcaattgcaaagtatctgaatacaatgccctgatgagaagaccttgctgccaaactatttacgtccttaagatt<br>atgtattcctaggctttcttcgattcataatgttcatgttcagctttagtcgttggaagttcgtagcgcccaataatctacatacctacgcgaattcataatctacatactctct<br>attgcagctgtaggtctatcactcctttcagcttcatgatttctcatgatttctaatgctacagcacttgttcttcttggattatccacccttgtcagattaggttccgtt<br>ttagttttgtagcatctgaactgcaatctctgcagtctacactgatttcttctcaatgtactttacagcagcaagataatatgcaaatacatacctccggcaaaccagacttaaagtttcc<br>attgaagacgagctgaagctgaagcttcctccctgcagtaagacactgatttcttctcaatcctgtaaccgttgcagcccttgcagcttcctttagctcttagtcgtatcaat<br>gcacacttcttatggagcttcctccctgcctgaacaatactgcctgaacatgcctaaaggaccaagtgctccttgcagtccctgcttatggactttgtatact<br>tccctgctacaacaatactgcctgaacaatctgcagctgcaacatgcctaaaggaccaagtgctccttgaaaaatatgtgacagcaccatataagta<br>tggaatgttctttgttatttccaatgtgtgtaggaatagctatcttcgcaagaggaataatgggacttgtatact |
| Contig40_gene_926 | 1139 | atgttaaaaatattggcagctgataaaatgacaaaaattaatagtcagataatgctcattgtaggtgtaatcatatgtctatgggat<br>agcattatctatcaaagcaacttttaggaacatcccctatttcatcgttcctgtcctatcaattgcctgtcctgactgtgaggagttta<br>caatagtttcaatgcacttcttgttatttcttgtttgctagaaagatcaccatctccaaatagctcagatgcttgtatgcgtcctc<br>tttgatatatgattgactccagtcttcagtcttctaatcttaattttccaaatcctacagattatatcagccaatgattctatgatcataagctgctt<br>tgtacttgcattgcttgcttattgaagtaaagtcaccatgcttccaggtgacgttcagttgtagccatcgctgaagttacaaata<br>gggactttggacagatcaagcattttttgacctaccacctgtatccattgcagcatcctatccattggcattggtatttttaggcaccttgagggggtc |

FIG. 9B-32

| | | |
|---|---|---|
| | | cgtgaaggaaccatatttgcagctattgttgtcggattaatcatccagttttatgacaggatatttgatataatattgatgcttatttggctga ttag |
| Contig40_gene_929 | 1140 | atgaacttagaaacaaagcattgaccttttaaatccattatcataatcgctatggtaattgtattcataatcattgcccttcctatgtgta tgcttaccaaaaattgccaagtcccagcatgactttatttctatacataggattaggccttatttcttcatttgaatttgataagcaatc tattgctaaacagattttaaaaaaggatctctcttttagattccttaaggacactataaaaattagcataagcaaaatccaaaaagcttca atctttgaatcctactcaagaaaggaaggaaatgattctggtctgtcatcatgttttaatggaatcatcctcagataatcaacatagttcgtcttggagg aataccattattctcagcaacaactaaggctgaagctgagcgtgcagaaagatatgctgcatcataaatcttctgcattattaacatactcc ttgcagaattcaataggattcacattatctattttagtatttttaggcttgcttttattttactcatcaagtatcatcaattggactcttttagtcattgcagtggc gtgttatctatatttaattacatttataggcgtacagcaataagctggcagcactggagctttaatccaatagaacttgtcatataggcgcat acttcgtctgctatagggtctcatagccatgcaatcagcatcagttgcaactgcgccgaaagcttttctactcaacccttacagatttttcactcacaca ttacattgaatgttcttggccatgtcaggtcaagcaactcttggaagggaaccattcaataacatctacaatattcggaccggctcttcttgacttgattgat tggaatgtgcattcaaatgctcttgatcgattcatttaaagacattgcacagcattcaaaagcataagaaag |
| Contig40_gene_941 | 1141 | atgctaccgtagacagttcctacccggattttcatacaaaccacctctcttcaggatacactattcaatacagtcatcacactcattctt tcttattttataatagcaatcataaagatgttaagaagataaaatagaccctatctccataatctctctcatactgttggccttatataaca gatctcatacgtcattgttgacatgggtctcatcacacagaaaaaacagtctttcttaataccccgccttcaatcatagagtcatactctcatacc attgcatcactgctattcagtctattcctagactaacatatcagtatctggtaatcacatatgtgctaatacaggtgctcaacaacatttgttgctgcagttcttcat acattatccattttcaaggacagcagcatgttttagcaaaatctctatatccaactattttgataatcattacaagtttctattgaaaattatagtcatcgttgc aactacagcgaacagcatatatgatcaatatttcgatgacgaaccatataaagtctattaaattaaccgtatttgtattaggattgcaccaggttga gaaactttttgactatgcaatagggtgtatag |
| Contig40_gene_953 | 1142 | ttgagcaacaatcaaatttctggttgttcctatgccttatctgatgaagcgataatgctcattcattgaaacaagatttcaataatga ttatggcatcttagccaaatatcttcaaatattcaaatattccttttcaaaaaatttgtattcaataactgattgcattcaataactgagactcttccaaataca atcagttcctatccaataacatccacgataactcaaggattgactcctcattcataaaaacatccgatctgtttataacaatacattaataaatgttcagtcattgaatga acctattaggcatttaagtataggctttcattcataacgaacatatgtgtactgcggcctcggcccttttataacatcttcgaaagcctcggattaagcctcatcacagagg acatagccaaaattgcaggaacaaatacaaagaaccagccttacgactatacaaggcctgcatcaaaaaggattcaatccctcagtatta aagtaaaatagctcagaccaatgacaaatgacttagctgtcgtgttctaagtaggaaaactatagttgggactgttttcccagcactgctttcctgtgatatgttatgagatgttgaac caattaaaagatagggtatcctaatgtaagcatagcaaattgaaaactatagttgggactgtttttccgatatgttcctatgaggttatttggct ttagcagggtaactgtaatttgccggctcctagcaatagtttgaatccaaactcacattcaaattccaaaagcattcaaaacccaccattatac atgaagcctaataataaattcatttccacgaaatgtcaaatatcctacaagcactgaaataacggaaata |
| Contig40_gene_957 | 1143 | atggttaaatgttcaaaatgtgggagtgaaaataagtctgaagcaaagtttgtcatagttgcggtgctaaattagataaggaccatataa tcttgatgcaaatcaagagagtatgttctacaacagcaaggctgctctgcctattatgaccatagcgctaattctggtgtt ccagttcagattccaccgaggaattgataatttagaatatgagaatatgagaatatatattttaaaaagatcattttgcttgctgtcttttatagtttta |

FIG. 9B-33

| | | |
|---|---|---|
| | | ttcatttttgtccttagctgctcaagcacttgatttgatatggaaccttatagcgaaataaaaccgcttatcataattattcaagtttggattt<br>agatgatgatgggcattatgcttggaagagcttgagtagagatagaaatattctaattctcaagtcaaagatgagtgatatcttaaaaaatccgata<br>agaatcgtaatcatctgataagagagcgctgagtatgatatgctgaactattatgtgaatgagcatttgaatgacatttaagactggagaaaaacgaa<br>aaaacaagtagttccagttctcagttctagtctaagctcagtctcagttccagttcatacaagtctccattaccaaccaagcggttcctcgatgatggagc<br>tgaaacatgtccgttctgcggtagtgaagcgtgtttatgaatctggaactcgtataaatgtgcgaatgtggtagaactattcaaatccagatg<br>atttagatttaaattatgatgagggctattattag |
| Contig40_<br>gene_958 | 1144 | atgaaaaaatgtagtaaatgtggttcagaaaatccagataatgctaaattttgtcataattgcggctcaagagatttgaacaaatgaaaatat<br>ttgtcctaaatgtggcaatccaatgaacggtcctttggtcgtgctggagcctggttctgttctgtatgaatggtcctttgtgctgtgtgct<br>aatgataagcctggttctgttctaactctaattctagttctgtgctggagccaatggtgtagctatagtctgtgattctttgctctagttctaatgataa<br>atctagttctagttctaactctaattctagtctaactcaattccagttctcaactatagtctgtctaactctaattctagtctaactcta<br>attctagttctaactctaattcaacatctctagttctcaatatatcaggttctcatgcttctctctgctaatcaatctaattcaaca<br>gcctctaccaaaaatcaatctaattcttttataatttgtcaatttattgaaggaaatgaaggcctgattaaagaaaatatgctgttgcta<br>tgttcctgttattcttttagttcttttataatttgtcacttcagaggctagtcgttaaacctgaatgtctgattcaagcattagttcatattc<br>accaattgacattgatgggatggaagattgtcacttcagaggctagtcagttgacttttatagtgatgtgaacctattcctcatcatcaagtag<br>aatgaagctgataagaacaacaatgttatctattccagttctcaagctcatctcaagctctcta |
| Contig40_<br>gene_960 | 1145 | gtggttataccagccttcaatgaagaagcgactgctagctcaagtgtaactgtagctcgcaagctatcatataagcgaagtcatagtgtgga<br>tgatgatcaactgcataaaactgtagagagaaggcaggagaactgtcataagccaggagccatataagcaccaaagtaaggggtagctatca<br>aaacaggattaaaaattccatggtcaattgctgataatagttgcctttatagatgcagatgtatccaattcactccaaaagatagcaagataatcaag<br>cctattttgaaggtaagacagacattaacagaccaaattgcacgggaaaagtggccgttgttacagagcttactgcaaaacctctttaagttt<br>ctcttccctgaattgtttgcatagtattgaacagcctttaagcgtcaattgcaggtcattgcacttaataataaatcaaatttgaaaaggactatg<br>gtgtggattgtgcataagtatgatgctgatgttcatgaataagaagcattttgaagttgatattggaagctgatattgcagaagacattcaacatgcaacatgctcttccctt<br>gccgattaacaacaaaatgcaaacgaagttgagaaccatcattcttgaactgctgctgcgtgcactgattatgccgtgtcactagtggatacccttgaaa<br>ttatatcagaatggccatcatggaattgcactgactatagccatatcctatgctataaaaatagttcaaagtcaattccatttaagaaggggatacaagtacg<br>tagtggctcttgttgaattgcactgactatagccatatcctgactatagtctctgatgtcttccactattttaagaaggggatacaagtacg<br>gcattaaagtcatttgtaagatgcacttcccctcctgtaatgctatcaggcctatatgttcaatgtctttccaccattcttatcagcagcaacatt<br>taatgatgcaggatatcagtgaagctactccagaaacttgtatattccccttcagatgactatcatcaaa |
| Contig40_<br>gene_962 | 1146 | ttgattgcacttgtcctttgctcctactgttttatcattgttcacttcttctgtaacgctgcattgttatttgtaggtatctttaatgattgt<br>gcaattgaaagaagttgattggaacaatatggttgtagctgcatcatgatgtcttaacctactcaatttccttag<br>gtatcgcatgggaattcgtcacctacgcgttgcagctcagctatccgctactgcaaagctaaagtcaagttcagtgtatgaaaccaacatt<br>ttgcagcatacgtgttcttcggactttag |
| Contig40_<br>gene_963 | 1147 | atgttaaataattttcaaattggatgaaaacatactgatataaaactgagttcttgcagtttgacaaccttttcttagcaatggcttatat<br>tttaggtgtaaaccaaccatgcttgctgaagtggaatgcctgcaacagagtatttcgcaactgctcttgctcaggggtatcttgtatca<br>tcatgggtcttgtttcaaatatcctgttcttccctgttatgtatgatgcattgttttacctatacaatacattggctatggtaac<br>acttgggaaactgcacttgcagctgatctcgtttcaagcataatcttttattaattaccattccggtttaaggagcaattcttaacgctct |

FIG. 9B-34

| | | |
|---|---|---|
| | | tccattgacttaaattagcgattggtgctggattggtttctctggctttcattgtttgaaggtgctgaattatcgtagcaccctg<br>ctactctcgtagtatgggaactatcttgtgctcctgcgtcttagctgtaatcgcatatgctacttgatgctatatacattaaaagtc<br>cctgcagctgtattcctgattgtaactcgcaatttagtgtaatctttacattgttcgttcggtgctggagatccattaatgcctgc<br>cattcctacagagttcattccttaattcgtacacttctgtagttggagcatttttaaaggatttcacaattgttcactaacatcctaacc<br>ttatcatgatttattctcattattattgtcattcctggtgttacttctttgatactactgaacctgatctcttagcaatcaatgttgttcgtgatgaa<br>gaagtaaggctgatgaattgacaaagcttcctggtgatgctataaagcggaatcattgtgctatcttaggtacttcaacctaactgcata<br>tgtagaaagtgcaacgtattggtctggtggtgaacaggtttaa |
| Contig40_<br>gene_966 | 1148 | atgaaagagtcagattacaataccattgattattgaagttttcgctattttcaatcatcatagcattgcatgtgtttctagtatgcccaaagc<br>aaaagtcatggcataaaagtatattcttttaaaaaaagaatataatcagtattgtaagttcggagttcctgtttttatatgataagcggagctcttcttttaaata<br>gggatattgaaatcggttctttttaaaaaaagaataaatagaaataaatagcattataacattataacattcatattcatagca<br>ttgactaaccataccagtgaacagcaaaacatatttgcttcagatgtattctgacaatctagtgttattaagcatacataatataaa<br>taaatattcaacattcatcattgaaagaaatcgatattcattcacatattatctttgcatcaataattatcatcaattatcaatcatcaattattactctttg<br>aaataaaaacaatattttactttgacttgtcatttccatatcctattcatattgtctacatccattagatatttgttttagtttatttacttatctataaaagactttaatctcagt<br>acaagcaagatgattgtcatttccatatcctattcatattgtctacatccattagatatttgttttagtttattactttctataaaagactttaatctcagt<br>tttgttgcagccaatcagtcatcatcctatcttcatgctagatgcagcttcatgaatcttcatagaatcctcatttagaaatcttcaaaattgttcttcagtaagcaggca<br>gcatatgaagctcaaaagtatattaattaatcatcatcttcttgctcagtcagtgattatcatttgtaatatatgtaaatacatata<br>aattccttgattcatcaataatcatcttcttgctcagtcagtgattatcatttgtaatatatgtaaatatcatata |
| Contig40_<br>gene_971 | 1149 | atgatattaggcacttattattaatcatgcctattttcaatagatgattaaggattgttcaatttaggaagttgaatatttcttggctatttggct<br>aattactgcatttttgacaatacttttattgatcgatccgtacctgacctactttacagaccaataggcatggtggtattaggatatt<br>atttaaggcatacggatagaaaaaatattcaatagcctccatatgcattagctttcttattgatggaatgattgttataatgctatgttcatat<br>ttcctatctagtccagagggaatgtatgtctttagatatttcattctttagcgattgaagtagttgaattttcaccctttataaggtcat<br>tgataaaaaagagcttaaaatctccataagaaaatggtttttaaaacatgctccattaaagtaacctgcttttagtcttgttcacatttagga<br>gccataatttattatgataatctttattaaatagagttccatattaaatagagttccatcttaggattatcggtgctaaatag<br>acatcttggctctattgctctattaaatagagttccatattaaatagagttccatcttaggattatcggtgctaaatag |
| Contig40_<br>gene_983 | 1150 | atggataatcaaatcaatgaattcaagaattgctttttattatcaatgattggagctgctgtggattagcaatatctggcgttatagcta<br>tgttgttactcaacggtggagaactctttttcaattctattaccttattagttgcaattctaatcatggaattccattcttgtattggaatatgaa<br>ttgattccgccataaagactcttttccaatatcttaaagagcatcaatcctaaattgaatacattcatggcattgttttaattactat<br>ttgttctaatctatatctggtatagtaagctcaaacctcctccaatatggctcaagcatatttcagctggggagctgattctgtcttta<br>tttcgtcagaatgtcggagggagctcaaacaagatttaaatgagagaataggacatggaaggcattgctgaaggctcaaagatttcaatatgccttcataatt<br>tctgtacatctccacaagattaaatgagagaataggacatggaaggcattgctgaaggcgcattgctgaatcctgatgcaaatgctattgcctgaagatctaaattgaccgaca<br>gtatttgcattgacccttccaggtgcaggtcaggtcattaagcatggaagagcatcaaccttgaagtcaagctgaagatcttgcctgaagatctaaattgaccgaca<br>atgtattgatgtgtttgcaaattgcgcattgaagtctgaagcacagactgtatttgttgttcccaatgatttcaatattatggtctatattatggtctataggtcatataat<br>acaccgattgtagaattgtaagcgaaggcacaggactgtatttgttgttcccaatgatttcaatattatggtctatattatggtctataggtcatataat<br>cgctccattgctatttatagacaatattgttcgctgaattgttcattattcgctgaattacttcagctgttcagtatttgaaccgatgataa |

FIG. 9B-35

| | | |
|---|---|---|
| Contig40_gene_988 | 1151 | atgacaattaaaaatatttcaaaacaagaaacaagaaagagattatgatagtgattactcaaataaggctcca<br>taaagaatcaagaatttaaaaactgcttaatgacaataaaggaaactattcaatcgtcattagtgcaattctactaatatcctttgattctct<br>ctattattgtgctgaacacagtttagaggaaggaagaacatacagacttcaaaccaataccaatacatcatagaagattataag<br>cgaaattacctaatatagtgagcgtgaggcattgggaagagctgagcttgcattgtcattgagaataaaagacccctgcttaactctcgtgatgactt<br>aaaggagataatagatgaaaactggctcaaaagaatcaggaatattatcaaaactatatattgaaataaactcctcaatcataggattgaaa<br>acactagcgatccattttcctataagttaaaacacatatattcaagtgtaaaggagacttttcctatggagatagatctttaggtgactctgattt<br>tgctataatctaaagatccagtacctgttctcttttgcgtgatgattcaagcttagaatagaaggacatagtcttttggtgactctgattt<br>tggaactcatgactccaatttctatgagaacatgaatcctcaatgaacgcaatgtatttatgccattctacgaccctatgcaggctagaagcatcatgagatgacaat<br>atgttgaaaactattcattctatgagagacaatttataaatctcaaagaccaatgaaaccgagacgagaccgagtgtcagtgcctgcgct<br>ggaagaatcatgaaaaactgcagagacaatttataaatctcaaagaccaatgaaaccgagacgagtgtcagtgcctgcgct<br>tgaccattatgcttgaaacatttataaatctcaaagaccaatgaaaccgagtgcagtgcctgcgct |
| Contig40_gene_989 | 1152 | gtgattgaaatgataaactagttaatgagctaaaaatagaccaaaaaggcttaatgtactcctcagaattgattctgtcctcatattgattat<br>attcatcataggaatcatgccaatataacagacacgtcaatgaattgggaggaagtccttagccaagagagctttcctccctagaggccataagcatag<br>aaagtgtagattatctcattgaacaatctctgaagtcaatgaattgttttttatgaaaatgaagagcagtagtgaattgtatcaagacgaatcata<br>ccagacttgccataatataaaaatctgtgaactaactcgtgaaaatgcttttcttatgaagaaaacagtagtgattgatgaagataataacctaactccatatcata<br>tatcaagctcttaagcttcaatctaatgatgacttgatcaatgaatcatctagtgatgttgtggctataaatagaacagttagatgtgactatcttagc<br>actctgatattgatataggttcaatgactttgagctttgtgctttttgcaaggtattttgcttgcagaacttagaatctaaaaaacgaactctgcaatcatgacagcaatgttaatctatc<br>aatttgtgatatataggttcaatgactttgagctttgcctttgcaaggtatttttgcttgcaagaacttagaatctaaaaaacgaactctgcaatcatgacagcaatgttaatctatc<br>taatcataagcaatgatcgaagtattttttgcttattatatagctcaatgtaaatagactatgaagaaatctatagaacaaggtatattaaaagcctaaacagaacaaggatgatatgaaagattaaaatgatgaggtgattgaa<br>attcgtcaataagcatgcaaatagtttattatatatagctcaatgtaaatagactactgaagaatctatagaacaaggatgatatgaagattaattattacttagttcg<br>ttaaatccgtttcttttgctgaagatatggtaaatatgatgaactactgaagaatctatagaacaaggatgatatgaagatgagttgattgaa<br>aacggttatggtagctatccataagaatatgactgatgagattgtatccaataatcagttgagatatgattatt |
| Contig40_gene_991 | 1153 | atgctagtaaaagatgcttagagactttatctgtgaccataagaattcaattgtatccatcttccttatgcgttcgcttatggcgtatccgtttac<br>aggaataaaatggagaagtggttggaatcacagatgtgcaacacactatgaagacacaaatcttgcagtggtggatatatgcgagaact<br>ttgataagatactctaaaagtataaagaacatggaagaggtcaagaacatggaagaggtcaagaatgccatagagaggtcaagaatgtcagagaagtctagtattgatacgggtagcaactacttcttcg<br>gaccagacataacctccatatactggaagaaaagcaagagaaagcagaccagagctctagaatgtgaaagaacttaatcctaacgacaagga<br>aggaatatggattgacaagcgcttgcagatgcaagatgcaagatgaagcagacctagtactatctacacccgagaagtacctgactcagcaagtcgactgactcagcaagtggctagtcattcatg<br>ccatccgagaattatatactctccagatatgcttactacctaccatagaatacaatagacgcaagaagacaatgtagggtaagcacaatggagcaggttgacacattgcagagttagacaagtgcattcatg<br>ccaagtaagggagctgatttgacatagagtacaatagtctactacctaccatagaatacaatagacgcaagaagacaatgtagggtaagcacaatggagcaggttgacacattgcagcaagagttcttcacagaacacag<br>agagctttagcgaattttccaattttccccaattatctttgttcatagtgcccttttaaccttgttccaaggaagacatgccaattcgttccaaggaaccaatttgtttatgtgccctttaaccacaatgagcaggtgattcttccacttgcaggctctcttttt<br>tgtttcaggaatttccccaattttatctttgttcatagttgacaatactcattctccaagcatgtcagcaatgtattcacttcat<br>attgaacactgaaggctatgggtatctcttcaccctttcatatctctccaagcatgtcagcaatgtattcacttcat<br>agcccttataagttaatagtctctcaccctttcatatctctccaagcatgtcagcaatgtattcacttcat |
| Contig40_gene_993 | 1154 | atgaagatgatacgtcaattcggggaatcctccatgctcttgtcgtcaatctaatctgttttttattttaatgaattaaatacatatttaccct<br>tcctaatcgtatttatgtctatataaagctatttttgagatactgcagtattaaaggaaagcctgattgctctttctatctgtctgtag<br>gggatttatgtgcaggtatcatttaggaaatatgaaattctcctaaagaccatctccctatggtatatcattccaggtactgcaattaggaatg |

FIG. 9B-36

| | | |
|---|---|---|
| | | agggaaacatctcttttggctcttttggctcaaggctagcacaccttcacattggtactttgtctcctgaatttaaagatcagagactag<br>cgaaaacattacagcatccctattttgactaggtacta=ccatattgcttgctgtaatcgctaaaggagtctgcatagccttggatttaaaa<br>gcataagcatttatgacttgttcttattcatttgcaggcttattcaactatcattatgctgcctattacaatgtttatctcacttaag<br>agctttgaaggaggctgggaccagacaatatacaactccattcattgcagctgtttgagactttcaccctccagcaatcatattaagcgt<br>aatcatagtgggattcattccatatctagtcaagtagtatgattgtctttgtagcggtaatatttgttacaatagcagcatttgattgcaggat<br>acacagcaaaaagcgatgtaaggcatatgtaaggcatcactcctgtacttcattgctcactcctggaacattgcaggtggaatattg<br>aatgattctcttacaacctttgcttaagaatcagacttactcactcttgttccactcttcaggtgaaagcggaggatggtaagcatattagg<br>agcaaggctatcatctggccttcactcaggtcttattgaccagtgctcagacctaagaagcatacagtagaga |
| Contig40_<br>gene_100<br>3 | 1155 | atgttacttacaatcttgctatttcacttgcagtagatcttcttctaggtgagttccaatgcagatacatcctgtagtatgattgaaaaat<br>aataagcttttttaagaatatctcaatcaaatacgacaataagatagccttgattctctcaattgttctccaattgttcatcacttattg<br>ttctaattccaatgctatagcaaggtatctcttgccatataatgatatgatgatttctattcaagctgatagcgatttgttcttcttacttca<br>acatttcagtcaagctgttgttgattctgccgtgattgtgaaaaggactaaggaacaataacttaaataaggcacgtcaggccgttagcta<br>tctgttagcctgacactattcaattgttgaataatgttgttgaatagagactttgatgtcataatactgctgttcttgctgcattt<br>caactgtattctatctattcaattgttgatacaatgattccatggagtaggatacaagactaagaaactctacaatacggttttattcagcgcattgatgatgc<br>atccataggggtttgttgatacaatgattccatggagtaggatacaagactaagaaactctacaatacggttttattcagcgcattgatgatgc<br>tttaaattacataccgcaaggttttctgcagtcctaattgacagtcctaattcaggatatacgatgcaacagtagctgagcattaaacattcagctagaagaaggagtt<br>gaaggatgcaaacaattgtgacagtcctaattcaggatatacgatgcaacagtagctgagcattaaacattcagctagaagaaggagtt<br>tatccttagggatataataatccaataaaatgttgattcattgcaagaacgatgaatcagcaagcaagcagcaacatattttagttacaatatt<br>cttcatgtttgtatttatgatttaatcttcttttaatgctttaa |
| Contig40_<br>gene_100<br>7 | 1156 | atgcttaaaagaaagatgctaagagatatattgaattataaagttcaattataatccattttatatccatcatcataggcattcatagggcgtatttgtattgc<br>cgactgactgactttctaaagcagcagatggttctgaagcctccaatgcatcattttaccagagagcaattagctgacgatgactaactatc<br>ttgttgatgacttcttcaaagcagtctacttgcttgcctggcgcaacacctatctaaatattatcctcttgaagcaatgaattaataagcgattctgaagg<br>aagccgatattacgctgcatatttgttgaaaacaacaccatatctaaatattatcctcttgaagcaatgaattaataagcgattctgaagg<br>tgtatggttagataaaactttcgctgatgctcgagagaatgttatagtgctgaaatctgaagatgggacaccattgcatttgaaagcaatgaattaaaatagaaagaga<br>ttagggatttaggctattctctccagagacaataactaactttaggtctgaaatctctgtagcttgatgacgccctgaaatctttccaggctattgtcctatcg<br>tataaagcattccatcagacaataactaactatttttaagtttcttaagttcatagtcgttcatatatagctaagcgccctgaaatctctcaggctattgtcctatcg<br>tttagagtaattatgaattgtatctgccccaatcaatcaatatagcgtaaatgcgtttcagatcaatcgccatcaaagaactcattaaacg<br>ctgttttcccaattctttttcactttgattcaatgctgatgcttcagtgactatgaagaatcatctctaatcaaagaactcattaaacg<br>cttaagctaatgagatttagcaataggtcaatagtcatccatttcatgatccaattttatttataagttccctgtttggctt |
| Contig40_<br>gene_101<br>2 | 1157 | atgaatcaaatgcccagtgaattcaattataacattatattgcaatgattggccttaccataggcataggcatagggaatatttggcgttcagcta<br>tgtattactctaatggagggagatccttctccatcccttatttttattgcaataatgttatgggaattcctttcttgatttagagtatggat<br>taggcttagcctaagacaagagagtttccaaagctgatgcatgatataccccgaattgagtaattgcttgatgttgtcatattcgtattc<br>acgttgtaattattacatatatggctgaatttacatagggattttgtatattcctaaacagcttagcttcggttgggaagcgatccaattcatt<br>cttcatgacttatgtggtggaactaggggagatatcccagttggaagcttctttcttctctactattggtaaggcttctactattgattattt<br>tttggttgtatccaatcgtgatgtggataggtgaaggaatcggaagaatttcaaccattctaatgccttgctattatataatgatttatctttt |

FIG. 9B-37

| | | |
|---|---|---|
| | | ttatactcattcacattgccaggatttgacattggaataaagacattgcttaagcctaattgtctctcttttagacattcacatctggcttgc<br>agcattcggacagacaatattcaccttaagcataggccaggcaatggtctataccttatgcaagctatttgctaggaattcctaagtcgatg<br>aagtattgcttgttattacaaacacctatatgaggttttcattgggtctttcaatacttgatatatgtcctaaagtcatca<br>atacctatagaaaaactaatcagtgaggaactgactgatatttgttatttccaaagatattgtgagatggttttgtaggtcagattat<br>agtccattgctattttatcaataactattgcaggatttactttccgcattggcattgttgagccttcctat |
| Contig40_<br>gene_102<br>2 | 1158 | atgaataaaaaattgattgaatatttgattatagcaacagttattattttaatcctttatggtgctattctcttattgattatcaatccaacgg<br>atatcagtttcgtatggtgaatgctactcatgtcatgaataatatctttgtccttcaagttctgcctattcagtcagtggagacacagtagaattta<br>gaaatggattaaacagtttctataatatggacgttagcaagctaaactcttcagatggtaaagttaaaaatatattgaatcaatattctaagttc<br>cataagtccgtacttttagatttcaatttgataaggatagtttatcctcttaataaggaagacgtttatctatttgatgaacaataggaatttgttgtag<br>tatctctgtcgattcatttgataagtagttggaagtcaggtggtaatatga<br>atactgtatatgaagtcaggtggtaatatga |
| Contig40_<br>gene_102<br>3 | 1159 | atgagtccatatgaactgataaagatgatgatgtgaagtggtaatctgtgtggttctcctgatgagagtcaagatttgatgtttcttagaaag<br>gctaaatgataaatcttttgaaaagaacgtctttagtattttcaaatattcacagaagcatgacgtattcatcagctattcaactcaaaaaactcagatatagcaaatgaga<br>tatgctaccttcttgaaaagaacgtcttgaatgctgattctttagtatttcaaatattcacagaatccaaaatattgaagtcattcagtctataa<br>atcaaatcaactaaaaatagtcgttttagtatttcaatacagagccttaaaattatgcaaatgacttcatttataaggtgctcaatgcatatattattaaaggctgcttaggcgctaatcaagcttagacggcttcatt<br>taagcctattattcatttcatttaatatgatcagtatggttactgacagttgtacacagcattatcacaaccataactcacaagtcagtgtactacaaactgaaaattcaagtcagatcaacagtaatcgacagttgcatatgctgatattatacaaagatctctgatattgtctttttattgttcttatgatatataaatgtaa<br>ccagaagacatatccaagcaacagaaaatcatgacattgttaggatttttataatgcgattccaacagtaatcgacagttgcatatcaatctttatgcaatttcatgtatcttttatgtatgtattataaatgtaa<br>ttaaccagatattctgttttaggactgatgtctttgataaggatctctttatgtatgtattataaatgtaa |
| Contig40_<br>gene_102<br>4 | 1160 | atgagtcatgatgtttttatatgtctatgatgagaagataaagattgtgcagagccattgtgccgtatctttgaagagaataatattaagacttg<br>gattcgctcaagagacgtatcttcaaagatgcagcccgaatctaacagaggctaacagaaatttccaaatgtttgtattgtctattcaaaga<br>atggaaagaacaccaattatattattaaatgaaacagacagcattttccaaaagaaattccaattacttttaagcttgatgagacaagcatt<br>ccaaaggatttggaatttatttattaaagaccaacagatgatattaagcttgattctaattcagtcaagacaattgaaagtctaaatcctcagaacaattgaaagtctaatcctcaaagaagaaaaacaata<br>agatattagatagaccaacagatgatattaagcttgattctaattcagtcaagacaattgaaagtctaatcctcaaagaagaaaaacaata<br>taaagaaagctattggagcagcggcttaatagcagcagtttaatagcagtttaattttaattttattgtaatagtgctacaggccagaacatcaccgat<br>acggtgtattctccatgatgtcaaccatgttgaagtgatgaatggccaaaggcaataagtatacgataatgccgaatcataatttgcc<br>aagtgattcgatagatactttatgaaccttcaattcttgatgataagaataagtgttgtttaaattaacctaacgccgatgagttaaat<br>caggcattatatgagtggtgatataaaaggtgatataagcatattggttaattaactgatataagcatgatataatactctcccaagag<br>gattataatcttggattgtag |
| Contig40_<br>gene_105<br>0 | 1161 | atgggtttgttaagcctcaccattcctatttaacaatccgcaaatggagaatcattatggcgcatttttagaatgttttagaatgctttc<br>tgtagtcttgattctaacatacaatagccaccaaatccaaagttaaagttataatcagaggccaacagtccgtaaaaccatatctggcaga<br>ttatcatatttccattctaggaatttcttgcactatattgcaatgtaatcccgcaaatgcaagaggattgattgtaatgata<br>tccgcattgcttggagaccatatgttggaataccctgtaggaataatagccgagtctgagatatggcatgggaggcattactgccttgcatg<br>tggccgttcaacaataatgctgaattgtaggagtctgtttataggatgtggtgaacgatggcgaattcctaaggccatataaggctgcactttaa |

FIG. 9B-38

| | | |
|---|---|---|
| Contig40_gene_105_2 | 1162 | tgcttctctatatagcggcttgacatgtttctaataaccatattaaccctcaaccaaaggagttcttattgctaatgcccttatgtctccaatg<br>acatttggcgctgttcttggaatcttcactcttcacctattttttaactgagaaaaaagaggaagcgatgaacaaactgtttctga<br>caataggaatacagacacacagaatataatgaatctcacaagaattgaatgaataaagataagttaaaagttagaacagaactagagg<br>aatacgacaaaaaattaatcaattgaacagaaattaaaggacaaataa |
| Contig40_gene_105_2 | 1162 | atgaatgaaccattaaggagcactcttggatccttaatccttgtttgttttgctaccttatcatgtttggatacaacattcatgaacgt<br>cagcattcctcagttgttgctgactgaacactgtagtgtagtaccatcaaacaatctcatcattctatctcatcactgcctcattcatgc<br>tcttaagtaccaagctcaggatatagttggtaaaaagaagctcttttaatcggtgctggaattatggcgtcgtacctgactgcagcatta<br>agtgccaatactctaatgttattatagaatggcattgctgaaggtataggcgttgcattgatgacacctgcagttccatcataagcgg<br>aacctatcaggtgaaaagtctacattcgccttgcaattgaaagcgcactgttgcaattgcagcagctatcggccgctctcggtgggtcg<br>ttacaacatactttcacttggagattaggatttgcagtggaattatatctcattgtagtctttgttcctctttgttatggtatttgatgctaactga<br>gctacaggatccaaaagcgaattgacattacagtgctcagattatcgtctagagacagaatctccgtgtagttctctctcctaggctgttgacctgaaatcaaaagaaaaggcaacg<br>taccgttgcttgatgtgttgaattattaaaagacgtattgccctatctcgattgcattcaacacagtttgacctgacctaggctttgcttctctt<br>tgcattgacagcccaaagctatctgcaaaactgaacacacaagatctcatgtcaatagatgtaatatcaa |
| Contig40_gene_105_3 | 1163 | ttgaaggaagtacggcctctaatgaagagattcgctccgcctttagatgatgaggcaaaatcacaggacaaacatgcgcgttctgtatgtgc<br>tatgtgattgcatctgtaggcttaacatgacctcaactgcagtcagtagctcagtaatcatcggtaatcatcctgatggaagcattctgcct<br>ctgcctatgcaagtggtgaccaatgaccgctccctctatgttttgaaagcatttaacgggattgcaatgcagatttgcagattattatatgatgtcagcagcc<br>atctcttttctcctcttccagttagagacagcaacagagagcttattgctagaacatctccattttatgatgtgttaatcgcattcttcgg<br>aggacttgcaggaatcataggacacagcagagtcagataggtaagcacatgctattgcaacagccctatgcctcctctat<br>gtacctgcgttatttaagtgcattgaagattgaagattccaaaattgaaggagtatacagaaaaagaatgaaaatccataagtgagaatgagttacgaat<br>tcaagccttatttttaagtcattgaagattccaaaattgaaggagtatacagaaaaagaatgaaaatccataagtgagaatgagttacgaat<br>actattttaa |
| Contig40_gene_105_6 | 1164 | atgagagacattgaagaacttaaaagaacaccaggactgtcacttagtgagaatatctattctttttattgcaaatcttatcgattgtatctaat<br>cagctttgattggatttcaccgtcaccaatctagcgcagtcatataatttcatattttcatagcatcttcaatgcagcaatatgcctctgg<br>taacaagatatacatgccccttatgttgaccttgaatcggagcactcttcctttaaacgaggggtcttgcctcttcggccatacttt<br>gcttagacatatcaggatgggaatagtcttgcccatcaacttgcctataatcgcctctatcaacccctatgcagcgaggatga<br>tggcacatatccaggctgtctcttgaagctgtagaagcccaacttaaaagaaaagagagattaaggattatcctggctaatcattgttgaaatcgatg<br>ggcttgcatgacgtgctcttggaagctgtgagaaggagtcatgcaactgtcaagtcaacaatgaaaacatccgccttcagatgattgaaa<br>ggaaaacaacaatcagatgatgcagttcagtgctctgagttacaaggtacaaggtctgaagaagaatatcagacgcttgcttgttgaa<br>atgggcaagcagatcaaacctcttcaggggatacagcaatgtcatatttacttcagcaaaataacagacctaggaagctttacaatgc<br>gctggttttcaatctttcaaatccaaggcgaatctcacgcgatatcgcacgtatagtaattttagtcatagaagacatgtccatgagtctattccaacttaa<br>gcaacagcatactaaatatccgtccaagaatccaaggcatcgcatatattccaacaaggccgaacaatg |
| Contig40_gene_107 | 1165 | Atgttagcccagattaggattaatatatgttttaggattactattcggccatatggtgcttaggtgtcgcattggcaatcgtgacattaaa<br>tttaataacgattcacactcatgtgaacactgtccctttgaatattcacctttggagtctcatatttaggatacggggttggagtctattcgaacgatctattccaacttaa |

FIG. 9B-39

| | | |
|---|---|---|
| 7 | | ttaaaaccgatacaattacaaagccaaactagataacagctaccacatctccctattttagtaagcatcatcatctgtgatttatctattca<br>acagtccaaggaatctcttttaacctatattctggttgatagattttatataatgatcctcttttattcatgagctttacacaatggcatt<br>tctctatggaataataaggcatttgatctgcaacagatatgattgttcgaaacaccaaaaaatcaaaagacatgttgacaagaaatatc<br>agcaatattctgcatgataatcatcacatcaatcctagcacatcattataactactgatgatacaacgtgcgaatcatagagttgata<br>gttttgggaatcttcctattctgcctatctgacaaagcattcggagtttggaatagcaattcccatgatgatataacaccgatcagcgaaggataatgcg<br>gaatttcattataatcacattatcctggagttgaatacgtattgctcctgttcctcattcctgcatttctatctttaagatatattgaagacaaagta<br>tagtattaatgtgggacctataataaccgatacgtattgctcctgttcctcattcctgcatttctatctttaagatatattgaagacaaagta<br>gttcagcctatctcatcatttccaaatcgaaggattcattaaggaaaatgagaagattgatgaagacggattggtaaagacctattccaagta<br>taccgatgagaagacagagattggaacacttgcccgctcatatacgaactgataaagcacataacaactata |
| Contig40_<br>gene_108<br>0 | 1166 | atgcaggtaacatatgcctattgttgatgtttgattgtaagttttttaattggagccagtaatcctgctccctattcagattgtagctccagt<br>aatcacatttgtcaatcttattattgatgatcggattgggaggaagcgtcctatgttctgttcgaaggcagaatttgatgatgaaaaagca<br>atagctacttttcagtatcaatcatatccctcatatccatcgggtattgattacgttgattacgttagagactctgtttttcaggaagcattgccagttc<br>ctatgctcttcacagcctgaattggttctccacagtgtccaatattcattgttgttcgttattgcattctatatgttatatgatgagctt<br>atcttattcataaggcggatgtatccccaactccattcagggctatactatactcttgtaggttccatttcaatttgcttttgacattattaca<br>ttaagttttcaatttgggcctaacagggggcgtcctgctaaacagctttcttttaattcattcattaaaagatagtactttcaggatttcttctgtcaac<br>aaggaacgtactttggaatttataaaattgctgtcataaactttttagttgcctttagtgtcatcaacacttttgtctcttttagtgtcttcttttattcataatctcaggatttcttctgtcaac<br>tcaactctatctgactttataaaagagagttgctgtcataaacttttagttgccttgcctcaatgtctccaatgtctctgtttttatttcatatttcctcaggcctgcttttaagtaag<br>agcagtcgttcatcatactataaaagagaccgcagatgttcctgtgtattgattgcatttgagaattttgcatttaagttatg |
| Contig40_<br>gene_108<br>3 | 1167 | atgtttaacaactataaagacaaactgaccggagatgataggaagatcctaatattgtttgtaatattagccatcttaacatagcctataacatcaa<br>catattcaagtatatggttgacatcaagacataaacatgccgtcaacaacatgccgcatcacaacgactttgtcaatcaactgtcaatcaactgtcaatcctagatttac<br>cttcaaccaggctcccaatcttaaaaagcgtgacagtcaattgacagttcaattcattatgaaataagctatcttatcatcatagccattcatcatagccatattcctcttcatatagccatattcctgatttaacattcctagc<br>ttctttaacaagtccatcaatggggaatcattatggctccatttggaatgttcaggatcctctctatctgctgcattaagcataaccattttca<br>cactaacaaagagttaaggcgtagtaaggagagagcccttccagcaatgcaagagcatgtcatgcagcattgttaataggcatgttccagcgatcatcatgttccagggatgcttgcaggccatatatt<br>ggaataccgtaggaatcatctctgagtctgagtctgagatgggaatgggaatgggaatctaatccacagatgagaaacaattcatcatccccagtcaaagcaggctttaatgttttttacgcgcttgagatgt<br>tctgctaccatatgacccgcaagacaaactgactcatcgctcgttgcaacctgaacctttatgggccgatgacatttcagcagtcctggaacccta<br>cttcagtctattgtaaattcatcctacataaatcagcttcagcttcatagcaggtggaacttgaatagcttaattaatcttttccagaga<br>attgaagaataaaataaaagcaaccaaccaaccgaaggagaacaaagtataaagttgaaagc |
| Contig40_<br>gene_109<br>5 | 1168 | atggaaactaaaaacctaatcatatgtacattaattattcttgtatgcctatgcctatttctcatatccatgaacgtcaggaaga<br>aaccatataacacatctaacaggccaatacctagagaggacacattaaaactatgcgataaggatggaaagataagcgatc<br>aaagattagcttaaagatccaatcaaaggatgaacttaatgacgatatagtcatttaaaaacagatgagatggtgaagcaatcaaac<br>ctgcaagggaaattatactctcatatcgatgaacaagccatatgggtatacctatagaattcattgtaagcctaa<br>ggaagtgagcaagctctaaaaccactagccacactacaactgccacatccaataatgagattagtgagtgactaagcagatgatgtta |

FIG. 9B-40

| | | |
|---|---|---|
| Contig40_gene_110_7 | 1169 | tagatggttggatccttcagaacatgaggtttctagagagtatttaggagagggtgagtatagagtcaattatgatgatgatattctagagtg<br>attgacagtgatgaaatgttttaagctatgatattag |
| Contig40_gene_110_9 | 1170 | gtgctttataggggctataaaaaaggaatggagtttgaaagttccagtatgcatttattgtttgcttaagtgccctgttattgctgcttta<br>tagcctatttaattaa |
| Contig40_gene_110_9 | 1170 | atgttaaaaaattaaagattattatagttggtgataggatggacaataaactattttacaggcattagcaatttttcattggcctaattat<br>aatatgcgcacttcttttatccgtgaactctgaactctgaactcctgaactcctgctattttatagcattactcttcatcccaatgttttttgctg<br>gaatcatcatgttttatcaaaagtccagagcttccagggctaaacttagattcggatggtttagctcaatagctgattataatcattgcttcagt<br>gcaatcatcctcttctcttgctttttatttctgcatatatcatgtatgcagaggttctagggagatgatatacctctcgaacagtagaagtgatgaggtcaaaatgtgg<br>catatttctccttgcatatatcatgtatgcagaggttctatgtgcatcatcatcaatcatcttctatcaatgccattgtatgatgatagcatattt<br>ttgacacagactctatgctgattttatccaataatcataatcttagaataaaaaacgaagaaagctttagaagagagcttttgatgtatgtgga<br>tcattatagctgctatgctgcgcatcacctgatattcataatcttagaataaaaacgaagaaagctttagaagagagcttgatgtatgtgga<br>tatgaaaaagggtaaaatatagattaataaccatattgtggtag |
| Contig40_gene_112_5 | 1171 | atgaaagtatcagtagtaacacctaactataatgtcttaaaatctttaaagcctattttgaaacctctagcttcaaagttagttcataggaagaga<br>gatcatcataatcgataatgcatcatctactgagtgcatctcagctcagctctgcatagtaagaataacatacacagtcctacgtataaagttgacataaaactta<br>taaaaatgataaaaatcttgatttgctcctgcagtcaatcaggcatttgctaaatccgaactcatcttatattctgtaacaatgatgta<br>gaactgaattaatactagaaaacttaatcatacatgaaagtaaagatccattcatgagattgaaggagtgaaactaggcatagtaggcgattgaca<br>acagtaccataagaagtaaataaggcctgcgatagaaatatccatacactaagaaactcatttgagaaaataggctcttttttgacgataat<br>ttcttgctattgtaagaaggagatatagatctttcattcagggctcaaataagttataagaaactacctagacccttaaatcatcatcattcatta<br>tgaagtgctacaagcggaaggcaaggtatagcaggctgcaaggctgcacagaaataaagttgatgatttataagagattttccaatttc<br>ctctaaagattgttaaattcatcttcatattcctgatttttcaaaaatacctcttcttttaaggaaggattcggttcaatctattggtcacagat<br>ggagtaaaaagggcttaagagaagaaggaatgaaaagaccacttgaatggaaacatgaaaattactttaagatagaatgagaaaagat<br>gattaagaacacatttggctactttaaaaaatag |
| Contig40_gene_112_6 | 1172 | atgagaaatataagacttatcaattattgttgttaattataacacctttaaattaacaaggacacactagatcctgttagctgaacctactca<br>ttatacatatgaaatattccttgtagacaacaaatcaacagtgacagcttcaaggaactctcaagaatactttaaaagtgaaacagaacgaggaa<br>tattaaaaatcattccaaaccaatccaacgatgttttgcaaaggcaaataatattgcaatagagcaagcaaggatttcatactctttta<br>aactcagacaccctatgaagcaatccactatcgacaagtgcatgattaacaacagacaaaggccacgatgatagatcattaggctgtaa<br>ggttccctcttgccgatggaagttcttgacaagtcttgacaagcctgcaagcgcagcttccaaacctcgcaagcttccaattgttcatatatatgtag<br>actagtgacaagacagattataatcttggatgatcttgatgatcttccatgtatcagagaacaggaggatgcatcctaaaaacaggdatatcgaggatggaa<br>gatagttactttcgccaggcagaataattcactataggagcaggagcaggaggataaaatataaaaaaatcaaaagatattatttattg<br>agttttatagggcaatgtatgtctttataaagcactatatacaaaaatataattcctgtaacattgcgtctatattggaattggagtt<br>ttgctagttttttaactagttagaaaatgcctcaggtctga |
| Contig40_gene_112_7 | 1173 | atgattaaagaaaatcagagaatattaaatgcaatactagtcatcatagacattattgtaattcttatctcactagcctttgcatactttgtaag<br>atccaagacaccacattctcagtaggagctccttccattcagttgactatttgcatattccacaatcgtttgcatattcctacttattctat |

FIG. 9B-41

| | | |
|---|---|---|
| 7 | | tatactacttcttttggtctttataagccattccgtaaccaatcatcaatattctctgtgctgagacattgtaaagtctgacataatgcattc<br>atcatcctggttgctattttgttcatcatcaactagcctaacttttcaaggatcatgctcttcttttaagcctatttgaatgattctcacaat<br>cgctgaaagggtattggtcgttcttgtattgagaatgatgagaacaaacaacctaacctgaagcatatgcttatcatcggaacaatgacttgg<br>cattcgagtttgcacataagatcaactctaaaactattgggatacaatattgccggatttttaggaagaagaaatataggcaaacgattt<br>gaaggaaccaagtttatagccaagtcgtgatgcagcttgatgactgcctcgtgttctaaagaccataagttgacaggtggtcatagccattccccttaagta<br>ttattaccatctaaacgaaatcgtggatgcatgtgagcatccatatccgctatgttccattggatgatgcctcaataagttcaagaagatagtctcagat<br>cttcagttgacatgcttgatgactagctattataatacgtaacgtaagccctcatgatgtataagttcagaagcatgaaggttcaggatg<br>tactttgtatccattgtagctattataacgtaacgtaagccctcatgatgtataagttcagaagcatgaaggttcaggatg<br>caagcaggaaagataggctataacgtaacgtaagccctcatgatgtataagttcagaagcatgaaggttcaggatg |
| Contig40_gene_113<br>0 | 1174 | atgttgattgctatgacttagaataattatatcctcaataatcataatgattctgcttggagtgctcttaaaaaatagacctctaaaaga<br>agaagatgtcgaaacactcaataatttagtaatcaatatatgctcaccctgtctcaattcacttcacttatattctacttaattatttgcttggataat<br>catctttgagtatttaacacttccactactactgtcttggaaatacaggtttttaggctatccgattacacagggatccatgcagcgaaggcct<br>gttaaaatatgagcatactctctgtgactgctccacctcaattgtgctatccattgtaatattgagcgttatctgattttgatgtgaattgaaggtgg<br>tatacgtcagtcttctgtgactactttgttccattatgtgatgccactacataagctattcatcattcatcttaataatattcgccattcgataacagatgtcgaact<br>ctttaagaaagatagctacttttgttgatgccactactaagctatcatcattcatcttaataatattcgccattcgataacagatgtcgaact<br>actgtagtcgttattgcctcattcataagctatcatcagctatgtcatcgctatgtatgtccttagggttatgcctgcttgaatcactgattcaatcata<br>ggaagtagtcttgcctcattcataagctatcatcagctatgtcatcgctatgtatgtccttagggttatgcctgcttgaatcactgattcaatcata<br>caatcgacttattgaagcggctatgtcatcgctatgatggctttgtttttagccataacttataagttgatcctcattgacttcagattgt<br>attttacttcgactttgttttgctttagtgactattccttgtttttttaatgtttatagtttaa |
| Contig40_gene_114<br>4 | 1175 | atgaacgaatatattattatgtaatagccttttctacttattgactattgcaattgtattttaaggcagacttgaaaattatgccttgaagt<br>caattttccccttttgatgtgaagacacagagattgagaggattttatagacagaatcgccaataggctccacgttttgaaatgtacatga<br>atataggaatcgtcatctctactgattgattcgatgtcgatctcgtgcttggtggcttggcttctcttaagacctgatgacgctcctacagtcagc<br>ctggttattccagggtggaagtgccagatgccagatctccaatatcatctcatcgtcttctattatttgcaattcttccaggagcttttgtagagc<br>gttcagtcatgaagaggaattgcaaggtgcaaggtgaaccgtcctttgtagtcctgagcgtcttgaggacgcattgtaataagcaggctactgaagacggcaatgc<br>ctgttatcatgatgctcatatcctcttgtagtcctgagcgtcttgtagtcctgagcgtcttgaggacgcattgtaataagcaggctactgaagacggcaatgc<br>aatcaattatctctgagggaatggtgatcaacggtcaaggagatgagatagcttccaattgaagtcaaatcctcaaaacagtcttaggatatatgga<br>ggcctaatcaaacgtgactgttctaacgatcaggagagtagcttccaattgaagtcaaatcctcaaaacagtcttaggatatatgga<br>gttcaggcacagttaatcaaataattctccggatttgcttggacacttcaacctgctccaatgaagccattgatgaggtc<br>gttctgatatactcttgaactttgctgtcggcacttgcttggacacttcaacctgctccaatgaagccattgatgaggtc |
| Contig40_gene_115<br>3 | 1176 | atgaaattcgattcagagacatctgtattgcttgtatcattccttacagcattctttgcagtgtttttagctgcagtagtcataggagttcc<br>agcaattgcaaatgagtttgaatgaacaatgtagttcaaatgattattacaatcgcattgcttgttgtagctatgttacgttcctgctg<br>gacagttgccggtaagttcggtgtcaaaaggtcttgcttgttggatattaatctttatcgtcggttcaatagagacgcctgctttttct<br>gccgaatcattcctctcttttaggtgattcaaggatcgagagggcattttcaaatgtgcttctatggcttgtcgttcaggcaatcaagcc<br>acaaagcagaagaaaggccctttgggcttactgtaactggggtttacctgcaggatccctttctccctgtaatatgcggattcctgtttataact<br>ttggatggagatccatgtttttacttacaattccatctctcattgtattgcgctaatgcttcctattgcgcaggatttgaagattccaggga |

FIG. 9B-42

| | | |
|---|---|---|
| | | gaaaatgataagattgactctataggatacatgatttatgcagtggaatattgctcttcatctatgattacaaacttgataaacgcttggg<br>tttgatttgtgttgtttgtaggctttatatgctcttgcctttgcatattatgaaacaagagtgacactcctgcatttaacatgagattgttta<br>agaatactaagtttgcatcctccaatgttgcggcattatgcagctatctgcagttgcagcactcactacatattgaattatcatttccagtat<br>gtaaḡgggatggaacgctcaaaaattgcagctattgaatgaccattgaatgcaactgcagccctagtgattttgatatct<br>taggatacatcctcaaaaattgcagctattgaatgaccattgaatgcaactgcagccctagtgattttgatatct |
| Contig40_<br>gene_115<br>4 | 1177 | atgaaattagattagaaacagttgtagtggcgtatcgtttattacttcattttttgcagtattttatcaaatgaattgtcataggggttcc<br>agctattgcacaagagtttgcaatgaataatgttattcaaaactggttcctacaatattcttcctgtgtagctatatttacagttcctgcag<br>ggcagatatcaggtaagtttggtgttaagagtcttgttggaggagtgcttgtctacctcttgctcataggggctgtgcttcattctct<br>actgagtcattcctccttttccgtatcctcaggtgcagggttgcattcttgaatgtgtctgctatgtgttgtacatgcagttaagcc<br>tcaaaatagggaaaggcacttggattacagtgactgggttatttggctacatcattgtcctgtaatttgcggattcctgttcataatc<br>tcggctgagatcaatgttctacttttgtaattccttcttgtatcgaatcggaatattgcattcatctatgattacaaccttaacaacaagcacagg<br>gaaaagacaagatcgatatgatcggatccattcatctatatgaatcggaatattggagcttgtattggagcttacaacctcatatgaaccattta<br>tcttatcctaacattcacatctcaaatactgcagactgcatgtcgatcattgtgagcttatattgcgttatgtgctgcacaacatctgaattatcatttccagtat<br>aaaatagaagttcacatctcaaatactgcagactgcatgtcgatcattgtgagcttatattgcgttatgtgctcaacaacatctgaattatcatttccagtat<br>gtaaggggatgggaatgcttcagagctgcaataggcatgcaatgcaattgcaataagtctcctatattcttatttctcacattcc |
| Contig40_<br>gene_115<br>6 | 1178 | atgctctttgtagagaatttaaagaatctctgtctgtttgaaatattggttcgtaagctattgaaaaagtaaaaaataccagaggactgttct<br>atttttagtcttcacctgcttttttgatataattttagctccaatattcattacaaatgatgtttcattgttaccattcatcattggcttaagaa<br>aggttgatagactcgatttgatttgatttatatgtttctcatattctcatgagacaattgcagctatctttcttgattctttgcctatatcgtgtatctgcagtgtttgattat<br>aatattgtaatgtatagtgttctcatattcatcagtcaaactgcagtaaactgcctatttgtcctctattctcagtctgtatctgcagtgtttgattat<br>tctatcctcttgttccaagcgatgcagtcagtaaactgcctatattgcctaaattgtgtattgataataagaacattacatctctaatctgttgtttaaaag<br>gtgttgattatttccttcttttgactttgggggttattgggaatcaatatgggggcttgtgcatcccagttattgcaatgttccgtatctgctgtcgtgattcagcactaa<br>tgataataggcaattgtggaatcaatatgggggcttgtgcatcccagttattgcaacttttaaatgttcgtctgctttatcctattgggagttgatgtttcattgttattcat<br>ttatgagcgataattgttaaatcgatatttgattatttcactatttctcctagttgcgtcttttatcctattggagtttgttattgtgagg<br>agcatgggggagtttaaatcgatatttgattatttcactatttctcctagttgcgtcttttatcctattggagttttatgtttattcat<br>taa |
| Contig40_<br>gene_116<br>1 | 1179 | atgtggttaatcattttgggaatatagaagaacttgattttctcccaaggagttgtacaggaggtgatcctaagatttaggtgattaag<br>tattcttgtagttatgtttattagtgttttgtaatcgtacagtcattacgttcagtcattacgttcaataccaatacataattccaatctattcaatctaattaatttattgcggtcttg<br>caatattcttttagttttccaagctgttttatgagctgttaggaacataagggtggataa |
| Contig40_<br>gene_116<br>2 | 1180 | atgattggaaacttatgctccattcactgcattgcttattttgaaacattgaaaccttattctatctctgaagttgtaatagcaggtgt<br>taattcattgtttgcttatatgctattgatagccgttgttgcttctcttaggaacatatggaacatatcaaacatgcaaactaacatgct<br>attatattgaaattatcggcggaatcgctatttattcattggtttagaatcaatgcttgaagcctttgaattcttta |
| Contig40_<br>gene_116<br>5 | 1181 | atgaaataaaagaatcaacaggtatgtcatttcactgtttaatatcattagggcctcaatcaatcaagcaaatctggg<br>aacatctccaatcatctgcctccatatgttcaagcctatctcttgaatatgagcgttgaacagtctgtttgatattaatgttatattcatac<br>ttgttcagataatcctccttagggagacttgaaaggagacagtatcttcagataattgtaggaacaatcttcctcctttcaattgacttca<br>atgacgcttgaacttttttaaatcctacaaactacattagccagttgccgtcctaagttgcgtcctaagttgttgttgttgttgcattgcgtattgct |

FIG. 9B-43

| | | |
|---|---|---|
| Contig40_gene_118_3 | 1182 | tgaggttcaaacagagagtggtctttcttcctcccgatggaatcattgtggctatttcaaggttctaataaggagttcctaagtaaaccttttctttgatacatcattagtgcttacagcagctattcttcaatagtttttcctaggctaccttgcaggagtccgtgaaggaaccataatttcagctgtaataattggcctatcgttaaagtgcttcagaagttcttaatcctatatcgaggctgtaattgaaaaataa |
| Contig40_gene_118_8 | 1183 | atgaatttcgaattctccattcttgattgttttttattgtctcctatttgttccaaacataatctgactaaattatcctaagattatgaaaatattcaaagagagaaataagatattgttaatccttgaacgtattgtgaagtgcaactgtgtattgcctgtatttgccttgttttgcggtctaaattagctggtcattattattattattttattctctaatgatgctttgtatgaggtttattggatagatactttatgtcaagccatacaatgaaggatatgtgtagtcttcaatatttgatccttccagttgccacattggtattcattatataatcataaaaagcagtgtaatcttaattaa |
| Contig40_gene_118_8 | 1183 | atgtctaattcgcaaaatgatggtttagaagatgtttccaaggagaacaatgaatctgctggtgaaatacagattcaactctaataaaaaactagattactaagatctatttcagaggtttttaaggaattagattctcaggaaaccaatgattctcaggaggcagaatctgaaagaatctcatcttagattctgaagatgctgcttctgaattagaatctgaagataaatattctcaataattttctgatgtagttctgatggtagaatttgaagaggaatatatcactactgcagaagaagaaatagatatctcgatgctctattcataagaaatcttagtaaaagagcttaagctaagctctatatacagaatcatattgtgatatctctctattctgtcgtgtgagatgaagctctatgagctcattgaagatgcttcattgaagctgaagatagttacgaagatgactcattgacagtgagatatcgatcaatcttatgagaagagctcttcttgatgagaatatgaaagttataaagtaaaatagtgttctttcagaggatgtttatcaagaaaaataaagattcctagtctcttcggtctataaaaatgattctccttattacacaagttttatcttgtgaaactgcaggtcttgactggaatttaatcatggtatatctctcaactccagttctgatagttgtagataatgttttatctgtgaaaccgcaggtcttgcagtctgcagtcttcttttaattatcattgtctcttaattatcgttcagtatcttgttcctctttaagattccttcttctctacaaagccgatcagtcttctctatgc |
| Contig40_gene_119_9 | 1184 | atggagataatgcctattatttcattttttatagggtaattcaatatatctccttgcattctgccacctgccaataattgcaggattagcctaaaagccgaatcaaagcaagacagaaatagtggccttcatataggctatttagatatatctgcactcatcattatctgacagattcttttacaaatattcttttaggtatatgtttatgtaaggtgccattgccgcatttctttgctcattatcatttgctctatccatatatgggaatattgatgttttttgactataatctatcttttgatcggttaatgtctgtagtggtaatgcaatagtgcaatgcatctgatgaatcatcagtgctttggcagattgctatagcggatatccatttctcttataactatgcttgtatcaagcagtccttgtacagtggtgctcttcagatttttcttgctttgcctgctttgtctctgcttggcattttataggtttacactcaattcaagtgttttataa |
| Contig40_gene_120_2 | 1185 | ttgaacgtatcatcggagttgatgaaactgccaaacgcagcatatgaattagaggatgggtcgattatgtccctatgaataatacagggcattattggtcattttcttaatattgcaggttaggtcaggtttaggtgcaattctcgaggcttcaaggcgcattagccttctgcactcttatgatcgttttagtactatctttgctggtgtgagtccacgttcttgcgttaattaatataacatgcattctgtgcatctgtttggcatctggcctcagagaaatatttggagatagggttcgcaagttcgtttaataattataacatgcattctcatatattcctatagccacattattccagttgataagattgctttcaagtttatccaaatttcggagcttgttttttatatggctgttttgcttattctgcattgatattaaatcaaatatctccgattccattataggtaagtttatctgcttactgacaaagccatttccaatgcatttgtaacatgtttgatccaagtcatatcaagcggtaaaaatgaaaaggataatgttatctatgggttattctatggatgcaatgtattattgagaagatacttgtgcatccaagcgcaattgttgccatattgccatgtcattttccatgacagcctcaagttttatgatcaccagcctcagttgatcagcctttcattgcagttaagaacattattggcaactattggctactgtaggattggtttttggcaatgtgcctatcagcagatatttgtgcagtattattgaataagcagtcaatagcattgattggttagcattggtgtactgtaggatcagtgttgcaatgtcaataatgtcttgttgttaatatgtccaatcacatcacaggggacacttccctcgtag |

FIG. 9B-44

| | | |
|---|---|---|
| Contig40_gene_121 0 | 1186 | tgcaagaataacaattgcagatgaattaggttaaatcaggataaactaaagactagacttaagatatccattc<br>atgttaagttaattaaagacaataaaggcttttatctcttatgctctattttatctcctaatttttatagttctaatctcatttaa<br>tatgattgtagatatggagatgcctagcttatccgaagacaacaatcaagacaagtcttatggagctgatgtcttcaaagatag<br>atggcaggattattccacattggagcgaatctcatatgttttatcctccaatgataattcgatagcctaaggaaggttaagatattcta<br>gatgattcttagcgctcatctggttctgactagcttatagagaaccattatctttttatagagactaataatttatggcctatgtctgtcatctgatgtgtga<br>ttattcaactgctgatgaggtttctctagctataagaaaacatgaaattattcttatagcttatatttcaaggcttaa |
| Contig40_gene_121 2 | 1187 | atggaagaacgtactgacttttttcaaatgaagttatctcgttcggagttgcaatctctgtctcagaaatagaggcaggaatacagcttgcttc<br>catgaacacccttgattccattggctacccttagctcttgctacttgccacatcatagggcatactgctatttctacaggacttataggtcacgtc<br>ttagattgaatgcaatggagaccatcaaatcaaccttgcaatttgcaatttgtccaaatctttccacattaaatgtattgcagcttatagcttgg<br>gtagctgtgctgaatgcaaggggcttcagcatgatggctgaattactacaacatcatttaacctgcattatcctgctcgcaatcat<br>tgcagtatggtttatgtaggagctttagaaggtcatctaagattactaccattatgatagtgcttacagcatttgcttacagcatttgaagcatcttgatatctgtaa<br>aactcttagggtccataatccaatgcttgcctattcaaaacattaattcaacagcattaagcttttggagcatctttgaaatttcaatagct<br>atgccaatctcatgcttcctgtgatttcagattataccaaagatgtggaaaaccagtaaacgcacattggtctctgcaatagcatataccat<br>agcaagccttgatgtatttttaggcatagaaatagttgcattgaaacaacaagcattgcacatcaatctccttgcagttcttggagctc<br>aaggagtgataattttagtgcttcaactgtaacctccaattttgtgagtgcataagtgcaataactttgcaataatatgatcattattggattcttatctttat<br>aatccaaagtgctaaatcattgcagagttgtaggtgagtgcagtgtgctccctgatctttctatctttctatcttctaaaggaagagagactgaaatg |
| Contig40_gene_121 3 | 1188 | atgaatgaacaataaaaacctaacaattcaagacatatcctgttatggacaatgctccatcacagtgctcattaccccgtaatttctgctttttgg<br>aatagaaacagcaatcctccctctgctgctactccaacacacttcaggtttttactgatttactgttagagatttaacagaagatcttccag<br>aaatccgtaaacattgggaaaaagaagaatatttcgattcaattacactggattcattgcatcagcagaacagttagattacatacataaaagac<br>atcatagactcaagataaagaaacaagataaatgcctgtatttgtgaccctgcatggcagacctatgagaatttctataatgattgattgaccaagaatt<br>tgcagataaaatggaagagctttgtaaattaggtgatttcattctccctaacaactgaagcatgcttatcctacataagccttggaaagaa<br>gctttacaaagaagaaatgctagagatgctaaagagcttaaagcattcactacaatgatatagttacaggatatgtatccatgaactggagatgtatt<br>tgcttcatcatttgtaggatcaaccatgttaggtaagtcccccttgacaggcaattcgaacaggcaattccagagttgtatgatcgtgttaaaatcaataataa |
| Contig40_gene_121 4 | 1189 | atgtggactggtccctattttttatctcaatgaaaccgcaagcctcatcaatcttttcctaggtttgattgtagcttgcttct<br>cgttaagataaaaatgacactacaaaaattgtactgatggcatttccacacttcgtattgccacctacagtagggttttttcctgc<br>tttatttttggtatcagaggacctataggaagcttctttttagactttcttgctgtaaagatagcatttcatggcctgcaactgttatagct<br>gcagtggttatgtctttttcctttaatgtatcgtttcgctagaggtgcattaaacaagttgattcaattattggatgccggcgtacattagg<br>tatgtctgagtggagagattcttttggaaatcttatttgcctgaaatgcttttgcctgaatcataagtggcggaatcattgcctatgcccgtggcttag<br>gagaattcggtctaccgcaatgcttgccggaaacattgccgacaactagaacactccctatggcggtttactctgaagtggctgctgaaat<br>atggaactcgtttgattatgttatattcatagtggccatatcattcattatgactatttttattgactatttttccatacgcaaggaaaacca<br>atgaaaaactag |
| Contig40_gene_122 | 1190 | atggctcaaaaagaattggatattcctgtagatgcatgcattgttcctcttgttccttcctttcctttcctcgttcctcgttgttcctcgtttcctcgtaagcttgatgaagt<br>ggaatccatcaatgtggacctaaacaccaataaggcccatatggttaaagaataatctctccagaacaatcgataagacagttgaatctg |

FIG. 9B-45

| | | |
|---|---|---|
| | 1 | tgggatttaccgttcgttggttccaaaggaggaagtggtcattcagattgctgaatgcattgtgcctcttgcgtgaacaatgttgaaagttccttcctcgt
gtagatggtgtggttgaggcaaatgccaatcttccaatcagaagttaccatcacatactataggacatgctcaatctaaaggagacctagagca
gacaatcgaaatgcttggattcgaatatcggccttgacgcttgacgctgacataatgatgacgcgaactggaaaggtatcaaaggacctagagca
aactatatagaatcatagtaggtctgtctttgccgtatacttatgcagcatgtcattccatattacaattcctcaattgactactggacaa
ctctcttaatcatagctatttccatcggattctctgtgtgcatctgttatgtaaggctgatgacatctcaagcataagaacctagatat
ggatgtaatgtattcaatgggtattctgccttcattcctcactaaggacgttatcttgaggcaaggagcagcaaatctcatcaagagcttatt
aatctgcagtgatgttgccttcattcctcactaaggacgttatcttgaggcaaggagcagaatagaagaaaatagatattgaggatatcaatattggaga
ggccttcagccaaaaacagcaacattaattacaagtgataggggcaatagcatgaagagggcaataagatagaagaaaatagatattgaggaattgatg
catattgcttgctttgtgaaagatacctgcagactcgattgtaggtcagctcttatttgacggtgaaagctatgttgatg |
| Contig40_<br>gene_122<br>2 | 1191 | atgatcggcataggggcaatactgctatttcctcgtccaatcgactatctctatagagaattcaattgttatggtaattccgcctttaat
ttcaatcatattaggagttcatttttcctcaaggatcagagaatatgacaaacttaaattcaagcatggatgatcatcaagcatatcatggc
tatggcagggctcttgttgagcaataatcatgatgcgttagatgctctcatgatgagtgcttttgaaatatctctgcatggacgga
agcggatttgaccatgttcagcgatgttgaatcctgtgaatcctgcctatgtgaacttctgaactgtgaagttgagtggtgtgaaatgggagagtggt
aatcatcttcataagcctactcattaagcctgatatgccattctgaacttcaagctatacaagtctgaagcaaggagaagaataagcaaatataa
aaaaatacccttaaaaaaaaccatgcaagatatgcatttatacccttataggtgtcattctatatctttatagcaggactccccttcttgattcc
ataaatcgacaatttcactacataccgcgaggaatgtcaataaagaatgcaaaattcaatatcaattctaccaaaaatgattctaatactcac
tatctttctaatgatattaggggctacactagtgcaataagcttcatgatgcaataaatcaacaatctttccccctgactgataatcatatgtcttgatgcttgggg
aactattgattgtaagcatcatattagggcaaacattgccctccaagtgagagcagcaatgtaattcacctcctagaaggacatagacacatcttg
attacaacaacaggagcaaacattgccctccaagtgagacgacgcagtaattacacaccctcaaaagacacacctatctg
tggttcttcagttccactgtaggtgctataagcttgtagtaattgttagagtaattcacactcttaaaaagacacactcttg |
| Contig40_<br>gene_123<br>1 | 1192 | atgggctcattggacacaggaataattgacctgctcctcctcaatcagacttccatctgacagagcttccatctgaacagcgaatcaagctgatatttac
attatttgtaatcacattcatgattggttctccagtaatgccaaatttcagacttctatgaagaaaaagatattcatccttgacgttcttc
tttttgaatagagatctgcctaatacagcagcatcataagcagacatagaattaatattttaggcagactcatacaaggattcggctgtggaggaata
ttcccagtagcggggggcctcttgtaggagcagcattaatccctatggctgaactggtgtgtttacaaataacattccattgcaatattctaattactct
aataggaggcctctcttgtaggagcagcaatagactaaacaataacaatttatagcgacctactctgccaatccatagtgcaatagaatggcatactgccaattagatctcgataatgcaaagctagcctattccaaggattacttcattctatttcttagtaatattcataattctaat
ttgcatgctacatactgccagactcagataacgcaatttaatgcgagctcaactctgccaatccatagtgcaatcgtgataccatctgccaagaatcgtgcatgcatagaaa
ccaatattcctaaagtagagaaaagcgaggttcaatctgccaatccatagtgcaatccttgaaaaatcctgataaaacaggtcaagcaccatctagagaa
cctatgctatgcaatactggaataatctactcttcagcaattttcatacaccatcgatttcttgaaaaatcctgataaaacaggtcaagaccagcttgcaagccttatg
ctgattccataatcttgagcaattgcagcaccgattctgcagcagatgtacaatcttagcagcacccaatcgatttcttgaaaaatcctgataaaacaggtcaagaccagcttgcatggaaac
aatgattcttgcaatgggcttattgcaatcttgcatgcaccgaatcttctcaagcaatctaattctttcataatagccggat |
| Contig40_<br>gene_123<br>2 | 1193 | atgcaaatgaaaatgtgagctaagtgagagagccaccggagatagcagttaagaaactggcaattccaatcattcattcattcctaaccgc
atcataacataatcgatgaatatccgtagccgcaggcttaggccaggcagcaattgccggaataggctttgtaacccaatattcatgatactaa
acggtgaagctaggtctctgaagcggtcaacaagcagcatagcaagaagcagtttgaactcgttttgtaggggctaaacaccgaggagcaaacaagtcagccacc
catgcccatttgtttgatctctatagcctcatttatagcctcataatcctaacatcataaatccttagcctcatccaagaccctcttcatccagaaccacatagctgaggcaaagcgg
acaatctctcagctagtgcaagactaaatacagaagcctctatcgaagcctctccacattcatgttgcaatagaagggattctccctg |

FIG. 9B-46

| | | |
|---|---|---|
| | | gagaagggacatgaaaaggcaatgtatgcagtaattgtatctgtaatattaaacacatgcctgacctatcttcatctacacattaggtatg<br>ggctcagcaggagcttccctgcaactatagtcagtctgcaggttcagcttcagccatagtcataatgtattggatactataaagaaagacacttggt<br>ccatgtggagctaaagaacttcaagttcgattcaaatatagcaaggacattctaaaagtaggaacattcctgcttcaatggacatgttcatgatgt<br>cactagctgtcagtcttcagtcttatctaatctcaacatagaagggagaattcggcatagctgcattcacatcaggtcaaaggctatacctattt<br>gcaataatgcctctaacatcaataggaagcctttgaacagcagtggcagtagcagtagcgcctatggagcaggaagcgcctatagccttatagccttttgctccacagc<br>tatttacggcgctaagtttggaatagccttgaacagcagtacaataatccttatagccttttgctccacagc |
| Contig40_<br>gene_123<br>9 | 1194 | atgaatatttcaagttttatttcagatgaaaaagttaatacaggaagacaagtcgaactgaactgaactcgaacttgcaatcatatttatgat<br>tttttacatactgtcatgtttgaagcatataatgtcggcttaagccccaacttatactatactcggcatgtcttaggaagccttatg<br>ctgcagtcgtcttcatgttctgcatggagtcgtggtattcgtgtggtattcttcttcattatcaaggcacagccaatgaacttgatgattaaaagaggaattatcctatat<br>ctcttaggccttttggtaaatgtcttgagtcttctgaattgaggattagcagttcaagcacaggaggtcttatgtgggcttaatgctggcttcttcctctattgg<br>aggactaataatcttttgtgttgtgacatcttggcattgagtttggcattttcacaataggaattgactttcccagttcgagatcgaagtttgcttcttcgtcac<br>ctatgattattaattgcagttataatgtctctcataggcagttcacaataggaattgtttatcttcccagttgcgggatacgttcggggacagtattcatcag<br>ttcattgagctaaaaacgacataccgccattctttaaaatactggcgatcctattgttgttggcttgtgcttcatcctcacgctattgggagag<br>agccaagacaaaaggaattctcactatcttaaaatactggcgatcctattgttgttggcttgtgcttcatcctcacgctattgggagag<br>tcttttcagaggatgttcacttatcttaaaatactggcgatcctattgttgttggcttgtgctataaatgccacgcattcatcgattatgctat<br>tgatttcagttatctgccagattcacttattctccaagttcttttcaacactaagccgcaatattaatgaaattaagtcacaatgttctatat<br>acctgtaacaataatcttaatcacttattctccaagattagtagttcaagttcttgcactattcatcatatttgtaagtctaatcaatgtcatact |
| Contig40_<br>gene_124<br>0 | 1195 | atgtattaattagcttttttgattagagtaaattaaccaattcaatgatgttgcactattcatcatatttgtaagtctaatcaatgtcaat<br>cttatgcctatactcaccagaatccaatgcatttctcgttttcaatgatatcattggaataggacacttattctaaatgcctattattaaacttcct<br>gcgaccccttcgcataaatgtgaaggccctgcaataattttagctccactagcaatgtccttgttacacagcctatctacaattat<br>accattgaagatgaagatccatctactacaggtcagtcttaaaggaaggcggttgataaggacttgttcacctcaaatcaatgattgataatacacata<br>cgttgagattgacggtcttgcatatgacgtcttaaagaaggcggttgataaggacgttgataaggacaggatatatgcctacctccaaatcaatgattgataatacacata<br>ccctaagaatgtgggagacagacctatcctcacaaacaggcaagcaagcaaggacagtgagtcaagtaacaacattggaagagagaatttcagatggaaatggct<br>tggattgaaaagaaaaacaacaatcagatgatgcaatgctctgagtgactcaagtaacaacattggaagagagaatttcagatggaaatggct<br>tcttgtagataatggagccagcagatcccaatctctctccggtgatacagacaactttgccgtattcgcctgtttattttacgacagcttgaatcata<br>tatacaacaaggcatggtttcggtaaaatgtgaaggccctaaagaaacatcagcctagatcaacagacaactttgccgtattcgcctgtttattttacgacagcttgaatcata<br>tcccaaataaagcacacgcagttttcgtcatgtcaatgtgaaggccctaaagaacatcagcctagatcaacagacaactttgccgtatagtagccagcgtcagccagcagttcaacctgaatcata<br>ggaaatcaacacctcaacattgattggagacatgtcggcgacattgacgttgcatattcaacctatttag |
| Contig40_<br>gene_124<br>2 | 1196 | atggatataagtgaataattggagatgcaattgcatatcctatacataattaaagcttagtaatttatatgattattgaatcattactgg<br>aatcttaggtggcgcaagtttcatggcttcatggcttactagcctaacaggcaaaaacgctcttgctgctgaggattgttgtatccttggagtatag<br>ttctcctcattggagcattattaatacaggatatgtttggatattggatattggatgtcctgaattgactta<br>gtaagacaagtttaaatgcagttaaattacttattgcagtcagcattgttctacatcacattttctgtctgcaattattgcttggtatgtttactctctt<br>agtaggggtatattaactgtctatttgttatgataattgtgtgacatattcgatggtaatgcaatatgcagattagcaaatatg<br>atagtttaggagaagcttagcaatcggtagcataggtgaagctattgtgtgacatatcaaaagtaggtgtaataaacttctgcaactattattatagtagtt<br>gtcattgcaatgatcgtatgcttatcttatctattatacgttataaattaaatagcctcattggagaattttattggtatattgctgtatacct<br>aacattcttcgccaataggcagcgtggtttattatacgttataaatagcctcattggagaatttattggtatattgctgtatacct |

FIG. 9B-47

| | | |
|---|---|---|
| Contig40_gene_124 9 | 1197 | atgaatatggattcagcgtaaaggatttaatgtacggctccggacaatacgtatttggaagtagtcatagctcttgttgtagcattctttt aaccggattacatgcgattatttgaatctactctggagaggcagagtatatcatatctcttgtatatgatggtctcttttgcaatagcct ccatcgggacacatgggttaaagatgacatatacggtgtattcaaggcctccaatctgtttaaggtcattatgatagtcattatcctc ttgcttcttatacagcagcatctgctgttgatgctatgtttgatctttaataatatcaatttatagctctcagttcagatttgcttatga ggcttcaaatcctctcttgtcctttttgaatctttcagcaatcttcattgagagagctcttcttgaggagaatcttattca ataggcttaagataagaaaaggagttatatttggagtggtggtatctcatcatccttgattatgccattcaattatccagaccattggct catataattacacttgcctattgataatgtgcttatgcattcccaataggggatctcttctaggaacagacaatctattgataaacatgtttgcacactcctcta taatctattgtcttatgtgatagtatacactccatagggatctcttctaggaggtccgttatgatttcactgtcatagtctgtgtttt caatagtatttgttccggcgtatatatttttattctcctataaagctgaatga |
| Contig40_gene_125 0 | 1198 | atggatttaatgtaacagacttcaatgttagataagaacaattaagcttaggaattattagtaggtattgtcattgtctttatttatccat agccctccttaatcatatatttccagttgatgatagtatgatgatttggcttgctttgatggtttgtattctctattcatttcttcctttatgctt aaaagtacctctgtctaaaacaggatttcaataaacatattgaaaggacaacagtcgtgaaatcttatgtgtcattatcaatatgttg tttgcttttttagtcttgctctatatttccacttcgatgcatacctttacttgtcgatgagtggttctatcctcgattttactcctac tgctattgatcctgcagttttctctattgaatcttccactccattataatcgctccaattgttcgattcgcatagacaagtgca ataggttaaagattagaacaggcattcttccgctatgttggctattggctttatcttagcataggtcataggcgcgaatgacaagtgca tttgtattgggaatgtgtatgtgttgttctttatcttaaaacagataataatattaatggcatgtctgttcattcctgaacaatctatattttac agtatgggactttattgcattggatgcaattgtttttccaaatgctgtattgacttttactcattccattttcttgattattaataa tcttattatataaggagattggtaaattactgctgaatag |
| Contig40_gene_125 2 | 1199 | atgttcctgantttacggctattcctacaggtacaagtctctgtagaaggtaacgatccattgccagaatttgatgatgt gattggcatgttttgacggcataaaggtttgcctgtctatctggatatgcgctggttccaataataatattcatggtctcttgcttttagtct ccagcgctattggaggatatggcgaattcgtattgatgcattgcttattactctctagccataatcgcgcttattgatgagcatg tttggagttgcaaaacatgctaattacgacggccgcattgcaaaggcatttgacattaagagattattgaaatcatacagtccgtcggcgttgt aagaagcgtagggcatatattgattcgatatgctatatctgacggcccatctcttatattgctctctcttgtattcgatttcttg gaataatcactggaacttaggtgcctatactgcacagcaggagcatatcattcagagaattatctcttaggttacttcttaatgctattcattgta agtcctatatttgattatgcaatcaagagttgctgattattataaccttcattaa |
| Contig40_gene_125 3 | 1200 | atggctagcagcattacagacattataaggaagacttaaatatccattcaatgacactagaaaagtattgattcttggctaatattcctcatctc tgggctcattctcccttttcacacagtcatgtgttttgattcatgaccttcagtcaatgctccccatacctccagttaatgaatgtttg catcaattcctccatcctaattcagcttttaatttcctgtcatgattgtaacattcatttgttcctttcacttcaggatacatatatgtt attaaatatgcaatagatggaagatacgaacctccagacttgcaatcctaagaacgattacgcacattaattgttggaat tgtttattccattgtgccagctcttatattcatcctggattgatgctgatggttaatgaagctcaggtgaagctgaacatgtttggactta tattgcttttgtttcattttattgttgcaatatctttgatatatttcaaatatggcctggggaagatttatcggagcctatgttcattgtaattgcaat gcattccaattttagtgagatctttgaatgatattcggagcaatatctactgagattgcttaggcagaagattggcatattgttcgatcgtttcttaatggcaat atttcaatgtcttttgtttattaagtccatatacagtattgcttgatcgtgttataaggagcattagtagtaa tattgactggtttgttattgtctggagtgatttttgagtgatgaagtttttgagatgattttagaaatta |
| Contig40_gene_125 5 | 1201 | ttggacatgtattcaatccttaaaatttaattgcttgatttttgagatgatttagaagttttgaaatgattttagaaatta ttataggtag |

FIG. 9B-48

| | | |
|---|---|---|
| Contig40_gene_125_7 | 1202 | atgctttctattttttatttaattctatcctaaaagaattctagttcaaatttaattataatcaagttcgaataggattctaa ttcagtaaataactcttcctctcttcagatgcttttaaaacgatttaaacagcatattcaaggtttctaagattatcacattctattgttt tagcaaacatactatttgtatctgcaatatacttgtattaagttattggatccatatccttcagttcatttgcccttattcgtgat ttcactggtttaggcttgatgtaacgctccttacctataacgtagttatctcaataatcgaagagttctctttagaggatctt cttacgaagattcaatcttgagcttgacactttgacatcttttatttcctgtctatctgcatgactgccatcctattttcctattttggaattcataactttgaggaatat tgggagctattcctcttgctgcgttccattcattgaatagaaattcattcatgaatagcattgttcattgcttaataatcatttgccattataactc atttcctttttgctgctcttagagctattgtattagagtgccctaaatcttttaaagaatag |
| Contig40_gene_125_8 | 1203 | atgttaaaattactggaaagaaataagagatttaataatatcattcattgtttgctttggcattctccattctttattcaaatcgatt taatgaattctattcattcatattccaatagtgcaatagagtaggtgccgattcatcttttcatgaatttggcatatgcactgcatatgcact atggatatttggcagaatatcaattatgcgaccactgacttgtcattgcattgtttcactgaagccgagttctgatcttttt gttgtcatatacagtcaagaatcaagagatctgagaagttcaaaagtgcctactcaggtctatcataagctttgatttgcttgctttga agtatttaaattcattattgcctatccacacagttcactactgatgatccaaagtttatcttgaatgctcttgttgttgtgatagttgccatatcgtt caacattaacttattgcttgtctatgcggttacctttgatag |
| Contig40_gene_125_9 | 1204 | atgcaaagaaagatgataaatacagtatgcctatgagtgggcaggtttagtaagataacttgatgacgaagtgtagtccaaagatagctcc agaatacgttattgcttaacagttattctcgtatcttttgttcatttttaagatactccatataa |
| Contig40_gene_126_7 | 1205 | ttgatgcattaaggcattagcaattagcaatttatctcgtaattgcgtaattgccatacacatgctacgcatgcctaagaattttgttatagcgaattggtgggaaa cttaccttcattgaattggaagatgaaggactcttgctcatagaattcccatagaatagtatatccattttattttgagcatcctcttaggaaccata taggagggattggaagattgaagaagctcatttcatatgatgcaattgatctgttgttttgttcaatagcaattctctatggagtatttatggaat tttcttctattgcaatagcctaaattatgatagatgggtacttgttgttggtactttaggagttgatgatttgtatttaacaaatgattttgcattctgatt tgatgatctttcttatttcctctgcttattatttaacatgcttgttgactatacattaggagttgaattccaatcagatttgcatactttt acaagtccgataggtttggtgttttaggctattattggcctttccgcctttgtccttgtcttgttttcaagaattctataatatattttgcattttgattat ttctcaagcctatgatgcttgtccttgttgttaagaattctataatattttaataaatatggcctgatgatctcttaataatcaagcctgatgattctttaataatca agttataggagttcctatgtcttggtttgccaggtagtgtcttgcgctttgcttgttgctgcctatctatagctgagcttcatttcaggaatatttaaaaac gtttatgcttatgcccaggtagtatcttttaggagtatctatggagcgcaggtttgagcggccattgcgccattgctatttagcaaatgctgctattagtattca gccagtcttatatatgattatattgttgtttctttactctgttcggtgattgtaatggctgtattaagta |
| Contig40_gene_127_1 | 1206 | atgagtgaaattcctttcctttctgtgataatctgttatttatctgctaatagcattgccaatctttgtttctttgtatcatttatgtt agtagatatcctggcacctatagatgttataaagaccattctaagtcctatatttcatctttgctgtgtcctgtaatgaattccatcg tcttacaataagcgctgcctagattatagcggcttgcttgtgtgctgccttatctatagctgagcttgttgagcttcatttcaggaatatttaaaaac cctcttgtctcctgatctttaggagtatctattggagtatctatggagcggccattgccatttagcaaatgctatttagcaaatgctgattca acttctgcctttgtcttgtcttggtcttattgcagtattcattacatttcaatatccaaagacatacaaaggccgaggaatttacctcctgtgctct ctggtactgcagtctctgcattctcttcaatgcattgattcaggagccaaattatgcagatccttatgataaattgcctcagattacctattgg |

FIG. 9B-49

| | | |
|---|---|---|
| | | cttatgggcagtctctctgcagttaatttgataagctgcaatgataatcattccattgtgtctggaataattgtcgtcatgatttaagatg<br>gcatttgaatgtcctctgcagttcctctctatgggtgatgaggaagcccaatcattggattgaacccatccagacttagattgattgtctgtactt<br>tagtaacatctgctgcagttcaatcagttggaattataggggcaagtattaggggcaagtattcctgtcttgtgttcctcatgactcgtataattgtaggtcagaccat<br>aagatacttattccagcttcattaagcactagttgtgttcctttattcctttactgctcagaagctagaaggctcatataccaatttcatatcaattcctat<br>tggtatttttaactgcaattattgtgttctttcttcctttattcctttactgctcagaaaggctattctgagtgaatt |
| Contig40_<br>gene_128<br>4 | 1207 | atgagcatgctcgagactcgagcctgcaagctcacaagaggacatggctgaaggcgatgtcgaaatcttgctgtcatatgcttgc<br>cataagcattgcaatgctacttctttttctttgcgcttgcagagccgactgttgcaggagtgattag |
| Contig40_<br>gene_129<br>9 | 1208 | gtggctatcctattgcattgatgagcatgttaggaatcggagaattgactcagaactacatattggcaatagtgagcggtatgatagccttgt<br>ggtttggtactacaacagagaagcacaacagcgatttgtgatgcggaaccaccaagtgcgactgcgagctcgctatgggggagacgaagcac<br>ttatatga |
| Contig40_<br>gene_130<br>0 | 1209 | atgataaccactgcgtagtagtgatattgttcaacagcataaccgagcagcaccctacttcatggagtggacgagatagggaatcgttcttgaatcgt<br>ttccatcaccatcgcctgcatttacatagcgatgatagacagatgagacgcaggagagaacgcaggaagagagcttgacacgatagaggactacataa<br>acaggaagctgaggagatagcgaacatgaagtattgagaacttgaggaattggaagaggaatga |
| Contig40_<br>gene_130<br>4 | 1210 | ttgggattttgggattgacaaccgattgcgaaatctcctgtccgttaggataccttatgcagacgtgattacagaagtctatggagag<br>gacagctcgaaggtcatattgcttggctcttgcaaacatattgctgattgtgctaccacatttgactgtctacatgcctatccaagctatt<br>ggacaggacagggagcgtatgctacatgttcgattcactcctagaaatggaccaacagtacctgttcaggttcatagcatacttggtggacagttcgtgaat<br>gcgagacttatggtgctcatcaagaaatggaccaacagtacctgttcatgaggacaatcgttcatagttgagcaatggagcaatcttttattcttatgcagtatgttgttaaggttacttggg<br>aagtgtgatgcagcctctgacatacaagtcaatcgcttggctagaagacggatag |
| Contig40_<br>gene_131<br>5 | 1211 | ttgaaggctattggagataacttctcagtggattatctccttttagcattattctctagtggacattttgatattggttgcatcgttctcaattc<br>ttatgtgtcatctcacctgagaatgtaaggaactgtgattgactatataagttacaggaaagttgatatttttggagacatccaaggagac<br>ctagaatgagttttgaagattatgtcttagacaattttgaagatgtaactggtgaactccacagaagacaggttgttgaatttgtctctcga<br>caagaggaaaggactcacctctgcaatgagatctcattgctgtgcctttgaagaagggagcaaggacgatatcgttgagatattgtgaa<br>tgagtattttgtggaggactataaggagaactggtttagagcaacacgagaatcttggttggaatgactggaagaactttgaagaagatag<br>ttgagaatgtgcgatgactccaaatcttttagaatcctttaggaatccaaatcttttagaatgactcctgtgctcttaatggagtattga |
| Contig40_<br>gene_132<br>7 | 1212 | atggagaaagtagaacaattaacaatagaacaatgaaagagaacgagaacattgaaagctgaacatttgaaagagctattaaagaagcaaaggaaca<br>atttgaaagagaaagaactgaacattttgaaagaagaaaggaacaatttgaaagagaaagaagagacgagaaagagagaatagaaaaagatgaaaaag<br>aagaaaagaaagaagaataggagagagaaagaaagatggagaaagatggataaaatagagaaagaagatagagaagaaatagaagaaaatagaagagag<br>aatgaaagaataggattaaaagagagagaaaagaaagaaagagtgaagaaaaaagaatgaaagaagattagaaaagcaaatga<br>aagaatagtattaaaagagagaagaaagaacgatgaatgagatatgaatattacaggtcaatagatacggtcaa<br>caggaaaaagtaaggtatgtggctcagcaattatggtcagcaattattccaattattggttatatattgttttatgtggaggaatgta |
| Contig40_<br>gene_133<br>9 | 1213 | atgctgaagacaaacttcggaatcaccaaggacacccctactgaccttgatggagtggtgccgctgaatgtcgacgatgtcaaggagctatcaggagcatt<br>ggacaggctcttgagaaggtgtgagaaggtggagacatggagacatgggagaatgctcgacaccacaacaggacacctgaacattgaagaaagaaacttccgtgttgcag<br>aaggcatgtgggagagatgttcactcactcactcatgtgaagatgacgctgaaccaagaggagacatcgtccaagaaactgtgtttgaagaac<br>cttgtcatgatagcgggtgcagtgcgttgagcggattgccactgtggctccaagcattgctctcctataagcattgctcctataagcgtctttgagatgtgggaagtgcgat |

FIG. 9B-50

| | | |
|---|---|---|
| | | aagaggacagcaggattcttgggactgatgaggttgcagagagacgcagtaacctttgaagtcaacattcctgacaatagctcagattgcaggcg<br>ctgacgcagctgtgtcttcagactgccgcaaacagcggttgactgcaagcttctgggcaatggctgctgcaatcttggctaacccttgactgg<br>gttgcagttgcacttatagccattgcagtagcagtctatgaggtcggaaagagttcggatggtgtctgataggctccatgattgtgctgt<br>ttggcaggaatccaaaggcttgagcgcctcataaacaatcctaacgtgcaaggattcctgaagacctgtctaacgcatgaatgacatat<br>gcgagcattggcaccagtcatcgattgggagactggggagactccttaggcaaggttgtgaatgccgtaaaatctgcttggaacgcattggaaggattgccggatt<br>ataattgacgttttcgacagttgggacctgtaggaatggttgtcatggcttttgagaatgattgtctgcatacttttaggtt<br>ccttcctatgctgtggacctgtaggaatggttgtcatggcttttgagaatgattgtctgcatacttttaggtt |
| Contig40_<br>gene_135_<br>2 | 1214 | atggatttaattttgaatatctgattgttttatttttattgttccacaaatatagcattttactaagatattctagtttaataaaataa<br>atttattccattgttgtttaggctatgctattagtattgcattaacttttgtatttctcctgaattacaaaggaatccatagatttta<br>ttccgtatattttatttgctgttagtgcttatcctaatctctatcttattgggcattgcttaggttaaaatcagataatctttcttatctggtcttga<br>gttgtttatatgcactattttattctcatctctatcttattgtattattttaaaatcaacaatctcaaaagacataatatgcagtcattggtg<br>attagctattctttctgtttgtagttatatttgctttatttgcttctatattgttatataactcttctagcgtaagagaatgattattcaatgtttgatcttttcta<br>aatatatgttttagaatttattttgcttatattgctatattataagcaattgtcatttgcttgttttagggttttatataatgattggttttaaaag<br>attcttactcctacatataaggtgctattataagcaattgtcatttgcttgttttagggttttatataatgattggttttaaaag<br>gctaaaaggaagtaa |
| Contig40_<br>gene_135_<br>3 | 1215 | atgatacttcaaggtacgaaatattgacttcgttcatccatattgttctgaaagctgctgcgcacctgttgtaattgttttagttagttatattcttt<br>aatctatgaaactttaagcttgcgatttttaaagctttaaagcatttaaatgatgttaacaaaagccattgaaatcgcaggatttgaaaaagttatgcaagaca<br>tttcaagctccgatagtcctgaagactttaaagcttggtcctgttatagagtccaagtaaacttattgaagagaagaaagaaattcttgtaaagataactgat<br>aattataattaggtccagaggcaagaaaagcttttgtcttcttggtacttaataccattagtcctgaagttcctgcttctgcttagtactggagatattacca<br>tatttagtaagattaggccctataattgcttttgatacaacttgctttttgatacattgtgcattagttatattgtttctaaatataggaagcaa<br>ctcttgccaatcctgacaattgcttttgatacaactgctgcagaggctattttagaaaaattgaatcagttttaa<br>tggtatgaagtgatttgactacaactgctgcagaggctattttagaaaaattgaatcagttttaa |
| Contig40_<br>gene_135_<br>4 | 1216 | atgttaagaaaagaaaacgtttagtagtagcgatgatgcgatggcgataaatcctgatatgatgctaagactcaggagtctcaagcacaacaggccacttctcaag<br>agggttttgatttttgccattatgcctcttcagtaatcctgatatgatgctaagactcaggagtctcaagcacaacaggccacttctcaag<br>tgagcacagtcaggactttaatagtagtgccaatgcaggtgcctcttagagcagtctgttattctgagtgtggaaaagtttataaagatcct<br>gatactgttaaattagtcatgtcagggttga |
| Contig40_<br>gene_135_<br>6 | 1217 | atgagttttaaaagtcctgcagatactgcaaaagtcagtgcatctgcagctacccgcaaaagtgaatgctatcataaaactgctatttagg<br>tttcttagcagtgcatacattgcattcggaggtttactgcagaagtagcaaatactgtgtctatgctgtggagttccagtaggtattctta<br>aattattattcgggacgtaaaactggttcctgtaggttaattatctgtgatcgtgaattatcactgtgactgtaaatcgtgtctcttcgttgctta<br>ggtcttagagacgtaaaactggttcctgtaggttaattatctgtgatcgtgaattatcactgtgactgtaggtaatgtttatgactatg<br>cgtacttgcttacttaactgttattatgtacccgaagcattcgctgcggtgcaattaccattgctaacactaaagcattagggtggagctacct<br>tcatgcagctgtaaatcaactgcttcttaacttggtacaatgtttccttagaggtatcggttgtaactggttagtgtattgttagctgtatac<br>ttagcttaacgctgctgacgatgtagtaggtaaattcctcggaatttggttcccaatcatgcgtttgtatgttgagcacagtgcgc<br>aacatgttctctcatcccattagtatctcttcttaggtgctgaagtaacctggcaacattcttcatcaacaacttaattcctgtaacctttaggta<br>acatcgttggtgctgtattcgtagcatgtgctactgtcgtcatacttacgcgactaa |
| Contig40_ | 1218 | atggcttaaacatagcttcagtcgttgatgcaagttttgatcaaccttttatcggacacaatgcacaggcggcttacaggtcttagagcctttt |

FIG. 9B-51

| | | |
|---|---|---|
| gene_137_8 | | ggtattgtaattacaatatttgaatgctgtttgactggaggtcaaatttagctttgataaaaggcggaatttgatgaaggtgaagca<br>atcattacttcacaactgcaatgcttgcaacaatagttctatcagttttgattttattgtatgcttttatttaaagatccttaatcta<br>ttgcatccgactgctggagcactgcctttatgtaaacgcaatttgcttcagaagttcatcagttcccaattgcaactatctggagtattatg<br>tcaatttattcgtgttgacgggcaaccgaatttgcttcaggagtaatattattgttgcaaatatatcaataatattagatatctctccttg<br>gtgtttttcatatggcatcgtttttccgaatgaaatttggactggatacgctcaacaattgaatattgtgtacttaaagtatcattttgattca<br>aaagaactttcgatcgttttgtattgtgatctatatcagaatttgtgatactggatacgctcaacaatgaagtaggtcttccagggcaag<br>catgggcttcttaatgtattgtgatctatatcagaatttaatgttgcgagtttagagagctggcttgatatattcaatgtatgtg<br>tggttgcattgcttttaataagcatttaatcatgggattcgcgaaacattgttcgtgtatattcactgcattcctcttaatatctgattctat<br>aatcttcatcatattgtgcgaaattcaattataataaccattgtctgttcggtgtatattcactgcattcctcttaatatctgatgtctatt<br>gatgttttcaaacttcaccaaacgctaatgatgattagtgtgaaaatgcgattagtatactcattgcat |
| Contig45_gene_1 | 1219 | atgaatatattaaaaaatctgccttgcaataaccgattgatattgccattctcttcacttgaaagatattcgctgatttcagcgccatatt<br>cttcataatcggctctattttaatatttatgtattgctaaagcttgttttctcatttcaatgactttttcaatgactgaacaatctgattccat<br>taagcacattcggtacattctcaatgctctatgctttgaagtcacatatctaaagccctttattcctgccattgtcacaagatattgccttgtg<br>atatggatttaggaataaataattcacctatccattatttgttcttcttacaacaactatgtcttacaattcaatattgaagatgtctatgc<br>aacttggtgatcgtctatatattgaattaccaacattggtctgtctcctacagatacattaattttaaacaaataagacattcttcttgaatag<br>gatttatattgatgataccaacattggtctgtctcctacagatacattaattttaaacaaataagacattcaaaataagccattcatttgcatt<br>tatgctgcaatttctatccatccttattgtaggatacgtaatgctataattgaaagattgaagtttatgccaagcttttacattcacattg<br>ttttatatttttgcaatattcaagcattcaagtttatataattgaaagattgaagtttatgccaagcttttacattcacattg<br>taataagcaatagcacagggaggcctataagttcttgaagttcttataatgaactag<br>ttagtaatatttgtattgtataattattgaagttttttaatgaactag |
| Contig45_gene_10 | 1220 | atgaatgaacagagacaaagcttctcaagatcattatatgatttttgcttaagttggccggttggtcttttgattctatgacccttgtcctatt<br>tacctttttgatttcacagcttcaatccagcttacatatctgcttacatataaatgccgaaatgcttgcattatgctttagattgtcctatttgctacaggattag<br>gggaatcattttggagcattagcatattcgtcattctctggttctattcagtcgtaagaagttattggaatgacaattctgtctattcgataggacactgctatgt<br>gcattctcatgtcatttcatttctctggttctattcagtcgtaagaagttattggaatgacaattctgtctattcgataggacactgctatgt<br>cgagacattccctgactatactccaggccaagttggagctttgagctttcatgcaatcaaggagctcctgttgagtcatattggcttcaatagtaggtgaa<br>tgataagccctattattgctgagaatgacattttggttctccatcattccggagcatcaacattgtttcaaaggaatacagaaagatattcct<br>gatgctgattaaaataaggatgatttgtaaacaagaacatattgttacctattcctggctccacctatcggcagagagaggggccttgcaa<br>tatatccttgtatgtgcatattcgtatgtctgcattcgtcgcgtgacttacaggatacatatgctgaatcagataagaataaggtcccagacctataat<br>tggttacaacctcccttgaatcatcacagtttcatcatgggaataagcattttggaggattcgttctctattctcagagctattcc<br>cctgcattcactactcacagtttcatcatgggaataagcattttggaggattcgttctctattctcagagctattcc<br>ggtattcatgttcctcacaggattcggaacaggattcttttggaggattcgttctctattctcagagctattcc |
| Contig45_gene_29 | 1221 | atgctaataatagtgtattaagacgtattgttctctaattaccaagcataacatacttagtatagaactaagtatttcctactacagagct<br>tgaaacagagtatgtagatgttcaattcaacaatgcttatgaaatgcttatgaaatcgataaagcgaatattactacagaaagtatcttcactaatc<br>tagttagagatgttggccgtgaaaatattccagaaaatcatagctttttatgaattgctccccgctcaaacaagatagatgaatatgccttagta<br>agcaagatcatcatgggaagtgacagatacatgtatgttgagctttcagagcctttcagagcctatatcatagattacttcacagacatatctaaggga<br>aatgggagattattgaaagaagcgaaacagagattgttcaagattgatgtctaaaaacgatcaataagaatacgatcaagcttgtgtaggga |

FIG. 9B-52

| | | |
|---|---|---|
| Contig45_gene_38 | 1222 | ttggattggataataacattcgtgtaaggcagcagcaggaatgactggcgctgcagccattgaaagatcaatcaagttcataaggaagttgga<br>gatgttccaggtgtggcattccattgacatagtggattccactagttccactcatcatcaactcttaattggacactccattaattggacaatctgaacatgcagaata<br>tcagcattatctattcattgacatagtggattccactaattccatcatccaaagcatgtaaaaacaagcttgtagagcttatgaccagctcaagg<br>agtttatgaaaactgtgaaggtcatattgaaggctaccgtgaaggtggagatgacctattgctcgttccaagtaaggagtggcaattcgt<br>gcaggccttgactgtgcatgttgttccatctaaataatgcgcaaaggtcaagataggtattggaagaagcagaagagaggcaggagaacgtgcaaa<br>cattgcagagggtattaaaggattgggcattgggcattaaaagatttgggcattaaagatttgggcat |
| Contig45_gene_52 | 1223 | atgagaaagtatttgaagcatcatagaagcttaaagtatccattcagagatttgaaaaatatattattgaattggctttcttctattaattgc<br>ttcttaggaaggaaattgccttcccagaggacccacagacagttgttttataggtgcactcttttttttgcaacaggatacg<br>gttcaaaaatcgtttatagcggattgaaggagaataticctccaaaactaagccatgtatggaaaaccattaaaaaaatcatacactactact<br>attatcatcattatgcatatgtcatattcattagtgttggagctctcttgaaacaggtatttccaccatggaaagtttataaggcattctattaa<br>aggaaatcattgcaatcattaaagagatggattcacttcaatagagcggttttatgataaattgaagattgcaccaattgcaccaattcgcaccattacca<br>ttcatcaatttagttaagggcatgttcacttcaatagagcggttttatgtataaattgaagattgtgaacagttgaaaaatttgaattcatcata |
| Contig45_gene_67 | 1224 | atggatttatttgctcattactctaaagtgtaaaatgattgaattatatatataattgatttgtttgttctaacattcttgctaccgtagcctt<br>cacttacttgtaagacatactctacgtgatcgtgatgcagatgtttcagatgcagtttgtcagtgaacatagacataaagcaggaactcccaccattg<br>gaggaatagctttcctatttgccattctcttatcagtctatgtctctattaggtctcttaagataaaggaatcaaaaggtctgtaaagatgattcaagttcctatagg<br>ggtgtaatggtggtcctcttcttgatgatctattagtctcttaagataaaggaatatcaaaggtctgtaaagatgatcttgttcctatagg<br>attattggcacttggccctggagagaggcaaggtaaccaccgacaagatcagtcatcgtataatcgcttgtataaggtatatgcctgactgttctggagatggaa<br>ttgttgctgaattccaatccagtatgagccaagcaagaccaagatcagtcatcgtataatcgcttatcaaatcaataaatctcattga<br>gtaacaaccctttgggggattcacttagcattgtctgccgcatcgtgccattctgttctgaaatttctatatcgtgaaatatgatatgattcctg<br>tggaatgatgattggctgccgcatcgttgcaattgcaattgtcttgattttgtctgccattccttacttgactgttgcctgttcccagatatattcatggtgccttgtatta<br>catttgcaatttactgcaatatgtctgtcatcttagggacattccttacttgactgttgtctgtcccggattgtatcagtcagtaataataagcct<br>gatacaggcacatataataaatctccttagagactttgcatcacacttgaactataaggataatctctg |
| Contig45_gene_72 | 1225 | ttgttaacccaataataaatgcattatcatatactccttccgtttctcttttatgaagatttcagacgatgagtagtgagaaaacaacagatact<br>tgcaatcatattgaatagtgccgcagcattacagcttacagcctgcaatcatatttttgagcattcatgacacagatgcagcatgcaatgcaatactcattg<br>gaacatatacagacagaaggtgaatgaactatcatcgtcttacaagcttcattttgatgtctctgtttttctttgactcttcctgcattc<br>agtcgtccacatccattcctgtcgtaatgattgtggctgagcctaatcgataagagaggaaatgacaatgacatactctagaaaagcaa<br>gttcctgatatttcttgattacaggttgcacttaaggtgtttcgcttaagtgttattttagccctgcttatggcctgtggacatttgtttt<br>actctttatgctttgagatgcagatagcaatgagatagcaagagtgcttttgagaagtttatttataa |
| Contig45_gene_83 | 1226 | gtgaatgatttaaaaaagttatatgtttgctgcaatttaattgttatttgttaggtattaacttttcatataatggttagacaccattaa<br>tactttaactcatgttaatttagattttaggtccaagcatgacaatgctaacgatcaaatcatattaaaatcggcagtagttcattaccaaat<br>taagcaaattttaccctggtaa |
| | | atggcactgattgagaaaaacgaactcttctttattggagaatcgtaaaaaaagatttgcagcaaaatataaagatttcgatattaggatatt<br>ttggagtattttaaaaccattatcaatcatgattttactacacatgatttttcaaactattactacaaacaattttcaaactatttcaactattgcgaagcattggcgcagttcattgattatatcccgtttcact |

FIG. 9B-53

| | | |
|---|---|---|
| | | ttttatccggaaaattatctcttgatttttttaattctgctacatcagtatcaatgatgtcacttaaagcaatataacatttaaaagaact<br>gctgcaccaaaactatttttacgttagcaggagtcgtttcagaattttcaagattttaatacctaataatattaattggtgtcatgattgt<br>gaccagatccccattttatatatggaatcaatgatagcaatatccgataatgtcattaatcattatgattactgaattagctaatactag<br>ctgttttatgtgtttactttcagacacatacaacatttatgggcgttattacattaatgttaatgtatgcatctgcaatattctatccaatgaac<br>ataatccctgaaccgtttcacggaataatgattttaaatccaattttttggttgtataggccaattagaattcttgtgctatgggaacaatacc<br>aagtaggatgaatatgttgaattagttcttttatcagtgattatttagtgttggaataatagtttcaagaaatttgagaaaagattactt<br>tgaaattttaa |
| Contig45_<br>gene_96 | 1227 | atggttagaaagcaagacgtcgaaaacgcaagaggaagatcctatgctgaactacaaaccttgtgatgcaatgcttgttcttgcatt<br>gggatttctcatcttgcagttatcggctgaacttacaaaagcgttatattcagtgatatgaccctcaggagcgacaggccactgagtcaa<br>ttaatcaaatcactaactactcaaggagaacagttaaacagtactccagacacatccaaaccagtcggagaaggttatgtagaacaagtaaa<br>gtttataaggattcgaaaacggtaatctgattagtgttgaaacttaa |
| Contig45_<br>gene_97 | 1228 | atgaactgatattcagcgtattgcagtaagcttgcagctatcctgcttctgcagctagagatattatatatcaaaattcttatatct<br>ttattaaagaagcatttgattcttgtactgtcttattctatcataatggctttgtgtcttgccctggcttctcactgagcagtccta<br>attcaacatctatagcttctataattctatatattatgtctgctgtattttgtttgctattttcactgtattgttagcttccatttgcaacagtctatgctccaag<br>tgtatcctcctgcattgtacagaactctctctcttaatcttctatgtcaattcaggactaattctgtgtgttctaatggctatattgatgtgtatat<br>ctttgcattgtaaggtcagatttgtgaggattatagagtgactcattagttgttgctcttataatgtgacactttt<br>tctactctatttccgatttcattattccaaatatgctccagtatttgcaaatcctcaacagagtgactttaatgcctattgagtcaatagttgttatggt<br>tgttccttatagcattgcttgattggggcctattagaagaagaactaatagattagaatga |
| Contig45_<br>gene_98 | 1229 | gtgattatattgcaatgacaattcctggtgttgacttcttaaccactgacttaatttcaacaagtcttttgatacctgtgttatcat<br>actattgttttgtagttgtgagatcttcagggtgcttcacttgaggcttatcatgaatacacttcaaggacaaaggtatctgtagatagcgtgtcca<br>atcgattctggagattccgattcaggtctgttcatgaagtctgaatcatagcaaactctccgattcctaagcttcaaaaggacattctg<br>cttaagatagcaagcacagagaaatatgagcccctacacgtatcggcccctacacttgcccgtaagctcatcgagaatgaagagggctaactgacaagtc<br>ccttgagatagcgtcaatacttgctgtaaacttgtccggcgttatgagtgttgtatcaacctgagtgtggtatcggttccggtgcttgttgctttatttca<br>aagcttagaaataggtgtatggaggaatatctatctaattctagatgtttatctgatgtttgattttatgctaaacattag |
| Contig45_<br>gene_99 | 1230 | atggattgtcactataccctattgcttgattaatcctataacattagtttttaagatagaaaataattatatataataatagc<br>catagacaccatatatgtgtttaataatatgagttttataaaccgctgaaaataagattcacttcagcatcagaaactcta<br>cagaaatattagctgaatccctattgacctgatttcgttcctccttgctcctaatctactgtttttaaccatttcaatctcccaagttt<br>ctaagataatcgactcttttttgaaatcttttgaacaattgacgtattcctttaaaagaccatcttgatgagattttaggattggccattct<br>tgtaatcctttgtatcaaccctttgaataatacctcttgatccaagcataaacagcatattcgacagcctatgttgtctatccacaatcacaa<br>ctgtaggatatggagacgtgcttcaaattcatatattgaaaagtaaaaggattttaatattgatattcggagtgctaatctttcagcaata<br>acaggagcaatgaccctctacttttgcaagaaaaatctaaacatgcacaaagactttaacattacagaaaatgacgacaatatccggcttcaaagga<br>agacttaagcttcaacagaaaatctaaacatgcacaatttaaagaagaagaattgttgaagagttaaaagagaaatggaatg<br>aaatgaaagaagaatttaagagaatctagacaattaaataaagaacttaaagagaagaagtttatttaatgagaattgaaaataatga |
| Contig45_ | 1231 | atgttattgcatgaacaggcattccagttgataggtgaatctatagttgttctatcatactataattgtcctaatact |

FIG. 9B-54

| | | |
|---|---|---|
| gene_114 | | tggaatcatactcctagaagaaacaaattggtattcctcactcattatcttgttgtgaatgtattcattcccctttgaagagtttggcta<br>atttcttaagattggatgacgcttggttgaccatattggaatagaggtgaggaataagtaaataagcaaagtttgaccagattcctcctgaa<br>gagaagataatcgttcttccacattgtcttcttagtctagaactgtgaggcaagcctaaggaaagcggatcaaatgcaaattctgtgaaagtg<br>tgcaataggaactatcaagtcaaaggcagagcctagtggatataaggtgttattgtacctgatccagcttgtaaagaagataatagagcaaa<br>acaagtcaagtcagttgtaggggttgcctgccatggatagatttgaaccagaccatgatggcactttcagactctatcctcaggagttcttta<br>tccacttctggctgttttgagacaagagtggatgtctctaaggtcttaagcacaatgggtattgtgatatagaataagcaaataatccattga<br>tgatgaaaaggacgactctgaagacataggtaggataaaacctagttaa |
| Contig45_<br>gene_143 | 1232 | atgaatttaacttaaacttcacaggtatatatgacatgattttaattttatcagagttcctattatgggctctgcagatacaattcctgagtctctgaggaccat<br>cgcattaatcacaggtatatatgacgtctaatccatgcaatagcagcataaaattcgattttataaagccattaatcaaattggacttgccg<br>gatttaaggaaaagctctttcaaaattgattctgaagagattatacagcatatacatttcattcttttagctcatatatcttaagccctattgtcagttcagttaacttatccaaggta<br>ataagatatcttcttcaaaattatacagcatatacatatcggtataaatcggtataatcggtataactcgtataatcggctgtggctcttatttgctcgcctatattttatacaccaaattga<br>tgaaatcaatataaagcttatcatcatctctgtgatgattgccattgccatgtaaatttcactaaatttcatgactaaaatcatttgctcttatttgctcttatttcagatatatttattgctctttaggacaatat<br>taattgtattattctctctgtgattcattaaattcactaaatcgtctacaacatatgaatcattgtcttctattgtcctatgaaatcattgtcttattgctgaataatgattgtacctgaggctacctttcaatcagatca<br>gcatatatgctagattcattgaaaaactatgaactctgcttaatctgcttgattttagctatctgaagtacgatcatcttagaagtagtgtgtctagagaaaagcttagttaa<br>cctaattacctctggttaactctgcttgattttagctatctgctttagctctgtgtcatgtttatgtactgatcatgctgcaggaaattt<br>caagcaatttaactgatctggttaatctgcttgattttagctctatgctttcatgctcttctatgctgtactgatcatgctgcaggaaattt |
| Contig45_<br>gene_146 | 1233 | atgaaaggacatgaaacttaaattacgattatgcttcttctatgctgttcttagcaattcagagattcaggaccattcgtttgtcctatccaatacatattcgtccaagattgttgaaagct<br>cctaggatacagaggattctacgattctacgaaatgcgaagcgagcccctgaactgctcaccaaatgtagcgaattagctcaagcggcaaacattccaaaacctaag<br>ctatgggttcattacttatccgaaagcgaagcgagcccctgaactgctcaccaaatgtagcgaattagctcaagcggcaaacattccaaaacctaag<br>gtaggcattcaaatacctgtgccaaatgcattgcatttgcatatggaagatccatatccaaacatacaatcgatatgccattacaactgttgttagtgccatac<br>tctgaccatgatgagcttaagcggtcttagccaggcggtcttagccaggcttcttaatctctccggagtgaacatgcggaggagcattaatcggcttttagct<br>cattaatctgctattattcctaggcaattgattgtactcttatctcaagagtaaggaatattatgcagatgcggaagcgtagagcttgatgtgatgcca<br>acctgaaaaattagcttcagctctttatagcttgtcatcctaggagttagagaatcaagatgttgaaggaaccaaagcat<br>tttcttaactgatatcagcaatgcaatgaaagaaatgaactaatgcatttcaggatcccagctgacttcaatcgcgatggagtgttattagcaagaagaattg<br>gatcagttaaaaaacaataatgtaaagatttcaggttccaataagattatgaaatgctctctcacacatccagcatgctaacactcgtctcactccaaaactaag<br>attagctgatatgaattaa |
| Contig45_<br>gene_150 | 1234 | gtgaaaaagatgatatgtccaaaatgtaatacagtaacgatgataatgaatgctgaataaatttgtgtttgcagctgaatacaactagaat<br>atgtcctaattgtaacactgcaaataagcaaattccaaatttgtcataagtggtactacctttaagccctgtagatacatttaaaaaggaa<br>ttatagaagaaaataacaagcaattcttcttagtacatacaagataccttataatctgcgcttttagttatttactgctatcgcgctgttaca<br>ggagtggctatttttcggtggtgacggcaatatggatcaattcaataatcccttggcaaatgacacatgaccatatgaccatagacaactaaataatta<br>tgccgtaaatcatgacaatgtaagccaaactcaaagtaactttacaagaaaaaccagatgaactgacaaccagaacaatacagactgtcaatcaga<br>ctgttgaaaataaaacaaactcaacagttcagcaaagtcaccagtcgaaaaagacaaaatgcaactaa<br>gaaagcataacaactacaacagttcagcaaagttcaacactgaaaagacaaaatgcaactaa |
| Contig47_<br>gene_1 | 1235 | atgaagcatagattaaatttagataagaagaccccaaattataatttgttgaaagaaatatttaaaattttgattcaagagaatcaaacaaat<br>attggtatcctatggttgatttaaaaactaaacagaacaatattttgctttataaatcatttttataagcatgttcttgaaattgacattccattca |

FIG. 9B-55

| | | |
|---|---|---|
| Contig47_gene_12 | 1236 | tcctaaatgaactcaaatccaatagaagactctgcaaattcctaatatttctgaagttctgactgcagatcaagtttataaatctttcagaa<br>ataaactctgaaaaactttataaaatcattaaacgaatctaaactcaagaatatggtcaaaaggaggaaaaaagactttcattgtcgatgc<br>gactccagtggacttgatatcaatttccgcagaataaaagagcaaagaacatctcaaaaaatgaatctcaaatggagttattctccctcta<br>aaggttattatattgatttaaagcgactgttgtgatgattacgattctatgaatcctgtttgcatttaatccattctgagctccaaatgat<br>gcaggacttttgagagatttagaaaaccttcaaaaagacaaatacaaagaagagatacattcagaaaaatcagaaccgactgtgacatttaa<br>taaaaactaccaaataggaatcagcaaaacaaagagaataatgaagaaaaagattatacaacaattaaaaanggaattaataagaaaaatagat<br>cctatccactagccgtatttaaaccaattaaaccaataagggcaaaatagaagattttttcaaattattaaaacaaggctgatatgagaaaatccacaaatatac<br>tcatgggagaaattaaaccaatagggcaaaattaaatgatttttggagcactgattatctcacaaggatttact<br>tctaaatcagtagaaaaaccgtttatctaaatgtattttggagcactgattatctcacaaggatttact |
| Contig47_gene_21 | 1237 | atgataggtgacgatgacttcttatgcagaatgcagctatcactatggagctagcgactcagagaagatgtatgaagaggctatgatggctc<br>ttcagactatgttccaagatactcatcaggaggcagctatggatcttcctctgtgcagaaagctcagagagcgtagccttgagtagctgcc<br>ttataggaattctaattgttcttggaatagttgttttgcaaacattgcattccagcaattactaattcattgtccagttcagtgacagtgat<br>gatttgaatattaccgatacatctattcaaaccagtataactcaaaaatcactaccgattatgatatcagattacataacaaagagaagcta<br>tgccagcagcatgccacaaatgttatttttctattcgaaaatgggaaagtattgtataatgacagccaatatgggaacttgctatctgggaag<br>tgccataacaataccattctatttgatgaaagcagactgcatgcaatattgaagtatataaaaccaattgattctgtgagtgtgcataccgtgaa<br>agagtgatgttgataataaaaatgttataaaagagttattaattatgatacattgtatgattaa |
| Contig47_gene_22 | 1238 | atgcagaactcatgacaaaatattgtagtagatgatacattcttgcaatactcttccaatagtcgaatagtgtcgagcattatata<br>ctcttgaaaagaagaagcattctaccaaacacatgaaaacacatgaaaatacataatcattgttgtatgatgcaataaatatccttttaattg<br>catttggcataattaccataccaccgtgggacaggttaa |
| Contig47_gene_26 | 1239 | atggataataataagaaatatactaataatcattattggaataatagtcctaatcgctgcagcaggattattctagtgatgttaacatcagaaaattatga<br>aagaatggagatagtgccaaacgggacaagcatatagatagtgtccattaaacaagaccacatatgatgagaattccagagcgctagagtttggcatt<br>gggacaaggggaatattagtcacatacaatagccatggagataaaacatttaagagtaagtgaattggcatttacactctaaataaataata<br>gaaactgagagaaaaggaaaatatcgatgattacctcttatgtaaatgccgatgagatatgggaaatcgagctattcgatgccattaaatt<br>acattataccggccaaattctattgcattccattagctatgttttccagtaaataagccggattttcaataacacaatgaaaactgcaacactgtgttccaacgacaggaggcagttc<br>atatgccaaatcaatccagtacaacagctatgcaaacactgatttgcaaatgccgttttcaactgtggaaaacctaactcagatcatcagcaaa<br>ggattatgtaaatgatgccaattttaagtgatgtcaaaacaacagtggaagagaaactgaattaatattgatgtgctaaatccgatttggagc<br>aatacattggaaagttgacttcataa |
| Contig47_gene_26 | 1239 | atgccattggatataattgaggatatatggaagtatacaacaaataaaacattcttttaattatttgtttattctactgtttttgtat<br>gttcatgcaaattttgatgaaatgaggatatcctatgcacttatctgtcaatgatacctttatattttcattgcagctatgaatgctataa<br>ctaaagatgtaattgataatggtaagcgattgcctaaaattaatcaaagatgtcattgtttttgggaataaaatcaactgttgttttattgta<br>tatctttcgtcaagggatatttttttccctagtatctttccatcatattcttgtaaatacgcttattttattgttgtgatttgcagtatttttcaccatgttcttcatgg<br>aacagcaccttattattttcatcataatcttgtaaatagcacactgcgcagttttggatgctttaagattaaaagattattgatataatcggatggaga<br>ctatatgcgaaacattatacagtaattatatttttattgggtttccattgctatagagacgagagactccattttgtcttgattatat<br>tttaaagtattttttaggtttattattgttcattactcaatattgggcatattgtcagttaatcagaatatataaattaaaacaaactaa |

FIG. 9B-56

| | | |
|---|---|---|
| Contig47_gene_35 | 1240 | atggatattagaaagtaattggaataatattaatcattttggtttaatcttttgcaatctacccagtttacagcgcccaagcagtctcatgat tgcaggagtagctctaatagcagccataattggtattggcttaatcctgacgattctccatatggagcatgatggctgagttcagcagcaaaatat tgctgggaatcatagcagccataatcggattcatgtctagtattttatagcaatagatggaatatcaagagccacagcaatattgacttaatcttaattga tttatactgatatttgtcggttttgcctagtatttttcacagccattatcacactgcagtctgttgaatctgtatgataatgaggaataaccttcctag atgcattatctgtgcttcttctcacttccacagccattatcacactgcagtctgttgaatctgtatgataatgaggaataaccttcctag caagtggcataattgatgaatga |
| Contig47_gene_36 | 1241 | atggataaagaaacaaaagaaccgtctaggagaaatcagagtcgcgatgaagaaatacggcttgataagatttaggcgaaagcgcaaaaacag gatacgcgaaagatgaggaagagagcctccattgatagcgaagttccagtcaagttccagacttgctcaggaacttgaacaacct tcatcaaactagcgcagctcttaagcacaagcctgacatgtagggaagacattgcaaacagcttgcaaccttcaggacgacaaccctgca atagctatgagcaggtaagcaatagttgaaaggagcttgaaggagacattgacgaactcttgcgaattctcacatgagcatcttgcaac cgcatctatcggacaggttcacgaagttcacctaaatacagggagcatgttgcagtcaagatccagaaagaggaatcacagacaagattgacc tggacataagatgaatacattgcaaaccgtgcagacagattaagcggcagattcatgaacatgcaaaggattgagatgaacttgtagacaatcaaatgtccacat gaccgcagcatccacaagaaatactgctactacaacaaagtccttacaacagcacatttatcaggagcaaaactgaatgacgtatatgcaagcgaagag tcagcaacctatcctaataactctgaaacacagccagacaatgtattgctgctacttggaccagcatcctctcatagagcatcatcaatagacgaccaacctcgcaga gaaaaatcattgacaaaaactcctgaagacaatgtattgctgctacctggtatgtggaacctgacgtatgtgatgatgtactgacatcttagact gcaatcttactcattatgaccaggacattgacgagtaatcaaccaattgatgtacatgtgacatcttagact |
| Contig47_gene_37 | 1242 | atgcagaaatagattgtttaaattgaagataggattacgatttccatttcataaaagaatccccatattcaaaatggctgcttgt cttattctttgttttataattggatccatcttatcaatgagcgatagttcaatgtttcatatgtgcatagtcttatcgatatcttata tatattcctagactggactataagcaataattagaagccatctctcaagagactgccctgcagtgcactttatcgacattcatcgatatcttata tatgcaataattatggagcaataatattgaatctgttgaatagtgagcaagcggaatcattgtttgatcctgaagcagtaggagctcttattaa gagcgtcttcattaatgggaagaattcatcaagttcttccagcatcttgcatcattcttgcatcaatatggtcatgtcatgttcatataccgtaaat tgtctgtggtgatttcagtcgcattgattttgcatgttatatgcaatatttatgccatgtttgcatcatttgcatgtcatgttcatatgcattgtcatacaa ggcttgatcaattttgagtttttttgcatacatcaagacaaaaatataattgtttcctatataaccattattgtacagatgcatttatctt tgcaatgctactgcttgactttggataa |
| Contig47_gene_41 | 1243 | atgatatgtccaagtgtgaagtggaagtgaaaataaggaagttctaaattctgtaaactgtggtggaaagttaactgtatagttctagacctaccag caccaatgctagtgctctcatctcaataagctcaatcaagagcaataagaatcttttgattgttgcaactataattatctgtgttgctgttgcaggg ctatcctttttatgagtgccagtccactgattatgagtggtggcaagcggttgaggctactaagcatcatcatcatcatcatccttctgaattcctatgac agttccaattcaaatgatgaaagtcagatgattcagcaagcaagtgaagattcagcaatattcggccgtgaatatataagaatcataatatg gggaagagttccaagaacagcatcaagatcagaagatcccaaagcatcagaatatttcctgaagcttgttactcatgttttctatgaagacagcaagttgacgagaatg gcttttgactgacaacagttaagagcttgtcagctcactagagaagcttgcagctactagagaactgttgcagaatacgttaacgtagataatgattatgttgac actcccgaccttgggaggagggatgaagcgttagaacaagagccgttcaacagagcgttcaaccagatgtttaa ctgtgctaaaaagtcaggaacagtgaacaagcaggtcaaccagatatgtttaa |
| Contig47_gene_46 | 1244 | gtgtctaaaaagaagaagagaataattgtcaaatagatgattgctctagtgaacttgtgcacctgtcagtcccttttcaaaagagggaatattatttt aattttcatcattgttttattcatgttctgtttttcttattatgactaatggattgattaa |
| Contig47_ | 1245 | atgacaaacttataaaagagaagttaaaggaataacgaggaaagtcctcaaagcttaagatagtaatgcatctctactttacaaa |

FIG. 9B-57

| gene_58 | | tcctccgattattgtattccttgttttattgattcattgtgctgcatcaatcgtttcaagtagtttcagctttgactgga<br>tgctattttgcaaatcgcgagatcatttcactgtatttgcatctgtcctcctatgcaatcataatctactggcaaagaagctgaatacagat<br>aaggacatctcaaatcgtgaagatcgcttcattcccctatcgtagggtgttgtcctacctgattgcttgtaatatcattttctcgaatt<br>gccaaactcctgacaattcttctctattatgtcgcaatcatgcttctcttggacctattgtgtcattatttgactttcactgttggaacatctgagcagg<br>caggattaagcgacctgagctgcctaatcatgctccttggacctattgtgtcattatttgactttcactgttggaacatctgagcagg<br>gtcaccttaaaagcatacaatggctcaggcaatagcggaggaatattcgtatcgtatccgtatcgttctatatcctttatatgcgcct<br>gtttaaatgagcgttccaggccttgtgccgttagcgcagaatcgttctgatcatatttgccctattggtgaaagctatcttatatgcgcct<br>ggctttggaaaaagaggattgatttctatattaagcgctatagtaagcgttttagtaacaatatttgcaggagatacattctcatgtataaggaat<br>cccctagcgcagtcttgattcttatattaagcgctatagtaagcgttttagtaacaatatttgcaggagatacattctcatgtataaggaat<br>cagcaggagcttgaaaggaaaacctatcaatagtgctctcacttgctcgcgttcgattgatatatgtgg |
| Contig47_gene_65 | 1246 | atgaaagaaagtatgctctccagactgtgagaaagtattagaaatgaatcagaaaacattagaaaagcagaatcatgttattgctgtgat<br>tgtgtctttattctcgtatggcatattcatgttctttaaataa |
| Contig47_gene_67 | 1247 | atgccatctgaaaagtgaaagaattaatgaaagccttaaaacaaagaagaagacaaattcttcaagcagacaaatatttgtatagctattgg<br>aacagtgtagtgtagctagcacattcttgctaaagatcctaatgagagcacagttgcaatagcgcatcattctttcataattactgtagtctac<br>caggatacgctgaaagcattcttgctaaaagatcctaatgagagcacagttgcaatagcgcatcattctttcataattactgtagtctac<br>ggattcttcataatcaactctaccttagagtgggaatcctaactatgtaacagatttcttaaagaagttacattcgcttattcaagcagctatgcctacagctacaaa<br>ctatcctgcttgcagtagagcaaagagctgagtatcctcctaagaattaaatatcatagagaagaattcataaatatatgaaaccagacatatttcgttc<br>ttaggagttcttatatgacactggagtatcctcctaagaattaaatatcatagagaagaagtcataaatagagtaaagcttcaagagataagacattagtta<br>caaacagaaggaagatataaaatccgacttgaagactccttgaagactcccttgaagactccttgatgatgatgtctgatccattagagaagacaagataagacatatagta<br>aattgattaaagagttaaagcgacgatgcatgctctgattgttatgaaaagaggaagaggaataattaa<br>gcacaagtggttatgagagagaactggtatgttgttattgaaaagagaagaggaataattaa |
| Contig47_gene_68 | 1248 | atggttccattgcagttttcagttttcctattcacttcagttgagttgaccctccttgaccctccttgaagtgagtgagtgtcctcttgaaccagcttgccatcattat<br>tccaacggcgtccctcgagcctatcagcatcagacaggagaacagctccattgtcagacaggatagttgtttttggatattagattagtgtttggattacagttgggg<br>gattctgcgagtctcttagcaaaatggttcctacagaaatcgatttcaattgttaaatgaggtatcgttgattgattttgtagcttgatatgcttgatatgcta<br>tttgcctccagtccgatgggagagtctttttgattccatcactttgcatactttgattcagcttgattgacgtattggaacatcctctgtattca<br>gcttgcgttggccgagcagcattgggggcttattatctttatatcttgacgcattgattgtcgattcagcttgattgaagcattgctttggataatgttgcttaggatagtgttgcttgata<br>aacttgtagtagttgatttgttttcagttccgatgcgactatagagctacatagagctaaattagttatatatgcctgagaaagataaaacaaatcttt<br>tgcataatttttgattttatatgcaattaaaatgcttgatcaattagcatcttgttagtctataa |
| Contig47_gene_69 | 1249 | atgaattaaaaataaacaattattccattgaataatattaatcattggagggtcttttatacttcttaagtggcatagaccaattcat<br>aagaccattaccccaacctattctaatgggctccctcaaaggtaagacatactattcttgttcttattggaataacaatcatcttgtccttcca<br>ttgagataatgagaggattcataactatcttatgaatctcattccagaaaagctaaggacaagacttttatttaagctctccttgatc<br>ttgttttaatacagcaatatcaggattagctgtagaattgtacttaagagcatctcttgggcttaactgaatacaactacttgtaatcatgaa<br>tcctagccttacaagcacaagctttctccattccatccattccattcttatatatcaatatttggaatctcttggaatcttcaatgaatcatattccagcag<br>gaatccataacaggaagctcattaagtagctatgcccaagtgtgataagcctgctctttatattgattcaataacttatatttctatggttcta |

FIG. 9B-58

| | | |
|---|---|---|
| | | tctaatcaaaggcgaaaggcagctctatgaatcctagaatacttttagcttttacaagcactcttggaataatcgattgattgacgaggcctcttttgcaac<br>tcctgcaatcggaggaatctatggaatcctatattgatgtacatgaagagattttagatgaattcagacttataactgaaaaagacaaaa<br>gagatgaataaaagagaaattaaatgaggaattaaggcgattaagtcaatcttaacaataacaataaaagaaatatttgaagattgccttg<br>cctcatattgcattgattctaataatcatcttaagttctctgttgcattctatgtgcatgtccagattcttatgaattcttatatctaatgg<br>ccacgatcttgatttagatgaatatgataacattaatatatcagaaaatggagataagagactgttgttcatcttt |
| Contig47_<br>gene_79 | 1250 | atggttaagattagtcgtaaaatagttttgatgaagcagtgaagaagaccctatgtcaggtgttgccaatctttgtggatgccatgttggttat<br>tgcagttggattgctgtgttttagtcattagctgtgaatatgcaatctatcattcaatgagatctatctcccagcaaaagcaagaggcta<br>ttgatgccatgaatcaggttattgaagttggatcaggggcaacaattaaatgagactccagatataagcaattcttcaggtgaaggctataccgaa<br>atggtaaggtttatcaggacccctaagacgggtaagctgataatgattgaaaattag |
| Contig47_<br>gene_80 | 1251 | gtgggtggagaattctaacttatatctttagacacactctagtcaaagtttacagattccagtaatcatcattcttacttatattcgctgttggagc<br>aatcatcctttaggaggcctaataagtcatagaagaatatagtcagataggccatctcagatgctgaatctcagatgctgaatcaacaagg<br>ctaatgacaaatctgagatttttatccattgtagactcttcagatattcaaactctcaaaagactgtttaagagagattacagattctgactgg<br>gacaatcaagagtgggcctgctaaaagatcaagatcaagtttacactccattccaatggctactgatcatatcagatatcatatgatgaaaaagcgcttgtcatacactgacataatcactcg<br>tatcggtcctacattagggcttatggaacactcattccaatggctcaggtccaggtcgctcagtccaggactctggatagtcatatgtcaaggcttgtgtaagcaagataaggcgaagatagcgaa<br>caattattgtagcattgatacaactgtgtaggtaggtgtcgtcaggtatcgttcaggtgtctcggtgtatataagcttaataagcttgaataagcttaataaattaa<br>tacattaacaatattgatgttttaactgatgtgtattgaataagcttaataattataa |
| Contig47_<br>gene_81 | 1252 | ttgggagaaaatgatagatctttgtcttcttcttagtgataataaaatatgacttagataatagtgctga<br>tttgaatagtttaaatcccaataactcttccatagcaatataattgcttaaattccaataaagaacaaataattattgctattgcaagaatcaaacagatcttaatgatg<br>atttaaacgattcagataactcttcctgataagtcctgacagttgcctgaaaacttcagtgtttcttgatgaaatatcatgataagcagttgaatgatgtgagatagatttctcc<br>gagcgcaataatcaaatctttcctgataagtcaaatcttcagtgtttcttgatgaaataaccgcttaaggaagattatggggatgcac<br>ccttgtatttgaaggatttcgctgactcgatatgcaacttgcatatcaataatccaatctacactcgaatcactgcaagaaaactcattcaagaata<br>ctgcattcaagctttctgcattactaagcttgtcttatgcatctacaatacactaccgcgaatttcaataggttaaagataaagcaagaataggttcagaagtattcattcaaaacgatttgcatctcacgcaaggtgaagg<br>gtctatctgattacattagcatctacaatatatccaatactaccgcgaatttcaataggttaaagataaacgaataatctaaatgaggcttggattatgatatagaataatcaataccatgttacagattccaccca<br>ctttagaagaacacactgattgtcttgttcatgcaattcaaagctgtaatgatcaaagcgtccagttgccattgtccagttgccattgtccagttatcaaagcgtagtcaagaaatcaataccatggtcctgttacagattccaccca<br>ataagaacagataatgccagcgctggtctgtagctcaaagctgtaatgatcaaagcgtagtcaagtcctattctattctattcttatgtcggtaatcaatctatgttacagattccaccca<br>agcagctgttgccagcgctggtctgtagctcaaagctgtaatgatcaaagcgtagtcaagtcctattctattcttatgtcggtaatcaatctatgttacagattccaccca<br>aagctcattgtgaccagcgctggcatgcatattatgattgcagtgacctcactgtcgaagaaacactcttatc |
| Contig47_<br>gene_86 | 1253 | atgctgatgaattgctacaataataagttcctagacttcctaggagtcattttagcaatagttcttttagcgtttgtagttattggtgc<br>aattattgtaattgtcgcaactagaccaatttttagatgttaccataatcttcatcctaatgcaagagtaagagcaagaaaaggaagattgtttg<br>atgagaacagatttcagaaagttgttgaagcaacaacgttgatgaaatcacaaactatctcagaggatctcctgactatgcagactacttggat<br>aattatacacttgaaaaaggcattggacattcaataacattaaagttttattgactgctaagcaagcaggattaaacgaagaagcaactgctgaccttttaa<br>agtaatggctaaaagtcagacatcaataacattaaagttttattgactgctaagcaagcaggattaaacgaagaagcaactgctgaccttttaa<br>ttcctactggttcttttatatgaagacttccacgacctgaaatatgaagaatatgaaaagactgaatagttgaccgacgtgatgtgtaactggcgttgttgcaggatttgcaggatagttgaccgacgtgatgtgtaactgtaactggcgt<br>ccagtatggaagaagcacttccagatatgaagaatatgaagaatatgaagaaagactggaatgtcctttccttggaatcagcattagatagtattactttatccaaattgct<br>cgcttccctgaaacccatctgattagaactatgaagctatcagccatacacatgattgataagctatcagccatacacatgattgataagctatcagccatacacatgattgatagctatcagccatacacatgatt<br>gagcaaaggctgatggttgattagaactatgaagctatcagccatacacatgattgatagtggatatcaatgattgtaagaatggaagcttaagaatggaagcttaagaatggaagcttaagaatggatctttatg |

FIG. 9B-59

| | | |
|---|---|---|
| Contig47_gene_88 | 1254 | gaagctgaagacgtcactggtgtcatttccggttgtattccggtttggaaggaaccaaatactcagacgtcctgttgaagtgcttcctgaatacaatgaaactgg<br>atctgtagctctctttgaaaaggcttagacaagttcttagtcgactctgcaaatcctattccatgaaaagc |
| Contig47_gene_89 | 1255 | atggtagaaattgctttaggtactgcttagcagcaattggtgctggtgtagcaattggttttgctgttaggttccggttaggacaaggtat<br>ggcagcagctgatctgttggagctgtgagcagaagataacgatatgttgctagaggtattatttctcagcattaccagaaactcaggctattt<br>acggattcttgattgctattttattactgtatctccaggattattaggtgagagaaggtctccacaactgcaggtattgtagctataggt<br>gtaggtgcatctattggatttgcaggttattatctcgatcattacagaaactcaagctattacagttcttgcatcttactatgtattcggtgaa<br>catgttcgaagagtattatctcctctgattacacagaaactcaagctattacagttcttgcatcttactatgtattcggtgaa<br>tcttaggttag |
| Contig47_gene_91 | 1256 | atgtaagcttaatgttataacttggacaaatacgctggtcctacgtcagtgcactcacgacgaggtattgtccaaataatgatattc<br>tgaacgtattcagcaagatcctaagctagcagacttttgaaaccttcaaaagttacacctatactggtagctgtcctcacttcttatgaaga<br>caagcgcacttccgatctctccggagatcgagatgccctcagaaggtcagtccttatgctgaatcaacattaagccagttgaggctgaacaaaggtattgaaga<br>cctaagagtcgaggatgttgatacagagaagtaaagcttatagcttgaatcaacattaagccagttgaggctgaacaaaggtattgaaga<br>taagttagccgcactagacagtgaagataccttacaggttgaatcaacataaagttagctcttagttctaaaaatcgatatgattgatctcttt<br>taagcgattcaaaagtactcctaccattgttggtaggatgctcagtcagctcagaaattcaaaagtgaatacagtaagattacagaggat<br>ctcttttacgaattggttcgagaagttcgagaagtttgaaactgaggagttacaaggagacgtacaatattcttgttgtcgtagcaacagagttaaggatgacatctataccttact<br>taggaaaaatgaattgaattcgagagtttgaaactgaggagttgaaagtgtagcagaagactaaggtgaggcgaccactgagggatgatgaagcgcacaatatgaaggcagtgcagagaaaacctgagcaagctca<br>aagtgaagataatccaagctaaagctgattttgaaagttgtagcagaaggacactgagggttgtctcttgaagcatgggcagaaactgagcaagctca<br>aagcataattgagactgctacagatgccacgttgccacgtgaaaacagaagaggttccagacaatgctgaagacg |
| Contig47_gene_92 | 1257 | atgagaaaattatatattattggctttttcagctctcttttaatcatttcagcctttggaatttatatgagtacctaaccaggtttagacattat<br>tgcatcatcccttgtgcttgtgttgcagtgttggttgttgacctcttgaacctgctgttttgaacctatcgattaaagcagctatctcattgacgat<br>tggattgtacttgtactgtatcactcacatttacgctttagtaagtcctatcaatctaattatgtcctctctcttgaattatttgttgctatagctgttta<br>gctatcttagaaaattaccagacaatatatattaagatactctacagatcttaa |
| Contig47_gene_99 | 1258 | atgaaaccaagatagttcgtgcaagtagtttgtcaagaggacaaaggaataatttatgaaatcatgttgcaaagctttttgaagatgctaaatacactgtcaagtccagga<br>taagaattatgtcctctcttaagaagacaaataattatgaaatcatgttgcaaagctttttgaagagtctaaatacactgtcaagtccagga<br>ttctagttaatgtggcctatttgcctacagtgttttgaattgaagtattctacgaccaagaaacttggataaggcgataagaatactcagattggaataa |

FIG. 9B-60

| | | |
|---|---|---|
| Contig47_gene_100 | 1259 | gctgtaggaaattatataggatatcacacttcattgctggattcattcattggaatgatcattattcacttataaccattctggaatgtctct<br>tgaaagataattccttggaatattcaatcaatcatttatataagcctgattgtgtataattggctattccag |
| Contig47_gene_103 | 1260 | atgagataacaaccaaaaggaagacaacaatgtggaggttatactccttccatggagtctctttttaattgctctatccgtttttccctaa<br>tggatgtgaagattga |
| Contig47_gene_116 | 1261 | atgaaaatcatgcaattcacgtaagaattcacgtaaagaattaaagaaagagaattgatatgaacttaattcaaaactacacaattatttaatcatagc<br>aataataattgcagttattatgacctatatgcatgaatgaataaaaaacccaatcattattgacttgcatactgccataattgtaattctagcta<br>atttatacctttactaagcttaaaaatag |
| | | atgtttgttgaagattaataataattatcaaattttatagaaagcagataagcgataaaaattaatttcttacaggaatattcttaa<br>ggcaggaatattcacttggcctctcaaatcattgctatattgttcatttcaatgttttacattgatattgcttgatgattgcattgttat<br>tttcatttgatattctattgctcatttccaattcaatggcttcaagcaatggcttgaaatagtcttgagaatgtcttgttgattgtc<br>gaagagcttgaaaactcaattccgactttttaagcaatggcttgaatgctgcggttgaatgaagtcttttgatgaatgcttttaggaatagg<br>agagcatgaaacgccaattatatgatgagctgcgcgtagttaaagattatctcataagagtggagagtcttgctgatgttatagtgat<br>cgaaaggcttgactcagtagttttaaaagggaaagaaagtcgtctgtaatgtcaatcatgttttggttttggcatctgtgt<br>gtcagtgatgattaagggctatgctgattgttggagtcttggagtcttggaatagtgtgcatatcaagtgccatctgtcaactgcccaacg<br>agctgtccctttgcttggggaatgttttggggtctattcctcattcctttatgaattgaacagatcaagtgccatctgtcaactgcccaacg<br>ttgctctgatctatctgatcattcatgttgcaggaattcctcattcattatctggactacctttcgattcgtaaactgatatt |
| Contig47_gene_123 | 1262 | atgaaatggagattattaaaaggattgggagcattgttggagcatttgtaggatgttttgtagtgatgctgcttgaacatatagccttgg<br>tccgcagaaacgtcagcttttccggaactgaaatcattaatgctttcggatcaataagttgtaggatgggcattgccttcagcgactcattt<br>atgaaaaagaggacattccattacctattcaagtcattccaaatgtaatcgattgggaaccctattgctgtagcagtctatttaggcttgg<br>atgccttagcttaggcataggctataaggcattaataataaaaaagataatagattatctaatgatttgatttgattcg<br>cacattcctagcaaggacattaataataaaaaagataatagattatctaatgatttgattaa |
| Contig47_gene_125 | 1263 | atggataagaaagattgttttcagtgtttcagtgtttcagtgtttcttcctttgtttcagtggcttagtctctgcagttgatgaaagaaatagctctgaaag<br>taagtaaactaatcgttattctgaaggccaaagccttatcctaatcgtgtccaaagaatagccttgtcaatgaatgaatgcaaagactattatgaaggatgaca<br>atgagacagttgcctggagtcctagtgagcgatgtcaacgtgtccaagccaaagaacttatatatgtgacgaataatagtatggacaactgagcgaactgatgcaagcaag<br>ctccttcaaatgcaccgatgtagccaagtagacgtcacgttggcatctaagctttgacgtttgaaatgggcattttgctctttaggaaacgttctttaggaaatgtagagtatcctaa<br>ggatgccctgtatgtcaagatgtcaagatgtcagaatacatcgcggaggaatatgtaacttttcagggcttaa |
| Contig47_gene_127 | 1264 | atgaaaggaatattcttaagaatattcttaagaatattgatgaataataataataataataatcagcattcaatcagcatttaatccaattgtaagctttgttcttcaatagg<br>cataattatcctcctccctttatgcggtttaaacattttaacattttaatgcatgttggatcctttacgaaatactgatggaataactttgccattgcca<br>atttgataacggctccacttttaaggagaacgtattaacagctctatattaacagaaatgaactttgtcactgatgaacgatttcaaatgaca<br>tttgttccgaagagaatctgcgacggagttttaatgaacatatatgcaggagtagtcattcctaaaaactgtcgaggatattcgttttc<br>aattgcgactgacaatcctaagcagcaggcaaaatgaattgtgtgaatgtgttgcaagcagtagccaaataataatcctagctctcaactaacagatctctgctgcaa<br>acagatttacatgcattgaatgcaatagtaaatcgattggcagcttatgaaaagtggggaatgcagaaaggtcttgcatca<br>ggtcccagcaactctctagcggaggctatcagctcactgaggctcacaacagttgaagctaataactcttcaggttccaaactatctttcaggttccaaactatctttgatgtgcatgaactcttgctgcaaacgcataacaaactgttcaagagg<br>gctcaattatataaaccagaaatctgaagaactgaaagaacttcaacgaaactcagcaggttccgatgaagtcgcagaccgatgcgcagaccatcgtaagtgcgagaccatcgtaagcgaagatg |

FIG. 9B-61

| | | |
|---|---|---|
| Contig47_gene_147 | 1265 | gtaaagactatgtagatgccagttgtgaacttgcaaatggaagtggcgaactggctaaaggttcttcacagttagcaaacgttctgttcaatt<br>ggctaacggttctgttcaattggcaaatggttctgttcttgcaagttgctgacggttctgttcaattggcgatggtt |
| Contig47_gene_150 | 1266 | atgttagacataccaaaagaagacctcaagttagaagatcattaaactagtgacaaagaggagatacagttatgaaaagctttagaagaagt<br>tggagcagactatatcgatgagcgagattgagattcgattcaatcaagagaagaggatatataggggactttataattaagacatcctc<br>ctaaagaacatcattactattcaggtgccaattcatcatcaggtccagttcaaataaaagacagtccagcaaatggatgatttaaaatgttat<br>atgagtgtttaggcccattgataataatcttgcaatagcaattcttttggggagttcttaaagaggtaa |
| Contig47_gene_151 | 1267 | ttgaccctgcctggagcatccattggtcttgcttgtttgatcctgagttgttgtccctttatacaattatagcatatgatgctgcattcgg<br>tcagatattctcttcattgagctttggaatggggctggattacattgcaagctatataccaaaggacatagacttgatttcaagtggattat<br>gtgttgttttgctaatagtcttttgaaaactttgcagcattaggggtttctcaattctagatatatgccctgagtctgagttgctgtt<br>tcaaagctgtatccaaggcacaacactgattttgttgttgcatatcctaagtgttaatattttaggaggtgtcgtttgatttgaggccact<br>attcttttttacagttatgttgcaggagtcacaagcatattgtctctcttcaatgtcttgccactcagctgagttattgcttagcattgcagac<br>atatttgtaaataatattatgtttttgttttcagtatttgttgtttcaaaccatcctttgttaaatatattgcccatcctttatattgataatatttaca<br>caatgctaaagccgatttttataaaactggttcaactgaattttgtagtagtttagagtattgcttgcaatattattgatatttgcatttatatttaca<br>aattataataatcttataaaaatggtgaattgttaaaacgatgaatgtttaaacgaagaagtaagtaa |
| Contig47_gene_154 | 1268 | atggctaatgaaatgaatgggcagcaatctgcatttgtactgtcagttctgcagttgattggtgaaatatctgagatatccata<br>tgtgcttattcaactataagtcctcatttacaaaggcctatcgtaaaatcaaaagcctaaattgaattttagtttagcgctccatcttcatcattgggg<br>tcgtctataactataagtcctcatttacaaaggctatcgtaaaaataagcctaaattgaattttatgttgattctcctgttgtcactttt<br>attatgacaattactattcaaccatatggcggtggatgaacaagttagctctcttaagtcttaaagctgtgggatcagatccaaatacatt<br>tttaacagttcattcaagtcgtcagttctcatcaagtgaatggcattcaaactttcaagctgtttcattcaatgatttcatatgctca<br>taatatgttcatttcccataggacttgatgaaggcttaggcgtgttgcccgatacttgttcccaatgctacttgttttttggttataaatga |
| Contig47_gene_157 | 1269 | atgccaaatcaaatgcttaaaagttcagtcagtcgttactgtactgcgaaaataaaaaccctatttatcatccaatttttaatatttgaatg<br>cataacaaataaagttggtgaatgaatgaaaacaccctagtcagtagtcgtgatagttctctttagttatttaggctatgattaaaggttactcaagacgtaa<br>tcaatgaggcaccagtctgcctaagataagccttaagaggttcaattcggagtgaaggaaccatcgtatacattctatctgaccata<br>caagcttcccttttagtttgattcctgcaatgaatcctcagtatatttcagatatttcaacaatttcctttatggaaatcgctcttg<br>gtttttttgagcatgatcctatcagcttcatactgactaagatcatcatgctcattgtctatgaacaatcttctatggaagaacaatcgttgaagatcgctctg<br>caatactagcagagaggaaaaacactaaaagcagtcatttgacttttaaaagaacaaaagaacagttgaaacaatcggttgaagcattataatagagattatatgt<br>gactatcacaagttagcgcgctgttgttttattttagtatttaccaccatctctagtgataaagcattaataagaaatcaagagacagccctcggg<br>atacaagcaattaa |
| Contig47_ | 1270 | atgagagaatccacaaatatctccaaatcagtagaaaaacgttatctatctaagtgaaatgtatttgggactgattatatcacaaggattta |

FIG. 9B-62

| gene_163 | | ctcaaaacgaccatacaacaatatctgaaactaa |
|---|---|---|
| Contig47_gene_165 | 1271 | atgaagcatagattaaattagataataaagacccaaattatatttgttgaagaaatatttaaattatggattctagaaaatccaaagtat<br>attagcatcctatggcttaaaactccaaaaagaacttgcaaataccttaatattctgaagtttgactgcagattcaagttatcagttttttcagaa<br>ttttaaacgagcttaaatccaaaaaacttataaaatgttttaaacgaatcttaaactcaagaatatggttaaaagaggaaaaaaaactttattgttgatgc<br>ataaactctgaaaaactctataaaatgttttaaacgaatcttaaactcaagaatatggttaaaagaggaaaaaaaactttattgttgatgc<br>gacccagtgacgtagatattaattccacagaataaaagactaaagaacatctgaaaatactcaatgagttattcatcctcta<br>aggttattatattgattaaagcaactgtttgtttagattctatgaatctgttgtatttgtatccactctgagctcaaacgat<br>gcaaaacttttcgaagaaatttagaaaaaccttcaaaaagacgaataatcaaaaggagacacattaatcttgataaggatattacagcta<br>a |
| Contig47_gene_166 | 1272 | ttgaatgaagcattgactaaattgctagacccttatgcaggattatataatgtcattctgcctaatgagttcgtttcaatgctagaggaatatccat<br>gattgaatctgttgccaccacattagatccttaaatagatgtcatgcttccatgaaccgatagtcaaagaggtaatgaagaagaaatgaaca<br>ttaaggaatctcttttcaaaacaaaaaacgcagttgtttattataaagaacatgcttaaagacacttcctccactttaacaaacagcgttcataag<br>ataacaatgagatatgaagcttcgctttgaaattgacagaatcatattgtgaaattgacaagtttcattgtgttgttataattgcagccctttct<br>gatgagctcttcaataactgaccattcaataggcctcaatgttatttgacatgcctttaattgcagttttagctatatagtgacttttattt<br>taggagccatagccgttgcaaattacatatacagcagataa |
| Contig47_gene_172 | 1273 | atgacaacaacagaatggctttatcatcaattctactaaattctgcttgatttaagcacaatcatcatatcaattatgtaataatcatagctgcagcaat<br>aatcataaaggtaggaagaaaaatcacttctaagaataggaaaagtatgaaaatcttactgccattatctcctaaaagacatccttaaat<br>atggaattattataattgcacttgcttgtttgattccaattttcatatctgaatatttgtaattggagataagaacgtccaagttggagaaccatagagat<br>atcgttttgctctaaggacatcgtatccaaaggttggttttagaaatacaacaatgattggtatggataacttaaggtaaccattccaaactctgttc<br>tgacgggagaaaggagccatccacaaaggttggttttagaaatacaacaatgattggtatggataacttaaggtaaccattccaaactctgttc<br>tttcaaccaaaacatataaaaacttcccaatgggagggattataggcttagctttgatgtgattgcctcatgactagagaataaatgaagaaggctc<br>aagcaaaagatgacagaggctatggaaaaatatgattataagatagagacctgcattttagctagagaataataaatgaagaaggctc<br>taagttgaaatcagcttttggataaatgattataagatagagacctggaaaaagctgtaatcttagaagaaagcaataaactaatttatgact<br>atctcatgatgaaaagaatgcaggcatcttaaggatgttaaataa |
| Contig47_gene_174 | 1274 | atgataagcaaagaaacatttgataaggacaaggcaaactttaaagaacatgctcctttaaggaataagcaatctgtcctttgctaaggaaatagacaatcctacactgcttca<br>aatagataactacatgaatttgcagggcattaagcgaaaaaccaaaaccggataagcttgctgtttgcttgccagcataggaacca<br>taattacaatctatattctttcatctatttttgaatggacataagcgcctttatcatacctcgtgcttttgatgtttatcctaatggaattcat<br>ttagtctcaaataagttgaactatcatgaaatatctcttagtacagggtcttagcagaatcatttaaggcttcagttttcctaagctatgcagg<br>agcccaggaaaaggttatagatatcctccttgtttatcgacatggagttccatttggtaaagagggtattgggacctttgatttcactgaat<br>tgcctcaaaagagagaaataaggggatcattacagtgacatcaattacaccaaatatcatcaaggggtcttcaaagtcaaaaaaagaaaatgaggaca<br>cagaaatagtcacatatgcatcaattctaggcatcattacgtgacatagccacctatataattgcattgatctttgaatctcataccccgcttcaactttcaa<br>tttaatggagataaattcatctaggcatcatgctatggctgaatgtctgcattcacactctttaggaagctattacgaaagatgt<br>ccttaagcgaaaagatagatgaccatgaaagatggtgaactatggttaacacagtacttggtgattatagaacagaagaacaagcagatttggttgttaa<br>ctttcatatgcagctagagagttctgattgaaaacagtacttggtatgcgtatcaaagcaagcagcagatttggttgttaa |
| Contig47_gene_179 | 1275 | atgaaatgaatgaaatgttgaaatgattacaggagacctaaaaaggcaatcaataaacttgctggcccttgatgcaagcatgctcttgat<br>tttttaataacattatagacagtatctggttgcagggcttggcctgaccctcttgctgaccctcttgctgcaatcggctatgtcacacctctcttatgggtgc |

FIG. 9B-63

| | | |
|---|---|---|
| | | ttgtaggatttgaaacgtatcggtgcaggtgcaacctcacttatctccgttatatcggagctgaaagagggatgatgcaaacaatgcagcg<br>attcactctgccatattaagtgtgtgttgtttcattgtttctcactgttctcactgtcattgccctttgatattagagtcctgcttaagctaatggtgctgg<br>gtctgtattgaaatatgcaatggactatgtgtgtgcctattgcactgttgctgttataattcttttcactgcccctatattgatacctcctatattgtggtgctttcaggg<br>ctgaaggagacattaaacggcaactgtgcctttgcaacagtcttgcaacagtcttgctccatgtcttgcatatatgattctagatcgatattcatgtatgtattggctgg<br>ggaattcaggtgctgccttgcaacagtcttgcaacagtcttgctccatgtcttgcatgatgctctattgatattcattaaaaagacacttatct<br>ctcatataatagaaaggatttccataattatatgctcaccctgttcagttcagttgcagttgcagttgggatataccgcaagcctgagcagttaatcatgg<br>ctgcacttgcagttacagtcattatatgctcaccctgttcagttcagttgcagttgcagttgctgcatatgtcagtggctgtatatcgaggatgagaataatctcatta<br>ggactcttgccagctattgagttgaactgctgcattacagtcacagtgttgcatatgtgcaagaaatgaaaacataaggactgcatg<br>cagatattcagttaagctagtgtctcatatcctcattatatgtatgcatattgctcttataattgcagatcaga |
| Contig47_<br>gene_181 | 1276 | atggatttatttcaactctactgttcaatgcacttgcaatgcaatgatgcctttagcgtttcctaacaaaggatcacctaagaacctcac<br>aaaaagccaagcttatgtttgaatatttcttgtggattcaggcttttaatgcctgttctcgatgctagaggaatccaacttgaatggc<br>tcattacaaccttgcaccttggttgcattcatactctctcttaatcggttcaaatatgattagagaaagtctctctgtgatgaagaggat<br>gagaaggactctgataagtttcattaaggaattgacatgcttgcttgctacaagcattgatgcattgacagttgagttgagttgaataacatatgcagt<br>actaaaagtagatattctaattcctatataataatgttggagttgtagcattatcttacaataattgactttattagtaaaaaataggaa<br>attactttggagacaagtttgagatagtcggtgagtgatcttaattctcttcttgcttgtaaaatactcctgaagtcttgaatttagttta<br>taa |
| Contig47_<br>gene_185 | 1277 | gtgagcagcactaacactgctgttgaaaataaacaggaagagaagaagctttcttaaaacaacaagtttctctaaaactgcaac<br>agaaggatttaagcaaaaggatataaggaataaaatcctgctacaaaaatatgctacaaaaagaagaaactgttgatgctaagctaagg<br>agctcctaaaaggaagctcctaaaagggaatcccctaaagaagttcatctgcggaataaaccttaaaaagattggaattatagcaataatcactaatcattctttat<br>aatattgttaaaaatcagatgaagttcatctgcggaataaaccttaaaaagattggaattatagcaataatcactaatcattctttat<br>cgcaggaatcggacttaatcaacatccaatgcagattccaacatgacaactgtgagtgatgaactatacagacggcatcatcaattcacctactctggtaact<br>ggtctgtatacaacatccaatgcagattccaacatgacaactgtgagtgatgaactatacagacggcatcatcaattcacctactctggtaact<br>agcgatgaaatcacttatgaaaaatcctatcagatgaactcactgtaaatgacactgcccattcctaaatgagaatcctgaatatcaagaggttaatgt<br>gggaggcgtcccagctccaacaatgtcaaaatctgacaatgcactcaagacttgacatctttgaataacaactgaaattcaaaatatgattaataatgtagtttaaggat<br>tcgttgcaaacaatgcaaacactgcaaacctgatacaagctatcaggaaaagcagttaccaagaagcagttaccaagagaaagctacgcaactataactatgaagacacaag<br>caattactaa |
| Contig47_<br>gene_187 | 1278 | ttgattttcagcaatctttgctgttggaatattgctaaggatataatagtccataagctaaatttcctttgtaaatcctcagaatatttgcc<br>tgaaggaaatacaacattgaagcaggttttattattttgatttaattctaatttttagttgtgtattcaaacttcttcttttgacaataata<br>tcatattgccaaacagtccgaattctatgtattcaattccttttagtattatagtttcagtatatagtttcagtatatagtatatagcaataatcatttatgacgtctct<br>aaaaaagcaaatattattgatattcctattcctcatcaattgcattcctattattggcgaatcttattattggcgaatctttaattgaatattggatttgt<br>acgtattcctgcattagtgtcattatatattatgaagttccatatttatactgataagttccatatttatactgataagtaatttgaaaaatcaatacttcttc<br>tcttttcaatagtgttcattagttttattataacattggttgtctgaaaacgaagatccattaaacgcattggttatggtctccaatgcatttaca<br>agcaaggatatacaattttaggtgaaagcactataggaaaaatagaacgtattggagtatattatctggagctgctac<br>agctactttgactgctgcaattttaattaacactttaatgctaaatagagaaatttgatgaaaatttgaagaatttaagtaatttccg<br>aataa |

FIG. 9B-64

| | | |
|---|---|---|
| Contig47_gene_190 | 1279 | ttgtatttagaattttggataatttagccattatcctcataattggagaactgctgacaggtggatctgacttggatc<br>gctagctgctgcaatatttaactatttccaatttagcattacaatccaaattgtgcattttattgttacagtcattttatcattcttcta<br>ggcctctcttaatcggcttaatgaaacacaattgataaaaatcaaacacagagcgattgattgaatgctatggaagatatt<br>gggcaaaaaatattggagcaataagcataaaggagagctgaaagccattcagatgaggagatatccaaaggagaagtaaaatat<br>agtatagatggagttaagttaaggttgaaaactctaa |
| Contig47_gene_191 | 1280 | atgatggatttaatttacatattaataattcattgcataatcgcatacaaagcataaagatcataagacctatgaaaaggggttgt<br>agaagattaggaaagtacaaccgaactgtagaaagagtctgaaacattgttattccattatagacaatcagaaaggttgacttaaggaac<br>aggtcgtagatgttcctcctcaagaggtaattacaaaggacaacaccgttgtagttgtagattgcgttatctttgcgaggtcatagatgcctc<br>aatgcagtatacaatgttgttaacttctctatcaggcaattaccaagctgcacaaaccaatctaagaaaatacatcggtggtgacttgacca<br>aacctgacttcaagagagatgatcaataacagaattgctgaaaccctttgatgttgcaactgacaaatgggaacaaaagttgtccgtgtagaaa<br>ttcaaagaataagaaacctccaaaggacatcgttgaagcaatgagtaaacaaatgaaagcgaaaagagctacaattctagagtcgaa<br>ggttataaggaatctgaaatcaaaaggtatcaggaaaattgccattgctgaggtctgtgaaaacattgctgatgaagcaaggtgaagcaagcaatgaagcaagttgc<br>agatgcaaacaaatatcaggaaattgccattgcattgtgaggctctgaaaacattgctgatgaaggcaacgaaatcacctataatctcaatgcagtaatcctacta<br>atgacctgattgcaatcaagtatctgaggaattgtcagaatttgtattgtatttacaagaactgatcctgaagcatttctactgcagtgagtttcaggaatc<br>ttaggctcagttggaggaattgcagaattgtttaaggacgatcctgaagcatttgaagaactttgaaagtataaagttctagaaaatgctaaaga<br>aacagcagataatgaatag |
| Contig47_gene_192 | 1281 | ttgggaggtgaaaaatgcaaaaatgaatgctgtgatattagagattatatattgacacttgttgttcttacctattcctttgacgctatgaattctg<br>gggtcttttaattgtaggatcattgtaggatatagctccgaaggaatattaggcgaatgcgaatgcgaatgcagccctggccaggagcattcgaa<br>caatcatatcagcaatcctattcattcataatcttgtcacaattggaggactgcaatgatgggattcctcggaggacttgctgattacagttca<br>ggaattacaagcttgattgatattgtattacaataataatcaaatatatgattgttatgaataactggtgctgtagtggagccttaagcggaga<br>aaaagaataa |
| Contig47_gene_193 | 1282 | atggtagatgcagaaaaaagcaaaaacaacctaaggaggagaataaacagtaaccttccagatatgatttgatttaaagcattaattttttggtgc<br>agcagcatatgcatttcccgcttgtttgcataccaatacaatctagacattttaatgtatttgcagcaatagtccaataggatata<br>ctgcaaaaactgaacttaaatcaatcattttaggaattgtaggtgcaactccactattatattagcttttcagcatgttaggatcatagga<br>tcaggtgaaatgcagatataatcatgacgtaattctcgaattctcggcattggcgcattggctgtgatcacctccaccagagataggca<br>aagaaatacagaaaagcagggggtattgtagtcgaaagaacaatttgaagacactggaagtgtcaaaagaatgttg<br>ctaacttattccttccaaaagcagaaggaaaaataa |
| Contig47_gene_209 | 1283 | atggccattggagttaaagagattagaatcactgatccataagtgttttattattgcctttaatatatgcctaatcatgggttgctcttt<br>tttagcaaaacctataaaattctataggtaaaagcaataaaggtagctgaaggagcaatgtttatttataggagttttaattgctaaattag<br>ctatttcgacgcgacaatccattgcattgatattttaatgcgcccctccttgatttacaactttgggattgccactccttatagcattg<br>ccgttgcttgcttttaggattagaagagaagtaatcggtatggcaagttccattgccgcgaacctaacttgggagtcattatcgacaagta<br>tgtttcaaatccctgagacaaggggagttttagccatttgtttatagactccattgcttgccatgctgcatcgccaagtcctttatcagcttcatatcaagcatat<br>gcatttcgctcatactaccatgccatgcttacctatgccattggagcctttgcaggatgccttgcaggatgcagtaacattctttcattgttaggcattacatgtcatattcat<br>catatacctgccatgccacccaaattgtataaatgttatctccaatcatggagccttgaggtaagggagggagacctattgatgacgaatatgctattgaag<br>gagtaaagatgataaaatatgctacttctgaggatttgagttctgaagattgaagattgggtcactttcctcgtactttctcaatcatcggc |

FIG. 9B-65

| | | |
|---|---|---|
| Contig47_gene_212 | 1284 | acagttggaaatttcataggttatcatacccctttgcttgatgtgttcatcggaatgctaatcattcaattattaccctatcggaatgtgcct tgagagataattccatgggatatcccatcaatcatttatataagttacttggtattttttagccattcctg atgaagcatagttaaatttagataataaagaccccaattatatttgttgaagaaatattttaaaatatgattctagaaatccaaaagtat attagcatcctatgatttaaaaactcttaaaatagaacaatatattacttttataatatgtctttgaattgacattccattca ttttaaacgagcttaaatccaaaaagaacttcgcaaatactcttaaatattctgaagtttgactgcagatcaagttataaaatttttcagaa ataaactctgaaaaacttatataaaatgtttaaacgaatcttaaactcaaggaatatgtgttaaaagaagagaaaaagactttatgttgatgc gaccccagtgacgtagatattaatttcaagcaactgttgttattagattatgattctatgaatcctgtttgtattttagtccactctgagctccaaacgat aaggttattatattgatttaaagcaactgttgttattagattatgattctatgaatcctgtttgtattttagtccactctgagctccaaacgat gcaaaacttttcgaagaatttttagaaaacctcaaaaaagacgaataatcagaaaagagacacatattcagcagcacatttgataaagatattacagcta taaaaactaccaaatcggaatcagcaaaaatcagcaaaacattccttcatttccaaaaagaaaaattcagcagaacccgattgatgacattttaa cttatccactagccgtatttaaccaatcagtagaaaaaacgtttatctaaatgtatttttgttctaatatcctgattatatcgaattctcttttaagcgaatcctatatgtttgattttat tcatggaaaaattaaacccatagggcaaatgaaatatctaaatgtatttttgttctaatatcctgattatatcgaattctcttttaagcgaatcctatatgtttgattttat tccaaatcagtagaaaaaacgtttatctaaatgtatttttgttctaatatcctgattatatcacaaggatttttact |
| Contig47_gene_219 | 1285 | atgtttgtaatatccttgattccttatttgacaatttctgttgctaataatccgaattctctttaagcgaatcctatatgtttgattttat tttggtgatattattccattctattttattatgagccggtatcgatcagcaagggcctataaaataatcttgttagcgataatcttgcgattttgatttgaagtttgattttgaaaaatg caataattattccattcatttctaattatataggattcattataggttttttagcatctctattgcaatcagcattgtctgttttgattcaatc gtaaggtcaattatattattccaattaaatag |
| Contig47_gene_220 | 1286 | atgaaaatggaaaactgatgaaaccaataggctggaagctttgataattgcaattattgtaacagttttggtttgcaatggtcc acagcctgaaaacgctaccaattgcaggaatttttagcttgaaagtttcatattttcacttcttgtcagttcctgtttgttgccaatctctgcaa tatccaccttgatatatgctcatgtgaaaaattga |
| Contig47_gene_226 | 1287 | atgagcataattgcaattttttctaggaataagtacttcattccctctttaggaattattgcagcatcgatatcttgactatcagtcttattgcttcaattttctgctcttaaacggaatatctgaagtggaatataaacactacaaaaggcttaaataccattattggactgataatgt tggttgtaagcttaggattgatattcaaccaagcataattcattcttaaccgctataaccatatctcaggaattttcttgataatcatt ggattggttgtgattgtgaaacagggaaaattgcttattctggatgggaattttattgaattctatagttgtaatctatataattcttgg aacttatatccaattcattgttctcgtttcattgattgtactgtagtgctactgtatattaaacttattaagtgacggttattaa |
| Contig47_gene_234 | 1288 | atgaacgccaatccaaaaatactttcttttacattctaatgattcagccttggaataaacactccattaagcattgtcggaatcatctcacaaat agcagagtattcaatacatcaatcaggaccttcagactctatgtaagctcatttgcatatgaacttaccattgcatatgcgattgttcatacctgttt tattttcaaaatacaatcgaaaaagaaccttgtaagcattttaacagtgtttgcaatatcaaacattgcaatatcttacaaaagcatttac atgcctctttcttagaatattatcagcatatttatccggcattcatatcaatagccctttacagttgcaagaaaatagcccaaaggaga agaacaagattatattacaaaaattctgcttgaatatcaatcaagttaggccttcctataacaacaggccttgaacaatattcaatt atcaagttgcaatgtcatgatcttttgaatatccttatcattaaatggacattgaataatggatgccaattgaataatggaatgccaatagagcaagcatagtatatata tatgaaatgccatttccagtctccaggtagtcagcagtaaagagacaagcaaccatctctcattcaatgccattagggagtctgtctccaatatttgaa cttggcttggaggaagttaatagcttaaaagagaagcaaccatctctcattgaatcttgagacggaatgggctacaatctcatcatttactccttatcta tttcaaattatctgattccagtcctaatattgatctataattgatctaatattggaatcttgagacggaatgggctacaatctcatcatttgaa agtaatcccagacagcccagaacttgcaaacggagttgttttaagcattttaaaatgaggaatagctcttgaa |

FIG. 9B-66

| | | |
|---|---|---|
| Contig47_gene_235 | 1289 | atgaatataaatggtgatttgatgaataaaaattactgtagacatattaatgttcatagcaataatagtgaatttctaagcctgcctatct<br>aattcatgaaatagttggagtgggattattgttttaattgcattacacttaaaatataacaaaggtatttaaaacaatagcaaagaaaat<br>ataaccttaaaaggcatgaagataggaaatcacaaaattcacatattcataaatcatcttcatattagtctaa |
| Contig47_gene_246 | 1290 | atggtcctgatttatataatccatttcaagggagctgaatcattaaacactcaatgaacatattcttcaccgatctgattattattgc<br>attcattcctcattgtatattcctgtaattgcatcaagattgttaaggacaggccctttcctcctattcatctcttacgggggatggaacttcagactct<br>actttaaggcattggcaattcctgtaatatattgtatatataatatattggggcagaatctctcattagatcagaaggcacatctcattctca<br>atagcccttttctgctgctgtcttgatttccgtgcctccaatgtattgcagaggaatatatattcgtggattatcatgcaaacattaggtc<br>atggattgggatacctcttatagccatagttttgcctcgaaacaaatgggttattggccatgaatgtcagcctcatactgcgaataattttctcttgctta<br>ttttagtattgcctggactggagcatcaaatcctctttccaattataagataggaggaattgtcattaataatattatgtataataat<br>gtattatgttggcaagaaaactgattgttttgtgtgaaatcccagaagactctcaaaatataggattattaaattttaa |
| Contig47_gene_248 | 1291 | atgcaggacttatctctgaattgttgcttgtcactctcttggctcctctgaacagtcagtcatagagtgtctgttttcagctcattcttta<br>tcaattccttcatcctactctgctgagaagtatgaggagcgagttgggaaggaacttcaagaaagcctagaaacattgcagcgaaatagtct<br>atatattccaatagtggtcatagtttataatagaagtgatctctcatactctgacatgtattttgataagatcttgacattcttgag<br>tatggatattccagaacaatctattaggtcttggtcttggtcttatgcttcaatgttaagctcaactaacattgaaaa<br>gatcaatggtgaaatcgttttagttgcaggaatatatctcttcatcagagaatgtgataaatgacttgaccatgcaagtgcataacatgt<br>tctttgctgatttttgactttttattgcaatacagtcagtagtgtttttagccctgtatttgtaatttccaatgtttaagaaaattcacaacaggaatac<br>tttaataagaagatgagattatgatgatgcagtgaatgatgatatatctaaagagcattatctaaacagtgatttttaatgataaggtcataacagatcctaacctg<br>tgacaccagttccttccatagggccaagagtataagagctataagagcattatctaaacagtgatttttaatgataaggtcataacagatcctaacctg<br>attccaatatgatgatatatcataatgatgattaaataattatcaaactcctcaagagattacctatctatgaagagagattattatctc<br>cataatccggaggatcctaataatccaataaagaaagaatcttaaaaagagtcaatcctgattctcattatgatgatgatgagactta<br>tataattgatgatgccaaaaacgacaattttttaa |
| Contig47_gene_250 | 1292 | atgaaaaaaccaggatttttaaaataaaattacaattattgacattctaataataatttgtatcattggagcagtggattcgcagtttaccatat<br>ggttgatgactcaacaaaggcttcagctaccctcttgactattcaacaaacaataagatgcttgaaacatatatgcttgaattattataagatg<br>gaaaaatagttacaagcagccttattgaactaaatcaaacacggcaagcctaaacaaatgaacgcacagtcctatggcttggagacaatcaa<br>acgataaggtaaacattgaaattaacaatgacgcaagcctatactgacagacttgtagtcagtgactcagtaagtctttttattgaaca<br>gataagctagagacaaatggagacaatgaaatcagtacgacatcgctatagatgaacagtcagtagcgtactgctcaaaattagcaaatgcattaaat<br>aaaataagaaacctgcattgcttaaagatgcttaaagaatggaacagtacactacattgaagtcaatagagccaatcagactgatttgaaatagctgacaa<br>tgtattaggagcttaaaggacagaagcgagatacaaattagaatctataattctacagcacaagattccatagacattcaaaatgcattta<br>atgtttaagcattgctaatacaagtcattaa |
| Contig47_gene_251 | 1293 | ttgaatttattgaaaatcaatgggtcaacagttatttaaggcttataccctagcgaaagattcctatcaattgtaaataagagtaagatctt<br>aaggaagagatattttcaccccttattgtttagtcacattcactcttttatacttcttgcaactgatccggtccaaggatttgcagacca<br>ctataatcattgcttttctaagctttttattggtcataatatttccaagattttattttgaataatcattaaatgatgaaact<br>aataccgacataaagaatcaaagactgataaaagcaagcaatgatcctcctatttaattcctacgatgtatattcctaggattcaatgcttagctt |

FIG. 9B-67

| | | |
|---|---|---|
| | | aattggaattgtcttttgttttaagcattgcctcgttgaggctgccaatactaaagtcctcattaagatattcacttaagccagcattta |
| | | caatgcctgtattttaatttcagttatccagttatgcgtgacttatgaacttgaatcagaataatcagccgcagccaaaca |
| | | agattcagattcttggtttaactgcaattgaactgtcctacactccaatatagaacccatcattgccatttactgatgat |
| | | tataataggatattatgtaaaatactatcagttggaggtcattttagtgcctgctcattggatgtgccattatgatattaa |
| | | gatcattgaatgagcttcaagggaatttcggactaatgcaaataactattctccacctaaactacaagcgccatgtacaacttacaatgatgtaacctactg |
| | | aattatatttcaggagaatttcggactaatgcatgaaagatgataagcagccgcatgcctaggacgatcttgacctagaatgatggtggcaa |
| | | actgatagcttggagaacagagagttactgtaacccctacattgctaggacagatgctagtggattcgtcgaaaac |
| Contig47_gene_252 | 1294 | atgcaatagaagaagttagaaatttggaagtgatcgcttctaaggacactcattcattaattggaagttaagcttattgccatctt |
| | | attaataatcgttttctgtgttttcagataggcctaatagttccacttgtattgaaatattctgtcattgtatctgtatctgcttgaattgt |
| | | cctttaaggacagcttaaaagaatagctctcttttttgccattcgttttgttatcgctttccagccattcatccacctgaaatatcatt |
| | | tggcaaggtcctatcctggttgtttataacagacactggttaaatggacagttctctttattgctagatttaatgctctgtttgacagctat |
| | | tgtcatccttcatcactccaccaatgcaggagttgttcaatcattttagaaagttgcaagagatctgctatgatttaacaatta |
| | | tggtcagattcctatttatcttttgatgatgaattaaggacatagcatagcatgatgatgctaagaacttgatcctttcaataagaagattccg |
| | | tataatgagagtcaagcagtggatatagacatagcatgatgttttaaggacatatgaaaaggagaaaccattattaagtatgccag |
| | | cagatgcttctcagacaattccagattattatcatgccaagacattatcatgccaagacactataaattattacttagcttgttataggcattgtca |
| | | ttgttttagaactgttgtattgttctattcgttctggcaatttggattattttaggcgttttctttatctttata |
| Contig47_gene_254 | 1295 | ttgattattgcattgtattgcgctgtattgtgaaatggcaaagcaaatctagatgcaaatctagatgaaaaacgtataccacttcttgcagtattagctgcagtatttt |
| | | tgcaattatgtctatgaacatgcctattccattgttaccagtgccacatggttggggcattgttgctatgttatttatggctcctgaag |
| | | ctgctcgtctcttgttattcactgacgtgcttgtcgtcttatcctcggagacgtggaattaccgcttagtgcaaatgtatttaacatg |
| | | gctatcgttggagagtgtgtgcgtcttgctctgtgctcttgagatgctattgcagaaatatccttcaatattcttaggcgcatggcttgc |
| | | aacattagttgcagcttgctgttgtcttgaaggagttattaacagttatttgtatattgtcttgaaatacacagaccagatctattgcatggacattaccatg |
| | | cattcattggttaattgaaggagtattaacagttattaacagttatttgtatattgtcttgaaaaatacacagatctattgcatggaatagaagaatag |
| Contig47_gene_256 | 1296 | atgcaaatctcaaatcaaatctcaaaatattagtttagcagtttagcaggtaatcctaatgtaggtaaaaccaccctattcaataatttgaccgtttaaaccaacatgtaggtaa |
| | | ctggcctgtaaaaccgtagcacaagcaaaagttcctataaacatagtgggaacgaagttgaagtaattgatttacctgtaactatgctttaa |
| | | gtgctcattcaattgaggaaattgtatcaagagactttatcgtagatgagactctgatgtaatgtgaacattataagtgcagcaaacatagaa |
| | | agaaacctgtatctgactgttcagatgatgagctcggagctaatttagtagttgcattgaatatgaatgtgataagtacgcccaagacaaggatatac |
| | | atcaatgcagataagcttttctgaattattgggagttccttgttgtttgttgaaattgaagcaaatagtgtataggtaaagagcaattgcttaaaacta |
| | | ttgaacaagcagctgcaaaccccgtagacccgtagacttcttcaaaaattggtttataacaatgaacttaaagagcatctcgctgaattgcagctgttata |
| | | gaagaagacaaaaacttacttagtttgatgttcctttcatcttggattgcaatcaaattgcttgaaaatgatgaaatgcttgaagagaagattgaaggatc |
| | | ttcaaaagaaacaatatagtaaatgaaactcaaaagatctctccaccaagccgaccacttgaaaagcatattggagaggcagtgaaggaggtaatcgcaaatg |
| | | caagatatgcattcattgacgattattaaaactctaaaagatctccttgtcatgccatatcgcttccctgtgaaacactttacttcggcgcacctttcattcctag |
| | | acaacaggatattgggcttcccgatatttccctttaggtggttgatgatgccataatcgctccttgagaaaacaatgcttcttcattcctag |
| Contig47_gene_258 | 1297 | atgtagacagacatgaaattgtagacaaatgtagaacaaacacttactttcgtaggaattgcaactgttgcagggcaaa |
| | | aatttaaaatcccaaaccactaaagattacgctgcaaaagaatggctaaagttctaacttgcaaaagcgacttagaagaatccattcaagaca |
| | | ttaaagacaatgcagaagacattcaaactgatgcaacaactgttgatgtgtaactgtaactgaagaagaataa |

FIG. 9B-68

| | | |
|---|---|---|
| Contig47_gene_265 | 1298 | atgaataatcaagattacgatactgaataagttcagaggttttacagtcaaatcaaatcaaattaatagatattttaattgatttaga<br>aagaaagcaagggctgttatgacttattgatagtctaacaacaagaaacaatacatagtttaaaatattactatatttttaaagagtaaatttcaaagaatagaatagaaatttcatcagatttggcttaataagaag<br>tgctgatgttgtaattgacactactga |
| Contig47_gene_271 | 1299 | atgttttatattgttgcttgtttatccttatccttcctaaataagacatgagaatgattattcatcaatctcaaagaactgccctatgc<br>attgcgccaattgtccactgtccactgaattaaggctgaaaaagcttgtttgatgtctcttgttgactcgtgtgttttatcaagg<br>aatttcaaggtcttgaggagtaaatatggtgaacaagtgaacaatctgtccattcaatcaaatattaatgctgaagatgttaatttgatat<br>agagtaatctatgagataactgcaagctctatgattaaacatatttcagaagcattttagctattttagcgcctgtgatttattcaataactgctcttcaagatgttccaagcagtgtgcttgttctttattctgtatgattgtcttccaatgataattgttt<br>ttagcatttgcaattaagaaaattagagcctaagctgtga |
| Contig47_gene_275 | 1300 | atgtttgatctattagcgcatgtttttattgaatagcaattggaacaggtacaggaatggttccaggcatccatgtaaacactgccgagcaat<br>catgtttgcatcatcaagattttctcttagttttgctttagttcctatctccgaattttctgatttatagttatatttccaaccccattaagcacctcacgctttgattg<br>agtttgttccatcaatgctcttcttgagtcccgaggggcactgcaagttctattctccaggacataggatggttttgaaggaagatctaag<br>gaagctatcagaatagttcacacttcagtagcgggtttggcgtctattgttggcgcattgttgccaatatttgccagtggcatatatgccattctgca<br>ggattcaaagcttacacttcgatgatactccgtttgttctattttagttagttgtgataatgctcaagtatagttaagcaatgaaggctcgcattatgtggt<br>ctatcttgttattgtattatcgcaggaggcactgcggagctatctgtaaatgatagctctcaattcctcaggaatttcattaatgtcacttcagtgg<br>ttatttgaattagcactattctttcgcaggaggcactgcgcaggacatctaagctaaaaatttctttctagcaaaatactacgattcgtaatcgataaggatac<br>aataagacattttcgcaggacgcagatgggatgacaacactaaaaattttcttctagcaaacagtgattgaatactcagacaccttattttcctaatagca<br>tatgtgaacaagcgcagatgggatgacaacactaaaaattttcttctagcaaacagtgattgaatactcagacaccttattttcctaatagca<br>atctatctgataggaaatcctagaagtggatttcagtgtatatgtcctattttgatatctgaattcagactctttgtctcattgatgatattcacttt<br>tgcttcttaattgcagtttcaatatcattgattattgctaaagctgggagacggcttttcaaacctaatgc |
| Contig47_gene_281 | 1301 | gtgacaacaatatttatttttgcgctttctcaaacctttataactcaattggcaaagcccacaataggattattatacgtttttggcct<br>attattttgccctttttggtgcattaggtgcatcattatcaaacgtagcaatagcaatagatgtttatcatgatatacctttgttcaaatactccctcag<br>ccatcacagcttttggagtttcttctttggcatatagcttttgtactccgattttaatcagatgagtacacaaacaagattgatacaatt<br>taccacctatgcctattttttagcaagcataatcatatggcggaatgattattcagtaggccacgaaatcctgcatatatcctaatcagccaga<br>tatagagaatcaataatcattcatcctctcttgaaccttaacaaacgttgcattcattatggtgcattatgtctttcattataatgtcatgacaatagctca<br>atccatagagacccctaaaaaatcagataatctcacataatccacaggcctaataatagttgtggcctaatgtatgctctatagacaaagccatt<br>catcatgagatacaaggtcaacgagataatgtcaacagacatattgcaaagttgtccgcaattttcattataattaccctaatcctttggatctttgag<br>ggctcgttccatagccagctttgactatgttgaaacagcattacactcaactcaccctccatctgatccgattcttgtgataagcgacata<br>atcataattctcttcattccaggaatcattcttccaggaatatcataagtagtcaagcccaatcacctcacacctcattttcgaaatcgaagg<br>attcatcaaggaagatgaaaagatagaagcggaaggctcattaagtctattcagaatatgtcaatgaacaga |
| Contig47_gene_284 | 1302 | atgagcaagaatagaattgaattgatctcgtaagctgtgatctcgtatttttaaccgttctgcttctatacattcatgcaacagatgaatctatattat<br>ctccctgattaatcccctattgactcctttcaagagtttcattcattcactttttattggacgtataggagttccattcttcttaa |

FIG. 9B-69

| | | |
|---|---|---|
| | | tgattacaggttatctattgcttgatagaacctatgacgatgagagagtcaaaagtttgaacaagagctgtaaggcttggtcatagttaca<br>atcatctggtccctgattatgcagtgagcatacagcttgtgactattccagcatacaagtcaatacaatagaagctgaaacctattcttcag<br>ccatatggtggtatatgccaatgattatcggtatgtatttatccatgcctttcgtgcctttatccgaatgcattgaaaaacttgatccagaacaattaacc<br>aagctacaacatcgtattctcctgccttccatcatatcgtaatgtaaatcgatccaatacatcgatattgagatgcaaggcttcagaattaaaaacatccaatac<br>tgccttggttcagtggaggagtatatggtatctataatttgcgttctcttccaatggtatgcattctctatagacttcagtttctcattatggtatgagttcc<br>gaggctgcttgcaatagtttcgtttataattgcattgttgaattatgttcaagaagagaaaggtcagagaggatttaagagagagagttgaatttttagccaaatat<br>cattatcctaaccgatcattgcttgaattatgttgaattatgttcaagaagagaaaggtcagagaggatttaagagaggagttgaatttttagccaaatat<br>tcatttgctgtgttttaataataaccagttatgcagctgcagttattattttatagaattcctaagttcggtaaat<br>acttggatacttttaaatcaaaattatgccactgtcttatggcaatgactttttattgataattgcctcgtcatcatccatcatgatttcatattgg |
| Contig47_<br>gene_286 | 1303 | atgaattatttaaatcaaaattatgccactgtcttatggcaatgactttttattgataattgcctcgtcatcatccatctatgatttcatattgg<br>atatgatcagtcatcaacaaggatgtgataagagggggcaagaaactgctaaaatacatcaaagagtgcaccatctatgaattaaaatgtg<br>ttatagtgcactcatatactctgcagttcaaacctagttatgttgaccttctcttattcctttttccagaattttcagattcctgcagattgaattagagcatgcc<br>cttacagataaactgaacattacaaatgtcactgcagcaaatatcctatattgattggcgaatatgtgtaataagtataatattaacctatat<br>ttttgtcttcttatgaaaattcacttgcaagactgtcagatgggggaaaattgcttgataatctatttaacttactatctccaatatgatccaattctta<br>acactataggctcgattacatacagattttgattttgcctcagttactagttggcgattacaagcttcttgcaataactatttaacttactatctccaatatgatccaattctta<br>ggattcctgattacatacagattttgattttgcctcgttactagttggattggaattggcaaatctataagatatataaat<br>taaaaatataaatctggataggccgacaaaaagagtgtttaa |
| Contig47_<br>gene_287 | 1304 | ttgttgcttgaactaataattgaaaactactagaaccattgcaagcatcatagttttctcaattccattaggaataggaaaatacattatgaa<br>taaatataaaagcatgaagtaaattacaaacaataagctacttcttcatattccgctgaatatatgccaaaagaaggaagtgaaacattaaagcaag<br>tatcctatttaatagtgctattttactcttcatattctcatatacagttttggccaatgcaaatagaaatctctcattttagaaatt<br>gtattgatgtatacattgcattgaaactacaaacagcctattccacatatgcaactgaaaaaacaagtactgttttcttttcttagtgcctatgtcaataagcatg<br>gttcctttttgaagaactacaaacaaatgtttagaataaccatattgctattattacaagtaatgatatgcagtttaggaagttcattcgtgtgaaattaaacagcat<br>aatatactgaaacaaatgtttagaataaccatattgctattattacaagtaatgatatgcagtttaggaagttcattcgtgtgaaattaaacagcat<br>tcaccgatcgattcaatagcaatgtctcaaatgcatttacaagtagtactgctacaatgacagttgctctcttcaaaacacttcaataaaagaatcaagg<br>actatttggttggagcggttatatcctttcaggagtgtactgctacaatgacagttgctctcttcaaaacacttcaataaaagaatcaagg<br>aaaatgaaaaacaaatgaagcacaatatgccgaattaaaagagtaatgattgaagaaataatgaggaaattaaagagatccttaaagagaacaat<br>ctgaaaaaaagactgaagaagaattgaaaaagaaattatagaaccgtaa |
| Contig47_<br>gene_294 | 1305 | atgcttgaaagtttaagaccattctcacaaaatattagaaccctatagccagccgattaaatataaatccaaatatttgtaactattataatttcgcc<br>atttttagctatataatctgcatttccttgctacgggaatttgattggcggagcattatcatcttcagcgatttttagatgttgttg<br>atggagctgtagcagataccaacaagatcaagcccattggtgcattctagactctacaatggacagatttgcagatgcaatcatattcatt<br>ggaataatctttggagtttattgtaatgttgttgttgttgagttttagcaatccattcagcaattacagtaagctatgtaaggcaagagccgaatc<br>acaaggagttgagtgcaatactggaatagccgaacgtgcagttagattgcatttcttatgtgggagcgtaattgcatcatattcaatgcag<br>atataatttcacatactttatctacactgtagttctttcatacttttacagtaggccaaagagttaccacgctgaaagctaaataa<br>aagaaaatcccacagaaagattgtag |
| Contig47_<br>gene_298 | 1306 | atgagttttgtccaaattgtggagtggaacgaaagaagaaggaagtcatttttgccatcattgtggctatgattatagagaagctaattcatctgg<br>gatgggctcagttctagttctgattcacaagtaaatcagaatcctagttttaattctcaagtaaatctatagtgtcacttatataagtcccaacaa |

FIG. 9B-70

| | | |
|---|---|---|
| Contig47_gene_300 | 1307 | agcaaatcctcataatttgctaagatcactggtatatattgtccttttaatacctgtattgcaatcgtaattgtatatatttgattta tctaaaatgaggaagttcataaacatggaattcatattatcggaatttctatagttgttcaatacttctatgattttctatgattggttaa |
| Contig47_gene_301 | 1308 | gtgattacagtgattgtcctgagattctgagtggctgtagatgatctgggagcttgctgtgataaaattgaatttatgttatgcagt aagtttatcgtttgcttaactttgaatataacaatatgtttttagcatgtaaataagatagatcataagttatctggtcaatagcaa ttgcaatgttttcctatctttaatcctatttgactactaatgtcttaaagaattcggataaggcaaatattgctcttcagtagcattggcagataa tttataatcgttgctatttgacaattttactataaatgcttgtatgttgaatgatcgttggctattttattttatccattgtgattgtcatgcttgttt tcagccatatgttacaacatcgtatttgtatttttcttattataaaaagcatggctaa |
| Contig47_gene_302 | 1309 | atgaacactaacagatttgaaacatttttgatgcgattatagcaatcataatcacagttctgtattaagttatcacagcctgcagctcctac cgttcctgcatttttagcctaaatgcaaggttttacttatgcaatctgtatttggccctttttatcattggtatgataatcataatttat tccaggtagttgaagagataaataatactgtattgattatatttatgccattcagatgttgcaatttcctctcttatttttctactggtg gcattgaatgtgaattcaattgctgctgagacaattgctggaatcaattttcctgaatacgattttcttcaatacttcttatgtctattttatgcggttta tagggctgaccctataagttgtatactccaggaatattttgtctgcattcttgctgatttgctgcttttcttttcaagacttcaaagactga |
| Contig47_gene_307 | 1310 | atgaggattgtgacaattgcaatagaggaatctgcctttgcaataggaatagtagcagctttttgcagcttatactatattcttgc tgaattgatttcagcaggattttcaatgatctgcttttattctaattgaattactctcttttattaggtattttgctaagttaggattttagagatcccattaataaatat aaattatcattccattgcgtatccagctcttggcgaatgtggaaatcttgctttcaagagctattggctgaatttgaaagctatcagaaaatca tagttaggcgctgttatgcctgtatcctggcgaaatgatggatgctgaatgtcttttcaatctagaaagcttatgcctgtcttgaaaagtatctgtt ctttatattggaattttatgactggtttttatttgtataaaatagttaa |
| Contig47_gene_310 | 1311 | atgaaatgtccgttgtgctgtgtgagaatccagatgctataaatttgtcatgatttgtgggaatccttgataatgctgattatgaaat gaataatgattaccccctctatgatgatttatcggttcatcggctcggcgtatatataatcgatatcatcgttggactttttatatttaagtg ccatatttgatcctccatatgcaattatgattgtaggatacttcgacccttttcagctttagtcttattagatactaactgaagcctctcctacttttagctcttcagtttgcaagcaatggaggaactctcttaaatgccaagaaaa acaatgttgataaagagtccacctaatataatcaattatggataacaacagatgaagttccaactcaatcaatcgaccacagccattcaaatcaacaatcaaaatcaaataat acaataaaaatctcaattataattgcttaactgtaatcagtgtattatttttgtgctgttttgatagcaggaggctattatattcctaccaaacagtagtagagcagcaccgaaacaaaatcaacaccgaacc tgctcctaaaaagctcagttaaagactcagatgaggatgtttaaaataagcgttaaaatagcgttttatacagcgtgatgctgctcgactgaatcaagaagattgctcgaaa atgttggtcagatgtactactgagttcagtaagttcagtcgttccagtggcagatgcattaagtattattatccagatcatgcttagtaactattagatagcaatgg taatgttttagacactcaagagttcatgagtgctaaaagtgctactcagacatttaa |
| Contig47_gene_316 | 1312 | atgaattatcaagaagaattaagtgattttgtgaacaatgtaaaagagtttaaagtagctaaaaaaccagacgtgaagaattttttgattt tcttaagttacagctattggtatagctatttgttaattgtttcattcggccaattattaggattataa |
| Contig47_ | 1313 | ttgggaaacgaggatatatgggtaatctatatgaaacagtccgaggaggactcctagagctgttggtagttcctttattcttatctcagtct |

FIG. 9B-71

| gene_328 | | ctttatgccaagcggatttaataatctgttttgtgatggtctatgtgcttaatagatgataatcggcagaaaacaattgctaattgc
cgattgagattggtcagcttgcaagaggaatagcatgcttttgtgtaatagattaggatatcctattaggatcctcatctatttggttgtc
cttttaatccagccaatgaatatgcagatatgcaacggaactgctgcagctacaaccattataatgagttttcttcactctttagctgttgt
gattatgcaagtaggtcctgtctctagagatacatccatattactacctttgcttgttttagttacatgtctagcttattgtccttggattcg
ctgaaagatcatgatgggtgaggtagtagtaaccatacctttgcaatatctttaggaatctgttttttatgtctcagcggatttatggaacttta
atattattcattgtaaccactggattgattgcatattggagaggtttaggtgactattttagaaagattctcttgaaatcaaccagtatgtgtgata
tttggagatattattatgatgtcttaactggagaggtttagggtgactatttagaaagattctcttgaaatcaaccagtatgtgtgata
atgagatatgattcgcctttgagacggttattgtataatcctattctcctaacctttgaaaagtgttcaaaaagatagtagaacaaaa
cgtgcagatttaagaaggttttattag |
| Contig47_gene_331 | 1314 | atgataaagcaaacattaggcttaaatgtagaagataaaaaatactacctgaagctaattatagaggctgtattaatcggtttattctcaggatt
cattgtatccctgtatcgacttgattagaccactcagaaagcatatatcctacatcctaaagtatatccaaggagactgacccctaatagttc
tatgttgtcatacttgcaatcatggagctttatcaccgcctttctgatgaagtgggaccccagagccagacgaagcggaattcctcagtcatg
ggagagttgaaaggatactttgatgtgacattggagcccatctgctcaattagagtgcgaacaattgcaaaatacctccaaacagcaaacagatctgatgaaagcgtcttt
tggaaggaaggccatctcgtgccaattgatgacattaggagcggctgctgcaacaattgagctgtaaatccccaaacagcaagactgatgaaagcgtctttgac
tagtgcggaagcgagcaggcttgtgtagtcgtttcagcagctgtttgtagtcgttaattgatctacatgtattctcggcaagccaactcttccattcacatc
agatcaatcgtcctgtagtcttgaatatttctgcgctattaactgctctagagaaaatgcagcttagaattcatcatgtttctccattatcgtcctcattaggatgatcagg
cagctgaaatgtgagagctctatgatgcacctagagcttgcacctcaccctgttcttgtaactgaattgctatcatgatcgatgatgcgcaaatacct
tctttaatattctgtttcggctcaagcgccccctgaagggataggtaatcggagcatata |
| Contig47_gene_338 | 1315 | atgaaagaagccttaatgataaaatgggatattgggataggttagggaataggggaagcataaagaaaagctataaagaaaagctagacatgctagg
tgccctaataatgattttttatgggaataacccatctctctcagcaggatgttctgttcaattaggatactgcagaactatgcaagcattaagcataa
tgccacacgctttcaaagccatacaaaaagccatacgaaaatagaacaatggaaactgcaaagcaagctctctcaacgattggtgcc
ttcctgatgctgccattcggaagctctgcaagctttatctgccattggctgagactttatcgagcaattgtgagtcgtacaccaggatcgaagcagccaagctccattagccagtga
aataggtgtcctcaaggacctcgtttgattacaagctttgattacaaagctttcattttactttgaatcatgccagatccattgatagcaattagattctgtaatctctga
cgattgtaggagcaggaattattggaatcgcttcattttacttgagaaatcatgccagatccattgatagcaattagattctgtaatctctga
accgtaggctgcttagacagtatcctggagcagtccctagagagaaaacttttattaacaatgacatgttaacttgcttgcttaccatctc
tggagcaataatggtattattctgtaatgtaa |
| Contig47_gene_365 | 1316 | atgaagcatagattaaatttagataataaagacccaattatattttgttgaaagaatatttaaatttggattctagaaatccaaagtat
attagcatcctatgatttaaaaaaactaaatagaacatatttacttttaaaatttatttaatttataagtatgttctttggaattgacattccatta
tttaaacgagcttaaatccaaaaaagaactttcgcaaatactttaatatttctgaagttttgactgcagatcaagtttataaatttttcagaa
ataaactctgaaaaatctataaagtttaaacagaatcttaaactcaagaaatatgttaaaagaaatcttgaaaaatcaagaacatctgaaaatcttaaactctaaaaaatcaagaacatctgaaaaaaaagactttattgtttatgc
gaccccagtgacctagatatatttaatttggatataaagtttaaacagaatcttaaactcaagaaatatgttaaaagaaaaaagactttattgttgatgc
aagttattattggattaaacaacatgtttgtattgattatagttgtattgattcatgatgtaatgcaacactgtttgtattccactctgagctccaaacgat
gcaaaacttttcgaagaaattttaagaaaacttcaaaaagacaataataacagaaaaagaacacattaatcttgataaggatattacagcta
taaaactaccaaatcagacagcaacaaaatcattccttcatttccaaagaaaattcagcagaaccgattgatgacattttaa |

FIG. 9B-72

| | | |
|---|---|---|
| | | cttatttactagccgtatttaacaaaacaaagagaataatgaaagaaaaagattatacaatagtttaaaatgaattaatgaaaaatagat<br>tcatgggaaaaatttaaaccaataaggggcaaaatagaagatttttcaaattattaaaacaaggcttgaatatgagaaatccacaaatatac<br>tccaaatcagtagaaaaaaccgtttatctaaatgtattttggagcactgattatatcacaaggatttact |
| Contig47_<br>gene_366 | 1317 | atgttgtggacagatttattgtttttggcgattgtttatattatgtggttgcaattttatactgtctgagaaggtcttaaagagcaggccaga<br>ggtcccgtaagtttttacatattatggtagtaatatgatatttgccatgccattcttctcagatcctgattatgctttattcattacct<br>tgcctgtaactgtggcactattcttccttacagagtactcccctattcagattgaaaacagcgtaccgaatccgacatgcattaggactcctc<br>ttttatgcattgattggtccatattgctctcttgtctcctaacatcatgctttgatcctaactatcttgattgtagcaatgcatcgttccatt<br>ggtatatgtgacgattgctgctctcttgttggagaaaatgggtacaatcaaatatcatgtatttggaggagaaaactgttgtaggttccc<br>ttgcaatgctttctgtaactgcagttgcaacattgtgaagctccagttatgtggtgttctacagttcaataggatacactcttcagagcttaattatgtat<br>atattgcttatatcagcagttgcaacattgtgaagctccagttatgtggtgtgtgacaacctactgttcctgctgtaacttccgttttgta<br>ttatattgttgcgaccgtcctctaa |
| Contig47_<br>gene_371 | 1318 | atgaatataaaagagtttatttatagaatccctaaaagacaataagaaactaataataggactatatgcattttttataatagtttcattgcagc<br>ttggattataaccggtccgaaaatgcaggccattgcaagccatgcaatgtaactgcaatgaatggtcctgagagcccaaagcgcaattgaacttt<br>tcatccataacgaacttgaggaatcattactacctgccatcagtatcttcttggaattgctgcaattgctaggatacaatgcattaaat<br>ttaggaagcattgacaattgctcattcaatcattcatgccaaatgagagaatcttatactcattacctaattcccatgaatattgaaattac<br>tgcaacagtccattcctcagtcgcagctggaatactattgttcctattcattgaggttcattgcattagaagcattagaagcaaggatacaaatgggcct<br>ctgacgcattgagatgactaaaaagacactgattcagacatagtctaatgtattgcaacaatcctcttacttattgccgctccaatcgaa<br>gcatattctcaactgcattctcagattttattatgggttttaggacttagataa |
| Contig47_<br>gene_385 | 1319 | atgaaatatctttttactcttttgaggatggatgcattattgcttcttgctcttactcactatttttattcgtatattgaatatgttccatgtt<br>ctttgagaaaagaagtcaaggcctattacaaggctcttgatacagatcaggatttttgatatgagtctctctttactattgtcatat<br>tgattatctatatcgagaggtctatattgattgccgttttatattatagtcattctagttcttcttgttccattattgacagtctattcctat<br>ttccatgcacataagatcattattcatgaaaggacaatccaaatgatatcatgaatccaacattgccaaccttctgacgttcattt<br>cggctcaacaagcatgataagatcattaggatcattgaagaggatccttttctgataaatgaagagctttcagattattgtgacttgcaattatcagtggagaca<br>ttgttgatggtcctctgctattgaagacgtcttggggcatgcaagggatgatgattttctcaccctctaagatgtgaatatgcctagctttactagaatacttgaaataatttttgttctagacgatgaggaattgaatgatcatgagtcgcagtagatatatt<br>tgaatgacattcatcttttgagacgtcttgggcatgcaaggccaagttgaagtagtcagcacagtgtattaggggattttcgttaaggaagataagg<br>tgaatattatcattcattttccatgtcctcaaaactggaggactttctaaatggattgacattgcattcaattgtcgccatactcatgaggccag<br>tccatccacttacttgagtctattccttttgtatggtactgattcagagatgtgtgtctcaaaattaagaa<br>tactgttaggctctatgatatctcttttagatgggtactgattcagagatgtgttgttctcaaaattaagaa |
| Contig47_<br>gene_388 | 1320 | atgatcttaaatcttattttaattatactaatcgcctaatttactcatatttcataatcctatacaatggtttaagaataatctgttga<br>aaggaaaaaagcagaagccagatacaaattaaagataactctgcttaaaatccctattttcaaaagatagcgaagacaaggctacagaat<br>ccgaagaggaaaagaagaaagatggaagaagaagtccaaaagacaaaaaggcctgatggaaaaatacaatgaaattaaacctatcctaaaa<br>gagctaattaaatcaaagaaagaacattcaagaacatctcaagacatttaaagaagaacattcaattgataatagtaaaaccgaagacacttgatactagg<br>cctaagcgactcttttcaccacagtcaagatgtcaagttggatatgtcaagttgataagcttgataagtctataggagctgatggtcaataggagctgatatagtaaaaagccagttcattaactgtag<br>atcctagatttacagagataatcactgatttttgaaggacaattggaattaaaatctactgaaatatatttatagcttaattttagta<br>agcaaaaaggacattagaagaattgattaagtaattatgcttataaaagcaaagataaaaagcaaagataaaagaagaagaaatgaaaactccaatgaaga |

FIG. 9B-73

| | | |
|---|---|---|
| Contig47_gene_393 | 1321 | attatataaagaaataaagacactgaaattaaagaaaactgaaattataaagaaagaaaagacactgaaattaaagaaaactcca<br>aagaagaattagataaaagaaaagacactgaaattaaagaaaactccaaagaaaactagataaaagaaaaggagaaaagaacttaa |
| Contig47_gene_393 | 1321 | atggatgatgaaactaataacaatcaatggaacgttcaacagttcaacaagcttcatacttgtcatggatccatcatagcattggcagggattggag<br>attttcctatcttatttatgaaaacgaggggcagctcgaggagtttgcgccaagagctcgatatttacaatatcaagtctgaatttgaaatatggcatgttatcctttc<br>ctaatattcatagtcctaatctgctatactgtcataatgtcctggacccttatccacatatgcttaacttacctgtagtcctattgaaggatcggcctcatattaa<br>tagtgttttcttttacaaccaccactcttcatatctcgaagggaataaataggggaatacattagtgacaaaatttcccctgcattgacatttgttctgtc<br>tctggcctcgatatattttcatatctcgaagggaataaataggggaatacattagtgacaaaatttcccctgcattgacatttgttctgtc<br>atcatcctttcagtcttgccctccaattgccaggatcgcaggaactggccttgcatatgtgcttgcatatgtgaaattctgatatctcttcagaggacagca<br>catttggctcactgcattgacttattgttctaatcagcctaatattctgaaattctgatgtctgttctcatatttgcattgctttgacatatgcaa<br>agcttatagacagcgcatggttattgttctaatcagcctgtaagcgacagcttctcattgatatttgtgttttccctaatgtattcaatgtgatgggctcatg<br>ttggaaagaacatgcctattacaagcctgtaagcgacagcttctcattgatatttgtgttttccctaatgtattcaatgtgatgggctcatg<br>ggcaacaataataggtccattgttcttttatgttatattatagggggatagttaggtgcattattgctcttatag |
| Contig47_gene_394 | 1322 | atggcaaacagtaatcagtctgaatgggatagtaacattgcattattttggcaatgatgttcctgcagttggttaggaaatatttgcgttt<br>tccaaatgttctatactcccacggtggagatcattcatgattcctatcgtatcctcctttaggaatatcattgtactgtgaat<br>atgctgtaggatacagattcaagctcctccaatcaaggttctatattctgtcaaagcaaattggagcctgctagcctgcttatcgcccaatc<br>gtctttctcataacaacatattacatgtagtggatggaacggatcaacaagatctgaatatctgttcctcatatgtggtcttcctatggtctttactgtcattat<br>cctttctcttctcaagcattgtccttcaatcaacagatttaaatgacggcataggtaagtaaggtactgcttcctttgcttgcttgattattgttgtt<br>gggctgttgcatgtacatattcactgaccttgcctgagcttcaataggctataccaaatttttactcctgattggagtgcctaactgacttgaatgt<br>acaatcgttttgtcgccttgacagatcgtattctccctagcttaggaatcctttttactcctgaagcacctcctgaagcctcaaat<br>ttggcttgctgccttttgacagatcgtattctccctagcttaggaaatgtccattcaattcgattttgaaatctccaatctttgttttatgacctta<br>taacagacaatgcttaatcgttgaccaactgcttactgagggaacaggctgcattgtgtttgttcctaaggtattcaatataatggtcttgggc<br>aacaggcattccattgaccaactgcttactgagggaacaggctgcattgtgtttgttcctaaggtattcaatataatggtcttgggc<br>tacaatcatcggtccgctcttcttcctatgcattcttttgctggtgtaacctctgtaatgcattgcttgagg |
| Contig47_gene_395 | 1323 | atgaattagacagtaacgtttaaaaccggattgattgagtcagtctatttctataatttcctttgttttatcattgtttattactagtgcaccaac<br>aggagtggataattctgctcgttctgtttcgaatttgacactgttctcttagcgatctgcttagcattattactaaagaaactattctat<br>cactattcgttggagtttttcgttgtgaattcagtgaattcaagtgattcaagttcagtaagtcatcatcagctctgcagttaagtcagtttagctatggt<br>ggtcaaatcatctcatgatgcgatgatgcatgaacgctgattgtcctccaatgctgatttgtcctccaatgtctgctcattggtggtaatccaatgcctccaattaacaaaat<br>gggaggcaaaagcgttagctgctaactcctgatgctgttgctgtaacactcctagaaaagctcaactagtactctcaacgtgttatgacaagctgttatgtat<br>tctttgatgactatgctaactccttgattgtagttcagtatgttattctcattgacaaccctgtgatcggtcttatcgggacagttgattactcaagtttcgaatcaat<br>gtaacgcaactgcagctccagttgcaggtatgctattgcttattattccagccatccctcagacattctcagacaagaaggcttgatctacaatcaaggcttgaatatcaaggtttcaattcattgttatctcgcag<br>cgctgaatgtaagcgattcggtccaatgaagaggcaggagaaaaggctcgtgcaagaaaagctgatgaacctgttaaatctccttgaagcaaccagc<br>ttaccctgtatgagttcggtccaatgaagaggcaggagaaaaggctcgtgcaagaaaagctgatgaacctgttaaatctccttgaagcaaccagc<br>tttgatgatgtaaaacctggaaggcattaaattatccgtatgaagtcatcatcctattgcagtctattcatttaatcatcggcgtcttatagcatt<br>ctactggagtggttacactacatccttaggcggtgaagaccaagcgctcattcatttaatgaaaacttctccat |
| Contig47_ | 1324 | atgaaaaacaacaagtaaaaacaatttttaaatctggttatcatcatatttaaggctatattgtttttgctttaggctcaatctgtaga |

FIG. 9B-74

| gene_408 | tattggaggagttcctaatgaacttaaatcacactatgtagacgaaacggtcttccttattcagtgaaatggactcatacttcaactacagga<br>tgaccagaattatatgacttatcatggatcatggatacttggtgacactaaggtaaacgtaccggtggatatgcattcatcttccctcaggtaggca<br>gtagtgattatcaaccgatgattgcttactgtctgtaattcctacttacatatcacaagaaggattacaacgactatgagcaattgcggcctcat<br>ttggactgggctattgttcctcactgttcctcactatattcacacacaattgcaggatttttcgatacagatatgtcaactaacctgccttattcttcata<br>tgattgtagtattaggtccaaacttaaaaactgataagctatcatacagaatcatatctccttattagcagtagcttcaatagcgctctattccttc<br>ctgtcttgtgaagcttaaaactgattgcttgctgtaatggctgttatgtgtcttctatttcaatattgaagatttttagaac<br>atggacaggttatatgtttttatgttgctgtaatggctgttatgtgtcttctatttcaatattgaagatttttagaac<br>cattaagaactatgaaataaactgaaatgctgattaatcagaaggattgttgctacattaattgttgttagtctaattggatta<br>ttattagccgtcggagtaggtgaattattgaaggtattaccggcctttcaccctcaagcagttgctgctgactgtagcctaa<br>cgtacttatttccgttgcgaaatgcaaattcctaattagtgactggaggacttgtagttcattcctcgcta |
| Contig47_gene_420 | 1325 | gtgataattattggaggattaaaaatatgaatgaaaccattaaggagaaattcttggttccactaatagtcgtgctcttgctcttttatgt<br>agcttagacgctacattcatgaatgtgagtatttcacaggttgttgttgactgaatactgacgtcagtacaattcaatcatgtcatttt<br>atactctcatcactgcagcatttatgctcttcttaagtctgcaaagcttcaagacatagtggataaaaagaactgtttttaatagtactgtctctttat<br>ggtgaggtacattcaccgcatcaataagtcaagtctgaatgttatttgttggatggcagcaattgaaggtgttgctggtgtcattaatgat<br>gcctgcaaccgttccatcataagtggaacatattctggtgaacaaatggaacatattctggtgaacatattgatatcgtttgtattttaata<br>ctgtaggcccactcttcgtgggtcatgaacctcattcgaacctctaaagattcacaactctgaatctagaagcgattagacatttcaggcgctataatcattatcgcttgtttatt<br>agtactaggtatctgtcactatctaaagattccacaacaagcataggcataattgaactattaaagacagaaattacgtgtaggaacatataattttgttatta<br>aaatcagaagaaagaatggtgtggggattattgcagtttccctattctgcaagttaacagaagtatttcgagtaaatgcattcaataatctggtgtgactactct<br>tcttaccttgcaatggtgtggggattattgcagtttcccctattctgcaagttaacagaaatttcattaatttcatagttcactactct<br>tccattaactttaggttgcttatttcgcagtattgctccaagtttaacagaaaattaagtcacaagaaaa |
| Contig47_gene_421 | 1326 | atgaacctaataaagtatctggaatattatcataattttaggattcataatttcataattttccctggtagttccgattagtatccatcat<br>gattgagttagctcatatttcaacattgatgcattgtcctcctttagattcaaccgaattctaccgactctaaccgaattcaccactcaataattattgcagcactcaatattctgcaatcatattcg<br>gttgctattcatatttcaacattgatgcattgtcctccttagattcaaccgaattctaccgactctaaccgaattcaccactcaataattgttatcttaatggtgcaattattcaccactttaagtgcactaatgtatgtgcca<br>ggtatctttcgaggagaaggctatcaagatgttcaaagattgcttcaatattgattaatctcaccaagtgtaagttaattattagcaccaaaaaattaa |
| Contig47_gene_422 | 1327 | atggtgttaatataaagtcaacattacttttggagaatataattaaagattcttctctatttattaggttcgctcgagtactattggcttatgcggattaactcttg<br>agtattagttgcaacattacttttggatggtaattgtttttaaactttattacagtttttaaacttattgttgtgcaatcgttacttacttcctcaatattcctgacaagttcctgtaggatct<br>tatttgcaatgttaattggatggtaattgtttttaaacttattacagttttaactttattgttgcaatcgttacttactaaatccttatctttctggcaatttcctgcaagttcctgagttaa<br>tgtggataatttattacagttttaaacttattacagtttgctaatgtcttacgagatttcttcactcatcaaattctttcctggcaagttctccgatattgaatcctcgattattgcatttg<br>tataatattatgacaaattatgcagtcagttgctcaagagatttcttcactcatcaaattctttcttgacaagttctccgatattgcatttg<br>aggcattgtctcaagcaatattgcaatcatagtacgtcagatattcagagtggtcaatattgcaaggctacttaagcagcaatattgcaaggctcagagcagcagatattgcaaggctcgacttaagcagcaatatatgcaagcatatatgcaaaacaattggtgtacg<br>taagtaattaggtaatcttattagtttcttgtaattagttggtgttatatagtgggatggttaaatctgttatattaactatgtccaacattatcaa<br>ttcttttcaattataataagcccatactagtagttcttgtcaaaggctactgattttattttcgattatagcttaa |
| Contig47_ | 1328 | atgaaattattaaggagaaaatccgaaaaaagttaaaagaagtttaatcgtatttattgataatatgataggaatatatctttataag |

FIG. 9B-75

| | | |
|---|---|---|
| gene_424 | | tattttaggtttaggagtcgaaattagccaaactggtgacatattcctttagtattattcctaggtatagtaaatgcaatactctgcctattt<br>taacaagaatagctatgccattttagtattgacctcgaatagttcattaaacggactcctctcaattactcgcaccatcattt<br>ggaatagaaatcaaaggtgctgcaatgatcttgcaccttaggaatgcgccgttacaacagtgctatctagcttaataacaattaatgatga<br>cagttcctattacagatccgttttaaatgatgcaaaaagaatgcaaaaatgcaaggatcaaggattatccagcgttatatcgttgaattgacg<br>gacttgcatataatgttttatgtgaagcagtgaaaagagacatgccaactcttaaaaaataatgaaggcgaagactacaatcttagaatg<br>tgggaaactgacttgtcttcccaaacggtcgcaagcaggcaatgtccgaatcagcaatgtgccggaatccttcatgaagctcatcgttgcattcagatgatgataaa<br>gagcaagcagatctaatttattctccaatccaagcaattgcacgtattgtctcattgtccttgcagatattgtaccgtacacaagactctataataag<br>atggagcaagcagatctaatttattctccaatccaagcaattgcacgtattgtctcattgtccttgcagatattgtaccgtacacaagactctataataag<br>gcatggtactcagtatttccaatccaagcaattgcacgtattgtctcattgtccttgcagatattgtaccgtacacaagactctgtcacaatcac<br>acattccatcaaaaacataaggccaagaatcaaccggtggaatagctgaatagcttatattccaacaagagctgctacaacg |
| Contig47_<br>gene_425 | 1329 | atggagattgctttgtctgtgaattaataattccaatttaatattgtgtgttattgcagttgcagaaattattcatgtaagattatt<br>gaatagtaaaagcagaatttaaatccaggagaatattcctgatgagaacttgaaacattaaagcaagttattatattggtaatgatgttaa<br>tattcttgtcttatattatagtatttgaaaatacatatgatagtccagctaagctattatcagtctgtttacaattcctgtcagtctatgtgct<br>ttaacttgattatagttatttgaaaataagatactttcttgcttatttgatgcatattctttgttcttcttgttttcaatgattttct<br>aatgattgcaataacaatcatactattcgctataagctttattaaagcttcattatcacactattgtggaaggtgttgaaccttttaaattctgct<br>ggcttggaataacaatcatactattcgctataagctttattaaagcttcattatcacactattgtggaaggtgttgaaccttttaaattctgct<br>gtaatgtttcaaatgcattacaagtaatgttatgcaatactggtcaatccttgtaacttgaccagttttagtttggagcgg<br>atacatcatatctgtgtagtactgcaacattaaccgctgcaattatgatgagacataatcaaaaacgtgaaaaagagtaaaaacaaacgtttag<br>atgagttggaatcattaattaaaaatagtaataataaagaataa |
| Contig47_<br>gene_428 | 1330 | atggattgcttttttatgttgtttgctgttgattgaggttgcttgcaggtttcatgcaggccttgggattggcgtgaattgtaat<br>cactccaatccaatattatcttttaacctcaatgatgtgatcctcaaaacgtcctaacgttacctcgcaacaagttcttgcagttctgtg<br>tcacgtgataaacagtacacgaaagtacacaacaatctaatagtaaaacagcacctaaaaccaatgatgtcttggttttgtaggtgcc<br>attctggtcagtcatatctcaatacatagatgttgaggtttaaagattttgttggtaatagtatgcaacagtatttagtttt<br>aataaatctcctacctcttagatatattcatacgatttgtgtgcagatattgagatatacaatatcgaacaacttcagcattcagcatc<br>gtcccgcaggagagcattatcatcaccgatttgtgtgcagatattgagatatacaatatcgaacaacttcagcattcagcatc<br>gcaaccacacttgcaggggtaatctgttatatgtttatccgattgctgtaacctatccacaaaatcatcctacaaattaaaagcgctgcagg<br>attcgtattttaacaataactagcattatttgcttgacgatggtgtaattaaaatcatcctacaaattaaaagcgctgcagg<br>taatcgtaatatcatatatgccttcaaatgtggtgtattcgacataatattaagcataatataa |
| Contig47_<br>gene_431 | 1331 | atgaatatattgcttatctttacttgcaattctatttgaaaccagtgccacatcactgttaaagttgctgaaggtttcactaaccattgcc<br>aacaatagcatcaatcatatattatacattatcattttacagtctcagcaactgcctaaaaacagcaccaataggagttgcatatgccatttggt<br>cagcattggaatcgtgcttgtgacaattgtaggattatcgcttcaaacagaccccctgattgggctgctatccttgacttttacttatcatt<br>ataggtgagggtgctaaatctattctcaaaaatgagcttacattaa |
| Contig47_<br>gene_433 | 1332 | atgaaaaagtttttgagtgttgcattaaattccaatggaaaacaatagtgtttatttcgcattaataatcattcagacatttcgttcaaatgga<br>aataattgatttgttcgtgcggctttatcatctcttctccaacaagagtggcttcaaaatcagcatatctgtcgtgagaaaatattccatatt<br>tcatttcaatgattgccgttatgtcatctctttctccaacaagagtggcttcaaaatcagcatatactgtcgtgagaaaatattccatatt<br>ctgatgaacttgcctcgtgaggaattgataaattcaggctagtacaaggctagttacaaggtcaaccagagtatgcctccgaacaggatttat |

FIG. 9B-76

| | | |
|---|---|---|
| | | agtgatgatactcgaacagttaatgcttattccagttacattcgtagcaattgtatatgaaatagcattgattgatggaacttatgcattatttt<br>tcttaggatttattggttgttccttttctgcaaatcaatgatatagctgcaggattccatttagaatgaaacagattgtgaaatattttcagagctaaaagacatatgtaaa<br>ctaaatttattattcttatcttaaaaatgtcatctatctatctatctataaaaagtcatctgataaaaatgtcatctatctatttaaaagtcatctgttacat<br>gaactcctatgataaaaatgtcatctatctatttaaaagtcatctgttaccat<br>tgcaatggttaattcaggatacaccattggattgaaactggattgaaacctggaatagtgtaattgatcttggtataatgtcatcact<br>actctagctaatattcctgcattaattgacagatgccacgtgcatatgccacttctgtgcgttggaggagtcttgaatattgaagataaaat<br>cataaaatccaatacaaatgataatctgaaggaatagagattgttgaggaggatagttgctcaagagctaagg |
| Contig47_<br>gene_438 | 1333 | atggattgcttttttatgtgttttgctgtcgtgaggttgctttcatggcaggttttcatggggattggcggtggaattgtaat<br>cactccaatccaatattatctttttaacctcagtcgatcgtgatcctaaaactaatagtaaaacagcacctaataaccaaggcttggtatggtgcc<br>tcacgatgataaacagtacacgaaagcaaacaaacaatctaatagtaaaacagcacctaaaaccaatgatggtcttggttttgtaggtgcc<br>atctggtgcagtcatatctctttagataatatatacgattttcgttgttgtaaagatttttgttggtgtaatatgcattgcatgctcaggattgatag<br>ataaaatctcctaactcttttagataatatatcgatttcgttgttgtaaagatttttgttggtgtaatatgcattgcatgctcaggattgatag<br>gtcccgcaggagagcattataatcacacgatttcgttgttgtaaagatttttgttggtgtaatatactatctgatcagcattaagcatc<br>gcaaccacactttgcagggtaactctgttatatgtttaggtgggttgttatccggattgccgattttcattagttatgtcaacttgcttca<br>attcgtattttaacaataacatagcattattgtatccggatatgctgctaacctatctaaaaaatcaatctactacaaatttaaaagcgctgcagg<br>taatcgtaatatcatatattgccttcaaatgatgggtgtattcgacataatattaagcataatataa |
| Contig49_<br>gene_6 | 1334 | atgaatttatataaggatatattctatctgcaggcttattctatatctatgcttcacatatccactgccatgccatt<br>ctgtgcaagatgctgtgaatcatcatatcatatcgtctgtctgcttcatgcctctcagtttgtagcctccaatgaatgcctgcttctttctc<br>tctttgtccaatgcttattgtagatgggcttgtgcagaagtataccgattatgaaagcacaaattcagaagattcataacaggcttcattttga<br>ttgcttatgtctatgatttctatttttacatgttgattgaacgctttatga |
| Contig49_<br>gene_9 | 1335 | gtgaagatattgaaaacttggattgaaaacttgatattattctatcaatactgattgtattgacatttcattcaacagcttcatttttgtt<br>ggatttgaacacaacctatataatttcatgcttttgtttgatcattatatgttggatcttatgtcttcatcatcttttaagctgcttaatt<br>cggatgacagaaaggcatatatgaggaaatatcttgattttttagcatcaatacctatgacctgtttttgctcccttcagttcattgcat<br>atcagtctttgataaacatagtcgtagacatagtcgttggcattatcattatgggcctggtgggcgtttcgaatcttgatctgcaatccaacctat<br>acatcctttgataaagtcgtagcatttcatgttcgtagtgggctcaacattcgcattgaatactttgatctgcaatcctaacctat<br>actacagcctatgttcgtatttcagacaataaccacagtagctcgttgattcatctgggctcaacagcgaccgtgatcgcagctgattggc<br>cttttgatgttggggtactcagtttcaattttcatacctcttaacgaaaggttcaaagatattcgtgaggaaatggatt<br>ccatgaaaagataaacacagtcaggaaaaaacaatttctgaagaaacaagaaagcaagatgttaccttatagatatgattgagaaaag<br>ttgctgaagttaaggaaagctaaacaaatccgaagaagcgtatagatttaccttatagatatgattgagaaaag<br>gaatag |
| Contig49_<br>gene_22 | 1336 | atgtcctatcaagaaaataatgcatctgacaagtctcttcaagataaagatatgaaagcgaagcagcgccaagatagaattgttaagacaagcat<br>aaaggtattgttaaatctaataattgttgcctcaagccacacatcggaattcttgtaaattccattgcaatcacttggatcagtaaaca<br>atctaactgattttctatcctcatattggcagcttggacttcagcaggctccagataaggagcatcttacggatacggccgt<br>attgaatatttgcatcgtaattattgcagctatcgttctttggcgaatcactgcattgatgaatcatgccaaagatcttaatcctga<br>tgttacaagctatactacagtttcattagtcatcgttcagtggcatgtgcagttgcagttgctaaattcatcatatttgggcgctacgttaagaatgttggagagg<br>aaatcaattcacaggcattggttgcatctgaagcgatgcgtttcttttgatgcatatttgtcatttcattgtcatttgattcagctttgagcagc |

| | | |
|---|---|---|
| gene_41 | | cgcagttctcttttagtaaagcctatgagcctggaagcggtttggagaattctttctacggtggtgcattcggatttgtagtttatgcgcttc<br>ctgctattatcactggtgcaaccgatcagaatggttagcaccctaaagatgaagcattccatgttcctgcccttgta<br>tcaatgaccatgcagggtaataagcatcataggaacaatcataggaaatatcctccacttcgacctgttataaactcaattcttttgaat<br>agtaattgcattcaatatcctgtaatatgagcgttacacggattaggctcatcaaatcgttcttgttgcaatcattcagccattgc<br>tcatgattggagtattgattatcacagcttttaacaactcagaaagcgtctttgagcttgaatattaacacctcttcaaggtaataata<br>gcaagtgcagtcttcttgcttgcaatctctattcattcattgtagaatcgaaaaagaacttaggattcgagcttggaaatcct<br>cagttcttcattcacatatgaacgaaggttccaagtcaatgaagagcttttcgacaatgctgaagaagcaattgacacactgttgggtct<br>gcagcttcagaaagccagacgagacggagatattaaggcattgattcattgccttcaccggaccctcttgagacattgaggttcaaatatg<br>cctacaatcctgcaaacagattgattcatttgcaatgttgcatgtgcacatgaatactcatcaaaggcaagcagattcgtcagat<br>taaaatcgagtcatcagtgagaaccgcattgaaaatatgaaaatactcatcaaaggcaagcagattcgtcagat |
| Contig49_<br>gene_75 | 1343 | ttgaaagcaggagttcttgtattcacaggagtctgttgctatcgaccatctcttctatccaatcatgtcttcttcgagcttgttattggagctat<br>tatgatcctatatttggatgaagtagtatccaaatgggattcgtagttcgtagttgtaggttttattcatgctgctgtgtagcagaacaattattg<br>taggtacatttaacttcttgccagtctccgtgcctcaacaactgcttcagtgtattcttcctgcattattcaatcaataattgtggagcacct<br>aattccaaatctcttgattccattgatttgctaccattgtagtgttcttgatagcagtatatggtgaagtatgagaatcgagattcctattcccca<br>cggcagagtaaagacacggtagaatcagagagggctagtagtaaagcatagcagtctctctatattggagaagtttcaggtgaaggctatcagc<br>gtgcgttcttgtaaacgtatccctattgcaagtgcatagcagtctctctacaacaaggaggttcagacctaagtctgtatcacgattc<br>ggacttgcttatgcttctcatggctaccacccctaacagcatagcagtcagttgtttccttaagtgtcaaagcaactctataactctgttattttaggctg<br>ttgtgtactctctcatggctaaagacaacttttatacaatcatgaaaaaatatattccaatcctggtggtttattcgtaggtattttg<br>cagttttattgcagaccttaccggagctcaatgttaggcggaggtacagttgctattgcttactgtaggtattgtatacaagctctacgaagagatcgctca<br>gcatttattgcagaccttaccggagctcaatgttaggcggaggtacagttgctattgcttactgtaggtattgtatacaagctctacgaagagatcgctca<br>agaacaacttatgagaatgcatccaatgttaagaaattcttaggaaacgattag |
| Contig49_<br>gene_77 | 1344 | atggcgtatcaaggtagttcttttttaggtattctctggcttcagcagttcgatgcaatgctattcgatgaatgctgtcctaatccttagttcaattgga<br>tccaactccaaatatcctgtacttactgtatttgtgatatctgcttttaatcatccctttgacagttactgcacagaaattatagtggaccaag<br>acaagatgaatgagatgcaagcaaattcaaaggcttgcagagaatttaagagaagctcaaaaagtggagatgctaaacaaatgcaaaagtt<br>caagcaaaacaacaagatatgatgcagacagagcaagttattgaaacagccagtcgttcattgattgtattccctccagctgttattatttccaatatggttcctatccttattaat<br>attcgattgatgtgtgcaatccgctataccgtcttcacttattgttgtatcctcacttgtgtgttgttagttggtattcattttgtacctttgaatgagtcaa<br>taggacaaatgcttttacgcgtgtaacataactaaccattccattttgtgttaggttggttatgtggtattcattttgtacctttgaatgagtcaa<br>atcattaggaaatttatgggattcaagaacggttctag |
| Contig49_<br>gene_83 | 1345 | atgccattccttataataacatgtctatttctgatattctcttcctcgaagcggaaaagtcatctccagcagggattcttttggaatcgtagtcac<br>cgcgactcatgcattacgtctctacacttcttcagagtgttaggtgttttcctatcctagattccagcccttacaacacctattgcaa<br>agatcttccactgtttgaaacactttaaggtcctaaatagtagttgatgataggcttttgatgtacaatacaatcttcatatttctaaatgag<br>attgatgtgatgcagaaggcacagaagacaagattaggtataattcctattggaattcattgcgttgatcgcttgtaagcaatatatt<br>tttaagatcattggaaaaaagcgaaacattgcaaaacagttttagattcaagaggctacgacgagagcttccggtttatataccgccaaggagg<br>aataa |
| Contig49_<br>gene_84 | 1346 | atggaaagaacaacacattaattattttagcagtcatttgtgctataatcttcatagcaccattagttatgtacagcggtcttggtgaagatgatgg<br>atacttcggcgcgagcgagcagacgatgcagctggcgaagctattggaagatctggttttaaaccatgttctcatcaatatgaagaaccacctcagtggtg |

FIG. 9B-79

| | | |
|---|---|---|
| | | aaatagaaagtttattattcgctcttcaagcagctataggtgcaatcattattggttacttcttcgcctactgagaggacaagtaagaagaatag |
| Contig49_gene_85 | 1347 | atgcacattatggaagatatttaccttgacatggtgtatcatatggttcgtcgtatcattcatcgttgtcgcttcgcttacgtatctatcaaataaaacaaattgtagatgaaacacctgactccaaggcattactgctgtcagtggagcattcatgtcatcttcatcttcatcttcatcttaaaactcccttcgttactggaagctgttctcaccctgttgtaacggattaggtgcagcattattcggccctgctgtaactgctgtactggaactatcgtactcttgttccaagcaatcttacttgctcacgcggattaaccactttagttgcaacacattttctcaatggtattataggcccattcgttgcttgctcgtatacaaagcttgcatcaaagctaatatttcatcaaccattgtcaatttcttgcagcattcttagtgactattaactatgtggctacttcattccaattagctttcgcattccctgcctcttttggcagcgcattaaaagcttacaaacaaaattattagacaaattaggtgtattagctcctaatgaagcatagaaggtatctttaaccgtaatcatatatgggacagattaaaagcttacaaaaccaaattattagacaaattaggtgtattagctcctaatgaagcataa |
| Contig49_gene_101 | 1348 | atgagcgtatttgattatatttgccatagagagaccgaaagaagcttcttttataagagacgcaatttccagtgtgcaagatgtacaggatttatataagtgaatagctagcatatcctatttaaatactttccattacttaactaacatctaacaacattagctattgaatcttcttattccatgtgcaattgatgacaagccaattgtttgagtgagagaaagcaataatgttctacgtttgattacaggcctttaggaggagtaggcttattgatatatgaagtggttttaaacttgtcttttaaatttattttattaa |
| Contig49_gene_133 | 1349 | atgtcaaagttttgtccgaaatgcggttgtgaaaatctagatgcgttcttttctgctggaatgtgcgcttctctcctagcattgaagaggttaaggaaaagtctttctcatggagctgaactgacaccttcaaagacttttaagttcaaattaaatgccatttaatcaggaaaccagtagttttcacagtccaactcaaattctaatgaacaaggcaattcaagcaagttaaaaatgtaataaatgaggcaaatcccgccaataatgacaatcaagactgtatctgttgcctgctcatattgtctttattgattgcattccatgtaattttaa |
| Contig49_gene_153 | 1350 | ttgattccttattataccctgccaagtcccttaaatgtatttaatgcgcatggacttaataactaatgaaaactcttcatgcatacctctagcacacttataaaggtattctcaggtatcattttagcatcctgagtgccattccactggaataatccttgatggtatgagaccttagacagattaagctcctaatcataagtatcctaaggcctattcctcatctcatgggtcttttggtttggtataggattatcctctgcagtattcgttatctttatcggttgtgttttctcagtactgtatacacaattgacggtgttaaaagaaccgataatgtattaatcgaagcagctcagactttagtgcaaacaattgggatatctgttcttaagattgtcctccatccactttgccttatatagtctctgacttaaggtaggtgtagcatagctttaatgtgtaccgtatctgctgagatgattgcttcaagcagaggttagttatatgatttctaactgcaagtcaattgttccagcctgaactgtgtagttggtatgatagttgtattgtataatcgtatttttgattagtatgtttagaaaagcgcaagagagaatattctgtaa |
| Contig49_gene_169 | 1351 | atgtcaagttaattcaattcctacttgccttaattgttatcgtcattgtatgtgggatctcttcattataagtactcgttggttatgccttggcttattggtaagcttgagcaggcggaaattattggaaaggacattcataagtcctccgtccattgctagctgaaatgggtggtattggtatatattcggattcatcataggatctttgccgaatatttctcttccagtttgaccttccagctttgtttctctctgttgttctttgttgaatcatcggcatggttgatgacttatgtcctcaaaggagaagctatcctcttttggcaggcatacaattatggtgggttgccctcctaatggtaggccttctatatatgatcatgatccgtatcatcttggaaagtagcagttcgattgcaggttgaatggaatagaatcaggcttgggttattttcaattcctttattataacaagtatcgaccttcaacaagtatcttggaaagtacccgtaccctatcattggggcgacaatatgcttgcaatcctcctgctgcaagtaaccgtaccttatcattggggcgacaatcgctcaatttgttattggaaggtaaagcacaatcaaaaagacttcattgtccttctaccgaacattatagatcagcgttaagtctacagtctggagtatgaaaggccgcagcaatccgactcagctaatgagacgcaagcttgtgggaataggcattatttttggtattcttggtatgaatgcctatcaggctgttattgagaaagccggtaactcatgatcatgatgattatacacttgcacagtttacagattcagacagattcagaagattatttctattattgggctgatgcctgggtaactcatgatcatgatgattatacacttgcacagtttacagattcagacagatt |

FIG. 9B-80

| | | |
|---|---|---|
| Contig49_gene_173 | 1352 | atggattcaaaggattaatcaacatagaactttattttgcacaatcatcatagtcatgattctgatagtgaacttcctatcctagagcatag catagattctgcaaatgtgatatggtgaaaactcccaatctgttgacggaaactattatacaatacttgtaagcagcaatagatcaagtaaatagcaataatg aaggatttcaaagaaaaataaaactcccaatctgttgacggaaactattatacaatacttgtaagcagcaatgaaataatattgaattcaac aacaagaagggaaaagctaaaatccagcccataatgagagccacatctatattcagcaaggcaattatacaatgaggaagcta cataattaaaagacccaacaaacaataatgagagccacatctataatcaagttctataataatcatgcaagtagaagaagtaa |
| Contig49_gene_191 | 1353 | atgacaaatatattaaaaaatgacagaatcaagtctgatttaaagatcatcgtggttgattatcgacgtattaggaatccttgtacc tcaatataagttaattgacttccaggagagctattttgctcccatttagtgcttcagctc tatctaggcagcaagcgaagaataggcagtcgtttaaaacagtaattgtttatatttcaacttcctatctgctatgtagctgtaact ggaagctatctcttccagttgcatgcatctcttgacagacgctagtagtgcagcacctgcgattgggagtcataagttccatgcttct taagatcttgcaaatctcttgcaatctctatcctaaggggattatttgaatcctcttggcctattgtaatagactatgcttaaagaaa ttgctagcgacagcacattggatgttttctccgactgcagtggcaagccagctgcgttaggggaattacaattgcctctataggatt atggcttgtatttagtgctgtatccgaaggagattaagacatttcatcaatacgtcaatgttcttatgcttgttggatgtattgcaac ggttgcattgtaacagacctatcattgcagcattgccttaaggcgcaatcctctaaaatagaggcttttgaaagattagccttgacaagactcattaaagt ctgcattcttaacaagaagctcagcagcaacaattcctgtaaacattcctgtacaacatttgccactgcccaagatcttattcaatagt atcctctagttccacaatcagttctatgtatcattccacttgcgttccctcgtgtagcaggaggtt ctcttgccttacaacaatgttctatgtatcattccacttgcgttccctcgtgtagcaggaggtt |
| Contig49_gene_201 | 1354 | atgataaagaagtgacaaatgtgatgatgaaataaccgattccctatttggcttaaagatgactattattcaggatatttctcttgattgc tgttatttttatgattttgaatacgacactcggtttcctcgtcatgggtacagtaataatagcggaattccaatgcttcttcttg ccatgacaagattgattcgcgaaaaaatgggttttcctcgtcatgggtacagtaataatagcggaattccaatgcttcttcttg gcagtgaagttgcatggattatgcattagttgctcttcttcttcagaaagaagttggactgtagagcgagctaagaaaggattgagaaatcttatcaattt aactccacagactgaagaagaatcgttggagatagcgaagcagtccctctcttgttgatcaatctatcatgactgggaatcattacctattgataaggaa gtgaaagcgttccggttccggtgatgatgaaatcataaaggcagctatggtgccattgacattaaggcaacagtcaagatggcaactgggaatcattacctattgataggaa gttgcatgaagtattttgcggtaccatgaaaaagcagctgatgaaagcagctccgactcaaaggaggtgactgttcttgtagtcttcttcttcagttgcattgcca gattgacctgtaaaggcagctagttgccaagcgacaaatattgaaaggagtgactgttcttgtagtcttcttcttcagttgcattgcca ttgcaatcgtagcttggctagttgcagccattggccaagcgacaaatattgaaaggagtgactgttcttgtagtcttcttcttcagttgcattgcca actgcattatgcagccattggtaacattaacttatgcattagcagtttcagtattatctcctttaaggatgatt tgtatttgataagactggtacattaacttatgcattagcagtttcagtattatctcctttaaggatgatt |
| Contig49_gene_205 | 1355 | atgatgagtcagctaataagatgaataagttgacgtttgaagaagcatgaacttaagaaccaagaccctgcttgcaataggactctctgcctt catattgattgtagtggttcttgtcagtttcttcattgacctgccattgacccctacaacgatcacaacgattgctcattgaatcagccaccttcccttgagc acctattcgtactgactggatgggaagagatgttcacacgtacaatcaaggggtttaggattaagtgtttcagataggattcttcgcttccata ttaagtagcatcattgctgttgcttagttttcctttagcttccaacacttcaaagcttcaacaaatattttagaccgattccgctttatatcttgcttatagatgtgttcctctc tattccgacatatttgcttatcattcttattcactggaaatcaaacgtatcaagacttcaagttggtgcattgcttcactcactgacat ctcttgctaggtccttaggcgtattgccattggaacatgaaatcaaactcaagacttcagagtttgtaacatctgaaagattaagaaaatccaagttctgatt gcaagaagcaaatcttgccattgtaacattgccattgtaacatctgaaagattaagaaaatccaagttctgattcatccagaaatcatgcacgaagctagtgtaac atcttaggttcggtttatctccacacgaaccggctatcgtatcattcttccgaatccatgaaatatcttccgaatcaatcttgcaactgttaattggtgtgg ctttattccctggttagcattattgcattcagttctgattgcttgctcttgatatattgcaggagaacatcaagaagatcagtagtcccgcaagcgcaat |

FIG. 9B-81

| | | |
|---|---|---|
| Contig49_gene_206 | 1356 | gattag |
| Contig49_gene_207 | 1357 | ttgcagttcttatcattcagtgaactcttcgttgtggaaccgttcttgtcgaacaggtattcatgtatcctgaatcggtcaggcagccgtttcagc<br>agtttgagaagcgagcgagtacctctgctgttggaaatcgttcttcagtgcgatatcgttattcttgttattgcgtaacctgattgcagatattctctata<br>actttgtagatccaagaataagagaaggtgaggaaaatgatga |
| Contig49_gene_207 | 1357 | atgtccctattaatccgttaacgctctatattccaatatgttgtaagccctgaaagattgcaactagaagacatattgggtgtaaatca<br>gccgattactgaaaactgatcaattgttaggaaatattatcactgtgaatttgaacttcctaatatacagaactcctgtattgcaggtaa<br>ttgctgaaagttcacagcatccctatcttgatgctaacagttggtgattcttggctttgcttaggagttcttgcaggattt<br>aaagagacttgattgataaggttgtaaggtatactgttacgtattgcaatctgcacctaccttgacttgcttgttgtaatggt<br>attcagtattatctggatggttccagtagcgggcgttccgatggggcgttcatcgcctatactcgtgacaagcttattgaagtaatgacaaccgaatt<br>tgatattgccggcattacgctgagcattttagagttgcatcaattgcactctatactcgtgacaagcttattgaagtaatgacaaccgaatt<br>tacttcctccttttgccaaggccaagagggaatccggatgacctttgattaa |
| Contig49_gene_217 | 1358 | atgaaaacataagacaaacactaagcaacatagaacaatagctcagtcctcaaaaagagcatacttccatattctcatcttcatattcct<br>gcttatagacgttactgtaaccttaccctccatcacatcacactgcagacattgtagatgtggaatacagacttcaactacataataa<br>gcgttgaacaatgatgatgaccatgttattgataggagttctagcaacaatagcgtatcctattttcaagcaagtatcagcagcatatga<br>aggactaaggaaataagctatgaaaagatactaaatctccaacttcgaacttaacaagatcaagatcatcctcataacacgtaatac<br>aaacgtatataccaaatacagatatctcttagcctgcttcttttacaaccatccatttgcacctatattaggaataggaagcatcatcaaggcaa<br>tgaacttgaacagacctcctatgattattgtagtgacattcgcctcagttgcaatactcctcgaataatattcataagaacagttccctac<br>tttaagtgatgcaggaacttattgacaagatcaaccagacatcaaggagaaataactgtggaatcgcagtaatcaaggcattcataaggcagga<br>ttacgagagaaagtttgaaaagacaaatgaggagttcaaggaagtaaatctccatgtattcaaaaccctcttcctaatgattctgcaatga<br>caatgatatttgaatgtgatgatagtcctatcttcctgatgcttggagattcgcaatgatttacaatcatgattccaagatactgactgaaccatcatagcattc<br>atccaatactccacacagattgtaatctcaattagtgacggaccaatagataagtataagatgagaatccacaatagaat<br>agagtcctgaatacagatacagatatcaattagtgacggaccaatagataagtataagatgagaatccacaatagaat |
| Contig49_gene_218 | 1359 | atggcaccaagaccaagagaagattgcctccggaaaagccaacaaatgtaaaggaagccatcaaaaacatattggactcctaatggatacaagct<br>aagctaagcataacagtcatttgcgtatcctcacactgtattcctcgtaataagccctcttgattggactagctacaactgcaatattcg<br>atggaataaactctgaaacatgaactgaaatcggaatatctaatcaaccttctaatcacagttgtgattctatcatagtgcagtcttctctat<br>ctccaagctatttcctcttggagataacaacagacatcagctataacagacagcatcaagaaagagttgattgaaaaatcaccacctatccatgggaga<br>gatggataaaaacacaagaggagaacatcttatcaaggataacaacgatgtagactcactacagacgacttaatcagacattcaaccaattgc<br>tctctggatgattacaatagttggagtcacatagtgcttccatcaataatgctgccaccaatgctgtgcttatcaattgca<br>tttaatcataacatttgtcacaaagcattcataaagcagcaggaagacagcctatataagcagctaacctatagggaagcctgaacgacagattgaagagtc<br>attacaggccatgaaatcattcgttcatcaatcaggaggacagtccatggaaacattatgtttcatcaatggatgtaatgttcatgtattcttgagcggtattc<br>ggaaatccaagttctattcaagcctctcccgccctctgaacttcatctcaatactctaaaacttcaatatgtgatagttcagttcttgagcggtattc<br>gtcttcagaatgcaatgtgttgaaggtgcagcagtgagagaatatttggatttagagagtagaaacgaagagacc |
| Contig49_gene_225 | 1360 | atgatattcgtaatcaattggttcctttatcattaagtgtggtaacattcctctcattccatcctgaggatttacaattctatttggagc<br>cgacttggctttcctgtattatcattggtcagcatgaattactcacccttcggtcctattggctattgtaaccgcattagcgt<br>cgcttaaggttatgaaggtcggtgttgataatcaagcctaaaatcgtatatgttttcttatagcaataaccgtattcggtgagca |

FIG. 9B-82

| | | |
|---|---|---|
| | | atgcacagatcattccatattgctatggttcatcgtctgttcatagtttatactatcattccaaatccttagcaaagtctatccttacaat cagaagatttaatgtttttccttgcagttagttgcattggtttgttgcttgagctttgttttccagatttaagcatgaagtttctctccat tgttaaggattcaagacttgctcagaactcttgcagtctaaaattgtaattgtaaatactcattgatgttcacgatcctgcttcatcc tattggctgacagtactgattgcagatttgcagatggttatattgcttcagtggttatattgcttcagattcttgccattcccattgtcttgg tcttttggtaaccaagaaggatacaatcgactatatgctgctcttcaggtatctcggttatgcatatgacttgagatttgacattgttatattgc ttttattagtctattacaatcataatggctgcttattgctccactggttatctgctcaggatcattgttgttcctcttacaaggacaattaggtaag gaagttcttttaattggttccctactgattttattgctcaagcgatcattgttgtcctcttacaggacaataaacgtatggcgctgct cacattcctgttcattaggctcttggtcttgctcatgttgactattagacgtgatagcaatgaagttttaa |
| Contig49_gene_227 | 1361 | atgaagaaagaaatagaatctacagatgttgaagtgatgaatcctaaacttaaactagattccactgtagaataatgaaattgacaa gactgaagaacttgacgcttcctctgaaattgatgaagaaagaacttctgcacttcctctgaatctgtcaaggatgaagaggataccaatctagtcattgacacagcca gtgaagtggttgaagcggatcgtgtggtaaagcataggataaaagcctaggttcgattacgacagttctgaatctgttacgatgcaatgcttgaagtcctccactctcat tatgttgaagaagtcatagtgtaagcaaacagtaggaatctgtgagaatcgtgaaacaattaaaaaagcagcaagaaatgttctctcttattggtgatccggtgtag cgaccaggtcatagtctcgctcaaggtagtgctgagtattgcctcctgaagtcttaagacaacaaggccaatgcaaaaagcgcgatgagaagaagatgatgat gtaagtcaatgctgattaggacagtccctgcagtctcaggccagcaagagaatgtcagcaaaaagtaggcaaaaaagcgccatatcattgcttgtaatattttt ccattgattaggacaagcctaagcaatacatgtctcctaaatattgtaaacaacgagataaaagatttgcaccattcatgatgctactggt ccatgcaaatcaagcctgcgcattgctcggtgatgtaagcacgacccttccaatctgaaggtcttgaacatgaaaactcaacagagc gattcaaggctcataaggagtttatacattgacgaatagtacaatgagtacatgaacatgaaactcaacagagc |
| Contig49_gene_231 | 1362 | atgagttcaggattaactataggattgctctctccttaataatttttgaattatagaaaacttgattctgcttcacggagtagtaaagccgc aatccacttaaactagaatggcttgcaatattcagttcagttagttgttgttggcgactcaatcgttaggaacagtatgtacaacattacaaaattatgaa ttacattgaattcattgcgcgatttgcaatattcgtattaggacttcgtattgcttatttgttgtaattaaatggcttacatattgttgttgga |
| Contig49_gene_232 | 1363 | atgtcattgcagaatcattgcagatcgtcagaatcattaaagaatatataaaaccattttagttattgatttttgtaattatttgaattattgttgctccaagtgt tattgaaggagcagatccttctctgttgcaggagcaagttgtcttgttgttcaattatgagttctttgaaccaaatcagcaa tgaatactctagacacattgaatttgcgattgcaatattgcgattctttcctttaatataccattgcttgga taa |
| Contig49_gene_242 | 1364 | atgtatttgactaagttttgtcctaaatgcgagagaagaacgaagatgtggctcaattctgcagtaactactgtcatgacttcaaggatgtgaa tcaaagaatgaagaatcgaaaagagaaacttcttccccttgtctgaacaaagatcttagtgccctgcaagaaaatgagattgattccg tcagcattcctctcactgccgaaacgctgacaagctgacaaagctgacaattctcaattgtatgactctctaatcttgaatacattgcctagccaccgaaatcctaactgat gggtcttttctatataattatcacttagtgaggtttaccaatctgccgatgattcgagggctatgacttaagcaagatctacgatgca atgcacattggttaaggagtatcatgataactatga |
| Contig49_gene_243 | 1365 | atgaatccattgaagacaatgcaagcgaaaagacaagcaaagactttcaaagagaaacagaccttgatgcatctgatgaagctgacataga cgaacagatagaaacactgaaaagaaacaagaactttagcgctaaccaagaagcttagcgccctgcaagagaaatggagattgattccg gaagggtcatggcttaactgctaatgttaaatattcttgactctcctaatctgtgactctttgaatacattgcctagccaccgaaatcctaactgat gccgactttcaagttcattagttcattagctgccaatattggtgtagcatggttgctgtttcatcttgctgccttcattctgatttaccatca tgaattattaaattaaatgcttaaatgctttacctagtgcttagcgacagtcatgttctattagtgcttagcgacagtcatgtcacagtcatgttctattagtgcttagcgacagtcatgttctattagcgacagtcatgttctattcacagtcacagaaccc |

FIG. 9B-83

| | | |
|---|---|---|
| Contig49_gene_247 | 1366 | ttattggaacatatcctgaattccgcttatcaaccaatatttttggaataataattgctagttattatattcttcctattgatgcttaattat gcatctaaaagaggattccttgatgaaggtaattgagaaagataagaaatatgtccatcacacattatatatcctaggattgcagtgat tattaaccttcttgactttagtgtgaatgtgaatgaaaactteattacttgttcttcctagtgcctattctctacaataaggatgtacgtttcaaat taaaaaataccgagtaa |
| | | atgcaagaaaaaattgacttggttcactgcctaaaaatcattttgaaattgagcattcctataatagcttctgcatcttcgatgcaatcta cggcatcgttgatatgctatgggtatcaaggataagtgtagaggcattttatgcaataggagtgtcaataccaatcacatctcatttctcat tcggtgattcaataggccaggaaccaatcaatgatgtcgtttcttataggagacactatgaaagcatgaaactgataacatgg atttctaatcgcaaatatcatatggtccctatgtccatcctgctctgtcttttgcatatgtattcatcttaaacatcatattggacccctatctctt attgatctttgattatatgtcctgattatcggttcaaatctccctataacattccagtcctgatgttttttacactcctgaagaccaagattcctttaagccgaaa gccgcttacgccagcgtcctatcctccctatactcgttggtaacagtggacaatgcattcgtacatttgttaatggtgttagcatctggaa aaggctatgggttgatgagcgtaacaggcattgttggagcgagcaattcgataagcgttgaagagtataagtatgtgctaa gatagcagtctgcacatcactcgttataatgattgtcttcttcgttagaaaactggcattggcctatttt |
| Contig55_gene_5 | 1367 | atgataaatagactaagaaaagactttgaagaataataaaaactcataatcttcctattggagtaattcttttcttttgcaatcaccaaac atttggcgggatcataatcccgacttaaagactcattgcaatattcatcgcttatcaataatcatcgcttttaaacgccctactttgccaactatcactt acctatccctaagtcttcatagttctgacctaggattctgaacctttcaatagacggagtcctcttctttatatagcatagcttatcatacctga gtgtccattaacggaatacatcttggaaaagagacattattttgaaaagagccctagaaagatgcccagctcatcccaaagatttgacataggaaccatcccaaatcatgattgacaaggcagccacagattgatctcttgg taccctatccgataactgataaatcaaaagaagccctagacaacggagatatgccaccctcaaatcatgattgacaaggcagccacagattgatctcttgg gaacgcatcttcaagcagaatcatcctccaaacagcctcccaagcagagatgccaagcacccaagatctgttctcaggagatgccaagcaagagtcttgtcattaatg gagcaagcagaatcatcctccaaacagcactgatgagcgaagcaagatatccaatgaaagcatcaatagcagcgattcagaaagcttattgtcattaatg tggtttattcttcatcaactccctaattgcaagaaatattggttctctcatctttgacagtgatatgaactgttactcaagagtcaggca tctgttcaagaaacattcagcctcgcctcaaataggaggattgaagtattttgtagcacgtgcaggaaccaatg |
| Contig55_gene_10 | 1368 | atgagtcaagcaagaaattagaaagggatgtatccagtagtaagcttatttaaaggtgaaaatgagttaagtagtattaacagtaatattaatga aaccaagttcaatgaaaatgactgatagcgatctaattctttggaacgcggttcattctgaatctgaatttattaaaagtttaatattgaaaa aaccaagtgagttgatatcgcaaatagaaatatctcaaacaatcaaacagtgtcaaacaagtttcaatacaaatatcaaatcatagaaaacattag |
| Contig55_gene_14 | 1369 | atgaaaaagatatatctttatttccaatcctgctgaataatgtttggatctacaggaatattcgttagaacattcgtagacgggaataga ttctacaacattgcttttcttgcgttttcaattgcaataattatatgctaattgtcttaactgtaaaagcctaataaagtgtcta aggaagatattccactattttctaatatgtgattatgcataccttggattaaacctatgctatattcatatattcaatgagagattacaagcatttccat gctcagttcctcttaagcactgccctgatcgggatgcatatgacaacggactactgacagcatgaaataatcggtccgctaaagtaatttccat aattctagtgattatcggatcaataccggtattacaatagcctcgaaatcaatcgatagggaaagcatcattacatattattcattgattata attacaatcgttacaataccgttacaaactttgacaaatcgaaagcttgtttggcaaatccggcaataatacttttattattgca |

FIG. 9B-84

| | | |
|---|---|---|
| Contig55_gene_27 | 1370 | ttcattgattcattgctctgcgcgtatattcttattacaatatccttaaccatttgatgcaggaactgtggtgattctatcctctgagagc<br>ctgtagctgccctcgtctttggtgcaatagtttataatgagattccaagccattgatgtttttgtgaataattataacaattattgcattgata<br>agcttgagtagaaaaatagagatgaaaagtgaataa |
| Contig55_gene_29 | 1371 | atgcacttattatggtttttatgtagctatcgtacttgccataagtgatgaatccatagcagaatagtgggctatgtcagagacttttacat<br>agttttggcggaatcataagcagttctctagattctgtaatgaaacttggattgtccatgaaggattagaagcattattccatatgatattcg<br>tatcaatagtctctcttttcattaaaaataggattttagcgcggcttaatccattcctattagatgtaagtcattcaatcgtcataagacatatg<br>ccatggttacctcatagagacattgcacttgttcattgaatgttcattcttatagccgtatttgattatag |
| | | atgaagcatagattaaattttagataataataagacccaaattatatttgttgaaagaaataattatgattctagaaatccaaaagtat<br>attagcatcctatggatttaaaaactttaaatagaacaatatttacttttaaaattatatttataagtatgttccttgaattgacatttcattca<br>ttttaaacgagcttaaatccaaaagaacttcgcaaatactttaaactctgaagtttgactgcagtcaagtttataaaattttttcagaa<br>ataaactctgaaaaacttatataatgtttaaacagaatcttaagaatatggttaaaagaagaaaaagactttattgttgatgc<br>gacccagtgacgtagatattaattccacagaaataaaagactaaagaacatctgaaaaattaatctcaaatgagttattcatcctcta<br>aagttatatattggattaagcaactgtgtattagatttctatgatcctgtttgtatttagtccactctgagctccaaacgat<br>gcaaaactttcgaagaaatttagaaaaccttcaaaaagcgaataatcagaaaggagacacattaactcttgataaggatattacaccta<br>taaaactaccaaatcgaatcagcaaatacaaaacaaagagaataatcattccttcattttccaaaagaaaaaattcagcagaacccgattgataacatttaa<br>cttatccactagcgtatttaaccaataaggcaaaatagaagattttttcaaattattaaaacaaggcttgaatatgagaaatccacaatatac<br>tcatggaaaaattaaacaataaggcaaaatagaagatttattttttggagcactgattatatcacaaggattttact<br>tccaaatcagtagaaaaccgtttatctaaatgtattttctactcatgtatttctactcatgtctgttctactcatgtatattttatgaaaaggagtaatttctgagga<br>aagatttggaagaaaaggaattattacaactctttttaa |
| Contig55_gene_41 | 1372 | atgactactgttgtatatacagtttcaaatgctgttctactcatgtgttctactcatgtataattattgaaaaggagtaatttctgagga<br>aagatttggaagaaaaggaattattacaactctttttaa |
| Contig55_gene_43 | 1373 | atgagaaaggaacgtattaaatcctatttggaattatatttgatctttgtaatttttagactgattcaatattatctcttgcctataca<br>aggccttcacttgactatgcagttttgtaaggctttgtaacaatctgttttctcctattaatcgaattcttttatgattatata<br>aatcagatgctaaagccaaatatttcaaagaacattccagattcctagatcgcttcaatcaccattcgattcaatcgcttcattcggttca<br>agttccattatacttaattggctcgtttcttacgttgctcagagtgtcgtcagagtgtttaggcgtaaatatagtaaaaaaatgtttgga<br>aaggttattaggcgtactcatgcagataagatatttattgtcatgcgttatagttgtcatattcactattctcttaactcttccggtcatg<br>aaaacatatccgacagttttttatttttgtgtgatcacctaaccactgtaggctatgcaatgaaggttaaatgagccttagcgaatttgtg<br>acattatttttaatattgtcggtattgtcggtgtattggtcttcagtactcactggtgtaacctcatcctctttatagataagatgctgaagaggcat<br>cagtgtgatgagaaagtctaatgagaattcagaagaattaagcaagaatatctgaattaaaagaaaacaagaaaagaattgctgaaattaaaa<br>aggaattggaaagtctaatgagaattcagaagaattaaagcaagaatatctgaattaaagagagttaattaaaagagaaaataataagtaa |

FIG. 9C-1

ORFs containing membrane-spanning domains identified from *M. ruminantium*: amino acid sequences

| ORF | SEQ ID No. | Amino acid sequence |
|---|---|---|
| Contig40_gene_28 | 332 | mkveimiigilllsnflyhhedgnpivqyvayiasllviilgff |
| Contig40_gene_32 | 333 | meksvillaavvsfvtaflanisvalpliarelamsniiqnwvatiyllpiamlsiplgkltskhglnksllagiilltigviiacfsinsel llsrviggigtalinvasmalivsavnpetrgqalglniagvvigislssapviggilviyhlgwqsifyimliplifsaylswslkdewtmydg piditgsiifsigililviygftivntwlgivllligililliafayfelrvnnpvfdvrlfknsrfsssniaslisytatfvityiltyhfqyi mgfdskfsgmllivtpvnmailaplsgrlsdridpqklaaigmgfvtvaltilcflnestplymillamflqgigyglfsspntnaimssvpk eetssasaslaavrviqgtlslgmltvifayimgnvaivpeyypllmessrlsciisavlcviavvaslvglrsddeyet |
| Contig40_gene_33 | 334 | mnskqktliilslsliillasiaavsavdytltnadmdyvvksngllhvheaitydfdsspngvyrdiplksgqsienlevyvdgayaeyqiip kgsgerikvylytdsskshklssdsvitvhyvydmpkvvkiyndigelqykvwgdewdedlenlqstitfpddeelqfwinpyfsnakarwae dhlkihsdfvgdgkyvearlipsefdsnaeyaqhinkngkdeiikigddkksqegfkslfsilnkvlvvlcfipgliylkfgrepkttyd aiyehepptddppayvngmigsglkdvgslnqeafqatimdlinrgkmgvsseedteftkttflttikdtsglkrfeadvinilkryelngnis lsymqdcirgesearyfqgrifeswkenfeneyfsedsfsrlfdkkgndylnyfaflliligiiafvasiffdfavtgstifvgvllvivgvvc lmlpsgiagkytdegklyeekwmkfkkylqdyslikehppesiviwnkylvyatalgvadevykamkmevysgsddyyrtndlymfyylgghr findsfntasstisaadnssvggigggsggggaf |
| Contig40_gene_36 | 335 | mnnkqktlaililllaivltsisaasavdykitnadvhldvedngilhvsenitylfksdghgvyrviplkadekmsyltvdvdgsyfeyniin rsgekevrvylykdkdltdygvsegstvtlkidyymenvvklfrdtglleyklwgeewdqvehlnakvtfpndeeieywinddsgktessfs gdtlyvkgsdipkgdyvearvliplgefdfdadyalhynhdasdevkkqeedfqkkqqyfntignllnviygililtplgiylkygrepkvss daiyehepptddspaifvnammsglskdvgkvdkkgfqatimdlinrdklgmeiaytnkkrpvslltvkstdglkdfemelidilrryeqngki nflymqqlsnrneayhfnrafnrwvsnfkvdylpddvlsryfntkgsdligkfkwialvagftgiigllltgswiplvlglililfvgvicfy lpssiggqytkegreyqqkwkrfekylkdfslikehppesvaiwneylvyatalgvadkvyksmkmevydgladgsnfssndlfvfyhiggir sldnsfvtvnniisadsssggigiggsgggggaf |
| Contig40_gene_37 | 336 | mnlkqkaiimlilsillmsaisasdykgsymdyvhmnvnengllvhvnesftyqmvspeseisiplyhgtnasienihirvndllvaydlkkgd tldelvihpkssdydydsestgtylldveveydienavkvyndvgaftyqinktdfngvslgmahirikfpgtqeheyfiipkegessaqwde dhfhmtnsqpakatviipldeldadakyaqhidsdgleaikndsfdlkysliqivnilikifviiafilpvaiylkygrepkvtldsiyehep ptddppffvnaimggtfrdvglvdtkafqatimdlinrgklsveteineknkqrtylvakstdgladyesdlisilrryeedgridlkhmels lyskseearyfrgrfnswghllysnyltddikaeyfedkgsklfkffayggllisvilflyclmfnqmeplpwvialfilssvlicipsafagh ytkkgkifkerwnnfkkylkdfsmmeeyppesvavwnkylvyatalgvadkvsntmkinfydglndetyrdndvfvfcdgngldligdsfsav sttldsdsggsdgvgggsgggggaf |

FIG. 9C-2

| | | |
|---|---|---|
| Contig40_gene_42 | 337 | mnitenqsdndekiltksfclifgallftalvmyalmstvteyassmgstatiaglvsgiyvfgglcsriysanalekkdwktlaliflsihf<br>lacilyffvdnvelllivrfihglgfgasanaivtiassilpkkrfgeafgyfmlgttiavglgpyisgffydiwgsfgsfllatvfsfialv<br>cvffldieryhpdekinnedilsdaesvgtesidanpikkqekekrsfiekifeidaipvslftaltalgvvsilsfyrlyaveldlvgpfslf<br>fliysvilvasrpiagkigdkngdkiicvigivaqsiglfliayapsdityicavcaalgfgtlnsacttivtrncsidrrpyaistflfc<br>dstigfgpallgcfvsatsgyapiyyisafitlmalpiclyslrnk |
| Contig40_gene_43 | 338 | mgekaqwdssIsfifamigaavg.gniwrfsyvlysnggsffipyfvaiaimgipflileygvgfsfkdsftnilkkidgrleivawililf<br>vfivviymvilswdmvyllitsftgwgvdtaayftntvggsadlakggiflipttiicvvlmwivlwfishrdvdkgigkvskvlipslfvim<br>giivfysitlpghmigidallrpnwrmlldvniwlaafaqiifslsmgaialtyasylpessrltdnvlivvasnslfeiftafgvfsilgy<br>mslnsgmalnklvtegtglvflvfpmifnvmgtvgrvlapllflailfagitsalgffepmlssasskfnlsrkrtatilsiigcafsilltt<br>gissylvgvidsfvnqfgillligvqciifawwygidhfipvlnengilvkgkiwkfiikyllpvvlfviwaygiftlfttaktfeimvdiii<br>ivavlilsfilshlnprgsnedna |
| Contig40_gene_47 | 339 | mkenkemnwkikfaiimfvlavliflarylicgdgeeiiaylwkhigfgipidililvalveeimgrkeheailekidmlmgtffseigndlia<br>elskanvnkantddlkaikswndkdydnklkelknnpvdfkaniapeeredflnrigsllvenreflvnlinnpnllekdefsslllalihld<br>eelarrgeltdikdadfnhlngdmkrvysklvewvyylkylnkhypymislairtnpfdseadvhvte |
| Contig40_gene_60 | 340 | mieelvtnmsitesgasasspifititilvftilligliyfvfkmyeqskptvesivliavitalatvgrliimsipavnlasfviimvgvvf<br>gkeegflvgaltafvsgifmgmgywvifqmlawglmgasagylasrfdslpfrfifgllwgflygwitdisaifysgtalqitpiialyingf<br>tydlithgvtnavllvvlydwfkkmftrakikylsnpsssdesidltn |
| Contig40_gene_62 | 341 | meltaihpgvylllyyfimvllafisdpyfvlsflalililiialqgvsselknimkffiplsvliilinpllnrtgahriylfngffityeai<br>aygilmslallivilvfssynrsvsyqemlyifskklpiismiivmalrfiplinsraievqklnnlkangvesdeedindsslednlseen<br>nlsdennskedsdsldleqfdsnissldigsdsrvfkkiksskrfgsiakeakvlgkimgitvswsleesmftaksmkargynsnertsylsy<br>kfgladiiflaiiivtvsilivigliqgygminiypsidfsfsdlpfniyyfafivfllpllylleikerflwr |
| Contig40_gene_74 | 342 | mndlisgiilyllifiilmvfafsmgilspyvgrreilisiiaigfvlgaigyffiypmyqdspyvlgnlqglftmeseilnlnipstsnisdv<br>tekilnqngvnsvstngfelttssinnetktyidsylkndsqierysigtnnisvdlkndasstatlgslvtwlsntvgvssefafvhikvnv<br>nanqvldikeylrdnhytivsvegpvqdtihyfydhlapdyvvmcitgiigvlvaiagiyvepltkfvrafrrgg |
| Contig40_gene_76 | 343 | msgfimvfftlllanyydlkygiipnklsvflmtfgilinvlilivlililisfpvililsfpvillllvykllrenklinlilafsnmkllikelstktvfindlkegmivedy<br>idilnhfytgsilnsfsfnsgillypkifsilinsillsfpvillllvykllrenklinlilafsnmkllikelstktvfindlkegmivedy<br>yfnsleifnlmeeltgneecynlkasqfkensyvlkssmaglitrddiklinfaymetlinfpnfkikmgvpfvpsltvgylvflafgdlvfl<br>istii |
| Contig40_gene_127 | 344 | msdknewgsnlsfvlamvgsavglgniwrypypvlysnggafyipylvaillmgipflileygvgynfkssfpkairkisskaeylgwllpts<br>vfiimiyysciIgwdgiyvilsffkgwgadpntffastllqssesvsgitnfipviaivmliswgivwyishkdleeglgrvskilvplfii<br>mlvivlfsltlpgamiglnelfspdwnlldfniwmaafgqiifslsgmsiaftyasytgkegdiintlaitfancafenfcalgvfsilg<br>ymslqsgtavadlvtqgtlvfrayptvlnvlgqyayvigplffitvylagltsilstieplsfsiqnkftwsrkktmtvlcligavlsmmya<br>tayggtllgvdayinqiailfgvileciyfawifkcenipilnersktiklgkwwvivkylplfitivwiggvldtindgstdqlivfg<br>iltvillgltalfthlpatneewdeteyrl |
| Contig40_ | 345 | midsfryalngiavslkdernlkiqmivmnlviiagfllkisrtewiiclilfalvlsaemintaienaidytremtvdkdnlariakcvsa |

FIG. 9C-3

| gene_131 | | gavlviaiasaivgliifipkvllll |
|---|---|---|
| Contig40_gene_145 | 346 | miwrekslkdvleiafaplffwlieigfalfvslfigvfidmiigieamv |
| Contig40_gene_168 | 347 | mvvlsagdtawvliatilvllmsipevaffysgltkrknvlntmfltfiafsiasilwvvygypfafgdvsisgliaqpahffmsgigiedlt<br>gtiptilfivfqltfagltaalisgsivgrmkvsawivfiiawtlvyvpiahwwgggflmqmgsldfaggtvvhinsgvtalalavlgrr<br>kdtsllphnlgysvlgagflwfgwmgfnggsalaanglaasailvsnvaaatalitwviidivkvgkptmlgaitggvaglvaitpaagfvdv<br>paaivigfvttfvsyfaiyylktrfgyddaldvfgvhglsgiwgaiatgifavpavggaagllygnpgqvtiqvisvivtivyaftisfilak<br>ildktmgirvdekteiegldtkihkesgyrl |
| Contig40_gene_173 | 348 | mnilnlpinilignisffasialilscvvndkreaykyqvieaIiltvssafflswtgiltmliaaarnylvmnerlssrlaIifiliitlii<br>cplintmgliglIpmigiliqlticnyylktikwikvafivnvliyavyfigiydlvscatqvitaiigfislvklikdekegnidsqpnn |
| Contig40_gene_174 | 349 | msddelyrraerkvdekigfykhlysyigvnlllfainaitsfgkwwfywvtifwgigivihflktfvltgklednreemiqkemekmkk |
| Contig40_gene_175 | 350 | mkrlfklvekyffilillavaiavvfpgsfdwvmgefmgininilligllfgmgttlkienfvnvfkrpkeillgvgaqyiimplvaigvas<br>lfginealtvglvlvgtvpggtasdvitflakgdlalsvsltavstvispiltplitlilignniafnpvdmfisivqivilpiaigllnyk<br>fpdfceelkdylpavsslviailvagvigankqailgssvviiaaivvqyfiamllgfvigylsgmkrkqmvtiaielafqnsglstslakth<br>fpalslatvpgalysvwqnfagsilayifrkyftdee |
| Contig40_gene_176 | 351 | mneehynkqllrdyqestdlsvydhreeidydedvdislcgcpdcaddhdhnhdhdhnhehshehehsysheheheshshehgh<br>ehgdehshehshdhdhghdhehehgdehshehshehesedtcgcgcddddchddleehshehdhshdhnehhehehdhhshehede<br>hhhneehshehshehdhehhehshdhdhshdhdhghdshdhdhghdscgcgechdddfslcacpdcaddddhgqeellaegkpli<br>ynrpigimvssgilfitghilefIsfsptivtiiymlgaliagyeiailayksIvkrhtvgpallvviaciasfiighgeegaavallyyiae<br>flediaehrakrsikslveiapetarvkvgdgeesrrieevkvgeivlvkpgdkvpldgevvygtssinqasitgeslpvtktvgdevfsgtv<br>nedgylevvvtkeakdsvinkivtlvkrsqlnrsttetmvekiskyytplmiiiaacvafvpplvfggdIidwiykalsimviscpcaflist<br>pigmvsaitsatkkgvlikgstyveemrnvkavifdktgtltegklelndininindeyseeivriaaslensshpiaqaivnyanekeigf<br>eeiedfrnvpgkgiigniggkqyyaaneslieqsgfnisqeeinqysaegktlifigdegsviasitvmdrirdnasevikdlksqgvktfml<br>tgdnkiaagkvadeigldyvysnllpedklniIdtlrnkfgdvamvgdgindapalaranigiamgaagsdvaietadvalmqddiskIpylf<br>slsqktmniikqnitlaivvkalfvilailiglitlmmsvgidglgltlvvilnsfriamvkdplf |
| Contig40_gene_183 | 352 | msesitpnggakysnnknkalaskkgndsyyknvlligspnvgksltfnkltgmtamvsnypgttvdidegnftyenktvhitdppglydlnt<br>iteeervakilvldlkrfdlmvhvvdaknieksidltlqlidagkevilvlnmmdelekmgatvdapslshelgipvvltaaqnrglddlkht<br>ivnydsienqilseskt1ldvdygrsieiaiseiqrnikgnypvskrylavslIegdedsedlmesedwdnlsqvigaqkakfdqpvkyltk<br>lrladyakhikssfttidsvniqdtdslgeklsrimihpfygliilacvlffglylivglvdfIentifggyinpavtsvvvgyipw<br>vpiqnlfvgeygivtlgltygfgiilpivslffivfsiledsgylprlallvdngfkriglsgrsvipfvlavgcgsmatmvtrtletkrern<br>iatmlmaltipcsaqIgvimallsarprsiwlwlavivfnfvviglylakrfvpgagpsffmelpplrwpklshiakktwtrIvmyikelipif<br>ilisviiwaldlvgifqwiiacvtpivnaiglpgstsssfvlgffrrdfgaaglmtiqnglgtvgqllvasvtltlflpcvaglmimikergvk<br>lagliavmsivlafsmgfivnfiltslnvvl |

FIG. 9C-4

| | | |
|---|---|---|
| Contig40_gene_188 | 353 | mivgilsiilaivvyfitppyiefylifvflipaialivpndaiknsraigaltfiilvivayfaisgmlgaydvltnmyvnglinstpstsd isacsngylmvliyalfnifcgalffkrtssidddvdeaf |
| Contig40_gene_215 | 354 | mascnigkkfiaeligtfflvffgtgaavtllisdsvtpgkagiglgllgglgdwiaialafgltvmaciylfgkisgahlnpavtiqllaskn isaidsiyyivaqvigaclgslllyvclgaqavtigglgatapgmgvgylpaliaecigtfflmlvvmqvavdekaepgfagisigmtvaavi ivlgaftgasinpartfgpylmdtllggtnfwgffpiyligpivgavlaailygylakgndacalpqpffee |
| Contig40_gene_218 | 355 | mylgssfafiapmvagvaiggksifsalmvvgliviyvaiailiratgkewinkllppvivgpmimviglclaptaigeigldqavvpinniiv alaafittaviairgkvivipfligilvayvvaallgmvdfsgffsaslfevpefympfinysfnptalltivpialvtmvehvgdhkvlg eigrdliqdpglnktllgdglatffaallggpanttygentsvvgltrvasiyvigltavfafifafsghltallaampnpviggvaillyg flavngvklliqeevdfnnnknivvaatmlviglggatlsvaqgdlsvsisgmalaaiagvlnlliperkednkfvpevk |
| Contig40_gene_220 | 356 | myiksffndlnltkkdgiyllaltvfsilytvhlidvnytlnfksdpfvylinglvyagmgghienysygmfltpvvsfltsllfrmgivdki aimivsgvisilgeiglyllfktkfnevysffgcilfasfhivltiwgggidipvcafsliitflfmvlavdknpkyyiptsifliisiftky dalfiipilflyyltkhdffnlvdlalsdrdelkivikinyikseefkyivislivvlifilfceviwsyganltfltqsqeslngfnsakaa rshfyyndkkfyirnlytffypqisqefsllipaiiagtvfnfaniirrkeypmvrdyktphfkyllvgliliilipialigfkyishmvtn valiticvllsladkfdidkrtfnldifflawifvfavffsfitikgqryliialpavvyfvlrtieeifnkfkdsnilkitliiiaaaiiv yslsfitfdgnfdternntaigevydylveydpdylnknlssdysygsrfgtwtlkkcvryvklgvidqsesdylivkhdnvslanyteiyra gkikiyqnnmydnssi |
| Contig40_gene_230 | 357 | maailcprcgkmndgsldfciycygtyfddyneednndnlffirsmtndgrpgkkqvvrlnempdnlqkpkhrlaillgylfailgglgfvfa iylitrkdknarrhgliqlvilliieyaligvlilinggldinmvldpfnmtrmnnitqlynssqmvvgsnisslfgf |
| Contig40_gene_246 | 358 | meelyymiylivfivgsilglllsykkhmepfiiseidvltlvlaivgwfllnhgligfvssvilltiaffcigrrpgygrketaigi lvavivwiltsgvifkf |
| Contig40_gene_247 | 359 | mnlmaqilinvviaflagslllgfhrkvmarvqlrpgppiiqyllhslkfffkketsfpktasmpfyvgitvilagiwvtgvivgpvckgslmi ifgiyaihkivehnagsssgspygklscvravfsaagelplfaviavvfllltgtmdiggiiqyqaangplafkiplaaimfftlvtkspysp faitkgkeiitgfetehfgmlrgyimfsesiawyillwlfltiffapigvvgyligmilicvitgfinattpmlnpnhsvmaqisiavicvvg siimiii |
| Contig40_gene_249 | 360 | mlienlggdflgtiplgldivilyinplhhiflfvtillftaliaisrtetqveamfgsldenkvavglkefkhrrflaiicgiatagamitgdlf nftlfmaligivnligivsavkqvevlnsayqygliammcglplfggaaiilaatgtlslfelasipanpmmifgalvmligvcgesgiapffa skaemfrtpgspfililhlssflivrfieilltil |
| Contig40_gene_250 | 361 | mvasvipqvvpafyssmyttalygglivafigligvamekrdiqililtdivglamlivvaavgtdlseallpglvvelaeimaiseilisr emrkadkdtsfspmpldmeimttapnfiallligygiflsgftggavaggivivlsrkvrglpifvldgvgaisgiswclwiigffff ilpqywllslfiaalgllkvaskigligilmreeygrk |
| Contig40_gene_253 | 362 | mlefinietismalmiigaigvllkkpldkiimvsvleaglflaivsfkyldvafltavldplsiivfllalikinkvrksklkedystldkl nistenleeksldknseggk |
| Contig40_gene_254 | 363 | myieligvitilmalravitknraekllyinvigfcvsalialyikttfgfvlaaffisstigsnaiayslkdledeisydkdmeerdeen |

FIG. 9C-5

| | | |
|---|---|---|
| Contig40_gene_255 | 364 | mdmiigiilaaviswinfvvvdtflglpeapgvkgaetvgysikerkgdlaggffggnilcspdasagtliaaigvyyalgiqggliaallvyi<br>gnrlcadpgyagtcgaltmtllifsfvgievemficgmviaiftiggihhptssrllgkiaksfgrytkye |
| Contig40_gene_256 | 365 | maivvaviiafalriplperpirfswttsalfptpifaigilaifyslnvywiydgliilsvivglasalfvkygfgdyifpkppqiedggnv |
| Contig40_gene_268 | 366 | meideliltyliiiavvailikifswllpifvilavayvlylyitenna |
| Contig40_gene_273 | 367 | mkkiiekhygihlnpndflpieeiksImqlyfllililyicimnffnfgisgelifinslidiilsvflvtiyydgstrgkiisifllpi<br>vsisyilfggsliryydfiripilylvvifynkfidyternnlgktilillsiiytgliltivlekqnpidavamvtnaitsngyaalgdse<br>ggvltsvflawggyiisgvatatlaadiihrnsrkkfrnmetkidnlenkidnleriivesqkenee |
| Contig40_gene_282 | 368 | msfltlilknpfrsksrailaiigigiatiialgaitdgmiasaddtlhaggcdftvsgkiestsssqmatfgtstidedyidkianvtgvk<br>daigmymtvlmttnspyfavvglpedygvsdltitegrmykndtneivigkiaseneekgvgdtitlddkkfkivgiyesgntlqddggfta<br>iknsqklskdegkissiyikvndqedvdkvrdritdkygdnlttisslsdlemtknmidmlngaslaisllaiiigavgliintmltsvfertr<br>elgvlkavgwsdekillmivgesivtivagiigsivgvigvellaaskimqllnpvysvdifvkafaialfvgiiggivpalksh |
| Contig40_gene_284 | 369 | mqtnkniesiigdpkkainrltyptilsmlImfannlidsmwvsglgaeplaalgfmsplylviigfgsgvgagansIisrligakrydesnn<br>aaihsiiialivsiiisiigmffldllvlfgagsvldyamdygmiifIssiillfpaivsslfraegdirratvplvvnailniifdpifiy<br>ifnwgvkgaaiatvlstlvnllmmlywylvkrdtfiklsleyfhskmeiykeilfvsipasleeliysivaicfnylimitagtmevavftvv<br>wrfvsiaflpcisigistitvagiayqarnyenfkttinystflsftitlicliffvfaypisetfnfisgdaemisrtaevIrimvfyniv<br>ipfggtavyvyqaigsgfkslaitilreliilsvflaylfgivlkmgifgvylgaivgmaigcfigftcikiyqgkfkkecesInqpv |
| Contig40_gene_287 | 370 | mfgkdkkensnekvlyegqpnlivysksifiavillglfflystgiqyignmqvymiestklplitryfaiavfviimvvilyiiikfslwts<br>ikytitesrvivekgiiifnkknympfntiqdvsrsqsilgkafsvgtitlysaydgkdmslkdvsnpkkiedlifenmrtthlrshnlyddsy<br>gnpynnsynnhnhwgydnygdsyqnrdfkpirpnsdekvhynrmedldleIvdvkerkrnIreirrkaknsrgnnynnqpidgpsnnynrn<br>snydpaynrnsnykqnpnynnrnnyddfgyddyesgynqrskrapqgnrgyskrnanqyrddsranhqhretiresyqrnpkyfaqnyekfh<br>qdnleaqnrggesfnempldsndyygmdddfisdeefdstinkamenigdnikfkpnnhsrvvnshedfdsrvvnshedfdsrmndsyddfa<br>sgsrhntdyansnqnrhynsnypddrgfrsnqsyegdyrqsrsnpyegdyrqsrpnrsyddgyhgsgsnpnynnsydqsnyyddyrqsnnp<br>prlnkqsssdnyhksnnrnrssnynrnsrsynnqenynsnyndmednsnnyeesdkkgkkkknkdsndllekhsrkfrrs |
| Contig40_gene_290 | 371 | matfkgfamkrlneigwvekevpecgpmdaiikptcvspctsdihtwegaigdrrdmilgheavgevvegsmvkkfkpgdrvivpaitpdw<br>ddeaaqrgfpsqtteplggwkfsnfkdgvfgerfhvnmadanltfipdglsdegacmltdmwstgmmgsenaniplggtvlvigigavglsai<br>agakclgagrlfaagtrpisvevakkygatdiinykngpideqvreltdgagvdsvviagnlentwaeaiksakaggtvsnvnylsgadnvl<br>iprvewgcgmsninitnglcpggavrmerladlalcgrqdpellvthkfkglekiedallmkdkpkdlikpvvmldid |
| Contig40_gene_301 | 372 | mlkqiirknftskykdsvlgilwsffnplitmallitaifssvfarnienfpvyfltgrcvidffnsgtkiamtslkknsgilnkifvpryvfa<br>lggifsefinflmsmivlivimivtrapfhlyaifsvipiailfililgvgltlsilctkftdieylykiftsllvyacaifypidivpqpir<br>qymelnpiygiiagfrefvmygrfpstklmlitfltsivififigvfikkygnritlel |
| Contig40_gene_326 | 373 | mgyltdlfkealvyplsnivtlililgvlltisfgvdvdfqliilifalisfvvslfmdgyslavikdavdfnvsmpafdimknfid<br>gvkvwvlkilyyiiptiitifvalltggvdailnifrfigenqellsnIntpaelinaipqeyiatfltslfitaivailyiifgllynigl<br>crlakydsfneginfkaiindikaigltyilwyiilfliifaisivmgliaaipyigiilInllfapflfllvnrslgllytkaegyng |

FIG. 9C-6

| | | |
|---|---|---|
| Contig40_gene_338 | 374 | medfkyyknkikeeiklafahnkyflivsalifilipmfvgyfysdqitpyiqpmvdtfeeniringtvtlstkslfannvevaiilyalsalga ilgivvlangglfigfyganfeltryvlltlphgifeisailiattggfvilsfvlnflynviypdysytdifdpyfsdakitvgqrfkssfk khghrikesfillcvsvilliiaafieanitipfaywicslfgisli |
| Contig40_gene_356 | 375 | makrnfseslgkivtllkkdftdvftknpvvpivllailiilpslyaliniqacwdpydntgnieiavanldngttfegeslnvgneiedelkg nddfywfvnetelregvkngtyysgilipknfsksiksittddphsaeleyivnrksnpmasklsdsaakavynkinakivqfinvvayskl gelqsalsqgaqmssgavqlsscgsaqvnsgasqvksgsnqvksaanqvqsggaevqsggeeikshasevksganqvsqgssqiqa gssqvqssakqldssvdvdklpsddlkhvvnsskqlanassnlagsssqlangsvqladqsgvlangsgasgsvrlangsvqla dgsvqlaegslslaagsqllansaayalfaaassslsgaasslssitqvdenqigsyiyspvtlneielnpvdnygsevapfylvlsmvqgali tcvmlrtqggstqgteyspsemyfgkllifmvmavlettvtligasilgiemsnpvlfvlsayfialvfmlicyslttsalqlglgkqiavlwlvfq isgtggiypiqlmgpilqavspympmthgitllreaalglvwsnyihsflliiamglitlillalikvfadkrahwfeeklnetdlfh |
| Contig40_gene_366 | 376 | mtvsflfvngaasvllnaidkekavtkiyimavifnvclnlvlipmfsydgeaistvlsvkyllsf |
| Contig40_gene_368 | 377 | mnqiksifkntgwlsvsqvitsicaflwtiiarylgvsdygivsfavsftglmgivmdlgistyitreiakhkdlvrkyfnniflfklilai ilfilsgllivmgyshltiivtlvftielifmsmttflngvfqafekvkyqaigailnssflligilitlgfdlgvisiafaytvaysiyfs ymflsyvktfsrphleldtnfireviksipfgltnfsyiydivmlsylagdyatglyksayniinvfttfvvyqsvifpvmskffke sqnlikvsyelsvkyllliiipisigiffyarpvvdliysnqyslastpvqiliwtvsflfvngaaavllnaidkektvtkiyiaaifnvcl nliliprfsydgaaiatvlseilitilltlyhifktdykpdlglliknviklivcgiilfvalyylnlslwfaipvgfivylisfltksiddnd ryvirelinr |
| Contig40_gene_378 | 378 | mtispkrilyldevrslaimlvvighlarlfsynynswlfcsgvfsltrigvplfftvsgsllltrkyevkfklekrfkrvclpffswiliyi vagvliwhydltfeyvvntafgvgdysalfwfiwsligvylilipvissfireegnwgaeylilitiilsllytfgffdypqmkynfrvlifnff pvlgyfimgsyihnkkfkysdkkmfaigcvlfivgicghfakiylkglgglslapidffdicvimetiglfiafkyastkwdkrkdarn |
| Contig40_gene_379 | 379 | mqeiefretklgevivlfasccsfgiyfshyilmryimyngflapirkthalifwlpvssiiiiglswlliyvmskipyvriasgvk |
| Contig40_gene_387 | 380 | meigeiitdslkypinnikaliliyivlgivagivlvltgvgvgagaiansaaatgivgigiiiffliylllilgyeldvinfgierrddapei dfarqitngikwyitcfiymlliptiimiilsyinqtlgglivgiiifiiaafallmaqcrlahtdslgealnipeaikditkvgiikiiavfli lviglvvsfiilglfsvlgdvgtyigailsgiftiylafvvfrasgllysdav |
| Contig40_gene_401 | 381 | maqikcpdcgkeqedtnkfckncganisnvkaeevkldldaapteekidintapteekldtdasevketpkapvenkkicskcghelnnekfc prcgqstasivpyeaktesggenndktcpscgtkvttekfcpncgskieekkpvqtgnapqkyrcncgnpidpkaeicpkcgvrqltvvkep lfsliislifpglgqfynngthkgiflliigaivsivltifvigvllymlvwlygmydaysttialnngeyvedklf |
| Contig40_gene_428 | 382 | mqrktlsrfdeivkilrkydmdkvlgqttrrnrispfrsgsenkellkedfperliltlqelgttfikfgqllstrpdlvgeriseelsqlhdd nppidfeeikviieedlggnlkdfftefsdtalatasiaqvheaklhsgervavkvqktnvqeivetdlnimkflanesdrfnttfkhlnpa vvkefdrsihkemdfdnelmnirhlrdnfihndkiivptiypdysservltmeyvdgvklseviagddpkynkiliadrmvrayfkqifldgf fhadphpgnifitddnsicfidfgmmgvldenfrgdlaelmicfsnrdidglinqliymnilnvktdisilkgdlndlfakyygvelsrfngv iedllflmqkydvmlpnefvlmarglsmveniglsldpididiveiikpfarklmiqkynpkkmvhnarntfftvehmlralpslvsktfykvd egeltinievkqiseitnqislaliliaalvigsslammveagpklfglplllgfvgftislalgvftvvryfmdf |

FIG. 9C-7

| | | |
|---|---|---|
| Contig40_gene_433 | 383 | maiimkhrlnldnkdpnyillkeifkimdsrksksilasygfknlnrtiftfkiifismffgidipfilnelkskkelrkyfnisevltadqv ykifseinseklikclnrilnsrnmvkrrgkktfivdatpvdldinfrrnkkskehlrklnlkwsyssskgyyigfkatvmdydsmnpvcil ihsgapndaglfeeileniqkrriirkgdtlifdkqyygyknyqigiqkykivpfifpkekfnrtlddiltyplavfnktkkimeekrlynk lkkellekldswekfkpirgkiedffqiietrleyernpqlyskis |
| Contig40_gene_465 | 384 | malelmnllisilgavyfmlpayvanlsglafggtpidgganyrdgnriigngvtwkgcingtligtlvgvvlgivgmyygdlstltggvid lhvygslfsglilgflmafgalfgdavgsfikrrmnlgsgqapapimdqldfvlgalifsllvvriswsffiiiclisillhlssntiayllgi kdvwy |
| Contig40_gene_471 | 385 | mfeftknelrdlviafivlsiafaianvkfdlhafisilpivmfgvgvgflihelghkyvankygykaefklwpigllialitsligwvfalp geakitaenideettgkialagpmaniglgllfiviaaitypllkssftlfeliylvstvgfsvnaflatfnlipfytldgtkvmkswsvkafiv afaiaainmlssmfigaenmilmligs |
| Contig40_gene_475 | 386 | mglittgmeqsvqttmnegaeitvtnitsigagtidsslvdelknitnvsrtagilsatdqnfvdmassndmsmesstrlyginradldle gikdingsffeegtkqaiigkqyaqmnnmsigdnisalgeefeivgvfetgvladsgvyvsletldevtgaegkvnqvivktdegvndtvva daiedkyenlttitseemsqmldnvigildavsvavsalaiivgaigivntmvmsvyertkeigvlksvgwksrkilkmiigetlvltilsgi vgsafgiliaevgvrlmgdtdfalgyspstfimafgitivvgliggiypaykasklaptealrye |
| Contig40_gene_481 | 387 | mikkktndkeqwfiyranlrtktlviglaaliiisifvcgyfirdiptnfasanqmpslehlfgtdwmgrdmfqrtiaglgisimvgfiasv lstiisivlglfssfnkfadeavagiidlfgsiphilllivsimfggvwgvimgvglthwtplarvlrsevkeiktkeyialsenlgrnkv wiaikhifpliisqiivgvilmfphaimheaaitflgfglpphepaigvilaesmhylsagywwlafypgisllivvlifdligenveklinp etaqs |
| Contig40_gene_482 | 388 | mnkqkiakyfgwklvrfvvlmiavaifsfvllldlspidpvnaylkgaavteagrailqqyfgtnvplpekifhwlmdllqgnlqtsliyrrpv mdviidkfmaslalmtiswilsgiigfalgvvagknkgswidkavkvycyaiqsapsfwvgmlismvfsvylgwfipigfgvpigvrstdatfi ewatrlviptltislvglapiamytrnelvqvlssdyvlfaksrgekgwalikdhglrnimlpaitlqflsfselfggavmveqvfsypgigq tavaaglqndvplflgivvisaifvfvgnlladisyyfidprikenefnd |
| Contig40_gene_487 | 389 | meflklkrskiflllsvlmavipallmyiatfadfdevqafdalftnvnmymsvlfavllifaiimaylfgreynehtlkmnltipisrgkfllsc flifllwllvlsvlsclssllfgfaagisgftvnllinsfaqllfanlllfltfspfvfislfvtnmvpamvggasltlvnmlvyggtwapyv pwvcpyliasgeiaeyginmllpyglvfatfivgivislylyftkkdvpl |
| Contig40_gene_495 | 390 | menhkalaipillaslalisfngieggvelkggslaelqltgstsvndlesqltkelntnnikvtsngenkvtvelennvnsstfskaid gkakvisyneigpvlseeamgqiyiamlfaflfmavtvfivfrepvpsvaiilaalcdilialgmsilhiplsiasvgallmligysvdtdi llttrllkregtvderarnamhtgltmscaaiaamgilyivtviimpeattlsnisavlvigligdilstwlmnlgilktyidwrqskkqdk fnidapksnesksskseedgksesksfkdrfkrskdddskdesesedsskdsesksdssndidsseeekssgkdkkssktksnkkgnkrktkks kkkgkggk |
| Contig40_gene_496 | 391 | masnlskffkdrqviilicliilisisisflgveqgldlkggssiqlqlehpvndstmkvvtsvldkrlnlygvtdvkvrssgdqmvivemag kspeeverlignppgifeakidnktvlvgsdvatvdapvvgesgewqvpftlttegakkfaelakgkgghevvmyldgkqiddhppalaeelas geavteqvtggaedvetakaesnevftvlktgslpvkihtvgsntvspelgqqfaggaliaglailgisavvyiryrraflaipilittls eiiilgvasiihwnidlaaiagliasvgtgvddqiiiitdevlhhddentrhrrtrtqmnvknalfiifasagtliaamlplayvgfargssg igtiagfafttiigvligvfitrpayakfielfvs |

FIG. 9C-8

| | | |
|---|---|---|
| Contig40_gene_498 | 392 | mwemvwpillvilsntiynictkstpgnvnafgtlmityitaailtaiifvflvkpenvmvelshvnwtsvvlgiaivglelayifafragwk vssasivaniglaivlvfvgailygenitlkqlggificavglflinmg |
| Contig40_gene_510 | 393 | mqeanedidlivnhpkqainklalplifsnffmvlnniidgiwvagigsnslaavgfvtplffamvgfanglgaganslisrcigaenygag nsaihsmnlsiivtfativlfativlvlflnpllmlmgageiieetsnygyilvgaysiflpammaaifrsegeinrasyplmlnaiinmildpifi yvlgwgvkgaafatvlagtfatlpmvywmfikqdsflkiklseyktnlkiykdilvvgipasieqfiifsvsilmnywltllagtlavaayta twrlvsigvspiigigvaaltvggaaygaknlknfktalnysailgiissiiicsiffvfaeqlsfifsysadsailaprvvdalrilcffil lmplgvisgnlfgamgkgtislvltiirsfilevifagifafvfdwadigiytglvcgnmcgsivsylyinyylkkhedyfivk |
| Contig40_gene_514 | 394 | mfiglapaivstvfimlsgsdllkkdfknkmigfykvkwlnviwavivfaivivcsillsllfgqpldqfsftesfsftgvgiagafititl asiieevgwkgycedsignymnwfwesmlfgvlwsfwhfplifisgtvqaglmvnplyvinffvsgipmgfvitwvylesdrsilacmifhff vnfmqekialtpetkcletivitvvailivmakkdmffetrhvgrlleynssqqq |
| Contig40_gene_526 | 395 | meesktrfegvesilgdpkkaiwklsiplliislfitslysvidavwvsslgadalagvgfvspifialmgingnlgagatsaiskyigegdkk ksdngavhaivitvivsifftlilflifitdiilsmgasntidyamdygvilvsgsilvilsnslygvilrgegdgnrtmyamlfasilnmildp ifiyylglgvkgaaiatlislifvnllfywfyikkdtylrpflsnyrfdkditvdilkvgfpaslelvnnalfaalfsllltvvastdavav ystgwrvvtiattpmlavgtalisvvaanygarryedillahrysmkiavlfgfiaaivvyfapqivsifaytgtsmrlssqliafslvivi yfptmgygvtstflfggtgngitamfqtlretvftlgfailiavvlggyeygawwgiilgelvvntitmfwadwhvkrlirsnn |
| Contig40_gene_535 | 396 | maglnlidsvmyypiliivmaiaglyfftktrgvqirlflesiriltteppdeegsisslqamlvstasrvgtgniigvstalclggpgacfwm wvmcigassafmestlaqiykrkdkegvfyggpayyiehglhkhkiallfcvfllatyavgfnmlcsfnlgstfmeypfyhpsitpiiigav laittcycllgggkrivsvtstlvpvmgvsyviiclivilfniqnvpvmflifrdafdfqsilggvagscmvygikrglysneagvgsapna sasadvshpakqglaqtlsvyidtlllctasalmclstgvvrdaavsgapyvqnaissvfgwigpilitvamilfaftslignlyytmnvlmf mnnekmpskrfvhifhiacsliifigaiipmdaawamaditmggmtlnlpvcllskaaidclkdyerqkkmglkpvfkassiglneeeldw wk |
| Contig40_gene_541 | 397 | mnvfrsfidilsdrtvnergyffsnkalfalflplvveqalefcvgladsmmvasigevaisgvslvdflvqllifsfsaiatggvaiagqyl gndepekacdasnqlvwfttilavimavlvlifrpflinlffggiepdvfntssiylsymaisipfiaiynsgaaifrtmnkanlpmqimfvc dilnvignaillfvfgfgvegvaiptvlaralaavimiyfvlqeryeihirktlrhkfdwvllrkvlnvgipygvengvfqlgriilislvst fgtiaiaansvgyaigifsvlpgfainlgitavisrcvghndyeqakfynkkililitifshlainllifallpyilqiynlspaasaltyqmv vwhgifavliwpiaftlpttfrgagdakwpmavslsvmficrialsyviadfmgvgvfgtwiamfidwyvraafyvryfsgkwmeyravgtn ls |
| Contig40_gene_544 | 398 | mrtlewednklklidqtklpdeltyycsnykqvitaikdmivrgapaigvsaafgmalaqlagedmekvavemknarptavnlmwavdrvmk aenmldealemaredintnlaigeygaeliddgdtvlthcnagalacvdygtalgvfrsafnggknlqvicdetrpggaslsvwemqegi pvklipdvrasgylmsigkidkvvigadrvahdgiankigsfmvalaakrfdipfyvaapistfdkeislifdteieerdpneviyggaricpe gtevinpafdivpkdlitgvitekgvfdlnnlekdfkelf |
| Contig40_gene_552 | 399 | mllskileellwgmgtsieifllltllfsiplglavaagrmssfkplqwfmkayisimrgtplmlqlivffgpyyifgmtlsrdyrmiavila ftinyaayfaeifrggiesipngqyeaaqvlgytrvqtffiiilpqvvkivlpsitnevitlvkdtslsfvlaipemffvakqiaaaeasisa lliaggfyyvfnalvaiimerfekrldyydt |
| Contig40_gene_561 | 400 | mnvfgiedpwiwgvyvllligmtlvcvaygalnwnned |

FIG. 9C-9

| | | |
|---|---|---|
| Contig40_gene_562 | 401 | mvgyvgylawkrtnssedflvagrethpyimalsygatfistaalvgfggvagkygmgilwlaflnilvgifiafvffgkrtrkmgkninslt fpeflgrrfdskflqyfsgvlifcampiyaavvligaarfmesslmldfnlalfilavicgyvlfgglkgvmytdalqgtimfigmlillvf iywvlggvteantaltnmahlyppdalaeggtgwtsfpklgspfwwtlvttiimgygigalaqpqlavrfmtvksnkelhrslligavfiavm tgtayivgslcnvyfygnfggiaidyvggnmdsiiptfistalpewfvyif1lsllaaamstlssqyhtqgtalghdivdafknrgttreytd eeilegsskeetrigfisvsgiliavvlsliliglilpggivalgtslfmglcaaaflpvycaalfwkratrkgaiagllsgtftslfllvf vykktavglgickaltgmdmlinvmpwysidvmvfaipvsviftvvvs11sppmdekvikrsfeglsee |
| Contig40_gene_565 | 402 | mldrlksislqnwiligmvlgitgvilnlyvhsqfidilildnvfylggnifikimkmlvvplvfcsivvgvasisdirkigtiggrtlily littalavsialliasfihpgaglhmaglatasnvstnvtitntilgmvpdnpinslangdmlpvilfgvlvgiilaklkeetetinkvfeeg ntlmmentsivmkfapigvfclmaktfatlgfdglmplskyvicvliglavgafivypslmviftrlnpikffkfysvmlfafssstsnati plnlekiselgvsrevssftiplgatinmdgtaimggvavmfaaqaygmdlgasalltviftavmasigtagvpsvglitlnmvftsiglpvd aigiimgidhildmfftavnvtgdaictiivsfknksidldvfngkkqaegss |
| Contig40_gene_570 | 403 | mfldrfslerndlnfrkynlailiaslllylllniyflssfgdffkfyfddlfaimvlfsflnlvfpykidnfwliviitifaaffweyvalfi kpgsvfdyldilayflsmviylliliyafegelnvsf |
| Contig40_gene_571 | 404 | medevidvedyevketaivvsddeedndysksndnnytsnttfrtatislsneklililalvaivliaiflltfc |
| Contig40_gene_574 | 405 | mvlicpilaeeahattvfltsdnvlghdedmqmlndikqietksngqitvivdenasnpgegtramnadcdiavtiayacagnlvdlgsysv qstkkiiyvnagsldltsinflrrsyddnwsssfaslqnpgqylydsgitllqpgqkfygetdngnldhcsseidgyiadevmkqvysngvi rkldsdylnrhkidpkylaedskkivdgfgtpmadsygsyttqqllymsasylvgysidvpqqfappenpaeysaftkgtysfneycemadiv vdymnehgkapdsisykgatisyydlvynfalltqddfdaahmnfpqnadfqkynsnlildilpiaiiivvliavaiiirklikkgrrgikri knrgkdnnyyrnqasgnrsrksrggsrdnysrnsarynnsrgnqsrksrnsgrprnsrnsrdsrnsknkrstklfhknvdldqydnsrskep krlnkkr |
| Contig40_gene_578 | 406 | mieeilktynttieglitneakerlekygpnkiqeqesdgllklflsqfadaliflliiaaiisylignhldavvivivviinsiigfiqeyr aenamqelkslvskeahvrregktkiipaekltigdivlieegnkvpadllvesydltidesllitgeseevrknadysnmgnleekirniss hyqeeelrekivsmnsnvlsgrgtgvviavgmdttigkiatmiqeedeetplakkvdklgkrigalsiavcigvffidffqdyniiegfmtav slavaaipegipavltitlalgmqkmaksnaivkklssvetlgsctfictdktgtltenrmtvredflldnksvlisglcnnakyetvdege yeslekdnnrarnsseedskktenskeesqlignptdiaaynfakghgfdkldpehsytrldeipfdsnrkrmsvivkketqneteyyiftkg apellnlsdriekdgnikeidsetiskinrkidemtnktlrviglsykqideedynkiknshndnkihdiqeelernliftgllgimdppra eaidavascqkagievvmitgdhkdtataiareigilskedceslskhvltgeeldrlnddeyrniveeikvyarvypeqkriiidilqskdh ivsmtgdgvndapalkkaaigvamgsgtevtkesadmiiqddnfativssikegrtiydnlkrflkfqlstnigailtitigsllpiptpftp iqllwiniimdgppaqslgleasednimerppergelldkktlikititisgivmtigtlslfiyelglnspygktkaitmaftvfvylqlfnal nyrsksnvknkmlifsligtfilqvliyvpylqiiifktcpiepfdwilviilsailivtdkianrlin |
| Contig40_gene_579 | 407 | mnliadiasglfwmslvmiggfivvialmtligkgssadf |
| Contig40_gene_602 | 408 | mrtevriagfgggvimagililgkaaslydninavqtgsygpearggasrteivvsdeeidypkvtspdilvamshealikymgdlkdegvli idpdmiveeeivdfvkehkiklyrapatktatedvglrivanivmigaivkvtnvvsvdaakkaildsvpkgtedkniqafeagyali |

FIG. 9C-10

| | | |
|---|---|---|
| Contig40_gene_608 | 409 | mdlknikiatiitiiafiiiglyaltevnyfsyknvvehddinasvviipsigvfekinnvsisgqvvidqmsnlptkgdvvlfghrtlqgsp flrldslkkgdivtlewpeigeinytvksskivpasyglylneshmeqdihnqeiylitchplgssaerlivvgelnstslinetaleenpha swawyitlgffalglivsflspeeerkilavviiitiilvyfclfpissqiwadqlgwlnsmmgvn |
| Contig40_gene_609 | 410 | msnrfnsfkkgiskvkniskvknispkikgnsnrkknnsknkrskstieyivpensplrknstdldsdsgffnsdyldipegvsytrpvgdlsegvty thpaddsydldgvdkryakyifgddlsdrnfkdprdssymedldnndglnnefgrnnfhksrnyadkrfnndldnngenykndsyldesysd fsfkkdldngylngdaylsnsdfsdfdkdylddsnfksshskkaslksngikskllnfkdglinkddnsksrfgkivfililflvlassmfyff vygpfgdelnleknaklnelntlykgpleahenayilknqiesendinelkkidilmyatkdwrtyhkskivsskdnfgrvmlaygdenknli msvkdanefvgdndgrvlsniqfekvdtiivppvsisrlqasaglisvgsivdiyslkdnysyggdedsnfessalnesseglvenqsedned lgggedisimpvdsnpeedsgfsqnqepdvsgatvlailrskdsgvidssisksntlvegnltdpyentssytndveelkasvfnsyddnka leyylnsygiklsnyermsnladidseyllevprsdvsfvinnmdnliltiptefapnwvigelnetyydniynydlnsssfi |
| Contig40_gene_610 | 411 | mrlksvgmgyflavsdaisilniafgflailmvidnnliyaslcillavvfdsvdgwvsrklnrvdplgfgmnidsladivsfgaapmailys igssisswagyliaivcmitlvcglirltrynviadkinyrgfvglpipatailvtyylsglfniavaavlmllasflmistirypkvdnyy liglgalmillllilpiqvfigpinlpalvlfvlalvymfmtfleffiddmtfdrdkasdkvsnvreiteskvsssvtnvkdvfknmkdting isnedldvglkedaeeekekevkeaeiveeve |
| Contig40_gene_616 | 412 | maidikrhkeklrqdepeiklvpfidilftllifivvtstfgaatvddngsgsgkpnmtdttgdaeyylipvaglqkvtvdgvdmsseikgna igvharvldggdvqiktsehaliikappgmspqeavhtpe |
| Contig40_gene_617 | 413 | miiemltdgfnmimemlqsgvityiillgiyglllisirkifylrkiskidateimgtitssmeqgaiealknishyknpvsrimsealki gynktevesmeqifivelskmtngisalktiielapflgligtvlgiwmtfknlgvnpdaaamaegiyialittiagltvaiilmpllytyi kgliddemdkielatkmtnwsyavikirryeklpcvvealqeadgivsvkeitdpysniqisfkpsmleksisniilekcdvkseiteskirg |
| Contig40_gene_635 | 414 | masfiptlnglgfayigakefknnwiegviyeipwfllfifvnnedigvffatigilgmavsfvrslyvykhkdilidddaesristeksi tsfwwifsviiflnglgliyvgfkrnvrgwilegaffeflwllffitpsnkalnsfiislgfigmilsvirtfmvyfeeermdggfysptavk keppaqnpientinsysennlsdddivpefkgyktqvedlkdafktkednvnnlskrftkeelsygrfksvvnefhktfysqadstltminl apeyservdetiknkiglmdsllgemnlleelilndglpeksdeeitelfemhnlinsvddynke |
| Contig40_gene_638 | 415 | mgikeffinkekrkivaiekdlnnnlsilggysmgikeyfiekidiilfillisiiaialdllgvdiygisliwiailfcgipifkeaaiglyte fdikadvlvtiaiisilligelfaaqcviavimaiggyleeytvsktragielvdltprkgrlienynksnesereisadiievgdilkvvpg etvpdgkiisgetsidgsvltgesipvdklegdevfsgtinlygsfvmkaikkgedsslqrliklvefsnpndaeivktadkwatlivviaf icavlalvftgeiiravtvlvvfcpcalvlatptaimasignlskrgilvkegitieklakvdrvvfdktgtltygkpltdvivydeeteek elihllaslenlsehplakaivkyymdnyddtlikisdfemiiakgvkanlngsnicagnleffkslgidipeefieeivspslekgataiyi akdsrflgcallsdvlrkdasdlvvqlrrikvvstlltgdnkqaaeyiakeadivdyqynclpedkistikkfgslklnvamigdgindapsl rqanvgismggvgsnisieasdvclvsddikyvphllalsrktirtinrgiafalilnilatvlamygmigpiegafvnigsviviysll lryeyan |
| Contig40_gene_657 | 416 | mwaqvnttialvpnianlglpytmvrflsaekdkekirdsfypmisltfistviiclliflifghpiadalfngsmqvlyittaisffacmnlm lityfrtfqemkrysiflvlqsyigvfvsiylytyagynietvvlgiltgyaavfimmaflivrhlgfsfgkwsnlkeqlafalptipsnvssw vvdssdkyvigillgsvavgcyspqyalgsilimflspfavllptilpehyekgdmaevdkylsysmkyylllltvpaavgmsvlskpllyiit tpeialggymvtpfvclgaifmgmygitnnlillleknt̲milglkwlwilvaisnivlnllivplnliigaaiatllcymlafgvtaiasrktmrl |

FIG. 9C-11

| | | |
|---|---|---|
| | | pfnrkelvkiliasaimgavvymmnpsgivnvlvailvgvvvyfailfvlkavtrkeigifkdlvk |
| Contig40_gene_659 | 417 | mkvvvcencgakyqlndddinafecsncsgslkelesfsdeeipkqsdessgsdsvlvycincglkfqiekddnindfecascggpldylsn kseesqesqisqdsgdsqgsdsyyetvsyvqsddiipihadpnysdsddipihaesdsqtpyyeeliesdeiyanqyeddqyvseyekvlqsd adsyyedeyddqyyqtdlqeegsqgislde lyytseypaydgtdeiipihaekrymedsqdsgfaygpngkyaedyleeeyieeeyvdsvee spyvevidipedelpetpvvltrqvlseedqrlfdrvnqmvfdspeeyeafkaarykyyvglldilkeeyllsmenefksgrsvknlikkg etvkqsnlyaddsdslvspetvelmksnrkyepkksnadviiiagffivivslayyffvsqimyvliafalglvilaygaykkyvfneylarg riirerllalpndfyvfyavgppqskdiinhvvvpgtgiftilsqrydskdyknklksdtetgdmlsesasigdyrqkntlelqtdydngs rfqfgneeihftqnsqikrkalelnedlaifldkkgfngiyiepligfvnddlailnviltnedlfidelfnkvirgrkrideltvakiarll syysancdvy |
| Contig40_gene_661 | 418 | mmfsniskdlnierkdylclfillvysaiitvllinfnesigiycsdvyiylynslvfarmgynntylylspldfglvelhflfrlgfvnevs iyavtgvfsifgslgiyvllkryfnsllslaggvlftsfslnllwwangtldpavglswvailfliladvespkyyilsfvflvlsiftryt clflipiflllylskhdlfgfldslisdrkeafsslrsfikteefrylmialvlalivavlfisvilyygaelsfleggstfasgskqalddy ahttdtlfyfhdlnflfsqkvifqenfiptltgasylaylilfilligisigiyrffnknksedkqfdnvnssisnlkefsfktshfktll yigll1slaialigfkinsiitiaflligl viif slkskgldrkdysvplfmigwflvyfifftflnikvnrylitvfpafiyfvilanei iglldgkslkigdlnlsniipivlvivlcmfsafstfstfednldfndykivadylidydgdyaskdiavfkqrtfnwlkdstiavttdqldf lessnityicdedlklenytkiynykdiflyervnn |
| Contig40_gene_662 | 419 | mnpyleiirpgnavmaaisvvlmmivghyydlpiilcavivfvctgagntindvfdykideinkpnrpipsgrislknarnysyllfaigiil sfvidyminsiwpsvivpavvimylyarnlkamplignitvatltgfcfviagtviacatsslrilfisiylglfalfmtlareivkdmedi egdklegartfpilygkkipsivsililivvttlmcpvlyifgifnvfymivmivpicmflycayslknppeevcakvsknlkiamlisfvaf vlgsfdwfsifaal |
| Contig40_gene_666 | 420 | mrkmdkrinfvsisrftllvaifllinkiqfhakildymalalaifaliciiilifiiqfkkglvefpikvvvetnvdkaladgaiteeqaeni pkrvvlnandifinlvfnlaianhfdllpvdlvreyipdippanlmrlyeksreldsddindyfrsqkflnkadvitrsdeiktylretypwmd dvtldntfdyfflgigng |
| Contig40_gene_668 | 421 | mskiknanknkkkesdqtiheleigkliknedvlyinnpdyfltfsdlleisdgidlienimilskdyvsfnrqyedekiscvelmeiteeyk enniegyisqsfdnsqfiinsyndititiivisndlevqkftdnlkvvnswkgfhnakinfggiilidhalspklliqlyktatkqkakffe slhmplhinnilnnedflviasnlpeetlnqdyimeigliditnmeyeddkldleefqeriedgvtiscedairkininigildyfvsegilig dlvelgmellenteptdelkeklktglksvsdrninalimaairleddfrkqrvreidlneklvhfypdeligvaianqisgtkgvlnyrry srhkpgilyglgpilsntfaglvagcmtkilee |
| Contig40_gene_677 | 422 | mecynhpdreavttcsvcgkavcpdcameiagnvyckdcvneivtqsimekastqapkeaaepiteevqeaeaveeaieepveiitpvqqeev eeiipetpkkapenfepeveyeteyvetydedgvedsyyenpeiipepepeykererivkeeakakeeeeiiepvhktedipkeaymddread fyeeqpskapskdleakyekyledlyydedeieeeiyeapktqkrrskprrpqredsyydechkrsprnysnqqeyinpreeefeeeefitp shsrkrarseetesyeelkriernyakeqeakenrfrrskkskkqkrpdyeyedeleniqemhsfpeyekedkigildilailivliiil |

FIG. 9C-12

| | | |
|---|---|---|
| | | ilyviylfrlngeyfsfidslglvrdpsgyisyvln |
| Contig40_gene_693 | 423 | mseeesvpqiivstddmaaainkldeaeekvefavgeyfqrlgqqngrdigilygiilglvilivsiefglvsamstmltslv |
| Contig40_gene_694 | 424 | mvrfsnkpntrgirnasnnveyrakllgregrlfagvistrfsgmaigiglalalavvipylaklcgl |
| Contig40_gene_695 | 425 | madkkpaadnwpvvsgdyivgdpespvavttlashnedipaaagaaiagpcktenlgiekvvaniisnpnirfllicgaevgghitgqsiqal hengcdpekkkitgatgaipfvenipmegverfqqqvelvdlidnedggaitakvkeciekdpgafeedamvievkegdddedegeeirpisa etallearirnidtqvklvgavqrnmagnysgkvqgimigliftlvigfllmapllga |
| Contig40_gene_696 | 426 | mvlpliqfipelnlnldpetgllgagggdliilsmdeingeiakveaaadelmnsldpnsaplgsfpgregnfviagtltnmvygfiigmfli maampiltamgvl |
| Contig40_gene_697 | 427 | mdqviaclgavcailwgvlairsvasyglgtgvpsigymslgigvigalagvgliaafklkglemlgpilalvfamliglivaivakkivgmk ipvmerctaeiagaaalavlgfssaaiaggysidllltavvapgfialfyilvtmaiqhpfnaclgpnedqvrtlkcgastafltmiitgilai saggyawfailvvgligwyvsfkmfvnasyeaaasvkwsglwpkvee |
| Contig40_gene_698 | 428 | mdlifiicvviagiimggvhfipvggapaamatatgvtgtamlaagagltglitaasmtgqpvwlivlagavgsmlmngitmlignfiyi fgvgvvpasgkaavdpitgwnqekyktpgteghgiptvcyisgiigglggaggglvywainefatanltgfdatviaglaailsvgmffins vtasyniggtiegfvdpkfkrlptgilacavvslvaaifmvlmiggi |
| Contig40_gene_699 | 429 | mdpitlgvvalmgaaatiagaaedlesdigsqsnpnsqvqlapqmghlhrminkaasgepvaygcwcgisgaiaalamgnglipivaiamgst vaalvhaiytvtshmgrivggsqfeqplfmdvltgslgpiaahgfiasfgivgiaylmtlpldglghpfplpllavlwgitigaigsstgdvh ygaeseyqkfdygggtpvaiqgdivtkaplgaknsidvgnfcakyggpltgfcfgliivfsfwitvvfgalggqivgiviviliaanyllek strakfgpyee |
| Contig40_gene_713 | 430 | mtiiskkvelielfydlifvyaisrltsiisepvnggiapfslfayiitsfvilqawlyftnyvnrygqwkweyviailnmiaviymantis stwnnyfvfnvsmlimlftvvflysvhaikekslkgaagnsitillvvcsiyiistlsilfghmdvviwlnvlailtgaflpfflkgkfdksi infphlierfelltiiitfgeavvgithffvnnnfdfvpilvflivigmfgsyvlqihylvdhhreerslrlmfshyfivisinlvtvafelih sgeinwipslmviislivfylsimankeyyydglelrkkdialmvlisligsiaillsvgsiygfligaliitlanfgvllnkygkfndn |
| Contig40_gene_722 | 431 | mfiifplfsanlisliligisvliifgiglayssfitheisgalssvmgifgivmiifglcfifainaisflvglgfyivafmlimiavvgflsd snvartgallylvlgivilliamfaaenplititiilgviliaggimgliygnei |
| Contig40_gene_727 | 432 | mrrecliiigtahvsqnsveevkealiedkpvvaieldrgryirlmnerngiveddqihitkiikenkvgflvttilsymqnkigdddidik pgsemigaidaaeetgsrialidrdinitlqrvlnhmstweklkfiygiigglissddeeldvealkeqsaideamgyfkeispgayealvne rdaylansilhipechviavvgaghkeginryldnpetipphselidmdkkggipwlkiilalipisfvvifflawmnghiegdivqfivis mimgflqsilsgsklasaiigglvaplithpllaagwfsglaeakfrkvrkqdinnigkiesfrdlwnnnifrillvvvgtnlgvslativi lpsqvfiplfmkifgg |
| Contig40_ | 433 | memdsliiiseilliiliilivinglfslaeiavvsarrirmqkncr |

FIG. 9C-13

| | | |
|---|---|---|
| gene_729 | | |
| Contig40_gene_731 | 434 | mllikgadvfvdgasnvaynlkiptiivgltivafgtsapeaavsitsafagtnaislgnvvgsnifnilavvgvsallgtltvdkvlikrdf pflvvssiglliatifgeisrlcgiiflililayvylvqearqdkeamseeievklsipkaaiyivigiagiiigsdlvvdsssyiasvfg lsdvligltivaigtslpelvtsitalkkgdngivignvlgssifnilfilgisgaimplpiapemvdillmtvitiigaafayknevdk egavlvalfilymafvilrn |
| Contig40_gene_740 | 435 | mdsddldwknsliaylwivmiwigkivndyriikihkn |
| Contig40_gene_747 | 436 | mplilvafasfiialdatfmnvsisplvidintdvgtigtiisfytlitasimlisskmgdvfgkkkifltgalvvglgafiasisqnaimlf igwsllegiggalmtpatisiisgtydgmrttalaissaivgiaaaigplfggvvttflswrygfvfelllilifrkripnfastaskk dlditgsllsaiglillvlgvlmisgktiglsigllliasiivligfglfekrrkangkmplfdvsllkdrnlsrgtlirllitaiamggslfsi siylgtvlkisafntgivllpltfgmlifsimapkfairlshkyamiigfsiaivgclllsygftltfrfidlpgmfiygaglgfpmalsvd talintppesgssasgfvstgqslgmsmgtaiigiliilvgavggmhdaintyapdkvtngefhdnvqgyfeklgnvnttelkhenslkekivs kvvqdamrlvmyvtalllaiggalftlkkqkikg |
| Contig40_gene_748 | 437 | mgnkeekkaargrfdeiigvakrhhlakllttneddedfevsdlryameelgpafiklgglllatrpdmvgndiaddlkllrdntpatpfeemr kviegelgkpleevysefneeplgsasigqvvratlkesgmevavkvqkpgiydvlvpdvkilnnlagtvdkhvsgsrtynlpamakefersi fkeldymeevrninkitnnfkdveyikipevypeycssklinmelidgyevtdlfdneieginnteiagytgsylkgvlidgffhadphpgn lfvtkdaklcyidfgmngvvndtfrsnfaqlilllldgnshhlinqllymniispegntdefredvddllnsyigvdldqmcgifdnlmnvmi nhniilprefimigrgllliedagnrldphfnltaeleefakkmirtkfepgnlvggfnyiveiehllkdlpdrlnstldkvekgelelnmn htglddlknqlsialivssailvgssialladkgpkvwdisaigtfgflfsailgaylvikyirk |
| Contig40_gene_764 | 438 | mvilgamiayglptpiankiqtkikypsisiflalilvviplilllfayvfyeitvfadvffnssdlagmdinnalnafvgnlpvelqgfikpym gslstglesalsyvlaytvtklvkgfsnvliqlfvlicsiyyftrdgdliwenifvfipnehkaffdrtfyeianvlksifyghfltaviigvm gqvgyyllgykfalflgiitgfqlipifgpwivywalaiyalfvagdivqavltvlwgfvlslsdmyirpvlasnyadmpslillvgfmagp yvfgivgfilgplilgvcyavikslkeelekdnwnsgdeegsdgdsedvkeisdnldevsddkkdsnedskdldlgieeki |
| Contig40_gene_770 | 439 | mkkiigiifiiiviggslvyknykdsqntvdksqesieisknqitmlipgdwveaksesnttaiaaadpaskdsagfssvniniekktsyn slsyefnnnykalgrdssydilyeqnvsiagtegmeagytssktgflkqhkaiwfkggddlyvilctapqskfaeeestfdfiinnlkfnnst n |
| Contig40_gene_771 | 440 | mklmqilknlerdyndgliseekylysnqyrhkidtidtsnrirtmggkkkvsprpyskyedanyqksrdederlvekyihnpesyninsrg kktksggtspwyialaviflllfafgagisfgifsentnsdvgdiiitasatindtafpevkqtkynrtsnytkyssnsysdyssgsynsyn syggsgyssgsggsgyssggsgyssggsgyssgsgysggsgsvsid |
| Contig40_gene_780 | 441 | msyeislisilevvltlliaflfigvlipgierkyvqariqpngpierkyvqariqppvtspglwasikflykeniqpnsmapglykampvlcfivvlaifivlm pynyqfmafssliaivgflikveevayvlmgslsesvmsanlrfpdhikgaarpdslvsiiedisskrslrmivfgsfplylalfvpaalsksi yladivayqqangpflftlagiigavvffvgymiilneypfsyikaksdviegpymelaskyrsfvyvtrgfliftlglvfsvlflgippvlf swkfiaavivslilpvimasisafspiftnkqlyptillvsamgvlaivialf |
| Contig40_gene_785 | 442 | mfvlanlligpliisviifgfvlgsrihldeknsfkftasgiilalliigalivsygigqfpyyndipiattflgalfglliigsallggrakgdh |

FIG. 9C-14

| | | |
|---|---|---|
| Contig40_gene_786 | 443 | maedkdlkttkkspnwnkdesspilkimvlpisfiiaslgimvilgghitpgggfqggamiagaiilsvvvytvngsplklshrfislleesvg alayvllglaglaltgsflynvggnlyglvppqaiaaifkypdltnagmvpylniavglkvlvglsaiviafsqfkklaeee |
| Contig40_gene_788 | 444 | mnnvsgamaaefllvglilaalffrhiniaacivvvilaailfftnmplaskikseqsdslekmlfyvlivlgilisviywglkyv |
| Contig40_gene_789 | 445 | mvvipilaalivnilggkdktvkafsiivglaipiiailaaigvqyfgghdpgllanslpsnlvgtlvasyntgivyifdnierififlmgiv aflsiftyftekkevsgpylylifmglasvialllsndifnmyvffeitaltqvgiivasstednyeialkylilgsiggpmllgvgfvlgt igsvnitdiiyaisnnfvdpyspglvigfalilfgwlysaglppfhtiksavyskarpngsailqgfsvlcmlafgiamykifayipgfntai ivfailamvlsiamsamevdfrrrmiaflavgelgfialgfgigtqmsiaaalfqaaneivitamlfigfgsiyyltntsdtrklgglivgdsl ngvmillggcalagvppfngfvsklmlvgaaleagytelalaivvsvviffftvkafhsvflepkpkdlkfvnekiprvtvfsvavllicl alglfpnivtdvfipfaggli |
| Contig40_gene_790 | 446 | mimdiqlaslfasgaliiigliaailfidniikkiigiafieegvnlfliciqykaggvviflpqmtadwfaqnsayplpqalvltsivigas tlavmlalamvlyrkhgtlsakeilgdek |
| Contig40_gene_791 | 447 | mieyilivavisailallqedllksailvgisgffiavlfhllapdvaltqaivegaivpvfialavyktkgga |
| Contig40_gene_792 | 448 | malglegmnlitiqslliliiaaigilrmdkdmpnvvyarihilgmidvagiiafiglgqplfaliyiflapllahalanayfhae ddlnnpvlnpnllneesdeseleesvdvaeqdgeepeesvdvaeqdgedsdseetsenveedsdseeeasnedvdnktteedvenlnnsegdd nd |
| Contig40_gene_793 | 449 | mimelllisecfliialvvflfasmriitykvsmgligtssltlaitlilicvgnmwgieffkdialvllligivgtiayatflrra |
| Contig40_gene_794 | 450 | mflsriyyaiaylvvlileiikatidmagrifkgdqydpivididtelkrpisqtilansitltpgtlsvdldsesqvikvaviaprdvkdii pfepyikgmle |
| Contig40_gene_795 | 451 | mssykghtifafilsllmfydpfaialaviganipdfdhefkrnhvllilisigmilsiflyllnlpiylgliiallgliflisshrgfthsil gavvisiaifllvyfgmdlssyfnlntitniplnyvilvgililflavlifInkqlasifillmlffitlvyfgivpvfkinvyslifsvflglf shmildsfspagikpfspfsdrkcykklglllfaliialylilfpnkldfyinliphfy |
| Contig40_gene_800 | 452 | mknrnvwriimseikkymedikknktglkgilvililfayqilgsyyimnininsiyytiitiatvygdiipvtplekffstslaltgigl iayiftiiitsfeenlhdirsgrhmekrlakmedhyilcgfgrvgtavyeelmkrnqkviliekenedkiediieetenvpfnanatedktlkk lnidkslgvivttgsdvdnlfivlttremnkdawiisraskkenikrlkhagankirlkhagankvispevsggtdiyfaavqpnlvhitqkhgidylerefe ilkkhnchlenieyhfpgiktpvtrtigvldeeekdhfidmvknnpevhesmdvmyetvngvhshwisgpdkshvdmvieelkkegnllgvnl dfkeineftkqfke |
| Contig40_gene_803 | 453 | mknkllifligaimaamlyfigidqvvdalkysnlwfvlavlliqftyflytwrwqiinksagmtlgiwklpmvlvslavnnitpsgr gggepvraylakeghykfedtfatviadraldtfpfvilailtiiailfsvslpvywivilvlcvvgitaivlillyvcineafgvrltewi lkitkrfyknyndalekriveavasfqstmnalirdkniiyyalplsfiiwvfeilrvyvvflafgakvspiligevfilaslvgmvpllpgg lgaidgvmilfysrsgitaslsaaatvversisfgmttilgliflmkygtsildasfklaesekaenleeitedceqkildqlsedgdksedsd enreeavlevldgepsievvdeeptlevideeptidvldekeeaidekvkn |

FIG. 9C-15

| | | |
|---|---|---|
| Contig40_gene_804 | 454 | mqglgvvlivptlvaliygeydpiapfmipcfvsfvlgtafskkfkdytklrkhgmlissfawlwasligasimvlslgipfvdaifenmsa wtgsgmtffvnvevlpksilflrsleqwlgglgviifigiliragtaasrlykseareekikpnitntlrkaleiylytavgilfilagl pifdainitftsistgomsiknanvgfyqdsivylismflmilgatsftihykivktkgkalfkdvqfqllitliivagaffiatnkmvpiee lftivsavtttganvvdphvlatwngstlivlmvlmliggssgstgglklriitvlkgmnltvtnlvspegrvvntrigkkinereikea sayivtflmflvfgwiimtmygydpftalfdvisiqsnnglstgivygglplpkltliflmwigrleiipvlvlfrtfygivnpkrrikqmk ktngndkktn |
| Contig40_gene_816 | 455 | mkkssiiiiffavfeiiaillfitlndifylfnftyigaclsiglylynvdskyskyarnfiqlaiglymlvylgiisrenmniegfwyylflg vfeaavihylvakilgpflfgrgwcgyacwtamildllpyktpnkldherknfgfiryilfiasligvglfmmnvpnlstvmfylfiagni vyytvgiilayalkdnrafckyicpttvflkigaryslikvkykrenciscnkcyrvcpmdvdicnndknkngteciclscakecgncalf l |
| Contig40_gene_825 | 456 | marhksnkrlnkgeeedpmsgaanlvdamlviavgllvflvisvnmqgivfnedntpeekqevmqqmqqvteleeqqelndtpdvsnssgkgy temgkvykdsstgklimveg |
| Contig40_gene_826 | 457 | mvtvipgsdlltsalnvvsqslqipvivfllifavyavitvggliseyssrkkvpvkiklidliyaisrsedvtelenilknaripknqkrvli niarsgelkkdsrealaeklieneedilekklqktdivtkigptlgmgtlipmgpglaalgsdvttlsnaiivafdttvvgigsgavayvv skvrrrwyeqylsnldalskavldrine |
| Contig40_gene_827 | 458 | mlwqfgilaavlvfgikiglavglanlskkylatvcigyggagvlilagissyfateiteliytynsifffiimavimilagiftirewkfekn ttaatcaaviapcpccfgsiivsilvaptvglgavdlsvyvaaalvltiivtyfassifvryvdkpypivlgnfmflgiyflisalvipni aimnksmgsisivsmeslagsivalvlivvigivfsrknnils |
| Contig40_gene_832 | 459 | marrrcnrrfeseeedpmagtanlvdamlviavgllvflvlawnmqsvlfneqltqeekqqvmdamnqemtevqeggilnetpdtsnatgqgy temgkvykdpstgklimvqnnsa |
| Contig40_gene_833 | 460 | mtlaigntlifadealyqganngifaifsntngtgfpfldssltaitqalqipviillifluavvtlgkllseylsrkkvpiklikemiys iydaqsaeeikrivnssdiqssqktilceladsehlgkksretlarrlidneedkitqnlqktdivtrigptlgmgtlipmgpglaalgtgd vttlasaitliafnttvigigagaayfaskirrrwfgeylanldalmdaildninkrddrle |
| Contig40_gene_838 | 461 | meiieliaiiiilvaaivfliyyyfqtvngsfdiddlkdhltiskreaatatvnldddeaeekvsvgkkikytfkdidksysnttdafskrld aflderseelienwslvttddleslekrcvtacdsiddlekrfseysnvtnekleldkrikaleedselleedaetiekeade |
| Contig40_gene_839 | 462 | maneilpseifilillvilafvviiialqwkkvrqsdntlklmekeielkkiamvekdlenkrlmenpislpseqqeqltgirdstakvmsdv gylhseinerlarleaqtelklkekmlaeiedkekklnkgk |
| Contig40_gene_888 | 463 | mekpqlvnfiakvledsgfkvyknfktsqqtvdiyavlptsmgdfgmvvacknydkewevgidvlkemevigkklkaskvsvvtssgfssqak ryaeerkiklvdrndlvalakkynkkqenepvrlrkespanidrdsfynrdvsrdyidnvngtqydaglnrvpnpydsyeeyesdidyyen qvggidlsgysayddlyraeflnrhpsnesnyngilliannrdpyvnskpssnsrlfsrnkateklsslnsrgytkntnnnrqrnsrttt vsrnkspsrnfissrdnalskfsrnesrssgglkemikpilgntivsiivvvayliafilgsivkvptygylgltelavalvlsyglvfytd rgsdvlvkgtliffislvvlmiliaf |
| Contig40_gene_890 | 464 | mdilqaiiiglvvgltefIpvssahlifiggalglsnvplafdvllhvgtlvavfvyffsdiiqmiqgffysildlrdqnfipeirrdpykk lawltiiatipvgvvgilfndieemftgltipaflllitgcllyvsqrmsgkidvqnitikeallmgcgqaiavlpgisrsgttiaaglfa gldkefaakfsfilsipailgaavvqlkdlsggnieigaclvgfivavisgyfaisflikivrekslfayycwivgvlvgsill |

FIG. 9C-16

| | | |
|---|---|---|
| Contig40_gene_905 | 465 | mmlnylfnilntntflnpkerviqgillfilmsvlsllfisfitlaspnlffpllisfellmlfglnislhsiytnyfnmlvsenpvllsy egivnllclslgafsfwlsiaifigpfwaffsfalawllplwimffrrdifnekskvisknsdkligyspiwfylfgcvslfipflvmfkiv ffskfnflalgliiitllletilifcpdywdkilpfdirtkkgtfiyfllslillscisiilykiv |
| Contig40_gene_912 | 466 | mlnlnkktiigvilcflilaipsfllgnlfpiiggpliailllgmiiasfwkdkgsaeeginftskyilqlavvflgfglnlgvivatgiqslpi iigtisialivayimmkvlkmernsailigvgssicggsaiaatapvigandeevaqsisiiffnviaaiifpmlgrmlgfstvngdafgif agtaindtssvtaaaatwdnmwglgsatldkaatvkltrtlaiipitlalsyiigkdngeksneegfslkrafptfiaffilasiittvavf lgvdaslfipmkeiskflivmamlaiglnsdivklvrtgkplllgascwiaitivsliiqhllgiw |
| Contig40_gene_920 | 467 | mseesssskvakgsailligvifrvggyiyrflmaslgpaaygilglttpfgqifqvlsaaglppaiakyvseynaldekdlarqtiftsl kimvflgiffgfimvfvaapiitnyhkpeallplqavglitpfsvivggfragfggvykmeyilytraieqifmilmatalvllglstlgav lgsvlgfvasaisavyifkrymgkyippanpdfkfplkdelklaktliffsipvtvaalaemgiysictllmgaflpaaaigyftaadpiarl plvvsnslattlpatseayalkdqvllekyvtapykygmffvipmcvgiaifargimglvyftnaaymngavslailvvgmtfysvytisgs ivqgignpripmyiligcvitlglgwyliplfgieggalattissfimmvpmfliqfrmtkthapysflikvtvaslimaivsiivpnnvyg itgivvcpivyvimvliktlshedvaefrkyanklgpirkyanklldfidkhssd |
| Contig40_gene_926 | 468 | mlkilaadkmdkklivryimlivgviimsmgialsikatlgtspissvpavlsiafpwtvgeftivfnallvifqmvllrkitisqaqmlvc vlfgymidfslllllnfpnptdyisqwilciiscfvlafgllievksditmlpgdgsvvaiaevtnrdfgqikpffdltivsiaailalvflgh legvregtifaaivvgliiiqfvdrifgynidaylad |
| Contig40_gene_929 | 469 | mnlenksidllnpfliiliamvivfliiialpmwyayqklpspsmdlflyiglglfiffegilsnllnrflkkdlsldslkdtikisisknpkk lsifesysrkemilvimvliigiilgiilgiilqiinivrlggiplpflsatlkaeaagkiwlasyiifipfinillaefnrdshyllvflgllfltlgyrtt piaivlsilitllyytrnikfkyqvlflglflviavalllaigfiavqaiswqhwslnpielvsyraaftlnvlghaisnqfatagklfystlt gffthtdprvlvggatlgrnhsitstifgpalldfglligmciqmlligfilktlhsiqkhkkevysafygillaqtiiwietgptdvvwify lliaivlmalfflkgssrdlea |
| Contig40_gene_941 | 470 | matvdsflpdfiqtffsgytifntviytlilllfliaiikmfkkikidpisilypiipyiflgsliralvdngvypktvflitpglyilvgl itiasllfslflynrknidyrtlsiigvillipnniimiprlnniipvlyvllitwliassiflvsliylpffkdrinlsiisahmfdasttfva veffnyseghvlantlyqlfdtsitmfpmkiivivavlyiidqyfddetiksllkltvfvlglapglrnfltmaigv |
| Contig40_gene_953 | 471 | msnnqisgcsyalyldgsdngsfignkifnndygilakysninlfknnsvfnnwiaiedsskynqflsnnihdryqgirliasnsalientv ynnylgilkysssfinksasvynntllnvqslndgeividqnmwycgpaalsiifeslglslsqediakiagtntngtslyglyqacikkgfn psvlkinssdlmtndlavllinedyhfsviysindtdivlndpsiglfvlsretfdemfsgyvldvepikdrvsnvsiakmktivgtvfpala ygglyalagvtviagslaiwnsnshynsksiqkphytwkpnnkifprnvkyptstgnngnrpkvsynpvtssisgnkyytnnkvytynyks snrkvsssnaaiiayqeaynyylstknnerakvekptnitsynyflkdvkafekgsykfslgpkgpdddlydsakivkalyrdatrnynygkf lintgnksrgicyiflatfeisfipaiiynqlsinp |
| Contig40_gene_957 | 472 | mvkcskcgsenkseakfchscgakldikdpynldgksreygsttgksagsasayydhsansggsssdstggidnfrnmsnfkkiifaccavfi vlfilslaaqalgfdmepysenktayhnyslidlddgalcleeieysnissskmsdifkksdknrnhlirgaeydmlnyvnehfkdlek kknektsssssssssgsssyksffttsgssddgaetcpfcgseavyesgnsykcaecgrtisnpddldlnydegyy |

FIG. 9C-17

| | | |
|---|---|---|
| Contig40_gene_958 | 473 | mkkcskcgsenpdnakfchncgskdfgtnenicpkcgesnvkeakfchkcgaslsnssgsssynptgmngpfgagandkpgsvmngpfga gandkpgsvmngpfgagangvadsfafdpssndksssssnsssnsssssnyssssnsnsssnsnsssnsnsssnsnsssnnggstassanq snstastknqsnstisstantgneqpqlkkicccyvpvillvlfifailnafpenfsatyddefyqldidgdgrlsleasqlnpgmsds sissyfneadknnngylighefddfysdvkpyssssssssnshkyssssssdydssdgyvltcpycgsealyesgsyykc adcgsiihnpddlelnyqegymdllapivqinlggv |
| Contig40_gene_960 | 474 | mvipafneeatvaqvvtvarklsyisevivddgstdktveeaeragatvishkgnggkgvaiktgfknshgdivafidadvsnftptkidki ikpilegktditktkfaresgrvteltakpllsffpelnyeqplsgqfagkrsalnkikfekdygrdvgivldadvhgisilevdigdiqhd mssladlnkmanevvrtiidravdygrvtmmdtlgnyirmaimglsliilglfmiffvpfiplvisvlvalvgialtiayiikvqrsipilr kgdtstalksfvkmhfpvivsgllililmlstflsaatfndgrisveltsrnfvyspsddyhqtisvrgpytidsaienetdmvrippdalstl emsandtmiidgeyysvntsregevdvfrlskavrhdldlyprevipnsrlaevfngvivnhninfmnssevmegyvqfsispkatnatffnl tldneslssvgnfkndsyytiaydddilcaftgddikkgnvtfeyagkdgmivfedrnntsirnfidsdrdsfvklytl |
| Contig40_gene_962 | 475 | mialvlaptvlsiftssvtaaalvivgilmivqlkevdwdnmvvaasvfmtiiinmlltysislgiawgfvtyavaaiatgkakefswimwlmv iifaayvffgl |
| Contig40_gene_963 | 476 | mlnkffkidenntdikteflagittflamayilgvnptmlaeggmpatgvffatalasgvscilmglvskypvglapgmgmnalftytiilam gntwetalaavfvssiifiliitisglreailnalpfdlklaigagigfflafigikgagivadpatlvgmgtilsapallavigililtlily ikkvpaavflglvitailgviftlfgfgagdplmpaiptefisfndtsvvgaflkgfsqlftnipnlimilfslltvtfdttgtliplanq cgfvdeeqkadgidkaflgdaisgiigailgtstltayvesatvlvveqv |
| Contig40_gene_966 | 477 | mervrlqyidllkffaifsiialhvflvwpkakvmgikvyslssivrfgvpvfimisgallnrdieigsflkkrinritypflffyiltfif ialtnhtheqgnifafrwyfwtilgvylsipiinkyiqhsslkeieyfiyifisifyqftyffeikqyfyltlflsplgylvlgyylskkd fnlstskmivisililfilstsikicgqlgyipitenfvasqsvilsswldvsfigilqaasfflcksiyeaskgifspikkflesniiskfv lsvsrasygmylinliptvivyyiqpmnltgsqvflaiplisiiiflvswiliviclckipylkyvsgys |
| Contig40_gene_971 | 478 | milgtylimplifnrwikdcsireveyflaiwllitcifdntlligfpvtltyftgpigmvvlgyylrhtdrkifnslpyalaflligmivimlc syflsspegmyvfdrysillaievvgiftlykvidkkelkifhkengffrrasfsiakysygiylchefimnifiiliflkhapfkvtlllvfv ctlgtswallallnrvpylnriigak |
| Contig40_gene_983 | 479 | mdnqnqwnsriafllsmigaavglgniwrysyvvysnggtffipylvailimgipflvleygifrhkdfsniksinpkleyiswalvli iyfvliylvivswdlvylgssinfswgadsalyfvqnvggssnlsmasfiipttismvlwicvwyishkdlnegigkaskilipllfgim afiivfaltlpgagigisalnpdwqmllnvniwlaafsqiifslsmgesisltyasylpegskltdnvlivvfancafevctafgifsilgy msytsgtpivelvseqtglvfvvfpmifnimgaighliapllfiailfagitsavavfepminstvhklnwsrkkavtvwsivgcivslllftt gissylvgivdsfitefclllliaiqsliftwfydiegvipilnendrvkvgktwvfvlvkyilpillffmwasgvyhlinantfelivygli tvfiililtyvftnipeks |
| Contig40_gene_988 | 480 | mtikkyfktrkgtkksvqerdydsdysnkglhkesriknlindnkgnysivisailllisfllilsliviintvleereehtdtiasnqyyiied ykrnlpnierealeelslyvienkrpcfnsrddlkeiidceklaqknqeyyqnyieinssiigientsdpfsykfktyissvkgdfsyeeide syvcnlkdpvpvlfcgddssfriedysllgdsdfgthdsnfenddsssnqkvfyghslakflrrhvenysfyenasspfiikrcpydpyk hhgddngrimkncrdngyyhesadgacylcrlegksgcdhygfetfinpqktnetgvsacgsdhvifsddiyppgvevivnsenglneilyld phghkvkygmsey |

FIG. 9C-18

| | | |
|---|---|---|
| Contig40_gene_989 | 481 | miemiklvnelkidqkglmyssellislilifiligimanitdsvnekvlsqeelssleaisiesvdyllnnpgspmnweeceginngivsrr<br>iipglainkksvengffyeesssdeeipnsisyiklklkqsnyddlinrnlfnstlkssitiyphsdidiiamgddlesssdvvainrtvrc<br>dylsnfviyrfndfelygenykktelcnhdsnvnlsnhsndrryfwlcknfrlyrsslnnynnyylisdssirhansyyileslnrtrddmerl<br>ndevielnpffaedmvnssneiysihfkvphddiddfktvmvaihknmtdeivsnnqlrydyfnsgevdfvlktayr |
| Contig40_gene_991 | 482 | mlvkkmlrdlshkigfvsiflmafigvffaftgingevvgitdvsthyyedtnladgwiygenfdkdtlkdiknmeevknahremvvdtvany<br>ssdpditlhilegkqeiskfhlfkgkdfnpndkegiwidkrfadardldigdkislkfdgktvsktirgliyspeyvyiqegsmipdfsqvg<br>yafmpskgadfdieynritidgkkeldakefssevsellgqytyaqfvprednvvstlqdeidqhnmfsgifpiifvmvalltllttmsrvi<br>ssqrtqigtlkamgydnttiilhylsygflsfagsllgliiigpllpylfypsmamyslpywgpawnlsfflvaalnviisvlvtfisvkt<br>indenpadsikpkvpkavssgimertkiwkmgfngrwnyrdakrnkvraimsifgvfacallimsafgmydsmndvqdwynqiynyhskly<br>ldenitdaqlstvvkdtngeenmeqalevkyrgnkhtasmtvyndselfrptdinrnyleidpdgvaisdrlaevlglkvgckvrwhlvgnpk<br>widseitqtystpfgqgiimsektyekyggddynystnvvltedkdiknytgvtsvstredivkgwednteamnlmvylifavilavvly<br>nlgllsftelqreiatlkvlgfntksirrlltqnlwfstigfilaipgayilmeammgstgadyfpiniyplnfiislimtfglsilvnll<br>fsrkikkvnmveslksne |
| Contig40_gene_993 | 483 | mkmirqfgessialvvnlilflingikyftlpnriyvyiklfledtdavlkeslialsicavgdlcagiilgnmefflktypglmviipgai<br>gmrgnifsgsrlsthlhigtlspefkrseilsenitaslilmvlsliltmvlsillaviakgvciafgfksisiydfvlisfiaglistiimlpitmf<br>islksfeggwdpdnittpfiaavgdfftlpailsviivgfisilipivkmivfvavlifvtiaallagytaksdvrhivrqstpvlficsllgt<br>faggilndsltllkngtllltlvplfsgesgglvsilgarlssglhsglidpvlrpkkhtvenfvailtlsvvmypvigflaesstiafgnig<br>vgilesmsisflagmilililmlivfyistisyrrgldpdniviplststdsistlllivvsllnvyf |
| Contig40_gene_1003 | 484 | mltillfslavdlllgefpmqihpvvwigkilsffknililykdnkiagllilsiaviivsslilvlipmaiaryllpyndmmiylfkliailll<br>tstfsvkllldsardvekdlrnnlnkarqavsylvsrdtnelnkehvisavietlsenipdsyvstvfyysivgilasilcgigdfdvillav<br>laafihrvdtmdsmvgyktkelynigfipahlddalnyiparfsgalivvsamflrlnwknalfimrrdanncdspnsgytmatvagalniq<br>lekegvytlgdninpinvdcielkavdlarltiflvtiffmfvfmdlillml |
| Contig40_gene_1007 | 485 | mlkrkmlrdiwnykvqfisifiiafigvffaqltaeadgfeasidsfyqrsnladgwiysnylvddflkqvyllgattsmerqlvvdsqael<br>dgkpditlhfvenntiskyyplegnelnisdsegvwldktfadarnlkigdtiafesngikiekkirglgyspenvyslvptqtvpnytargf<br>aymsykafpsdnityvinvkfdgrpeifsellsyrldgyyelylpqsnqysvnavsdsiahqslnavfpilftlismlmlsvtmkriisnq<br>rtqigvlkangfsnrsiahymssgfieklaiwkrlsfnirwnyrdikrnrfkslmtivgvmgctillisgfavyeqmeiskdwyfndvnhfesklvidd<br>eppsqikpkppkmvssgfieklaiwkrlsfnirwnyrdikrnrfkslmtivgvmgctillisgfavyeqmeiskdwyfndvnhfesklvidd<br>ntdlsqidsiahkvngdeimessielkgdanfasllvlndtdlitmtndnrekidipknevsiskkmadildlkvgdtidchlldsnklvki<br>ridrihstpftqglvmsadkyeelgfnftptsiitsehvnksydgvkstiysednvrgwdqmqktsmmiitsilflaivlavvilynmnllsf<br>iemendiatlkvlgfkskylktlklatgfffiivgfilglpvayyilltllmpafgnkiylipnisvlmafsfliivsfivmnlyfsrkirk<br>ldmvdalktfe |
| Contig40_gene_1012 | 486 | mnqnaqwnsiitfilamigltiginiwrfsyvlysnqggsffipyfiaimvngipflileyglgfslkksfsklmhdirpefeviawmlvif<br>vfivviyymvliigwdfvyflnsfsgwgsdpnsffmtyvggtreisqigrlllptlicttvlwiifwfvsnrdvdegikistilmplfiim<br>ififlysftlpgfdigiktllkpnwslldihiwlaafgqtiftlsigqamvytyasylprnsklvdevllvvitnlyevfiaigvfsilgy<br>mslkssipieklisegtglifvvfpkifsemgfvgqilgpllflsilfagftsalalfepflsslcdkfnlsrrkgvtlivavicsipfst<br>gissylvgivdkfvndfgilililigvqaiifgwfygvekvmpvlnelstfkvgkswftikyllpvliiiiwvngvvglfsntnsfelivdlii |

FIG. 9C-19

| | tfvvvgfsvlftklgvke |
|---|---|
| Contig40_gene_102_2 | 487 | mnkklieyliliatviililygcyslidyqsngyqfrmvnatdsmniscpssaysvsgdtvefrnglnsfynmdvsklnssdgkvknilnqys kfhksgtldlknetcyvltveleddkgfnyhsmiisvdsfdkdslsfnkeatvylfdgnnrefvvdtvygsqvvi |
| Contig40_gene_102_3 | 488 | mspyelikddgevvnlggspdesqdfdvslerlndksladsdgdgkhdvfisystknsdianeicyllekngleclwiaprnissgknyvdeia dgikstkivvlvfskysqeskyvnnevmmafsynkpiisfnidqtepndimgyylkvaqwlpaypnpksqyetlvtdalklcnerprtvitsl dgfipediskqknwislilftpiywasfiymglvskkkswtllgflyaiptvigllllyfqvftrlfliypifrlfnlfilcwilailhgl virneflgrysvlglmsfdkdlfeylgmyykm |
| Contig40_gene_102_4 | 489 | mshdvficydeedkdcaeaicrifeenniktwirsrdvsskdaarnlteairnskcfvlysknkntnyiinetdiafskeipililfkldet sipkdlefiliskkkivayphskrqlktlvketsdildrptddikldsnsvktiersnpkrkennikkaigaaaliaavllililylfvivptgq nitdsgyfsmdvthvevdelakgnkytiygesynlpsdsdryfmnlqffddknvyvennstadefksgiiwsgdinkgdikhigfkltdmdn kilsqedynlgl |
| Contig40_gene_105_0 | 490 | mgllsltisyfnksangeslwapflemfrmlsvvllityiatksksfkviirggqsrktiiwqiiifsilgilasyctmdvngipanargliv misallggpyvgipvgiiagvwrygmggitalacgvatimagivgslvyrwndgeflrpykaallmllysgfdmflitiltpqpkgvlianal yapmtfgavlgillftlfltekkeeaeksdeqtvsdnrntdtqnineisqelneykdkvkkleqkleeydkkfnqleqklkdk |
| Contig40_gene_105_2 | 491 | mnetikehswiplilvcfatfiialdttfmnvsissvvadlntdvstiqtissfytlitasfmlstklqdivgkkklfligagivgvgtlta alsantlmlfigwallegiggalmtptavsiisgtyqgekltfalaiesalvaiaaaigplfggvvttyftwrlgfavefiivlivfalqgki pyfeatgskselditgaiisfvglvlfvmgilmltddttfsiainmaaglivlalfalfeikrkrkgnvplldvelilkdrnlrvgtlrllvnl amggalfavsvylgsvlalsafntgltlpmtlglllfaltapklsakinhkilmsigcliisigciilsgftmatsmlelmpglfvlgagl gfvmalgvdialsnipgeqnnasgivttgqtlgqsmgtailgvllilgiggisnavdtyvpdqsgnatfehdvyegfqsissindvkaens tignivklsig |
| Contig40_gene_105_3 | 492 | mkedtasneeirsrlldggkitgtnmrvlvcamviasvglnmsstaviigamlisplmgsilasayasvtndrpllgkhltgfamqiiisvta aaifflspvkeptvellartspsfydvliaffgglagiigqtrsdkvstvipgvaiatalmpplctcgysiangrwdmllgagylflincyf iflsssllilsalkipklkeytekewkihkwrmsygilf |
| Contig40_gene_105_6 | 493 | mrdieelkktpglslkrylilfianliglylisfgldftvtnlgrviiffisifnaaiwplvtriymplmvwtfgigallnggvfaffgp yfgldisgwgivlapltialitivlstlmdaeddgtyyqavlreaqtkrkgeikdypglliveidglaydvlleavekgvmptvksmidnkth ilkkwetdlssqtgasqagilhgnnenitafrwiekennqmmqcsgvtkvkvleerisdgnllvengasrsnlfsgdtdnvifftskitdl rklyngawfsifsnpsefarivlviedmvheiysqlkhsilnirprisrgiayiptragtnvfmreintetligdmligdidvaystylgyd eiahhsgvrdedvwfalkgmdkqirrliygnkyspreyefviqsdhgqtngatfkqryggsfedfvksllphetniyakmssnedhfaevyip fkdridkfknrn |

| | | |
|---|---|---|
| Contig40_gene_1077 | 494 | mlapdlgiiyvlgllfgpygalgvalaivtlnlingftlmetlpfeiftfgvsylgyrlwysgfktdtitkpkldnsyhislflvsiiicgfi ystvqgisfnlifwvdrfyimilfyfmsfttmaflygiigiwicnrydcfetpkkskrhvdkriyqaifcmiiitsiilatsfittddtvri lelivlgiflfayltkpfeyditpndkdtisgrimrnfiiitfilgvlgiaismisysaysqsdnvylvlmwgpiitdtvlliflipcifilr yiedkvvqpissfskiegfikenekidedglvktyskytdekteigtlarsytelikhnnnyienireiegekerinaeldiatkiqesslpe npiktndftvegysipakevggdffdyymvddenlaivigdasgkgipaailsmitqfmiknflkqtlnpsevlyslnnqlsennpecmfitl wlgiyntrtkkvrfangghnpplvkedkfkyldidtglvlgitgdfdyineeiilkdelivytdgitdatdedsniygedrilkflnefkgd evpikplisdvntfskgvveqfddmtllclklnk |
| Contig40_gene_1080 | 495 | magniclfvdglivsfligasnlapiqivapvitfvnliywmigiggsvlcsvakaefddeksnsyfsvslislisigvlitviglifsgsia qflcssqpelvsgvsqvsqyfialvigmpflcymmslsyfiradgipqlpfraiilianivnicfdiiyikfnlgitgaalatstgylvgsilisy yffkkertlefiklkanaffkfikkivtsgfssastqlyltlklvinflvglyvvqksgvvafgicynslfilylfligtaqtmspivsvyfk eedysgvdyiikrslkivvasslalsvlfifypqallflysvkdpadvpvlnalrifaisyvgtaitflytfyaqalqknrlstiislegf llpisaavilsfaigngiwisfaiaelltilfifaysrninktngeytgffinkhndervfeytingnieeavnllqrksqklpylg |
| Contig40_gene_1083 | 496 | mfnnykdkltgdrkililfvilaifnialyinifkymvdikdinmavihdfvtincailiilgftstrlpnlkkrdssiyeisyliiigllsit isffnksingeslwapylemfrilsvvliltflatktksfkavvrgdrsrktiisqiilcsvlgilasyftmdinglpanaralvvmisgllg gpyigipvgiiisgvwrysmggptalacaiatilagitgsiihrwngnefispvkagllmffysgfemflltiltprptglivasnlygpmtfa avlgillfslfldekkekaetdtdgdedkkielmseeleeykikangtegelkeykdkveklegelneikgki |
| Contig40_gene_1085 | 497 | metknliiicvtliiivclglfliishmngeethitiltsqyltegdtlklklcdkdgkgiadqksikigskdgnfndivktdengesqi qnlqrqnytliakydgtsqyegygltyefivspkeveqsskttstttatsnngdyasdykaddvidgwdpsehevsreylgegeyrvnyddg ysrvidsdgnvlsygy |
| Contig40_gene_1087 | 498 | mlyrgykkgmefgkfqyafivclsalficllyslfn |
| Contig40_gene_1099 | 499 | mlkklkiiivgdrmdnklflqafskffigliiicallfipagtlnypngwlfiallfipmffagiimfikspellrrrlnadeeeeqkivil isaiiflafilaglnfrfgwfk.nsliiiiasvifllayimyaevlreneylsrtvevnegqnvvdtglygivrhpmytstiflfsmplvl dsifsfivmliypiiiifrikneeklleeeldgyveyekrvkyrlipylw |
| Contig40_gene_1125 | 500 | mkvsvvtpnynglkflnayfetlafqsrfieeiiiidnastdascdlieeyinspsykidiklikndknlgfapavnggirlakseliysvnn dvelefntietligsmersieegknpfsiqskmiqyhnrsliddagdeynilaytkklgdgspidnynekreifsscagaalyrksilekigl fddnffayvedidlsfragingyrnylepksiiyhygsatsgsrynefkirlaarnnvwmiyknfpiplkivnfififlgffikylflrkgf gsiylggvkeglrerkgiekthfewknwknyfkiewkmikntfgyfkk |
| Contig40_gene_1126 | 501 | mrnidlsiivvnyntfkltrdtidsclaephtyeiflvdnkstddsleklqeyfksetergilkiilpnqsndgfakanniaiegakgdfil llnsdtlmkqstidkcmdyitdkghddidalgckvsladgsldkackrsfpnpansfyklfhinvsdkndynldlddgiyeidclvgafm lvrrttidevglldaffmygedidwcyrikqagwkivyfgqaeiihykgassedkntkkrnpkiiyefyramyvfykkyhtkkynflvniav yigigvllvfnlvrnafrs |

FIG. 9C-21

| | | |
|---|---|---|
| Contig40_gene_112 7 | 502 | mikenqrlnailvliidiivlislglayfvrfkttifsvggslpfsdyfiftivcliptyillyyffglykpfrnqssifsgaedivksdim afiilvailfiinqpnfsriml11lslfgmiltiaervlvvlvlrmmrtnnlnlkhmlligdndlafefahkinsktylgyniagflgrkeni gkrfegtkfigsfddiprvlkthkfdrvviaiplkyyyhlneivdaceeegikaeiipdyykylpakpsvdmlddmpiinirvplddafnkf kkivsdyfvslvaliiitspimiltaiaikiespgpiifkqerigyngkpfmmykfrsmkvqddeeeksqwttkddprktrigtfirkwsidel pqffnvlkrdmsvvgprperpyfveefkktipkymvkhqvrpgltglaqvngyrgntsikkrieydiryvenwslaldvkimfwtvfrrnkna y |
| Contig40_gene_113 0 | 503 | mliamdfriiilsiiimllgvllkkidllkeedvetlnnlviniciclpclifnalytadvslipslsiltstitslivgvftyilllklfaw dnvkiwsllvtvlgntgflgypitgqiygseglirayfcdcstsitfvilsvllllifdgelkvalrkiatfvplwsivlgilfnifaipit dvgttvvgylgdatiplimisiglslnisglknnlkevslasfiklilypfvalgvmallgitgfnhtigllieaamssamiglvlaityklddp hltsdciftsstlfglvtiplflmfiv |
| Contig40_gene_114 4 | 504 | mngiyyyviaflliwtiaivfkgrlenyglevnfpllmwktqrlrgfidrianraprfwkwymnigivistgfmilmavalvyslktlmdapt vslvipgvevpgspifipflsglialatvlivhefshgilarvekikinsigllifailpgafvepdeeelkglnrpsrmriyvagsmanltl aaialavimnlissfvpavfeddgivisrltedgnainylsegmvikginnysvsdgasyqkavstlrpnqtvtltdgeysfqlksnpqnk slgymgvgaqvnglispdfdnkfytpllwgimsltdllfwiyflnfavgtfnllpmkpldghlfedllsyitseniyekpvvtfmsffmgili vvslvvgfvgvpf |
| Contig40_gene_115 3 | 505 | mkfdsetsvllvsfltaffavflaagivigvpaianefgmnnvvqnwiitiallvvamftlpagqlsgkfgvkrsllvgvlifivgsigacla fsaesflffrviggiggafsnvasmamvqaikpqsrgkalgltvtgvylagslspvicgflvnfgwrsmfyftipflliicialmlwkipgd wktyendkidsigymiyavgillfiygftnlinawglicvvvgfilllafayyetrvdtpafnmrlfkntkfassnvaalcsylavaalttil nyhfqyvrgwnaqmsglilivtpiimafmapnsgklsdrihpqklaaigmtiataalvililfldantpiwliivamvlqgvgmglfttpntna imssvppketpnasaagsamrtiggtmslglltlvfawimgslklssqyagmvvqasqivciictiicvvaifaslvgiksdefniekps |
| Contig40_gene_115 4 | 506 | mkldletvvvavsfitsffavflsngivigvpaiaqefamnviqnwvptiffivvaiftvpaggiskfgvkksllggvlvylfasigavls fstesflfrilggagvaflnvsamamvhavkpqnrgkalgftvtgvylatslspvicgflvhnlgwrsmfyfvipflvicvlmafkipge wktyekdkidmigsilygigilafiygfttllttstglliltiaglamlvvfgayelrqkspvfnmmlfknkkftssniaalcsyiavmvvttil nyhfqyvrgwnaqtagmiliitpiimaimapnsgklsdkihpqklaaigmsiatvalllltfldgntpiyfvilamilggigmglfsspmna imssvppkdaptasagsatmrtiggtmslglltlvfawvmgslplatkyagmvvqasqiicgictvacilaifaslvgvkskdkfntdrpt |
| Contig40_gene_115 6 | 507 | mlfveilknlsvfeilvrklkvkntrglvlfivlflvftcffssifitndvsliifvpftiialrkvdrdliifavsmetiaanvgcmvlpiga phnivmymvshipfqsfflillpyivvsavfliilsffvpsdavnlpkfgkveinkegffkrvlfgvdyflltfialfvlignlenitffnl lfkkwiigneviwgvvasqfisnvpaaillsgfstnyeailivginigglgtliasmanlisykilvrehgefkirylliftflnvvlfillg vyvfih |
| Contig40_gene_116 1 | 508 | mwliifgnienlilssggvvgvdpkilgglsilvvimfvigtvitdvaiqysnlinfigglaiflgfqavyeavrnirgg |
| Contig40_gene_116 2 | 509 | mdwkpyapftallifgnienlilssegviagvnsfvllilsliavawllgtgtnyaikyadyieliggiaililglesmleafgil |

FIG. 9C-22

| | | |
|---|---|---|
| Contig40_gene_116 | 510 | meikrinryiylfslflislgasisikanlgtspiiclpyvsslilnmsvgtvclifnvifilvqiillrgdferrqylqiivgtifslsid fsmtlvtflnptnyisqfavlmlscvvafgvllevqtevvflppdgiivaiskvlnkefpkvkpffdtslvltaailsivflgylagvregt iisaviigpivkvlqkffnpyieaviek |
| Contig40_gene_118 | 511 | mnfefsilglfllllfvpniiwtkfipkdyenyskrenkillilerigevatvvfalfcgakfswsllliiifilmalyevywiryfmssht mkdmcdsllmiplpgatlpviafflfgiysnsiflvissillaighigihynhkkqcnln |
| Contig40_gene_118 | 512 | msnsqndgledvskgnnesagentdstsnkktrftsksisevfkeldsqetndsilldsedaaselesedkysnienylseaeseeildass eaesldassdvefeediildstaeeeideiipihneykdldeseafntesideeeisesseldnyvesivnekddlssdelvdskenldavgg degsmsvkdienasfeaedtsldaedyeddsidsedidqsyeeelldenmkvikvnnassedvlskknkgflssfgsikmdssfiitvlsfiv glgilimgifylnsssdrvvdnvlsgetaglavflliiiglliiigfsilrflsstkadqssmldmfksirdidyddvkddnisrddfdsvfss vfgkekrsdfsnddgqkssvdknlfdeddeisdedidalysdsnlnktasstknstgiqdtnlieedlddsfdmidsdnsedfdndtdledd nvsdlkdkyskynfddddapskpqfkksvdiskfdddglseeeleaerrkaeeleekkrriiggtnfdnslrk |
| Contig40_gene_119 | 513 | meimpiisffigvisilspcilptlpiiagfslkaeskaeivafilglfsiftiiifitgfftilfryivyvrviaaflllimgilmffdyn lsfgsvksrsgegivnsfilgfltsvawadcysgylislitmlvssplyavfnifiyvfgfaltlvlclaiskidlekliyksgyipkifa vliigafymfytsigvfl |
| Contig40_gene_120 | 514 | meriigvdetaktpayeledgvdyvpmnkyrallvhflniaglgpifgaigqalfgpsaflwivlgtifaggvhdffegamsvrndglsmpgi iskylgdrvrkffavlliiitcilvasvfasgsadllssltnidihiwlvaifiyfliatlfpvdkiiqkiypifgalffimavllisalilnp nyslpefttagilyltdkaifpflfvtiacgaisgfhasqapivarcvknekdmhmvfygamviegilaliwatiamsffhgqpqlasiygssp siavkemsialigtvglvlaliqvvicpitsqdtslrsaritiadelqlnqdklktrlkisiplflvsfgltfidfslvwryfawsqlivaia vllaatvylidnkkhfivtfapalfctvvaiayilqaseglrldpflsnvisvivalalsvyfilkyrkqpnttt |
| Contig40_gene_121 | 515 | mlslikdnkgflsliidailslflllifivlisfnmivdmempslsednqfktsqdlmelmsskidgrdystlerisyvlssndnsiasrrevkn ilddffsahlgsdykyfietnqlngyvlssdgdystadevslairngynysyklyifka |
| Contig40_gene_121 | 516 | meertglfsngviwfgvaisvseieagiqlasmntldsiwlplvighiiggilllfstgligarirlnametikstfgnyskffstlnvlqli awvavlnaqgasalmginipisfspltciilsaiiavwvyvglirrsskittimmivitallvlilsvkllgvhisnalpiqninstalsfwsife isiampiswlpvisdytkdvenpvngtlvsaiaytiaslwmyflgieivgigttsiaqsillagliagvillvlstvtsnfvaansagesak aifnrinpkiagvvsaisailaisgimdhyigflyliasvfapmaavllvsfylskeetgnariwywnifawlagfivyqatvnldsiflgp tllavisailayipillknksklpnisk |
| Contig40_gene_121 | 517 | mnetiktltiqdiscyqgcsitvalpvisafgietailpsavlsthtsgftdftvrdltedlpeirkhwekegiffdsiytgfiasaeqldyi kdiidsrlkenglvfvdpamadhgefyngfdqefadkmgelcklgdfilpntteacfilhkpwkesftkeenlemakelkaftkryvilkgye eedkmgmivldkiedtidivynekinyvshgtgdvfassfvgstmlgkspsaaakiageftkkaiektigdethtygvkfeqaipelydllks i |
| Contig40_gene_121 | 518 | mmdwspifismktaslsifitffigliivawllvkikndttkivldgiftlpivlpptvvgffilyifigirgpigsffldffavkiafswpatv iaavvmsfplmyrsargafkqvdsnlldagrtlgmsewkifwkilfanalpgiisggilayarglgefgatamlagniaggtrtlpmavysev aagnmgtafdyviifvaisfiaifimdyfsirkenqwkn |

FIG. 9C-23

| | | |
|---|---|---|
| Contig40_gene_122_1 | 519 | maqkeldipvdgmhcsscsllveksigkldevesinvdlntnkahmvlkdnlspetidktvesvgftvpkeevviqiagmhcascvnnvekfl prydgvveananlsnqkvtityyrdmlnlkeigktiemlgfeyigldgeldimdeeeryqkdlrgklyrilvglvfagilmaimhfhitippl tmqqlsliiaifpfcyvsmpilkagwnsfkhknldmdvmysmgilvafvssvlgtfniildssfmfyesavmlpsfltigryleararkrkss sikeliglgpktatlitsdeegnsiekeidiedinigdillvpgekipadsivvdgesyvdeamitgepvpklkkegidvfsgtinqdgalk ieaqkigsetvlsqiiqlvekagskppvqrlankivswfipvvltiaivvfclwyfvagaglifsltclisvlvvacpcslgiatptavtvg vgraaeygilikngetlesskdvdvcvfdktgtitegkpevadietfdmagdkflqvlssvennsnhpiaksilnrfksdnlkiteegkddla llevsdfenitgkglkanvvvdennssvlagnlklmesegvetdevldkfntfvseakttivmaidgeikgiitlmdkikdnsksaidelhk mgietymltgdnektastvanevgidnvianvlpndkldkvqelqkegkrvlfvgdgindapalsqadvgvamgngtdiamesgdivimegdl envvasigfskkvmtrikenlfwafaynmllvpaaagllfllfgivfkpewaglamalssvtvislsllkryvppikrnkv |
| Contig40_gene_122_2 | 520 | migigailllfplpidlfyrefnyyygvipplisilgvifsgfreydklkfkhgmiissiswlwaglvgaiimmllidvsfvdaffenisaw tgsgltmfsdveslpmsilfrsveqwigglgvviifislllikpgtsafklykseaaredrikpniknltlkktmgiyaiytvigvlylliaglp lfdsinltfttisaggmsiknanigfyqndivyiltiflmilgatsftvhykmaktkgkaildiqfqllvsilsaiaiaiitklapmdvv fhvvsaitttganiappsemaawappaliiivlmlmggssgstvgaiklvrvitlksthlavtnivspgrfvkisgksinegemkeass ymavyifflaiswiimtyytndpfntlfdvvstlgnvglstgiisgelgtipkvvliflmwlgrleiipllltigigfetfnqslrfvkrrmn rkikpn |
| Contig40_gene_123_1 | 521 | mgsldtgiigpvlpsieqsfhltresswiftlfvitfmigspvmakfsdfygrkifilfdvlfgigscliaasisielifiigrligfgcg gifpvagafvgdgfpleergkalgilgsvfgisaiggplvgaalipygwnwcftinipialfliifawyilpdsdndrklkidyigilllsll aiflsyglnqidssnfiaslslnvlpflvifiilipifkvekkaeesivpihmlknkeisiacietlcygiiyssaifipslvilsmgidd qlaslmipilganavaapilgkildktgskklmamgtmilaigliaialypsnlfifiiagclgvglvtligaplryivlteakpyergag qaivnmlssagqliggaliggliasftgilgyqvsliiaaivaliafaftlrkgrdeqiatmkanq |
| Contig40_gene_123_2 | 522 | manenvelmrgapeiavkklaipimismlltasynidgifvaglgqaaiagigfvtpifmilngvsvglgsgatssisrfvgaknheganks athallifliasiiltiiflfigepllrtygasgqslaeglkygsplflgftfmfangsgilrgegdmkramyavivsvilntcldpifiy tlgmgsagaslativssagsaivimywilikkdtwvhvelknfkfdsniakdikvgipasmdmfmnslavslylifistigqefgiaaftsg qrlylfaimpltsigsavaavgsavgaygarngdylsrthiygakfgiafgtavtilliafapqlatifaytpetaplvpeitqflriaslcipl tgagmcssflyggigkgtismwtiireviftvsatyilgivlgwglvgiwtglaigritasilnftfarftikkirenfgt |
| Contig40_gene_123_9 | 523 | mnisslfsdekvntgrqveldiakafaliifmiflhtvmiveaynvglsptytylignvlgrpyaavvfmfcmgvgvvysrhsqwnlmikrgli lyllgllvnvfefflphylagylgvnaeafplfggliifcvdilafaglafilmgilrkfevsnkamiliavimsligsftigidfgipavcs ffghfigaknghtafplfnwfifpvagyvwqqyfirakdkreffkywpillivafayffissrywggvfsedvhlyyflntldavfciinaha figlcywisdylpdsitkffstlsrnineiyiaqwfyipvtiilityfskglvfddlvttivsicmliistvtalayrklrtkg |
| Contig40_gene_124_0 | 524 | mylisffglgvkltnfndvalfiiifvslinailwpiltrilmpflvlsfgigtlilngllinfcgplfginvegpalilaplamsfvttalst iltiedegsyyrsvyrdaekkrkgevkdypgliiveidglaydvlkeavdkgymptlksmidnthtlrmwetdlssqtgasqagilhgnedi tafrwiekknnnqmmqcsgvtqvttleerisdgnglivdngasrsnlfsgdtdnviftfskilnirklynkawfsvfsnpsnfarivclfiyd mtleiisqikhsvkninrprikrgiayiptraatnvfmreintstlligdmmvgdidvaystylgydeiahhsgvrdedswyalkgmnkqierli ntnkytprkyefviqsdhgqtngatfkqryggsfedyvkslipkemkmfakmssnedhyaesflpfsrknddlidekdleelgdseeivlasg nlamiyltgwdyrlsieeinkffpelipgiveneyvgfivirsdegdlamgkkgiynldtgdiiggnplegfgkniarhlkrnssfkytpdil vnsfydcendevcafeelvgshggvggsqskpfilypsgwnvsdeeivgaesiykilkenlkklkeysndntalekecsnde |

FIG. 9C-24

| | | talekeystalee |
|---|---|---|
| Contig40_gene_124_2 | 525 | mdiseiigdaiaypihnikalvlviymiigiitgilggasfmglimsltgknalaaggfgilgvlvlligallitgyqldivkfgierrddgpgi dlvrqvlnavklllvslvyyivpaliawvlftllgrgiltvlivmiislifafaefmaicrlakydslgealalgealgdiskvgviklati iivvviamivcfillyyyklnsligqillgifavyltffanraagllysda |
| Contig40_gene_124_9 | 526 | mnmdfsvkdfnvrlrtiriwevvialvvafflitgftcdyfgiysgeaeyiifflynumvffaiasigthgfkddiygvfkasnlfkvimivipn mlaffiqqhlagfdamfmninllalpvsdlayeasnpllflfeffsaifiapiseelffrgilfnrlkirkgvifgvvvssiifglchfnyp dhlahiiytclfgmclcilylrtdnllinmfahflynllsyvivytpigdlflggpfmdftvlvllfsivfvpayifyfsiklk |
| Contig40_gene_125_0 | 527 | mdfnvtdfnvrlrtiklrellvgiviafilslallilifpvmdsyddlalmvfvffifflyalkgtsglkqdfnklferdnsreilyvliin mlafviaifstfdayltladsewvsildftptaidpavflfesftsiiiapileelvfrgvlfnrlkirtgllpamlissflfaighefgg mtsafvfgmcmcvlylktdnilmgmsvhflnnliftvwdlfaldaivfqmpvlpltllislisglllilylykeigkllae |
| Contig40_gene_125_2 | 528 | mflxygysyrvtkvsvegmingndplpefddvigmfvdgikvclvylgyalvpliifmvfalvssaiggygesvlmafgsiitllaiigayvm smfgvanmanydgalakafdikeileliqsvgvvrsvgayiglaiictaifmivgllifvfgfgiitgtlgsytaaggifiagiilgyflm lfivspyllimqsrvagllynlh |
| Contig40_gene_125_3 | 529 | masitdiikeglkypfndtrkvlilgliflisglislftqyvvydsmtlmvnaspytsvngmfasippsnsalifiswivtfillfltsgyly dvikyaidgryelpdfgnifailknglrtlivgivysivpalifilglmlmvneasgeavnmfglilfvsfivaifiylieviaishmvend slksafqfseifdiismqwgrfigalifafiviaiismffgmifgaistgigilifdsalvstlvssiltglllspyisialgrmfgsvykea ise |
| Contig40_gene_125_6 | 530 | mdmisilkilialifemilevfemildsfrnyyr |
| Contig40_gene_125_7 | 531 | mllffiykfnsisknssnfnyssnrdsnsvnnsslsdafrndlnsifkvskiyhillfivlanilfvsaiyfvlsylgsisiiqfnaplf gdftglgfdvtllylitvvlspiieeflfrgiflrrfnleldnltlailissvlfgichnfggilgailfgicvsilyvksrnvlvpilahf innlisfllaligienfihgnsivialiiiilaiisnfvlfraivlewpksfke |
| Contig40_gene_125_8 | 532 | mlkftgkeirdliisflvialafsilysnrdfngilflfpivaigvgagfifhelghkfaamhygywaeyqlwptglvialvssffgfifaap gavviysqgmeksenglvslagpavnivlgliflglnslgqvtdynqyialicllgtrinfflatfnllpippldgskvlswnalvwivaf aisvillvyggylg |
| Contig40_gene_125_9 | 533 | makkddkysmpmsgaglvryfddesvgpkiapeyvialtvilgifcfilrysi |

FIG. 9C-25

| | | |
|---|---|---|
| Contig40_gene_126_7 | 534 | mdalralailicviaihayacsrnfviselvgnlpslnwiiiqfsgntfrigvdiflmlsgalslgrdwkmkdffahrfprivypflfwsillg tiflllsyydsfnvissfdlvsianyfygvfmgiidfakpywyfwmilgiylimpvfnkwilhsdlddllyflffwlitclfdytlgvefpir lsyftspiglvvlgyylrytrriilnnqyfalfliilfssllmlvlsalystdthfynfniysilvsmevigvfllfknfykfnlnigffsrpd gffnksvyalarysygiflihnaficvlvhylgntgippvlymiilfvvsllcsvivmavlsripylnrvigvk |
| Contig40_gene_127_1 | 535 | msenssfsvdnlviylllialpiflffvsfmlgrypvapidviktilspifpslavspelnsivftirlpriiaallvgaalsiagasfqgif knplvspdligvsmgagfgaaiailanagnaliqlsafvfgliavfitfsisktykaggilllvlsgtavsaffnalisgakfmadpydklpq itywlmgslsavnfdklamiiiplvlgiiivvmilrwhlnvlsmgdeeagslglnpsrlrliviiactlvtsaavsisgiigwiglvvphmtri ivgpdhkilipaslsigasflllidnisrtfisieipigiltaiigvplflyllrkgysewn |
| Contig40_gene_128_4 | 536 | msmladfeparlhkrtwaerhdveilaviclaisiamlllffalaeptvagvi |
| Contig40_gene_129_9 | 537 | maillplmsmlgigeltqnyilaivsgmialvvwyyneknhnsdlvsgttkcdcelcyggddeali |
| Contig40_gene_130_0 | 538 | mittgvvilfnsitehpyfmewdeiglvlgivsitiaciylamidrwkerrkkeeldtiedyinrkaeeianmkvlrkleeleee |
| Contig40_gene_130_4 | 539 | mgfwglttdcgnllfplglymadvitevygertarrvillglfanillivattltvympypsywtggayaymfgftprivlagfiaylvgqf vnarlmvlikkwtnskylfmrtigstlggelcdscicssiayygivpnsgillfilmqyvvkvtwevvmqpltyksiawarkdg |
| Contig40_gene_131_5 | 540 | mkaigdnfsvdyllialfssgdlilvaivlnsygvispenvrelvidyisyrkvdifwrhlrrprmsfedyvldnfeemetgeltreqvvefv srgerkgltfcneifiavplkkgskddiveilwneyfvedykenwleqhenlgwndwkkllkkeivenggddfqifrnhlidcvlmey |
| Contig40_gene_132_7 | 541 | mekveqliekierererteqferaikeakeqfererteqfererkerlerekrekerekiekererkerlernrikieerererikrnerir renernriksdkrerekseekrikrnerirkanernsikrekrerernrvmtideyyrsigygstgkskvwsaiiipillviciililmfyg ggm |
| Contig40_gene_133_9 | 542 | mlktnfgitkdtltdlgwsgaaddvkgyqealdkalekggmdgmldtttghletlkknfrvagrhvgemftpyidmavqklnglketcpglf enlvmiagavsgfatvapsiapmisvfgdvgsaikrtagflglmevaedavtlkstfltiaqiagadaavlqtaansgltasfwamaaailan pltwvavaliaiavavyevgksfgwwsdigsmigavwagiqrlwsafinnpnvqgflkdlsnawndicealapvidwarkawaelfppsatgs fdivraiidvfgqlgdflgkvvnavksawnalggfagflpmllgpvgmvvmalrmivcillgcsppgivpalqktqsvfmsvfgaiaefiggav snvvailtriisaltgiftrvssivstylakmissvviswassivskaksasskfltnvvnyfsklpskvwnhlkniiqkvtswatsivskgkn aaskfltavvnhfsklpgkvgtyvsntasrissgankwvsnarskasstvsavtgpisklpgkvynefmgigsrmlsagsalvskarqigsnl vsgllnamnihspgtiqqkvvaefentlsrvgsmdstaldvggsvgnsivrgftdfgldtgsfnadystdynlnrknddnldvnikqelefvf dfknlpndvdedkllemlkemvtdksviqalvsnpdfgsmdtkvknsiiakvkrargv |

FIG. 9C-26

| | | |
|---|---|---|
| Contig40_gene_135_2 | 543 | mdlifeylivfillfatniafllryssfnknkfipfvlgyailvfaltfvfssInlqkesidfipyilfavsalmllisiryvgfgknygind dkvvlygtilssflsigalalgksdnlflsglelailsvviflvykiskifnnakrpyyavigeymflefllllaltfssvreldysmf gsfliltptykvlymiiaivillvlgvlyndwvlkrlkrk |
| Contig40_gene_135_3 | 544 | milqgteiltsfihivsesllapvvivlvifliyailsfggflnewftkkplksaglekllqdisssdspedlkavidasalykeqkellvki tdnylgpearkafasklieeeesnlllkittktdilvrlgpifgllgtliplgpplsalgtgdittlaqsltiafdttvtgltigalgylvsk yrkqwyesdlttetiaeailekInqf |
| Contig40_gene_135_4 | 545 | mlrkrkrfsddgdedpmsgisnlsdamlvlalglflifaimalqvnpdmwaktqesqaqqatsqvstgqdfnssanagasleqsgysevgkvyk dpdtgklvmvgg |
| Contig40_gene_135_6 | 546 | msfkspadtakavasaatakgempiiklailgflagayiafggllaevantgaiaggvpvgiskllfgavfpvglimvvicgselftgdvmfm tmglidgktdimgllknwrgswvfnligglfvayvlayltgimvpeafaggaitiantkalggatfmaagkstasltwvqcflrgigcnwlvc lavylanaaddvvgkffgiwfpimafvcigfehsvanmffiplglfIgaevtwaqffinnlipvtIgnivgaavfvacaywfvylrd |
| Contig40_gene_137_8 | 547 | malniasvvdasfvstfighnaqaalqvleplvllitifewlfglggqilalnkkaefdeggsnhyfttamlativlsvllllvcflfkdsli nllhptagalpyvnayspylfisfpiatilgvlcqfirvdgqpnfasgvvivaniniiildylflgvfhmgiegaslammigyavgllctlky hfdskrtfrfvfselkfgtwirstieiikiglpgasmgffnvlliyinnlivgvlgelgldifnvcvvalllisilimgfaetlssivpiyy aqndfynlhivrnsiiitlvcsviftaflliypdgllmffklhqtandglvenairiyslafipmafstmllfyyegiertvesgiitvise flgplffftyllypfigitsvwlsfplgfilsivavsiyvkvverkdseysglffirrgliektrnytleskndavksemfnhlkslnvddssi etldkiigtifdsnnekvhveillidygdkivinmkdegnrevmdieksfsqdkikvsevlgfnnveylidga |
| Contig45_gene_1 | 548 | mniiknlplaitglilalslgkifadfsaiffiigsilifmvllklvfhfndffnelnnliplstfgtfsmalmwstylkplflplsqdia fviwilgiiihlsiilfftnnyvlnnfniedvyatwwivyigitmaaitapahglskygfiffgigfilmiptlvlvsyryinfkqiddqnkp ficiyaailsilivgyvnamtingtflsliyigavifyifaiiqafkfiiierlkfmpsfsaftfpfvisaiatgeaykffgldilnylfyiq afialilvifvlynylkflmn |
| Contig45_gene_10 | 549 | mneqtklskdhymifglswagwvfdfydlvlftflisqlqsslhinaemlalclglslfatglggiifgalgdkygrkkvlewtilvysigtl lcafswsfyslvlfrfitglgvggewatggiqiyisetfpdnlrakfgafmqsgapvgvilasivggmispiigwrmtflvsiipaitiliry lkesdvwiknkddfvnknifgefkqlvskeyrkiflislvlcifgmsaywftyswlptylaeerglamvttslgiiligcgdftgytgfva erigrrpaftiysfimgisiamltcwnqidkvpdlimvfmfltgfgtgfggfgslfselfptkirntgvgtvfnlargvqfitpmiitfvg ayydlsygiaiaaifaflvgiwiwvfpetkgtaindld |
| Contig45_gene_29 | 550 | mannsvlrrivslitkhnilsigtkyfptteleteyvdmfnytqtmlmeidkanittesiftnlvrdvgrenipenhsfyellpaqnkideya lvskiimgsdrymyvelsepsyiidyftdiilrengeiierseteivsrlmskndairiaiklvgigldnnirvraaagmtqaaaiersikfn kevgdvppgvaftklggeyalvldtpfklqgsehaeyqhylfidivdstnfiskhgknklvelmtsvkefmencghiegyreggddliarfps kgvairagldcawfilnngakvkigigrsrreageraniaegikgfgaltlivfdlanglyayyvpsdfsrtlcelfttkkgklvtaflvfi lcyllavlgfglygilvfiivvayytlk |
| Contig45_gene_38 | 551 | mrkvfesiiealkypfrdwkniivigflliiaslgrklpfpedpqqtvvfigalllilfiqtgygskivysglkgenippklrpipkliwegfk kiiiiiyvhimvifisvgktqlsannipiailfvlggtylImvgglInryfhhgkfikafylkeiiaiikkigfwdmisivicamisqtl tistfinlvkgmftsielviciiafflapialmstkrlisinIrriIssdedlekfaf |

FIG. 9C-27

| | | |
|---|---|---|
| Contig45_gene_52 | 552 | mdylliitkcdkmdlnyiivlfvltflatvaftyfvrhtlrdadvsdspivsehrhkagtptmggiaflfailfivsiyyrntniliasfiml tggvmglldd11g1kikeyqkvknvsdsvvpiglldlgpgeearvttdkakkqvygyvdegkleivaeipikyepsektkiivqllpglfla ltgvvttlggftlgilaypiciialgsinslnlidgmdglaagivaiasfscciyayicgnmdmipafailtgiclgflvfnrypasifmgd tgsfvlgtgyavavilgdipyfgvlalavpivsviislmhrahinlpveplhhtlnykgisevkivlsywlltvlvcaigilaklyifa |
| Contig45_gene_67 | 553 | mfnpiialsyissgffmkisddeydeknnkilailifgivcgaftalassmstdaacifiailignilaqkvdgihhvvtmlsflivlvflglp afsrpsilvvmicvagalidekgndneilyekskflmyffdyrfalkvvilalalfglvdiwtfvyflcfeiayeiarvlfekfil |
| Contig45_gene_72 | 554 | mndlkklyvllailiviyvginfsyngldtintlthvnldlgpsmdnandanhikigsssftklskiftw |
| Contig45_gene_83 | 555 | malieknelflleeivknfaakykdsilgifwsilkpllimilltiifsnlfggslenypyflsgkliifdffnsatsvsmmslkgninilk rtaapkhiftlagvvseflnflitliliiligvmivtrspfyilesmiaiipimsliimitgislilavlcvyfsdiqhlwgvitlmlmyasaif ypmniipepfhgimilnpifwviggfrilvlwgtipsrmmnlnlvllsvilvfgiiivfkkfekkitlkf |
| Contig45_gene_96 | 556 | mvrkkarrrkrqeedpmagtnlvdamivlalgflifavigwnlqsvifsdmdpqergatmesinqitnvtqgeqlnstpdtsnqsgegyveq gkvykdsktgnlimvet |
| Contig45_gene_97 | 557 | melifsvfavislaaillligielglislskffnislkkhlilvlaysiiifavivilspsyeavlnstfysfyyyiimgfvclalglitlfywsk mewyppalkcllyfdfvpislsmlistalmapsfafkvqnfslnltmvnsglilvvlmailmvifylfsdfvedyrvthyaiiigslllifa layfvlgfiipnmapvfanpsteltlmpiesivmvvliallilglgalfrkrtnrle |
| Contig45_gene_98 | 558 | miilamtipggdfilttgnlisqsllipvviillvfvvvvisigglliyeytsrtkvsvddvsnlileisdsgsvdsmksaianspipklqkd illkiastgnmspntreafarklieneeglatdksleitdiitrigptlglmgtlipltgltgllalsgvntlseslivafdttvvgisgala yviskrnrwyeeyisn1dv1sdavidfmakh |
| Contig45_gene_99 | 559 | mglslyllldliliftlvfkiennlyyiliaidtilcviliyefynrfktaenkihfsirnsteilagipidliflpfapnltvfltifnll kflkiiglfleffetidvflkkthldeilglailvilvstlgiylyldfdpsinsifdslwfvlstittvgygdvlpnsyigkvigiliilfgvli fsaitgamtsyfarkvfatkdfnitenddnirllkedlsfnkknlnnanekidkinndveklkrelnemkeelresrqlnkelkeeivilnen lknk |
| Contig45_gene_114 | 560 | mlheqafqligesivvlvvliiiliiliiallliglillrrnklvfpsliifvvnvfyspiksianflrlddalvdhigievrnkvnkpkfdqip peekiiivlphclrsrdceaslkesgiktcfcgkcaigtikskaepmgykvfivpgssfvkkiieqnkfksvvgvachvdlnqtmmalsdfypq gvllstsgcfetrvdvskvlstigyyeykeknksiddekddsedigrikps |
| Contig45_gene_143 | 561 | mnfnlkdmilifirgflmgsadtipgvsggtialitgiyerlihaissikfgfikplikldfagfkeklfeeidfelfiplvlgigiavltls kvirylqnytaytfsfflglilasayilytkldeinikliiliigiilsyifvglnpiaanhslivlffsgmiaicamilpgisgsflll lgqyaymidsinsInfteiivfiagafigilgfskilnylenyesatmafligimigtlrlpfnqitsnltgswliclilaiigvvlivvle kkls |
| Contig45_gene_146 | 562 | mkgtwklklrlwlsmavmfglvyvlimlagnflgyrgfygfyaiaglfvlflqyifgpkivessmgvhylseseapelhqmvaelaqaanipk pkvgisntmvpnafaygrskrsghvcvtkgilglldhdelkavlgheishkhndmaittvvsaiplicyylgflsifsgggdnnnggali gflaliayflgqlivlfisrvreyyadagsvelgcqpeklasalyklvygaaripegeikdvegtkaffltdisnarneindlsqldfnrdgv iskeeldqlknnnvkisgsnkimemlsthpdmlkrikrladmn |

FIG. 9C-28

| | | |
|---|---|---|
| Contig45_gene_150 | 563 | mkkmicpkcntvnddnekfckncglqlnttricpncntankpnskfchkcgttlspvdtfkkgileentsnsffstykipiicalvillaiga vtgvaifggdgnnginsiiplandtyddtnlnnygvnhdnvsqtqsdnftenqtdnltdnqtvnqtvenktkatvqntdnnktsnndtnkt kvysektnttnssakvntektkcn |
| Contig47_gene_1 | 564 | mkhrlnldkkdpnyillkeifkimdsreskqilvsygfknlnrtifafkiifismffeidipfilnelksnrrlckflnisevltadqvykif seinsekliksInrilnsrnmvkrrgkktfivdatpvdldinfrrnkkskehlkklnlkwsyssskgyyigfkatvvmdydsmnpvcilihsg apndaglfeeilenlqkrriirkgdtlifdkgyygyknyqigiskykiipfifpkekfsrtlrlddiltyplavfnktkrimeekrlynnlkxe liekidswekfkpirgkiedffkllkgglnmreihkytlksvektvlnvflgaliisgffysktigglsen |
| Contig47_gene_12 | 565 | migdddffmqnadyhygasdsekmygrgydgssdyvpryssggsygssgaessedgslgkyclig lvflgivvfanigipaitnslsssvt vddlnitryiysnqynskittdygyqitykersygqhatnvifysknqkvlyndsqymgtcylgevpyilyfdgkadyaifevyktqfdsgec iyrervdvdnknvikefinydtlydd |
| Contig47_gene_21 | 566 | maelmdkifvvigyilailfpivgiivgallyflkkedafyqthgkyilivgiamiainilliafgiltippvqv |
| Contig47_gene_22 | 567 | mdnrnililigiilvliaaagiilvmltsenyermeivpngtsidvplnkttydgefqsarvhwdkgilvtynshedknilrvselgiytlnk iietgekenidgftsyvinadeileielfdaiklhytgkfyciplangttgdviiicsndrdeavhmaksiqyknvfpvnsdfnntietvenl seylestvndyanstdfdnavstvenltgnlessakdyvndanlsdvkttveektginiddaksdleqyiglkits |
| Contig47_gene_26 | 568 | mpldiiediwkyttnnktflliilvlfylfcmfmqifdemrisyalylsmipyifiagygmaitkdvidngkrlpkilikdvivlgikstvvf ivylsvqgiffslvsylcnfpiidvedlldffetapllfhhnlvntlifivvdfavfyftmfmemglakladtgrfldafnlikikkiidi igwrlyakhytviifllwvfslliidvetpffvldyifkvflgllllfitqywgigavyriykiktn |
| Contig47_gene_35 | 569 | mdirkvigililglifaiypvysaqavswiagvaliagfgigilildgfsiwsmmagvsaakillgiiaaligfmflykvdalsfiiayqfyi igfilifvgllgifiaidgisrataliltlilgiiiciicaffslsqplytavivgicmimegitflasgiide |
| Contig47_gene_36 | 570 | mdketkerlgeiraamkkygfdkilgesaknrirgkdeeeeslildsevpvkfrimlqelgttfiklgqlistrpdmvgedianelanlqddn paisyeqvkaiverelegdidelfaefshehlatasigqvheatlntgehvavkiqkegitdkidldirimkyianradrlsgelkkvnlpgv meefdrsihkeidynefmnmqriemnfvdnpnvhipatypkycttkvltmefiagaklndvyasegedfdkllaktvidsylqgllidgff hgdphpgnimilednvlcyldlgmmgtfdedfkrnlaeaillimdqdidgvinglmymdildydidtkplkrdlndlfgryfgvdlnrfdgil gdllkimqeygvvlpnelvtmargvsmveaiahnldpeidifeslkpiakriarerldpkrylkskksniilyehmfralpqlltrtvhkien eelqfrfevditdkvsivalvsalivgssvvsfgprafdmpvisiigyliailsivgirkfvlk |
| Contig47_gene_37 | 571 | mteidwfkfedrdydfpfykknphiskmgwlvlffvfiigsilsmsdklsysilcciviivpvlyfldwdykaifrkpslkdialavalfigy liyaiimgailesvgivssgilidpgsidwtvliksvfslmgeefikflpfiffllrvlykytdnrklsvvisvalvmamfaslhaynwvmfiya lfiggfgsifeffayiktkniivsyithyctdafifamlllglg |
| Contig47_gene_41 | 572 | micpscgsenkegskfckncgerltdssrptstnasassqsksnknlllicatiiicvavvagailfmsggstdyevasgeatndhsssalns ydssnndesgddsasasedssdsadeynknhkwgksfgeaseyfpeasetvvthvfyeadidgngfltdnefkdfkslvsftrkyaadvtnn dyvdtpdlwegdgsvrtrycadhgriavgsddrcpycakkgqdsrtrsgstryv |
| Contig47_gene_46 | 573 | mskkedncqiddcssgtcapvspfskegilflifiivlflfillwtngli |

FIG. 9C-29

| | | |
|---|---|---|
| Contig47_gene_58 | 574 | mtklikrevkreyneespiklkianaistftnppiiciciplfllisfvlasngnpfsssfsfdwmlfakceiislvfasvlpmaiiiywakkln tdkdisnredrfipllivgvlsyligfvisffelpnfltilllcyavntfivmlitslwkisihttglsgpvaalimllgpvialimllgpigalfgllypvl iwsrvtlkkhtmaqaiaggifgfvftvgesylymrlfkmsvpglvplaecfwiifalvacpivlgicgllekrgiesviraklfhllafigfa afyfygpssavlililsaivsvlvtifagdtfswykgisrglerenlsivlslacgliwiyvamnyfniesaiiativafvgaiaepvaiky arykfpmksllgndgnksiessvvalivtmiilllftqnvfvsiavgllvclietfvpkelenlvipvacaiilgfllhy |
| Contig47_gene_65 | 575 | mkervcspdcekvlemnqkninirksrimlfavivvfilvwayfmffk |
| Contig47_gene_67 | 576 | mpsekvkefneslktkegrdkffkqifciaigtvvgvatyafclyfnlaifgwniglalspltagyaesilakkilnestgaisafilfiltv vygffisnstlgfniitagsavviiqaamptatnyllavgvgiltyvtgflkklhsalykgykkifkrepkraeryyqkqasqvhafydenl dinslgvlimtleyppkelniieqkgiyetrhifgskqkediksgledsleeevinrvklardktlvklikevkadgcnglmlhttyetlgt ekgdhiaqvvmrgtgiviekeeeey |
| Contig47_gene_68 | 577 | mvplqfflftsvgvdpslammvsigtslaiiiptassgayhqkknksivrpgirlavfgiiggfcggllanmvptrilqmifaclllfvald mlfgsrsdgekalidfnllnggivgfsigiiisgliggvfipslcilfgfslieaigtssvfiaftaigglisyiytgfgvnpmpyclgy vslinfvviivlfsvpmatigaklvyklpekrlkqifailiiymaikmlgfdpisillgl |
| Contig47_gene_69 | 578 | mnlkinkyipfgiililgslyflsgidqfirpftqpilmgsskgkdilffvlfgitiilssigdnerihnylmnlsipeklkdkdfylkls lilflitaisglavelyralsglqinwntilvimpsltstsflhshlyksifgiilgiflshipagihtgsslssyapsvislfilipityi smvlsnqrrkaasrillaftstlgiiglidgglfatpaiggiygiilimyneeildgisdfitekcdkrdgikeklneelraiksifnnknikk ylkialphialililllifsvafygacpdsyeliisnghdldleydtlnisengdrtvvhlsnqynemelfk |
| Contig47_gene_79 | 579 | mvkisrknsfdesseedpmsgvanlvdamlviavglvlflviswnmgsiifnedlspqqkqeaidamnqvievdqgqlnetpdisnssgegy temgkvyqdpktgklimien |
| Contig47_gene_80 | 580 | mgggiltyildtlsqslqipvliiflliifavgaililgglireyshrktisdaemrniidainkandkseilsivdssdipnsqktvlreitds dwdnesrvglakkllissrekrlekrlsytdiitrigptlgimgtllpmgplaalgtgdvvtlsnaiivafdttvvgisgalayviskirrr wyseyinnidvltdvvlnklnkl |
| Contig47_gene_81 | 581 | mgendrsclnsccsllkyslgdnknndldnsadlnslnpnsnnclnsnknnccnycyknqtdlnddlndsdncpdsfakktninhdkqlndgeid fsernnqiflispenfsvffdennrlkedyggctlvfegdfaelgiidisypytritakensfkntafklsasdielsnlnisldkefkdney agilvlsdyisiynitlnytvpantgfciyskgegfrritdlslinntiftgnnlneawdygifldktdnalvygnslgsylplcednwyn neygavskmssagfvaqscndlklssneintyvtdstqssfamdscilydcsdltverntlyledidsqdgknntlhgfdlylcddaiiafnn idlftmggndgrkitsplqvngpsdniriaynnitssnfgsncgiyshnfygdthleiisnfidvagfansgewsllsgievqdsddviwnnt iivtnlgdfkynnkvygisysqnrnynstfnvqynnittngyyavylgkddypvvnstvknnvlntyitgnpavsiandnknnpivnntdn efkniksssfpkwlknflrqdtkvdkdfswitdainpqsngtgfsndtgntgliindgsdtvgnnsegsdsivngtsangtgngtsgnat epqnpiddnqgdnsqgssssdnstgsqtdnedsnqnntdptdskptnntdvpvnptntdkpvnstepvpandtepvpandtgpv pdnktdnpvnntepvqedanktdsdntepinttkdnsteinktesdddtnqtvlkdddlpkeshensqdnknpsddeekstpdsgnelt dpessnesespqnqeensensnddssepsstvgdshsdsasspglsdasssknayeldkpvedlvtksvdyislagicivtlllllfgykrqkd ieged |

FIG. 9C-30

| | |
|---|---|
| Contig47_gene_86 | 582 | madeiatiisslglsneaflaivllafvvigaiivivatrpildvypylhpnarvrarkgrlfdekqiselveannvdeitnylrgspdyady ldnytlekaldiqlgetydmvsrmapkeiqssfkvmakksdinniksllitakqaglneeatadlliptgslyedierltdadgvtgvvagldg teyapvleealpeyektgmvlplesaldkyylskllassetpsdenkqilysyvgngvdvaniklliralkadgldyeaispymidsgylrew klkdlmeaedvtgvisglegtkysdvlvevlpeynetgsvalfekaldkflvdsaksysmkkpigipiigflsqkevevknlkviarakrea dfpiskiremlv |
| Contig47_gene_88 | 583 | mveialgtalaaigagvaigfaglgsglgqgmaaagsvgavaednddmfargiifsalpetqaiygfliaill1vfsgllggeglstaqiva igvgasigfaglgsgmggmaaassvgaivednddmfargiifsalpetqaiygfliaillmvffggilg |
| Contig47_gene_89 | 584 | mrklnvitldkyagptvsalhdegivqindiseriqqdpklaellkpskvtpytgklssllmktsalsdllgdalseqgslkdtlmsfispdl pvpkevedvdtesfiayaestlsqveaetkgiedklaaldseesklesnkslasklknldmdlallsdskytstivgritaesagkfkseysk itedlfyelvpddekeynilvvvvanefkddiytllrknefekfetedlqgrpdslisscesrqiaiesersgakadlkvvaekwddevlalk eqlenekeknevfatfaetdktvvleawvpeknleqagsiieatdghvimeteevpdnaedvpvlqenctyakpyellvemysplkyneidp tlfvaitypffgfcltdagygilvaligfilyrgmgkvnrtmhdgglliliasgiwsiilglftngflgdmwtriglglpalptvidsinafk fpatilviavigiiytnigffilgaidnlrygekkeaigsqivwfvfelgiililglflptfgmigmalgavliiaalgmliwangayglmd vfgfmgdvlsyarllalclatggiamtvniltnmvndmipfvgivlaiiifigghianflfqvlgagvnalrlnyveffsqfymggknsygaf kakrgftkvkk |
| Contig47_gene_91 | 585 | mrkiillafsallilglwnymsvpkpgldiiasslvlvavgwtlamsvfepnwikaaifidglvfvlvsitflvspinyvfllfgiilvaia vlaylrklpdnilryfyrs |
| Contig47_gene_92 | 586 | mkpkivrardkevmnqlaklfeeskytvksqdknyvllkknygnplihlpfiliglffnafailvnvayfaysvfkksnvilitteknededg nplefddvgeievfydqetwdkaielsrle |
| Contig47_gene_99 | 587 | maigvkeikitdtisillipliyalviglalylakpikfigrkqskvaegamvlfigvlitklaissgqiasifqvgpalliqqignlgtli alpialffgfrrevigmtssicrepnlgvviidkygfkspetrgvlavfvigsilgtpfisflssisaslipmhpyayamasgvgsasmnaaal aplmhmfpsmatdleafagcsnlsfcfgiymcifvslplaermykwlsphighdkeetiddeyaiegvkhdkyaskeelssgkikrwatfli ifsftvavgnyigyhtslldsfigmiiislititlgmsleriipwniqsiiyisligiivaipgmptadfivrvysqidltticctaflayvgia igndweefkkigwrgiiitlivisgtylcsagiahltlvatgmv |
| Contig47_gene_100 | 588 | meitkrkttmwrlysfhgglflialsvfslngced |
| Contig47_gene_103 | 589 | mknhaisrkefkerridmelnskhytilliaiiiavimtymtgiknpiiiglcilaiivilanlyltklkk |
| Contig47_gene_116 | 590 | mfvedlinnisnfiesrlsdkilifiqeyflkagiftlasqiiailfisivftlilalmiallsfdilmaillaifiplilsfilfvfikser rreelensipdflrqlasmlrvgmslenalvdlsehgnglplydelrrvveirmgksfdesfrnmakrldskdlersfkiilnahksgglad visdvsddlramlilkrerkssvmnsimflvlasvvaapfalgmvgvyssfmielnrssaicqlaptvaliylihsilaglialimygdik kgvkfsipitalafflfylinvfglsffgf |
| Contig47_gene_123 | 591 | mkmeiikrigiqafvgcfvvmlvmvlgtyslgpqnvsfsgteiinaffgsivvgwafafsgliyekediplpiqvifqmviglgtlfavavyl gwmpislgipiitwiviaiafaavfwlgfylyytflardinkkielsndfd |

FIG. 9C-31

| | | |
|---|---|---|
| Contig47_gene_125 | 592 | mdkkmivsvafllliLavalvsvfdesnssesxvnlivysegpkslselvneiktqdyyegydnetvawmeslgnkkfyygdgiivimsatda sklpslyvtdvelfehfecnvlekrslgnveypkdvlyvknvkyigeeygnfsga |
| Contig47_gene_127 | 593 | mkgnilknideliksdfksafsnpivvlvligiiilpslyaviniyacwdpygntdevvfaianldngstfkgdyinignelvtefknnndfk wtfvseenlrtgvfngtyyagivipknlsenvvsiatdnpkqakleyvvnvktnpvaskltdsaanriymalnakivkiidlaayeklgelqk glasgsqqlssggyqlqsgsaqissgshqvssgakqvkdgkqqvstgaetvkskasdldegaqtvqegsnyinqkseelqqgsdevqaaadps lmpdgpvkdyvdasvelangsgelakgsqlangsvqlangsvqladgsvqladgsvqaladgsvslaagaqllssyavqalftass slgatanelgsvtginktlignylyapialereemfsvpdygsdiapfyivlsmvvgailtcvmlktgstkysalemyggklvlfvilsi lqacvtiigcnilgihivnlplfifscilvsvvfmilvysiisalgvqkaiavvllvlqisatggiypiqimhgffqtlysympmtygitlv reaglgtvwsnywpalailfaigiitvivallikvkadkashyfekrleesglf |
| Contig47_gene_147 | 594 | mldipkedpqvrrfiklvkeegysyekaleevgadyiderdweyfgfnqregdyrdfynlrhppkehhylsgsnssgssnkrqsskwddlk cymsvlgplliifaiaiilwgvfkgg |
| Contig47_gene_150 | 595 | mtlpgasiglaelfdpdwsllynysiwmaafgqiffslslgmgagftfasytkrdidlissglcvvlanslfenfaalgvfsilgymslesgv avsklvsqgttlifvaypkvfnilggvalilgpllffftvyvagvtsilssfevlsisisiqdkfafsrkkattalcivgglasmvfatsaggyll siadifvnnimvlfsvivqtilfawvfkaerlvdfnaksrflklgrwwlilvkyicpilltviwigelynlikmgstefvvilgvllailli fafiftirpaktdewfkteerik |
| Contig47_gene_151 | 596 | manenewgsnlafvlamigsavginiwrypyvlysnggafyipyliailvlaiplililleygvvynyksssftkaivkikpklefygwilpvv tfimtiyystilgwdgiyfilsffkgwgsdpntfltvsllqadsisgilnfipviaismifiwlliiwfishrnldeglgrvaryfvpnaffg yk |
| Contig47_gene_154 | 597 | mpnqmlkgsvryctenktlfliviqfliifecitnkvggimktsvilvllvilgyglkvtqdvinggtslpkislkellnfgvkgtivytfyl tiqaslllgisiamnfpefeleemilnlhetielffehdpisfilfilllliivygtiffmeialailadgetlkaafdfkrikrtvetigwk eyaedytkivaavvilvfingyfhsygwisiligvltdilaftveyrgigniyrgyqkingetaledtsn |
| Contig47_gene_157 | 598 | mvvqehicineekiqehslqlkslesdadfkdkrmdelyrkidkieekldvinnninnfllrnsqenkkmeirltkietdiqnqklesqrria rmgialtaitilliniyfkimh |
| Contig47_gene_163 | 599 | mreihkytpksvektvylnvflgaliisqgfyskttiggqlsen |
| Contig47_gene_165 | 600 | mkhrlnldnkdpnyillkeifkimdsrksksilasygfknlnrtiftfkiifismffgidipfilnelkskkelrkyfnisevltadqvykif seinseklikclnrilnsrnmvkrrgkktfivdatpvdvdinfhrnkktkehlekinlkwsysskgyyigfkatvvldydsmnpvcilvhsg apndaklfeeillenlqkrriirkgdtllifdkgyys |
| Contig47_gene_166 | 601 | mnealtklldlmqdynvilpnefvsmargismiesvattldpkidvmasiepivkevmeermnikeslsnkkgslvyyknmlktlppltnsv hkinngdmklrfeidridhivskfslvviiaallmsssitmtinrgpmlfdmpliavlgyivtfilgaiavanyiysr |
| Contig47_gene_172 | 602 | mttewlyqilnlldlstiisiliviiiaaaiiiklgekslirriekkyeinltahyllkdilkygiiiialailinligidlqniilslgivs ivigfaskdivsnfisgifvigdknvgvgetieidgrkgaitkvgfrnttmigmdnfkvtipnsvlstktyknfpmgedyrlrldvilphgfd ifeykqkmnteamekyeyinkdkepvilareineegskveisfwindykdrdpgkavileesnkliydylmdeknagilrivk |

FIG. 9C-32

| | | |
|---|---|---|
| Contig47_gene_174 | 603 | misketfdkdkanfkgtyrpllkeidnptllqidelhgiagalsgknqnihnnilillasigtitiifffiyfewdisafiipcvlimfiilg ihlvsnklnyhdkyleyrvlaeslrlqffisyagagekvididlpwfiehgvplvkevlgtldftelpqkreirdnwiihqkkyhegalqkskk kmrtqkivtyasitvtiatyiialifeylipastfnlngdiihlgiklamagmsaftlflgsyygkmslsekiddhermvelygiiedrirte getdeilsyaareflienstwyayqsknkpdlvv |
| Contig47_gene_179 | 604 | memnenvemitgdpkkainklawpliasmliiflnniidsiwvaglgpdplaaigyvtplfmvlvgfgngigagatslisryigaekrddann aaihsailsvvvslvltviallilleslklmgagsvlkyamdygviilflftapilippifggafraegdikratvpialvavinmildpifmy vfgwgisgaafatglapcfglcmmlywifikkdtylsynrkdfhnnlnmykdilvvgipasleqlimaalavtvnymiltvsgsvavaytag wriislglipaigvgtaaitvtgvaygakkyenirtacrysvklgiissiivcillfifadqiayifsyseasahllpliagfiqlmciifly vpfgatagnvfqglqkgttsfvlttfrefvlvlvfayllgfvfhmgetgiyygmliggfigsviayygyieyyvdrlikgkvkgsdi |
| Contig47_gene_181 | 605 | mdfistllaialamdafsvsltkgftlknltksqalwfgiffggfqalmpvlgwlggiqlewlittfapwvafilliilgsnmireslsgde edekdsdkfsfkeltllaiatsidafavgityavlkvdilpliimigvfaftiiglylgkkignyfgdkfeivggvilillgvkillgelg ilvi |
| Contig47_gene_185 | 606 | msstntavenkqereeaflkqtskpsfsktategfkqkdkgiknpatkynmpkkeetvdakakeapkreapkkeikrespkkevkkeapkkei kpnivkksdegssginlkkiglialilililiagiglnqmqnttdevmnytdgiinftysgnwsvynntnadsnmtdlafktdktligf ttiqsdeityekilsdvndtahslngeileygevnvggvpaqeiistqdgqysrylcilhdgvyycfvannaksdnqnltslnttelqnmin sisfkdvvagdtanldtsyqessygeesydnynyedtsny |
| Contig47_gene_187 | 607 | mifaaifavgillrdkivhklnffvnpqnylpeeeiqtlkqvyylililivccilnfffdnniilpnspefyvfnsfldiivsvyiaiiyd gskkskillifllipipsiafllfgeslieywdfvripallyimkifydkfhiytdkynleksillifsivfisfiitlvaenedplnalvmvs naftskgytilgestigkidsiflvwggyiisgaatatltaailikhfnakiekfdekfeeleklise |
| Contig47_gene_190 | 608 | mylefwiilaliilligelltggfyllsiglgslaaaifnyfqfsitiqivafilvtvifiilsrplfnrlnrntidkksnterlginqeame digqknigaisikgevwkaisdeeiskgeevkiigidgvklkvekl |
| Contig47_gene_191 | 609 | mmdliyilililiailiayksikilirpyekgvverlgkynrtverglnivipfietirkvdlreqvvdvppqevitkdntvvvdcvifcevid afnavynvvnfyqaitklaqtnlrniigdleldqtltsremintelretldvatdkwgtkvvrveiqrieppkdiveamskqmkaermkrati lesegykeseikkaegdkqskilaaqaeeaikqvadankyqeiaiaegkarateitynaihagnptndliaikylealeniadgratkiflp tevsgilgsvggiaelfkddpealekfesikvlenaketadne |
| Contig47_gene_192 | 610 | mggekmakmnavilgfiiltlvvylffgryefwgllivgfivgyiahegilgmwnaalagafgtiisailfiilvtiggtammgflgglagft vsgitslidivftiikymivmgitgavggalsgeke |
| Contig47_gene_193 | 611 | mvdaekakqpkerknknsnlpdidfkalifgaaayaffplvayqynldilmvfaaigplyigytaktelksiilgivgatpllylafsgmlgs ygsgemadiimtvgilglgalmgyfggylyrdrqrnkakaggivvedtpkkekqfedtgsvkknvanlflpksrrkk |
| Contig47_gene_209 | 612 | maigvkeiritdtisvllplliyalimglalflakpikfigkkqskvaegamvlfigvliaklaissgqsidilifnvgpsliqligdigtli alpvaligfrrevigmassicrepnlgviidkygfkspetrgvlaifvigsiigtpfisflssicislipyhpyafamasgigsasmnaaal vplvhmypamatqleafagcsnilsfclgiymcifislplaeklykwlspiigkgegrtiddeyaiegvkddkyatsedlssgkierwvtflv lfsiigtvgnfigyhtplldvfigmlliisitligmclerilpwdipsiliyisllgifllailpgvptsdiiityvsqielttictaflayvgia igndweefkkigwkgiliailvisgtylgsasianlvlfvtgmi |

FIG. 9C-33

| | | |
|---|---|---|
| Contig47_gene_212 | 613 | mkhrlnldnkdpnyillkeifkimdsrksksilasygfknlnrtiftfkiifismffgidipfiilnelkskkelrkyfnisevltadqvykif seinseklikclnrilnsrnmvkrrgkktfivdatpvdvdinfhrnkktkehlekinlkwsysskgyyigfkatvvldydsmnpvcilvhsg apndaklfeeilenlgkrriirkgatlifdkgyysyknyqigiskykiipfifpkekfsrtlrlddiiltyplavfnktkrimkekrlynslkme lmkkidswekfkpirgkiedffkllkgginmreihkytpksvektvylnvflgaliisgfysktaigqlsen |
| Contig47_gene_219 | 614 | mfvislipyltifvanqpnsllseslygldfilvdiilfimsrylikinenseyldknailiipfifliigfliigflcyppiaisivcli tivrsilysik |
| Contig47_gene_220 | 615 | mkmenlmetnrleafydaiiaivtvlvlelpqpetatiagilalkvsyftylvsflvcqslaispldicsceкn |
| Contig47_gene_226 | 616 | msiiaifIgliviafplgliaasdiglsvllsifillngiseveynttkglIntiiglimlvvsglIifnpsifsfitaitylagifli iiglvivgnrenkykfwmgilgillgviyililgtyihnsfvlgsligiwlvatgilnllsdgy |
| Contig47_gene_234 | 617 | mnanpkillyilmisalgintplsivgiiisgiaeyfntsiaisglyvssfttiaicglfipvlfsknyrkrtfvsiltvfaisniaiiftks iyiasffrilsaifypafisialtvceeiapkgeeqdyitkillgisigsivglpittgtlifnygvamswifainlisliiiiffpkikg kaksyempfsslksketllatigimmnpigasivynyqpyflqvvshvytyklsifliyglfsifgtwlggkliakrdkatilifqlicggv fvllylfanylipvllilifgildgmynlIgiyiessvipdspelangvflsilnggialgiaiggflvdgfgimsififgalflilafiil yyiigimkmplkys |
| Contig47_gene_235 | 618 | mningdlmnkkitvdilmfiaiivefslspiliheivgvgllfliahlkynkryfktigkgkynlkrtlnliniglIasllitisgifss qkslkgmkignhkishihksssylv |
| Contig47_gene_246 | 619 | mgpdfliisifkggaeslntsmniffttdliiiiafipslyiaskivkdrpfssyssrggwnfrlyfkalaipvilyilyilgaesllgsegtsh fsiaflavllisvplgciaeeyifrgiimqtlgswigiplaivigaiiftlghgydalglletlvlgiayffawktngieissalhtannf sigIfimlgleasnssfqlydkiggivyllilciimyvvgkktdwfgeipedsgmigllnf |
| Contig47_gene_248 | 620 | maglisgivalftswlgvsgtvigsvfssflyqflssysaekyeervgegtsrkprnigseivyifpivvivievifilscmhyyfdkifdi leygifqnnlfrlmgligliaIgvyplIsstniekingeivlvagiylfirgmvdindltmqvhnmffadfdffialivvlalvfvifnvlrns tqeyfnkedgdydavndeftqkrfskprrkskarkidtssfhkgqeykehylnsdfndkghnqspnpdsnmddyhnddlnnygtpqedlpiye eeiiylhnpedpnnpikkrilkrvnpdshyddcdetyiiddakndnf |
| Contig47_gene_250 | 621 | mkkpgilnkitiidililiiciigavgfavyhmvdddstkasatsfdystnnkmletymnyykdgkivtssligtksntgekiemngtvlwlgd nqndkvnieinndgkpilagfykdtpnadvfieqisletngdsyanitdfvvspkeiknlkeiiskipndteyeistsiaidldldsvtaqkla nalnknkpcilvknsgtvilevnranqtdfeiadnvlgdfkgqtseigiriynstaqdsidiqnafnvlsiantsh |
| Contig47_gene_251 | 622 | mefienqwnsyfkglypserflsivnkskilkeeifsplivlvtflfillatdpvprdlqttiiiaflsffigaiifprfilnnqlnqlnd etntdnkesktdkskqiplfnsydvysigfclsligivflfisiasvgglpilkssIrysIkpaftmpvflipgilmashylngyknneis rsqtrfrflvltaigigtvltlgyrtpiiailImmiiigyygkliawrtevtvtptllgqmlvdfgklgvavemcllgflgtgykivkitensfyia lyglIltysivgvetgildigilayffisafiyfavilkdkgiriy |
| Contig47_gene_252 | 623 | maieevrnleviaskdtiihnlegrvkliailIIivfcvfsdrlivplvleifllivmylaelsfkdsfkriallpfggfviafqpfihpgn iiwqgpypwlfitdtgInwtvIlfarlivcItaivilsstspmqevvqsfrkIgmprdlamiltimvrflfifvdelrdirqsmksrnfdpfn kkipykwrvkqvgysiammflkayekgetiylsmasrcfsdnsrlyhaktligkheyiflacvigivivlevlfysqnldylgvslsl |

FIG. 9C-34

| | | |
|---|---|---|
| Contig47_gene_254 | 624 | miialyfagkwakanldekripllavlaagifaimsmnmpipfgtsghmvggalvaivfmapeaavlvftavlliqalffgdggitalganvf nmaivggcvglytykglngliigkypsiflgawlatlvaavvcalemaiagtfplsvgvasmalyhafigliegvltvivifalekyrpdllaw nre |
| Contig47_gene_256 | 625 | manlkiglagnpnvgkttlfnnltglnqhvgnwpgktvaqakgsykhsgnevevidlpgnyalsahsieeivsrdfivdedsdvivnlidaan iernlyltvqmmelganlvvalnmnkyaqdkgytinadklsellgvpvveieansdigkeqllktieqaaanpvdsskklvynnelkehlael gavieedknlldvpsswiaikllendeiveekiegsskrnnivnetqkvkdhlkgifgegseevianaryafidglikesltkpdhlkttise kidrivtnrilgfpiflvimyamfeivftgapfqdlideffgilgdaiigslgetmlssflvngliggvglvflpqiillfliisfledc gylaraafvmdklmhkfvglhgkafipmllgigcgvpgimatrmenekdrlitmlivpfmscsarmpvylllvgaffaaneslvifslllg ilvavivafilrkttfkemdapfvmelpdykiptirgliemhtlekswgfikkagtiilvasiviwmlsyfpagveygsadsaigtigqviapv faplgfgewqpavallfglvakevvvgtfsslfgvaeegaeiaaamhgiftpltayvfmvfvllyipcfaalgaikqetggwkypllmagltl vvayvvafivymiglglglg |
| Contig47_gene_258 | 626 | mvdrheivdkmyenkhtllfvggiataivgakilksqttkdyaakgmakvltcksdleesiqdikdnaediqtdakaaqkeaicvdvteeee |
| Contig47_gene_265 | 627 | mnnqdydtgissevftvksniklidifnlilekkaravmdlfdsltnketihnessiiiigtyftgiaiakylsyngfknitivdiyphlegf idsnlgdpidvnksskgkfkeniefssdiglirsadvvidtt |
| Contig47_gene_271 | 628 | mffilfalfilylpkirhendyssiskelpyalrqlstelragkslfdaldsivdsdygvlsrefsrvleeikygetsenaflnlekrvnska lsrviyeilasirigrgscpiqiniiaedvnfdmrmklkeyseklnafimiytlflailapviiltmllaasvvigdivpssllfilyglffpm iivflafaikklepkl |
| Contig47_gene_275 | 629 | mfdllaacfigiaigtgtgmvpgihvntagaimfassgfllsflspeflcivmvsmsiahaliefvpsmllgvpeegtassilpghrmvlegr skeairivsvggfgaivvilmlpifavalpflqdlskpytwmiltvvsilmiyklsngrlafmwsillfvlsgilgwimlgtpisssgislmc tfsglfgistilfslndsssiphqnkyydfvidkdtiksifaggtagailgflpgfpaggsiiaqgvcgtsadgddtknfllansglntsdt lfsliaiylignprsgiavymsyliseftlshlmiftfaslivssisliiclklgdgfsnlmggvdyrkslsisvillmlviylifaiiyegpi lyltlalitstamglliphylgvskshlmgvlilpaiiiymqmfm |
| Contig47_gene_281 | 630 | mttifyfalsqtfitqlglqspqigllyvfglifgpfgalgaslsnvaidvyhgytfvqilpsaiisfgvsllayklwysgfksdeytkprld tiyhlclflasiiicgmiysvghgnlayilispdieesiilpsflnftnvafimgiagiwlfkrtnlietpkkserrinknlyrlifsllmvm tivsfifiirnsdnltiitgllivvalmyaymtkpfiheigevnensiiakivrnfiiitlilgffgglvsiasfdyvetsitlniylhlmpi lvisdiiiilffipgiiilkyigdnvvkpitsfseiegfikedekieaeglikvyseyvneqneigtlarsytelinhnnyieniqkiegek ertnaeldiatniqaaalpteaiktdafivngyskpakevggdffdyyelddgnlaivigdasgkgvpaalvamitqvvikqtlinnhdpsev lfslnnqlcvnnpesmfitlwlgiynktnkkltfsnaghnpplikengkfkyldiesgivlgimedfqyedeeitidgelvtytgdgitdannn dgemygedrlleffnkfksdkdpilpllkdindftkdtegfddmtllylkvnd |
| Contig47_gene_284 | 631 | msknriewidlvralailtvlyihatdgiyiissdlipywtpfsrvfqfislfigrigvpffimitgyllldrtyddervkkfwnksckglvi vtiiwsliyavsiqlvayssiqvntieagnlffshmwympmiigmylsmpfvanalknfdprtinqativfsclafllpfisivcemqglqnv niqyclgfsggvygiyilgwlvkkglfkkyssnslrllaivsfiicvlfqwyafsidfsflwyefpfiltgsfalfelcsrrekvrgfrgv eflakysfavflihnlfrliilpmvvlpytepvkailwlliitsyaaaviiyripkfgkfilymr |

FIG. 9C-35

| | | |
|---|---|---|
| Contig47_gene_286 | 632 | mnylnqnyatvfmngndflliiasliimififgygsvitkdvirggkklpkiyikectiygikcvivaliysavgtlvmvdlshrflpefele haltditgtlqmftannpiligeyvvisililtyifvffmeislarladggkllesfnllaikrcidtigwkkytidytkllaitiltylqyg fqflgffdyitdlifgllvfiiqfigigqiykiykikkysnldrptkksv |
| Contig47_gene_287 | 633 | mleliienlletiasiivfliplgigkyimnkikkheskftnnrlInpaeympkeevetlkqvsylivlflififfiysfwpmanmkffsfl eivlmvyialnidysnwknkvlfflvpygsiawflfeeltnsifdifhmiillyfmkvyyekfreytetngligitillftiifisfiltmi vegvspidsiamvsnaftsngyavlgssfggklnsillvwsgyilsgvgtatmtvallskhfnkrikenektneaqvaelkemiernneeike ilkennlekkteeelekkiiep |
| Contig47_gene_294 | 634 | mleslrpfltkilepiasrlninpnivtiispflalisayffatgnliggalfillsgfldvvdgavaryhnrsspfgafldstmdrfadaii figilfggycnwfvgvlaihsaitvsyvkaraesggvecntgiaeravrlililmvgaviafifnsdiiftyflyjlvvlsyftvgqrvyhvwk elnkkkipqrrl |
| Contig47_gene_298 | 635 | msfcpncgverkegshfchhcgydyreanssgmgssssssdsqvnqpsfnsqvnqsstynvptkqnphnfakitgyilsflipvfaivigiyl ilskneevhkhgiiiigisivvqilsmifmmg |
| Contig47_gene_300 | 636 | mitvvleipmavdgswgallldikiefivyavsfivcfnfwnynnnvfsmvnkidhkviwsigiamffislpylttfvalnpdaflpsflyg ldfiivailtiftinalknsdkanialqialadnqpyvttivfvifgmivgyfiyplaiviaclfsiitlwlisyykhg |
| Contig47_gene_301 | 637 | mntnrfetffdaiiaiiitvlvlklsqpaaptvpaflalnarfityaicylalfiiwydnhnlfqvveeinntvliiyaiqmfaisllpyfat wvalnvnsiaaetmfgidflalililyvlsiyavyradpyncgisknnfrkiycyipliivligifnklyslysrniclhsdctllaflfkts kt |
| Contig47_gene_302 | 638 | mrdcsncnreesclIqkvagiimvfgslyyilaelisagffndslintylfhtiselgvpvansplsflmnsafiligitlllgyfakfrdfii kykliisilavitalgviivgfiihagnpltdgyhslgavmailggnvmlilvsramaefesyqkitfillgifivfwimffnleslympvfe rlsvytliiwnfmtgfylykns |
| Contig47_gene_307 | 639 | mkcpvcgcenpdgykfchdcgnplimpdydemndypsfdskkliiiigyiiailfgwgtfilsaifgsygfigflffpgfmlnskdsnirk hayiqlaimivgilatflvlfr |
| Contig47_gene_310 | 640 | micpecgaenqdsakfckqcgtslnpvatmkktnsdesrpiksgifnennsspssfeakgsggdnknliiicltviicavliaggliflsngs nngndssdvgnsislpdnsvnqtddsqnqtdtepapkkssvsdmkilsgsfttgssIsdktwcsvvyekyagedvkisvlysrdgsdinggk ivpknvgsdgtvsvpsadafkyypdchalvtiydsngnvldtqevimsaksgtqtf |
| Contig47_gene_316 | 641 | mnygeelsdfwkqckrvlkvakkpdreeffdfskvtaigialigvfvivlfgqllgl |
| Contig47_gene_328 | 642 | mgkrgymgnlyetvrggtpravgivpfililsifmpsgfnnlvlvmglcaliddiigrktianlpieigqlargigmlcviglgypimgvssil vvlliqpmniadmqpgtaaattiimsfftllaviimqvgpvleihpyyyplivtclaycpldfagkimmgevgnhtfaislgicfyalggf igtlilfivttgliaylrrynlsrflinklhipnptfgdlfmdvltgggdlfrkillksnqydvdneililalgfrrllynpyspnlekvvq kdsrtkradlrrfy |

FIG. 9C-36

| | | |
|---|---|---|
| Contig47_gene_331 | 643 | mikqtlglnvedkkyylkiiieavligifsgfivslyrlgidhsesilsyilkyiqgdltlivlwfvilaimglitallmkwdpdslgsgipq vmgevkgyfdvtwwktliakfiggtltalgglslgregpsvqlgamaakgvskylpnsktdekrllvcgsgaglaatfsaplagfiftleein kgfdrsivlvglvsavvavlvsnvffgqspifpftslnlpleyfwllivlgiaigilgyinvgmikaaemwdklsflpleikfiivtgi vglflpevlgggysmmhlielslpplsvlivlligkyllllcfgssapggifypvlvigayigaifsaivipifginplyaykfimismaam fassvrtpitavvliaemtgvtnsivamivvvilayiiptildndpiyetllmrllkknkgidfdktksvleeyvvpmdcaligtkiwelpip ksamvvsvvrsgntlipdenlelkyadelfiimqntypednnkieslliynnwkee |
| Contig47_gene_338 | 644 | mkealminwgyvllfilgaisykrksldmlgalimifmgitiifsagvswfilivlffilsimatrfskpykkeigqyektrtaknvisngl vaflmaafgsyylplaggfigavatatadtlaseigvlqeprlitsfkkvpagtdgaisilgtsaaivgagiigiasfllgimpdpliaikis visgtvgcfidsilgavlerrnfinnehvnllatisgaligilsvm |
| Contig47_gene_365 | 645 | mkhrlnldnkdpnyillkeifkimdsrksksilasygfknlnrtiftfkiifismffgidipfilnelkskkelrkyfniseultadqvykif seinseklikclnrilnsrnmvkrrgkktfivdatpvdvdinfhrnktkehlekinlkwsysskgyyigfkatvvldydsmnpvcilvhsg apndaklfeeilenlqkrriirkgdtliifdkgyysyknyqigiskykylpfifpkekfsrtlddiltyllavfnktkrimkekrlynslkme lmkkidswekfkpirgkiedffkillkgglnmreihkytpksvektvlnvflgalliisggfysktaiqqlsen |
| Contig47_gene_366 | 646 | mlwtdfivlaivyiyvvaifilsekvlksrpevsrkflhimvgnmifampffsdpwimllfitlpvtvalffiteyspiqiensvtesghalg llfyallwsillfvypimldpnylwivamaivplvygdgfaalvggkwgtikyhvfggektvvgslamlsvtavlsvfvwfyssigytlpel nlwyillisavatlcealsyggvdnltvpavtsvlyyivatvl |
| Contig47_gene_371 | 647 | mnikelfieslkdnkkliiglyaffiivfiaawiitgpkmqaiasnvtamngpggaqssaielfihnelggiltylasvffgiaaivllgyna lnlgsigqlfnhfmpnggilylyliphgifeitatvlgsaagillfiwrfikafrskdtngasdafemtkktligsivlmviatillia apieayfstafsefimgflglr |
| Contig47_gene_385 | 648 | mkylfllfgglddiyllltilfgilnvmpmffeeksrpitrldtisgfwimslfylfvililyiggvyidwpfyliviivllvpltvy syfhahkilihertiqmdninedliniahlsdvhfgstrhdkiirdlsdklkelsdycdllalisgdivdgssaieeddflplkdvnmpivftpg nhdsyldiedvfgacrnagiivlddegmefgnlnifgmtfifgmtrkfeefevvstgvlgdfvkedkvnliifhvpknwedfsklgfdiqlsg hthggqfhpltwicdllwynrglfkaniggkdrylhvttgvgsmdypfrwgtdseivvlkrknd |
| Contig47_gene_388 | 649 | mlnliliiliallilfissllyngirilltvekekaearylkitllkipiftkdssedkateseeekeedgeeeeskdkglmekyneikpi lkeliksskelkkylkdilksidikkleghliglsdsfttvkiaswiwsigaivnskpvsltvdprfteiitdfegglelkinilkilifys lilvskkdireliklkiviaykkakdekenekensneelykkekdteikenskeelykkekdteikenskeeldkkeeldkkee ket |
| Contig47_gene_393 | 650 | mddetnngwnsstsfilvmvgsiialagiwrfsyliyenggsflipyilaivimvipllvleefgvgfkykaslprifyniksefeivawfi lflifivlicytcimswdliyivlislfkgwgnnpsvffttllhstsnpyglltylvpigliliwaliyfisrreinrgislvtkfslalt fvlviilsvfalqlpgsrtglmaifnpnweylldyniwltafglifsyglaygiastyssylpedsklidsawvivlislifeilmsvlifa llghmalgknmpitslvsdsfslifvvfpnvfnvmgswatiigplffmvifigglgalfalieplanaicekfiwtkdraiktlvlaglfasf ifatgmgeyflrivdgfiitqfai:lvvlveihvfgwlfldlddirnvlnnnsriklgkywwylikfaipillliviwilgvynliitgdrqsllv qsilasiiivplaltvapfngeyslgsitggynyfrdsgddeeaksnskpdlksrftsrftskdndvdngtegyeektyvektiddyegydg vvaitdeeensslksrfswdkfkksngknvlnnvdlsakefdppsddydydyetyklv |

FIG. 9C-37

| | | |
|---|---|---|
| Contig47_gene_394 | 651 | mansngsewdsniafillamigsavglgniwrfpnvlyshggsfmipyivslfllgisfvlveyavgyrfkssllkvlysvksklepvawfia<br>livflittyyicvvgwdliyvlsftkawgsnpdlffssivlqstdsiegllhivpmvfisvlalwavawyiiqkdlndgigkvskllipll<br>iivvtivlfsltlpgasigytgiftpdwsaltdlnvwlaafgqivfslslgmsialtyasylpegskltdnalivafsnsgfeifnsigifsi<br>lgfmtlntgipfdqlvtegtglafvfpkvfnimgpwatiigplfflcilfagvtsvmallevvcysisekfnfsrrksativcligfivsvi<br>fttsagsmilgifdaflnniallfavlleciifgwiynfdnlietlnnnsnikvgkvwknvikfilpicic |
| Contig47_gene_395 | 652 | mnldsnvktglivaisilifivsllfitsaptgvdnsarfgiltllpplialalafitketilsfvgvfvgefmvsvsdlniissavnafla<br>mggiiscmadpwnagivlqcllggvigliltkmggakaladalakradtprkaglitefglcvfddyanslivgpimrpvmdklkvsrek<br>lafvvdataapvagialistwigleisllitqgfesigmnvsgfgiflqtipfrfynlilifivisavtlyefgpmkeaekrararkadepvk<br>sleatsfddvkpvegiklswwnaiipiavlligaliafywsgyttllggedqalihlmktsplsfngifealsasdasvalfgaallasivai<br>vmavlqkiltieealsewiggmktivitgvilllawslggvigdigtadylvgilkdtipvfilptlifilgalisfatgtsygtmsilmplt<br>iplawavnpdmgfvivctsgvltgaifgdhcspisdttilssmgtscdhidhvrtgiyyaifvasisliffgyipagfgipwyisipvaivvdv<br>slglrr |
| Contig47_gene_408 | 653 | mekqqvktilksvviiailllivfglraqsvdiggvpnelkshyvdenglpyfsemdsyfnyrmtenymdhgyfgdtkvngtgwdmhsyfpsg<br>ravgdyqpmilayvtsflygiinmfqemsllevafwtgaivsslaviptyiftrritndygaiaaslivvlgpnyishtfagffdtdmfnitlp<br>lfflilffvealktdklsyriifsllavasialyslswtgymfyvavmvlvmivffvlcfyfnieilepfknygnklewlinqkelfatlivlv<br>vgliiiavgvggiiegitgltgftlqagaadvwpnvlisvaemqipnlvtgglvgsflantggvvngvvgivclfgvliviytfvqrlfr<br>lnsvkvkgdtakphkskrkatsvrteqkrfsvslkdigsfgstdeinkskrhtvlylslffwivssaiavtgqtrfiqvlvvpmgicagifv<br>gyavdvyvknnvdndkvllliaviasililalpitqiaygldnamtiglvvlvillaisaiviyakksikdsdvsikkalvvlitlalvsptvc<br>gafqttaatvpgssdpmwfamdyvkenstndtviiswwdfgylfqvasdhptsfdggsqtgdraywvgksltttsdyaqskgilqmlattgsna<br>smllseytgsnvtavhaldetlgksrseaqkiltskynlltndqakavvkqshpsnpnnvsfvlssdmigkagwwsyfgswnfdtlnstnyqyy<br>mandyvpikqntggniltilnesgiiyqavvnrgkngtnettaqmetiwdnnrskidlngteynplkasnliciensyltvnktlnkdgnytly<br>llgsgddytailmdnnlkdsvftrlfllggiggdtfelsnmqdgvswtlrdgssnsddagsq |
| Contig47_gene_420 | 654 | miiigglknmetikenswvplivvalasfivaldatfmnvsisqvvvdlntdvstiqsimsfytliitaafmllsaklqdivdkklifligta<br>lygvgtftasisssagmlfvgwaaiegvagalmmpatvsiisgtysgekrtvalaivgvmgavaaavgplfggvmttflswrygfaveliivf<br>vilifrnsiphfeptesrsdldisgaiisfiglvllvigilslskdfttsigiivvglialvafayfeirrkrngkvplldmelfkdrnlrvg<br>tiilllsylamgglfavslflqsvlqlnafntgvttlpltlgllifavlapsltekishkkimaigclmisyqfrldttlwtllp<br>gllvlgaglgfimalctdislsnipaesqnnasgvnstgtslgesmgtavigilllgvmggistavdtyapdhsgdeqfqlevanyfqkvat<br>iddlkqdstlvdvaniiqntmafvmqvtalimgvvflltlrlkdnkikq |
| Contig47_gene_421 | 655 | mepnkvsgilsillgllifilfplvssglvsimigvsllfgiasiltefsalniiiglailifgllfifnidalsfligfgfyiigilmilig<br>vagifagegvskiasllililgvialglggfsltqpifaavligvalitqgvrlyvapkn |
| Contig47_gene_422 | 656 | mgvnmeimeiikdsflfpsknlgtfsiyvvlsvlvatffggifsyllgfigseyilliggltlvfamligwvmsgyeisiiksgidldevpe<br>fkwwdnfitgflnfivaivyfiipafivgvvgylinindklmavaqeisslypniflltsspdiafealsqaiielivplailivalivfvif<br>lflqsmaearlantgslsealnifeaakdikrigvrkvlilvflvfliigvigmvtsvifnyvptlsilsilispylvffaqratgllysdia |

FIG. 9C-38

| | | |
|---|---|---|
| Contig47_gene_424 | 657 | meiikgkeipkkslkrslivfignmigiylisilglgveisqtgdiflvlflgivnailwpiltriampflvlftfgigsliinglilqllap sfgieikgaamilaplgmaavttvlsslitindssyyrsvlndakknaknevkdypgvliveidglaynvlceavekgdmptlkkmiesedy nlrmwetdlssqtqasqagilhgmnegivafrwieksngnqmqcgisnvpelekrisdgngllvengasrsnlfsgdtdnviftfskimdf gklynkawyssvfsnpsnfarivslfladivreiwsqithsiknirprinrgiayiptraatnvfmreintstlligdmnvgdvdvaystylgyd eiahhsgvrdsdawialrqmdqqikhltdankysprdyqfviqsdhgqtngatftqryggtfedfvkslipedmtmfakmtsnddhfvgdytp farkdkkiekekeeakelsdsevilasgnlamiyltqwtnrlsyeelnsyfpelipglinneyvgfilvksqehgdlaigkngtyyldrdei dgenpllgfgdnivkhlkrtssfehtpdilvnsfydeeadevcafeelvgshggaggdqskpfilypsswnvsddeligaeniykllkenlae lkk |
| Contig47_gene_425 | 658 | meifkvvceliipilifgvlfavgkfihvrllnsksrilnpgeyfpdeeletlkqvyylvmmliffafilyimivqanevfaiavlqilvsvy valtldysylknkilffllvpfeaiiflvfndflmiwpiylmhilvyayfikvvyfdkfrkytetnglgitilllfaivfisfiitlfvegvep lnsavmvsnaftsngyailgnsgigkltslvlvwsgyiisgvtatltaaimmrhnqkrekelnkrldelesliknsnnke |
| Contig47_gene_428 | 659 | mdllfyvvlliggcfagfmagllgigggivitpiqyylltsigcdpktsltvtfatglavicvtminstrkhkqmnlivkqhlkpmmvfgfv gailgavisqyidvevlkilfgvicivstvflvlikspstsldniktdaglfysiafacglasgligpaggafiipifvaylrypintigtts alsiattlagvicyivlgwgvqglpdfslgyvnllgfvflititsiivsgyaanlskkinptklkalqvivisyiglqmmgvfdiilsii |
| Contig47_gene_431 | 660 | mnniayllailfetsatsllkvaegftkplptiasiilyilsfyslsncIktapigvayaiwsalgivltvigliafkqtpdwaailglil iiigvglnlfskmslh |
| Contig47_gene_433 | 661 | mkkflsvalkfqwktivfifaliiiiqtfvqmeiidlfgaaltgvkeqnvdllfksglymlmytvismiavyviisflttrvassksaytvrekif hilmnlpreeidkfkisglvtrstgmsseqgfivmileqlmlipvtfvaivyeialidgtyalfflgfigvlsaliifrmkqiveiffrakk tygkinllflskindiagripfnkgeyevefekacensydknviyiksqcylgpilmwglyvlvlvtlamvnsgytigfetdsvidsfiilvy vayfittlanipalidrwprayatsvrleevlniedkiiksntndnlkeieiveediageakgiwderkgisekftallkedkakvrismill tistlcmvyapkvagktvdllasnwnstndpaiyislalllvlysvgylfklppkrimgatgekvaydlrvklfdkldavgsdfiqenskglv lsrlnndvmnirefvsskfteiyaqilfivfvivlivmtdfrlsliylvilpvyavcfyvcdvksknyydghqmlgrlmsyferglsnrdsf hekgfkkmnqtvidyyvksknvtnfmvpvttllniskitvyiagiyflagneiqigtllavimggllitdpikklssmatietsfssikri faiidykndk |
| Contig47_gene_438 | 662 | mdllfyvvlliggcfagfmagllgigggivitpiqyylltsigcdpktsltvtfatglavicvtminstrkhkqnnlivkqhlkpmmvfgfv gailgavisqyidvevlkilfgvicivstvflvlikspstsldniktdaglfysiafacglasgligpaggafiipifvaylrypintigtts alsiattlagvicyivlgwgvqglpdfslgyvnllgfvflititsiivsgyaanlskkinptklkalqvivisyiglqmmgvfdiilsii |
| Contig49_gene_6 | 663 | mnlykdifylagfichqkpersfhishcqlpfcarccgiiisviasfilaqfvafpmnalafllfvpmivdglvqkytdyestnfrrfitgfl fgfayvvyfymfglnal |
| Contig49_gene_9 | 664 | mkilktwiekldiilsilivldisflasflldlnttyinfmllfdttlcwilivsfifkllnsddrkaymrenyldflasipmdlvllpfss lhisliniviivrflrlllfkesykyvkkfkatsfdkvvalfivivvgstfaleyfdpaipnlyyslwfvfqtittvgfgdvipespvggl ialgllmvgvlmfsiftasfaylfnekvfreenedfhekintvrenlaenkerveeirqstlststseeiaevkeklnkseeniknleeridyli dmiekke |

FIG. 9C-39

| | | |
|---|---|---|
| Contig49_gene_22 | 665 | msyqennasdkslqdkdmkakqrqdrivktsiigivvnlilvafkatigilvnsiaitldavnnltdalssiitiigaklagrapdkehpygy grieyfasviiaaivlwagitalmeswpkifnpdvtsyttvslvivavavkfilgryvknvgeeinsqalvasgsdaffdailsfstliaa lvsiffhislegilgviiisivliikasidmlketvdsmigervdsklsrdikeaicefpqvygayglslhnygpdsmegsvhievddsitalei hnltrlismkifnefsiiltvgiyarnddfkdirndlyeitskydevieihgflaypeeklitfdiivdfdadreevkdkildeikslhpdft ycmiddydlsd |
| Contig49_gene_28 | 666 | mnreerdrigtrasavaiignilltvlnisvglmsgsyalisegahtisdiatsviayvgfkigsrpadkehplghgraeaisgliivflsi vaieviqgafhklffggalevpdpiavvmafvgilvnlfmssyiirlgkkarspaivadgkhqrvdifaslaifiginvsqyypmldpiigi figaliartavivaidnlnnimgklpsdelikeirdvansvtdvcsahdikvnyfgsyatvalhvelppdmslreahkithrvqdkilenvdm vqavhvhpcpegvqydhsqlldeds |
| Contig49_gene_32 | 667 | mketlikefkdlkeetgqasvelilligsilvitiicgtyvfnvnskingqfnqtmtkarlflinkv |
| Contig49_gene_33 | 668 | msaneieifesgngmnrlpretvfeqikrnfvqlkdetsgqgaaeyillfggvivialagliiyrsyfsnntsglnatqdinsirdnmsnvl |
| Contig49_gene_34 | 669 | msdsldlftgvlltaiglvliygsliyrlidlvlilgvltlfglykllpaffmrllssrksssrnklskanvsqdsllkagieeinnfldge dnkensksvlrapressldapnqmtfeeymsksktdyatnyspkevkpifkdrdvdeskqvlrtkpvkeekskfklpsfkrnsskkpksrnfa frkdkdterspdklyftpnyenpmmvspkpkkksenklrlsdspkrskeiseealasvgttetvdnnasddsysympkemdelivpideidl dgpqeapiytlsqsentlynnviyddvdsdfyitpihaesnednspdeegdyegqdlylevepedtsygndlyietepednyygndlyiete pednyyddediyiesyeeeqsyedddgyitveasdddipiprpkeistpqslprptsiastnpiskkevgsnlsrphkkvstlprpsvssnlq rphkkaestdavsvkdeskaaeasiakpkpiakpkpvakpkpkeapksdelisskeeldqiiqdpkdntiqidpnnpeslpipklinsyvvcek giltsqeafeevashssqeilleaptikdmgerflssiadiktriivqefdladisyvllsslikkgveiktlpmvnsfnligddshaliis nsmdeddfeygavytdkpsidnikelfesswsiandldignlnese |
| Contig49_gene_39 | 670 | mdttvktvsihlvaavvaaiistaftlgwfgfknnvfafvigvvilyfigqyckafgeeisgfstwlwdgilpfgffwfilwtiltnyl |
| Contig49_gene_41 | 671 | mssvaglskyirtlpkakstflmiivlsfiigavlflvkpmslgsglenffyggafgfvvyglpaiitgatdqkwvstlkginlkmkhsmfla lvsmtmagvisiigtiignilhfdlfinsilfgiviafafnilviwsvtrirliksvlvaliqpllmigvlliitsflnnlesvfelgiftff kviiasavfllaiysfisisvespmkknlgfgaleilsffishmnegsksieelfdnageaidtlvgvcsfrkpdgdikalfispcvhpgplgd iggsnmptilanrfdsfamvahgpsthdfnpvssdeivkiessvrtalenmeysskasrfvryshkkanigtqffnngcvmlstfapsgsddi efavglatmiesqkeleidnpilvdchnsfnaekgvvlpgnpelfglldtikliekkdleheikvgcystdlggfgkhegigdsgiktmviev dggrtayvlfdsnmmelgyretifnavedleideievmttdthsvntlsagynpvgtvekekiieyvvresiieaiddletveagtrterienl ktfgpnnstelistissivsvskiaaplifimaiifviwiylf |
| Contig49_gene_75 | 672 | mkagvlvftgslvaidpsfypimllqlivigaimilyldevvskwgfgsgvglfiaagvaetiivgtfnflpasaasttasgilpafiqsiigg apnfqilipliativvfliavygesmrieipishgrvkghgrirgavgkyplkfiyasnmpviltsallvnvsliaslfqklgfpifgevsgg raisglalwlttpnsisvlftnplrvlfyaivflgccvlfswlwveisgslsakevakqlynsgiqipgfrsskrqlytimkkyipaltiigg lfvgilafiadltgalgggtgvlltvgivyklyeeiaqeqlmemhpmlrkflgnd |

FIG. 9C-40

| | | |
|---|---|---|
| Contig49_gene_77 | 673 | mayqgsfllgislqpvfdamnavlnplvqldptpnnpvltvfvisalislltvtaqkilvdqdkmnemqanskalqkelreaqksgdakqia kvgakqtdmmqdqsevmksfrpmivtmvpillifdwmwqsairslivvfppavyyctltpifhslgqmlyggnittipfgvgwlwwyfictf gmsqiirkfmgfkngf |
| Contig49_gene_83 | 674 | mafliitclflifffgsgkvlyqtgfgivvtddswhyglytffrvlgcfplgflalttpiakifhcletlkvpkivieigllmyntififl neidvmqkaqktrlgynsywnslqclgslvsnifrslekseltlqnslsdsrgydgelpvyippkee |
| Contig49_gene_84 | 675 | merttllilavicailfiaplvmysgleddgyfggaddaageaieesgfkpwfssiweppsgeiesllfalqaaigailigyffgywrgqk ee |
| Contig49_gene_85 | 676 | mhimegylpltwcliwfvvsfivvaygiyqikqivdetpdskallavsgafmfilsslklpsvtgscshpcgnglgaalfgpavtavlativl lfqaillahggltlganifsmqiigpfvawlvykacikanisstiaiffaaflgdlltyvatsfqlafafpapsfgsaltkflvifavtqvp laigegiltviiwdrlkaykpkllidklgvlapnea |
| Contig49_gene_101 | 677 | msvfdyichrrpersffykgrqfpvcarctgfyisgiasilifkyfplpntlttlaigilllipcaidgtsqlfemresnnvlrlitgllggv glimiyevvlnfvflnfiy |
| Contig49_gene_133 | 678 | mskfcpkcgcenldeasfclecgaslpsieevkersshgagtshgstfssnlneengfngetssfsqsnsnsneasnsskfknvineanpann dnqdyaicclvifvlllliaflcnf |
| Contig49_gene_153 | 679 | mipyyilpsplnvfnaawtlitngklfmhtsstlikvfsgiilasvvaiplgilgwyetldrlssliisilrppiswipfsilwfgigls savfvifigcvfsvlvytidgvkrtdnvlieeaqtlgannwdillkivlpstlpyivsglkvgvsialmctvsaemiassrglgymiltasql fqpgtvvvgmivigilgilfdygfrkagerifw |
| Contig49_gene_169 | 680 | msslisiptlplivialicgilsfistrlvmpwlligkleqaeiigkdihkssrpivaemggigigfliigifagiilfpvltfqlvvllvv llvgiigmvddlivlsskekllflflagiplwwvappnvgllymimipiavsitsnltnmlaglngiesglgvismtsltisciilgkydvai ismtmlgtllaflyynkypakvfpgdtgtlligatiaaiafigrvkliafivlpniidaalkfysagvmerqhnptqlnedgklvrpeqgf kslirlvlrkpvdektavmmiwgigiifgilgiilvallmpgvthdqtfaqfihlkdyfyylg |
| Contig49_gene_173 | 681 | mdskglinielffctliiivmiiivnfpilehsidsandmdensqgrflinsistsidqvnsnnegfskkiklpqsvdgnyytilvssneiile fnnkkgkakiqpinlvdsknrtlskaqlynggsyiikktltnnneshiynqssiiimqveg |
| Contig49_gene_191 | 682 | mnkyikkwtesslilkiigliigsvlgivpqykligilpqelfvtalkaiapllvfilvasalsrasegigsrfktvivlylfstflsamva vtgsylfpvgmhltdasdvaapggigevissmlkifanplqslsgqdylgilfwalviglclkkiasdstldvfsdladatslavrgiiqfa pigimglvfsavsesglsifigyglvlllvgciatvafvtdpiiaafalrrnpypvltclkesgitafftrssaanipvnmrlcerlgldk dfysisiplgstinmegaavtitvmtlavchtlgisvdlpttivlciistlaacgssgvaggslllipmacslfgipsdismqaiavgfiigv vqdscetalnssgdalfsataeyhdrvkrgedmnflgefakdkakq |
| Contig49_gene_201 | 683 | mikkvtnvideitdclflglkmtiisgiflliavifmifgidtpiylnpawgtviisgipmlllamtrlirekwvssalliaiamvasllgei faagevawimalgalledwtverakkglrnlinltpqtgrrivgdseevisvdeirigdvlrilpgesvpvdgeiikgsssldqsimtgeslp idkevgdevfcgtmnmygaidikatslgensslqklidlvkaadekqaptqriadkwatwlvpvalaiavawlvtgnieergvtvlvvfcpca lilatptaimaaigqatkygvliksgealetlgalntlvfdktgtltygnlavsdiislkddldemdvlrivasceklsehplakaivnyane akvdieepedfkmypgkgvvcknsyghicagnskflnennidfnigskddldvdslinhlkgegkasiivalngeilialigldvmredskam ieslhdlgtetvlltgdntetanyfasrlgikvygnllpqekldwierfkdegkkvcmigdgvndapalktadvsvamgsvgsdvaieaadi allgddigkipylkklsnstlftikaniiismtinavaivcsvlglinpvtgaivhnagsclvvlnaallydrkfddsikridtenvehshyh |

FIG. 9C-41

| | | |
|---|---|---|
| | | fhndgehshshegirlidEiktdngikhmhihkhalnrqsceayhn |
| Contig49_gene_205 | 684 | mdesankmnkfdvlgsmnlrtktllaiglsafilivvlvsffidptsittdwsimnqppslehlfgtdwmgrdmftrtikglglsvqigffa<br>silssiiavalaflssfnkyldsfvswlidvflsiphilllilisialgggafgvlvgvafthwtslarvlraeikriktsefvtiserlgks<br>kfwiarkqilplvisqvivgtilifphaimheasvtflgfglsphepaigiilsesmkylatgnwwlalfpglallilvllfdiagenikkml<br>dpasand |
| Contig49_gene_206 | 685 | mqflsfselfggtvlveqvfmypgiggaavsaglrsdvplllgivifsaifvycgnliadilynfvdpriregeeng |
| Contig49_gene_207 | 686 | mspinpvnayisnmvvspekiakleaywgvnqpiteklinwlgniitgdfgtsliyrtpvlqviaekftaslilmltswvisgilgfalgvla<br>gfkrdtwidrvvkvycyvlqsaptfwiallvvmvfsiylgwfpvsggvpigalsqdvsffdwlkhlilpaftlsilgvasialytrdklievm<br>ttriyflllpkakrgirmdld |
| Contig49_gene_217 | 687 | mknirqtlstigkmlsplkksipsiflififlllidvycnltlpsytadivdvgiqntdfnyiisvgtmmmtmvligvlatialsyfsskvsaa<br>ygrdlreisyekilkfsnfelnkisrssllitrntndvyqiqiflgilftillfapilgigsiikamelgtdllwiivvtfasvaillgiifir<br>tvpyfkvmqelidkingtsreilmgmpvikafirqdyeeerfektneefkevnlhvfktlflmipamtmilnvmivlilyfgaydaingkilt<br>gtiiafiqystqivisflmlggftimiprilvsgrrvgevlnteisisdgpidkidenptiefknvgysypgseketlkdisfklekgkttai<br>iggtgsgkstilnlipriqdvteggilvndknikeyklstlrerisytpqkailfggtvrsnmqvgkedatdeeiekalniaqvdfiesldde<br>vtqgasnfsggqkqrlsiarsimdkrdfylfddcfsaldmnteakvkenlkdlkesssililisqristimdadeiivldegkiildkgghdyly<br>kncdiykeivssqiersedliydneetasftidsssikkaagqk |
| Contig49_gene_218 | 688 | maprprippekptnvkeaiknifgllmgyklklsitvicgilstvfsvispllglattaifdggjnsqnmnleyiinllitvvilyliisavf<br>sylqsyflleittdisynlrkeliekithlsmgemdkntrgdilsritndvdslqtglnqtfnqllsgvitivgvtimmlsiniwltlativl<br>ipiaflliitfvtkhsqdyytkqltyrgslngieesftgheliirsynqeeqsmetfrednenwyeqewkskfysslsaplmnfisnfqyviia<br>vlgavfvlqnaiavgdilafiqysknftttpiqqitrvmnmvqtamaaserifgfleieneenpskekiekindsitfenvtfgytkdepvikn<br>ltftakkgekiaivgetgagkttivkllmrfydvdddgeikidgvninsydkhsvrslvgmvlqdtwlfndtiynnikygkldateeeisask<br>eahadhfirqipegyqselnedvdnishgqkqlltiartiisnkqliildeatssvdtrtekiigkamdklmekrtsfviahrlstvrdadki<br>iviedgriieeggsheelleqkgyyyntlntqrreniv |
| Contig49_gene_225 | 689 | mifvinlvplslsvvtflslflsggftilfgadlaflvlsfgqheftphfgpiallaivtalaslkvmegsgvdisrlknivyvflialtvfg<br>gamhrsflllwfiglfigytiisksfrqksiltirrilmfflaalvafgllelvsrilsmevfspllrisrlaqnslaslklvigntqlighd<br>passywsdstgfadgyislpmqfilmfglpfllmfglpflffgllvtkkdtidymlpgifgyaydfgyltfvilllvlftiiigilvlreyrlkreknn<br>kkylgkevlligsltfiagaiglflfnrtingmalltflflgslvlahvvtirrdsnevlsgqi |

FIG. 9C-42

| | | |
|---|---|---|
| Contig49_gene_227 | 690 | meekkiestdvevneskdlnldstvenneidkteeldasseideneelgtssevretividtasevveadvvsetidssesvkdeeedsnpld veyveedgkrrikpmldyeslsntseievppllidqvigheesvetikkaakqrrnvlligdpgvgksmlakgmaellppevledvlvypnge dsnyplirtvpagqgkkivkankanaksgdekkmmitmfataaifvlgilyqrifealiaallvifismqikpkannmspkllvnngdkrfap fmdatgahagallgdvrhdpyqsgglgtpahervesgmihkahkgvlyideigtmsmktqqellsamqekkyaitgqsenssgamvrsqavpc dfvlvasgniqvlegmhiamrsrirgygygvfmkdymedteenrkklvqfvaqevkndgriphfatdaldeiileakrragrknaltlrlrel gglvrssgdvaieegadivtaehvvtakrfartleqqivdrsiiqrkeysvfhssggkigmvnglavmgdrsgivmpiaaemapansknegki ivtgklgeialdsvqnvsaiikkytqvdisnhdihvqflqsydgvegdsasvsitaavisavegipidqsialtgslsvrgdvmpiggataki eaaaeagikkvllpksnmedvmlekkyedmieivpietiedvleniliingskkeklinknernqwsshkqgly |
| Contig49_gene_231 | 691 | mssgltigllsliifgnienlilasggvvkaanplklaifslicvscwliigtvctqglqnygiyiefiggfaifvlglqsmieaaarg |
| Contig49_gene_232 | 692 | msfaeslkeykpflgllifgnienlvlaaggviegadpflvagasvcfviiwqfigvfgtksamkysrhiefiggfaifvlgiqsmlpliygl lg |
| Contig49_gene_242 | 693 | myltkfcpkcgeenedvaqfcsnyghdfkdvnqrmkeskrenssfplsgtkillcivllivliiaaflftggnadkpqnitmikentygftfv nrgvlfynyhldevlpicrmisramtlrqdstmqmthwlrsimiti |
| Contig49_gene_243 | 694 | mksiednasektkqklqkkgkkiddiseadideqietlekenkklkryqrildalqekmeidsgrvmgltdgifsivmtlliifgitlpsteil tdaglssfissilpnigvtlvsfillasfwiyhhefiklkclnlvylwlsmfylatvcfipfttligtypefrlstnifginillviiffli mlnyaskrgfldeeviekdkkyvhhtlyliilglaviinlldfsvnenfiylffvpliistirdvrfklknte |
| Contig49_gene_247 | 695 | mqekidlvslpkksfwklsipiliafcifdaiygivdmlwvsrisveafyaigvsipitslifsfgdsigggtnsmmnsrfigtgdyesayntli hgilianiiwlilvlclifaggilfkvddadsyillifdymvpmiifayvffilnnlfsetfgaegnshtptliligsnilnildpififdlnl gikgaayasvlsslitfsvlmflythgrtkiplsrkyfkfrsyilveifkvtfpnfiddaiwsftmsfinviligtmgeigpilysvsnkirs llnaptkgygrglmsvtghlfgaeqfdklkemykyvlkiavctslvimivffvrnwafglfsitgmdneifwiavggiimmtilpfstissk mldgfgkslysllititkvaieialislltqylkdgssvligiilseiissivyykflgylfdhfdkkyefkytvkaftikrkdkrekrreri rqnieekklrkeekkeefrqnieekklrkeekkeefrqnieekkmrkeekkeefrqnieekkarkeekkeefrggleerkekrkekid |
| Contig55_gene_5 | 696 | minrlrkdfgriiklliifllileviiffaitqtfggiilpdiktafaliialsilnallwptitylsirffivltigftflidgvllylislfi pgvsingialfsipllligllssmlsilsnliinidddytyyryilekemkvihrnipkkegflfleidglsyriikealdngdmptlkswidkgshr liswetdlsqtsssqagilhgnnnipafrwvekdhenriissngrtdskliekrisngkgllslngasrsnlfsgdakdhlltfsrfsdse sinsnswfylystpyviarilvlfifdmimellsrvrhlfkniqprlkwrglkyfvaragtnvvlreatttfligdvfagehnviyatymgyd eiahhsgiedfdsfyslrqidkqfkhienainnsnrdykivlsdhgsngpsfkqkfdislndllseflpenitvhsilhsnddhfskefsi nhlgsenlekldkrventkekldikidntkekldhridntkekldhridntkekldhridntkekldttkekldh ridntkeridsnldytkekintsfdgelintwdklikfknkssnkafldklrkkrtlinndepiidrinnvsedlsedlevnielskekitsd kaaqtivlssgnlgliyftdwsnrmsyeqiedafpglinqlashdgigfvmvksdiygtlvfsndnlfyleseeyvgenfldkfgkntvqklk rtdkfahvpdilvnseynmetnevyafeeligshggiggtqqypfilcpsnweseeifgaenvykffmkeinkswnqsknk |
| Contig55_gene_10 | 697 | msqarnlekdvssskayfkgenelsinsninetkfnemtdsdsnffgtrfilnlslillklilkkqmkvisqieiisnnqktskqfqyklllqkt l |

FIG 9C-43

| Contig55_gene_14 | 698 | mkkiylifpilagimfgstgifvrtltengidsttllflrfsialiymliaivltdkslikvskediplflicglciclglnlcynnsintvpl slaavllstapvfvvifayfifnekissakvisiilvligcilttglleesmipitsiglisgigsaifwaiytiasrksidrgkhtftilfy sliitivtipftnfgqiesfvlanpanniiflllhslisfalpyilitislnhldagtvvilssgepvaalvfgaivyneipsplmfcgiii tiialislsrkiemkse |
| --- | --- | --- |
| Contig55_gene_27 | 699 | mhllwfyvaivlaisdeihsrivwgyvrdfyivfggiisssldsvmetwivheglealfhmifvsivffslkigflaalihflldvshsivir hmpwlphralhfvieclffiavfgl |
| Contig55_gene_29 | 700 | mkhrlnldnkdpnyillkeiikimdsrksksilasygfknlnrtiftfkiifismflgidisfilnelkskkelrkyfnisevltadqvykif seinseklikclnrilnlrnmvkrrgkktfivdatpvdvdinfhrnkktkehlekinlkwsyssskgyyigfkatvvldydsmnpvcilvhsg apndaklfeeilenlqkrriirkgdtlifdkgyytyknyqigiskykyiipfifpkekfsrtrlddiltyplavfnktkrimkekrlynslkme lmkkidswekfkpirgkiedffkllkqglnmreihkytpksvektvylnvflgaliisqgfysktiqqlsen |
| Contig55_gene_41 | 701 | mttvvytvsnavlmlfyswynlyekgviseerfgrknynysf |
| Contig55_gene_43 | 702 | mrkeriksylgiifdllvildlililifislpiqgihlidyagfvrafdlticflllieffygiyksdakakyfkehfldliasipfdlivfalf gsssilnlarflrlvrvvrvfravnivkkyglekvirrthadkifiviavivviftillitlsghenisdsfyfvvitlttvgynegfnepl akfvtlflivgvlvfstitgvtssffidkmleegisvdenlhfinqklnfheremektrkelaeikkeleksnenseelkqeiselkelike nnk |

VACCINES AND VACCINE COMPONENTS FOR INHIBITION OF MICROBIAL CELLS

RELATED APPLICATIONS

This is a continuation application under 35 U.S.C. § 120 of U.S. patent application Ser. No. 12/678,976, entitled "Vaccines And Vaccine Components For Inhibition Of Microbial Cells," which has a filing date of Mar. 24, 2010, which is a 35 U.S.C. § 371 national phase application of International Application No. PCT/NZ2008/000249, which claims the benefit of U.S. Provisional Application No. 60/975,104, filed Sep. 25, 2007, U.S. Provisional Application No. 60/989,840, filed Nov. 22, 2007, and U.S. Provisional Application No. 60/989,841, filed Nov. 22, 2007, the contents of all of which are hereby incorporated herein by reference in their entirety.

INCORPORATION BY REFERENCE

The Sequence Listing submitted in an ASCII text file, in accordance with 37 C.F.R. § 1.821(c) and (e), is incorporated by herein by reference. The text file name is "218991-30006.txt", the date of creation of the text file is Nov. 21, 2016, and the size of the ASCII text file in bytes is 3,066,000.

FIELD OF THE INVENTION

The invention relates to components from microbial cells which are useful for antibody production, including peptides, polypeptides comprising these peptides, polynucleotides which encode these peptides or polypeptides, and antibodies directed to these peptides, polypeptides, or polynucleotides. The invention also relates to expression vectors and host cells for producing these peptides, polypeptides, polynucleotides, and antibodies. The invention further relates to methods and compositions, especially vaccine compositions, for detecting, targeting, and inhibiting microbial cells, especially methanogen cells, using one or more of the disclosed peptides, polypeptides, polynucleotides, antibodies, expression vectors, and host cells.

BACKGROUND OF THE INVENTION

In New Zealand, agricultural activity accounts for the majority of greenhouse gas emissions. Therefore, reducing agricultural emissions of greenhouse gases is important for meeting New Zealand's obligations under the Kyoto Protocol. The Protocol requires reduction of greenhouse gases to 1990 levels by the end of the first commitment period (2008-2012). To this end, agricultural sector groups and the New Zealand government established the Pastoral Greenhouse Gas Research Consortium (PGGRC) to identify means for reducing New Zealand's agricultural greenhouse gas emissions.

An important part of the PGGRC's activities has been research into reducing methane emissions from New Zealand's grazing ruminants. Mitigating methane emissions from ruminants is of commercial interest for two reasons. First, failure to meet commitments under the Kyoto Protocol will force the government to purchase carbon credits. This is currently estimated to cost $350 million. Second, methane production results in the loss of 8-12% of the gross energy produced in the rumen. This energy could be used, instead, to improve ruminant productivity.

Methane is produced in the rumen by microbes called methanogens which are part of the phylum Euryarchaeota within the kingdom Archaea. Most methanogens grow on $CO_2$ and $H_2$ as their sole energy source, but some can use acetate or methyl compounds for growth. Several different genera of methanogenic archaea exist in the rumen, but species of the genus *Methanobrevibacter*, especially *M. ruminantium*, and *M. smithii* are thought to be the predominant methanogens in New Zealand ruminants. *M. ruminantium* is currently the subject of a genome sequencing project funded by the PGGRC. The project is the first genome sequencing of a rumen methanogen and it aims to build a better understanding of the biology of *Methanobrevibacter* to discover targets for inhibition of methane formation.

Reducing methane production in the rumen requires the inhibition of methanogens or the inactivation of their methanogenesis pathway. A means of inhibiting methane production is to identify specific molecules that inhibit methanogen cells. This may be achieved, for example, by use of agents which target methanogens. In one approach, vaccines can be prepared to target microbial cells. Therefore, it would be useful to identify components, especially cell-surface components from microbial cells, including peptides and polypeptides, and related polynucleotides and antibodies, that can be used for anti-microbial vaccines.

SUMMARY OF THE INVENTION

The invention features isolated peptides, polypeptides, and polynucleotides of *M. ruminantium*, particularly cell-surface components of *M. ruminantium*, as well as expression vectors, host cells, and antibodies, and methods of use thereof, as described in detail herein.

The invention specifically features an isolated peptide comprising, for example, at least a fragment of one amino acid sequence selected from the group consisting of SEQ ID NO:1-702. In a particular aspect, the peptide comprises at least a fragment of an amino acid sequence of any one of SEQ ID NO:45-260 and 332-702. In a further aspect, the peptide comprises at least a fragment of an amino acid sequence of any one of SEQ ID NO:10-17. In another aspect, the peptide is a fragment, for example, comprising at least one amino acid sequence encompassing an extracellular domain of any one of SEQ ID NO:10-17, 45-260, and 332-702.

The invention specifically features an isolated polypeptide comprising, for example, at least one amino acid sequence selected from the group consisting of SEQ ID NO:1-702. In a particular aspect, the polypeptide comprises the amino acid sequence of any one of SEQ ID NO:45-260 and 332-702. In a further aspect, the polypeptide comprises the amino acid sequence of any one of SEQ ID NO:10-17. In another aspect, the polypeptide is a fragment, for example, comprising at least one amino acid sequence encompassing an extracellular domain of any one of SEQ ID NO:10-17, 45-260, and 332-702.

The invention additionally features an isolated polynucleotide comprising a coding sequence for at least one peptide. In one aspect, the polynucleotide comprises a coding sequence for at least a fragment of an amino acid sequence selected from the group consisting of SEQ ID NO:1-702. In a particular aspect, the polynucleotide comprises a coding sequence for at least a fragment of any one of SEQ ID NO:45-260 and 332-702. In a further aspect, the polynucleotide comprises a coding sequence for at least a fragment of any one of SEQ ID NO:10-17. In another aspect, the polynucleotide comprises a fragment of a coding sequence, for example, least one amino acid sequence encompassing an extracellular domain of any one of SEQ ID NO:10-17, 45-260, and 332-702.

The invention additionally features an isolated polynucleotide comprising a coding sequence for at least one polypeptide. In one aspect, the polynucleotide comprises a coding sequence for at least one amino acid sequence selected from the group consisting of SEQ ID NO:1-702. In a particular aspect, the polynucleotide comprises a coding sequence for any one of SEQ ID NO:45-260 and 332-702. In a further aspect, the polynucleotide comprises a coding sequence for any one of SEQ ID NO:10-17. In another aspect, the polynucleotide comprises a fragment of a coding sequence, for example, least one amino acid sequence encompassing an extracellular domain of any one of SEQ ID NO:10-17, 45-260, and 332-702.

In an additional aspect, the invention features an isolated polynucleotide comprising, for example, a nucleic acid sequence selected from the group consisting of SEQ ID NO:703-1373. In a particular aspect, the polynucleotide comprises the nucleic acid sequence of SEQ ID NO:703-710. In another aspect, the polynucleotide is a fragment or an oligonucleotide comprising, for example, the nucleic acid sequence encompassing an extracellular domain as encoded by any one of SEQ ID NO:703-710, 737-931, and 1003-1373. In addition, the invention encompasses an isolated polynucleotide, or fragment thereof, which hybridizes to any one of the nucleic acid sequences of SEQ ID NO:703-1373. The invention further encompasses an isolated polynucleotide comprising the complement, reverse complement, reverse sequence, or fragments thereof, of any one of the nucleic acid sequences.

The invention features an expression vector comprising a polynucleotide of the invention. In one aspect, the expression vector comprises a coding sequence for at least a fragment of an amino acid sequence selected from the group consisting of SEQ ID NO:1-702. In a particular aspect, the expression vector comprises a coding sequence for at least a fragment of at least one of SEQ ID NO:45-260 and 332-702. In a further aspect, the expression vector comprises a coding sequence for at least one amino acid sequence of at least one of SEQ ID NO:10-17. In another aspect, the expression vector comprises a coding sequence for at least one amino acid sequence encompassing an extracellular domain of any one of SEQ ID NO: 10-17, 45-260, and 332-702.

The invention also features a host cell, for example, a microbial host cell, comprising at least one expression vector.

The invention specifically features an antibody directed to a peptide, polypeptide, or polynucleotide as disclosed herein. In certain aspects, the antibody is directed to an amino acid sequence selected from the group consisting of SEQ ID NO:1-702. In alternate aspects, the antibody is directed to at least a fragment of a polypeptide sequence selected from the group consisting of SEQ ID NO:10-17, 45-260, and 332-702. In a particular aspect, the antibody binds to at least a fragment of the peptide sequence of any one of SEQ ID NO:10-17. In a further aspect, the antibody binds to at least a fragment of the polypeptide sequence of any one of SEQ ID NO:45-260 and 332-702. In an alternate aspect, the antibody binds to at least a fragment of a peptide or polypeptide encompassing an extracellular domain of any one of SEQ ID NO:10-17, 45-260, and 332-702. In another aspect, the antibody includes one or more fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention additionally features modified peptides or polypeptides, e.g., for at least one of SEQ ID NO:1-702, including biologically active alterations, fragments, variants, and derivatives, described herein. Also featured are polynucleotides encoding these modified peptides or polypeptides, as well as alterations, fragments, variants, and derivatives of the disclosed polynucleotides; antibodies raised using these modified peptides, polypeptides, or polynucleotides; expression vectors comprising these polynucleotides; and host cells comprising these vectors. Further featured are modified antibodies, including biologically active alterations, fragments, variants, and derivatives, described herein. In specific aspects, the compositions and methods of the invention employ these modified peptides, polypeptides, polynucleotides, antibodies, or corresponding expression vectors or host cells.

The invention features a composition comprising an isolated peptide or polypeptide, e.g., at least one of SEQ ID NO:1-702. Also featured is a composition comprising an isolated polynucleotide, e.g., at least one of SEQ ID NO:703-1373. The invention additionally features a composition comprising an antibody, e.g., directed to a peptide, polypeptide, or polynucleotide sequence disclosed herein. Further featured is a composition that includes an expression vector, or host cell comprising an expression vector, in accordance with the invention. The composition can include any one of the biologically active alterations, fragments, variants, and derivatives described herein. The compositions can include at least one cell inhibitor (e.g., as a fusion or conjugate), and can be formulated, for example, as pharmaceutical compositions, in particular, vaccine compositions.

The invention also features a composition of the invention as part of a kit for targeting and/or inhibiting microbial cells, especially methanogen cells, in accordance with the disclosed methods. The kits comprise: a) at least one composition as set out herein; and b) optionally, instructions for use, for example, in targeting cells or inhibiting cell growth or replication for methanogens or other microbes.

The invention also features a method for producing a peptide or polypeptide, e.g., at least a fragment of any one of SEQ ID NO:1-702, the method comprising: a) culturing an expression vector or host cell comprising an expression vector, which comprises at least part of a coding sequence for at least one peptide or polypeptide under conditions suitable for the expression of the peptide or polypeptide; and b) recovering the peptide or polypeptide from the culture. In particular aspects, the peptide or polypeptide comprises at least one amino acid sequence selected from the group consisting of SEQ ID NO:1-702, or modified sequences thereof.

The invention also features a method for producing an antibody, e.g., directed to at least a fragment of any one of SEQ ID NO:1-702, the method comprising: a) culturing an expression vector or host cell comprising an expression vector, which comprises at least part of a coding sequence for at least one antibody or antibody fragment under conditions suitable for the expression of the antibody or antibody fragment; and b) recovering the amino acid sequence from the culture. In particular aspects, the antibody or antibody fragment is directed to at least one amino acid sequence selected from the group consisting of SEQ ID NO:1-702, or modified sequences thereof. In an alternate aspect, the antibody is produced by administration to a host animal, as described in detail herein.

The invention additionally features a method for producing an antibody, e.g., directed to at least a fragment of any one of SEQ ID NO:1-702, which comprises a fusion or conjugate with at least one cell inhibitor. Such method comprises: a) culturing an expression vector or host cell comprising an expression vector, which comprises a coding sequence for at least one antibody or antibody fragment under conditions suitable for the expression of the antibody or antibody fragment; b) forming a fusion or conjugate to the antibody or antibody fragment (e.g., by expression of the fused sequence or chemical conjugation to the cell inhibitor); and c) recovering the fusion or conjugate.

In particular aspects, the antibody is directed to at least a fragment of any one of SEQ ID NO:1-702, or modified sequences thereof. In further aspects, the inhibitor is selected from anti-methanogenesis compounds (e.g., bromoethanesulphonic acid), antibodies and antibody fragments, lytic enzymes, peptide nucleic acids, antimicrobial peptides, and other antibiotics as described in detail herein. In an alternate aspect, the antibody is produced by administration to a host animal and then conjugated, as described in detail herein.

In addition, the invention features a method of inhibiting (e.g., inhibiting growth or replication) of a microbial cell, in particular, a methanogen cell, comprising: contacting the cell with antibody or antibody fragment, e.g., directed to at least a fragment of any one of SEQ ID NO:1-702, or an antibody fusion or conjugate, or any modified antibody. As another method, the cell is inhibited by administration of a vaccine composition as described in detail herein.

The invention further features a method of inhibiting (e.g., inhibiting growth or replication) of a microbial cell, in particular, a methanogen cell, comprising: a) optionally, producing or isolating at least one antibody as disclosed herein; and b) contacting the cell with the antibody. In a particular aspect, the antibody is directed to at least a fragment of any one of SEQ ID NO:1-702, or a modified sequence thereof. In certain aspects, the antibody further comprises at least one cell inhibitor, attached, for example, as a fusion or conjugate. In other aspects, the antibody is administered to a subject as a composition, e.g., a vaccine composition.

Additionally, the invention features a method of inhibiting (e.g., inhibiting growth or replication) of a microbial cell, in particular, a methanogen cell, comprising: a) optionally, producing or isolating at least one peptide or polypeptide as disclosed herein; and b) administering the peptide or polypeptide to a subject to induce an immune response thereto. In a particular aspect, the peptide or polypeptide comprises at least one amino acid sequence selected from the group consisting of SEQ ID NO:1-702, or a modified sequence thereof. In other aspects, the peptide or polypeptide is administered to a subject as a composition, e.g., a vaccine composition.

The invention furthermore features a method of detecting and/or measuring the levels of a polypeptide, in particular, a cell surface polypeptide, or corresponding peptides or polynucleotides, comprising: 1) contacting a sample from a subject with an antibody directed to the polypeptide (e.g., at least a fragment of any one of SEQ ID NO:1-702, or a modified sequence thereof), or a corresponding peptide or polynucleotide (e.g., at least a fragment of one of SEQ ID NO:703-1373, or a modified sequence thereof); and 2) determining the presence or levels of the antibody complex formed with the corresponding polypeptide, peptide, or polynucleotide in the sample. Such methods can also be used for detecting and/or measuring the levels of a microbial cell, in particular, a methanogen cell.

The invention also features a method of detecting and/or measuring the levels of a polynucleotide, in particular, a polynucleotide encoding a cell surface component, comprising: 1) contacting a sample from a subject with a complementary polynucleotide (e.g., a sequence complementary to at least a fragment of any one of SEQ ID NO:703-1373, or a modified sequence thereof); and 2) determining the presence or levels of the hybridization complex formed with the polynucleotide in the sample. Such methods can also be used for detecting and/or measuring the levels of a microbial cell, in particular, a methanogen cell.

In particular aspects, the methods of the invention utilize in vivo or in vitro expression components. In other aspects, the methods employ peptides, polypeptides, polynucleotides, or antibodies produced by recombinant, synthetic, or semi-synthetic means, or by endogenous means.

Other aspects and embodiments of the invention are described herein below.

BRIEF DESCRIPTION OF THE DRAWINGS

This invention is described with reference to specific embodiments thereof and with reference to the figures.

FIGS. 1A-1C. Comparison of Methanobacteriales genomes (FIG. 1A); *M. ruminantium* genome statistics (FIG. 1B); Genes predicted to be involved in methanogenesis in *Methanobacteriales* species (FIG. 1C).

FIG. 2. Vaccination protocol.

FIG. 3. Sheep antibody responses to vaccination with *M. ruminantium* cell wall preparation and peptides designed against *M. ruminantium* mtr and cell surface proteins.

FIG. 4. Peptide sequences used for antibody production.

FIGS. 5A-1 to 5A-9 and FIGS. 5B-1 to 5B-4. ORFs selected for antibody production: Nucleotide sequences (FIG. 5A-1 to 5A-9); Amino acid sequences (FIG. 5B-1 to 5B-4).

FIGS. 6A, 6B-1 to 6B-7, and 6C-1 to 6C-3. ORFs encoding methanogenesis pathway enzymes identified from *M. ruminantium*. Annotation (FIG. 6A); Nucleotide sequences FIGS. 6B-1 to 6B-7); Amino acid sequences (FIGS. 6C-1 to 6C-3).

FIGS. 7A-1 to 7A-5, 7B-1 to 7B-51, and 7C-1 to 7C-39. ORFs for cell surface proteins identified from *M. ruminantium*: Annotation (FIGS. 7A-1 to 7A-5); Nucleotide sequences (FIGS. 7B-1 to 7B-51); Amino acid sequences (FIGS. 7C-1 to 7C-39).

FIGS. 8A-1 to 8A2, 8B-1 to 8B-21, and 8C-1 to 8C-11. ORFs encoding the biosynthesis of exopolysaccharides identified from *M. ruminantium*: Annotation (FIGS. 8A-1 to 8A2); Nucleotide sequences (FIGS. 8B-1 to 8B-21); Amino acid sequences (FIGS. 8C-1 to 8C-11).

FIGS. 9A-1 to 9A-20, 9B-1 to 9B-84, and 9C-1 to 9C-43. ORFs comprising membrane-spanning domains identified from *M. ruminantium*: Annotation (FIGS. 9A-1 to 9A-20); Nucleotide sequences (FIGS. 9B-1 to 9B-84); Amino acid sequences (FIGS. 9C-1 to 9C-43).

DETAILED DESCRIPTION OF THE INVENTION

Definitions

Figure 1C:
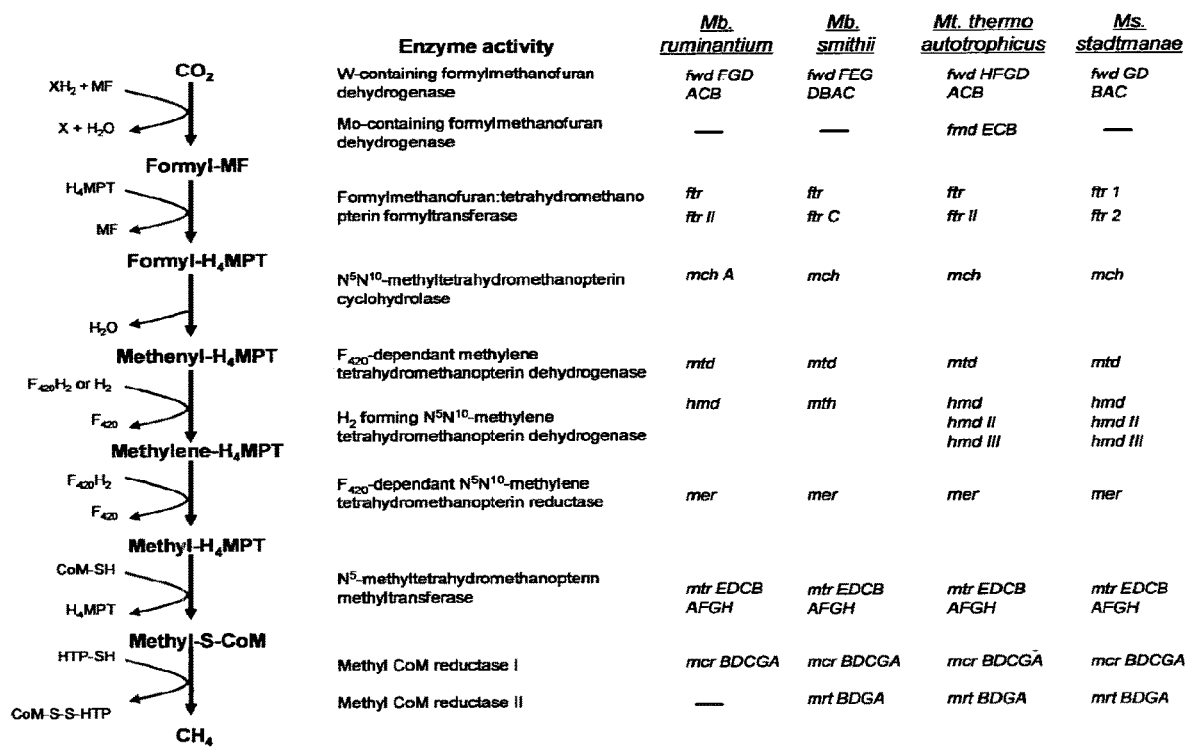

The term "antibody" should be understood in the broadest possible sense and is intended to include intact monoclonal antibodies and polyclonal antibodies. It is also intended to cover fragments and derivatives of antibodies so long as they exhibit the desired biological activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library.

Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., one or more mouse, human, or ruminant sequences. Further included are camelid antibodies or nanobodies. It will be understood that each reference to "antibodies" or any like term, herein includes intact antibodies, as well as any fragments, alterations, derivatives, or variants thereof.

"Altered" nucleic acid sequences encoding peptides, polypeptides, or antibodies, as used herein, include those with deletions, insertions, or substitutions of different nucleotides resulting in a polynucleotide that encodes the same or functionally equivalent sequence. The encoded peptide, polypeptide, or antibody may also be "altered" and contain deletions, insertions, or substitutions of amino acid residues which produce a silent change and result in a functionally equivalent sequence. Deliberate amino acid substitutions may be made on the basis of similarity in polarity, charge, solubility, hydrophobicity, hydrophilicity, and/or the amphipathic nature of the residues as long as the biological activity (e.g., cell association, membrane association) or immunogenic/immunological activity is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to a sequence of an oligopeptide, peptide, polypeptide, protein or antibody, and any fragment thereof, and to any naturally occurring, recombinant, synthetic, or semi-synthetic molecules. The sequences of the invention comprise at least 5, 10, 15, 20, 25, 30, 35, 40, 45, 50, 100, 150, 200, 250 amino acids, preferably at least 5 to 10, 10 to 20, 20 to 30, 30 to 40, 40 to 50, 50 to 100, 100 to 150, 150 to 200, or 200 to 250 amino acids. Sequences retain the biological activity (e.g., effect on cell growth and/or proliferation) or the immunogenicity/immunological activity of the amino acid sequence. "Amino acid sequence" and like terms are not limited to the complete, native amino acid sequence associated with the full-length molecule, but include also any fragments, alterations, derivatives, and variants thereof.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The terms "biologically active" or "functional," as used herein, refer to a peptide or polypeptide retaining one or more structural, immunogenic, or biochemical functions (e.g., cell association, membrane association) of a naturally occurring sequence.

The terms "cell inhibitor" or "inhibitor," as used herein, refer to agents that decrease or block the growth or replication of microbial cells, especially methanogen cells. A cell inhibitor can act to decrease or block, for example, cellular division. An inhibitor can decrease or block, for example, DNA synthesis, RNA synthesis, protein synthesis, or post-translational modifications. An inhibitor can also decrease or block the activity of enzymes involved in the methanogenesis pathway. An inhibitor can also target a cell for recognition by immune system components. Inhibition of a cell also includes cell killing and cell death, for example, from lysis, apoptosis, necrosis, etc. Useful inhibitors include, but are not limited to, anti-methanogenesis compounds (e.g., bromoethanesulphonic acid), antibodies and antibody fragments, lytic enzymes, peptide nucleic acids, antimicrobial peptides, and other antibiotics as described in detail herein.

The terms "complementary" or "complementarity," as used herein, refer to the natural binding of polynucleotides under permissive salt and temperature conditions by base-pairing. For the sequence A-G-T, the complementary sequence is T-C-A, the reverse complement is A-C-T and the reverse sequence is T-G-A. Complementarity between two single stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "derivative", as used herein, refers to the chemical modification of a nucleic acid encoding a peptide, polypeptide, or antibody, or a nucleic acid complementary thereto. Such modifications include, for example, replacement of hydrogen by an alkyl, acyl, or amino group. In preferred aspects, a nucleic acid derivative encodes a peptide, polypeptide, or antibody which retains a biological or immunogenicity/immunological activity of the natural molecule. A derivative peptide, polypeptide, or antibody is one which is modified by glycosylation, pegylation, or any similar process which retains one or more biological function (e.g., cell association, membrane association) or immunogenicity/immunological activity of the sequence from which it was derived.

The term "homology", as used herein, refers to a degree of complementarity. There may be partial homology (i.e., less than 100% identity) or complete homology (i.e., 100% identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (e.g., Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction.

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

A "methanogen," as used herein, refers to microbes that produce methane gas, which include *Methanobrevibacter, Methanothermobacter, Methanomicrobium, Methanobacterium*, and *Methanosarcina*. Specific methanogens include, but are not limited to, *Methanobrevibacter ruminantium* (i.e., M1 strain, or strain DSM1093), *Methanobrevibacter smithii, Methanobrevibacter acididurans, Methanobrevibacter thaueri, Methanobacterium bryantii, Methanobacterium formicicum, Methanothermobacter marburgensis, Methanothermobacter wolfeii, Methanosphaera stadtmanae, Methanomicrobium mobile, Methanosarcina barkeri, Methanosarcina mazei, Methanococcoides burtonii*, and *Methanolobus taylorii*. All methanogen genera and species are encompassed by this term.

"Microbial" cells as used herein, refers to naturally-occurring or genetically modified microbial cells including archaebacteria such as methanogens, halophiles, and thermoacidophiles, and eubacteria, such as cyanobacteria, spirochetes, proteobacteria, as well as Gram positive and Gram negative bacteria.

The term "modified" refers to altered sequences and to sequence fragments, variants, and derivatives, as described herein.

"Nucleic acid sequence" or "nucleotide sequence" as used herein, refers to a sequence of a polynucleotide, oligonucleotide, or fragments thereof, and to DNA or RNA of natural, recombinant, synthetic or semi-synthetic, origin which may be single or double stranded, and can represent sense or antisense strand, or coding or non-coding regions. The sequences of the invention, preferably, comprise at least 12, 15, 30, 45, 60, 75, 90, 105, 120, 135, 150, 300, 450, 600, 750 nucleotides, preferably at least 15 to 30, 30 to 60, 60 to 90, 90 to 120, 120 to 150, 150 to 300, 300 to 450, 450 to 600, or 600 to 750 nucleotides, or at least 1000 nucleotides, or at least 1500 nucleotides. It will be understood that each reference to a "nucleic acid sequence" or "nucleotide sequence," herein, will include the native, full length sequence, as well as any complements, fragments, alterations, derivatives, or variants, thereof.

The term "oligonucleotide" refers to a nucleic acid sequence of at least 6, 8, 10, 12, 15, 18, 21, 25, 27, 30, or 36 nucleotides, or at least 12 to 36 nucleotides, or at least 15 to 30 nucleotides, which can be used in PCR amplification, sequencing, or hybridization assays. As used herein, oligonucleotide is substantially equivalent to the terms "amplimers," "primers," "oligomers," and "probes," as commonly defined in the art.

The term "polynucleotide," when used in the singular or plural, generally refers to any nucleic acid sequence, e.g., any polyribonucleotide or polydeoxribonucleotide, which may be unmodified RNA or DNA or modified RNA or DNA. This includes, without limitation, single and double stranded DNA, DNA including single and double stranded regions, single and double stranded RNA, and RNA including single and double stranded regions, hybrid molecules comprising DNA and RNA that may be single stranded or, more typically, double stranded or include single and double stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences, or iRNAs such as siRNAs. It will be understood that each reference to a "polynucleotide" or like term, herein, will include the full length sequences as well as any complements, fragments, alterations, derivatives, or variants thereof.

A "peptide" and "polypeptide," as used herein, refer to the isolated peptides or polypeptides of the invention obtained from any species, preferably microbial, from any source whether natural, synthetic, semi-synthetic, or recombinant. Specifically, a peptide or polypeptide of the invention can be obtained from methanogen cells, such as *Methanobrevibacter* cells, in particular, *M. ruminantium*, or *M. smithii* cells. For recombinant production, a peptide or polypeptide of the invention can be obtained from microbial or eukaryotic cells, for example, *Escherichia, Streptomyces, Bacillus, Salmonella*, yeast, insect cells such as *Drosophila*, animal cells such as COS and CHO cells, or plant cells. It will be understood that each reference to a "peptide" or "polypeptide," herein, will include the full-length sequence, as well as any fragments, alterations, derivatives, or variants, thereof.

"Peptide nucleic acid" or "PNA" as used herein, refers to an antisense molecule or anti-gene agent which comprises bases linked via a peptide backbone.

The term "ruminant," as used herein, refers to animals that have a rumen as a special type of digestive organ. Ruminants include, but are not limited to, cattle, sheep, goats, buffalo, moose, antelope, caribou, and deer.

The terms "stringent conditions" or "stringency," as used herein, refer to the conditions for hybridization as defined by the nucleic acid, salt, and temperature. These conditions are well known in the art and may be altered in order to identify or detect identical or related polynucleotide sequences. See, e.g., Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (e.g., within a range from about 5° C. below the melting temperature of the probe to about 20° C. to 25° C. below the melting temperature). One or more factors may be varied to generate conditions of either low or high stringency different from, but equivalent to, the above listed conditions.

The term "subject" includes human and non-human animals. Non-human animals include, but are not limited to, birds and mammals, such as ruminants, and in particular, mice, rabbits, cats, dogs, pigs, sheep, goats, cows, and horses.

The terms "substantially purified" or "isolated" as used herein, refer to nucleic acid or amino acid sequences that are removed from their cellular, recombinant, or synthetic environment, and are at least 60% free, preferably 75% free, and most preferably at least 90% free or at least 99% free from other components with which they are associated in their environment. "Isolated" polynucleotides and polypeptides have been identified and separated from at least one contaminant molecule with which they are associated in their natural state. Accordingly, it will be understood that isolated polynucleotides and polypeptides are in a form which differs from the form or setting in which they are found in nature. It will further be appreciated that "isolated" does not necessarily reflect the exact extent (e.g., a specific percentage) to which the sequence has been purified.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

"Vaccines" as used herein include all components and compositions for stimulating the immune response in a subject. Particularly useful in this regard are subunit vaccines, including peptide vaccines, and also vectored vaccines, nucleic acid vaccines, and edible vaccines. Vaccines can be used to establish or strengthen an immune response to an antigen, particularly a microbial antigen. In particular aspects, vaccines comprise antigens that evoke host-protective reactions, e.g., antibody formation, T helper, and T cell responses. Vaccines can also comprise antibodies, for example, for passive immunization.

A "variant" of a peptide, polypeptide, or antibody, as used herein, refers to an amino acid sequence that is altered by one or more amino acids. A variant polynucleotide is altered by one or more nucleotides. A variant may result in "conservative" changes, wherein a substituted amino acid has similar structural or chemical properties, e.g., replacement of leucine with isoleucine. More rarely, a variant may result in "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunogenic/immunological activity may be found using computer programs well known in the art, for example, LASERGENE software (DNASTAR).

The invention also encompasses variants which retain at least one biological activity (e.g., cell association, membrane association) or immunogenicity/immunological activity. A preferred variant is one having substantially the same or a functionally equivalent sequence, for example, having at least 80%, and more preferably at least 90%, sequence identity to a disclosed sequence. A most preferred variant is one having at least 95%, at least 97%, at least 98%, or at least 99% sequence identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100. A useful alignment program is AlignX (Vector NTI).

DESCRIPTION OF THE INVENTION

Figure 7B-17:
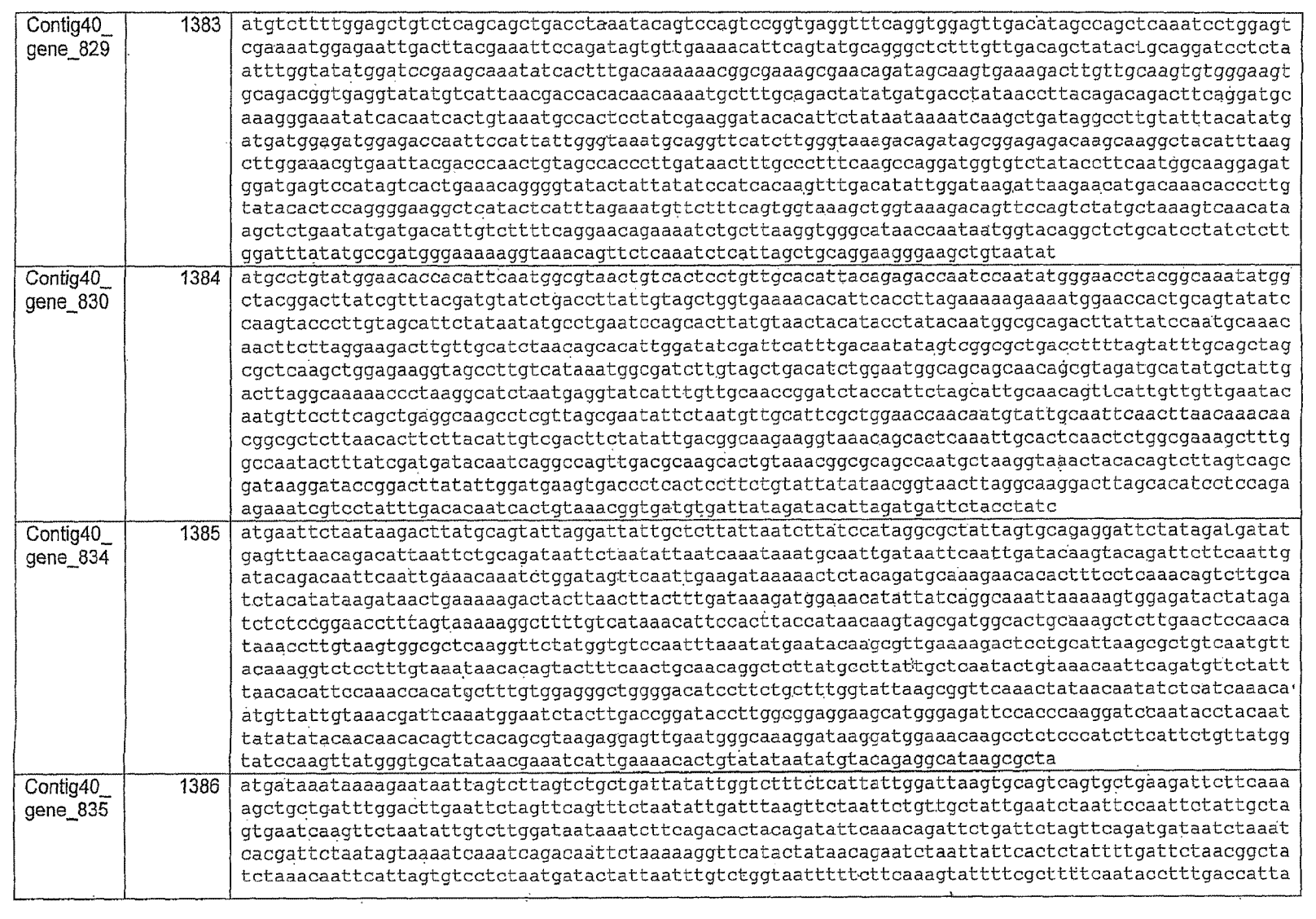

Methane is produced in the foregut of ruminants by methanogens which act as terminal reducers of carbon in the rumen system. The multi-step methanogenesis pathway is well elucidated, mainly from the study of non-rumen methanogens, but the adaptations that allow methanogens to grow and persist in the rumen are not well understood. *Methanobrevibacter ruminantium* is a prominent methanogen in New Zealand ruminants. As described herein, the genome of *M. ruminantium* has been sequenced and shown as approximately 3.0 Mb in size with a GC content of 33.68%. All of the components of the methanogenesis pathway have been identified and comparison of these gene sequences with those from *Methanobacterium thermoautotrophicum* and *Methanosphaera stadtmanae* indicates methanogenesis gene organisation is conserved within the *Methanobacteriales* (FIG. 1C.). The genome contains many large surface proteins with characteristics that indicate that they may mediate association with other rumen microbes. In various aspects of the invention, the identified polynucleotides and polypeptides can be used as a means for inhibiting methanogens and/or methanogenesis in the rumen, and to further elucidate the role of *M. ruminantium* in methane formation. Particularly useful are the disclosed polynucleotides and polypeptides identified as components involved in methanogenesis (FIGS. 6A-6C), as cell surface components (FIGS. 7A-7C), as components involved in exopolysaccharide biosynthesis (FIGS. 8A-8C), as components with membrane spanning domains (FIGS. 9A-9C), as well as the polynucleotides and polypeptides used for antibody production (FIGS. 5A-5B).

Peptides, Polypeptides, and Polynucleotides

The invention encompasses peptides and polypeptides, including those comprising at least one of SEQ ID NO:1-702, and fragments, variants, and derivatives thereof. The peptides and polypeptides of the present invention may be expressed and used in various assays to determine their biological activity. The peptides and polypeptides may be used for large-scale synthesis and isolation protocols, for example, for commercial production. Such peptides and polypeptides may be used to raise antibodies, to isolate corresponding amino acid sequences, and to quantitatively determine levels of the amino acid sequences. The peptides and polypeptides can be used for vaccines for targeting and inhibiting microbial cells, especially methanogen cells. The peptides and polypeptides can also be used for preparing antibodies to inhibit the growth or replication of such cells. The peptides and polypeptides of the present invention may also be used as compositions, for example, pharmaceutical compositions, especially vaccine compositions. In particular aspects, slow-release ruminal devices can be used in conjunction with the peptides, polypeptides, antibodies, and compositions (e.g., pharmaceutical compositions, especially vaccine compositions) of the invention.

The peptides of the present invention comprise at least one sequence selected from the group consisting of: (a) peptides comprising at least a fragment of an one amino acid sequence selected from the group consisting of SEQ ID NO:1-702, or fragments, variants, or derivatives thereof; (b) peptides comprising a functional domain of at least one amino acid sequence selected from the group consisting of SEQ ID NO:1-702, and fragments and variants thereof; and (c) peptides comprising at least a specified number of contiguous residues of at least one amino acid sequence selected from the group consisting of SEQ ID NO:1-702, or variants or derivatives thereof. In one embodiment, the invention encompasses an isolated peptide comprising the amino acid sequence of at least one of SEQ ID NO:1-9. All of these sequences are collectively referred to herein as peptides of the invention.

The polypeptides of the present invention comprise at least one sequence selected from the group consisting of: (a) polypeptides comprising at least one amino acid sequence selected from the group consisting of SEQ ID NO:1-702, or fragments, variants, or derivatives thereof; (b) polypeptides comprising a functional domain of at least one amino acid sequence selected from the group consisting of SEQ ID NO:1-702, and fragments and variants thereof; and (c) polypeptides comprising at least a specified number of contiguous residues of at least one amino acid sequence selected from the group consisting of SEQ ID NO:1-702, or variants or derivatives thereof. In one embodiment, the invention encompasses an isolated polypeptide comprising the amino acid sequence of at least one of SEQ ID NO:1-9. All of these sequences are collectively referred to herein as polypeptides of the invention.

The invention also encompasses an isolated polynucleotide that encodes a peptide or polypeptide of SEQ ID NO:1-702. The isolated polynucleotides of the present invention have utility in genome mapping, in physical mapping, and in cloning of genes of more or less related cell surface components. Probes designed using the polynucleotides of the present invention may be used to detect the presence and examine the expression patterns of genes in any organism having sufficiently homologous DNA and RNA sequences in their cells, using techniques that are well known in the art, such as slot blot techniques or microarray analysis. Primers designed using the polynucleotides of the present invention may be used for sequencing and PCR amplifications. The polynucleotides of the invention can be used for preparing expression vectors and host cells for vaccines to target and inhibit microbial cells, especially methanogen cells. The invention further encompasses the use of the polynucleotides for the production of antibodies to inhibit the growth or replication of such cells. The polynucleotides of the present invention may also be used as compositions, for example, pharmaceutical compositions, especially vaccine compositions. In particular aspects, slow-release ruminal devices can be used in conjunction with the polynucleotides, vectors, host cells, and compositions (e.g., pharmaceutical compositions, especially vaccine compositions) of the invention.

The polynucleotides of the present invention comprise at least one sequence selected from the group consisting of: (a) sequences comprising a coding sequence for at least one amino acid sequence selected from the group consisting of SEQ ID NO:1-702, or fragments or variants thereof; (b) complements, reverse sequences, and reverse complements of a coding sequence for at least one amino acid sequence selected from the group consisting of SEQ ID NO:1-702, or fragments or variants thereof; (c) open reading frames contained in the coding sequence for at least one amino acid sequence selected from the group consisting of SEQ ID NO:1-702, and their fragments and variants; (d) functional domains of a coding sequence for at least one amino acid sequence selected from the group consisting of SEQ ID NO:1-702, and fragments and variants thereof; and (e) sequences comprising at least a specified number of contiguous residues of a coding sequence for at least one amino acid sequence selected from the group consisting of SEQ ID NO:1-702, or variants thereof; and (f) sequences comprising at least a specified number of contiguous nucleotides of any one of SEQ ID NO:703-1373. Oligonucleotide probes and primers and their variants are also provided. All of these polynucleotides and oligonucleotide probes and primers are collectively referred to herein, as polynucleotides of the invention.

It will be appreciated by those skilled in the art that as a result of the degeneracy of the genetic code, a multitude of nucleotide sequences encoding the peptides or polypeptides of the invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to naturally occurring amino acid sequences, and all such variations are to be considered as being specifically disclosed.

Nucleotide sequences which encode the peptides or polypeptides, or their fragments or variants, are preferably capable of hybridizing to the nucleotide sequence of the naturally occurring sequence under appropriately selected conditions of peptide or stringency. However, it may be advantageous to produce nucleotide sequences encoding a peptide or polypeptide, or its fragment or derivative, possessing a substantially different codon usage. Codons may be selected to increase the rate at which expression of the peptide or polypeptide occurs in a particular prokaryotic or eukaryotic host in accordance with the frequency with which particular codons are utilized by the host. Other reasons for substantially altering the nucleotide sequence encoding peptides or polypeptides and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode the peptides or polypeptides, or their fragments or variants, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a peptide or polypeptide, or any variants or fragment thereof. Also encompassed by the invention are polynucleotide sequences that are capable of hybridizing to the claimed nucleotide sequences, and in particular, those shown in SEQ ID NO:703-1373, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase Amersham Pharmacia Biotech (Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) the ABI Catalyst and 373 and 377 DNA Sequencers (Perkin Elmer), or the Genome Sequencer 20™ (Roche Diagnostics).

The nucleic acid sequences encoding the peptides or polypeptides may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotides or fragments thereof which encode peptides or polypeptides may be used in recombinant DNA molecules to direct expression of the peptides or polypeptides, or fragments or variants thereof, in appropriate host cells. Due to the inherent degeneracy of the genetic code, other DNA sequences which encode substantially the same or a functionally equivalent amino acid sequence may be produced, and these sequences may be used to clone and express peptides or polypeptides. The nucleotide sequences of the present invention can be engineered using methods generally known in the art in order to alter amino acid-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, introduce mutations, and so forth.

In another embodiment of the invention, natural, modified, or recombinant nucleic acid sequences encoding peptides or polypeptides may be ligated to a heterologous sequence to encode a fusion protein. For example, it may be useful to encode a chimeric sequence that can be recognized by a commercially available antibody. A fusion protein may also be engineered to contain a cleavage site located between the peptide or polypeptide of the invention and the heterologous protein sequence, so that the peptide or polypeptide may be cleaved and purified away from the heterologous moiety.

In another embodiment, sequences encoding peptides or polypeptides may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the polypeptide itself may be produced using chemical methods to synthesize the amino acid sequence, or a fragment thereof. For example, polypeptide synthesis can be performed using various solid-phase techniques (Roberge, J. Y. et al. (1995) Science 269:202-204; Merrifield J. (1963) J. Am. Chem. Soc. 85:2149-2154) and automated synthesis may be achieved, for example, using the ABI 431A Peptide Synthesizer (Perkin Elmer). Various fragments of peptides or polypeptides may be chemically synthesized separately and combined using chemical methods to produce the full length molecule.

The newly synthesized peptide or polypeptide may be isolated by preparative high performance liquid chromatography (e.g., Creighton, T. (1983) Proteins Structures and Molecular Principles, WH Freeman and Co., New York, N.Y.). The composition of the synthetic peptides or polypeptides may be confirmed by amino acid analysis or sequencing (e.g., the Edman degradation procedure; Creighton, supra). Additionally, the amino acid sequence of the peptide or polypeptide, or any part thereof, may be altered during direct synthesis and/or combined using chemical methods with sequences from other proteins, or any part thereof, to produce a variant molecule.

In order to express a biologically active peptides or polypeptides, the nucleotide sequences encoding the sequences or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the peptide or polypeptide and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding the peptides or polypeptides of the invention. These include, but are not limited to, microorganisms such as bacteria transformed with recombinant phage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. For bacteria, useful plasmids include pET, pRSET, pTrcHis2, and pBAD plasmids from Invitrogen, pET and pCDF plasmids from Novagen, and Director™ plasmids from Sigma-Aldrich. For methanogens, useful plasmids include, but are not limited to pME2001, pMV15, and pMP1. The invention is not limited by the expression vector or host cell employed.

The "control elements" or "regulatory sequences" are those non-translated regions of the vector-enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In bacterial systems, a number of expression vectors may be selected depending upon the use intended for the peptide or polypeptide. For example, when large quantities of peptide or polypeptide are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding a polypeptide may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like.

pGEX vectors (Promega, Madison, Wis.) may also be used to express peptides or polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned peptide or polypeptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

Specific initiation signals may also be used to achieve more efficient translation of sequences encoding the peptides or polypeptides of the invention. Such signals include the ATG initiation codon and adjacent sequences. In cases where sequences encoding a peptide or polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed peptide or polypeptide in the desired fashion. Such modifications of the sequence include, but are not limited to, acetylation, carboxylation, glycosylation, phosphorylation, lipidation, and acylation. Post-translational processing which cleaves a "prepro" form of the peptide or polypeptide may also be used to facilitate correct insertion, folding, and/or function. Different host cells which have specific cellular machinery and characteristic mechanisms for post-translational activities are available from the American Type Culture Collection (ATCC; Bethesda, Md.) and may be chosen to ensure the correct modification and processing of the sequence. Specific host cells include, but are not limited to, methanogen cells, such as *Methanobrevibacter* cells, in particular, *ruminantium*, or *M. smithii* cells. Host cells of interest include, for example, *Rhodotorula, Aureobasidium, Saccharomyces, Sporobolomyces, Pseudomonas, Erwinia* and *Flavobacterium*; or such other organisms as *Escherichia, Lactobacillus, Bacillus, Streptomyces*, and the like. Specific host cells include *Escherichia coli*, which is particularly suited for use with the present invention, *Saccharomyces cerevisiae, Bacillus thuringiensis, Bacillus subtilis, Streptomyces lividans*, and the like.

There are several techniques for introducing nucleic acids into eukaryotic cells cultured in vitro. These include chemical methods (Feigner et al., Proc. Natl. Acad. Sci., USA, 84:7413 7417 (1987); Bothwell et al., Methods for Cloning and Analysis of Eukaryotic Genes, Eds., Jones and Bartlett Publishers Inc., Boston, Mass. (1990), Ausubel et al., Short Protocols in Molecular Biology, John Wiley and Sons, New York, N.Y. (1992); and Farhood, Annal. NY Acad. Sci., 716:23 34 (1994)), use of protoplasts (Bothwell, supra) or electrical pulses (Vatteroni et al., Mutn. Res., 291:163 169 (1993); Sabelnikov, Prog. Biophys. Mol. Biol., 62: 119 152 (1994); Bothwell et al., supra; and Ausubel et al., supra), use of attenuated viruses (Davis et al., J. Virol. 1996, 70(6), 3781 3787; Brinster et al. J. Gen. Virol. 2002, 83(Pt 2), 369 381; Moss, Dev. Biol. Stan., 82:55 63 (1994); and Bothwell et al., supra), as well as physical methods (Fynan et al., Int J Immunopharmacol. 1995 February; 17(2):79-83; Johnston et al., Meth. Cell Biol., 43(Pt A):353 365 (1994); Bothwell et al., supra; and Ausubel et al., supra).

Successful delivery of nucleic acids to animal tissue can be achieved by cationic liposomes (Watanabe et al., Mol. Reprod. Dev., 38:268 274 (1994)), direct injection of naked DNA or RNA into animal muscle tissue (Robinson et al., Vacc., 11:957 960 (1993); Hoffman et al., Vacc. 12:1529 1533; (1994); Xiang et al., Virol., 199:132 140 (1994); Webster et al., Vacc., 12:1495 1498 (1994); Davis et al., Vacc., 12:1503 1509 (1994); Davis et al., Hum. Molec. Gen., 2:1847 1851 (1993); Dalemans et al. Ann NY Acad. Sci. 1995, 772, 255 256. Conry, et al. Cancer Res. 1995, 55(7), 1397-1400), and embryos (Naito et al., Mol. Reprod. Dev., 39:153 161 (1994); and Burdon et al., Mol. Reprod. Dev., 33:436 442 (1992)), intramuscular injection of self replicating RNA vaccines (Davis et al., J Virol 1996, 70(6), 3781 3787; Balasuriya et al. Vaccine 2002, 20(11 12), 1609 1617) or intradermal injection of DNA using "gene gun" technology (Johnston et al., supra).

A variety of protocols for detecting and measuring the expression of the peptides or polypeptides of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay can be used with monoclonal antibodies reactive to two non-interfering epitopes on the peptide or polypeptide, but a competitive binding assay can also be used. These and other assays are described, among other places, in Hampton, R. et al. (1990; Serological Methods, a laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences encoding the peptides or polypeptides, or any fragments or variants thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Expression vectors or host cells transformed with expression vectors may be cultured under conditions suitable for the expression and recovery of the peptide or polypeptide from culture. The culture can comprise components for in vitro or in vivo expression. In vitro expression components include those for rabbit reticulocyte lysates, *E. coli* lysates, and wheat germ extracts, for example, Expressway™ or RiPs systems from Invitrogen, Genelator™ systems from iNtRON Biotechnology, EcoPro™ or STP3™ systems from Novagen, TNT® Quick Coupled systems from Promega, and EasyXpress systems from QIAGEN. The peptide or polypeptide produced from culture may be secreted or contained intracellularly depending on the sequence and/or the vector used. In particular aspects, expression vectors which encode a peptide or polypeptide can be designed to contain signal sequences which direct secretion of the peptide or polypeptide through a prokaryotic or eukaryotic cell membrane.

Other constructions may include an amino acid domain which will facilitate purification of the peptide or polypeptide. Such domains include, but are not limited to, metal chelating domains such as histidine-tryptophan (e.g., 6X-HIS) modules that allow purification on immobilized metals, protein A domains that allow purification on immobilized immunoglobulin, and the domain utilized in the FLAG® extension/affinity purification system (Immunex Corp., Seattle, Wash.). Useful epitope tags include 3XFLAG®, HA, VSV-G, V5, HSV, GST, GFP, MBP, GAL4, and β-galactosidase. Useful plasmids include those comprising a biotin tag (e.g., PinPoint™ plasmids from Promega), calmodulin binding protein (e.g., pCAL plasmids from Stratagene), streptavidin binding peptide (e.g., InterPlay™ plasmids from Stratagene), a c-myc or FLAG® tag (e.g., Immunoprecipitation plasmids from Sigma-Aldrich), or a histidine tag (e.g., QIAExpress plasmids from QIAGEN).

To facilitate purification, expression vectors can include cleavable linker sequences such as those specific for Factor Xa or enterokinase (Invitrogen, San Diego, Calif.). For example, the vector can include one or more linkers between the purification domain and the peptide or polypeptide. One such expression vector provides for expression of a fusion protein comprising a peptide or polypeptide of the invention and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3: 263-281) while the enterokinase cleavage site provides a means for purifying the peptide or polypeptide from the fusion protein. A discussion of vectors which contain fusion proteins is provided in Kroll, D. J. et al. (1993; DNA Cell Biol. 12:441-453).

Antibodies and Vaccines

The antibodies of the invention may be produced using methods which are generally known in the art. In particular, purified peptides, polypeptides, or polynucleotides may be used to produce antibodies in accordance with known methods. Such antibodies may include, but are not limited to, polyclonal, monoclonal, chimeric, and single chain antibodies, Fab fragments, and fragments produced by a Fab expression library. Neutralizing antibodies, (i.e., those which inhibit function) are especially preferred for use with vaccines.

For the production of antibodies, various hosts including goats, rabbits, rats, mice, humans, and others, may be immunized by injection with a peptide, polypeptide, polynucleotide, or any fragment thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, polypeptides, or fragments used to induce antibodies have an amino acid sequence comprising at least five amino acids and more preferably at least 10 amino acids. It is also preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin and antibody produced against the chimeric molecule.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

In addition, techniques developed for the production of "chimeric antibodies", e.g., the combining of mouse antibody genes and human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120-3).

Those of skill in the art to which the invention relates will appreciate the terms "diabodies" and "triabodies". These are molecules which comprise a heavy chain variable domain (VH) connected to a light chain variable domain (VL) by a short peptide linker that is too short to allow pairing between the two domains on the same chain. This promotes pairing with the complementary domains of one or more other chains and encourages the formation of dimeric or trimeric molecules with two or more functional antigen binding sites. The resulting antibody molecules may be monospecific or multispecific (e.g., bispecific in the case of diabodies). Such antibody molecules may be created from two or more antibodies using methodology standard in the art to which the invention relates; for example, as described by Todorovska et al. (Design and application of diabodies, triabodies and tetrabodies for cancer targeting. J. Immunol. Methods. 2001 Feb. 1; 248(1-2):47-66).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments which contain specific binding sites may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having binding specificity. Numerous protocols for competitive binding or immunoradiometric assays using either polyclonal or monoclonal antibodies with established specificities are well known in the art. Such immunoassays typically involve the measurement of complex formation between a peptide, polypeptide, or polynucleotide and its specific antibody. A two-site, monoclonal-based immunoassay utilizing monoclonal antibodies reactive to two non-interfering epitopes is preferred, but a competitive binding assay may also be employed (Maddox, supra).

The antibodies described herein have the ability to target and/or inhibit cells and are also useful as carrier molecules for the delivery of additional inhibitory molecules into microbial cells. The chemistry for coupling compounds to amino acids is well developed and a number of different molecule types could be linked to the antibodies. The most common coupling methods rely on the presence of free amino (alpha-amino or Lys), sufhydryl (Cys), or carboxylic acid groups (Asp, Glu, or alpha-carboxyl). Coupling methods can be used to link the antibody to the cell inhibitor via the carboxy- or amino-terminal residue. In some cases, a sequence includes multiple residues that may react with the chosen chemistry. This can be used to produce multimers, comprising more than one cell inhibitor. Alternatively, the antibody can be shortened or chosen so that reactive residues are localized at either the amino or the carboxyl terminus of the sequence.

For example, a reporter molecule such as fluorescein can be specifically incorporated at a lysine residue (Ono et al., 1997) using N-α-Fmoc-Nε-1-(4,4-dimethyl-2,6 dioxocyclohex-1-ylidene-3-methylbutyl)-L-lysine during polypeptide synthesis. Following synthesis, 5- and 6-carboxyfluorescein succinimidyl esters can be coupled after 4,4-dimethyl-2,6 dioxocyclohex-1-ylidene is removed by treatment with hydrazine. Therefore coupling of an inhibitory molecule to the antibody can be accomplished by inclusion of a lysine residue to the polypeptide sequence, then reaction with a suitably derivatised cell inhibitor.

EDC (1-ethyl-3-(3-dimethylaminopropyl) carbodiimide hydrochloride) or the carbodiimide coupling method can also be used. Carbodiimides can activate the side chain carboxylic groups of aspartic and glutamic acid as well as the carboxyl-terminal group to make them reactive sites for coupling with primary amines. The activated antibody is mixed with the cell inhibitor to produce the final conjugate. If the cell inhibitor is activated first, the EDC method will couple the cell inhibitor through the N-terminal alpha amine and possibly through the amine in the side-chain of Lys, if present in the sequence.

m-Maleimidobenzoyl-N-hydroxysuccinimide ester (MBS) is a heterobifunctional reagent that can be used to link an antibody to cell inhibitors via cysteines. The coupling takes place with the thiol group of cysteine residues. If the chosen sequence does not contain Cys it is common to place a Cys residue at the N- or C-terminus to obtain highly controlled linking of the antibody to the cell inhibitor. For synthesis purposes, it may be helpful for the cysteine to be placed at the N-terminus of the antibody. MBS is particularly suited for use with the present invention.

Glutaraldehyde can be used as a bifunctional coupling reagent that links two compounds through their amino groups. Glutaraldehyde provides a highly flexible spacer between the antibody and cell inhibitor for favorable presentation. Glutaraldehyde is a very reactive compound and will react with Cys, Tyr, and His to a limited extent. The glutaraldehyde coupling method is particularly useful when a polypeptide contains only a single free amino group at its amino terminus. If the antibody contains more than one free amino group, large multimeric complexes can be formed.

In one aspect, the antibodies of the invention can be fused (e.g., by in-frame cloning) or linked (e.g., by chemical coupling) to cell inhibitors such as antimicrobial agents. Included among these are antimicrobial peptides, for example, bactericidal/permeability-increasing protein, cationic antimicrobial proteins, lysozymes, lactoferrins, and cathelicidins (e.g., from neutrophils; see, e.g., Hancock and Chapple, 1999, Antimicrob. Agents Chemother. 43:1317-1323; Ganz and Lehrer, 1997, Curr. Opin. Hematol. 4:53-58; Hancock et al., 1995, Adv. Microb. Physiol. 37:135-175). Antimicrobial peptides further include defensins (e.g., from epithelial cells or neutrophils) and platelet microbiocidal proteins (see, e.g., Hancock and Chapple, 1999, Antimicrob. Agents Chemother. 43:1317-1323). Additional antimicrobial peptides include, but are not limited to, gramicidin S, bacitracin, polymyxin B, tachyplesin, bactenecin (e.g., cattle bactenecin), ranalexin, cecropin A, indolicidin (e.g., cattle indolicidin), and nisin (e.g., bacterial nisin).

Also included as antimicrobial agents are ionophores, which facilitate transmission of an ion, (such as sodium), across a lipid barrier such as a cell membrane. Two ionophore compounds particularly suited to this invention are the RUMENSIN™ (Eli Lilly) and Lasalocid (Hoffman LaRoche). Other ionophores include, but are not limited to, salinomycin, avoparcin, aridcin, and actaplanin. Other antimicrobial agents include Monensin™ and azithromycin, metronidazole, streptomycin, kanamycin, and penicillin, as well as, generally, ß-lactams, aminoglycosides, macrolides, chloramphenicol, novobiocin, rifampin, and fluoroquinolones (see, e.g., Horn et al., 2003, Applied Environ. Microbiol. 69:74-83; Eckburg et al., 2003, Infection Immunity 71:591-596; Gijzen et al., 1991, Applied Environ. Microbiol. 57:1630-1634; Bonelo et al., 1984, FEMS Microbiol. Lett. 21:341-345; Huser et al., 1982, Arch. Microbiol. 132:1-9; Hilpert et al., 1981, Zentbl. Bakteriol. Mikrobiol. Hyg. 1 Abt Orig. C 2:21-31).

Particularly useful inhibitors are compounds that block or interfere with methanogenesis, including bromoethanesulphonic acid, e.g., 2-bromoethanesulphonic acid (BES) or a salt thereof, for example, a sodium salt. Sodium molybdate (Mo) is an inhibitor of sulfate reduction, and can be used with bromoethanesulphonic acid. Other anti-methanogenesis compounds include, but are not limited to, nitrate, formate, methyl fluoride, chloroform, chloral hydrate, sodium sulphite, ethylene and unsaturated hydrocarbons, acetylene, fatty acids such as linoleic and cis-oleic acid, saturated fatty acids such as behenic and stearic acid, and, also lumazine (e.g., 2,4-pteridinedione). Additional compounds include 3-bromopropanesulphonate (BPS), propynoic acid, and ethyl 2-butynoate.

Further included as antimicrobial agents are lytic enzymes, including phage lysozyme, endolysin, lysozyme, lysin, phage lysin, muralysin, muramidase, and virolysin. Useful enzymes exhibit the ability to hydrolyse specific bonds in the bacterial cell wall. Particular lytic enzymes include, but are not limited to, glucosaminidases, which hydrolyse the glycosidic bonds between the amino sugars (e.g., N-acetylmuramic acid and N-acetylglucosamine) of the peptidoglycan, amidases, which cleave the N-acetylmuramoyl-L-alanine amide linkage between the glycan strand and the cross-linking peptide, and endopeptidases, which hydrolyse the interpeptide linkage (e.g., cysteine endopeptidases) and endoisopeptidases that attack pseudomurein of methanogens from the family Methanobacteriaceae.

Additionally, PNAs are included as antimicrobial agents. PNAs are peptide-nucleic acid hybrids in which the phosphate backbone has been replaced by an achiral and neutral backbone made from N-(2-aminoethyl)-glycine units (see, e.g., Eurekah Bioscience Collection. PNA and Oligonucleotide Inhibitors of Human Telomerase. G. Gavory and S. Balasubramanian, Landes Bioscience, 2003). The bases A, G, T, C are attached to the amino nitrogen on the backbone via methylenecarbonyl linkages (P. E. Nielsen et al., Science 1991. 254: 1497-1500; M. Egholm et al., Nature 1993. 365: 566-568). PNAs bind complementary sequences with high specificity, and higher affinity relative to analogous DNA or RNA (M. Egholm et al., supra). PNA/DNA or PNA/RNA hybrids also exhibit higher thermal stability compared to the corresponding DNA/DNA or DNA/RNA duplexes (M. Egholm et al., supra). PNAs also possess high chemical and biological stability, due to the unnatural amide backbone that is not recognized by nucleases or proteases (V. Demidov et al., Biochem Pharmacol 1994. 48: 1310-1313). Typically, PNAs are at least 5 bases in length, and include a terminal lysine. PNAs may be pegylated to further extend their lifespan (Nielsen, P. E. et al. (1993) Anticancer Drug Des. 8:53-63).

In one particular aspect, the antibodies of the invention can be fused or linked to other antibodies or fragments thereof. The added antibodies or antibody fragments can be directed to microbial cells, or particularly methanogen cells, or one or more cell components. For example, cell surface proteins, e.g., extracellular receptors, can be targeted. In certain aspects, the antibodies or antibody fragments can be engineered with sequences that are specifically expressed in subjects, for example, human or ruminant sequences. Also included are chimeric antibodies, for example, monoclonal antibodies or fragments thereof that are specific to more than one source, e.g., one or more mouse, human, or ruminant sequences. Further included are camelid antibodies or nanobodies.

The antibodies of the invention find particular use in targeting a microbial cell, in particular, a methanogen cell. In certain aspects, the antibodies can be used to associate with or bind to the cell wall or membrane and/or inhibit growth or replication of the cell. As such, the antibodies can be used for transient or extended attachment to the cell, or to mediate sequestration or engulfment of the cell, and/or lysis. To effect targeting, the microbial cell can be contacted with an antibody as isolated from a host organism, or produced by expression vectors and/or host cells, or synthetic or semi-synthetic chemistry as described in detail herein. Alternately, the antibodies can be produced by the host organism itself in response to the administration or the peptides, polypeptides, or polynucleotides disclosed herein. It is understood that the antibodies of the invention, as well as the corresponding polynucleotides, expression vectors, host cells, peptides, and polypeptides, can be used to target various microbes, for example, *Methanobrevibacter ruminantium*, which is the primary methanogen in ruminants, and *Methanobrevibacter smithii*, which is the primary methanogen in humans. In particular aspects, the antibodies, or corresponding polynucleotides, expression vectors, host cells, peptides, or polypeptides, are delivered to subjects as a composition described in detail herein, for example, through use of a slow-release ruminal device.

In various aspects, the agents of the invention (e.g., one or more peptides, polypeptides, polynucleotides, and antibodies) can be included in a composition, for example, a pharmaceutical composition, and especially a vaccine composition. The composition comprises, for example: a) an isolated peptide or alteration, fragment, variant, or derivative thereof; b) an isolated polypeptide, or an alteration, fragment, variant, or derivative thereof; c) an isolated polynucleotide, or an alteration, fragment, variant, or derivative thereof; d) an expression vector comprising this polynucleotide; e) a host cell comprising this expression vector; or (f) an antibody, or an alteration, fragment, variant, or derivative thereof. The compositions of the invention can be specifically packaged as part of kits for targeting, and/or inhibiting microbial cells, especially methanogen cells, in accordance with the disclosed methods. The kits comprise at least one composition as set out herein and instructions for use in targeting cells or inhibiting cell growth or replication, for methanogens or other microbes.

For vaccines, a number of approaches can be used to increase antigen immunogenicity, for example, by use of antigen particles; antigen polymers and polymerization; emulsifying agents; microencapsulation of antigens; killed bacteria and bacterial products; chemical adjuvants and cytokines; and agents for targeting antigens to antigen presenting cells (reviewed in Paul, Fundamental Immunology, 1999, Lippincott-Raven Publishers, New York, N.Y., p. 1392-1405).

To render antigens particulate, alum precipitation can be used. With the use of aluminium hydroxide or aluminium phosphate, the antigen in question becomes incorporated into an insoluble, gel-like precipitate or else is bound to preformed gel by electrostatic interactions. Antigens can be subjected to mild heat aggregation. Antigens exhibiting self-assembly can also be used. Liposomes, virosomes, and immunostaining complexes (ISCOMs) are also useful for forming particulates.

To promote polymerization, nonionic block copolymers can be used as additives to adjuvants, e.g., polymers or polyoxypropylene and polyoxyethylene, with which antigen can be associated. These are found as components of complex adjuvant formulations by both Syntex (SAF-1, Syntex Adjuvant Formulation-1) and Ribi Chemical Co. Carbohydrate polymers of mannose (e.g., mannan) or of $\beta$1-3 glucose (e.g., glucan) can be used in similar fashion (Okawa Y, Howard C R, Steward M W. Production of anti-peptide antibody in mice following immunization of mice with peptides conjugated to mannan. J Immunol Methods 1992; 142:127-131; Ohta M, Kido N, Hasegawa T, et al. Contribution of the mannan side chains to the adjuvant action of lipopolysaccharides. Immunology 1987; 60:503-507).

Various agents can be used for emulsification, including water-in-oil emulsions, such as Freund's adjuvants (e.g., Freund's incomplete adjuvant), or other mixtures comprising tiny droplets of water stabilized by a surfactant such as mannide monooleate in a continuous phase of mineral oil or other oils, such as squalane. An alternative approach is to use oil-in-water emulsions, such as MF5963 (Chiron), or other mixtures comprising oil droplets of squalene and a mixture of emulsifying agents TWEEN80 and SPAN85, and chemical immunomodulators such as derivatives or muramyl dipeptide, e.g., muramyl tripeptide-phosphatidyl ethanolamine (MTP-PE) (Valensi J-P M, Carlson J R, Van Nest G A. Systemic cytokine profiles in Balb/c mice immunized with trivalent influenza vaccine containing MF59 oil emulsion and other advanced adjuvants. J Immunol 1994; 153: 4029-4039). Small amounts of polysorbate 80 and sorbitan trioleate can also be used in the mixtures. As another example, SAF-165 (Syntex) can be used, or other oil-in-water mixtures comprising Pluronic L121, squalene, and TWEEN80.

Microcapsules, in particular, biodegradable microcapsules, can be used to prepare controlled-release vaccines (Chang T M S. Biodegradable, semi-permeable microcapsules containing enzymes hormones, vaccines and other biologicals. J Bioeng 1976; 1:25-32; Langer R. Polymers for the sustained release of macromolecules: their use in a single step method of immunization. Methods Enzymol 1981; 73:57-75). Cyanoacrylates are another form of biodegradable polymer. For example, poly(butyl-2-cyanoacrylate) can be used as an adjuvant for oral immunization (O'Hagan D T, Palin K J, Davis S S. Poly (butyl-2-cyanoacrylate) particles as adjuvants for oral immunization. Vaccine 1989; 7:213-216). Microcapsules are useful for the mucosal administration of vaccines. Particles of very small size (nanoparticles) are particularly suitable. Digestion in the stomach can be countered by enteric coated polymers, and coating with substances that increase intestinal absorption, as needed.

Various bacteria, other than killed *M. tuberculosis*, can be used as adjuvants. Where the killed bacterial preparation is itself highly antigenic, the adjuvant properties extend to the co-administered antigen. Useful organisms include *Bordetella pertussis, Corynebacterium parvum*, and *Nippostrongylus brasiliensis*. Peptide and lipid components of bacteria can also be used. Exemplary components include acetylmuramyl-L-alanyl-D-isoglutamine, or muramyl dipeptide (MDP) (Ellouz F, Adam A, Ciorbaru R, Lederer E. Minimal structural requirements for adjuvant activity of bacterial peptidoglycans. Biochem Biophys Res Commun 1974; 59:1317-1325), MDP (murabutide) (Chedid L, Parant M A, Audibert F M, et al. Biological activity of a new synthetic muramyl dipeptide devoid of pyrogenicity. Infect Immun 1982; 35:417-424), threonyl MDP (Allison A C, Byars N E. An adjuvant formulation that selectively elicits the formation of antibodies of protective isotypes and cell-mediated immunity. J Immunol Methods 1986; 95:157-168), and MTP-PE. Lipid adjuvants can comprise LPS endotoxins of gram-negative bacteria, such as *Escherichia, Salmonella*, and *Pseudomonas*. In certain approaches, the lipid A structure can be chemically modified to lower toxicity but retain adjuvanticity, e.g., as for monophosphoryl lipid A (MPL) (Johnson A G, Tomai M, Solem L, Beck L, Ribi E. Characterization of non-toxic monophosphoryl lipid. Rev Infect Dis 1987; 9:S512).

Various chemicals can be used as adjuvants, including polynucleotides, such as poly-I:C and poly-A:U, vitamin D3, dextran sulphate, inulin, dimethyl dioctadecyl ammonium bromide (DDA), avridine, carbohydrate polymers similar to mannan, and trehalose dimycolate (Morein B, Lövgren-Bengtsson K, Cox J. Modern adjuvants: functional aspects. In: Kaufmann S H E, ed. Concepts in vaccine development. Berlin: Walter de Gruyter, 1996:243-263). Also included are polyphosphazines (initially introduced as slow release-promoting agents) and a *Leishmania* protein, LeIF. Cytokines can also be used as adjuvants, for example, IL-2, IL-4, IL-6, IL-10, GM-CSF, and IFN-g.

For targeting antigen presenting cells, C3d domains, Fc domains, and CTB domains can be used (Dempsey P W, Allison M E D, Akkaraju S, Goodnow C C, Fearon D T. C3d of complement as a molecular adjuvant: bridging innate and acquired immunity. Science 1996; 271:348-350; Sun J-B, Holmgren J, Czerkinsky C. Cholera toxin B subunit: an efficient transmucosal carrier-delivery system for induction of peripheral immunological tolerance. Proc Natl Acad Sci USA 1994; 91:10795-10799; Sun J-B, Rask C, Olsson T, Holmgren J, Czerkinsky C. Treatment of experimental autoimmune encephalomyelitis by feeding myelin basic protein conjugated to cholera toxin B subunit. Proc Natl Acad Sci USA 1996; 93:7196-7201).

Specific adjuvants for mucosal delivery, e.g., CT, LT, and Fragment C of tetanus toxin, can also be used (Elson C J, Ealding W. Generalized systemic and mucosal immunity in mice after mucosal stimulation with cholera toxin. J Immunol 1984; 132:2736-2743; Holmgren J, Lycke N, Czerkinsky C. Cholera toxin and cholera B subunit as oral-mucosal adjuvant and antigen vector systems. Vaccine 1993; 11:1179-1184; Clements J D, Hartzog N M, Lyon F L. Adjuvant activity of *Escherichia coli* heat-labile enterotoxin and effect on the induction of oral tolerance in mice to unrelated protein antigens. Vaccine 1988; 6:269-277; Gomez-Duarte O G, Galen J, Chatfield S N, Rappuoli R, Eidels L, Levine M M. Expression of fragment C of tetanus toxin fused to a carboxyl-terminal fragment of diphtheria toxin in *Salmonella typhi* CVD 908 vaccine strain. Vaccine 1995; 13:1596-1602).

Therapeutics and Diagnostics

The peptides, polypeptides, polynucleotides, and antibodies of the present invention are considered to have health benefits. In particular aspects, vaccines that target methanogens can be used to restore energy to the subject that is normally lost as methane. The invention therefore relates to a pharmaceutical composition (especially a vaccine composition) in conjunction with a pharmaceutically acceptable carrier, for use with any of the methods discussed above. Such pharmaceutical compositions may comprise a peptide, polypeptide, or antibody in combination with a cell inhibitor. Alternatively, the pharmaceutical compositions may comprise a polynucleotide, expression vector, or host cell as described in detail herein. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject alone, or in combination with other agents, drugs (e.g., antimicrobial drugs), or hormones.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.). The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilising agents may be added, such as the crosslinked polyvinyl pyrrolidone, agar, alginic acid, or a salt thereof, such as sodium alginate.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical formulations suitable for parenteral administration may be formulated in aqueous solutions, preferably in physiologically compatible buffers such as Hanks' solution, Ringers solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. For administration of a composition of the invention, such labeling would include amount, frequency, and method of administration.

Pharmaceutical compositions suitable for use in the invention include compositions wherein the active ingredients are contained in an effective amount to achieve the intended purpose. For any compound, the therapeutically effective dose can be estimated initially either in cell assays, e.g., in microbial cells, or in particular, in methanogen cells, or in animal models, usually mice, rabbits, dogs, or pigs, or in ruminant species such as sheep, cattle, deer, and goats. The animal model may also be used to determine the appropriate concentration range and route of administration. Such information can then be used to determine useful doses and routes for administration. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for polynucleotides than for polypeptides. Similarly, delivery of peptides, or polypeptides, polynucleotides, or antibodies will be specific to particular cells, conditions, locations, etc.

The exact dosage will be determined by the practitioner, in light of factors related to the subject that requires treatment. Dosage and administration are adjusted to provide sufficient levels of the active agent or to maintain the desired effect. Factors which may be taken into account include the severity of the disease state, general health of the subject, age, weight, and gender, diet, time, and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. The compositions can be co-administered with one or more additional anti-microbial agents, including anti-methanogenesis compounds (e.g., bromoethanesulphonic acid), antibodies and antibody fragments, lytic enzymes, peptide nucleic acids, antimicrobial peptides, and other antibiotics as described in detail herein. Co-administration can be simultaneous or sequential, or can alternate with repeated administration.

Particularly useful for the compositions of the invention (e.g., pharmaceutical compositions) are slow release formulas or mechanisms. For example, intra-ruminal devices include, but are not limited to, Time Capsule™ Bolus range by Agri-Feeds Ltd., New Zealand, originally developed within AgResearch Ltd., New Zealand, as disclosed in WO 95/19763 and NZ 278977, and CAPTEC by Nufarm Health & Sciences, a division of Nufarm Ltd., Auckland, New Zealand, as disclosed in AU 35908178, PCT/AU81/100082, and Laby et al., 1984, *Can. J. Anim. Sci.* 64 (Suppl.), 337-8, all of which are incorporated by reference herein. As a particular example, the device can include a spring and plunger which force the composition against a hole in the end of a barrel.

As a further embodiment, the invention relates to a composition for a water supplement, e.g., drenching composition, or food supplement, e.g., ruminant feed component, for use with any of the methods discussed above. In particular aspects, the food supplement comprises at least one vegetable material that is edible, and a peptide or polypeptide of the invention. Alternatively, the food supplement comprises at least one vegetable material that is edible, and a polypeptide or peptide, or a polynucleotide encoding a peptide or polypeptide disclosed herein, for example, as an expression vector or host cell comprising the expression vector. In particular, the composition further includes a cell inhibitor, as fused or linked to the resultant sequence. The preferred vegetable material include any one of hay, grass, grain, or meal, for example, legume hay, grass hay, corn silage, grass silage, legume silage, corn grain, oats, barley, distillers grain, brewers grain, soy bean meal, and cotton seed meal. In particular, grass silage is useful as a food composition for ruminants. The plant material can be genetically modified to contain one or more components of the invention, e.g., one or more polypeptides or peptides, polynucleotides, or vectors.

In another embodiment, antibodies which specifically bind the peptides, polypeptides, or polynucleotides of the invention may be used to determine the presence of microbes, especially methanogens, or in assays to monitor levels of such microbes. The antibodies useful for diagnostic purposes may be prepared in the same manner as those described above. Diagnostic assays include methods which utilize the antibody and a label to detect a peptide or polypeptide in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring levels of a peptide, polypeptide, or polynucleotide are known in the art (e.g., ELISA, RIA, and FACS), and provide a basis for diagnosing the presence or levels of a microbe, especially a methanogen. Normal or standard levels established by combining body fluids or cell extracts taken from normal subjects, e.g., normal humans or ruminants, with the antibody under conditions suitable for complex formation. The amount of standard complex formation may be quantified by various methods, but preferably by photometric means. Quantities of peptide, polypeptide, or polynucleotide expressed in subject, control, and treated samples (e.g., samples from vaccinated subjects) are compared with the standard values. Deviation between standard and subject values establishes the parameters for determining the presence or levels of the microbe.

In another embodiment of the invention, the polynucleotides may be used for diagnostic purposes using particular hybridization and/or amplification techniques. The polynucleotides which may be used include oligonucleotides, complementary RNA and DNA molecules, and PNAs. The polynucleotides may be used to detect and quantitate gene expression in samples in which expression may be correlated with the presence or levels of a microbe. The diagnostic assay may be used to distinguish between the absence, presence, and alteration of microbe levels, and to monitor levels during therapeutic intervention.

In one aspect, hybridization with PCR probes may be used to identify nucleic acid sequences, especially genomic sequences, which encode the peptides or polypeptides of the invention. The specificity of the probe, whether it is made from a highly specific region, e.g., 10 unique nucleotides in the 5' regulatory region, or a less specific region, e.g., in the 3' coding region, and the stringency of the hybridization or amplification (maximal, high, intermediate, or low) will determine whether the probe identifies only naturally occurring sequences, alleles, or related sequences. Probes may also be used for the detection of related sequences, and should preferably contain at least 50% of the nucleotides from any of the coding sequences. The hybridization probes of the subject invention may be DNA or RNA and derived from the nucleotide sequence of SEQ ID NO:703-1373, or complements, or modified sequences thereof, or from genomic sequences including promoter and enhancer elements of the naturally occurring sequence.

Means for producing specific hybridization probes for DNAs include the cloning of nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like. The polynucleotides may be used in Southern or northern analysis, dot blot, or other membrane-based technologies; in PCR technologies; or in dipstick, pin, ELISA assays, or microarrays utilizing fluids or tissues from subject biopsies to detect the presence or levels of a microbe. Such qualitative or quantitative methods are well known in the art.

In a particular aspect, the nucleic acid sequences may be useful in various assays labelled by standard methods, and added to a fluid or tissue sample from a subject under conditions suitable for hybridization and/or amplification. After a suitable incubation period, the sample is washed and the signal is quantitated and compared with a standard value. If the amount of signal in the test sample is significantly altered from that of a comparable control sample, the presence of altered levels of nucleotide sequences in the sample indicates the presence or levels of the microbe. Such assays may also be used to evaluate the efficacy of a particular vaccination regimen in animal studies, in clinical trials, or in monitoring the treatment of a subject.

In order to provide a basis for the diagnosis of the presence or levels of a microbe, a normal or standard profile for expression is established. This may be accomplished by combining body fluids or cell extracts taken from normal subjects, with a polynucleotide or a fragment thereof, under conditions suitable for hybridization and/or amplification. Standard levels may be quantified by comparing the values obtained from normal subjects with those from an experiment where a known amount of a substantially purified polynucleotide is used. Standard values obtained from normal samples may be compared with values obtained from samples from subjects treated for microbial growth. Deviation between standard and subject values is used to establish the presence or levels of the microbe.

Once the microbe is identified and a vaccination protocol is initiated, hybridization and/or amplification assays may be repeated on a regular basis to evaluate whether the level of expression in the subject begins to decrease relative to that which is observed in the normal subject. The results obtained from successive assays may be used to show the efficacy of vaccination over a period ranging from several days to months.

Particular diagnostic uses for oligonucleotides designed from the nucleic acid sequences may involve the use of PCR. Such oligomers may be chemically synthesized, generated enzymatically, or produced in vitro. Oligomers will preferably consist of two nucleotide sequences, one with sense orientation (5'.fwdarw.3') and another with antisense orientation (3'.fwdarw.5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate expression include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotides described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents. In one embodiment, the microarray is prepared and used according to methods known in the art such as those described in PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619).

In one aspect, the oligonucleotides may be synthesized on the surface of the microarray using a chemical coupling procedure and an ink jet application apparatus, such as that described in PCT application WO 95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may include, for example, 24, 48, 96, 384, 1024, 1536, or 6144 spots or wells (e.g., as a multiwell plate), or more, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs are appropriate probes. Therefore, in one aspect, mRNA is used to produce cDNA which, in turn and in the presence of fluorescent nucleotides, is used to produce fragments or antisense RNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and oligolabeling kits (Amersham Pharmacia Biotech) well known in the area of hybridization technology.

In another embodiment of the invention, the peptides or polypeptides of the invention or functional or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the peptide or polypeptide and the agent being tested, may be measured.

One technique for drug screening which may be used provides for high throughput screening of compounds having suitable binding affinity to the peptide or polypeptide of interest as described in published PCT application WO84/03564. In this method, large numbers of different small test compounds are synthesized on a solid substrate, such as plastic pins or some other surface. The test compounds are reacted with the peptide or polypeptide, or fragments thereof, and washed. Bound peptide or polypeptide is then detected by methods well known in the art. Purified peptide or polypeptide can also be coated directly onto plates for use in the aforementioned drug screening techniques. Alternatively, non-neutralizing antibodies can be used to capture the peptide and immobilize it on a solid support.

In another technique, one may use competitive drug screening assays in which neutralizing antibodies capable of binding the peptide or polypeptide specifically compete with a test compound for binding to the peptide or polypeptide. In this manner, the antibodies can be used to detect the presence of a test compound which shares one or more antigen binding sites with the antibody.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1: Genome Size Estimation

*Methanobrevibacter ruminantium* strain M1$^T$ (DSM1093) was grown on BY+ medium (basal medium, Joblin et al., 1990) which consists of [g/l] NaCl (1), $KH_2PO_4$ (0.5), $(NH_4)_2SO_4$ (0.25), $CaCl_2.2H_2O$ (0.13), $MgSO_4.7H_2O$ (0.2), $K_2HPO_4$ (1), clarified rumen fluid (300 ml) $dH_2O$ (360 ml), $NaHCO_3$ (5), resazurin (0.2 ml) L-cysteine-HCl (0.5), yeast extract (2), and Balch's trace elements solution (10 ml) (added trace elements; Balch et al., 1979) which consists of (g/l) nitrilotriacetic acid (1.5), $MgSO_4.7H_2O$ (3), $MnSO_4.H_2O$ (0.5), NaCl (1), $FeSO_4.7H_2O$ (0.1), $CoCl_2.6H_2O$ (0.1), $CaCl_2.2H_2O$ (0.1), $ZnSO_4.7H_2O$ (0.1), $CuSO_4.5H_2O$ (0.01), $AlK(SO_4)_2.12H_2O$ (0.01), $H_3BO_3$ (0.01), $Na_2MoO_4.2H_2O$ (0.01), $NiSO_4.6H_2O$ (0.03), Na$_2$SeO$_3$ (0.02), and Na$_2$WO$_4$.2H$_2$O (0.02). Genomic DNA was extracted by freezing cell pellets under liquid N$_2$ and grinding using a pre-chilled, sterilised mortar and pestle. Cell homogenates were imbedded in agarose plugs and subsequent manipulations were carried out in the plugs to reduce the physical shearing of genomic DNA. Digests were performed with restriction endonucleases and DNA fragments were separated using pulsed-field gel electrophoresis (PFGE).

Example 2: DNA Cloning and Sequencing

The DNA of the M. ruminantium genome was sequenced by Agencourt Biosciences Corporation (Massachusetts, USA) using a random shotgun cloning approach (Fleischmann et al., 1995) and by Macrogen Corporation (Rockville, Md., USA) using pyrosequencing. Briefly, libraries of M. ruminantium DNA were constructed in Escherichia coli by random physical disruption of genomic DNA and separation of fragments by gel electrophoresis. Large fragments in the 40 Kb range were retrieved from the gel and used to generate a large insert fosmid library. DNA fragments in the 2 to 4 Kb range were recovered and used to generate a small insert plasmid library. Clones resulting from both large and small insert libraries were grown, and their fosmid or plasmid DNA was recovered and sequenced using high throughput sequencing technology. A sufficient number of clones were sequenced to give a theoretical 8 fold coverage of the M. ruminantium genome. Additional sequence coverage was obtained by pyrosequencing of randomly sheared genomic DNA fragments (Macrogen Corporation) to a final theoretical genome coverage of approximately 10 fold.

Example 3: Sequence Assembly and Annotation

DNA sequences were aligned to find sequence overlaps and assembled into contiguous (contig) sequences using Paracel Genome Assembler (Paracel Inc, Calif., USA) and the Staden package (Staden et al., 1998) in combination with sequence from both standard and inverse PCRs. Contigs were analysed using the open reading frame (ORF) finder GLIMMER (Gene Locator Interpolated Markov Model ER Delcher et al., 1999) and each ORF was analysed by gapped BLAST (Basic Local Alignment Search Tool (Altschul et al., 1997) against the National Center for Biotechnology Information (NCBI) non-redundant nucleotide and protein databases.

The contigs from the 8 fold draft phase sequence were joined at random by artificial linking of sequences to generate a "pseudomolecule" and submitted to The Institute for Genomic Research (TIGR, DC, USA) for autoannotation. The contigs assembled from the 10 fold pyrosequencing were reanalysed using GLIMMER and ORFs were autoannotated using GAMOLA (Global Annotation of Multiplexed On-site Blasted DNA sequences; Altermann and Klaenhammer, 2003). Automated annotations were subsequently verified manually. ORFs were categorised by function using the clusters of orthologous proteins (COG) database (threshold 1e-02) (Tatusov et al., 2001).

Protein motifs were determined by HMMER (hypertext transfer protocol://hmmer.wustl.edu) using PFAM HMM and TIGRFAM libraries, with global and local alignment (hypertext transfer protocol://pfam.wustl.edu) and standard and fragment-mode TIGRFAM HMMs models (hypertext transfer protocol://world wide web.tigr.org/TIGRFAMs) respectively (threshold 1e-02). tRNAs were identified by using TRNASCAN-SE (Lowe and Eddy, 1997) and nucleotide repeats were identified using the KODON software package (Applied Maths, Austin, Tex., USA) and REPUTER (Kurtz and Schleiermacher, 1999). Genome atlas visualizations were constructed using GENEWIZ (Jensen et al., 1999). Pathway reconstructions from the predicted M. ruminantium ORFeome were carried out in conjunction with the KEGG (Kyoto Encyclopedia of Genes and Genomes, Kanehisa et al., 2004) on-line database using in-house developed software (PathwayVoyager; Altermann and Klaenhammer, 2005).

Example 4: Sequencing Results and Analysis

Size estimation of the M. ruminantium genome by restriction enzyme digestion of genomic DNA and sizing of fragments via PFGE, indicated a single chromosome of approximately 2.5-2.9 Mb. Initial sequencing of large and small insert clones (6 fold draft coverage) and assembly of the sequence into contigs indicated that a 40 Kb region of the genome was highly over-represented (>20 fold), particularly within the small insert library. This was possibly due to a high copy number plasmid (although no extrachromosomal DNAs had been identified) or a lysogenic bacteriophage that had replicated during the growth of the culture used for DNA extraction. Because of this large sequence bias, additional sequencing was carried out (2 fold theoretical genome coverage) for only large insert clones yielding a final 8 fold coverage from Sanger sequencing. The 8 fold draft phase sequence was assembled into 756 contigs which were linked via 105 scaffolds. Further pyrosequencing was carried out to an additional ~10 fold coverage and incorporation of these sequences into the assembly resulted in the contig number dropping to 27. Subsequent gap closure using inverse and long range PCR techniques reduced the contig number to 14.

The combined length of the 14-contig sequence indicate that the genome is slightly larger (2,920,443 bp) than the size estimated by PFGE (FIG. 1A) and significantly larger than its closest relative, M. smithii (1.9 Mb). The % G+C of 32.7 is close to the reported 27.5% to 31.6% range reported for M. ruminantium strains (Balch et al, 1979). Analysis of the sequence predicts 2672 ORFs and the total number of hits to protein families (TIGRFam and PFam) and Clusters of Orthologous Groups (COGs) are reported in FIG. 1B. All of the genes predicted to be involved in methanogenesis from H$_2$+CO$_2$ and formate are present (FIG. 1C; and FIGS. 6A-6C). However, the draft sequence of M. ruminantium lacks a methyl coenzyme reductase II (mcr II or mrt) system. In other methanogens, the mcr II cluster encodes an isoenzyme of the methyl CoM reductase I enzyme which is up-regulated during growth at high partial pressures of H$_2$ (Reeve et al., 1997). H$_2$ is used rapidly in the rumen and does not accumulate to high levels, so M. ruminantium appears to be adapted to use low levels of H$_2$ via the mcr I system only.

Comparison of the draft M. ruminantium genome with the closely related M. smithii and Mt. thermoautotrophicus reveals several regions of difference. Some of the gene differences encode very large surface proteins of the asparagine/threonine-rich large protein family that may contain CPOMP and DUF11 repeat sequences (chlamydial polymorphic outer membrane proteins, and domain of unknown function, respectively) that are likely to mediate interactions with surfaces or other microorganisms in the rumen environment (see FIGS. 7A-7C). Similar repeat sequences are also found in large surface proteins encoded in both the Ms. stadtmanae and M. smithii genomes (Samuel et al., 2007).

M. ruminantium has previously been reported to produce a capsule (Smith and Hungate, 1958) and sequence analysis shows that it encodes more than 50 genes (glycosyl transferases (GT), other transferases, epimerases and transporters) involved in the synthesis and export of exopolysaccharides confirming that it decorates its surface with polysaccharides (see FIGS. 8A-8C). *M. ruminantium* has at least 30 glycosyl transferases (6 GT1, 21 GT2, 2 GT4 and 1 GT66; see FIGS. 8A-8C) compared with 28 in *M. smithii* (1 GT1; 22 GT2; 4 GT4 and 1 GT66) and 41 in *M. stadtmanae* (2 GT1; 26 GT2; 12 GT4 and 1 GT66) (Samuel et al, 2007; Fricke et al., 2006; Coutinho and Henrissat, 1999). This is a relatively large number of genes devoted to encode surface polysaccharides by these organisms and suggests that this is an important factor for survival in gastrointestinal environments.

Nucleotide repeat analysis revealed the presence of at least two Spacer Interspersed Direct Repeats (SPIDRs) regions in the *M. ruminantium* genome. SPIDRs are nucleotide repeats (usually less than 40 nt) made up from identical units separated by heterologous sequences and were first characterised in prokaryotes (Jansen et al., 2002). The *M. ruminantium* SPIDR I has a unique genetic arrangement which consists of two identical repeat structures flanking a 17 kb region harbouring a cluster of associated cas-genes. Similar repeat structures have been found in several methanogen genomes. *Methanocaldococcus jannaschii* contains 18 copies of a multicopy repetitive nucleotide element (Butt et al, 1996) which consist of a long (391-425 bp) repeat segment followed by up to 25 short (27-28 bp) repeat segments which are themselves separated by 31 to 51 bp of unique sequence. The *Ms. stadtmanae* genome contains a 4.8 Kb region in which a 30 bp element is repeated 59 times (Fricke et al., 2006). *Mt. thermoautotrophicus* contains two extended repeats (3.6 and 8.6 kb in size) that contain a 372-bp repeat sequence, followed by 47 and 124 copies of the same 30 bp repeat sequence separated by unique sequences 34 to 38 bp in length (Smith et al., 1997). The biological function of these SPIDRs is unknown, although a current hypothesis speculates that this system is a functional analog of the eukaryotic small interfering RNA systems and represents a defence system against foreign replicons that functions on the antisense RNA principle (Jansen et al., 2002; Haft et al., 2005; Godde and Bickerton, 2006; Makarova et al., 2006).

Figure 9B-77:
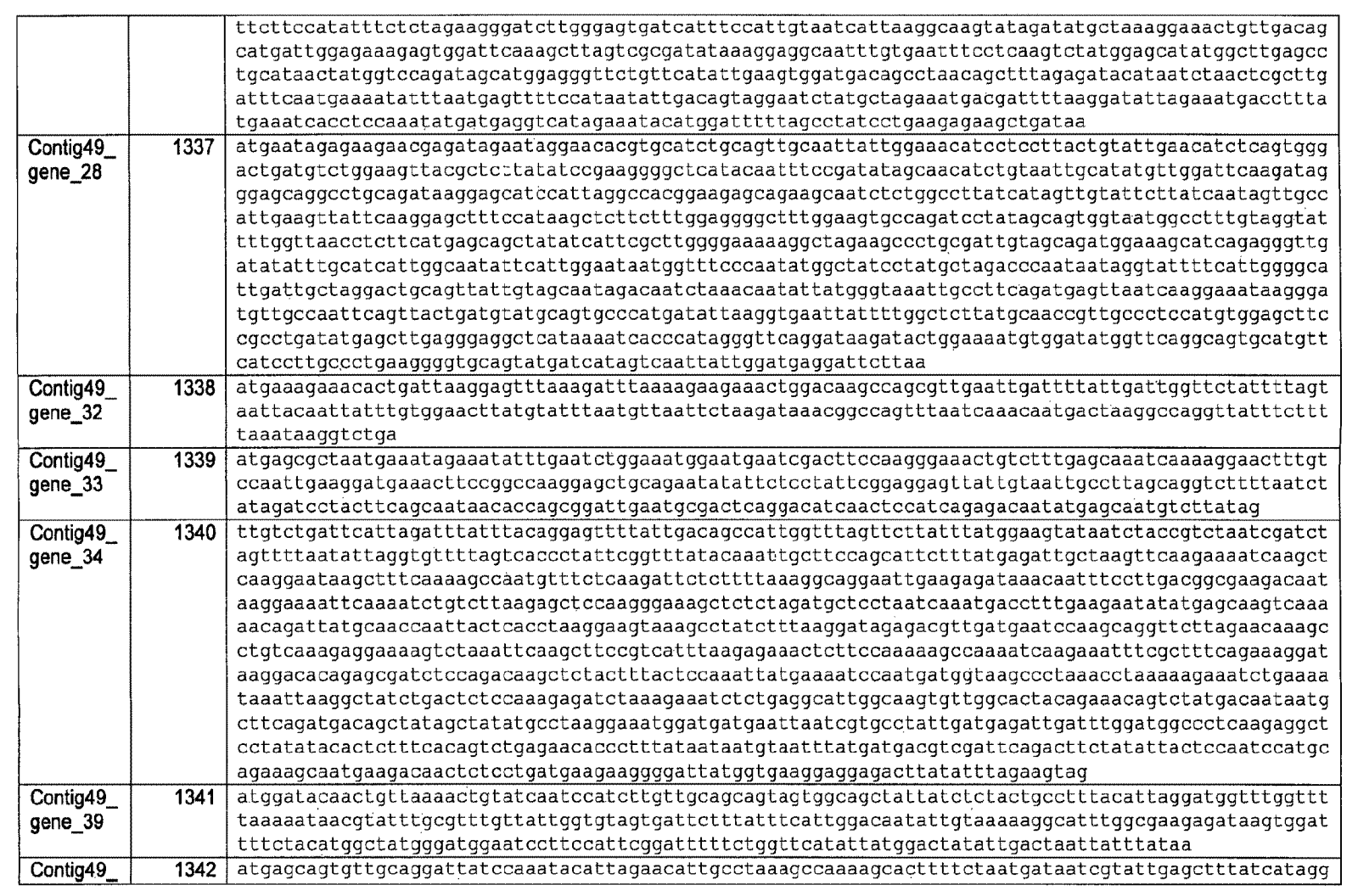

The *M. ruminantium* genome also encodes a large number of ORFs predicted to encode proteins with membrane-spanning domains, which consequently are expected to contain regions that are exposed on the cell surface (FIGS. 9A, 9B and 9C).

Example 5: Antibody Production and Testing

Preparation of cell walls from *M. ruminantium*: Cell walls from *M. ruminantium* were prepared by freezing cell pellets under liquid $N_2$ and grinding using a pre-chilled, sterilised mortar and pestle. The finely ground cells were resuspended in trypsin-phosphate buffer (40 mg trypsin/200 ml of 0.1 M phosphate buffer, pH 7.9) and incubated at 37° C. for 2 hours. The preparation was then centrifuged at 48,000 g for 30 minutes at 4° C., and the resulting pellet was washed twice with sterile distilled $H_2O$ and freeze dried.

Antibody production: Nine peptide sequences which were predicted to be located external to the cell were identified from the *M. ruminantium* genome sequence and selected as potential antigens. Five milligrams of each of these peptides were synthesized (Invitrogen) and their purity checked by mass spectroscopy. The peptides and their coding sequences are shown in FIG. 4. The full nucleic acid and amino acid sequences are shown in FIG. 5. Two milligrams of each peptide remained unconjugated for ELISA and 3 mg was conjugated to Keyhole Limpet Hemocyanin (KLH) for animal immunisation.

The vaccination programme is summarised in FIG. 2 and proceeded as follows. Each immunization used one sheep (1-3 years old) which was pre-bled to give 2-5 ml of preimmune serum on Day 0. This was followed by primary intradermal (ID) injections of 200 μg of conjugated peptide in CFA (Complete Freund's Adjuvant) at 10-15 sites on Day 0. Intradermal (ID) injections of 200 μg of KLH-peptide in IFA (Incomplete Freund's Adjuvant) at 10-15 sites were made on Day 14, and 200 μg of KLH-peptide in CFA at 10-15 sites on Day 28. A further five intradermal (ID) injections of 200 μg of KLH-peptide in IFA at 10-15 sites were made on Days 56, 70, 84, 98 and 112. Four test bleeds (2-5 ml) were made on Days 42, 56, 84, and 112. A production bleed giving approximately 1,000 ml of antisera was made at the end of the standard protocol.

The antibody titer was determined with an enzyme linked immunosorbent assay (ELISA) with peptide-GGG (goat gamma globulin) bound in solid phase (0.1 μg/100 μl/well) on high binding 96 well plates. The serum was first diluted 50 fold and then further diluted in 2-fold serial dilutions. The ELISA Titer was calculated as the estimated dilution factor that resulted in an OD at 405 nm of 0.2 and was derived from nonlinear regression analysis of the serial dilution curve. Detection was obtained using an HRP conjugated secondary antibody and ABTS substrate.

The sheep antibody responses to vaccination are shown in FIG. 3. All sheep sera had titres at 6 weeks which were at least 32-fold greater than pre-immunisation (1:1600). The most antigenic preparation was the mtrD peptide which had a titre 1024-fold greater than the pre-immunisation level. The least immunogenic preparations were the mtrE peptide, the ORF508 and ORF819 surface protein peptides. The *M. ruminantium* cell wall preparation induced a good antibody response (256-fold higher than preimmune levels) but this was not sustained longer than 15 weeks despite several booster shots.

Antibody binding to *M. ruminantium* cells: An ELISA assay was used to measure antibody binding to *M. ruminantium* cells as follows. MaxiSorp ELISA plates (Nunc) were coated with *M. ruminantium* whole cells (40 μl of cells into 2 ml of sodium carbonate buffer) and with *M. ruminantium* cytosolic protein fractions. The serum samples were diluted 1/20 (25 μl into 475 μl diluent) in PBS Tween 20 containing 1% w/v casein, and incubated at room temperature for 1 hour. The plate was washed 6 times with PBS Tween 20. A negative control serum was included, and this was obtained from a sheep which had not had colostrum as a lamb.

For detection the conjugate used was donkey anti sheep/goat IgG HRP (Batch 061005 Star 88P by Serotec) and 50 μl of a 1/5000 dilution (2 μl into 10 ml diluent) was added to each well. The 3,3',5,5' tetramethylbenzidine (TMB) substrate was then added (50 μl/well) and the reaction incubated at room temperature in dark for 15 min. Stop solution (0.05 M $H_2SO_4$, 50 μl/well) was then added and the plate read at 450 nm.

*M. ruminantium* growth inhibition test: The immune serum samples were thawed in the anaerobic hood, and 0.1 ml from each of 10 samples was placed in a 1.5 ml microcentrifuge tube. The mixture (1 ml) was incubated at room temperature with the lid open in the anaerobic hood overnight to remove any dissolved oxygen. The preimmune serum served as a negative control. The combined serum sample (0.3 ml) was added into 5 ml of growing *M. ruminantium* culture in Hungate tubes in triplicate in the anaerobic hood. Gas (80% $H_2$ and 20% $CO_2$) was pumped into the Hungate tubes and the cultures were incubated at 39° C. on a shaker (100 rpm). Methanogen growth was monitored by measuring the OD at 600 nm with a spectrophotometer and by gas chromatograph determination of hydrogen usage and methane production.

ELISA assays showed that antibodies generated from each of the antigens bound to *M. ruminantium* cells fixed to microtitre plates. Antibodies were shown to bind to *M. ruminantium* cells in vitro, although single antibody preparations added to *M. ruminantium* cultures did not inhibit methanogen growth or reduce the amount of methane formed. However, a preparation consisting of pooled samples of antisera from each of the 10 different antigens, appeared to increase cell aggregation when added to *M. ruminantium* cultures.

Example 6: Overview

*Methanobrevibacter ruminantium* was chosen for genome sequencing because of its prevalence in the rumen under a variety of dietary conditions (based on cultivation and molecular detection data), the availability of cultures, its amenity to routine growth in the laboratory, and the relatively large amount of previous studies and background literature available for this organism. A significant number of the genes within the *M. ruminantium* have been assigned a function, and have thereby allowed a detailed picture of this organism's lifestyle within the rumen. *M. ruminantium*'s dependence on simple substrates ($H_2+CO_2$, formate) and its interaction with the rumen environment via surface proteins and exopolysaccharides are important targets for inhibition. Similarly, the SPIDRs hold promise for both specific targeting of *M. ruminantium* and for future genetic manipulations to assist in determining gene function. The sequence data elucidates the metabolism of this organism and how it interacts with other microbes, and points to conserved systems and components among methanogens that can be inactivated to prevent or reduce methane formation in the rumen.

REFERENCES

Altermann E, Klaenhammer T R (2005) PathwayVoyager: pathway mapping using the Kyoto Encyclopedia of Genes and Genomes (KEGG) database. *BMC Genomics* 6:60-66.

Altermann, E., and T. R. Klaenhammer. 2003. GAMOLA: a new local solution for sequence annotation and analyzing draft and finished prokaryotic genomes. Omics 7:161-169.

Altschul S F, Madden T L, Schaffer A A, Zhang J, Zhang Z, Miller W, Lipman D J (1997) Gapped BLAST and PSI-BLAST: a new generation of protein database search programs. *Nucleic Acids Research* 25, 3389-3402.

Balch W E, Fox G E, Magrum L J, Woese C R, Wolfe R S (1979) Methanogens: reevaluation of a unique biological group. *Microbiological Reviews* 43, 260-296.

Baresi, L. and Bertani, G. 1984. Isolation of a bacteriophage for a methanogenic bacterium. In *Abstracts of the Annual Meeting of the American Society for Microbiology*. Washington D.C.: American Society for Microbiology, p. 133.

Bickle, T. A. and D. H. Kruger. 1993. Biology of DNA restriction. Microbiol. Rev. 57:434-450.

Bult C J, et al. (1996) Complete genome sequence of the methanogenic archaeon, *Methanococcus jannaschii*. Science 273, 1058-1073.

Coutinho P M, Henrissat B (1999) Carbohydrate-active enzymes: an integrated database approach. In 'Recent Advances in Carbohydrate Bioengineering' (Eds H J Gilbert, G Davies, B Henrissat and B Svensson) pp. 3-12 (The Royal Society of Chemistry, Cambridge) (Carbohydrate Active Enzymes database, hypertext transfer protocol://world wide web.cazy.org/).

Delcher A L, Harmon D, Kasif S, White O, Salzberg S L (1999) Improved microbial gene identification with GLIMMER. *Nucleic Acids Research* 27, 4636-4641.

Fleischmann et al., 1995. Whole-genome random sequencing and assembly of *Haemophilus influenzae* Rd Science 269:496-512.

Fricke W F, Seedorf H, Henne A, Kruer M, Liesegang H, Hedderich R, Gottschalk G, Thauer R K (2006) The genome sequence of *Methanosphaera stadtmanae* reveals why this human intestinal archaeon is restricted to methanol and $H_2$ for methane formation and ATP synthesis. *Journal of Bacteriology* 188, 642-658.

Godde J S, Bickerton A (2006) The repetitive DNAe called CRISPRs and their associated genes: evidence of horizontal transfer among prokaryotes. *Journal of Molecular Evolution* 62, 718-729.

Haft D H, Selengut J, Mongodin E F, Nelson K E (2005) A guild of 45 CRISPR-associated (Cas) protein families and multiple CRISPR/Cas subtypes exist in prokaryotic genomes. *PLoS Computational Biology* 1:474-483.

Jansen R, Embden J D, Gaastra W, Schouls L M (2002) Identification of genes that are associated with DNA repeats in prokaryotes. *Molecular Microbiology* 43, 1565-1575.

Jansen R, van Embden J D, Gaastra W, Schouls L M (2002) Identification of a novel family of sequence repeats among prokaryotes. *OMICS: A journal of integrative biology* 6, 23-33.

Jensen, L. J., Friis, C. and Ussery, D. W. 1999 Three views of microbial genomes. Res. Microbiol. 150, 773-777.

Joblin K N, Naylor G E, Williams A G (1990) Effect of *Methanobrevibacter smithii* on xylanolytic activity of anaerobic ruminal fungi. *Applied and Environmental Microbiology* 56, 2287-2295.

Kanehisa M, Goto S, Kawashima S, Okuno Y, Hattori M (2004) The KEGG resource for deciphering the genome. *Nucleic Acids Research* 32, D277-D280.

Kiener, A., Konig, H., Winter, J. and Leisinger, T. 1987. Purification and use of *Methanobacterium wolfei* pseudomurein endopeptidase for lysis of *Methanobacterium thermoautotrophicum*. J. Bacteriol. 169, 1010-1016.

Knox, M. R. and Harris, J. E. 1986. Isolation and characterisation of a bacteriophage of *Methanobrevibacter smithii*. In *Abstracts of the XIV International Congress on Microbiology*. Manchester: International Union of Microbiological Societies.

Kurtz S, Schleiermacher C (1999) REPuter: fast computation of maximal repeats in complete genomes. *Bioinformatics* 15, 426-427.

Lowe T M, Eddy S R (1997) tRNAscan-SE: a program for improved detection of transfer RNA genes in genomic sequence. *Nucleic Acids Research* 25, 955-964.

Loenen, W. and N. Murray. 1986. Modification enhancement by restriction alleviation protein (Ra1) of bacteriophage lambda. J. Mol. Biol. 190:11-22.

Lucchini, S., F. Desiere, and H. Brussow. 1999. Comparative genomics of *Streptococcus thermophilus* phage species supports a modular evolution theory. J. Virol. 73:8647-8656.

Luo, Y. N., Pfister, P., Leisinger, T. and Wasserfallen, A. 2002. Pseudomurein endoisopeptidases PeiW and PeiP, two moderately related members of a novel family of proteases produced in *Methanothermobacter* strains. FEMS Microbiol. Lett. 208, 47-51.

Makarova, K. S., Aravind, L. and Koonin, E. V. 1999. A superfamily of archaeal, bacterial, and eukaryotic proteins homologous to animal transglutaminases. Protein Sci. 8, 1714-1719.

Makarova K S, Grishin N V, Shabalina S A, Wolf Y I, Koonin E V (2006) A putative RNA-interference-based immune system in prokaryotes: computational analysis of the predicted enzymatic machinery, functional analogies with eukaryotic RNAi, and hypothetical mechanisms of action. *Biology Direct* 1:7-32.

New Zealand Statistics 2005 (www.stats.govt.nz)

New Zealand's Greenhouse Gas Inventory 1990-2004. The National Inventory Report and Common Reporting Format. (2006) Ministry for the Environment. Hypertext transfer protocol://www.mfe.govt.nz/publications/climate/nir-apr06/nir-apr06.pdf.

Rawlings, N. D., Morton, F. R. and Barrett, A. J. 2006. MEROPS: the peptidase database. Nucleic Acids Res. 34, D270-D272.

Reeve J N, Nolling J Morgan R M, Smith D R (1997) Methanogenesis: genes, genomes and who's on first? *Journal of Bacteriology* 179, 5975-5986.

Samuel B S, Hansen E E, Manchester J K, Coutinho P M, Henrissat B, Fulton R, Latreille P, Kim K, Wilson R K, Gordon J I (2007) Genomic adaptations of *Methanobrevibacter smithii* to the human gut. *Proceedings of the National Academy of Sciences USA* 104, 10643-10648.

Smith D R, et al. (1997) Complete genome sequence of *Methanobacterium thermoautotrophicum* ΔH: Functional analysis and comparative genomics. *Journal of Bacteriology* 179, 7135-7155.

Smith P H, Hungate R E (1958) Isolation and characterization of *Methanobacterium ruminantium* n. sp. *Journal of Bacteriology* 75, 713-718.

Staden R, Beal K F, Bonfield J K (1998) The Staden Package. *Methods in Molecular Biology: Bioinformatics Methods and Protocols* 132, 115-130.

Tatusov R L, Natale D A, Garkavtsev I V, Tatusova T A, Shankavaram U T, Rao B S, Kiryutin B, Galperin M Y, Fedorova N D, Koonin E V (2001) The COG database: new developments in phylogenetic classification of proteins from complete genomes *Nucleic Acids Research* 29, 22-28.

All publications and patents mentioned in the above specification are herein incorporated by reference. Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the spirit and scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10590170B2). An electronic copy of the "Sequence Listing" will also be available from the USPTO upon request and payment of the fee set forth in 37 CFR 1.19(b)(3).

What we claim is:

1. A vaccine composition comprising a polypeptide comprising the amino acid sequence of SEQ ID NO: 165, and an adjuvant.

2. The vaccine composition of claim 1, wherein the polypeptide comprises a conjugate or fusion molecule.

3. A kit for reducing methanogen growth or methane production in a ruminant comprising a vaccine composition of claim 1.

4. A method of vaccinating an animal against a methanogen, comprising administering to said animal, a vaccine composition according to claim 1.

5. The method of claim 4, wherein the methanogen is *Methanobrevibacter ruminantium*.

6. The method of claim 4, wherein the animal is a ruminant.

7. The method of claim 4, wherein the ruminant is selected from the group consisting of cattle, sheep, goats, buffalo, moose, antelope, caribou, and deer.

8. A method of reducing methane emissions from a ruminant, comprising vaccinating the ruminant against a methanogen according to claim 4.

* * * * *